US011434522B1

(12) United States Patent
Hunter et al.

(10) Patent No.: US 11,434,522 B1
(45) Date of Patent: Sep. 6, 2022

(54) DETECTION OF CHROMOSOME INTERACTIONS

(71) Applicant: Oxford Biodynamics PLC, Oxford (GB)

(72) Inventors: Ewan Hunter, Oxford (GB); Aroul Ramadass, Oxford (GB); Alexandre Akoulitchev, Oxford (GB)

(73) Assignee: Oxford Biodynamics PLC, Oxford (GB)

( * ) Notice: Subject to any disclaimer, the term of this patent is extended or adjusted under 35 U.S.C. 154(b) by 729 days.

(21) Appl. No.: 15/738,476

(22) PCT Filed: Jun. 24, 2016

(86) PCT No.: PCT/GB2016/051900
§ 371 (c)(1),
(2) Date: May 23, 2018

(87) PCT Pub. No.: WO2016/207653
PCT Pub. Date: Dec. 29, 2016

(30) Foreign Application Priority Data

Jun. 24, 2015 (GB) ..................... 1511079
Jun. 26, 2015 (GB) ..................... 1511080
Nov. 5, 2015 (GB) ..................... 1519555

(51) Int. Cl.
*C12Q 1/68* (2018.01)
*C07H 21/00* (2006.01)
*C12Q 1/6827* (2018.01)
*C12Q 1/6886* (2018.01)

(52) U.S. Cl.
CPC ......... *C12Q 1/6827* (2013.01); *C12Q 1/6886* (2013.01); *C12Q 2521/501* (2013.01); *C12Q 2523/101* (2013.01); *C12Q 2537/159* (2013.01); *C12Q 2600/106* (2013.01)

(58) Field of Classification Search
CPC ................................. C12Q 1/68; C07H 21/00
See application file for complete search history.

(56) References Cited

U.S. PATENT DOCUMENTS

| 10,508,303 | B2 | 12/2019 | Ren et al. |
| 2007/0238094 | A1 | 10/2007 | Chaussabel et al. |
| 2010/0075861 | A1 | 3/2010 | De et al. |
| 2010/0130373 | A1* | 5/2010 | Dekker .............. C12N 15/1072 506/9 |
| 2018/0274015 | A1 | 9/2018 | Akoulitchev et al. |
| 2019/0071715 | A1 | 3/2019 | Ramadass et al. |

FOREIGN PATENT DOCUMENTS

| WO | 2005/118873 A2 | 12/2005 |
| WO | 2007/093819 A2 | 8/2007 |
| WO | 2008/084405 A2 | 7/2008 |
| WO | 2009/147386 A1 | 12/2009 |
| WO | 2012/159025 A2 | 11/2012 |
| WO | 2015/077414 A1 | 5/2015 |

OTHER PUBLICATIONS

Figueroa-Romero et al. PLOS One 7(12) :e52672 (Year: 2012).*
Imakae et al., Iterative correction of Hi-C data reveals hallmarks of chromosome organization. Nature Methods 9(10) : 999 (Year: 2012).*
Lajoie et al., The Hitchhiker's guide to Hi-C analysis: Practical guidelines. Methods 72 :65-75 (Year: 2015).*
Jeznach, M., et al., "Breast cancer: development of early non-invasive diagnostics to reduce disease mortality and psychological outcomes," Psychoonkologia, vol. 2: 35-49 (2013).
"Systemic Epigenetic Biomarkers for ALS Improve Early Diagnosis, Treatment and Trials," International Pharmaceutical Industry Magazine; Spring 2016, vol. 8 Issue 1.
Press Releases from Oxford BioDynamics from Aug. 10, 2009 to Apr. 25, 2016.
Tests look at the development of type 2 diabetes to predict the progress of the condition; The Diabetes Research & Wellness Foundation; Apr. 21, 2016.
Hughes, E., "Oxford BioDynamics expands biomarker discovery programme for ALS," EPM Magazine; Jan. 28, 2016. <<https://www.epmmagazine.com/news/oxford-biodynamics-expands-biomarker-discovery-programme-for/ >>.
Youdell, M., et al., "Development of Novel ALS Treatment on the Basis of Mechanisms of Cellular Chronological Life Span Control," Poster at the 12th annual Northeast ALS Consortium (NEALS); Oct. 7, 2013.
Williams, M. T., et al., "Fcg Receptor Targeting Reduces Bone Disease in a Pre-clinical Model of Multiple Myeloma," 57th American Society of Hematology Meeting in Orlando; Dec. 9, 2015.
Babu, D., et al., "3D Genome Organization in Health and Disease: Emerging Opportunities in Cancer Translational Medicine," Nucleus 6:5, 382-393; Sep./Oct. 2015.
Hunter, E., et al., Development of Epigenetic Profiling of ALS Patients with Chromosome Conformation Biomarkers Offers Novel Signatures for Non-invasive Diagnostic and Prognostic Stratifications; Annual 2015 ALS Consortium Conference in Tampa, Florida; Nov. 6, 2015.
"Biotechnology firm Oxford BioDynamics earns Technology Innovation Award for biomarker discovery platform EpiSwitch™," Press Release From Oxford BioDynamics of Oct. 22, 2015.
"Amyotrophic Lateral Sclerosis (ALS) patients could benefit from a new tool being developed by Oxford Biodynamics partly funded by the UK government," Press Release From Oxford BioDynamics of Dec. 16, 2014.
Akoulitchev, A., "Epigenetics and New Approaches in Molecular Diagnosis," CMR Seminar Announcement poster at SingHealth, Jan. 23, 2012.
Pchejetski, D., et al., "Validation of a New Epigenetic-Based Prognostic Blood Test to Predict Prostate Cancer Aggressiveness," Annals of Oncology, 24 (Supplement 9): ix31-ix65, 2013.
New Frontiers in Epigenetics: Genomic Biomarkers with EpiSwitchTM Technology, Oxford Biodynamics Breast Cancer Presentation at SingHealth, National Cancer Centre, Singapore (NCCS), Jan. 23, 2012.

(Continued)

*Primary Examiner* — Ethan C Whisenant
(74) *Attorney, Agent, or Firm* — Elmore Patent Law Group, P.C.; Joseph C. Zucchero; Carolyn S. Elmore

(57) ABSTRACT

A method of determining the epigenetic chromosome interactions which are relevant to a companion diagnostic.

5 Claims, 9 Drawing Sheets

Specification includes a Sequence Listing.

(56) References Cited

OTHER PUBLICATIONS

Akoulitchev, A., Chinese language Abstract O-065. Annual Meeting of Japanese Association of Breast Cancer Screening, Okinawa. Nov. 30, 2012.
Akoulitchev, A., "Clinical evaluation of EpiSwitch OBD-27, a Breast Cancer Screening Tool, based on Epigenetics Concept on Japanese population," English translation of Abstract O-065. Annual Meeting of Japanese Association of Breast Cancer Screening, Okinawa. Nov. 30, 2012.
Campus Internal Grant Report (Academics year 2010-11). Journal of Saitama Medical University, 2012, vol. 39, No. 1, p. 4-8.
Goodyear, C., et al., "Epigenetic Chromosome Conformations Predict MTX Responsiveness in Early Rheumatoid Arthritis Patients". Presentation made at ACR/ARHP Annual Meeting (Nov. 6-11, 2015 in San Francisco, CA), publicly disclosed earlier on Mar. 31, 2014 at 'The Scottish Early Rheumatoid Arthritis (SERA) Meeting' in Perth, Scotland.
Bastonini, E., et al., "Chromatin barcodes as biomarkers for melanoma," Pigment Cell Melanoma Res., 27: 788-800 (2014).
Alshaker, H., et al., "Development of a new epigenetic-based blood test to stratify prostate cancer patients according to risk groups," International Journal of Molecular Medicine, 34 (Suppl S9) (2014).
Sun, J., et al., "A Novel Suppressive Long Noncoding RNA within the IGF1R Gene Locus Is Imprinted in Acute Myelocytic Leukemia," Blood, 124(21): p. 3592 (2014). Retrieved from the internet May 21, 2020. <<https://ashpublications.org/blood/article/124/21/3592/97498/A-Novel-Suppressive-Long-Noncoding-RNA-within-the?searchresult=1>>.
Oxford BioDynamics Website (2013-2014) http://web.archive.org/web/20131209081232/http://oxfordbiodynamics.com/applications/predictive-biomarkers.
Kubiak, M., et al., "Can chromatin conformation technologies bring light into human molecular pathology?" Acta Biochimica Polonica, 62(3): 483-489 (2015).
Mukhopadhyay, S., et al., "Formation of distinct chromatin conformation signatures epigenetically regulate macrophage activation," Intl. Immunopharmacol., 18: 7-11 (2013).
Cheng, J. X., et al., "Disease-Associated Chromatin Conformation and Therapeutic Implications in Leukemia," Blood, 122(21): 4892 (2013).
Jakub, J. W., et al., "A pilot study of chromosomal aberrations and epigenetic changes in peripheral blood samples to identify patients with melanoma," Melanoma Research, 25: 406-411 (2015).
Carini, et al., "Epigenetic Chromosome Conformatons Predict MTX Responsiveness in Early Rheumatoid Arthritis Patients", Annual Meeting of the American-College-of-Rheumatology (ACR) and Association-of-Rheumatology-Health; San Francisco, CA, USA; 2015, vol. 67, Suppl. 10. Retrieved from the Internet: URL:http://acrabstracts.org/abstract/epigenetic-chromosome-conformations-predict-mtx-responsiveness-in-early-rheumatoid-arthritis-patients/ [retrieved on Sep. 8, 2016].
Jakub, J. W., et al., "Diagnostic Value of Epigenetic Chromatin Conformation Changes Identified in Peripheral Blood to Differentiate Early Stage Melanoma From Healthy Volunteers and Other Cutaneous Malignancies," WSA 2013 Annual Scientific Session, 2013.
Crutchley, J., et al., "Chromatin conformation signatures: ideal human disease biomarkers?", Biomarkers in Medicine, vol. 4, No. 4, Aug. 1, 2010 (Aug. 1, 2010), pp. 611-629.
Byers, R. J., et al., "Subtractive hybridization: Genetic takeaways and the search for meaning", International Review of Experimental Pathology, Blackwell Scientific, Oxford, GB, vol. 81, No. 6, pp. 391-404 (2000).
Ranganathan, P., et al., "Wil! pharmacogenetics allow better prediction of methotrexate toxicity and efficacy in patients with rheumatoid arthritis?" Annals of the Rheumatic Diseases, British Medical Association, GB, vol. 62, No. 1, Jan. 1, 2003 (Jan. 1, 2003), pp. 4-9.
Plant, D., et al., "Genetic and epigenetic predictors of responsiveness to treatment in RA," Nature Reviews, Rheumatology, vol. 10, No. 6, Jun. 1, 2014 (Jun. 1, 2014).
Wessels, J., et al., "A clinical pharmacogenetic model to predict the efficacy of methotrexate monotherapy in recent-onset rheumatoid arthritis", Arthritis & Rheumatism, vol. 56, No. 6, Jun. 1, 2007 (Jun. 1, 2007), pp. 1765-1775.
Martin, P., et al., "Capture Hi-C reveals novel candidate genes and complex long-range interactions with related autoimmune risk loci", Nature Communications, vol. 6(10069), www.nature.com/naturecommunications, Nov. 30, 2015 (Nov. 30, 2015).
Verlaan, D. J., et al., "Allele-Specific Chromatin Remodeling in the ZPBP2/GSDMB/ORMDL3 Locus Associated with the Risk of Asthma and Autoimmune Disease," The American Journal of Human Genetics, 85, 377-393 (2009).
Shulha, H. P., et al., "Human-Specific Histone Methylation Signatures at Transcription Start Sites in Prefrontal Neurons", PLoS Biol 10(11): e1001427.
McCord, R., et al., "Chromatin signatures of DLBCL subtypes" [abstract] in: Proceedings of the 105th Annual Meeting of the American Association for Cancer Research; Apr. 5-9, 2014; San Diego, CA. Philadelphia (PA): AACR; Cancer Research 2014;74(19 Suppl):Abstract 462. doi:10.1158/1538-7445.AM2014-462 [retrieved Aug. 20, 2018] <URL: http://cancerres.aacrjournals.org/content/74/19_Supplement/462.
Wikipedia, "Chromosoma conformation capture" as at Apr. 28, 2014 [retrieved Aug. 20, 2018] <URL: https://en.wikipedia.org/w/index.php?title=Chromosome_conformation_capture&oldid=606170436.
Wang, S., et al., "Disease mechanisms in rheumatology—tools and pathways: defining functional genetic variants autoimmune diseases", Arthritis and Rheumatology 67(1): 1-10 (2015).
Xu, Z., et al., "Mapping of long-range INS promoter interactions reveals a role for calcium-activated chloride channel ANO1 in insulin secretion", PNAS, 111(47): 16760-16765 (2014).
Dekker, J., et al., "Capturing chromosome conformation", Science, 295: 1306-1311 (2002).
Mitchell, R. M., "A CSF biomarker panel for identification of patients with amyotrophic lateral sclerosis", Neurology, 72(1): 14-19, (2009). Epub Nov. 5, 2008.
Mitchell, R. M., "Plasma biomarkers associated with ALS and their relationship to iron homeostasis", Muscle Nerve, 42: 95-103 (2010).
Woollacott, I. O. C., et al., "The C9ORF72 expansion mutation: gene structure, phenotypic and diagnostic issues", Acta Neuropathol., 127(3): 319-332 (2014).
Salter, M., et al., "Initial Identification of a Blood-Based Chromosome Conformation Signature for Aiding in the Diagnosis of Amyotrophic Lateral Sclerosis.", EBioMedicine, 33: 169-184 (2018). doi: 10.1016/j.ebiom.2018.06.015. Epub Jun. 23, 2018.
Goodyear, C., et al., "Epigenetic Chromosome Conformations Predict MTX Responsiveness in Early Rheumatoid Arthritis Patients". Presentation made at ACR/ARHP Annual Meeting (Nov. 6-11, 2015 in San Francisco, CA).
Liao, K. P., et al., "Environmental influences on risk for rheumatoid arthritis," Curr. Opin. Rheumatol., 21: 279-283 (2009).
Bottini, N., et al., "Epigenetics in rheumatoid arthritis: a primer for rheumatologists," Curr. Rheumatol. Rep., 15, 372 (2013).
McInnes, I. B., et al., "The pathogenesis of rheumatoid arthritis," N. Engl. J. Med., 365(23): 2205-2219 (2011).
Liu, Y., et al., "Epigenome-wide association data implicate DNA methylation as an intermediary of genetic risk in rheumatoid arthritis," Nat. Biotechnol., 31(2): 142-147 (2013).
Nakano, K., et al., "DNA methylome signature in rheumatoid arthritis," Ann. Rheum. Dis., 72(1): 110-117 (2013).
De La Rica, L., et al., "Identification of novel markers in rheumatoid arthritis through integrated analysis of DNA methylation and microRNA expression," J. Autoimmun., 41: 6-16 (2013).
Viatte, S., et al., Genetics and epigenetics of rheumatoid arthritis, Nat. Rev. Rheumatol., 9(3): 141-153 (2013).
Hider, S. L., et al., "Can clinical factors at presentatian be used to predict outcome of treatment with methotrexate in patients with early inflammatory polyarthritis?" Ann. Rheum. Dis., 68: 57-62 (2009).

(56) References Cited

OTHER PUBLICATIONS

Farragher, T. M., et al., "Early treatment with, and time receiving, first disease-modifying antirheumatic drug predicts long-term function in patients with inflammatory polyarthritis," Ann. Rheum. Dis., 69: 689-695 (2010).

Bakker, M. F., et al., "Early clinical response to treatment predicts 5-year outcome in RA patients: follow-up results from the Camera study," Ann. Rheum. Dis., 70: 1091-1103 (2011).

Barrera, P., et ai., "Drug survival, efficacy and toxicity of monotherapy with a fully human anti-tumour necrosis factor-α antibody compared with methotrexate in long-standing rheumatoid arthritis," Rheumatology, 41: 430-439 (2002).

Deng, W., et al., "Do chromatin loops provide epigenetic gene expression states?" Curr. Opin. Genet. Dev., 20(5): 548-54 (2010).

Kadauke, S., et al, "Chromatin loops in gene regulation," Biochim Biophys Acta., 1789(1): 17-25 (2009).

Christova, R., et al., "P-STAT1 mediates higher-order chromatin remodelling of the human MHC in response to IFNγ," J. Cell Sci., 120(18): 3262-3270 (2007).

Watanabe, T., et al., "Higher-Order Chromatin Regulation and Differential Gene Expression in the Human Tumour Necrosis Factor/Lymphotoxin Locus in Hepatocellular Carcinoma Cells," Mol. Cell. Biol., 32: 1529-1541 (2012).

Harismendy, O., et al., "9p21 DNA variants associated with coronary artery disease impair interferon-γ signalling response," Nature, 470(11): 264-268 (2011).

Rau, R., et al., "Benefit and risk of methotrexate treatment in rheumatoid arthritis," Clin. Exp. Rheumatol., 22: S83-S94 (2004).

Kosaka, N., et al., "Unraveling the Mystery of Cancer by Secretory micro RNA: Horizontal microRNA Transfer between Living Cells," Front. in Genet., 2: 97 (2012).

Rozen, S., et al., "Primer3 on the WWW for general users and for biologist programmers," Methods Mol Biol., 132: 365-386 (2000).

Biotechnology firm Oxford BioDynamics expands its biomarker discovery programme for ALS diagnosis; International Pharmaceutical Industry (IPI); Jan. 15, 2016. http: <<www.ipimediaworld.com/biotechnology-firm-oxford-biodynamics-expands-its-biomarker-discovery-programme-for-als-diagnosis/>>.

Press Release of Jun. 2, 2016: Oxford BioDynamics picks Malaysia to conduct a biomarker discovery programme for diabetes and pre-diabetes.

Cobb, J. et al., "Genome-Wide Data Reveal Novel Genes for Methotrexate Response in a Large Cohort of Juvenile Idiopathic Arthritis Cases", The Pharmacogenomics Journal, vol. 14, Apr. 8, 2014, 356-364.

Fullwood, M. et al., "An Oestrogen-Receptor-α-Bound Human Chromatin Interactome", Nature, vol. 462, Nov. 5, 2009, 58-64.

Li, G. et al., "Extensive Promoter-Centered Chromatin Interactions Provide a Topological Basis for Transcription Regulation", Cell, vol. 148, Jan. 20, 2012, 84-98.

Sandhu, K. et al., "Large-Scale Functional Organization of Long-Range Chromatin Interaction Networks", Cell Rep., vol. 2, No. 5, Nov. 29, 2012, 1207-1219.

Youdell, M., et al., "Development of Novel ALS Treatment on the Basis of Mechanisms of Cellular Chronological Life Span Control," Poster at the 12th annual Northeast ALS Consortium (NEALS); Oct. 7, 2013. Exhibit A—document providing enlarged sections of poster.

Goodyear, C., et al., "Epigenetic Chromosome Conformations Predict MTX Responsiveness in Early Rheumatoid Arthritis Patients", Presentation made at ACR/ARHP Annual Meeting (Nov. 6-11, 2015 in San Francisco, CA), publicly disclosed earlier on Mar. 31, 2014 at 'The Scottish Early Rheumatoid Arthritis (SERA) Meeting' in Perth, Scotland. Exhibit B—document providing enlarged sections of presentation.

Williams, M. T., et al., "Fcg Receptor Targeting Reduces Bone Disease in a Pre-clinical Model of Multiple Myeloma," 57th American Society of Hematology Meeting in Orlando; Dec. 9, 2015. Exhibit C—document providing enlarged sections of poster.

Hunter, E., et al., Development of Epigenetic Profiling of ALS Patients with Chromosome Conformation Biomarkers Offers Novel Signatures for Non-Invasive Diagnostic and Prognostic Stratifications; Annual 2015 ALS Consortium Conference in Tampa, Florida: Nov. 6, 2015. Exhibit D—document providing enlarged sections of presentation.

Akoulitchev, A., "Clinical evaluation of EpiSwitch OBD-27, a Breast Cancer Screening Tool, based on Epigenetics Concept on Japanese population," English translation of Abstract O-065. Annual Meeting of Japanese Association of Breast Cancer Screening, Oklnawa. Nov. 30, 2012. Exhibit E—English translation of Akoulltchev, Abstract O-065, Annual Meeting of Japanese Association of Breast Cancer Screening, Okinawa. Nov. 30, 2012.

Brites, N. and Vaz, A.R., "Microglia centered pathogenesis in ALS: insights in cell interconnectivity," Frontiers in Cellular Neuroscience, 8(Article 117): 1-24 (2014).

Fontana, L., et al., "Extending Healthy Life Span—From Yeast to Humans," Science, 328: (5976), 321-326 (2010).

\* cited by examiner

DETECTION OF CHROMOSOME INTERACTIONS

RELATED APPLICATIONS

This application is a US National stage entry of International Application No. PCT/GB2016/051900, which designated the United States and was filed on Jun. 24, 2016, published in English.

This application claims priority under 35 U.S.C. § 119 or 365 to GB Application No. 1511079.4, filed Jun. 24, 2015, GB Application No. 1511080.2, filed Jun. 24, 2015 and GB Application No. 1519555.5, filed Nov. 5, 2015. The entire teachings of the above applications are incorporated herein by reference.

FIELD OF THE INVENTION

The invention relates to detecting chromosome interactions.

BACKGROUND OF THE INVENTION

Health care costs are spiralling and so there is a need to treat people more effectively using existing drugs.

SUMMARY OF THE INVENTION

The inventors have investigated the use of epigenetic chromosome interactions as the basis of or for use in conjunction with companion diagnostics, and in particular in the detection of epigenetic states to determine responsiveness to therapy (e.g. pharmaceutical therapy), predisposition to disease/conditions, and/or monitoring residual disease. The inventors' work shows the role played by epigenetic interactions in a diverse set of conditions and provides methods for identifying the relevant chromosomal interactions. The invention includes a method of identifying relevant chromosomal interactions based on looking at the chromosome interactions present in subgroups of individuals. The invention also includes using the identified chromosome interactions as the basis for companion diagnostic tests.

Accordingly a first aspect of the invention provides a method of determining the epigenetic chromosome interactions which are relevant to a companion diagnostic that distinguishes between subgroups, comprising contacting a first set of nucleic acids from the subgroups with a second set of nucleic acids representing an index population of chromosome interactions, and allowing complementary sequences to hybridise, wherein the nucleic acids in the first and second sets of nucleic acids represent a ligated product comprising sequences from both of the chromosome regions that have come together in the epigenetic chromosome interaction, and wherein the pattern of hybridisation between the first and second set of nucleic acids allows a determination of which epigenetic chromosome interactions are specific to subgroups in the population, wherein the subgroups differ in a characteristic relevant to a companion diagnostic.

Preferably, in the first aspect (and/or any other aspect) of the invention:
- the subgroups are subgroups in a or the animal (e.g. mammal or nematode worm) population, most preferably subgroups in a or the human population; and/or
- the first set of nucleic acids is from at least 8 individuals; and/or
- the first set of nucleic acids is from at least 4 individuals from a first subgroup and at least 4 individuals from a second subgroup which is preferably non-overlapping with the first subgroup, and/or
- the second set of nucleic acids represents an unselected group of chromosome interactions; and/or
- the second set of nucleic acids is bound to an array at defined locations; and/or
- the second set of nucleic acids represents chromosome interactions in least 100 different genes or loci; and/or
- the second set of nucleic acids comprises at least 1000 different nucleic acids representing at least 1000 different epigenetic chromosome interactions; and/or
- the first set of nucleic acids and the second set of nucleic acids comprise nucleic acid sequences of length 10 to 100 nucleotide bases; and/or
- the method is carried out to determine which locus or gene is relevant to said characteristic relevant to a companion diagnostic;

and/or
- the subgroups differ in respect to:
  (i) responding to a specific treatment and/or prophylaxis (in particular to a specific pharmaceutical treatment and/or prophylaxis), and/or
  (ii) predisposition to a specific condition, and/or
  (iii) the presence of residual disease which may lead to relapse;

and/or
- the first set of nucleic acids is generated in a method comprising the steps of:
  (i) in vitro cross-linking of chromosome regions which have come together in a chromosome interaction;
  (ii) subjecting said cross-linked DNA to restriction digestion cleavage with an enzyme; and
  (iii) ligating said cross-linked cleaved DNA ends to form the first set of nucleic acids (in particular comprising ligated DNA);

and/or
- said characteristic relevant to a companion diagnostic is:
  (i) responsiveness to methotrexate (or to another rheumatoid arthritis drug) in rheumatoid arthritis patients, and/or
  (ii) responsiveness to therapy for acute myeloid leukaemia, and/or
  (iii) likelihood of relapse in melanoma.

Preferably, in the first and/or other aspects of the invention, the feature " . . . the nucleic acids in the first and second sets of nucleic acids represent a ligated product comprising sequences from both of the chromosome regions that have come together in the epigenetic chromosome interaction . . . " can comprise or be: " . . . the nucleic acids in the first and second sets of nucleic acids are in the form of a ligated product(s) (preferably a ligated nucleic acid(s), more preferably ligated DNA) comprising sequences from both of the chromosome regions that have come together in the epigenetic chromosome interaction".

A second aspect of the invention provides a companion diagnostic assay method which selects a subgroup having a characteristic relevant to treatment and/or prophylaxis (in particular pharmaceutical treatment and/or prophylaxis), which method comprises:
(a) typing a locus which has been identified by the above method as having an epigenetic interaction characteristic to the subgroup, and/or
(b) detecting the presence or absence of at least 5 epigenetic chromosome interactions, preferably at at least 5 different loci, which are characteristic for:

i. responding to a specific treatment and/or prophylaxis (in particular a specific pharmaceutical treatment and/or prophylaxis), and/or
ii. predisposition to a specific condition, and/or
iii. the presence of residual disease which may lead to relapse.

Preferably, in the second aspect (and/or any other aspect) of the invention:

the method comprises step (a) as defined in the second aspect of the invention, wherein:
(1) said locus is a gene, and/or
(2) a single nucleotide polymorphism (SNP) is typed, and/or
(3) a microRNA (miRNA) is expressed from the locus, and/or
(4) a non-coding RNA (ncRNA) is expressed from the locus, and/or
(5) the locus expresses a nucleic acid sequence encoding at least 10 contiguous amino acid residues, and/or
(6) the locus expresses a regulating element, and/or
(7) said typing comprises sequencing or determining the level of expression from the locus;

and/or the method comprises step (b) as defined in the second aspect of the invention, wherein:
5-5 to 500, preferably 20 to 300, more preferably 50 to 100, epigenetic chromosome interactions are typed, preferably at at least 5 different loci; and/or
the presence or absence of 5 to 500, preferably 20 to 300, more preferably 50 to 100, epigenetic chromosome interactions, preferably at at least 5 different loci, are detected.

Other preferred or particular features of or in the second aspect (and/or any other aspect) of the invention include the following:

The companion diagnostic assay method of the second aspect of the invention can particularly be used to detect the presence of any of the specific conditions or characteristics mentioned herein.

Preferably, the companion diagnostic method of the second aspect of the invention is used to detect:
responsiveness to methotrexate (or another rheumatoid arthritis drug) in rheumatoid arthritis patients,
responsiveness to therapy for acute myeloid leukaemia (AML) patients,
likelihood of relapse in melanoma,
likelihood of developing prostate cancer and/or aggressive prostate cancer, and/or
likelihood of developing and/or having a predisposition to a neurodegenerative disease or condition, preferably a dementia such as Alzheimer's disease, mild cognitive impairment, vascular dementia, dementia with Lewy bodies, frontotemporal dementia, or more preferably Alzheimer's disease, most preferably beta-amyloid aggregate induced Alzheimer's disease, and/or
a comparison(s) between dementia patients (preferably Alzheimer's disease patients, more preferably Alzheimer's disease patients with beta-amyloid aggregates) and cognitively-impaired patients without Alzheimer's disease, in particular with respect to memory and/or cognition; in all cases preferably in a human.

Preferably, in the second aspect and in all other aspects of the invention, the disease or condition (in particular in a human) comprises:

an inflammatory disease, preferably rheumatoid arthritis; in particular in a human;
a blood cancer, preferably acute myeloid leukaemia (AML); in particular in a human;
a solid cancer/solid tumour, preferably melanoma, prostate cancer and/or aggressive prostate cancer; in particular in a human; and/or
a neurodegenerative disease or condition, preferably a dementia such as Alzheimer's disease, mild cognitive impairment, vascular dementia, dementia with Lewy bodies, frontotemporal dementia, or more preferably Alzheimer's disease such as beta-amyloid aggregate induced Alzheimer's disease; in particular in a human, and/or
responsiveness to immunotherapy, such as antibody therapy, preferably anti-PD1 therapy.

In one embodiment responsiveness to therapy, preferably anti-PD1 therapy, is detected in any of the following cancers, preferably of the stage or class which is indicated and/or preferably with other indicated characteristics such as viral infection:

DLBCL_ABC: Diffuse large B-cell lymphoma subtype activated B-cells
DLBCL_GBC: Diffuse large B-cell lymphoma subtype germinal center B-cells
HCC: hepatocellular carcinoma
HCC_HEPB: hepatocellular carcinoma with hepatitis B virus
HCC_HEPC: hepatocellular carcinoma with hepatitis C virus
HEPB+R: Hepatitis B in remission
Pca_Class3: Prostate cancer stage 3
Pca_Class2: Prostate cancer stage 2
Pca_Class1: Prostate cancer stage 1
BrCa_Stg4: Breast cancer stage 4
BrCa_Stg3B: Breast cancer stage 3B
BrCa_Stg2A: Breast cancer stage 2A
BrCa_Stg2B: Breast cancer stage 2B
BrCa_Stg1A: Breast cancer stage 1A
BrCa_Stg1: Breast cancer stage 1.

The condition or characteristic may be:
responsiveness to IFN-B (IFN-beta) treatment in multiple sclerosis patients, and/or
predisposition to relapsing-remitting multiple sclerosis, and/or
likelihood of primary progressive multiple sclerosis, and/or
predisposition to amyotrophic lateral sclerosis (ALS) disease state (in particular in humans), and/or
predisposition to fast progressing amyotrophic lateral sclerosis (ALS) disease state, and/or
predisposition to aggressive type 2 diabetes disease state, and/or
predisposition to type 2 diabetes disease state, and/or
predisposition to a pre-type 2 diabetes state, and/or
predisposition to type 1 diabetes disease state, and/or
predisposition to systemic lupus erythematosus (SLE) disease state, and/or
predisposition to ulcerative colitis disease state, and/or
likelihood of relapse of colorectal cancer for ulcerative colitis patients, and/or
likelihood of malignant peripheral nerve sheath tumours for neurofibromatosis patients, and/or
likelihood of developing prostate cancer and/or aggressive prostate cancer.

A third aspect of the present invention provides a therapeutic agent (in particular a pharmaceutical therapeutic agent) for use in the treatment and/or prophylaxis of a condition in an individual (in particular in a human individual), wherein said individual has been identified as being in need of said therapeutic agent by the method of the second aspect of the invention. The third aspect of the invention also provides the use of a therapeutic agent (e.g. pharmaceutical therapeutic agent) in the manufacture of a medicament (in particular a pharmaceutical composition comprising the therapeutic agent) for use in the treatment and/or prophylaxis of a condition in an individual (in particular in a human individual), wherein said individual has been identified as being in need of said therapeutic agent by the method of the second aspect of the invention. The third aspect of the present invention also provides a method of treatment and/or prophylaxis of a condition in an individual (in particular in a human individual and/or an individual in need thereof), comprising administering a therapeutic agent (e.g. pharmaceutical therapeutic agent and/or an effective amount of a therapeutic agent) to the individual, wherein said individual has been identified as being in need of said therapeutic agent by the method of the second aspect of the invention.

Preferably, in the third aspect (and/or other aspects) of the invention, the therapeutic agent (in particular pharmaceutical therapeutic agent) comprises:

a pharmaceutically active agent (e.g. compound or biologic/biological agent such as a protein or antibody) suitable for use in the treatment and/or prophylaxis of an inflammatory disease; in particular in a human;

preferably a pharmaceutically active agent (e.g. compound or biologic/biological agent such as a protein or antibody) suitable for use in the treatment and/or prophylaxis of rheumatoid arthritis (RA); in particular in a human; wherein preferably the pharmaceutically active agent comprises methotrexate; hydroxychloroquine; sulfasalazine; leflunomide; a TNF-alpha (tumor necrosis factor alpha) inhibitor, in particular a monoclonal antibody TNF-alpha inhibitor such as infliximab, adalimumab, certolizumab pegol or golimumab, or a circulating receptor fusion protein TNF-alpha inhibitor such as etanercept; or a T cell costimulation inhibitor such as abatacept; or an interleukin 1 (IL-1) inhibitor such as anakinra; or a monoclonal antibody against B cells such as rituximab or tocilizumab;

or a pharmaceutically active agent (e.g. compound or biologic/biological agent such as a protein or antibody) suitable for use in the treatment and/or prophylaxis of a blood cancer, preferably acute myeloid leukaemia (AML); in particular in a human; or a pharmaceutically active agent (e.g. compound or biologic/biological agent such as a protein or antibody) suitable for use in the treatment and/or prophylaxis of a solid cancer/solid tumour, preferably melanoma, prostate cancer and/or aggressive prostate cancer; in particular in a human; or a pharmaceutically active agent (e.g. compound or biologic/biological agent such as a protein or antibody) suitable for use in the treatment and/or prophylaxis of a neurodegenerative disease or condition, preferably a dementia such as Alzheimer's disease, mild cognitive impairment, vascular dementia, dementia with Lewy bodies, frontotemporal dementia, or more preferably Alzheimer's disease such as beta-amyloid aggregate induced Alzheimer's disease; in particular in a human.

A fourth aspect of the invention provides a method of identifying an agent which is capable of changing the disease state of an individual from a first state to a second state comprising determining whether a candidate agent is capable of changing the chromosomal interactions from those corresponding with the first state to chromosomal interactions which correspond to the second state, wherein preferably the first and second state correspond to presence or absence of:

(i) responsiveness to a specific treatment and/or prophylaxis (in particular a specific pharmaceutical treatment and/or prophylaxis), and/or (ii) predisposition to a specific condition, and/or (iii) a residual disease which may lead to relapse.

A fifth aspect of the invention provides a method of determining the effect of a drug comprising detecting the change in epigenetic chromosome interactions caused by the drug, wherein said effect is preferably the mechanism of action of the drug or are the pharmacodynamics properties of the drug, and wherein said the chromosome interactions are preferably specific to:

(i) responsiveness to a specific treatment and/or prophylaxis (in particular to a specific pharmaceutical treatment and/or prophylaxis), and/or (ii) predisposition to a specific condition, and/or (iii) a residual disease which may lead to relapse.

Additionally or alternatively, according to a preferred embodiment of all aspects of the present invention, the present invention does not relate to a method of determining responsiveness to a specific therapy (in particular a specific pharmaceutical therapy) for rheumatoid arthritis in a subject (e.g. a mammalian such as human subject), comprising detecting the presence or absence of 5 or more (in particular 7 or more, or 10 or more, or 15 or more, or 20 or more) chromosomal interactions; wherein said chromosomal interactions are in particular at 5 or more (for example 5) different loci; and/or wherein said detecting in particular comprises determining for each interaction whether or not the regions of a chromosome which are part of the interaction have been brought together.

DETAILED DESCRIPTION OF THE INVENTION

Figure 1:
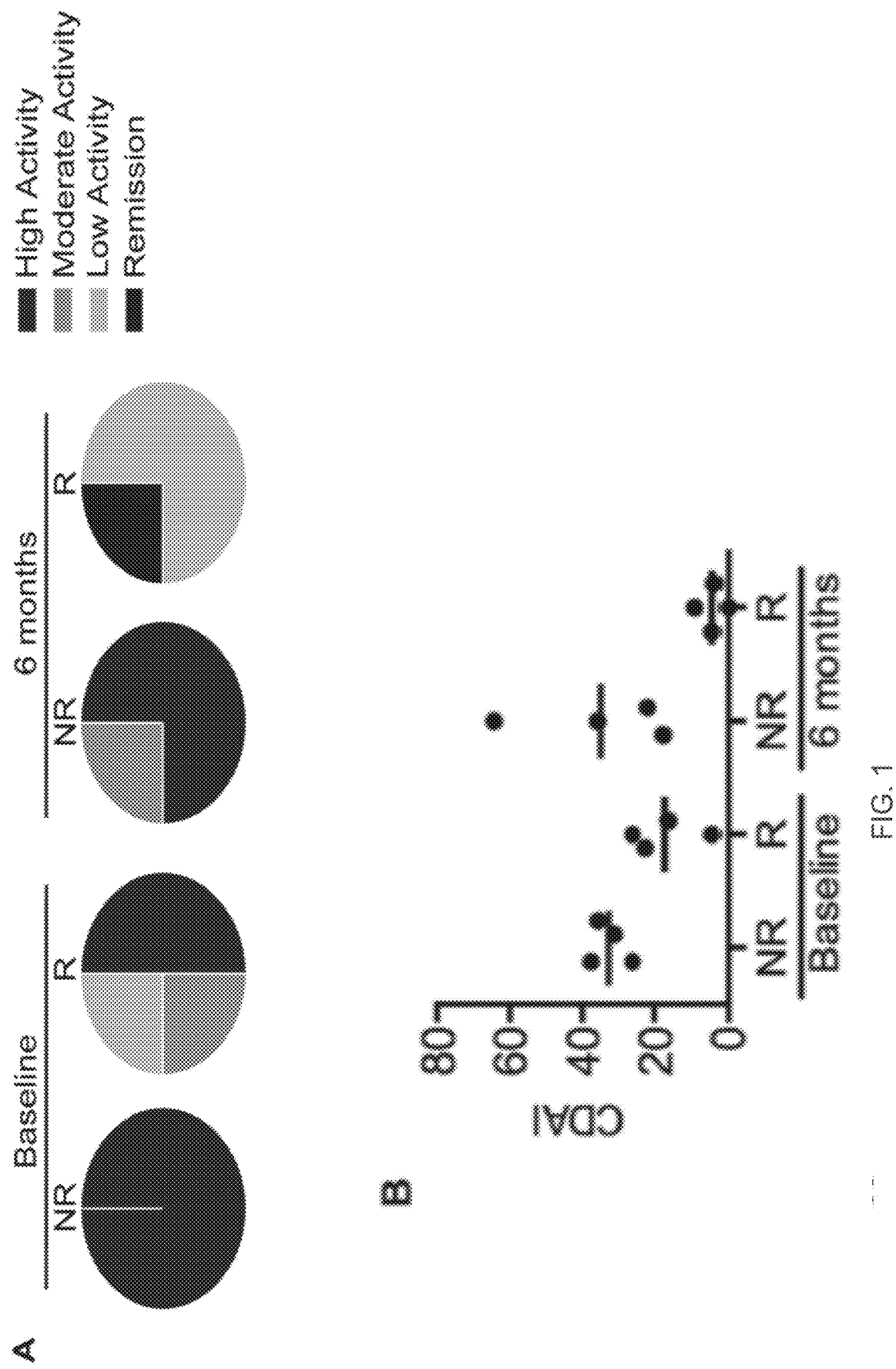
FIG. 1 is a figure comprising pie-charts and graphs relating to: Chromosome Conformation Signature EpiSwitch™ Markers discriminate MTX responders (R) from non-responders (NR). A discovery cohort of responder (R) and non-responder (NR) RA patients were selected based on DAS28 (Disease Activity Score of 28 joints) EULAR (The European League Against Rheumatism) response criteria (see methods). (A) Pie charts show the clinical interpretation of CDAI scores for both R and NR patients at baseline and 6 months. (B) CDAI scores of R and NR patients at baseline and 6 months. (C) EpiSwitch™ array analysis of peripheral blood mononuclear cells taken at diagnosis from R and NR, and healthy controls (HC) identified 922 statistically significant stratifying marker candidates. Further analysis revealed that 420 were specific for NR, 210 to R and 159 to HC. Pie charts show the proportion in relation to the 13,322 conditional chromosome conformations screened. All markers showed adjusted p<0.2. (D) Hierarchical clustering using Manhattan distance measure with complete linkage agglomeration is shown by the heatmaps. Marker selection using binary pattering across the 3 groups (R, NR and HC) initially reduced the 922 EpiSwitch™ Markers to 65 and then the top 30 markers.
Figure 1:
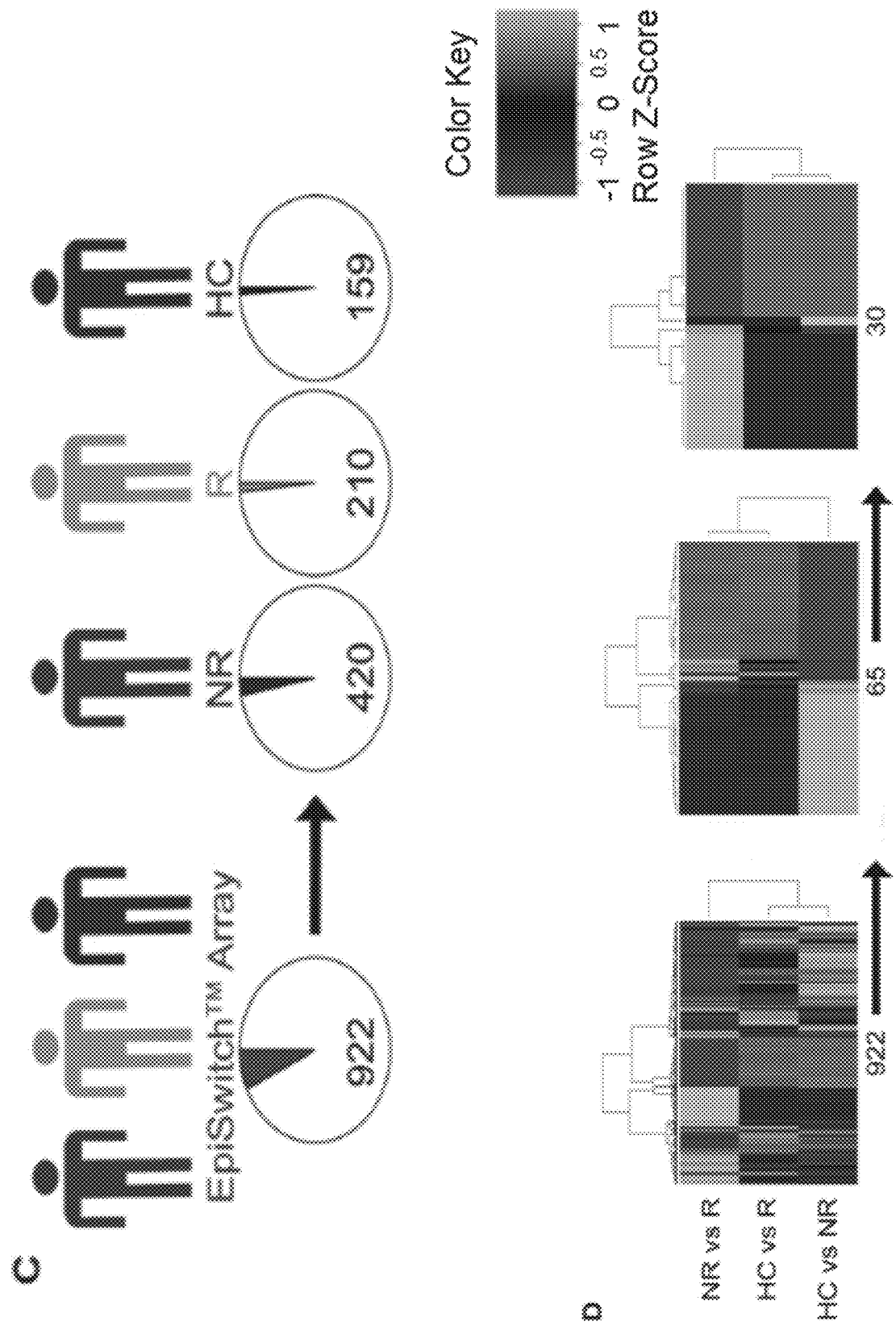

The invention has several different aspects:
- a method of identifying chromosome interactions (in particular epigenetic) relevant to a companion diagnostic, in particular that distinguishes between subgroups;
- a companion diagnostic method;
- a therapeutic agent for use in treatment and/or prophylaxis of an individual (e.g. treatment and/or prophylaxis of a condition in an individual, e.g. human individual), wherein said individual has been identified as being in need of the therapeutic agent in particular by the companion diagnostic method of the invention;
- a method of screening for (identifying) an agent, in particular a therapeutic agent, which is capable of changing the disease state in or of an individual, comprising determining whether a candidate agent is capable of changing chromosomal interactions, in particular chromosomal interactions relevant to or associated with the disease state;
- a method of determining the effect of a drug comprising detecting the change in epigenetic chromosome interactions caused by the drug.

Epigenetic Interactions

As used herein, the term 'epigenetic' interactions typically refers to interactions between distal regions of a locus on a chromosome, said interactions being dynamic and altering, forming or breaking depending upon the status of the region of the chromosome.

In particular methods of the invention, chromosome interactions are detected by first generating a ligated nucleic acid that comprises sequence(s) from both regions of the chromosomes that are part of the chromosome interactions. In such methods the regions can be cross-linked by any suitable means. In a preferred embodiment, the interactions are cross-linked using formaldehyde, but may also be cross-linked by any aldehyde, or D-Biotinoyl-e-aminocaproic acid-N-hydroxysuccinimide ester or Digoxigenin-3-O-methylcarbonyl-e-aminocaproic acid-N-hydroxysuccinimide ester. Para-formaldehyde can cross link DNA chains which are 4 Angstroms apart.

The chromosome interaction may reflect the status of the region of the chromosome, for example, if it is being transcribed or repressed in response to change of the physiological conditions. Chromosome interactions which are specific to subgroups as defined herein have been found to be stable, thus providing a reliable means of measuring the differences between the two subgroups.

In addition, chromosome interactions specific to a disease condition will normally occur early in the disease process, for example compared to other epigenetic markers such as methylation or changes to binding of histone proteins. Thus the companion diagnostic method of the invention is able to detect early stages of a disease state. This allows early treatment which may as a consequence be more effective. Another advantage of the invention is that no prior knowledge is needed about which loci are relevant for identification of relevant chromosome interactions. Furthermore there is little variation in the relevant chromosome interactions between individuals within the same subgroup. Detecting chromosome interactions is highly informative with up to 50 different possible interactions per gene, and so methods of the invention can interrogate 500,000 different interactions.

Location and Causes of Epigenetic Interactions

Epigenetic chromosomal interactions may overlap and include the regions of chromosomes shown to encode relevant or undescribed genes, but equally may be in intergenic regions. It should further be noted that the inventors have discovered that epigenetic interactions in all regions are equally important in determining the status of the chromosomal locus. These interactions are not necessarily in the coding region of a particular gene located at the locus and may be in intergenic regions.

The chromosome interactions which are detected in the invention could be caused by changes to the underlying DNA sequence, by environmental factors, DNA methylation, non-coding antisense RNA transcripts, non-mutagenic carcinogens, histone modifications, chromatin remodelling and specific local DNA interactions. The changes which lead to the chromosome interactions may be caused by changes to the underlying nucleic acid sequence, which themselves do not directly affect a gene product or the mode of gene expression. Such changes may be for example, SNP's within and/or outside of the genes, gene fusions and/or deletions of intergenic DNA, microRNA, and non-coding RNA. For example, it is known that roughly 20% SNPs are in non-coding regions, and therefore the method as described is also informative in non-coding situation. In one embodiment the regions of the chromosome which come together to form the interaction are less than 5 kb, 3 kb, 1 kb, 500 base pairs or 200 base pairs apart.

The chromosome interaction which is detected in the companion diagnostic method is preferably one which is within any of the genes mentioned in the Tables herein.

However it may also be upstream or downstream of the genes, for example up to 50,000, 30,000, 20,000, 10,000 or 5000 bases upstream or downstream from the gene or from the coding sequence.

The chromosome interaction which is detected may or may not be one which occurs between a gene (including coding sequence) and its regulatory region, such as a promoter. The chromosome interaction which is typed may or may not be one which is inherited, for example an inherited imprinted characteristic of a gene region.

Types of Clinical Situation

The specific case of RA (Rheumatoid Arthritis) illustrates the general principles. There are currently no tests that clinicians can use a priori to determine if patients will respond to methotrexate (MTX) when the patients are first given the drug. Since a significant number (about 30%) of patients do not respond to MTX, being able to predict whether a patient is a responder or non-responder will increase the chances of successfully treating RA, as well as saving time and money.

This is one example of how the inventors visualise the present invention to be used. More broadly speaking, the aim of the present invention is to permit detection and monitoring of disease. In more detail, this technology allows stratification based on biomarkers for specific phenotypes relating to medical conditions, i.e. by recognising a particular chromosome confirmation signature and/or a change in that particular signature.

The methods of the invention are preferably used in the context of specific characteristics relating to disease, such as responsiveness to treatments and/or prophylaxes, identification of the most effective therapy/drug, monitoring the course of disease, identifying predisposition to disease, and/or identifying the presence of residual disease and/or the likelihood of relapse. Therefore the methods may or may not be used for diagnosis of the presence of a specific condition. The methods of the invention can be used to type loci where the mechanisms of disease are unknown, unclear or complex.

Detection of chromosome interactions provides an efficient way of following changes at the different levels of regulation, some of which are complex. For example in some cases around 37,000 non-coding RNAs can be activated by a single impulse.

Subgroups and Personalised Treatment

As used herein, a "subgroup" preferably refers to a population subgroup (a subgroup in a population), more preferably a subgroup in a or the population of a particular animal such as a particular mammal (e.g. human, non-human primate, or rodent e.g. mouse or rat) or a particular nematode worm (e.g. *C. elegans*). Most preferably, a "subgroup" refers to a subgroup in a or the human population.

Particular populations, e.g. human populations, of interest include: the human population overall, a or the human population suffering from a specific condition/disease (in particular inflammatory disease e.g. RA, blood cancer eg AML, solid cancer eg melanoma or prostate cancer (PC), or neurodegenerative disease/condition e.g. Alzheimer's disease (AD)), the human healthy population (healthy controls), the human population which is healthy in the sense of not suffering from the specific condition/disease of interest or of study (eg RA, AML, melanoma, PC or AD), the human population (e.g. either healthy and/or with a specific condition/disease e.g. RA, AML, melanoma, PC or AD) who are responders to a particular drug/therapy, or the human population (e.g. either healthy and/or with a specific condition/ disease e.g. RA, AML, melanoma, PC or AD) who are non-responders to a particular drug/therapy.

The invention relates to detecting and treating particular subgroups in a population, preferably in a or the human population. Within such subgroups the characteristics discussed herein (such as responsiveness to treatment and/or prophylaxis; in particular responsiveness to a specific treatment and/or prophylaxis of one or more conditions or diseases, and/or responsiveness to a specific medicine or therapeutically active substance/therapeutic agent, in particular in the treatment and/or prophylaxis of one or more conditions or diseases) will be present or absent. Epigenetic interaction differences on a chromosome are, generally speaking, structural differences which exist at a genomic level. The inventors have discovered that these differ between subsets (for example two, or two or more subsets) in a given population. Identifying these differences will allow physicians to categorize their patients as a part of one subset of the population as described in the method. The invention therefore provides physicians with a method of personalizing medicine for the patient based on their epigenetic chromosome interactions, and provide an alternative more effective treatment and/or prophylaxis regime.

In another embodiment, threshold levels for determining to what extent a subject is defined as belonging to one subgroup and not to a or the other subgroup of the population are applied. In one preferable embodiment wherein the subgroups comprise responders versus non-responders of a therapy for the treatment and/or prophylaxis of a particular disease, said threshold may be measured by change in DAS28 (Disease Activity Score of 28 joints) score, in particular for rheumatoid arthritis.

In one embodiment, a score above 1.2 units indicates a subject falls into the responder subgroup, whilst a score below 1.2 units indicates a subject is defined as a non-responder.

Typically a subgroup will be at least 10%, at least 30%, at least 50% or at least 80% of the general population.

Generating Ligated Nucleic Acids

Certain embodiments of the invention utilise ligated nucleic acids, in particular ligated DNA. These comprise sequences from both of the regions that come together in a chromosome interaction and therefore provide information about the interaction. The EpiSwitch™ method, described herein, uses generation of such ligated nucleic acids to detect chromosome interactions.

One such method, in particular one particular method of detecting chromosome interactions and/or one particular method of determining epigenetic chromosome interactions and/or one particular method of generating ligated nucleic acids (e.g. DNA), comprises the steps of:

(i) in vitro crosslinking of said epigenetic chromosomal interactions present at the chromosomal locus;

(ii) optionally isolating the cross-linked DNA from said chromosomal locus;

(iii) subjecting said cross-linked DNA to restriction digestion with an enzyme that cuts it at least once (in particular an enzyme that cuts at least once within said chromosomal locus);

(iv) ligating said cross-linked cleaved DNA ends (in particular to form DNA loops); and (v) identifying the presence of said ligated DNA and/or said DNA loops, in particular using techniques such as PCR (polymerase chain reaction), to identify the presence of a specific chromosomal interaction.

One particularly preferable method of detecting, determining and/or monitoring chromosome interactions and/or epigenetic changes, involving inter alia the above-mentioned steps of crosslinking, restriction digestion, ligating, and identifying, is disclosed in WO 2009/147386 A1 (Oxford Biodynamics Ltd), the entire disclosure of which (in particular claims 1, 2, 3, 4, 5, 6, 7, 8, 9, 10, 11, 12, 13, 14, 15, 16, 17, 18, 19, 20 or 21 of which) are incorporated herein by reference as though fully set forth. Claim 1 of WO 2009/147386 A1, which can be used in those methods of the present invention which involve a ligated product(s) and/or a ligated nucleic acid(s), discloses a method of monitoring epigenetic changes comprising monitoring changes in conditional long range chromosomal interactions at at least one chromosomal locus where the spectrum of long range interaction is associated with a specific physiological condition, said method comprising the steps of:—

(i) in vitro crosslinking of said long range chromosomal interactions present at the at least one chromosomal locus;

(ii) isolating the cross linked DNA from said chromosomal locus;

(iii) subjecting said cross linked DNA to restriction digestion with an enzyme that cuts at least once within the at least one chromosomal locus;

(iv) ligating said cross linked cleaved DNA ends to form DNA loops; and (v) identifying the presence of said DNA loops;

wherein the presence of DNA loops indicates the presence of a specific long range chromosomal interaction.

PCR (polymerase chain reaction) may be used to detect or identify the ligated nucleic acid, for example the size of the PCR product produced may be indicative of the specific chromosome interaction which is present, and may therefore be used to identify the status of the locus. The skilled person will be aware of numerous restriction enzymes which can be used to cut the DNA within the chromosomal locus of interest. It will be apparent that the particular enzyme used will depend upon the locus studied and the sequence of the DNA located therein. A non-limiting example of a restriction enzyme which can be used to cut the DNA as described in the present invention is Taq I polymerase.

Embodiments Such as EpiSwitch™ Technology

The EpiSwitch™ Technology relates to the use of microarray EpiSwitch™ marker data in the detection of epigenetic chromosome conformation signatures specific for phenotypes. The present inventors describe herein how the EpiSwitch™ Array Platform has been used for discovery of chromosome signature pool of potential biomarkers specific for particular disadvantageous phenotypes subgroups versus healthy controls. The inventors also provide examples of validated use and translation of chromosome conformation signatures from microarray into PCR platform with examples of several markers specific between subgroups from the cohorts tested on the array.

Embodiments such as EpiSwitch™ which utilise ligated nucleic acids in the manner described herein (for identifying relevant chromosome interactions and in companion diagnostic methods) have several advantages. They have a low level of stochastic noise, for example because the nucleic acid sequences from the first set of nucleic acids of the present invention either hybridise or fail to hybridise with the second set of nucleic acids. This provides a binary result permitting a relatively simple way to measure a complex mechanism at the epigenetic level. EpiSwitch™ technology also has fast processing time and low cost. In one embodiment the processing time is 3 hours to 6 hours.

Samples and Sample Treatment

The sample will contain DNA from the individual. It will normally contain cells. In one embodiment a sample is obtained by minimally invasive means, and may for example be blood. DNA may be extracted and cut up with standard restriction enzymes. This can pre-determine which chromosome conformations are retained and will be detected with the EpiSwitch™ platforms. In one embodiment wherein the sample is a blood sample previously obtained from the patient, the described method is advantageous because the procedure is minimally invasive. Due to the synchronisation of chromosome interactions between tissues and blood, including horizontal transfer, a blood sample can be used to detect the chromosome interactions in tissues, such as tissues relevant to disease. For certain conditions, such as cancer, genetic noise due to mutations can affect the chromosome interaction 'signal' in the relevant tissues and therefore using blood is advantageous.

Properties of Nucleic Acids of the Invention

The disclosure herein mentions first and second nucleic acids. In addition the nucleic acids are used in the companion diagnostic method and in other embodiments to detect the presence or absence of chromosome interactions (for example by binding to ligated nucleic acids generated from samples). The nucleic acids of the invention typically comprise two portions each comprising sequence from one of the two regions of the chromosome which come together in the chromosome interaction. Typically each portion is at least 8, 10, 15, 20, 30 or 40 nucleotides in length. Preferred nucleic acids comprise sequence from any of the genes mentioned in the tables, in particular where the nucleic acid is used in an embodiments relevant to the condition relevant for that table. Preferred nucleic acids comprise the specific probe sequences mentioned in the tables for specific conditions or fragments or homologues of such sequences. Preferably the nucleic acids are DNA. It is understood that where a specific sequence is provided the invention may use the complementary as required in the particular embodiment.

The Second Set of Nucleic Acids—the 'Index' Sequences

The second set of nucleic acid sequences has the function of being an index, and is essentially a set of nuclei acid sequences which are suitable for identifying subgroup specific sequence. They can represent the 'background' chromosomal interactions and might be selected in some way or be unselected. They are in general a subset of all possible chromosomal interactions.

The second set of nucleic acids may be derived by any suitable method. They can be derived computationally or they may be based on chromosome interaction in individuals. They typically represent a larger population group than the first set of nucleic acids. In one particular embodiment, the second set of nucleic acids represents all possible epigenetic chromosomal interactions in a specific set of genes. In another particular embodiment, the second set of nucleic acids represents a large proportion of all possible epigenetic chromosomal interactions present in a population described herein. In one particular embodiment, the second set of nucleic acids represent at least 50% or at least 80% of epigenetic chromosomal interactions in at least 20, 50, 100 or 500 genes.

The second set of nucleic acids typically represents at least 100 possible epigenetic chromosome interactions which modify, regulate or in any way mediate a disease state/phenotype in population. The second set of nucleic acids may represent chromosome interactions that affect a diseases state in a species, for example comprising nucleic acids sequences which encode cytokines, kinases, or regulators associated with any disease state, predisposition to a disease or a disease phenotype. The second set of nucleic acids comprises sequences representing epigenetic interactions relevant and not relevant to the companion diagnostic method.

In one particular embodiment the second set of nucleic acids derive at least partially from a naturally occurring sequences in a population, and are typically obtained by in silico methods. Said nucleic acids may further comprise single or multiple mutations in comparison to a corresponding portion of nucleic acids present in the naturally occurring nucleic acids. Mutations include deletions, substitutions and/or additions of one or more nucleotide base pairs. In one particular embodiment, the second set of nucleic acids may comprise sequence representing a homologue and/or orthologue with at least 70% sequence identity to the corresponding portion of nucleic acids present in the naturally occurring species. In another particular embodiment, at least 80% sequence identity or at least 90% sequence identity to the corresponding portion of nucleic acids present in the naturally occurring species is provided.

Properties of the Second Set of Nucleic Acids

In one particular embodiment, there are at least 100 different nucleic acid sequences in the second set of nucleic acids, preferably at least 1000, 2000 or 5000 different nucleic acids sequences, with up to 100,000, 1,000,000 or 10,000,000 different nucleic acid sequences. A typical number would be 100 to 1,000,000, such as 1,000 to 100,000 different nucleic acids sequences. All or at least 90% or at least 50% or these would correspond to different chromosomal interactions.

In one particular embodiment, the second set of nucleic acids represent chromosome interactions in at least 20 different loci or genes, preferably at least 40 different loci or genes, and more preferably at least 100, at least 500, at least 1000 or at least 5000 different loci or genes, such as 100 to 10,000 different loci or genes.

The lengths of the second set of nucleic acids are suitable for them to specifically hybridise according to Watson Crick base pairing to the first set of nucleic acids to allow identification of chromosome interactions specific to subgroups. Typically the second set of nucleic acids will comprise two portions corresponding in sequence to the two chromosome regions which come together in the chromosome interaction. The second set of nucleic acids typically comprise nucleic acid sequences which are at least 10, preferably 20, and preferably still 30 bases (nucleotides) in length. In another embodiment, the nucleic acid sequences may be at the most 500, preferably at most 100, and preferably still at most 50 base pairs in length. In a preferred embodiment, the second set of nucleic acids comprise nucleic acid sequences of between 17 and 25 base pairs. In one embodiment at least 100, 80% or 50% of the second set of nucleic acid sequences have lengths as described above. Preferably the different nucleic acids do not have any overlapping sequences, for example at least 100%, 90%, 80% or 50% of the nucleic acids do not have the same sequence over at least 5 contiguous nucleotides.

Given that the second set of nucleic acids acts as an 'index' then the same set of second nucleic acids may be used with different sets of first nucleic acids which represent subgroups for different characteristics, i.e. the second set of nucleic acids may represent a 'universal' collection of nucleic acids which can be used to identify chromosome interactions relevant to different disease characteristics.

The First Set of Nucleic Acids

The first set of nucleic acids are normally from individuals known to be in two or more distinct subgroups defined by presence or absence of a characteristic relevant to a companion diagnostic, such as any such characteristic mentioned herein. The first nucleic acids may have any of the characteristics and properties of the second set of nucleic acids mentioned herein. The first set of nucleic acids is normally derived from a sample from the individual which has undergone treatment and processing as described herein, particularly the EpiSwitch™ cross-linking and cleaving steps. Typically the first set of nucleic acids represent all or at least 80% or 50% of the chromosome interactions present in the samples taken from the individuals.

Typically, the first set of nucleic acids represents a smaller population of chromosome interactions across the loci or genes represented by the second set of nucleic acids in comparison to the chromosome interactions represented by second set of nucleic acids, i.e. the second set of nucleic acids is representing a background or index set of interactions in a defined set of loci or genes.

Library of Nucleic Acids

The nucleic acids described herein may be in the form of a library which comprises at least 200, at least 500, at least 1000, at least 5000 or at least 10000 different nucleic acids from the second set of nucleic acids. The invention provides a particular library of nucleic acids which typically comprises at least 200 different nucleic acids. The library of nucleic acids may have any of the characteristics or properties of the second set of nucleic acids mentioned herein. The library may be in the form of nucleic acids bound to an array.

Hybridisation

The invention requires a means for allowing wholly or partially complementary nucleic acid sequences from the first set of nucleic acids and the second set of nucleic acids to hybridise. In one embodiment all of the first set of nucleic acids is contacted with all of the second set of nucleic acids in a single assay, i.e. in a single hybridisation step. However any suitable assay can be used.

Labelled Nucleic Acids and Pattern of Hybridisation

The nucleic acids mentioned herein may be labelled, preferably using an independent label such as a fluorophore (fluorescent molecule) or radioactive label which assists detection of successful hybridisation. Certain labels can be detected under UV light.

The pattern of hybridisation, for example on an array described herein, represents differences in epigenetic chromosome interactions between the two subgroups, and thus provides a method of comparing epigenetic chromosome interactions and determination of which epigenetic chromosome interactions are specific to a subgroup in the population of the present invention.

The term 'pattern of hybridisation' broadly covers the presence and absence of hybridisation between the first and second set of nucleic acids, i.e. which specific nucleic acids from the first set hybridise to which specific nucleic acids from the second set, and so it is not limited to any particular assay or technique, or the need to have a surface or array on which a 'pattern' can be detected.

Companion Diagnostic Method

The invention provides a companion diagnostic method based on information provided by chromosome interactions. Two distinct companion diagnostic methods are provided which identify whether an individual has a particular characteristic relevant to a companion diagnostic. One method is based on typing a locus in any suitable way and the other is based on detecting the presence or absence of chromosome interactions. The characteristic may be any one of the characteristics mentioned herein relating to a condition. The companion diagnostic method can be carried out at more than one time point, for example where monitoring of an individual is required.

Companion Diagnostic Method Based on Typing a Locus

The method of the invention which identified chromosome interactions that are specific to subgroups can be used to identify a locus, which may be a gene that can be typed as the basis of companion diagnostic test. Many different gene-related effects can lead to the same chromosome interaction occurring. In this embodiment any characteristic of the locus may be typed, such as presence of a polymorphism in the locus or in an expressed nucleic acid or protein, the level of expression from the locus, the physical structure of the locus or the chromosome interactions present in the locus. In one particular embodiment the locus may be any of the genes mentioned herein in the tables, in particular in Tables 1, 3, 5, 6c, 6E, 18a, 18b, 18c, 18d, 18e, 18f, 22, 23, 24 or 25 (in particular Tables 1, 3 and/or 5), or any property of a locus which is in the vicinity of a chromosome interaction found to be linked to the relevant condition.

Companion Diagnostic Method Based on Detecting Chromosome Interactions

The invention provides a companion diagnostic method which comprises detecting the presence or absence of chromosome interactions, typically 5 to 20 or 5 to 500 such interactions, preferably 20 to 300 or 50 to 100 interactions, in order to determine the presence or absence of a characteristic in an individual. Preferably the chromosome interactions are those in any of the genes mentioned herein.

In one particular embodiment the chromosome interactions which are typed are those represented by the nucleic acids disclosed in the tables herein, in particular in Tables 6b, 6D, 18b, 18e, 18f, 22, 23, 24 or 25 herein, for example when the method is for the purpose of determining the presence or absence of characteristics defined in those tables.

Specific Conditions

The companion diagnostic method can be used to detect the presence of any of the specific conditions or characteristics mentioned herein. The companion diagnostic method can be used to detect responsiveness to methotrexate (or another rheumatoid arthritis drug) in rheumatoid arthritis patients, responsiveness to therapy for acute myeloid leukaemia (AML) patients, likelihood of relapse in melanoma, likelihood of developing prostate cancer and/or aggressive prostate cancer, and/or likelihood of developing beta-amyloid aggregate induced Alzheimer's disease.

In one embodiment the method of the invention detects responsiveness to immunotherapy, such as antibody therapy. Preferably the responsiveness to antibody therapy of cancer is detected, for example in immunotherapy using anti-PD-1 or anti-PD-L1 or a combined anti-PD-1/anti-PD-L1 therapy.

Preferably the cancer is melanoma, breast cancer, prostate cancer, acute myeloid leukaemia (AML), diffuse large B-cell lymphoma (DLBCL), pancreatic cancer, thyroid cancer, nasal cancer, liver cancer or lung cancer. In such embodiments detection of chromosome interactions in STAT5B and/or IL15 are preferred, such as described in the Examples. The work in the Examples is consistent with the fact that response to immunotherapy is a feature of the immune system epigenetic set up rather than cancer identity. ['Anti-PD-1' is an antibody or antibody derivative or fragment that binds specifically to PD-1 (programmed cell death protein 1). 'Anti-PD-L1' is an antibody or antibody derivative or fragment that binds specifically to PD-L1 protein which is a ligand of PD-1.]

The method(s) and/or companion diagnostic method of the invention can be used to:
responsiveness to IFN-β (IFN-beta) treatment in multiple sclerosis patients (in particular in humans), and/or
predisposition to relapsing-remitting multiple sclerosis (in particular in humans), and/or
likelihood of primary progressive multiple sclerosis (in particular in humans), and/or
predisposition to amyotrophic lateral sclerosis (ALS) disease state (in particular in humans), and/or,
predisposition to fast progressing amyotrophic lateral sclerosis (ALS) disease state (in particular in humans), and/or
predisposition to aggressive type 2 diabetes disease state (in particular in humans), and/or
predisposition to type 2 diabetes disease state (in particular in humans), and/or
predisposition to a pre-type 2 diabetes state (in particular in humans), and/or
predisposition to type 1 diabetes disease state (in particular in humans), and/or
predisposition to systemic lupus erythematosus (SLE) disease state (in particular in humans), and/or
predisposition to ulcerative colitis disease state (in particular in humans), and/or
likelihood of relapse of colorectal cancer for ulcerative colitis patients (in particular in humans), and/or
likelihood of malignant peripheral nerve sheath tumours for neurofibromatosis patients (in particular in humans), and/or
likelihood of developing prostate cancer and/or aggressive prostate cancer (in particular in humans), and/or
likelihood of developing and/or predisposition to a neurodegenerative disease or condition, preferably a dementia such as Alzheimer's disease, mild cognitive impairment, vascular dementia, dementia with Lewy bodies, frontotemporal dementia, or more preferably Alzheimer's disease, most preferably beta-amyloid aggregate induced Alzheimer's disease; in particular in a human; and/or
a comparison between dementia patients (preferably Alzheimer's disease patients, more preferably Alzheimer's disease patients with beta-amyloid aggregates) and cognitively-impaired patients without Alzheimer's disease, in particular with respect to memory and/or cognition; in particular in humans.

Preferably the presence or absence of any of the chromosome interactions within any of the relevant genes mentioned in the tables are detected. For example in at least 1, 3, 10, 20, 50 of the genes mentioned in any one of the tables. Preferably the presence or absence of chromosome interactions represented by the probes sequences in the Tables is determined in the method. For example at least 1, 3, 10, 20, 50, or 100 of the relevant chromosome interactions from any one of the tables. These numbers of genes or chromosome interactions can be used in any of the different embodiments mentioned herein.

The Individual Tested Using the Companion Diagnostic Method

The individual to be tested may or may not have any symptoms of any disease condition or characteristic mentioned herein. The individual may be at risk of any such condition or characteristic.

The individual may have recovered or be in the process of recovering from the condition or characteristic. The individual is preferably a mammal, such as a non-human primate, human or rodent.

The individual may be male or female. The individual may be 30 years old or older. The individual may be 29 years old or younger.

Screening Method

The invention provides a method of identifying an agent which is capable of changing the disease state of an individual from a first state to a second state comprising determining whether a candidate agent is capable of changing the chromosomal interactions from those corresponding with the first state to chromosomal interactions which correspond to the second state, wherein preferably the first and second state correspond to presence or absence of:

responsiveness to a specific treatment and/or prophylaxis, and/or predisposition to a specific condition, and/or a residual disease which may lead to relapse.

In one embodiment the method determines whether a candidate agent is capable of changing any chromosomal interaction mentioned herein.

The method may be carried out in vitro (inside or outside a cell) or in vivo (upon a non-human organism). In one embodiment the method is carried out on a cell, cell culture, cell extract, tissue, organ or organism, such as one which comprises the relevant chromosome interaction(s). The cell is The method is typically carried out by contacting (or administering) the candidate agent with the gene, cell, cell culture, cell extract, tissue, organ or organism.

Suitable candidate substances which tested in the above screening methods include antibody agents (for example, monoclonal and polyclonal antibodies, single chain antibodies, chimeric antibodies and CDR-grafted antibodies). Furthermore, combinatorial libraries, defined chemical identities, peptide and peptide mimetics, oligonucleotides and natural agent libraries, such as display libraries (e.g. phage display libraries) may also be tested. The candidate substances may be chemical compounds, which are typically derived from synthesis around small molecules which may have any of the properties of the agent mentioned herein.

Preferred Loci, Genes and Chromosome Interactions

For all aspects of the invention preferred loci, genes and chromosome interactions are mentioned in the tables. For all aspects of the invention preferred loci, genes and chromosome interactions are provided in the tables. Typically the methods chromosome interactions are detected from at least 1, 3, 10, 20, 30 or 50 of the relevant genes listed in the table. Preferably the presence or absence of at least 1, 3, 10, 20, 30 or 50 of the relevant specific chromosome interactions represented by the probe sequences in any one table is detected.

The loci may be upstream or downstream of any of the genes mentioned herein, for example 50 kb upstream or 20 kb downstream.

In one embodiment for each condition the presence or absence of at least 1, 3, 5, 10, 20 of the relevant specific chromosome interactions represented by the top range of p-values or adjusted p-values shown in Table 48 are detected. In another embodiment for each condition the presence or absence of at least 1, 3, 5, 10, 20, 30 or 50 of the relevant specific chromosome interactions represented by the mid range of p-values or adjusted p-values shown in Table 48 are detected. In yet another embodiment for each condition the presence or absence of at least 1, 3, 5, 10, 20, 30 or 50 of the relevant specific chromosome interactions represented by the bottom range of p-values or adjusted p-values shown in Table 48 are detected. In another embodiment for each condition the presence or absence of at least 1, 2, 3, 5 or 10 of the relevant specific chromosome interactions from each of the top, mid and bottom ranges of p-values or adjusted p-values shown in Table 48 are detected, i.e. at least 3, 6, 9, 18 or 30 in total.

Particular combinations of chromosome interactions can be detected (i.e. determining the presence of absence of), which typically represent all of the interactions disclosed in a table herein or a selection from a table. As mentioned herein particular numbers of interactions can be selected from individual tables. In one embodiment at least 10%, 20%, 30%, 50%, 70% or 90% of the interactions disclosed in any table, or disclosed in relation to any condition, are detected.

The interactions which are detected may correspond to presence or absence of a particular characteristic, for example as defined herein, such as in any table herein. If a combination of interactions are detected then they may all correspond with presence of the characteristic or they may all correspond to absence of the characteristic. In one embodiment the combination of interactions which is detected corresponds to at least 2, 5 or 10 interactions which relate to presence of the characteristic and at least 2, 5 or 10 other interactions that relate to absence of the characteristic.

The probe shown in table 49 may be part of or combined with any of the selections mentioned herein, particularly for conditions relating to cancer, and responsiveness to therapy, such as anti-PD1 therapy.

Embodiments Concerning Genetic Modifications

In certain embodiments the methods of the invention can be carried out to detect chromosome interactions relevant to or impacted by a genetic modification, i.e. the subgroups may differ in respect to the genetic modification. Clearly the modification might be of entire (non-human) organisms or parts of organisms, such as cells. In the method of determining which chromosomal interactions are relevant to a biological system state the first set of nucleic acids may be from at least two subgroups, one of which has a defined genetic modification and one which does not have the genetic modification, and the method may determine which chromosomal interactions are relevant to, and/or affected by, the genetic modification. The modification may be achieved by any suitable means, including CRISPR technology.

The invention includes a method of determining whether a genetic modification to the sequence at a first locus of a genome affects other loci of the genome comprising detecting chromosome signatures at one or more other loci after the genetic modification is made, wherein preferably the genetic modification changes system characteristics, wherein said system is preferably the metabolic system, the immune system, the endocrine system, the digestive system, integumentary system, the skeletal system, the muscular system, the lymphatic system, the respiratory system, the nervous system, or the reproductive system. Said detecting chromosome signatures optionally comprises detecting the presence or absence of 5 or more (e.g. 5) different chromosomal interactions, preferably at 5 or more (e.g. 5) different loci, preferably as defined in any of the Tables. Preferably the chromosomal signatures or interactions are identified by any suitable method mentioned herein.

In one embodiment the genetic modification is achieved by a method comprising introducing into a cell (a) two or more RNA-guided endonucleases or nucleic acid encoding two or more RNA-guided endonucleases and (b) two or more guiding RNAs or DNA encoding two or more guiding RNAs, wherein each guiding RNA guides one of the RNA-guided endonucleases to a targeted site in the chromosomal sequence and the RNA-guided endonuclease cleaves at least one strand of the chromosomal sequence at the targeted site.

In another embodiment the modification is achieved by a method of altering expression of at least one gene product comprising introducing into a eukaryotic cell containing and expressing a DNA molecule having a target sequence and encoding the gene product an engineered, non-naturally occurring Clustered Regularly Interspaced Short Palindromic Repeats (CRISPR)-CRISPR associated (Cas) (CRISPR-Cas) system comprising one or more vectors comprising:

a) a first regulatory element operable in a eukaryotic cell operably linked to at least one nucleotide sequence encoding a CRISPR-Cas system guide RNA that hybridizes with the target sequence, and b) a second regulatory element operable in a eukaryotic cell operably linked to a nucleotide sequence encoding a Type-II Cas9 protein, wherein components (a) and (b) are located on same or different vectors of the system, whereby the guide RNA targets the target sequence and the Cas9 protein cleaves the DNA molecule, whereby expression of the at least one gene product is altered; and, wherein the Cas9 protein and the guide RNA do not naturally occur together, wherein preferably each RNA-guided endonuclease is derived from a Cas9 protein and comprises at least two nuclease domains, and optionally wherein one of the nuclease domains of each of the two RNA-guided endonucleases is modified such that each RNA-guided endonuclease cleaves one strand of a double-stranded sequence, and wherein the two RNA-guided endonucleases together introduce a double-stranded break in the chromosomal sequence that is repaired by a DNA repair process such that the chromosomal sequence is modified.

Typically the modification comprised a deletion, insertion or substitution of at least 5, 20, 50, 100 or 1000 bases, preferably up 10,000 or 1000,000 bases.

The modification may be at any of the loci mentioned herein, for example in any of the regions or genes mentioned in any of the tables. The chromosomal interactions which are detected at other (non-modified) loci may also be in any of the loci mentioned herein, for example in any of the regions or genes mentioned in any of the tables.

Embodiments relating to genetic modifications many be performed on any organism, including eukaryotes, chordates, mammals, plants, agricultural animals and plants, and non-human organisms.

Methods and Uses of the Invention

The method of the invention can be described in different ways. It can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:

the locus may be any of the loci, regions or genes mentioned herein, and/or wherein the chromosomal interaction may be any of the chromosome interactions mentioned herein or corresponding to any of the probes disclosed in the tables, and/or wherein the ligated product may have or comprise (i) sequence which is the same as or homologous to any of the probe sequences disclosed herein; or (ii) sequence which is complementary to (ii).

The method of the invention can be described as a method for detecting chromosome states which represent different subgroups in a population comprising determining whether a chromosome interaction is present or absent within a defined region of the genome, wherein preferably:

the subgroup is defined by presence or absence of a characteristic mentioned herein, and/or the chromosome state may be at any locus, region or gene mentioned herein; and/or the chromosome interaction may be any of those mentioned herein or corresponding to any of the probes or primer pairs disclosed herein.

The invention includes detecting chromosome interactions at any locus, gene or regions mentioned herein. The invention includes use of the nucleic acids and probes (or primers) mentioned herein to detect chromosome interactions, for example use of at least 10, 50, 100 or 500 such nucleic acids or probes to detect chromosome interactions in at least 10, 20, 100 or 500 different loci or genes.

Tables Provided Herein

Tables herein either show probe (Episwitch™ marker) data or gene data representing chromosome interactions present in a condition (the first mentioned group) and absent in a control group, typically but not necessarily healthy individuals (the second mentioned group). The probe sequences show sequence which can be used to detect a ligated product generated from both sites of gene regions that have come together in chromosome interactions, i.e. the probe will comprise sequence which is complementary to sequence in the ligated product. The first two sets of Start-End positions show probe positions, and the second two sets of Start-End positions show the relevant 4 kb region. The following information is provided in the probe data table:

HyperG_Stats: p-value for the probability of finding that number of significant EpiSwitch™ markers in the locus based on the parameters of hypergeometric enrichment Probe Count Total: Total number of EpiSwitch™ Conformations tested at the locus Probe Count Sig: Number of EpiSwitch™ Conformations found to be statistical significant at the locus FDR HyperG: Multi-test (False Discovery Rate) corrected hypergeometric p-value Percent Sig: Percentage of significant EpiSwitch® markers relative the number of markers tested at the locus log FC: logarithm base 2 of Epigenetic Ratio (FC)

AveExpr: average log 2-expression for the probe over all arrays and channels

T: moderated t-statistic p-value: raw p-value adj. p-value: adjusted p-value or q-value B—B-statistic (lods or B) is the log-odds that that gene is differentially expressed.

FC—non-log Fold Change

FC_1—non-log Fold Change centred around zero

LS—Binary value this relates to FC_1 values. FC_1 value below −1.1 it is set to −1 and if the FC_1 value is above 1.1 it is set to 1. Between those values the value is 0

The gene table data shows genes where a relevant chromosome interaction has been found to occur. The p-value in the loci table is the same as the HyperG_Stats (p-value for the probability of finding that number of significant EpiSwitch™ markers in the locus based on the parameters of hypergeometric enrichment).

The probes are designed to be 30 bp away from the Taq1 site. In case of PCR, PCR primers are also designed to detect ligated product but their locations from the Taq1 site vary.

Probe Locations:
  Start 1—30 bases upstream of TaqI site on fragment 1
  End 1—TaqI restriction site on fragment 1
  Start 2—TaqI restriction site on fragment 2
  End 2—30 bases downstream of TaqI site on fragment 2
4 kb Sequence Location:
  Start 1—4000 bases upstream of TaqI site on fragment 1
  End 1—TaqI restriction site on fragment 1
  Start 2—TaqI restriction site on fragment 2
  End 2—4000 bases downstream of TaqI site on fragment 2

The following information is also provided in the tables:
  GLMNET—procedures for fitting the entire lasso or elastic-net regularization. Lambda set to 0.5 (elastic-net)
  GLMNET_1—lambda set to 1 (lasso)
  Fishers P-value—Exact Fishers Test P-value
  Coef—Logistic Regression Coefficient, if you raise e (e^X) to power of the coefficient you get the odds ratio for the variable
  S.E.—Standard Error
  Wald—Wald Equation Statistic. Wald statistics are part of a Wald test that the maximum likelihood estimate of a model coefficient is equal to 0. The test assumes that the difference between the maximum likelihood estimate and 0 is asymptotically normally distributed
  Pr(>|Z|)—P-value for the marker within the logistic model. Values below <0.05 are statistically significant and should be used in the logistic model.

Preferred Embodiments for Sample Preparation and Chromosome Interaction Detection Methods of preparing samples and detecting chromosome conformations are described herein. Optimised (non-conventional) versions of these methods can be used, for example as described in this section.

Typically the sample will contain at least $2\times10^5$ cells. The sample may contain up to $5\times10^5$ cells. In one embodiment, the sample will contain $2\times10^5$ to $5.5\times10^5$ cells Crosslinking of epigenetic chromosomal interactions present at the chromosomal locus is described herein. This may be performed before cell lysis takes place. Cell lysis may be performed for 3 to 7 minutes, such as 4 to 6 or about 5 minutes. In some embodiments, cell lysis is performed for at least 5 minutes and for less than 10 minutes.

Digesting DNA with a restriction enzyme is described herein. Typically, DNA restriction is performed at about 55° C. to about 70° C., such as for about 65° C., for a period of about 10 to 30 minutes, such as about 20 minutes.

Preferably a frequent cutter restriction enzyme is used which results in fragments of ligated DNA with an average fragment size up to 4000 base pair. Optionally the restriction enzyme results in fragments of ligated DNA have an average fragment size of about 200 to 300 base pairs, such as about 256 base pairs. In one embodiment, the typical fragment size is from 200 base pairs to 4,000 base pairs, such as 400 to 2,000 or 500 to 1,000 base pairs.

In one embodiment of the EpiSwitch method a DNA precipitation step is not performed between the DNA restriction digest step and the DNA ligation step.

DNA ligation is described herein. Typically the DNA ligation is performed for 5 to 30 minutes, such as about 10 minutes.

The protein in the sample may be digested enzymatically, for example using a proteinase, optionally Proteinase K. The protein may be enzymatically digested for a period of about 30 minutes to 1 hour, for example for about 45 minutes. In one embodiment after digestion of the protein, for example Proteinase K digestion, there is no cross-link reversal or phenol DNA extraction step.

In one embodiment PCR detection is capable of detecting a single copy of the ligated nucleic acid, preferably with a binary read-out for presence/absence of the ligated nucleic acid.

Homologues

Homologues of polynucleotide/nucleic acid (e.g. DNA) sequences are referred to herein. Such homologues typically have at least 70% homology, preferably at least 80%, at least 85%, at least 90%, at least 95%, at least 97%, at least 98% or at least 99% homology, for example over a region of at least 10, 15, 20, 30, 100 or more contiguous nucleotides, or across the portion of the nucleic acid which is from the region of the chromosome involved in the chromosome interaction. The homology may be calculated on the basis of nucleotide identity (sometimes referred to as "hard homology").

Therefore, in a particular embodiment, homologues of polynucleotide/nucleic acid (e.g. DNA) sequences are referred to herein by reference to % sequence identity. Typically such homologues have at least 70% sequence identity, preferably at least 80%, at least 85%, at least 90%, at least 95%, at least 97%, at least 98% or at least 99% sequence identity, for example over a region of at least 10, 15, 20, 30, 100 or more contiguous nucleotides, or across the portion of the nucleic acid which is from the region of the chromosome involved in the chromosome interaction.

For example the UWGCG Package provides the BESTFIT program which can be used to calculate homology and/or % sequence identity (for example used on its default settings) (Devereux et al (1984) Nucleic Acids Research 12, p 387-395). The PILEUP and BLAST algorithms can be used to calculate homology and/or % sequence identity and/or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W5 T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) oi 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more bases, such as less than 10, 15 or 20 bases (which may be substitutions, deletions or insertions of nucleotides). These changes may be measured across any of the regions mentioned above in relation to calculating homology and/or % sequence identity.

Arrays

The second set of nucleic acids may be bound to an array, and in one embodiment there are at least 15,000, 45,000, 100,000 or 250,000 different second nucleic acids bound to the array, which preferably represent at least 300, 900, 2000 or 5000 loci. In one embodiment one, or more, or all of the different populations of second nucleic acids are bound to more than one distinct region of the array, in effect repeated on the array allowing for error detection. The array be based on an Agilent SurePrint G3 Custom CGH microarray platform. Detection of binding of first nucleic acids to the array may be performed by a dual colour system.

Therapeutic Agents

Therapeutic agents are mentioned herein. The invention provides such agents for use in preventing or treating the relevant condition. This may comprise administering to an individual in need a therapeutically effective amount of the agent. The invention provides use of the agent in the manufacture of a medicament to prevent or treat the disease. The methods of the invention may be used to select an individual for treatment. The methods of the invention, and in particular the companion diagnostic assay method, may include a treatment step where a person identified by the method may then be administered with an agent that prevents or treats the relevant condition.

The formulation of the agent will depend upon the nature of the agent. The agent will be provided in the form of a pharmaceutical composition containing the agent and a pharmaceutically acceptable carrier or diluent. Suitable carriers and diluents include isotonic saline solutions, for example phosphate-buffered saline. Typical oral dosage compositions include tablets, capsules, liquid solutions and liquid suspensions. The agent may be formulated for parenteral, intravenous, intramuscular, subcutaneous, transdermal or oral administration.

The dose of agent may be determined according to various parameters, especially according to the substance used; the age, weight and condition of the individual to be treated; the route of administration; and the required regimen. A physician will be able to determine the required route of administration and dosage for any particular agent. A suitable dose may however be from 0.1 to 100 mg/kg body weight such as 1 to 40 mg/kg body weight, for example, to be taken from 1 to 3 times daily.

Forms of the Substance Mentioned Herein

Any of the substances, such as nucleic acids or therapeutic agents, mentioned herein may be in purified or isolated form. The may be in a form which is different from that found in nature, for example they may be present in combination with other substance with which they do not occur in nature. The nucleic acids (including portions of sequences defined herein) may have sequences which are different to those found in nature, for example having at least 1, 2, 3, 4 or more nucleotide changes in the sequence as described in the section on homology. The nucleic acids may have heterologous sequence at the 5' or 3' end. The nucleic acids may be chemically different from those found in nature, for example they may be modified in some way, but preferably are still capable of Watson-Crick base pairing. Where appropriate the nucleic acids will be provided in double stranded or single stranded form. The invention provides all the of specific nucleic acid sequences mentioned herein in single or double stranded form, and thus includes the complementary strand to any sequence which is disclosed.

The invention also provides a kit for carrying out any method of the invention, including detection of a chromosomal interaction associated with a particular subgroup. Such a kit can include a specific binding agent capable of detecting the relevant chromosomal interaction, such as agents capable of detecting a ligated nucleic acid generated by processes of the invention. Preferred agents present in the kit include probes capable of hybridising to the ligated nucleic acid or primer pairs, for example as described herein, capable of amplifying the ligated nucleic acid in a PCR reaction.

The invention also provides a device that is capable of detecting the relevant chromosome interactions. The device preferably comprises any specific binding agents, probe or primer pair capable of detecting the chromosome interaction, such as any such agent, probe or primer pair described herein.

Preferred Therapeutic Agents for Use in the Invention for Specific Stated Condition A. Predisposition to Relapsing-Remitting Multiple Sclerosis (RRMS)

Drugs used to treat the condition:
Disease modifying therapies (DMT):
Injectable medications
Avonex (interferon beta-1a)
Betaseron (interferon beta-1b)
Copaxone (glatiramer acetate)
Extavia (interferon beta-1b)
Glatopa (glatiramer acetate)
Plegridy (peginterferon beta-1a)
Rebif (interferon beta-1a)
Oral medications
Aubagio (teriflunomide)
Gilenya (fingolimod)
Tecfidera (dimethyl fumarate)
Infused medications
Lemtrada (alemtuzumab)
Novantrone (mitoxantrone)
Tysabri (natalizumab)
Managing relapses:
High-dose intravenous Solu-Medrol® (methylprednisolone)
High-dose oral Deltasone® (prednisone)
H.P. Acthar Gel (ACTH)
Steroids:
Methylprednisolone B. Likelihood of Primary Progressive Multiple Sclerosis (PPMS)

Drugs used to treat the condition:
Steroids
Immunosuppressive therapies such as total lymphoid radiation, cyclosporine, methotrexate, 2-chlorodeoxyadenosine, cyclophosphamide, mitoxantrone, azathioprine, interferon, steroids, and immune globulin.

Copaxone
Ocrelizumab (Genetech).
C. Predisposition to fast progressing amyotrophic lateral sclerosis (ALS) disease state
  Drugs used to treat the condition:
    Riluzole
    Baclofen.
D. Predisposition to type 2 diabetes disease state
  Drugs used to treat the condition:
    Metformin
    Sulphonylureas such as:
      glibenclamide
      gliclazide
      glimepiride
      glipizide
      gliquidone
    Glitazones (thiazolidinediones, TZDs)
    Gliptins (DPP-4 inhibitors) such as:
      Linagliptin
      Saxagliptin
      Sitagliptin
      Vildagliptin
    GLP-1 agonists such as:
      Exenatide
      Liraglutide
    Acarbose
    Nateglinide and Repaglinide
    Insulin treatment.
E. Predisposition to type 1 diabetes disease state
  Drugs used to treat the condition:
    Lantus subcutaneous
    Lantus Solostar subcutaneous
    Levemir subcutaneous
    Novolog Flexpen subcutaneous
    Novolog subcutaneous
    Humalog subcutaneous
    Novolog Mix 70-30 FlexPen subcutaneous
    SymlinPen 60 subcutaneous
    Humalog KwikPen subcutaneous
    SymlinPen 120 subcutaneous
    Novolin R injection
    Toujeo SoloStar subcutaneous
    Apidra subcutaneous
    Humalog Mix 75-25 subcutaneous
    Humulin 70/30 subcutaneous
    Humalog Mix 75-25 KwikPen subcutaneous
    Novolin N subcutaneous
    Humulin R injection
    Novolin 70/30 subcutaneous
    insulin detemir subcutaneous
    Levemir FlexTouch subcutaneous
    Humulin N subcutaneous
    insulin glargine subcutaneous
    Apidra SoloStar subcutaneous
    insulin lispro subcutaneous
    insulin regular human injection
    insulin regular human inhalation
    Humalog Mix 50-50 KwikPen subcutaneous
    insulin aspart subcutaneous
    Novolog Mix 70-30 subcutaneous
    Humalog Mix 50-50 subcutaneous
    Afrezza inhalation
    insulin NPH human recomb subcutaneous
    insulin NPH and regular human subcutaneous
    insulin aspart protamine-insulin aspart subcutaneous
    Humulin 70/30 KwikPen subcutaneous
    Humulin N KwikPen subcutaneous
    Tresiba FlexTouch U-100 subcutaneous
    Tresiba FlexTouch U-200 subcutaneous
    insulin lispro protamine and lispro subcutaneous
    pramlintide subcutaneous
    insulin glulisine subcutaneous
    Novolog PenFill subcutaneous
    insulin degludec subcutaneous
F. Predisposition to systemic lupus erythematosus (SLE) disease state
  Drugs used to treat the condition:
    Non-steroidal anti-inflammatory drugs (NSAIDS): ibuprofen, naproxen and diclofenac.
    Hydroxychloroquine
    Corticosteriods
    Immunosuppressants: azathioprine, methotrexate, mycophenolate mofetil and cyclophosphamide.
    Rituximab
    Belimumab.
    Corticosteroids: prednisone, cortisone and hydrocortisone
    NSAIDs: indomethacin (Indocin), nabumetone (Relafen), and celecoxib (Celebrex)
    Anti-inflammatories: aspirin and acetaminophen (Tylenol)
    Disease-Modifying Anti-Rheumatic Drugs (DMARDs): hydroxychloroquine (Plagenil), cyclosporine (Gengraf, Neoral, Sandimmune), and azathioprine (Azasan, Imuran).
    Antimalarials: chloroquine (Aralen) and hydroxychloroquine (Plaquenil).
    BLyS-specific Inhibitors or Monoclonal Antibodies (MAbS): Belimumab (Benlysta).
    Immunosuppressive Agents/Immune Modulators: azathioprine (Imuran), methotrexate (Rheumatrex), and cyclophosphamide (Cytoxan).
    Anticoagulants: low-dose aspirin, heparin (Calciparine, Liquaemin), and warfarin (Coumadin).
G. Predisposition to ulcerative colitis disease state
  Drugs used to treat the condition:
    Anti-inflammatory drugs: Aminosalicylates—sulfasalazine (Azulfidine), as well as certain 5-aminosalicylates, including mesalamine (Asacol, Lialda, Rowasa, Canasa, others), balsalazide (Colazal) and olsalazine (Dipentum) and Corticosteroids—prednisone and hydrocortisone.
    Immune system supressors: azathioprine (Azasan, Imuran), mercaptopurine (Purinethol, Purixam), cyclosporine (Gengraf, Neoral, Sandimmune), infliximab (Remicade), adalimumab (Humira), golimumab (Simponi) and vedolizumab (Entyvio).
    Other medications to manage specific symptoms of ulcerative colitis:
      Antibiotics
      Anti-diarrheal medication
      Pain relievers
      Iron supplements.
H. Likelihood of relapse of colorectal cancer for ulcerative colitis patients
  Drugs used to treat the condition:
    Aminosalicylates
    UC steroids
    Azathioprine
I. Likelihood of malignant peripheral nerve sheath tumours for neurofibromatosis patients
  Treatment
    Treatments for MPNST include surgery, radiotherapy and chemotherapy.

J. Likelihood of developing prostate cancer and/or aggressive prostate cancer
  Drugs used to treat the condition:
    luteinising hormone-releasing hormone (LHRH) agonists
    anti-androgen treatment
    combined LHRH and anti-androgen treatment
    Steroids
    Other medical treatments:
      Abiraterone
      Enzalutamide
      docetaxel (Taxotere®)
      carboplatin or cisplatin chemotherapy
K. Alzheimer's disease:
  Drugs used to treat the condition:
  Donepezil
  Rivastigmine
  Galantamine
  Memantine

PUBLICATIONS

The contents of all publications mentioned herein are incorporated by reference into the present specification and may be used to further define the features relevant to the invention.

Specific Embodiments

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent SurePrint G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent SureScan Scanner and the resultant features extracted using the Agilent Feature Extraction software. The data is then processed using the EpiSwitch™ array processing scripts in R. The arrays are processed using standard dual colour packages in Bioconductor in R: Limma*. The normalisation of the arrays is done using the normalised within Arrays function in Limma* and this is done to the on chip Agilent positive controls and EpiSwitch™ positive controls. The data is filtered based on the Agilent Flag calls, the Agilent control probes are removed and the technical replicate probes are averaged, in order for them to be analysed using Limma*. The probes are modelled based on their difference between the 2 scenarios being compared and then corrected by using False Discovery Rate. Probes with Coefficient of Variation (CV)<=30% that are <=-1.1 or =>1.1 and pass the p<=0.1 FDR p-value are used for further screening. To reduce the probe set further Multiple Factor Analysis is performed using the FactorMineR package in R.

*Note: LIMMA is Linear Models and Empirical Bayes Methods for Assessing Differential Expression in Microarray Experiments. Limma is a R package for the analysis of gene expression data arising from microarray or RNA-Seq.

The pool of probes is initially selected based on adjusted p-value, FC and CV<30% (arbitrary cut off point) parameters for final picking. Further analyses and the final list are drawn based only on the first two parameters (adj p-value; FC).

EXAMPLES

The invention is illustrated by the following non-limiting Examples.

Statistical Pipeline

EpiSwitch™ screening arrays are processed using the EpiSwitch™ Analytical Package in R in order to select high value EpiSwitch™ markers for translation on to the EpiSwitch™ PCR platform.

Step 1

Probes are selected based on their corrected p-value (False Discovery Rate, FDR), which is the product of a modified linear regression model. Probes below p-value <=0.1 are selected and then further reduced by their Epigenetic ratio (ER), probes ER have to be <=-1.1 or =>1.1 in order to be selected for further analysis. The last filter is a coefficient of variation (CV), probes have to be below <=0.3.

Step 2

The top 40 markers from the statistical lists are selected based on their ER for selection as markers for PCR translation. The top 20 markers with the highest negative ER load and the top 20 markers with the highest positive ER load form the list.

Step 3

The resultant markers from step 1, the statistically significant probes form the bases of enrichment analysis using hypergeometric enrichment (HE). This analysis enables marker reduction from the significant probe list, and along with the markers from step 2 forms the list of probes translated on to the EpiSwitch™ PCR platform.

The statistical probes are processed by HE to determine which genetic locations have an enrichment of statistically significant probes, indicating which genetic locations are hubs of epigenetic difference.

The most significant enriched loci based on a corrected p-value are selected for probe list generation. Genetic locations below p-value of 0.3 or 0.2 are selected. The statistical probes mapping to these genetic locations, with the markers from step 2, form the high value markers for EpiSwitch™ PCR translation.

Array Design and Processing

Array Design

1. Genetic loci are processed using the SII software (currently v3.2) to:
   a. Pull out the sequence of the genome at these specific genetic loci (gene sequence with 50 kb upstream and 20 kb downstream)
   b. Define the probability that a sequence within this region is involved in CC's
   c. Cut the sequence using a specific RE
   d. Determine which restriction fragments are likely to interact in a certain orientation
   e. Rank the likelihood of different CC's interacting together.
2. Determine array size and therefore number of probe positions available (x)
3. Pull out x/4 interactions.
4. For each interaction define sequence of 30 bp to restriction site from part 1 and 30 bp to restriction site of part 2. Check those regions aren't repeats, if so exclude and take next interaction down on the list. Join both 30 bp to define probe.
5. Create list of x/4 probes plus defined control probes and replicate 4 times to create list to be created on array
6. Upload list of probes onto Agilent Sure design website for custom CGH array.
7. Use probe group to design Agilent custom CGH array.

Array Processing

1. Process samples using EpiSwitch™ SOP for template production.
2. Clean up with ethanol precipitation by array processing laboratory.
3. Process samples as per Agilent SureTag complete DNA labelling kit—Agilent Oligonucleotide Array-based CGH for Genomic DNA Analysis Enzymatic labelling for Blood, Cells or Tissues
4. Scan using Agilent C Scanner using Agilent feature extraction software.

Example 1: A Method of Determining the Chromosome Interactions which are Relevant to a Companion Diagnostic that Distinguishes Between Non-Responders and Responders of Methotrexate for the Treatment of Rheumatoid Arthritis Source: Glasgow Scottish Educational Research Association (SERA) cohort.

Introduction to and Brief Summary of Example 1

Stable epigenetic profiles of individual patients modulate sensitivity of signalling pathways, regulate gene expression, influence the paths of disease development, and can render ineffective the regulatory controls responsible for effective action of the drug and response to treatment. Here we analysed epigenetic profiles of rheumatoid arthritis (RA) patients in order to evaluate its role in defining the non-responders to Methotrexate (MTX) treatment.

Reliable clinical prediction of response to first-line disease modifying anti-rheumatic drugs (DMARDs, usually methotrexate (MTX)) in rheumatoid arthritis is not currently possible. Currently the ability to determine response to first line DMARDs (in particular, methotrexate (MTX)) is dependent on empiric clinical measures after the therapy.

In early rheumatoid arthritis (ERA), it has not been possible to predict response to first line DMARDs (in particular, methotrexate (MTX)) and as such treatment decisions rely primarily on clinical algorithms. The capacity to classify drug naïve patients into those that will not respond to first line DMARDs would be an invaluable tool for patient stratification. Here we report that chromosome conformational signatures (highly informative and stable epigenetic modifications that have not previously been described in RA) in blood leukocytes of early RA patients can predict non-responsiveness to MTX treatment.

Methods:

Peripheral blood mononuclear cells (PBMCs) were obtained from DMARD naïve ERA patients recruited in the Scottish early rheumatoid arthritis (SERA) inception cohort. Inclusion in this study was based on diagnosis of RA (fulfilling the 2010 ACR/EULAR Criteria) with moderate to high disease activity (DAS28≥3.2) and subsequent monotherapy with methotrexate (MTX). DAS28=Disease Activity Score of 28 joints. EULAR=The European League Against Rheumatism. ACR=American College of Rheumatology. MTX responsiveness was defined at 6 months using the following criteria: Responders—DAS28 remission (DAS28<2.6) or a good response (DAS28 improvement of >1.2 and DAS28 3.2). Non-responders—no improvement in DAS28 (50.6). Initial analysis of chromosome conformational signatures (CCS) in 4 MTX responders, 4 MTX non-responders and 4 healthy controls was undertaken using an EpiSwitch™ array containing 13,322 unique probes covering 309 RA-related genetic loci.

Differentiating CCS were defined by LIMMA* linear modeling, subsequent binary filtering and cluster analysis. A validation cohort of 30 MTX responders and 30 non-responders were screened for the differentiating CCS using the EpiSwitch™ PCR platform. The differentiating signature was further refined using binary scores and logistical regression modeling, and the accuracy and robustness of the model determined by ROC analysis**.

*Note: LIMMA is Linear Models and Empirical Bayes Methods for Assessing Differential Expression in Microarray Experiments. Limma is a R package for the analysis of gene expression data arising from microarray or RNA-Seq.

**Note: ROC means Receiver Operating Characteristic and refers to ROC curves. An ROC curve is a graphical plot that illustrates the performance of a binary classifier system as its discrimination threshold is varied. The curve is created by plotting the true positive rate against the false positive rate at various threshold settings.

CCS EpiSwitch™ array analysis identified a 30-marker stratifying profile differentiating responder and non-responder ERA patients. Subsequent evaluation of this signature in our validation cohort refined this to a 5-marker CCS signature that was able to discriminate responders and non-responders. Prediction modeling provided a probability score for responders and non-responders, ranging from 0.0098 to 0.99 (0=responder, 1=non-responder). There was a true positive rate of 92% (95% confidence interval [95% CI] 75-99%) for responders and a true negative rate of 93% (95% CI 76-99%) for non-responders. Importantly, ROC analysis to validate this stratification model demonstrated that the signature had a predictive power of sensitivity at 92% for NR to MTX.

We have identified a highly informative systemic epigenetic state in the peripheral blood of DMARD naïve ERA patients that has the power to stratify patients at the time of diagnosis. The capacity to differentiate patients a priori into non-responders, using a blood-based clinical test, would be an invaluable clinical tool; paving the way towards stratified medicine and justifying more aggressive treatment regimes in ERA clinics.

Detailed Version of Example 1

The capacity to differentiate patients a priori into responders (R) and non-responders (NR) would be an invaluable tool for patient stratification leading to earlier introduction of effective treatment. We have used the EpiSwitch™ biomarker discovery platform to identify Chromosome Conformation Signatures (CCS) in blood-derived leukocytes, which are indicative of disease state and MTX responsiveness. Thereby we identified an epigenetic signature contained in the CXCL13, IFNAR1, IL-17A, IL-21R and IL-23 loci that provide the first prognostic molecular signature that enables the stratification of treatment naïve early RA (ERA) patients into MTX R and NR. Importantly, this stratification model had a predictive power of sensitivity at 92% for NR to MTX. This epigenetic RA biomarker signature can distinguish between ERA and healthy controls (HC). This combinatorial, predictive peripheral blood signature can support earlier introduction of more aggressive therapeutics in the clinic, paving the way towards personalized medicine in RA.

RA is a chronic autoimmune disease affecting up to 1% of the global population. Pathogenesis is multifactorial and characterized by primarily immune host gene loci interacting with environmental factors, particularly smoking and other pulmonary stimuli. The exposure of a genetically susceptible individual to such environmental factors suggests an epigenetic context for disease onset and progression. Recent studies of chromatin markers (e.g. methylation status of the genome) provide the first evidence of epigenetic differences associated with RA. However, to date neither genetic associations, nor epigenetic changes, have provided a validated predictive marker for response to a given therapy. Moreover, clinical presentation only weakly predicts the efficacy and toxicity of conventional DMARDs. MTX[8], the commonest first-choice medication recommended by EULAR (The European League Against Rheumatism) and ACR (American College of Rheumatology) management guidelines, delivers clinically meaningful response rates ranging from 50 to 65% after 6 months of treatment. Such responses, and especially the rather smaller proportion that exhibits high hurdle responses, cannot currently be predicted in an individual patient. This begets a 'trial and error' based approach to therapeutic regimen choice (mono or combinatorial therapeutics). The ability to predict drug responsiveness in an individual patient would be an invaluable clinical tool, given that response to first-line treatment is the most significant predictor of long-term outcome.

Herein we focused on epigenetic profiling of DMARD-naïve, ERA patients from the Scottish Early Rheumatoid Arthritis (SERA) inception cohort in order to ascertain if there is a stable blood-based epigenetic profile that indicates NR to MTX treatment and thus enables a priori identification and stratification of such patients to an alternate therapeutic. The source Epigenetic modulation can strongly influence cellular activation and transcriptional profiles. Conceivably, the mode of action for a drug could be affected by epigenetically modified loci. We have focused on CCS, also known as long-range chromatin interactions, because they reflect highly informative and stable high-order epigenetic status which have significant implications for transcriptional regulation. They also offer significant advantages[15] and early functional links to phenotypic differences[16], and have been reported as informative biomarkers candidates in oncology and other disease areas.

We used early RA (ERA) patients provided by the Scottish early rheumatoid arthritis (SERA) inception cohort. Demographic, clinical and immunological factors were obtained at diagnosis and 6 months. Inclusion in this study was based on a diagnosis of RA (fulfilling the 2010 ACR/EULAR Criteria) with moderate to high disease activity (DAS28≥3.2) and subsequent monotherapy with MTX. Responders were defined as patients who upon receiving MTX achieved DAS28 remission (DAS28<2.6) or a good response (DAS28 improvement of >1.2 and DAS28≤3.2) at 6 months. Non-responders were defined as patients who upon receiving MTX had no improvement in DAS28 (≤0.6) at 6 months. Blood samples for epigenetic analysis were collected at diagnosis. (DAS28=Disease Activity Score of 28 joints.)

We used a binary epigenetic biomarker profiling by analysing over 13,322 chromosome conformation signatures (CCS) (13,322 unique probes) across 309 genetic loci functionally linked to RA. CCS, as a highly informative class of epigenetic biomarkers (1), were read, monitored and evaluated on EpiSwitch™ platform which has been already successfully utilized in blood based stratifications of Mayo Clinic cohort with early melanoma (2) and is currently used for predictive stratification of responses to immunotherapies with PD-1/PD-L1.

Identified epigenetic profiles of naïve RA patients were subject to statistical analysis using GraphPad Prism, WEKA and R Statistical language. By using EpiSwitch™ platform and extended cohort of 90 clinical samples we have identified a pool of over 922 epigenetic lead biomarkers, statistically significant for responders, non-responders, RA patients and healthy controls.

To identify a pre-treatment circulating CCS status in ERA patients, 123 genetic loci (Table 1) associated with RA pathogenesis were selected and annotated with chromosome conformations interactions predicted using the EpiSwitch™ in silico prediction package. The EpiSwitch™ in silico prediction generated 13,322 high-confidence CCS marker candidates (Table 1). These candidates were used to generate a bespoke discovery EpiSwitch™ array (FIG. 5) to screen peripheral blood mononuclear cells isolated at the time of diagnosis (DMARD-naïve) from 4 MTX responders (R) and 4 MTX NR, all clinically defined after 6 months therapy (FIG. 1A, B and Table 2), and 4 healthy controls (HC). To identify the CCS that differentiated R, NR and HC, a LIMMA* linear model of the normalized epigenetic load was employed. A total of 922 statistically significant stratifying markers (significance assessed on the basis of adjusted p value and EpiSwitch™ Ratio) were identified. Of the 922 lead markers, 420 were associated with NR, 210 with R and 159 with HC (FIG. 1C). Binary filtering and cluster analysis was applied to the EpiSwitch™ markers to assess the significance of CCS identified. A stepwise hierarchical clustering approach (using Manhattan distance measure with complete linkage agglomeration and taking into account R vs NR, HC vs R & HC vs NR) reduced the number of significant markers from 922 to 65 and finally resulted in a 30-marker stratifying profile (FIG. 1D and Table 3).

*Note: LIMMA is Linear Models and Empirical Bayes Methods for Assessing Differential Expression in Microarray Experiments. Limma is a R package for the analysis of gene expression data arising from microarray or RNA-Seq.

Figure 2:
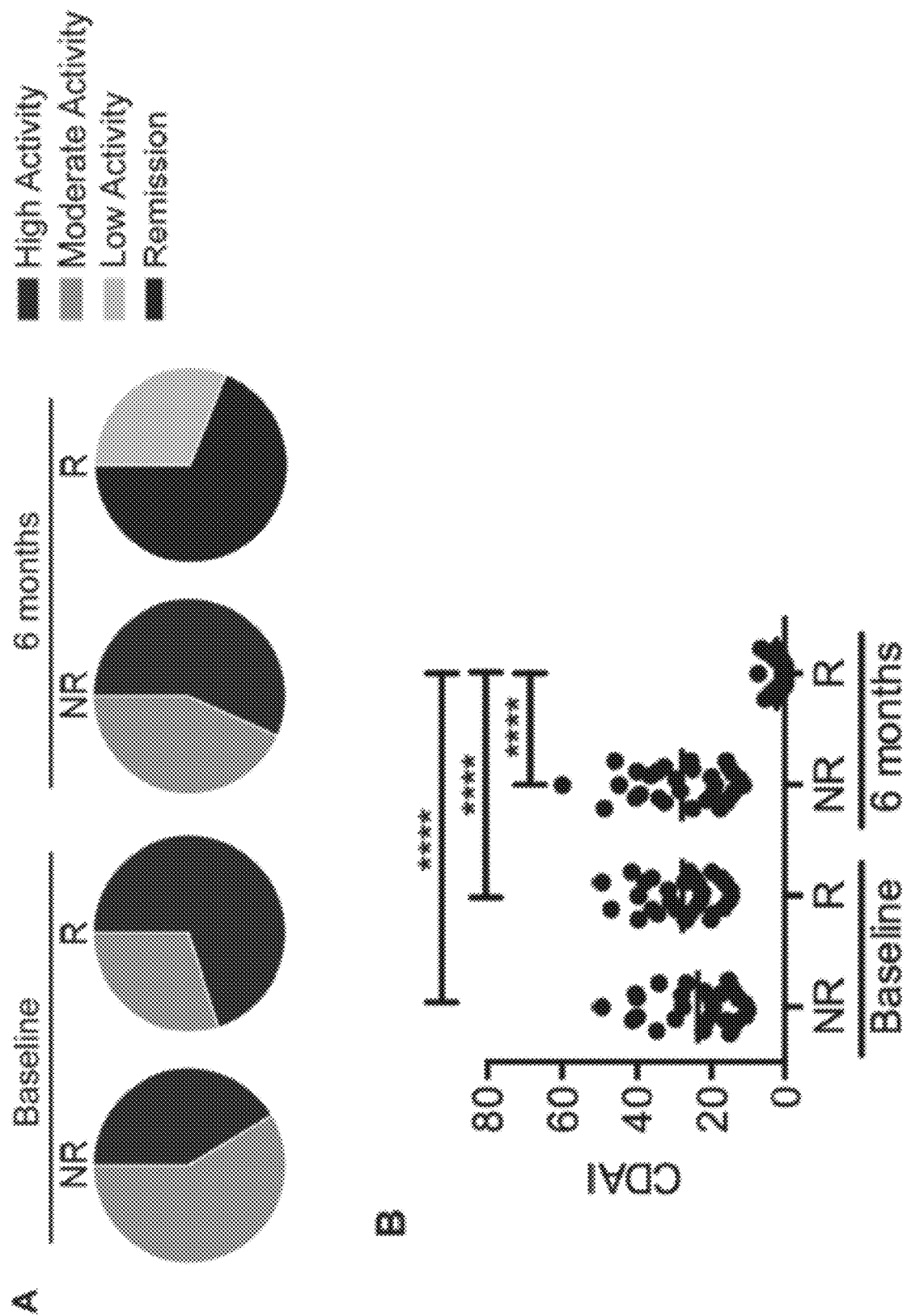
FIG. 2 is a figure comprising pie-charts and graphs relating to: Refinement and validation of the Chromosome Conformation Signature EpiSwitch™ Markers. The validation cohort of responder (R) and non-responder (NR) RA patients were selected based on DAS28 (Disease Activity Score of 28 joints) EULAR (The European League Against Rheumatism) response criteria (see methods). (A) Pie charts show the clinical interpretation of CDAI scores for both R and NR patients at baseline and 6 months. (B) CDAI scores of R and NR patients at baseline and 6 months. ****$P<0.0001$ by Kruskal-Wallis test with Dunn's multiple comparison post-test (C) Correlation plot of the classifying 5 EpiSwitch™ markers. The red box indicates the markers that define NR whilst the orange box indicated markers that define R. (D) Principle Component Analysis (PCA) for a 60 patient cohort based on their binary scores for the classifying 5 EpiSwitch™ markers.
Figure 2:
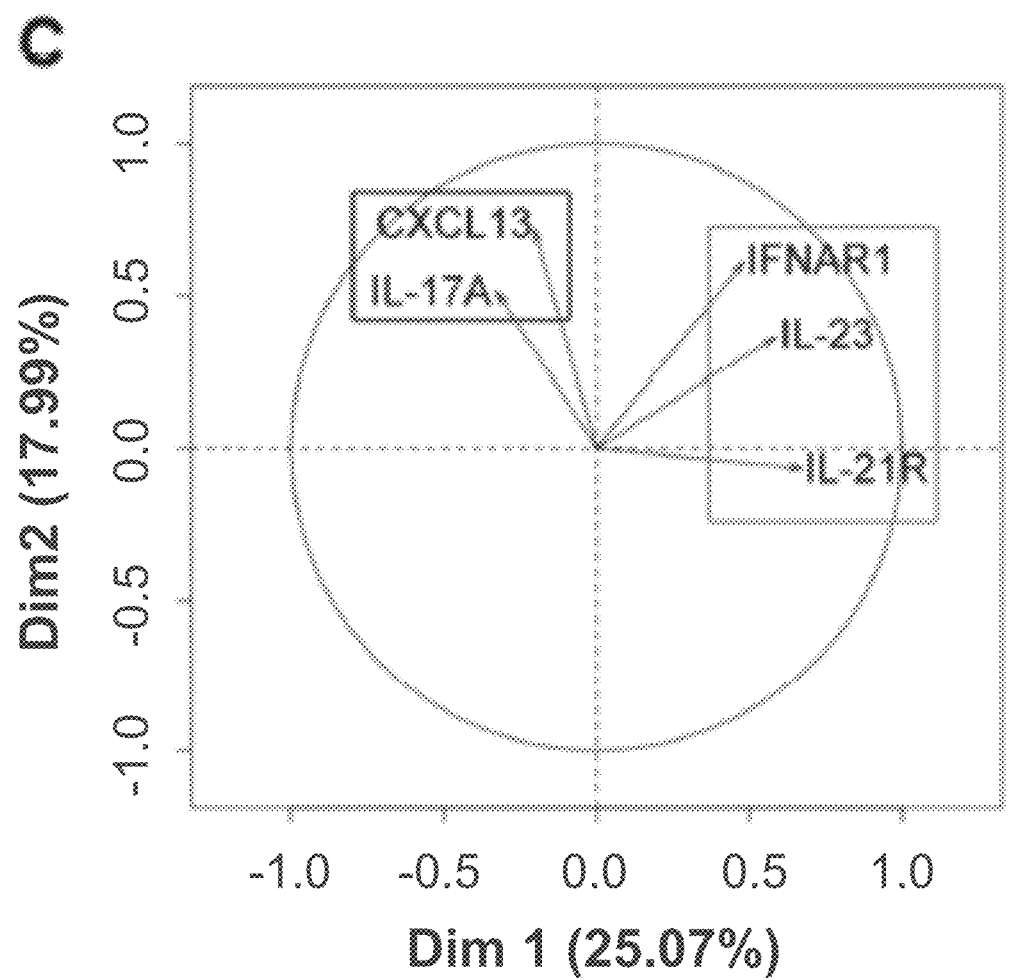
Figure 2:
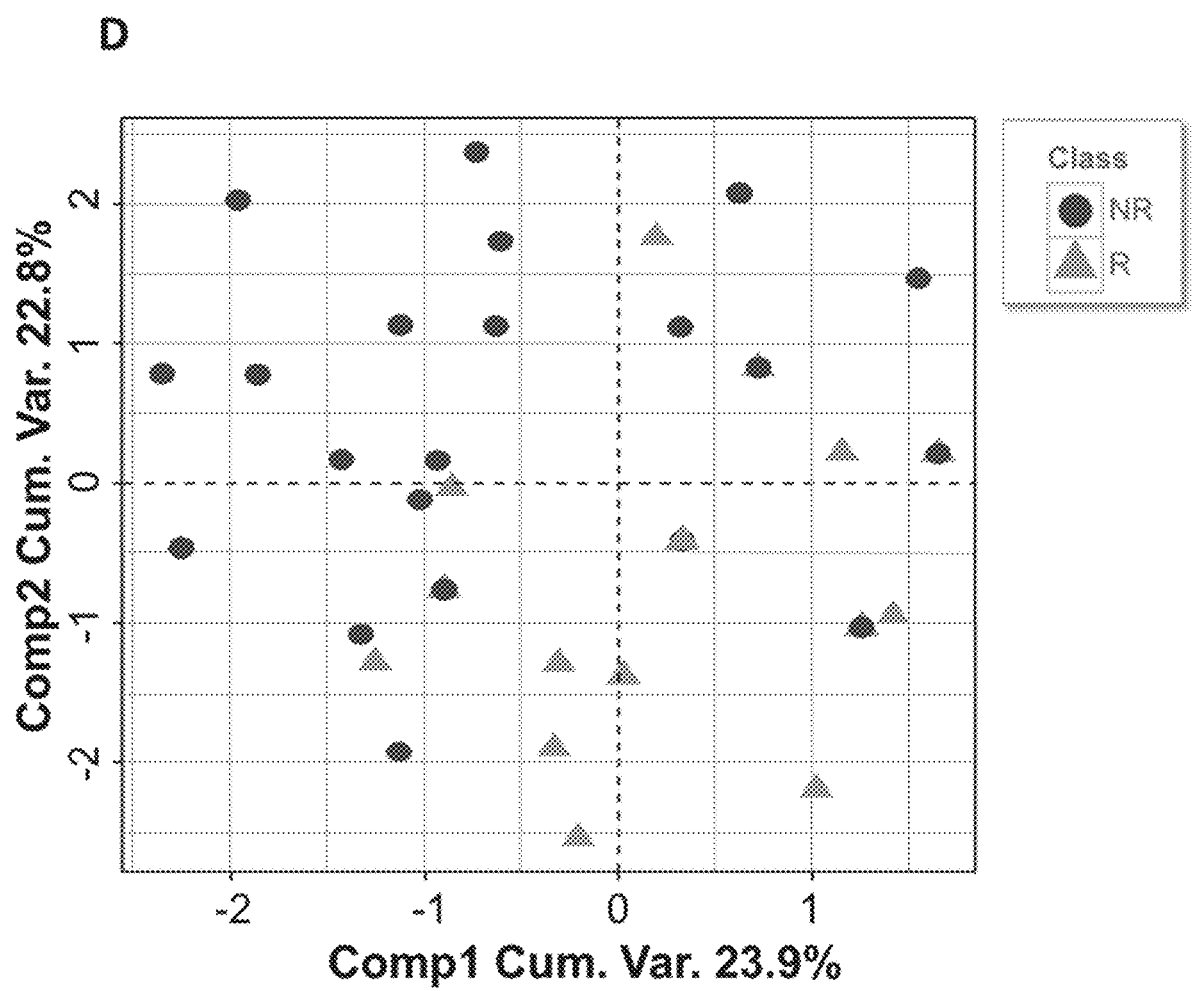
Figure 5:
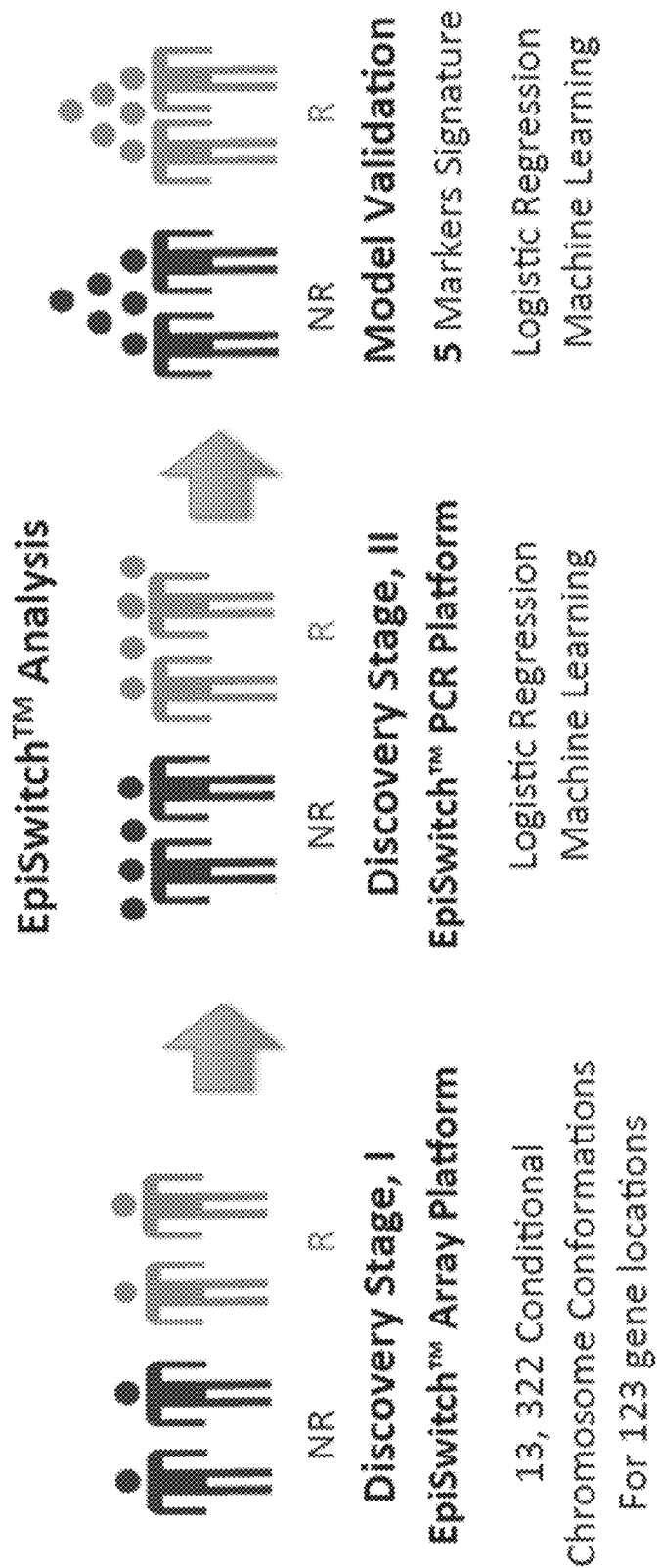
FIG. 5 is a Scheme illustrating the Design for Discovery and Validation of Epigenetic Stratifying Biomarker Signature for DMARDS Naïve ERA patients, who were confirmed within 6 months of MTX treatment as responders (N) or non-responders (NR). Epigenetic stratification was based on conditional chromosome confirmations screened and monitored by EpiSwitch™ Array and PCR (polymerase chain reaction) platforms. Disease specific epigenetic nature of the identified biomarkers was confirmed by stratification against healthy controls (HC). Validation was performed on 60 RA patients (30 responders and 30 non-responders) and 30 HC.

To refine and validate the CCS signature, the 30 identified markers were screened in a second ERA patient cohort of R and NR (FIG. 2A, B and Table 4) in a stepwise approach, using the EpiSwitch™ PCR platform (FIG. 5). In the first instance, the entire 30 CCS markers were run in 12 ERA patients (6 R and 6 NR). The best differentiating CCS markers were identified by applying a Chi-squared test for independence with Yate's continuity correction on the binary scores, revealing a 12-marker CCS profile (Table 5). These 12 CCS markers were run on an additional 12 ERA patients (6 R and 6 NR) and the data combined with the previous 12 ERA. Combining the 24 patient samples (12 R and 12 NR) a logistic regression Model in the WEKA classification platform (using 5-fold cross validation to score the discerning power of each marker) was built and run 10 times by random data re-sampling of the initial data set to generate 10 different start points for model generation. The markers with the highest average scores were selected, thus reducing the profile to the 10 best discerning CCS markers (Table 5). The 10 CCS markers were used to probe a further 36 ERA samples (18 R and 18 NR). Combining all data (30 R and 30 NR), and using the same logistical regression and score calculation analysis, revealed a 5 CCS marker signature (IFNAR1, IL-21R, IL-23, IL-17A and CXCL13) that distinguished MTX R from NR (FIG. 2C, Table 5). CCS in the CXCL13 and IL-17A loci were associated with non-responders whilst CCS in the IFNAR1, IL-23 and IL-21R loci were associated with responders. This was an intriguing profile given the central role postulated for the IL-17 axis in human autoimmunity.

Importantly, the composition of the stratifying signature identifies the location of chromosomal conformations that potentially control genetic locations of primary importance for determining MTX response. Principal component analysis (PCA) of the binary scores for the classifying 5 EpiSwitch™ CCS markers provided clear separation of ERA patients based on their MTX response (FIG. 2D). The model provided a prediction probability score for responders and non-responders, ranging from 0.0098 to 0.99 (0=responder, 1=non-responder). The cut-off values were set at 50.30 for responders and 20.70 for non-responders. The score of 50.30 had a true positive rate of 92% (95% confidence interval [95% CI] 75-99%) whilst a score of 20.70 had a true negative response rate of 93% (95% CI 76-99%). The number of observed and predicted patients per response category (R or NR to MTX) is shown in Table 6. With the EpiSwitch™ CCS marker model, 53 patients (88%) were classified as either responder or non-responder.

TABLE 6

Observed and predicted number of R and NR to MTX monotherapy at 6 months using the EpiSwitch ™ CCS model
Predicted response

| Observed responder | Non-response | Undefined | Responder |
|---|---|---|---|
| Non-responder | 25 | 3 | 2 |
| Responder | 2 | 4 | 24 |

Notes to Table 6:
Cut off levels were chosen based on the probability of response to MTX of (approximately) >0.70 for NR and <0.3 for R. NR and R were defined as described in the methods.

Figure 3:
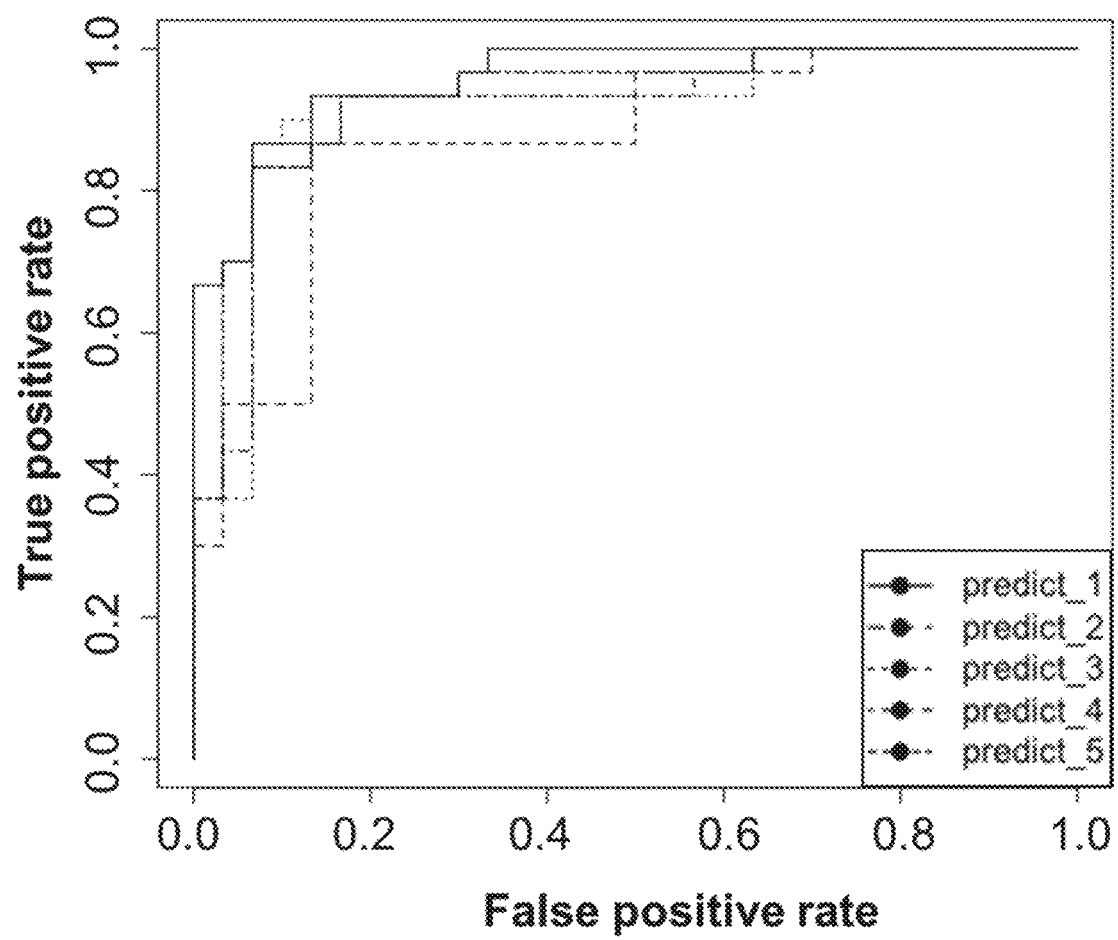
FIG. 3 is a figure comprising graphs relating to: Prognostic stratification and model validation for response to methotrexate (MTX) treatment. (A) Representative examples of 5 selected Receiver Operating Characteristics (ROC) curves from 150 randomisations of the data using the 5 CCS marker logistic regression classifiers. (B) Factor Analysis for responder (R) and non-responder (NR) RA patients vs healthy controls (HC) using EpiSwitch™ CCS markers selected for discerning MTX responders from MTX non-responders.
Figure 3:
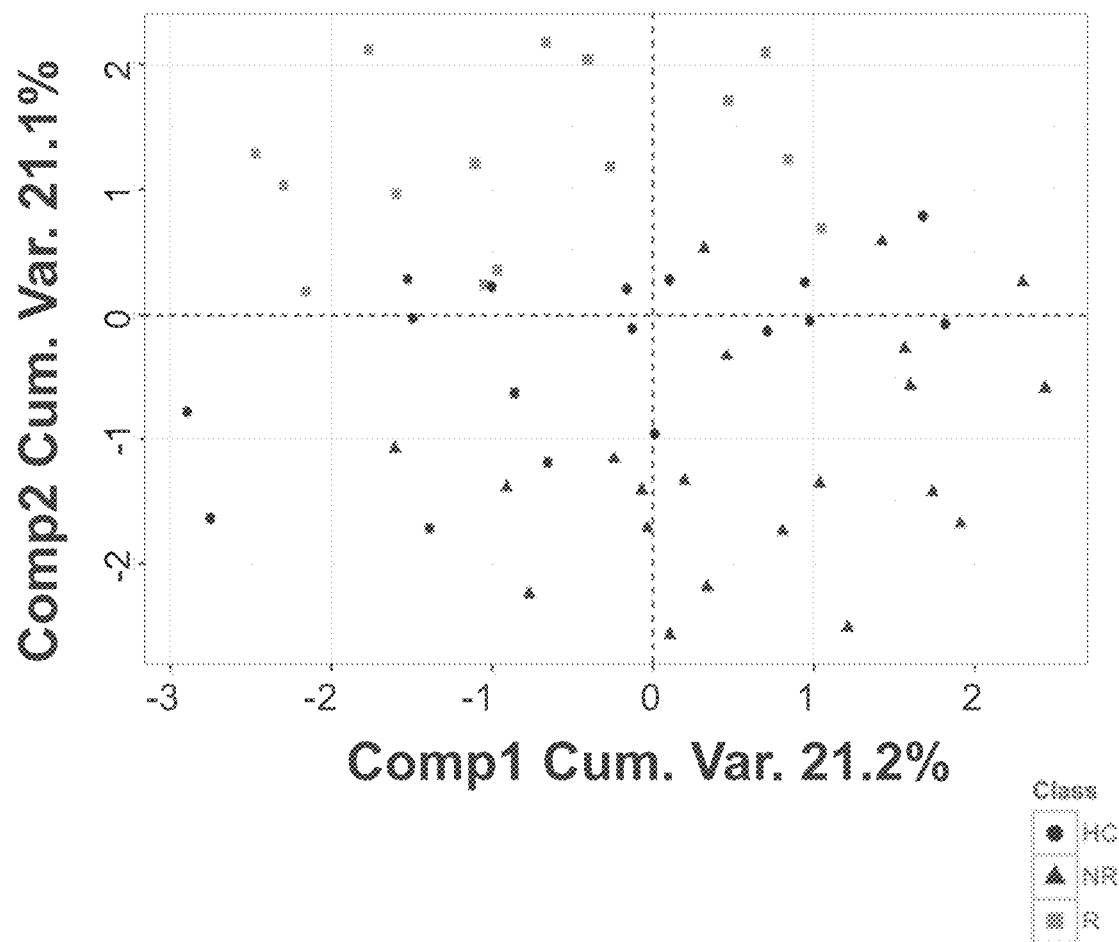
Figure 4:
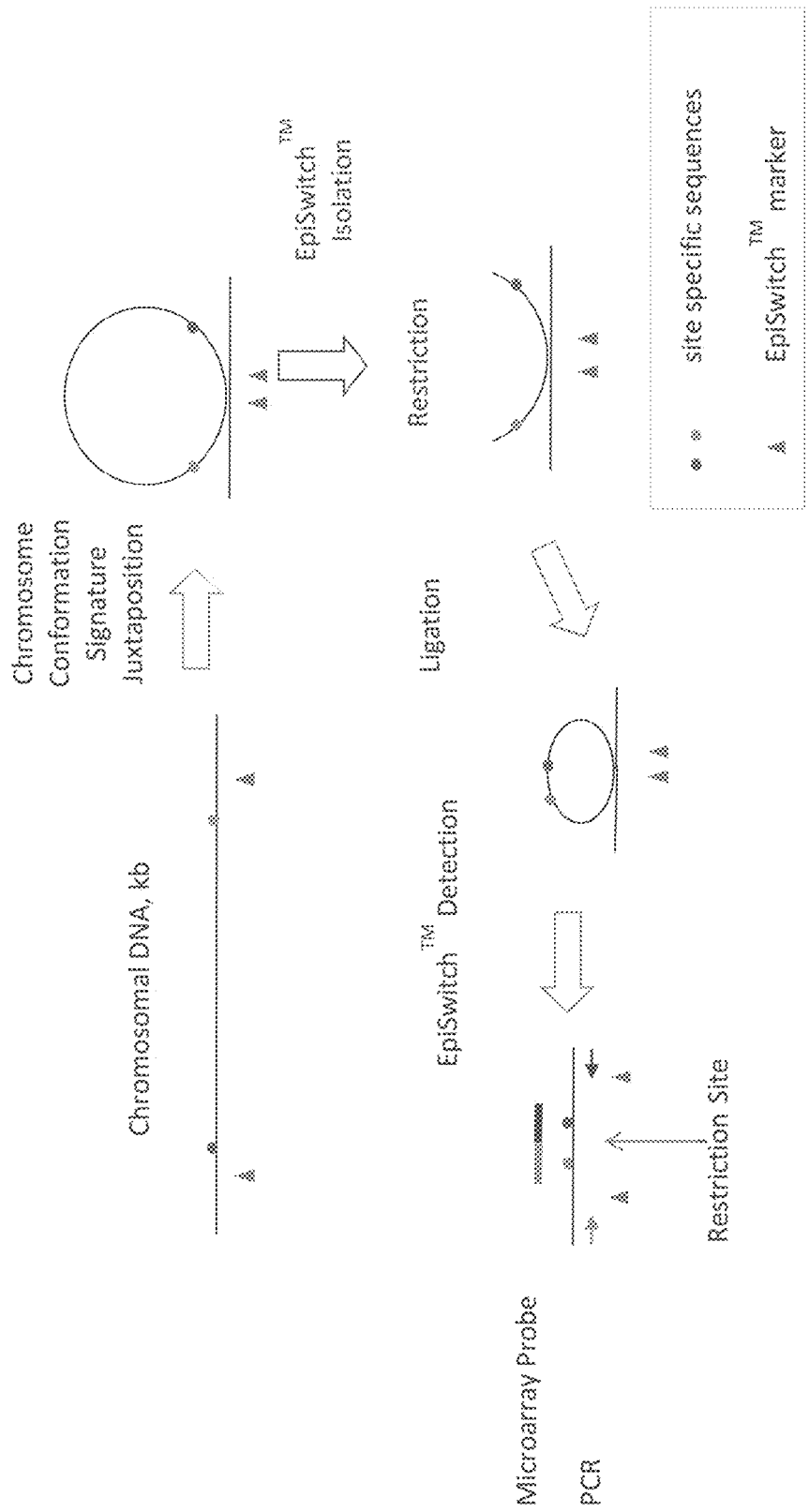
FIG. 4 is a Schematic diagram of the 3C extraction process. 3C means chromatin conformation capture, or chromosome conformation capture.

In order to test the 'accuracy' and 'robustness of performance' of the logistic classifying model that determined the 5 EpiSwitch™ CSS markers, 150 ROC** curves (with unique start points) were generated by random data re-sampling of the R and NR data (FIG. 3A). This resulted in the data being split into training (66%, equivalent to 6000 known class samples) and test (34%, equivalent to 3000 unknown class samples) groups; importantly the same split is never seen in the data for cross validation. The average discriminative ability (AUC) of the model was 89.9% (95% CI 87-100%), with an average sensitivity (adjusted for response prevalence) for NR of 92% and an average specificity for R of 84%. To determine the predictive capability of the model, the average model accuracy statistics were adjusted for population R/NR to MTX using Bayes prevalence theorem[21]. Using a 55% MTX response rate, the positive predictive value (PPV) was 90.3% whilst the negative predictive value (NPV) was 86.5%. If the response rate was adjusted to 60%, this decreased the PPV to 87% whilst increasing the NPV to 89%.

**Note: ROC means Receiver Operating Characteristic and refers to ROC curves. An ROC curve is a graphical plot that illustrates the performance of a binary classifier system as its discrimination threshold is varied. The curve is created by plotting the true positive rate against the false positive rate at various threshold settings.

As an independent evaluation of the discerning powers of the selected 5 EpiSwitch™ CCS markers, factor analysis of mixed data (FAMD) incorporating 30 HC was performed. This illustrated that the signature not only has the power to differentiate between MTX R and NR but also retains sufficient disease-specific features to differentiate between healthy individuals and RA patients (FIG. 3B).

Example 1—Table 6D and 6E—Stratifying Between RA-MTX Responders and Non-Responders Table 6D, and continuation Table 6E, presented hereinafter after Tables 6b+6c from Example 1A, show inter alia a list of about 54 DNA probes (60mers) and their DNA sequences. These probes represent some of the probes used in Example 1. Without being bound, most of the probes illustrated in Table 6D+6E are thought likely to be significant to/useful in stratifying between RA-MTX responders and RA-MTX non-responders. The shown probes were investigated further by PCR. P Value=Probability value; adj.=adjusted.

Example 1—Conclusion

In conclusion, our study of the epigenetic profile classification of DMARD naïve ERA patients on the basis of prospective clinical assessment for R/NR has identified a consistent epigenetic signature, which discriminates an epigenetic state that is conducive and non-conducive to MTX response. This is to our knowledge, the first example of a stable and selectively differentiating blood based epigenetic biomarker in early RA patients that appears disease related (versus healthy controls) and that can predict non-responsiveness to first-line MTX therapy. This model offers direct and practical benefits with a validated classifier based on 5 conditional CCS and their detection by the industrial ISO-13485 EpiSwitch™ platform, which has the potential to be routinely available in the near future within clinical practice. Importantly, by adopting this predictive signature it should be possible to stratify MTX naïve ERA patients into R and NR cohorts. This offers the potential to accelerate patient progression through the currently approved treatment strategy for ERA seeking earlier use of effective therapeutics, hence leading to a 'personalised' treatment regime. Furthermore, it is conceivable that alternative CCS signatures are present in RA patients (and patients with other autoimmune diseases) that could be used to justify fast-tracked biological treatment regimes in the clinic. This would have far reaching socio-economic implications, providing more cost effective and robust therapeutic approaches.

Example 1—Material and Methods

Example 1—RA Patient Population

ERA patients in this study are part of the Scottish early rheumatoid arthritis (SERA) inception cohort. Demographic, clinical and immunological factors were obtained at diagnosis and 6 months (Table 1). Inclusion in the inception cohort was based on clinical diagnosis of undifferentiated polyarthritis or RA (≥1 swollen joint) at a secondary care rheumatology unit in Scotland. Exclusion criteria were previous or current DMARD/biological therapy and/or established alternative diagnosis (i.e. psoriatic arthritis, reactive arthritis). Inclusion in this study was based on a diagnosis of RA (fulfilled the 2010 ACR/EULAR criteria for RA) with moderate to high disease activity (DAS28≥3.2) and subsequent monotherapy with MTX. [DAS28=Disease Activity Score of 28 joints. EULAR=European League Against Rheumatism. ACR=American College of Rheumatology.] Responders were defined as patients who upon receiving MTX achieved DAS28 remission (DAS28<2.6) or a good response (DAS28 improvement of >1.2 and DAS28≤3.2) at 6 months. Non-responders were defined as patients who upon receiving MTX had no improvement in DAS28 (50.6) at 6 months. Blood samples were collected at diagnosis (Baseline) in EDTA tubes and centrifuged to generate a buffy layer containing PBMCs, which was harvested and stored at −80° C. Local ethics committees approved the study protocol and all patients gave informed consent before enrolment into the study.

Example 1—EpiSwitch™ Processing, Array and PCR Detection. Probe Design and Locations for EpiSwitch™ Assays Pattern recognition methodology was used to analyse human genome data in relation to the transcriptional units in the human genome. The proprietary EpiSwitch™ pattern recognition software[18, 20] provides a probabilistic score that a region is involved in chromatin interaction. Sequences from 123 gene loci were downloaded and processed to generate a list of the 13,322 most probable chromosomal interactions. 60mer probes were designed to interrogate these potential interactions and uploaded as a custom array to the Agilent SureDesign website. Sequence-specific oligonucleotides were designed using Primer3[23], at the chosen sites for screening potential markers by nested PCR. Oligonucleotides were tested for specificity using oligonucleotide specific BLAST.

Example 1—Chromatin Conformation Signature Analysis from Patient PBMC's

Template preparation: Chromatin from 50 µl of each PBMC sample was extracted using the EpiSwitch™ assay following the manufacturer's instructions (Oxford BioDynamics Ltd). Briefly, the higher order structures are fixed with formaldehyde, the chromatin extracted, digested with TaqI, dilution and ligation in conditions to maximize intra-molecular ligation, and subsequent proteinase K treatment. EpiSwitch™ microarray: EpiSwitch™ microarray hybridization was performed using the custom Agilent 8×60 k array using the Agilent system, following the manufacturer's instructions (Agilent). Each array contains 55088 probes spots, representing 13,322 potential chromosomal interactions predicted by the EpiSwitch™ pattern recognition software quadruplicated, plus EpiSwitch™ and Agilent controls. Briefly, 1 µg of EpiSwitch™ template was labelled using the Agilent SureTag labelling kit. Processing of labelled DNA was performed. Array analysis was performed immediately after washing using the Agilent scanner and software. In order to compare all the experiments the data was background corrected and normalized. Since each spot in the array is present in quadruplicate, the median of the four spots of each probe in the array was calculated and its log 2 transformed value was used for further analysis. The coefficient of variation and p-value was calculated for each probe replicate. EpiSwitch™ PCR detection: Oligonucleotides were tested on template to confirm that each primer set was working correctly. To accommodate for technical and replicate variations, each sample was processed four times. All the extracts from these four replicates were pooled and the final nested PCR was performed on each sample. This procedure permitted the detection of limited copy-number templates with higher accuracy. All PCR amplified samples were visualised by electrophoresis in the LabChip* GX from Perkin Elmer, using the LabChip DNA 1K Version2 kit (Perkin Elmer) and internal DNA marker was loaded on the DNA chip according to the manufacturer's protocol using fluorescent dyes. Fluorescence was detected by laser and electropherogram read-outs translated into a simulated band on gel picture using the instrument software. The threshold we set for a band to be deemed positive was 30 fluorescence units and above.

Example 1—Statistical Methods and Packages

GraphPad Prism and SPSS were used for all statistical analyses of clinical data. The chi-square test and Fisher's exact test (for categorical variables), the t-test for independent samples (for continuous normally distributed variables), and the Mann-Whitney U test (for continuous variables without normal distribution) were used to identify differences. The level of statistical significance was set at 0.05, and all tests were 2-sided. R (and appropriate packages) were used for evaluation of EpiSwitch™ data. This included Stats package for Chi-square test and GLM (logit), ROCR package for ROC curves from WEKA odds probabilities, gplot & stats package in R for Heatmaps. FactorMiner package was used for PCA and Factor plots. Weka was used for Attribute Reduction, data randomisation and re-sampling, Logistic Model Classifier, AUC calculations and model accuracy calculations.

TABLE 1

Example 1- Selected genes for EpiSwitch ™ Array

| GENE | Description | Comments | Number of identified EpiSwitch ™ sites |
|---|---|---|---|
| ABCB1 | ATP-binding cassette, sub-family B (MDR/TAP), member 1 | MTX related genes | 56 |
| ABCG2 | ATP-binding cassette, sub-family G (WHITE), member 2 | MTX related genes | 84 |
| ADORA2A | Adenosine A2a receptor | MTX related genes | 72 |
| AFF3 | AF4/FMR2 family, member 3 | RA SNP association | 140 |

TABLE 1-continued

Example 1- Selected genes for EpiSwitch™ Array

| GENE | Description | Comments | Number of identified EpiSwitch™ sites |
|---|---|---|---|
| AMPD1 | Adenosine monophosphate deaminase 1 | MTX related genes | 24 |
| ApoE | Apolipoprotein E | Apolipoproteins | 96 |
| ATIC | 5-aminoimidazole-4-carboxamide ribonucleotide formyltransferase/IMP cyclohydrolase | MTX related genes | 32 |
| BLK | B lymphoid tyrosine kinase | RA SNP association | 196 |
| BTNL2 | Butyrophilin-like 2 (MHC class II associated) | Associated with RA via exome sequencing | 44 |
| C5orf30 | Chromosome 5 open reading frame 30 | RA SNP association | 96 |
| CCL2 | Chemokine (C-C motif) ligand 2 | Cytokines & Chemokines | 404 |
| CCL21 | Chemokine (C-C motif) ligand 21 | Cytokines & Chemokines | 28 |
| CCL3 | Chemokine (C-C motif) ligand 3 | Cytokines & Chemokines | 52 |
| CCL5 | Chemokine (C-C motif) ligand 5 | Cytokines & Chemokines | 52 |
| CCR1 | Chemokine (C-C motif) receptor 1 | Cytokines & Chemokines receptors | 172 |
| CCR2 | Chemokine (C-C motif) receptor 2 | Cytokines & Chemokines receptors | 164 |
| CCR6 | Chemokine (C-C motif) receptor 6 | Cytokines & Chemokines receptors | 56 |
| CD28 | Cluster of Differentiation 28 | RA SNP association | 132 |
| CD40 | Cluster of Differentiation 40 | RA SNP association | 148 |
| CD80 | Cluster of Differentiation 80 | Cell surface | 76 |
| CHI3L1 | Chitinase 3-like 1 (cartilage glycoprotein-39) | Extracellular | 64 |
| CHUK | Conserved helix-loop-helix ubiquitous kinase | NFKB | 92 |
| CIITA | Class II, major histocompatibility complex, transactivator | NLR pathway | 80 |
| CLEC12A | C-type lectin domain family 12, member A | Other | 52 |
| CLEC16A | C-type lectin domain family 16, member A | Other | 108 |
| COL2A1 | Collagen, type II, alpha 1 | Collagens | 100 |
| CTLA4 | Cytotoxic T-lymphocyte-associated protein 4 | RA SNP association | 68 |
| CX3CL1 | Chemokine (C-X3-C motif) ligand 1 | Cytokines & Chemokines | 92 |
| CXCL12 | Chemokine (C-X-C motif) ligand 12 | Cytokines & Chemokines | 80 |
| CXCL13 | Chemokine (C-X-C motif) ligand 13 | Cytokines & Chemokines | 80 |
| CXCL8 | Chemokine (C-X-C motif) ligand 8 | Cytokines & Chemokines | 48 |
| CXCR3 | Chemokine (C-X-C motif) receptor 3 | Cytokines & Chemokines receptors | 72 |
| CXCR4 | Chemokine (C-X-C motif) receptor 4 | Cytokines & Chemokines receptors | 56 |
| DHFR | Dihydrofolate reductase | MTX related genes | 72 |
| ESR1 | Oestrogen receptor 1 | FLS MTX responsive genes | 140 |
| FCGR2A | Fc fragment of IgG, low affinity IIa, receptor (CD32) | RA SNP association | 100 |
| FCGR3B | Fc fragment of IgG, low affinity IIIb, receptor (CD16b) | RA SNP association | 192 |
| FCRL3 | Fc receptor-like 3 | Other | 68 |
| FPGS | Folylpolyglutamate synthase | MTX related genes | 56 |
| HTR2A | 5-hydroxytryptamine (serotonin) receptor 2A, G protein-coupled | Other | 80 |
| ICAM1 | Intercellular adhesion molecule | FLS MTX responsive genes | 132 |
| ICOS | Inducible T-cell co-stimulator | RA SNP association | 200 |
| IFNAR1 | Interferon (alpha, beta and omega) receptor 1 | Cytokines & Chemokines receptors | 80 |
| IFNg | Interferon, gamma | Cytokines & Chemokines | 52 |
| IKBKB | Inhibitor of kappa light polypeptide gene enhancer in B-cells, kinase beta | NFKB | 128 |
| IL-10 | Interleukin 10 | Cytokines & Chemokines | 48 |
| IL-15 | Interleukin 15 | Cytokines & Chemokines | 76 |
| IL-17A | Interleukin 17A | Cytokines & Chemokines | 32 |
| IL-18 | Interleukin 18 | Cytokines & Chernokines | 64 |
| IL-1a | Interleukin 1 alpha | Cytokines & Chemokines | 196 |
| IL-2 | Interleukin 2 | Cytokines & Chemokines | 44 |
| IL-21R | Interleukin 21 receptor | Cytokines & Chemokines receptors | 60 |
| IL-23 | Interleukin 23 | Cytokines & Chemokines | 56 |
| IL-23R | Interleukin 23 | Cytokines & Chemokines receptor receptors | 104 |
| IL-2RA | Interleukin 2 receptor, alpha | Cytokines & Chemokines receptors | 100 |
| IL-2RB | Interleukin 2 receptor, beta | Cytokines & Chemokines receptors | 72 |
| IL-32 | Interleukin 32 | Cytokines & Chemokines | 44 |
| IL-4 | Interleukin 4 | Cytokines & Chemokines | 32 |
| IL-4R | Interleukin 4 receptor | Cytokines & Chemokines receptors | 76 |
| IL-6 | Interleukin 6 | Cytokines & Chemokines | 48 |
| IL-6ST | Interleukin 6 signal transducer (gp130, oncostatin M receptor) | Cytokines & Chemokines receptors | 72 |
| IL-7 | Interleukin 7 | Cytokines & Chemokines | 72 |
| IL1RN | Interleukin 1 receptor antagonist | MTX related genes | 28 |
| IRAK3 | Interleukin-1 receptor-associated kinase 3 | Signalling | 80 |

TABLE 1-continued

Example 1- Selected genes for EpiSwitch ™ Array

| GENE | Description | Comments | Number of identified EpiSwitch ™ sites |
|---|---|---|---|
| IRF5 | Interferon regulatory factor 5 | Signalling | 76 |
| ITGA4 | Integrin, alpha 4 (antigen CD49D, alpha 4 subunit of VLA-4 receptor) | Cell surface | 100 |
| ITPA | Inosine triphosphatase (nucleoside triphosphate pyrophosphatase) | MTX related genes | 56 |
| JAG1 | Jagged 1 | FLS MTX responsive genes | 84 |
| M-CSF | Colony stimulating factor 1 | Cytokines & Chemokines | 96 |
| MafB | V-maf musculoaponeurotic fibrosarcoma oncogene homolog B | Transcription factors | 52 |
| MAL | Mal, T-cell differentiation protein | TLR pathway | 68 |
| MEFV | Mediterranean fever | Other | 76 |
| MMP14 | Matrix metallopeptidase 14 | Matrix Metalloprotineases | 92 |
| MMP2 | Matrix metallopeptidase 2 | Matrix Metalloprotineases | 212 |
| MMP9 | Matrix metallopeptidase 9 | Matrix Metalloprotineases | 68 |
| MTHFD1 | Methylenetetrahydrofolate dehydrogenase (NADP + dependent) 1, methenyltetrahydrofolate cyclohydrolase, formyltetrahydrofolate synthetase | MTX related genes | 80 |
| MTHFR | Methylenetetrahydrofolate reductase (NAD(P)H) | MTX related genes | 52 |
| MyD88 | Myeloid differentiation primary response gene 88 | TLR pathway | 80 |
| NFAT | Nuclear factor of activated T cells | Transcription factors | 204 |
| NFATC2IP | Nuclear factor of activated T-cells, cytoplasmic, calcineurin-dependent 2 interactingprotein | RA SNP association | 84 |
| NFKB1 | Nuclear factor of kappa light polypeptide gene enhancer in B-cells 1 | NFKB | 96 |
| NFKB2 | Nuclear factor of kappa light polypeptide gene enhancer in B-cells 2 (p49/p100) | NFKB | 64 |
| NFKBIB | Nuclear factor of kappa light polypeptide gene enhancer in B-cells inhibitor, beta | NFKB | 120 |
| NFKBIA | Nuclear factor of kappa light polypeptide gene enhancer in B-cells inhibitor, alpha | NFKB | 88 |
| NLRP1 | NLR family, pyrin domain containing 1 | NLR pathway | 108 |
| NLRP3 | NLR family, pyrin domain containing 3 | NLR pathway | 128 |
| PADI4 | Peptidyl arginine deiminase, type IV | RA SNP association | 168 |
| PRDM1 | PR domain containing 1, with ZNIF domain | RA SNP association | 120 |
| PRKCQ | Protein kinase C, theta | RA SNP association | 216 |
| PRKCZ | Protein kinase C, zeta | Other | 184 |
| PSTPIP1 | Proline-serine-threonine phosphatase interacting protein 1 | Cytoskeletal | 96 |
| PTGS2 | Prostaglandin-endoperoxide synthase 2 (prostaglandin G/H synthase and cyclooxygenase) | Signalling | 52 |
| PTPN22 | Protein tyrosine phosphatase, non-receptor type 22 | RA SNP association | 196 |
| PXK | PX domain containing serine/threonine kinase | RA SNP association | 296 |
| RBPJ | Recombination signal binding protein for immunoglobulin kappa J region | RA SNP association | 296 |
| REL | V-rel reticuloendotheliosis viral oncogene homolog A | NFKB | 92 |
| RFC-1 | Replication factor C (activator 1) 1, 145 kDa | MTX related genes | 52 |
| RGMB | RGM domain family, member B | FLS MTX responsive genes | 80 |
| RUNX1 | Runt-related transcription factor 1 | RA SNP association | 212 |
| SH2B3 | SH2B adaptor protein 3 | RA SNP association | 124 |
| SHMT | Serine hydroxymethyltransferase 1 (soluble) | MTX related genes | 68 |
| SLC19A1 | Solute carrier family 19 (folate transporter), member 1 | MTX related genes | 76 |
| SPRED2 | Sprouty-related, EVH1 domain containing 2 | RA SNP association | 336 |
| STAT4 | Signal transducer and activator of transcription 4 | Signalling | 128 |
| SUMO1 | SMT3 suppressor of mif two 3 homolog 1 | SUMO | 132 |
| TAGAP | T-cell activation RhoGTPase activating protein | RA SNP association | 92 |
| TLR1 | Toll-like receptor 1 | TLR pathway | 204 |
| TLR2 | Toll-like receptor 2 | TLR pathway | 52 |
| TLR4 | Toll-like receptor 4 | TLR pathway | 52 |
| TNF | Tumour necrosis factor | Cytokines & Chemokines | 68 |
| TNFAIP3 | Tumour necrosis factor, alpha-induced protein 3 | RA SNP association | 180 |
| TNFRSF11B | Tumour necrosis factor receptor superfamily, member 11b | Cytokines & Chemokines receptors | 80 |
| TNFRSF13C | Tumour necrosis factor receptor superfamily, member 13C | Cytokines & Chemokines receptors | 52 |
| TNFRSF14 | Tumour necrosis factor receptor superfamily, member 14 | RA SNP association | 112 |
| TNFRSF17 | Tumour necrosis factor receptor superfamily, member 17 | Cytokines & Chemokines receptors | 44 |
| TNFRSF1A | Tumour necrosis factor receptor superfamily, member 1A | Cytokines & Chemokines receptors | 72 |
| TNFRSF1B | Tumour necrosis factor receptor superfamily, member 1B | Cytokines & Chemokines receptors | 72 |
| TNFSF11 | Tumour necrosis factor (ligand) superfamily, member 11 | Cytokines & Chemokines | 52 |
| TNFSF13 | Tumour necrosis factor (ligand) superfamily, member 13 | Cytokines & Chemokines | 48 |
| TRAF1 | TNF receptor-associated factor 1 | RA SNP association | 120 |
| TRAF6 | TNF receptor-associated factor 6 | RA SNP association | 72 |
| TYMS | Thymidylate synthetase | MTX related genes | 48 |
| WISP3 | WNT1 inducible Signalling pathway protein 3 | Signalling | 88 |

Example 1 - Table 2. Patient Characteristics - Discovery Cohort

| | Baseline | | | 6 months | | | Healthy |
|---|---|---|---|---|---|---|---|
| | Non-responder | Responder | P value | Non-responder | Responder | P value | control |
| Age - years | 55 ± 6.1 | 55 ± 19.7 | >0.99 | — | — | — | 52 ± 13.3 |
| Males - no. (%) | 1 (25) | 1 (25) | 1 | — | — | — | 3 (38) |
| Caucasian - no. (%) | 4 (100) | 4 (100) | — | — | — | — | 8 (100) |
| Body mass index - kg/m² | 29.5 ± 0.96$ | 25.0 ± 4.88 | 0.19 | — | — | — | — |
| Patient global assessment (VAS, 0-100 mm) | 54.3 ± 33.5 | 39.3 ± 30.2 | 0.53 | 54.5 ± 20.0 | 9.3 ± 6.2 | 0.029 | — |
| Physician global assessment (VAS, 0-100 mm) | 55 ± 29.7 | 38.5 ± 17.8 | 0.38 | 32.5 ± 20.2 | 8.8 ± 7.0 | 0.068 | — |
| Number of swollen joints (0-28) | 11.3 ± 5.3 | 4.8 ± 3.9 | 0.09 | 15 ± 10.7 | 2.0 ± 2.8 | 0.057 | — |
| Number of tender joints (0-28) | 10.5 ± 7.7 | 4.8 ± 6.4 | 0.2 | 11.25 ± 10.6 | 0.5 ± 1.0 | 0.029 | — |
| CDAI | 32.7 ± 5.2 | 17.3 ± 9.6 | 0.03 | 35.0 ± 21.2 | 4.3 ± 3.7 | 0.03 | — |
| DAS28-CRP | 5.1 ± 0.2 | 4.2 ± 0.77 | 0.06 | — | — | — | — |
| DAS28-ESR | 5.5 ± 0.5$ | 4.6 ± 0.9$ | 0.4 | 5.3 ± 1.3 | 2.8 ± 0.7 | 0.016 | — |
| RF (IU/ml) | 35.4 ± 25.6 | 321 ± 140$ | 0.06 | — | — | — | — |
| CCP (U/ml) | 10.3 ± 7.2 | 340 ± 0$ | 0.06 | — | — | — | — |
| Current smoker - no. (%) | 2 (50) | 1 (25) | — | — | — | — | — |
| Previous smoker - no. (%) | 1 (25) | 1 (25) | — | — | — | — | — |
| Non-smoker - no. (%) | 1 (25) | 2 (50) | — | — | — | — | — |

The Fisher exact unconditional test is used to assess differences in proportions between the two groups. To examine differences in continuous variables between the two groups, the independent samples t-test or the Mann-Whitney U-test (depending on distribution of data) is used.
$n = 3

Example 1 - Table 3. 65 Selected genes from EpiSwitch™ Array analysis

| Gene | Probes* | adj. p value | EpiSwitch™ ratio | HC_NR_MTX | HC_R_MTX | NR_R_MTX | Association |
|---|---|---|---|---|---|---|---|
| 19_55449062_55451429_55484960_55486708_RF | 19_55449062_55451429_55484960_55486708_RF | 0.079228864 | −1.43395525 | 0 | −1 | −1 | R |
| C5orf30 | C5orf30_Site5_Site2_FF | 0.079228864 | −1.24257534 | 1 | −1 | −1 | R |
| CHUK | CHUK_Site7_Site2_RF | 0.079228864 | −1.32868581 | 1 | −1 | −1 | R |
| CXCL13 | CXCL13_Site1_Site3_RR | 0.079228864 | −1.29833859 | 0 | −1 | −1 | R |
| TLR1 | TLR1_Site4_Site7_FR | 0.079228864 | −1.43064593 | 1 | −1 | −1 | R |
| 11_47175706_47180170_47251505_47252468_FR | 11_47175706_47180170_47251505_47252468_FR | 0.083312472 | −1.20859706 | 1 | −1 | −1 | R |
| C5orf30 | C5orf30_Site4_Site2_FF | 0.084204721 | −1.20024867 | 1 | −1 | −1 | R |
| TLR1 | TLR1_Site9_Site2_FF | 0.086622849 | −1.37554182 | 1 | −1 | −1 | R |
| FCRL3 | FCRL3_Site9_Site7_FF | 0.090200643 | −1.25121814 | 1 | −1 | −1 | R |
| SH2B3 | SH2B3_Site6_Site5_FF | 0.090200643 | −1.32868581 | 1 | −1 | −1 | R |
| 12_69705360_69711928_69799162_69800678_RF | 12_69705360_69711928_69799162_69800678_RF | 0.097224197 | −1.20580783 | 1 | −1 | −1 | R |
| IL-23R | IL-23R_Site5_Site8_FF | 0.108787769 | −1.26868449 | 1 | −1 | −1 | R |
| CLEC12A | CLEC12A_Site6_Site1_FR | 0.112869007 | −1.22264028 | 0 | −1 | −1 | R |
| IL-17A | IL-17A_Site3_Site1_RR | 0.115042065 | −1.16473359 | 0 | −1 | −1 | R |
| CXCL8 | CXCL8_Site7_Site6_FR | 0.118123176 | −1.13288389 | 0 | −1 | −1 | R |
| MyD88 | MyD88_Site5_Site1_FR | 0.129904996 | −1.18372449 | 1 | −1 | −1 | R |
| PRDM1 | PRDM1_Site6_Site2_RR | 0.144057138 | −1.19195794 | 1 | −1 | −1 | R |
| MMP2 | MMP2_Site8_Site9_FF | 0.146105678 | −1.2.0859706 | 1 | −1 | −1 | R |
| SPRED2 | SPRED2_Site4_Site8_RF | 0.149371667 | −1.38510947 | 1 | −1 | −1 | R |
| C5orf30 | C5orf30_Site4_Site8_RF | 0.150085134 | −1.17826714 | 1 | −1 | −1 | R |
| 19_10294661_10295285_10370560_10371551_RR | 19_10294661_10295285_10370560_10371551_RR | 0.153140631 | −1.20859706 | 1 | −1 | −1 | R |
| TNFRSF13C | TNFRSF13C_Site3_Site6_FF | 0.15333898 | −1.20580783 | 1 | −1 | −1 | R |
| IL-23 | IL-23_Site4_Site5_FR | 0.160960834 | −1.18099266 | | −1 | −1 | R |
| NFKBIB | NFKBIB_Site8_Site9_FR | 0.168381727 | −1.23114441 | 1 | −1 | −1 | R |
| TNFRSF13C | TNFRSF13C_Site1_Site6_FF | 0.16921449 | −1.1198716 | 1 | −1 | −1 | R |
| CD28 | CD28_Site5_Site9_RR | 0.171723501 | −1.14340249 | 1 | −1 | −1 | R |
| NFKB1 | NFKB1_Site4_Site8_RR | 0.185725586 | −1.20024867 | 1 | −1 | −1 | R |
| CHUK | CHUK_Site3_Site5_RF | 0.188137111 | −1.13076939 | 1 | −1 | −1 | R |
| TLR1 | TLR1_Site9_Site3_FR | 0.188137111 | −1.19747871 | 1 | −1 | −1 | R |
| M-CSF | M-CSF_Site5_Site6_FF | 0.191292635 | −1.20859706 | 1 | −1 | −1 | R |
| NFKBIB | NFKBIB_Site1_Site8_FF | 0.191922112 | −1.12766093 | 1 | −1 | −1 | R |
| 11_47175706_47180170_47202910_47204016_FF | 11_47175706_47180170_47202910_47204016_FF | 0.192002056 | −1.20580783 | 1 | −1 | −1 | R |
| PRDM1 | PRDM1_Site6_Site1_RR | 0.194604588 | −1.18970712 | 1 | −1 | −1 | R |
| TNFRSF14 | TNFRSF14_Site4_Site1_RR | 0.082014717 | 1.526259209 | 0 | 1 | 1 | NR |
| SH2B3 | SH2B3_Site3_Site2_FF | 0.083312472 | 1.228303149 | −1 | 1 | 1 | NR |
| MyD88 | MyD88_Site2_Site4_FR | 0.086246871 | 1.211392737 | 0 | 1 | 1 | NR |
| MafB | MafB_Site2_Site4_FF | 0.090511832 | 1.170128253 | −1 | 1 | 1 | NR |

Example 1 - Table 3. 65 Selected genes from EpiSwitch™ Array analysis

| Gene | Probes* | adj. p value | EpiSwitch™ ratio | HC_NR_MTX | HC_R_MTX | NR_R_MTX | Association |
|---|---|---|---|---|---|---|---|
| PRKCZ | PRKCZ_Site6_Site3_RF | 0.093763087 | 1.316462719 | 0 | 1 | 1 | NR |
| IFNAR1 | IFNAR1_Site2_Site4_RR | 0.093849223 | 1.228303149 | −1 | 1 | 1 | NR |
| NFAT | NFAT_Site2_Site10_FR | 0.093849223 | 1.208597056 | −1 | 1 | 1 | NR |
| NFAT | NFAT_Site5_Site10_RR | 0.094393734 | 1.25411241 | −1 | 1 | 1 | NR |
| MAL | MAL_Site2_Site6_RF | 0.095094028 | 1.274560627 | 0 | 1 | 1 | NR |
| FCGR2A | FCGR2A_Site3_Site6_RR | 0.096581892 | 1.170128253 | −1 | 1 | 1 | NR |
| IL-32 | IL-32_Site5_Site4_RF | 0.097224197 | 1.205807828 | 0 | 1 | 1 | NR |
| MTHFD1 | MTHFD1_Site1_Site7_RF | 0.114751424 | 1.175547906 | −1 | 1 | 1 | NR |
| TLR2 | TLR2_Site1_Site5_RR | 0.120590183 | 1.217003514 | −1 | 1 | 1 | NR |
| NFAT | NFAT_Site6_Site10_RR | 0.129631525 | 1.211392737 | −1 | 1 | 1 | NR |
| ICAM1 | ICAM1_Site4_Site9_FR | 0.131386096 | 1.180992661 | −1 | 1 | 1 | NR |
| NFAT | NFAT_Site5_Site10_FR | 0.133034069 | 1.170128253 | −1 | 1 | 1 | NR |
| MTHFD1 | MTHFD1_Site5_Site7_RF | 0.144559523 | 1.156688184 | −1 | 1 | 1 | NR |
| MTHFR | MTHFR_Site6_Site4_RR | 0.150085134 | 1.170128253 | −1 | 1 | 1 | NR |
| ICAM1 | ICAM1_Site4_Site1 FF | 0.151103565 | 1.140763716 | −1 | 1 | 1 | NR |
| MTHFD1 | MTHFD1_Site1_Site7_RF | 0.114751424 | 1.175547906 | −1 | 1 | 1 | NR |
| NFAT | NFAT_Site11_Site10_RR | 0.158903523 | 1.197478705 | −1 | 1 | 1 | NR |
| NFAT | NFAT_Site10_Site9_RF | 0.160614052 | 1.197478705 | −1 | 1 | 1 | NR |
| MafB | MafB_Site5_Site2_RF | 0.167291268 | 1.164733586 | −1 | 1 | 1 | NR |
| NFAT | NFAT_Site7_Site10_RR | 0.169766598 | 1.189207115 | −1 | 1 | 1 | NR |
| FCGR2A | FCGR2A_Site3_Site7_RR | 0.180386617 | 1.125058485 | −1 | 1 | 1 | NR |
| MafB | MafB_Site6_Site2_RF | 0.186948332 | 1.107008782 | −1 | 1 | 1 | NR |
| ADORA2A | ADORA2A_Site1_Site7_FR | 0.191209559 | 1.138131035 | −1 | 1 | 1 | NR |
| MMP9 | MMP9_Site2_Site3_FR | 0.192328613 | 1.132883885 | −1 | 1 | 1 | NR |
| COL2A1 | COL2A1_Site7_Site2_FF | 0.193661549 | 1.112136086 | −1 | 1 | 1 | NR |
| TNFRSF1B | TNFRSF1B_Site1_Site7_FR | 0.19556991 | 1.154018752 | −1 | 1 | 1 | NR |
| FCGR2A | FCGR2A_Site3_Site2_RR | 0.197822331 | 1.117287138 | −1 | 1 | 1 | NR |
| IL-21R | IL-21R_Site5_Site2_RR | 0.199109911 | 1.125058485 | 0 | 1 | 1 | NR |

Example 1 - Table 4. Patient characteristics-Validation Cohort

| | Baseline | | | 6 months | | | |
|---|---|---|---|---|---|---|---|
| | Non-Responder | responder | P value | Non-Responder | responder | P value | Healthy control |
| Age - years | 58 ± 14.5 | 54 ± 13.2 | 0.26 | — | — | — | 45 ± 15.4 |
| Males - no. (%) | 10 (33) | 13 (43) | 0.6 | — | — | — | 11 (37) |
| Caucasian - no. (%) | 30 (100) | 28 (97)$ | — | — | — | — | — |
| Body mass index - kg/m² | 28.3 ± 5.4 | 27.4 ± 4.6$$ | 0.48 | — | — | — | — |
| Patient global assessment (VAS, 0-100 mm) | 48 ± 30.2 | 62 ± 23.0 | 0.05 | 64 ± 23.2 | 11 ± 12.9 | <0.0001 | — |
| €Physician global assessment (VAS, 0-100 mm) | 46 ± 22.7 | 54 ± 21.0 | 0.19 | 39 ± 6.4 | 6.4 ± 6.1 | <0.0001 | — |
| Number of swollen joints (0-28) | 5.8 ± 3.7 | 8.3 ± 4.3 | 0.006 | 6.0 ± 5.2 | 0.2 ± 0.48 | <0.0001 | — |
| Number of tender joints (0-28) | 8.4 ± 6.2 | 7.9 ± 5.2 | 0.97 | 11.6 ± 7.7 | 0.4 ± 0.72 | <0.0001 | — |
| €CDAI | 23.6 ± 10.9 | 27.8 ± 9.8 | 0.13 | 27.9 ± 12.6 | 2.3 ± 2.2 | <0.0001 | — |
| #DAS28-CRP | 4.8 ± 1.0 | 5.1 ± 0.9 | 0.27 | 5.0 ± 0.8 | 1.8 ± 0.44 | <0.0001 | — |
| §DAS28-ESR | 5.2 ± 0.8 | 5.2 ± 1.0 | 0.98 | 5.3 ± 0.8 | 1.8 ± 0.45 | <0.0001 | — |
| ₣RF (IU/ml) | 196 ± 244 | 138 ± 155 | 0.48 | — | — | — | — |
| ∞CCP (U/ml) | 244 ± 201 | 314 ± 798 | 0.25 | — | — | — | — |
| #C-reactive protein (mg/liter) | 25.8 ± 33.7 | 23.4 ± 30.0 | 0.40 | 12.7 ± 12.2 | 5.5 ± 5.6 | 0.005 | — |
| §Erythrocyte sedimentation rate (mm/hour) | 35 ± 19.8 | 22.6 ± 16.2 | 0.02 | 23 ± 18.6 | 8.5 ± 5.6 | 0.0004 | — |
| ¶Whole Blood cell count | 8.4 ± 2.2 | 7.5 ± 1.7 | 0.09 | 7.6 ± 2.4 | 6.5 ± 1.7 | 0.07 | — |
| ¶Lymphocytes | 1.9 ± 0.59 | 1.7 ± 0.78 | 0.09 | 1.8 ± 0.76 | 1.7 ± 0.95 | 0.31 | — |
| ¶Monocytes | 0.63 ± 0.16 | 0.59 ± 0.22 | 0.50 | 0.59 ± 0.45 | 0.52 ± 0.13 | 0.38 | — |
| ¶Eosinophil | 0.18 ± 0.14 | 0.19 ± 0.13 | 0.55 | 0.19 ± 0.15 | 0.17 ± 0.12 | 0.89 | — |
| ¶Platelets | 332 ± 107 | 307 ± 86 | 0.34 | 299 ± 103 | 270 ± 79 | 0.25 | — |
| Current smoker - no. {%} | 10 (33) | 4 (14) | — | — | — | — | — |
| Previous smoker - no. (%) | 10 (33) | 9 (31) | — | — | — | — | — |
| Non-smoker - no. (%) | 10 (33) | 16 (55) | — | — | — | — | — |

The Fisher exact unconditional test is used to assess differences in proportions between the two groups. To examine differences in continuous variables between the two groups, we used the independent samples t-test or the Mann-Whitney U-test (depending on distribution of data).
$One patient "other" (non-white, non-South East Asian, non-Indian Sub-Continent, Non-Afro-Caribbean), one patient did not give an answer.
$$n = 25 in responders for BMI
€Baseline - n = 29 non-R, n = 30 R; 6m - n = 30 non-R, n = 29
Baseline - n = 26 non-R, n = 29 R; 6m - n = 21 non-R, n = 29
§Baseline - n = 19 non-R, n = 23 R; 6m - n = 19 non-R, n = 22
₣Baseline - n = 13 non-R, n = 23 R
∞Baseline - n = 26 non-R, n = 29 R
¶Baseline - n = 29 non-R, n = 27 R; 6m - n = 28 non-R, n = 25

Example 1 - Table 5.12 Selected genes from EpiSwitch1 ™ PCR

| Gene | EpiSwitch Marker | adjusted.p.value | EpiSwitch ™ ratio | HC_NR_MTX | HC_R_MTX | NR_R_MTX | Association |
|---|---|---|---|---|---|---|---|
| C5orf30 | C5orf30_Site5_Site2_FF | 0.079228864 | -1.242575344 | 1 | -1 | -1 | R |
| IFNAR1 | IFNAR1_Site2_Site4_RR | 0.093849223 | 1.228303149 | -1 | 1 | 1 | NR |
| IL-17A | IL-17A_Site3_Site1_RR | 0.115042065 | -1.164733586 | 0 | -1 | -1 | R |
| CXCL13 | CXCL13_Site1_Site3_RR | 0.079228864 | -1.298338588 | 0 | -1 | -1 | R |
| IL-21R | IL-21R_Site5_Site2_RR | 0.199109911 | 1.125058485 | 0 | 1 | 1 | NR |
| IL-23 | IL-23_Site4_Site5_FR | 0.160960834 | -1.180992661 | 0 | -1 | -1 | R |
| MafB | MafB_Site6_Site2_RF | 0.186948332 | 1.107008782 | -1 | 1 | 1 | NR |
| FCGR2A | FCGR2A_Site3_Site2_RR | 0.197822331 | 1.117287138 | -1 | 1 | 1 | NR |
| CLEC12A | CLEC12A_Site6_Site1_FR | 0.112869007 | -1.222640278 | 0 | -1 | -1 | R |
| PRKCZ | PRKCZ_Site6_Site3_RF | 0.093763087 | 1.316462719 | 0 | 1 | 1 | NR |
| MafB | MafB_Site2_Site4_FF | 0.090511832 | 1.170128253 | 1 | 1 | 1 | NR |
| C5orf30 | C5orf30_Site4_Site2_FF | 0.084204721 | -1.200248667 | 1 | -1 | -1 | R |

TABLE 6

Example 1- Observed and predicted number of R and NR to MTX monotherapy at 6 months using the EpiSwitch ™ CCS model.

| | Predicted response | | |
|---|---|---|---|
| Observed response | Non-responder | Undefined | Responder |
| Non-responder | 25 | 3 | 2 |
| Responder | 2 | 4 | 24 |

Notes to Table 6:
Cut off levels were chosen based on the probability of response to MTX of (approximately) >0.70 for NR and <0.3 for R. NR and R were defined as described in the methods.

Example 1A—RA Analysis: MTX Responders Vs Non-Responders: Work Subsequent to Example 1

Following on after Example 1, in Example 1A, a biostatistical hypergeometric analysis was carried out, using the "Statistical Pipeline" method(s) at the beginning of the Examples section in the present specification, to generate further refined DNA probes stratifying between MTX responders vs MTX non-responders, for RA patients on MTX monotherapy.

Example 1A Results: Table 6b (and continuation part Table 6c) hereinafter discloses Probe and Loci data for RA-MTX—DNA probes stratifying between responders (R) and non-responders (NR). B=B-statistic (lods or B), which is the log-odds that that gene is differentially expressed. FC is the non-log Fold Change. FC_1 is the non-log Fold Change centred around zero. It is seen that Table 6b+6c includes the sequences of 25 refined preferable DNA probes (60mers) for identifying MTX responders (MTX-R), and of 24 refined preferable DNA probes (60mers) for identifying MTX responders (MTX-NR), from the hypergeometric analysis.

Example 1A - Table 6b. Probe and Loci data for RA-MTX - probes stratifying between responders and non-responders.

| FC | FC 1 | Loop LS detected | 60 mer |
|---|---|---|---|
| 0.5774097 | -1.7318725 | -1 MTX-R | TGTTTTTTGGCTGCATAAATGTCTTCTTTCGAAATAATCATCAAAATATTTTTCATTGAC (SEQ ID NO:1) |
| 0.6052669 | -1.6521636 | -1 MTX-R | CACCCCCATCTCCCTTTGCTGACTCTCTTCGATGAATCCATTTTTTTGGAAATAGATGAT (SEQ ID NO:2) |
| 0.6567507 | -1.5226477 | -1 MTX-R | CACCCCCATCTCCCTTTGCTGACTCTCTTCGAACTGTGGCAATTTTAACTTTTCAAATTG (SEQ ID NO:3) |
| 0.6624775 | -1.5094851 | -1 MTX-R | CACCCCCATCTCCCTTTGCTGACTCTCTTCGAGGCATGATTTGAGTCTTGACAGAAGTTC (SEQ ID NO:4) |
| 0.6628804 | -1.5085678 | -1 MTX-R | TGCCAGTATTTTATTGAGGATTTTTGCATCGAGATTGGGTTGCATCATGTTGGCCAGGCT (SEQ ID NO:5) |
| 0.6850588 | -1.4597286 | -1 MTX-R | TGTTTTTTGGCTGCATAAATGTCTTCTTTCGAACTCATGGGCACAAGCAATCCTCCCACC (SEQ ID NO:6) |
| 0.6868153 | -1.4559955 | -1 MTX-R | TGCCAGTATTTTATTGAGGATTTTTGCATCGAACAGATGGAGGGAAGAGGGGATAGCTCC (SEQ ID NO:7) |
| 0.6890053 | -1.4513676 | -1 MTX-R | TGCCCTAGAGATCTGTGGAACTTTGAACTCGAGTCAAAGAGATATCAAGAGCTTCTATCA (SEQ ID NO:8) |
| 0.6943398 | -1.4402171 | -1 MTX-R | CACCCCCATCTCCCTTTGCTGACTCTCTTCGAGGGCAGAATGAGCCTCAGACATCTCCAG (SEQ ID NO:9) |
| 0.6963019 | -1.4361587 | -1 MTX-R | TCTCCTGCCTGATTGCCCTGCCAGAACTTCGATTTGGGCTATAGTGTTGTTCCAGTCTAA (SEQ ID NO:10) |

Example 1A - Table 6b. Probe and Loci data for RA-MTX - probes stratifying between responders and non-responders.

| FC | FC 1 | LS | Loop detected | 60 mer |
|---|---|---|---|---|
| 0.7008036 | -1.4269334 | -1 | MTX-R | CACCCCCATCTCCCTTTGCTGACTCTCTTCGATCTTGAAGAGATCTCTTCTTAGCAAAGC (SEQ ID NO:11) |
| 0.7132593 | -1.4020146 | -1 | MTX-R | CACCCCCATCTCCCTTTGCTGACTCTCTTCGAAATATTTTTGCTTGAGCTCCTGTCTCAT (SEQ ID NO:12) |
| 0.7141705 | -1.4002258 | -1 | MTX-R | TAGGCGCACATGCACACAGCTCGCCTCTTCGACCCAGGAAGATCCAAAGGAGGAACTGAG (SEQ ID NO:13) |
| 0.7156204 | -1.397389 | -1 | MTX-R | CCCCCACCCCCATCCCAGGAAATTGGTTTCGATGAGAGAAGGCAAGAGAACATGGGGTCT (SEQ ID NO:14) |
| 0.7183721 | -1.3920362 | -1 | MTX-R | TGCCAGTATTTTATTGAGGATTTTTGCATCGAGTTCAAAGTTCCACAGATCTCTAGGGCA (SEQ ID NO:15) |
| 0.7189408 | -1.390935 | -1 | MTX-R | CTAAAAATTACATCCAGGAAATGAGATATCGAAAGAAGACATTTATGCAGCCAAAAAACA (SEQ ID NO:16) |
| 0.722487 | -1.384108 | -1 | MTX-R | TAGGCGCACATGCACACAGCTCGCCTCTTCGATGTACAAGCTGCCTATTGATAGACTTTC (SEQ ID NO:17) |
| 0.7254458 | -1.3784627 | -1 | MTX-R | AAAGTTGTGCAATCAGGCAAGTCAAGATTCGAAAGAAGACATTTATGCAGCCAAAAAACA (SEQ ID NO:18) |
| 0.7374119 | -1.3560941 | -1 | MTX-R | CACCCCCATCTCCCTTTGCTGACTCTCTTCGAGTGGTGAGCAGCCAAACCAGGGTTCACT (SEQ ID NO:19) |
| 0.7374768 | -1.3559748 | -1 | MTX-R | GGGTCTTGCTATGTTGCCCAGGCTGGCCTCGAGATCAGCCTGGGCAACACGGTGAAAACC (SEQ ID NO:20) |
| 0.738555 | -1.3539954 | -1 | MTX-R | CTGGTTTAGTCTTGGGAGAGTGTATGTGTCGAGTTAAGCCATCTGCAAATAGCAAGAGAG (SEQ ID NO:21) |
| 0.7415639 | -1.3485014 | -1 | MTX-R | AGCCTTGCATCCCAGGGATGAAGCCCACTCGAGATATAGATTGAGCCCCAGTTTTTGGAG (SEQ ID NO:22) |
| 0.7422652 | -1.3472274 | -1 | MTX-R | ATCGTGTGGGCTGTGTGTGGCAGACTGTTCGAAATCGGAAGCCTCTCTGAAGGTCCAAGG (SEQ ID NO:23) |
| 0.7430431 | -1.3458169 | -1 | MTX-R | TGCCAGTATTTTATTGAGGATTTTTGCATCGAATTCCTGGGTTTATATCCCAATCATTGT (SEQ ID NO:24) |
| 0.7432273 | -1.3454835 | -1 | MTX-R | CACCCCCATCTCCCTTTGCTGACTCTCTTCGATATTGGTGTATATTCAAAGGGTACTTGA (SEQ ID NO:25) |
| 1.6553355 | 1.65533547 | 1 | MTX-NR | TGATCACTGTTTCCTATGAGGATACAGCTCGAGGGGCAGGGGCGGTCCTGGGCCAGGCG (SEQ ID NO:26) |
| 1.4321012 | 1.43210121 | 1 | MTX-NR | AACTTATGATTCTAATCTTGAATGTCTGTCGATCTATGAGGAAATGCCCCCAGCCTCCCA (SEQ ID NO:27) |
| 1.4179763 | 1.41797626 | 1 | MTX-NR | CATAATGCATGTGCATGAAAACTAATCTTCGATCTATGAGGAAATGCCCCCAGCCTCCCA (SEQ ID NO:28) |
| 1.4150017 | 1.41500165 | 1 | MTX-NR | ATCAGTAAGCTGGTCAGCTACCCATGAATCGATCTATGAGGAAATGCCCCCAGCCTCCCA (SEQ ID NO:29) |
| 1.3755396 | 1.37553964 | 1 | MTX-NR | GTGTCCCAATTTCTAGTGCACTGTGAACTCGACCTCGCGGGAGGGTGCCAGGCCGCATC (SEQ ID NO:30) |
| 1.366009 | 1.36600904 | 1 | MTX-NR | CCGGGGCTTCTCGTTTAAGAATTCTTTGTCGATCTATGAGGAAATGCCCCCAGCCTCCCA (SEQ ID NO:31) |
| 1.3611955 | 1.36119553 | 1 | MTX-NR | GTCTTTGAAGAAGGACTAATGCTTAGTATCGAGTGCAGCGCCGGTGGGCCAGCACTGCTG (SEQ ID NO:32) |
| 1.3408009 | 1.34080092 | 1 | MTX-NR | GTTCATTTAAACATTTTATTATGTATATTCGAGGGGCCAGGCTTTTATACCCCCATCTGA (SEQ ID NO:33) |
| 1.3350815 | 1.33508153 | 1 | MTX-NR | TTCTCCACAGCCGGCCGGTCCTTGGCAGTCGAGGGGCAGGGGCGGTCCTGGGCCAGGCG (SEQ ID NO:34) |

Example 1A - Table 6b. Probe and Loci data for RA-MTX - probes stratifying between responders and non-responders.

| FC | FC 1 | Loop LS | detected | 60 mer |
|---|---|---|---|---|
| 1.3191431 | 1.31914307 | 1 | MTX-NR | GCAACACATACAACGACTAATCTTCTTTTCGACGCCGAGGAGCTCTGCAGTGGGGCGTA (SEQ ID NO:35) |
| 1.3183444 | 1.31834441 | 1 | MTX-NR | GTAGGTGCTGAGTAAGTGAGCACTTGCCTCGAGGGGCAGGGGCGGTCCTGGGCCAGGCG (SEQ ID NO:36) |
| 1.3164851 | 1.31648512 | 1 | MTX-NR | CAGAAAGACCTTGCAATCATACGGTGCTTCGACGCCGAGGAGCTCTGCAGTGGGGCGTA (SEQ ID NO:37) |
| 1.3056925 | 1.3056925 | 1 | MTX-NR | TACTGTGCTGTGCTCGTCAAAGAGTATGTCGATCTATGAGGAAATGCCCCCAGCCTCCCA (SEQ ID NO:38) |
| 1.2876529 | 1.2876529 | 1 | MTX-NR | CAGAAATTAATCAAATGCAAGTGCACCCTCGACCACCCAAGGGCTGAGGAGTGCGGGCAC (SEQ ID NO:39) |
| 1.2777853 | 1.27778527 | 1 | MTX-NR | AAGGGACCTAGTCCCCTATTAAGATTTCTCGAGGGGCCAGGCTTTTATACCCCCATCTGA (SEQ ID NO:40) |
| 1.2773474 | 1.2773474 | 1 | MTX-NR | CCTGCCGAGACACGGGACGTGGGATTGCTCGATCTATGAGGAAATGCCCCCAGCCTCCCA (SEQ ID NO:41) |
| 1.2754233 | 1.2754233 | 1 | MTX-NR | CCAAAGCTCGCTTTCTTAACCACTATGCTCGAGGGGCCAGGCTTTTATACCCCCATCTGA (SEQ ID NO:42) |
| 1.2747737 | 1.27477371 | 1 | MTX-NR | TGAATTGTGTAGCGTAAGAATTTATATCTCGAAGTTTGTGAACTGGCAGGTGGACGGGGA (SEQ ID NO:43) |
| 1.2710171 | 1.2710171 | 1 | MTX-NR | ACCTGATCTGGGGAAGATTAGGAATTGTTCGAAACCAATTTCCTGGGATGGGGGTGGGGG (SEQ ID NO:44) |
| 1.2689263 | 1.26892631 | 1 | MTX-NR | GCAAGAGGATCTCTTGAGGCCCAGGAGTTCGAGGGGCCAGGCTTTTATACCCCCATCTGA (SEQ ID NO:45) |
| 1.2665372 | 1.2665372 | 1 | MTX-NR | TATCAAGTGATCCAAAAGGCTGCCAGTGTCGAGGGGCAGGGGCGGTCCTGGGCCAGGCG (SEQ ID NO:46) |
| 1.2648953 | 1.26489531 | 1 | MTX-NR | AAGGGACCTAGTCCCCTATTAAGATTTCTCGAAACCAATTTCCTGGGATGGGGGTGGGGG (SEQ ID NO:47) |
| 1.2592485 | 1.25924848 | 1 | MTX-NR | TATGGACTTTGTAGTCTCATATCAAAGCTCGAAACCAATTTCCTGGGATGGGGGTGGGGG (SEQ ID NO:48) |
| 1.2559537 | 1.25595366 | 1 | MTX-NR | AAAAATAATCTGGCTCTACACTTAGGATTCGAAACCAATTTCCTGGGATGGGGGTGGGGG (SEQ ID NO:49) |

Example 1A - Table 6c. Probe And Loci data for RA-MTX

| | | Probe Location | | | | | 4 kb Sequence Location | | | | |
|---|---|---|---|---|---|---|---|---|---|---|---|
| FC | FC_1 | Chr | Start1 | End1 | Start2 | End2 | Chr | Start1 | End1 | Start2 | End2 |
| 0.5774097 | −1.7318725 | 12 | 69702274 | 69702303 | 69759619 | 69759648 | 12 | 69702274 | 69706273 | 69759619 | 69763618 |
| 0.6052669 | −1.6521636 | 7 | 22743265 | 22743294 | 22801876 | 22801905 | 7 | 22739295 | 22743294 | 22797906 | 22801905 |
| 0.6567507 | −1.5226477 | 7 | 22743265 | 22743294 | 22769055 | 22769084 | 7 | 22739295 | 22743294 | 22769055 | 22773054 |
| 0.6624775 | −1.5094851 | 7 | 22743265 | 22743294 | 22757576 | 22757605 | 7 | 22739295 | 22743294 | 22757576 | 22761575 |
| 0.6628804 | −1.5085G78 | 1 | 67644699 | 67644728 | 67729398 | 67729427 | 1 | 67640729 | 67644728 | 67725428 | 67729427 |
| 0.6850588 | −1.4597286 | 12 | 69702274 | 69702303 | 69805129 | 69805158 | 12 | 69702274 | 69706273 | 69805129 | 69809128 |
| 0.6868153 | −1.4559955 | 1 | 67644699 | 67644728 | 67672222 | 67672251 | 1 | 67640729 | 67644728 | 67672222 | 67676221 |
| 0.6890053 | −1.4513676 | 1 | 67673763 | 67673792 | 67752422 | 67752451 | 1 | 67669793 | 67673792 | 67748452 | 67752451 |
| 0.6943398 | −1.4402171 | 7 | 22743265 | 22743294 | 22766800 | 22766829 | 7 | 22739295 | 22743294 | 22762830 | 22766829 |
| 0.6963019 | −1.4361587 | 4 | 123383001 | 123383030 | 123399247 | 123399276 | 4 | 123379031 | 123383030 | 123399247 | 123403246 |
| 0.7008036 | −1.4269334 | 7 | 22743265 | 22743294 | 22765456 | 22765485 | 7 | 22739295 | 22743294 | 22765456 | 22769455 |
| 0.7132593 | −1.4020146 | 7 | 22718635 | 22718664 | 22743265 | 22743294 | 7 | 22718635 | 22722634 | 22739295 | 22743294 |
| 0.7141705 | −1.4002258 | 12 | 48397660 | 48397689 | 48423816 | 48423845 | 12 | 48397660 | 48401659 | 48423816 | 48427815 |
| 0.7156204 | −1.397389 | 17 | 32738857 | 32738886 | 32777305 | 32777334 | 17 | 32738857 | 32742856 | 32777305 | 32781304 |
| 0.7183721 | −1.3920362 | 1 | 67644699 | 67644728 | 67673763 | 67673792 | 1 | 67640729 | 67644728 | 67669793 | 67673792 |
| 0.7189408 | −1.390935 | 12 | 69702274 | 69702303 | 69766052 | 69766081 | 12 | 69702274 | 69706273 | 69762082 | 69766081 |
| 0.722487 | −1.384108 | 12 | 48397660 | 48397689 | 48412400 | 48412429 | 12 | 48397660 | 48401659 | 48412400 | 48416399 |
| 0.7254458 | −1.3784627 | 12 | 69702274 | 69702303 | 69806507 | 69806536 | 12 | 69702274 | 69706273 | 69802537 | 69806536 |
| 0.7374119 | −1.3560941 | 7 | 22743265 | 22743294 | 22773903 | 22773932 | 7 | 22739295 | 22743294 | 22769933 | 22773932 |

Example 1A - Table 6c. Probe And Loci data for RA-MTX

| FC | FC_1 | Chr | Probe Location Start1 | End1 | Start2 | End2 | Chr | 4 kb Sequence Location Start1 | End1 | Start2 | End2 |
|---|---|---|---|---|---|---|---|---|---|---|---|
| 0.7374768 | −1.3559748 | 19 | 55449063 | 55449092 | 55486679 | 55486708 | 19 | 55449063 | 55453062 | 55482709 | 55486708 |
| 0.738555 | −1.3539954 | 17 | 32622187 | 32622216 | 32745745 | 32745774 | 17 | 32618217 | 32622216 | 32745745 | 32749744 |
| 0.7415639 | −1.3485014 | 13 | 43129388 | 43129417 | 43181041 | 43181070 | 13 | 43125418 | 43129417 | 43181041 | 43185040 |
|  |  | 10 | 104130466 | 104130495 | 104156468 | 104156497 | 10 | 104126496 | 104130495 | 104152498 | 104156497 |
| 0.7430431 | −1.3458169 | 1 | 67614064 | 67614093 | 67644699 | 67644728 | 1 | 67614064 | 67618063 | 67640729 | 67644728 |
| 0.7432273 | −1.3454835 | 7 | 22743265 | 22743294 | 22798802 | 22798831 | 7 | 22739295 | 22743294 | 22798802 | 22802801 |
| 1.6553355 | 1.65533547 | 1 | 2460436 | 2460465 | 2486982 | 2487011 | 1 | 2456466 | 2460465 | 2486982 | 2490981 |
| 1.4321012 | 1.43210121 | 10 | 6391740 | 6391769 | 6577853 | 6577882 | 10 | 6391740 | 6395739 | 6577853 | 6581852 |
| 1.4179763 | 1.41797626 | 10 | 6520005 | 6520034 | 6577853 | 6577882 | 10 | 6516035 | 6520034 | 6577853 | 6581852 |
| 1.4150017 | 1.41500165 | 10 | 6427823 | 6427852 | 6577853 | 6577882 | 10 | 6427823 | 6431822 | 6577853 | 6581852 |
| 1.3755396 | 1.37553964 | 18 | 74845065 | 74845094 | 74866978 | 74867007 | 18 | 74845065 | 74849064 | 74863008 | 74867007 |
| 1.366009 | 1.36600904 | 10 | 6470268 | 6470297 | 6577853 | 6577882 | 10 | 6466298 | 6470297 | 6577853 | 6581852 |
| 1.3611955 | 1.36119553 | 20 | 44704386 | 44704415 | 44720665 | 44720694 | 20 | 44700416 | 44704415 | 44716695 | 44720694 |
| 1.3408009 | 1.34080092 | 17 | 32551069 | 32551098 | 32617664 | 32617693 | 17 | 32551069 | 32555068 | 32617664 | 32621663 |
| 1.3350815 | 1.33508153 | 1 | 2486982 | 2487011 | 2540813 | 2540842 | 1 | 2486982 | 2490981 | 2536843 | 2540842 |
| 1.3191431 | 1.31914307 | 12 | 66647072 | 66647101 | 66696510 | 66696539 | 12 | 66647072 | 66651071 | 66696510 | 66700509 |
| 1.3183444 | 1.31834441 | 1 | 2476023 | 2476052 | 2486982 | 2487011 | 1 | 2472053 | 2476052 | 2486982 | 2490981 |
| 1.3164851 | 1.31648512 | 12 | 66663907 | 66663936 | 66696510 | 66696539 | 12 | 66663907 | 66667906 | 66696510 | 66700509 |
| 1.3056925 | 1.3056925 | 10 | 6556987 | 6557016 | 6577853 | 6577882 | 10 | 6556987 | 6560986 | 6577853 | 6581852 |
| 1.2876529 | 1.2876529 | 12 | 6268999 | 6269028 | 6304632 | 6304661 | 12 | 6268999 | 6272998 | 6300662 | 6304661 |
| 1.2777853 | 1.27778527 | 17 | 32617664 | 32617693 | 32708031 | 32708060 | 17 | 32617664 | 32621663 | 32704061 | 32708060 |
| 1.2773474 | 1.2773474 | 10 | 6442502 | 6442531 | 6577853 | 6577882 | 10 | 6442502 | 6446501 | 6577853 | 6581852 |
| 1.2754233 | 1.2754233 | 17 | 32529051 | 32529080 | 32617664 | 32617693 | 17 | 32529051 | 32529080 | 32617664 | 32621663 |
| 1.2747737 | 1.27477371 | 19 | 45364170 | 45364199 | 45397229 | 45397258 | 19 | 45360200 | 45364199 | 45397229 | 45401228 |
| 1.2710171 | 1.2710171 | 17 | 32689356 | 32689385 | 32738857 | 32738886 | 17 | 32685386 | 32689385 | 32738857 | 32742856 |
| 1.2665372 | 1.2665372 | 1 | 2486982 | 2487011 | 2556784 | 2556813 | 1 | 2486982 | 2490981 | 2552814 | 2556813 |
| 1.2648953 | 1.26489531 | 17 | 32708031 | 32708060 | 32738857 | 32738886 | 17 | 32704061 | 32708060 | 32738857 | 32742856 |
| 1.2593382 | 1.25933818 | 1 | 110420097 | 110420126 | 110472386 | 110472415 | 1 | 110416127 | 110420126 | 110472386 | 110476385 |
| 1.2592485 | 1.25924848 | 17 | 32553720 | 32553749 | 32738857 | 32738886 | 17 | 32549750 | 32553749 | 32738857 | 32742856 |
| 1.2559537 | 1.25595366 | 17 | 32522613 | 32522642 | 32738857 | 32738886 | 17 | 32522613 | 32526612 | 32738857 | 32742856 |

Example 1A - Table 6cc. Continuation of Tables 6b and 6c (RA-MTX)

| probe | Gene Locus | Probe_Count_Total | Probe_Count_Sig | HyperG_Stats | FDR_HyperG | Percent_Sig | logFC | Ave Expr |
|---|---|---|---|---|---|---|---|---|
| 12_69702273_69705360_69759618_69766081_RR | 12_69702273_69705360_69759618_69766081 | 4 | 2 | 0.034576041 | 0.5118640615 | 50 | −0.7932332744 | −0.792332744 |
| IL-6_Site4_Site5_FF | IL-6 | 48 | 13 | 7.18E−05 | 0.014530844 | 27.08 | −0.724356533 | −0.724356533 |
| IL-6_Site4_Site2_FR | IL-6 | 48 | 13 | 7.13E−05 | 0.014530844 | 27.08 | −0.606582168 | −0.606582168 |
| IL-6_Site4_Site3_FR | IL-6 | 48 | 13 | 7.18E−05 | 0.014530844 | 27.08 | −0.594056548 | −0.594056548 |
| IL-23R_Site4_Site2_FF | IL-23R | 104 | 19 | 0.000550011 | 0.054890393 | 18.27 | −0.593179555 | −0.593179555 |
| 12_69702273_69705360_69805128_69806536_RR | 12_69702273_69705360_69805128_69806536 | 4 | 2 | 0.034576041 | 0.518640615 | 50 | −0.545700188 | −0.545700188 |
| IL-23R_Site4_Site3_FR | IL-23R | 104 | 19 | 0.000550011 | 0.054890393 | 18.27 | −0.542005944 | −0.542005944 |
| IL-23R_Site3_Site7_FF | IL-23R | 104 | 19 | 0.000550011 | 0.054890393 | 18.27 | −0.537412982 | −0.537412982 |
| IL-6_Site4_Site1_FF | IL-6 | 48 | 13 | 7.18E−05 | 0.014530844 | 27.08 | −0.526286321 | −0.526236321 |
| IL-2_Site2_Site4_FR | IL-2 | 44 | 7 | 0.059144295 | 0.772691596 | 15.91 | −0.522215223 | −0.522215223 |

-continued

| Example 1A - Table 6cc. Continuation of Tables 6b and 6c (RA-MTX) |||||||||
|---|---|---|---|---|---|---|---|---|
| IL-6_Site4_Site1_FR | IL-6 | 48 | 13 | 7.18E−05 | 0.014530844 | 27.08 | −0.512918 | −0.512918 |
| IL-6_Site6_Site4_RF | IL-6 | 48 | 13 | 7.18E−05 | 0.014530844 | 27.08 | −0.487501401 | −0.487501401 |
| COL2A1_Site2_Site5_RR | COL2A1 | 100 | 15 | 0.013266079 | 0.488432899 | 15 | −0.485659509 | −0.485659509 |
| CCL2_Site6_Site14_RR | CCL2 | 404 | 58 | 9.15E−06 | 0.003705017 | 14.36 | −0.482733674 | −0.482733674 |
| IL-23R_Site4_Site3_FF | IL-23R | 104 | 19 | 0.000550011 | 0.054890393 | 18.27 | −0.477196734 | −0.477196734 |
| 12_69702273_69705360_69759618_69766081_RF | 12_69702273_69705360_69759618_69766081 | 4 | 2 | 0.034576041 | 0.518640615 | 50 | −0.47605502 | −0.47605502 |
| COL2A1_Site2_Site4_RR | COL2A1 | 100 | 15 | 0.013266079 | 0.488432899 | 15 | −0.468956553 | −0.468956553 |
| 12_69702273_69705360_69805128_69806536_RF | 12_69702273_69705360_69805128_69806536 | 4 | 2 | 0.034576041 | 0.518640615 | 50 | −0.463060243 | −0.463060243 |
| IL-6_Site4_Site2_FF | IL-6 | 48 | 13 | 7.18E−05 | 0.014530844 | 27.08 | −0.439457343 | −0.439457343 |
| 19_55449062_55451429_55484960_55486708_RF | 19_55449062_55451429_55484960_55486708 | 4 | 2 | 0.034576041 | 0.518640615 | 50 | −0.439330382 | −0.439330382 |
| CCL2_Site10_Site13_FR | CCL2 | 404 | 58 | 9.15E−06 | 0.003705017 | 14.36 | −0.437222819 | −0.437222819 |
| TNFSF11_Site4_Site2_FR | TNFSF11 | 52 | 12 | 0.000677659 | 0.054890393 | 23.08 | −0.431357024 | −0.431357024 |
| NFKB2_Site5_Site2_FF | NFKB2 | 54 | 9 | 0.026686973 | 0.518640615 | 16.67 | −0.42999336 | −0.42999336 |
| IL-23R_Site5_Site4_RF | IL-23R | 104 | 19 | 0.000550011 | 0.054890393 | 18.27 | −0.428482185 | −0.428482185 |
| IL-6_Site4_Site5_FR | IL-6 | 48 | 13 | 7.18E−05 | 0.014530844 | 27.08 | −0.428124668 | −0.428124668 |
| TNFRSF14_Site4_Site1_FR | TNFRSF14 | 112 | 14 | 0.063886514 | 0.784061767 | 12.5 | 0.727123624 | 0.727123624 |
| PRKCQ_Site11_Site4_RR | PRKCQ | 213 | 31 | 0.000852984 | 0.057576386 | 14.55 | 0.518133451 | 0.518133451 |
| PRKCQ_Site7_Site4_FR | PRKCQ | 213 | 31 | 0.000852984 | 0.057576386 | 14.55 | 0.503833375 | 0.503833375 |
| PRKCQ_Site9_Site4__RR | PRKCQ | 213 | 31 | 0.000852984 | 0.057576386 | 14.55 | 0.50080374 | 0.50080374 |
| 18_7845064_74846657_74864995_74867007_RF | 18_74845064_74846657_74864995_74867007 | 4 | 2 | 0.034576041 | 0.518640615 | 50 | 0.459997712 | 0.459997712 |
| PRKCQ_Site2_Site4_FR | PRKCQ | 213 | 31 | 0.000852984 | 0.057576386 | 14.55 | 0.44996703 | 0.44996703 |
| CD40_Site10_Site9_FF | CD40 | 142 | 17 | 0.062222744 | 0.784061767 | 11.97 | 0.444874319 | 0.444874319 |
| CCL2_Site11_Site10_RR | CCL2 | 404 | 58 | 9.15E−06 | 0.003705017 | 14.36 | 0.423095044 | 0.423095044 |
| TNFRSF14_Site1_Site8_RF | TNFRSF14 | 112 | 14 | 0.063886514 | 0.784061767 | 12.5 | 0.41692785 | 0.41692785 |
| IRAK3_Site2_Site5_RR | IRAK3 | 75 | 11 | 0.036066824 | 0.521680846 | 14.67 | 0.399601038 | 0.399601038 |
| TNFRSF14_Site6_Site1_FR | TNFRSF14 | 112 | 14 | 0.063886514 | 0.784061767 | 12.5 | 0.398727315 | 0.398727315 |
| IRAK3_Site4_Site5_RR | IRAK3 | 75 | 11 | 0.036066824 | 0.521680846 | 14.67 | 0.396691209 | 0.396691209 |
| PRKCQ_Site3_Site4__RR | PRKCQ | 213 | 31 | 0.000852984 | 0.057576386 | 14.55 | 0.384815172 | 0.384815172 |
| 12_5268998_65272753_6301795_6304661_RF | 12_6268998_6272753_6301795_6304661 | 2 | 2 | 0.006428387 | 0.289277402 | 100 | 0.364743757 | 0.364743757 |
| CCCL2_Site10_Site5_RF | CCL2 | 404 | 58 | 9.15E−06 | 0.003705017 | 14.36 | 0.353645409 | 0.353645409 |

| Example 1A - Table 6cc. Continuation of Tables 6b and 6c (RA-MTX) ||||||||
|---|---|---|---|---|---|---|---|
| PRKCQ_Site8_Site4_RR | PRKCQ | 213 | 31 | 0.000852984 | 0.057576386 | 14.55 | 0.353150952 | 0.353150952 |
| CCL2_Site12_Site10_FR | CCL2 | 404 | 58 | 9.15E-06 | 0.003705017 | 14.36 | 0.350976141 | 0.350976141 |
| ApoE_Site3_Site6_FR | ApoE | 96 | 17 | 0.001508547 | 0.081621699 | 17.71 | 0.350241172 | 0.350241172 |
| CCL2_Site7_Site6_FR | CCL2 | 404 | 58 | 9.15E-06 | 0.003705017 | 14.36 | 0.345983436 | 0.345983436 |
| CCL2_Site2_Site10_FR | CCL2 | 404 | 58 | 9.15E-06 | 0.003705017 | 14.36 | 0.343608292 | 0.343608292 |
| TNFRSF14_Site1_Site9_RF | TNFRSF14 | 112 | 14 | 0.063886514 | 0.784061767 | 12.5 | 0.340889449 | 0.340889449 |
| CCL2_Site5_Site6_FR | CCL2 | 404 | 58 | 9.15E-06 | 0.003705017 | 14.36 | 0.339017988 | 0.339017988 |
| M-CSF_Site8_Site3_FR | M-CSF | 96 | 13 | 0.042613318 | 0.595117032 | 13.54 | 0.332665749 | 0.332665749 |
| CCL2_Site11_Site6_FR | CCL2 | 404 | 58 | 9.15E-06 | 0.003705017 | 14.36 | 0.332562994 | 0.332562994 |
| CCL2_Site12_Site6_RR | CCL2 | 404 | 58 | 9.15E-06 | 0.003705017 | 14.36 | 0.328783229 | 0.328783229 |

| probe | t | P. Value | Adj. P. Value | B | FC | FC_1 | LS | Loop detected |
|---|---|---|---|---|---|---|---|---|
| 12_69702273_69705360_69759618_69766081_RR | −6.352796842 | 0.001540038 | 0.2362361 | −0.525734091 | 0.577409703 | −1.731872526 | −1 | MTX-R |
| IL-6_Site4_Site5_FF | −4.707112783 | 0.005590201 | 0.249035946 | −1.652257403 | 0.605266944 | −1.652163579 | −1 | MTX-R |
| IL-6_Site4_Site2_FR | −6.460394591 | 0.001429141 | 0.2362361 | −0.464821575 | 0.656750743 | −1.522647688 | −1 | MTX-R |
| IL-6_Site4_Site3_FR | −8.583674236 | 0.000391843 | 0.2362361 | 0.497776542 | 0.662477542 | −1.509485133 | −1 | MTX-R |
| IL-23R_Site4_Site2_FF | −4.111539379 | 0.009661387 | 0.255484712 | −2.16568129 | 0.662880374 | −1.508567818 | −1 | MTX-R |
| 12_69702273_69705360_69805128_69806536_RR | −11.32682228 | 0.000106595 | 0.2362361 | 1.272674673 | 0.68505884 | −1.459728628 | −1 | MTX-R |
| IL-23R_Site4_Site3_FR | −5.42869826 | 0.003062642 | 0.238248996 | −1.109864705 | 0.686815287 | −1.455995548 | −1 | MTX-R |
| IL-23R_Site3_Site7_FF | −5.114255946 | 0.00395047 | 0.245648426 | −1.336115162 | 0.689005315 | −1.451367613 | −1 | MTX-R |
| IL-6_Site4_Site1_FF | −9.186377243 | 0.000285762 | 0.2362361 | 0.704172073 | 0.694339754 | −1.440217119 | −1 | MTX-R |
| IL-2_Site2_Site4_FR | −5.718310426 | 0.002446187 | 0.2362361 | −0.914385499 | 0.696301857 | −1.436158743 | −1 | MTX-R |
| IL-6_Site4_Site1_FR | −7.365051101 | 0.000791901 | 0.2362361 | −0.003263498 | 0.700803556 | −1.4269334 | −1 | MTX-R |
| IL-6_Site6_Site4_RF | −10.39123759 | 0.000160265 | 0.2362361 | 1.051647199 | 0.71325932 | −1.402014627 | −1 | MTX-R |
| COL2A1_Site2_Site5_RR | −5.378633994 | 0.003186918 | 0.238248996 | −1.144888013 | 0.714170522 | −1.400225814 | −1 | MTX-R |
| CCL2_Site6_Site14_RR | −8.467642183 | 0.000417345 | 0.2362361 | 0.455161713 | 0.715620353 | −1.397388986 | −1 | MTX-R |
| IL-23R_Site4_Site3_FF | −4.678820538 | 0.005731165 | 0.249035946 | −1.67524497 | 0.71837212 | −1.392036205 | −1 | MTX-R |
| 12_69702273_69705360_69759618_69766081_RF | −6.933158571 | 0.001041262 | 0.2362361 | −0.21283591 | 0.718940848 | −1.390935016 | −1 | MTX-R |

Example 1A - Table 6cc. Continuation of Tables 6b and 6c (RA-MTX)

| | | | | | | | | |
|---|---|---|---|---|---|---|---|---|
| COL2A1_Site2_Site4_RR | −4.969850387 | 0.004457667 | 0.247336967 | −1.44516118 | 0.722486957 | −1.384108032 | −1 | MTX-R |
| 12_69702273_69705360_69806536_RF | −8.264131154 | 0.000467027 | 0.2362361 | 0.378009148 | 0.725445811 | −1.378462712 | −1 | MTX-R |
| IL-6_Site4_Site2_FF | −9.296613034 | 0.000270277 | 0.2362361 | 0.739375667 | 0.737411927 | −1.356094149 | 1 | MTX-R |
| 19_55449062_55451429_55484960_55486708_RF | −3.343380062 | 0.021128841 | 0.2949434 | −2.923926031 | 0.737476825 | −1.355974814 | −1 | MTX-R |
| CCL2_Site10_Site13_FR | −6.961047822 | 0.001022576 | 0.2362361 | −0.198730934 | 0.738554956 | −1.353995383 | −1 | MTX-R |
| TNFSF11_Site4_Site2_FR | −3.690911039 | 0.01466314 | 0.27772544 | −2.567190834 | 0.741563929 | −1.348501404 | −1 | MTX-R |
| NFKB2_Site5_Site2_FF | −7.280958467 | 0.000834343 | 0.2362361 | −0.04262056 | 0.742265202 | −1.347227376 | −1 | MTX-R |
| IL-23R_Site5_Site4_RF | −5.623009709 | 0.002631353 | 0.2362361 | −0.977392524 | 0.743043107 | −1.345816939 | −1 | MTX-R |
| IL-6_Site4_Site5_FR | −7.957232876 | 0.000555975 | 0.2362361 | 0.255568458 | 0.743227265 | −1.345483471 | −1 | MTX-R |
| TNFRSF14_Site4_Site1_FR | 3.49919083 | 0.017894673 | 0.286624284 | −2.761197677 | 1.655335471 | 1.655335471 | 1 | MTX-NR |
| PRKCQ_Site11_Site4_RR | 3.441802618 | 0.019015331 | 0.289191715 | −2.820609109 | 1.432101206 | 1.432101206 | 1 | MTX-NR |
| PRKCQ_Site7_Site4_FR | 3.563003996 | 0.016736154 | 0.282950401 | −2.695857596 | 1.417976256 | 1.4.17976256 | 1 | MTX-NR |
| PRKCQ_Site9_Site4_ RR | 3.901543743 | 0.011859009 | 0.26637802 | −2.362004516 | 1.415001654 | 1.415001654 | 1 | MTX-NR |
| 18_7845064_74846657_74864995_74867007_ RF | 3.62562346 | 0.015682006 | 0.282950401 | −2.632482122 | 1.375539636 | 1.375539636 | 1 | MTX-NR |
| PRKCQ_Site2_Site4_FR | 3.494064593 | 0.017991649 | 0.286624284 | −2.76647964 | 1.366009039 | 1.366009039 | 1 | MTX-NR |
| CD40_Site10_Site9_FF | 3.596360937 | 0.016164851 | 0.282950401 | −2.662006295 | 1.36119553 | 1.36119553 | 1 | MTX-NR |
| CCL2_Site11_Site10_RR | 4.037430853 | 0.010378328 | 0.256491595 | −2.234032001 | 1.34080092 | 1.34080092 | 1 | MTX-NR |
| TNFRSF14_Site1_Site8_RF | 3.395381579 | 0.019980609 | 0.289483909 | −2.869115138 | 1.335081534 | 1.335081534 | 1 | MTX-NR |
| IRAK3_Site2_Site5_RR | 4.778321582 | 0.005252968 | 0.249035946 | −1.594997683 | 1.319143065 | 1.319143065 | 1 | MTX-NR |
| TNFRSF14_Site6_Site1_FR | 3.546617882 | 0.017025241 | 0.283912444 | −2.712563011 | 1.318344409 | 1.318344409 | 1 | MTX-NR |
| IRAK3_Site4_Site5_RR | 6.129428964 | 0.001804535 | 0.2362361 | −0.656668121 | 1.316485115 | 1.316485115 | 1 | MTX-NR |
| PRKCQ_Site3_Site4_ RR | 4.130430098 | 0.009487914 | 0.255484712 | −2.148419919 | 1.3056925 | 1.3056925 | 1 | MTX-NR |
| 12_5268998_65272753_6301795_6304661_ RF | 3.5905166 | 0.016263314 | 0.232950401 | −2.667922157 | 1.287652904 | 1.287652904 | 1 | MTX-NR |
| CCCL2_Site10_Site5_RF | 4.378884995 | 0.007511833 | 0.255484712 | −1.92743217 | 1.277785266 | 1.277785266 | 1 | MTX-NR |
| PRKCQ_Site8_Site4_RR | 4.981896454 | 0.00441255 | 0.247336967 | −1.435937375 | 1.277347404 | 1.277347404 | 1 | MTX-NR |
| CCL2_Site12_Site10_FR | 4.528090618 | 0.006555946 | 0.251096737 | −1.800021979 | 1.275423299 | 1.275423299 | 1 | MTX-NR |
| ApoE_Site3_Site6_FR | 5.557940873 | 0.002767294 | 0.2362361 | −1.021147938 | 1.27477371 | 1.27477371 | 1 | MTX-NR |
| CCL2_Site7_Site6_FR | 3.556342165 | 0.016853001 | 0.283624894 | −2.702643166 | 1.271017097 | 1.271017097 | 1 | MTX-NR |
| CCL2_Site2_Site10_FR | 4.809544682 | 0.005112639 | 0.249035946 | −1.570158657 | 1.268926312 | 1.268926312 | 1 | MTX-NR |
| TNFRSF14_Site1_Site9_RF | 3.734122588 | 0.014030572 | 0.276682133 | −2.524417542 | 1.266537198 | 1.266537198 | 1 | MTX-NR |
| CCL2_Site5_Site6_FR | 4.192080779 | 0.008946373 | 0.255484712 | −2.092541211 | 1.264895314 | 1.264895314 | 1 | MTX-NR |
| M-CSF_Site8_Site3_FR | 4.605504441 | 0.006116205 | 0.249035946 | −1.735449183 | 1.259338177 | 1.259338177 | 1 | MTX-NR |

| Example 1A - Table 6cc. Continuation of Tables 6b and 6c (RA-MTX) | | | | | | | |
|---|---|---|---|---|---|---|---|
| CCL2_Site11_Site6_FR | 3.935674905 | 0.011465355 | 0.262959895 | -2.329538136 | 1.259248484 | 1.259248484 | 1 | MTX-NR |
| CCL2_Site12_Site6_RR | 3.876162824 | 0.012161863 | 0.267229746 | -2.386288494 | 1.255953655 | 1.255953655 | 1 | MTX-NR |

TABLE 6D

| Example 1 - Stratifying between RA-MTX responders and non-responders | | | |
|---|---|---|---|
| Probes | NR_R_P.Value | NR_R_adj.P.Val | Probe sequence 60 mer |
| TNFRSF14_Site4_Site1_FR | 0.001232118 | 0.079419805 | TGATCACTGTTTCCTATGAGGATACAGCTCGAGGGGCA GGGGGCGGTCCTGGGCCAGGCG (SEQ ID NO: 50) |
| TNFRSF14_Site4_Site1_RR | 0.002061691 | 0.082014717 | AACCTGGAGAACGCCAAGCGCTTCGCCATCGAGGGGCA GGGGGCGGTCCTGGGCCAGGCG (SEQ ID NO: 51) |
| TNFRSF1A_Site2_Site5_FR | 0.004469941 | 0.093849223 | CTACCTTTGTGGCACTTGGTACAGCAAATCGACGGGCC CCGTGAGGCGGGGCGGGACCC (SEQ ID NO: 53) |
| TNFRSF1A_Site1_Site5_FR | 0.005468033 | 0.09532964 | CATCAATTATAACTCACCTTACAGATCATCGACGGGCC CCGTGAGGCGGGGCGGGACCC (SEQ ID NO: 54) |
| TNFRSF14_Site4_Site8_FR | 0.005244102 | 0.094393734 | TGATCACTGTTTCCTATGAGGATACAGCTCGAAGATTA GGTAAAGGTGGGGACGCGGAGA (SEQ ID NO: 55) |
| RUNX1_Site7_Site2_RR | 0.001313112 | 0.079419805 | GAAAGGTAATTGCCCCCAATATTTATTTTCGAAACAGA TCGGGCGGCTCGGGTTACACAC (SEQ ID NO: 55) |
| TNFRSF14_Site1_Site8_RF | 0.003725772 | 0.090200643 | TTCTCCACAGCCGGCCGGTCCTTGGCAGTCGAGGGGCA GGGGGCGGTCCTGGGCCAGGCG (SEQ ID NO: 56) |
| 18_74845064_74846657_74864995_74867007_RF | 0.001604249 | 0.079419805 | CGTGTCCCAATTTCTAGTGCACTGTGAACTCGACCTCG CGGGAGGGGTGCCAGGCCGCAT (SEQ ID NO: 57) |
| PRKCZ_Site8_Site6_FR | 1.26726E-05 | 0.079228864 | CCTCTCTTCTAAAAGGTCTCAACATCACTCGACTGGAG AGCCCGGGGCCTCGCGCCGCTT (SEQ ID NO: 58) |
| RUNX1_Site5_Site2_RR | 0.000540863 | 0.079228864 | GTTTCCCCTTGATGCTCAGAGAAAGGCCTCGAAACAGA TCGGGCGGCTCGGGTTACACAC (SEQ ID NO: 59) |
| PRKCQ_Site7_Site4_FR | 0.003958472 | 0.090816122 | CATAATGCATGTGCATGAAAACTAATCTTCGATCTATG AGGAAATGCCCCCAGCCTCCCA (SEQ ID NO: 60) |
| 18_74756101_74757557_74845064_74846657_RR | 0.003489147 | 0.089578901 | AGATGTGTAAGTCACCAGGGAGTGCATTCGCGACCTCG CGGGAGGGGTGCCAGGCCGCAT (SEQ ID NO: 61) |
| PRKCQ_Site10_Site4_FR | 0.004639159 | 0.093849223 | GTAATGGTGCCATCATAGCTCAAGCTCCTCGATCTATG AGGAAATGCCCCCAGCCTCCCA (SEQ ID NO: 62) |
| PRKCQ_Site10_Site4_RR | 0.007812066 | 0.108064059 | AATACAAAGGATGGTATATTTTGCATATTCGATCTATG AGGAAATGCCCCCAGCCTCCCA (SEQ ID NO: 63) |
| PRKCZ_Site8_Site9_FR | 0.000560117 | 0.079228864 | CCTCTCTTCTAAAAGGTCTCAACATCACTCGATGGTGC GGGAGGTGGCCGGCAGGGTTGG (SEQ ID NO: 64) |
| MTHFD1_Site5_Site1_RF | 0.000404338 | 0.079228864 | ATAATTCTTCCTGGCACATAATAAGTATTCGAATCGGG GCGGTTCCGGCGTGGGTTTCAG (SEQ ID NO: 65) |
| NFAT_Site6_Site1_FF | 0.000514351 | 0.079228864 | TCTAAAGGGATTTCCACTATATGTAGATTCGAGGGGCG TGTGCGCGCGTGGCGGGCCCG (SEQ ID NO: 66) |
| PRKCQ_Site11_Site4_RR | 0.006796573 | 0.102494645 | AACTTATGATTCTAATCTTGAATGTCTGTCGATCTATG AGGAAATGCCCCCAGCCTCCCA (SEQ ID NO: 67) |
| TNFRSF1A_Site5_Site6_FF | 0.011987094 | 0.126537326 | GAGGTGGGCAGATCACGGGTCAGGGTATCGAGGCCCA TCACTGGCGGGGAGACGGGAGG (SEQ ID NO: 68) |
| 18_74845064_74846657_74864266_74864995_RF | 0.008686097 | 0.111746517 | ACTGAATATGAAAAAAAATGTAAAAATTATCGACCTCG CGGGAGGGGTGCCAGGCCGCAT (SEQ ID NO: 69) |
| PRKCQ_Site7_Site4_RR | 0.011239245 | 0.123381356 | GATTTTATAGCAAATTTACAAAAATGAGTCGATCTATG AGGAAATGCCCCCAGCCTCCCA (SEQ ID NO: 70) |

TABLE 6D-continued

Example 1 - Stratifying between RA-MTX responders and non-responders

| Probes | NR_R_P. Value | NR_R_adj.P. Val | Probe sequence 60 mer |
|---|---|---|---|
| PRKCZ_Site5_Site9_RR | 0.002885944 | 0.086622849 | ACCAAGAGTTGGACCCCCTTTTTGATGTTCGATGGTGC GGGAGGTGGCCGGCAGGGTTGG (SEQ ID NO: 71) |
| MAL_Site4_Site2_FR | 0.000818457 | 0.079228864 | TATATTGCTATCTACTAGCAAAGGATAATCGAAGAGGT TCAGGGCGGTGCCCGCGGCGCT (SEQ ID NO: 72) |
| PRKCQ_Site9_Site4_RR | 0.003669785 | 0.090200643 | ATCAGTAAGCTGGTCAGCTACCCATGAATCGATCTATG AGGAAATGCCCCCAGCCTCCCA (SEQ ID NO: 73) |
| TNFRSF14_Site3_Site8_FR | 0.000995361 | 0.079228864 | TGAAAACAGTTCATCCTGAGTTTCAGTCTCGAAGATTA GGTAAAGGTGGGGACGCGGAGA (SEQ ID NO: 74) |
| IFNAR1_Site2_Site4_RR | 0.004801376 | 0.093849223 | GTGCAGAGCGAGAGCGGGGCAGAGGCGGTCGAAACTGG GAGAATTCATCTGAAATGATTA (SEQ ID NO: 75) |
| IL-21R_Site5_Site2_RR | 0.034533931 | 0.199109911 | GAGGCAGGCAGATCATGAGGTCAGGAGTTCGAGCCCTG GACCCCAGGCCAGCTAATGAGG (SEQ ID NO: 76) |
| 19_10326358_10327821_10368389_10370560_RR | 0.000174676 | 0.079228864 | GCTCACTGCAACCTCCACCTCCCAGGTTCGCGAACCTC CTGATAACTTCAGCATTAACAG (SEQ ID NO: 77) |
| 19_55449062_55451429_55484960_55486708_RF | 7.78E-05 | 0.079228864 | AGGGTCTTGCTATGTTGCCCAGGCTGGCCTCGAGATCA GCCTGGGCAACACGGTGAAAAC (SEQ ID NO: 78) |
| TLR1_Site4_Site7_FR | 0.000969535 | 0.079228864 | TGTAATATAAGCATAGCTCACTGCAGCCTCGAAGCATT TGTACGACATTCTCATCTTCTT (SEQ ID NO: 79) |
| IRF5_Site8_Site2_FF | 0.000148986 | 0.079228864 | ACAGAGGAGCGAGGCCCGATCCTTACTTTCGAACTCCT GACCTCGTGATCTGCCCACCTC (SEQ ID NO: 80) |
| SPRED2_Site4_Site8_RF | 0.018236449 | 0.149371667 | GGGTTTCACCATGTTAGCCAGGATGGTCTCGATCTCCT GACCTCATGATCCGCCTGCCTC (SEQ ID NO: 81) |
| IKBKB_Site5_Site8_FR | 0.013123191 | 0.130076121 | GCATTTCACCATGTTGGTGAGGCTGGTCTCGAAGAGTT CACACGTGTCCAAATTTGGTGG (SEQ ID NO: 82) |
| TLR1_Site9_Site2_FF | 0.002914123 | 0.086622849 | CTGGGATCACAGGCATGTGCCACCATGCTCGACAAGAA TAGTCTCCTTGTTTCTGAACAT (SEQ ID NO: 83) |
| CD28_Site1_Site9_RR | 0.003257956 | 0.088621062 | GTATTTCTGGTTCTAGATCCTTGAGGAATCGAGCAGAA GGAGTCTCTCCCTGAGGCCACC (SEQ ID NO: 84) |
| 12_10289678_10290500_10350455_10351677_RF | 0.001491578 | 0.079419805 | CGAGGCGGGCGGATCACGAGGTCAGGAGATCGACCCCC ACGTTCTCACCACCTGTTTCTT (SEQ ID NO: 85) |
| CD28_Site1_Site8_RR | 0.007644106 | 0.107723492 | GTATTTCTGGTTCTAGATCCTTGAGGAATCGACCTCCT GGGCTCAACCTATCCTCCCACC (SEQ ID NO: 86) |
| CXCL8_Site2_Site6_RF | 0.002891692 | 0.086622849 | GGGTTTCACTGTGTTAGCCAGGATGGTCTCGACCTCCC TGGCTCAAGTGATCTTCCCACC (SEQ ID NO: 87) |
| IL-23R_Site4_Site3_RF | 0.001588257 | 0.079419805 | TGCCCTAGAGATCTGTGGAACTTTGAACTCGATATATG AAAATAGTTTTTTAATTATAAA (SEQ ID NO: 88) |
| RBPJ_Site14_Site13_FF | 0.010539749 | 0.118804917 | GGTGGGGGAATCACTTGAGGTCAGAAGTTCGAGACCAT CCTGGGCAACATGGTAAAACCC (SEQ ID NO: 89) |
| CHUK_Site7_Site2_RF | 0.000132328 | 0.079228864 | AATGGCACGATCACGGCTCACTGCAGCCTCGAATGTTA CTGACAGTGGACACAGTAAGAA (SEQ ID NO: 90) |
| SH2B3_Site6_Site5_FF | 0.003743845 | 0.090200643 | GAGTTTTGCCATGTTGCCCAGGCTGGTCTCGAGAACAG CCTGGCCAACATGGTAAAACCC (SEQ ID NO: 91) |
| IRAK3_Site7_Site5_FR | 0.00056928 | 0.079228864 | AGGTCTCACTATGTTGCCCGGGCTGGTCTCGACGCCGA GGAGCTCTGCAGTGGGGCGTA (SEQ ID NO: 92) |
| CD28_Site4_Site2_RF | 0.014801185 | 0.136839161 | GGGTTTCACCATGTTGGCGAGGCTGGTCTCGAACTCCT GACCTCAGGTGATCCGCCTGCC (SEQ ID NO: 93) |
| CD28_Site5_Site6_FR | 0.007402719 | 0.106291976 | GGTGGGTGGATCACCTGAGGTCAGGAGTTCGACCTAAG GGTGGTCATAATTCTGCTGCTG (SEQ ID NO: 94) |
| 19_39424583_39425930_39445791_39449626_FF | 0.001743055 | 0.079577656 | GGGTCTCACAGCCTTCAGAGCTGAGAGCCTAGGCTTCA GTGAGCCATAATCACGCCACTA (SEQ ID NO: 95) |

TABLE 6D-continued

Example 1 - Stratifying between RA-MTX responders and non-responders

| Probes | NR_R_P. Value | NR_R_adj.P. Val | Probe sequence 60 mer |
|---|---|---|---|
| IL-1a_and_IL-1b_Site1_Site7_RF | 0.002815998 | 0.086622849 | CTTTGGGAGGCCAAGGTGAGTGGATTGCTCGACATCTC ATTTGATAGGATTAAGTCAACG (SEQ ID NO: 96) |
| IRAK3_Site7_Site1_FF | 0.00166033 | 0.079419805 | AGGTCTCACTATGTTGCCCGGGCTGGTCTCGAACAGCA GCGTGTGCGCCGACAGCGCGCC (SEQ ID NO: 97) |
| C5orf30_Site2_Site8_FR | 0.00524841 | 0.094393734 | TCTGTCGCCCAGGTTGGAGTACAGTGGCTCGAGGATGT CCTATTTTGCCACCTTATCTAA (SEQ ID NO: 98) |
| CXCL13_Site1_Site3_RR | 6.56394E-05 | 0.079228864 | TTATATCTCCTACCTCCAAGCCTGGCAGTCGATTCCAA AGTGAAGCAAAAAAAAAACTTC (SEQ ID NO: 99) |
| 14_55507409_55508411_55583475_55586339_RF | 0.003368236 | 0.088703855 | AAAGACCCTGTCTCTAAATAAATAGAACATCGAGATCA TGCCACTGCACTCCAGCCTGGG (SEQ ID NO: 100) |
| 14_91450408_91451505_91524833_91527062_FF | 0.004287708 | 0.093190996 | GGGGTTTTTCCATGTTAGTCAGGCTGGTCTAATGGCTC CCTTACCTTGCTGGCTGTGGGC (SEQ ID NO: 101) |
| IL-23_Site4_Site5_FR | 0.021765214 | 0.160960834 | AGTGGCATGATCACAGCTCACTGCCACCTCGAAACCAA ACCCTGTGACTTCAACACCCAA (SEQ ID NO: 102) |
| IL-17A_Site3_Site1_RR | 0.009698852 | 0.115042065 | CCCTCCCTCAACATGCAGGGATTACAATTCGAAGATGG TCTGAAGGAAGCAATTGGGAAA (SEQ ID NO: 103) |

Example 1 - Table 6E. Stratifying between RA-MTX responders and non-responders

| Probe Location | | | | | 4 kb Sequence Location | | | |
|---|---|---|---|---|---|---|---|---|
| Chr | Start1 | End1 | Start2 | End2 | Chr | Start1 | End1 | Start2 | End2 |
| 1 | 2450436 | 2460465 | 2486982 | 2487011 | 1 | 2456466 | 2460465 | 2486982 | 2490981 |
| 1 | 2457910 | 2457939 | 2486982 | 2487011 | 1 | 2457910 | 2461909 | 2486982 | 2490981 |
| 12 | 6443253 | 6443282 | 6472689 | 6472718 | 12 | 6439283 | 6443282 | 6472689 | 6476688 |
| 12 | 6452140 | 6452169 | 6472689 | 6472718 | 12 | 6448170 | 6452169 | 6472689 | 6476633 |
| 1 | 2450436 | 2460465 | 2539015 | 2539044 | 1 | 2456466 | 2460465 | 2539015 | 2543014 |
| 21 | 36117642 | 36117671 | 36260589 | 36260618 | 21 | 36117642 | 36121641 | 36260589 | 36264588 |
| 1 | 2436982 | 2487011 | 2540813 | 2540842 | 1 | 2486982 | 2490981 | 2536843 | 2540842 |
| 18 | 74345065 | 74845094 | 74866978 | 74867007 | 18 | 74845065 | 74849064 | 74863008 | 74367007 |
| 1 | 1977899 | 1977928 | 2066129 | 2066158 | 1 | 1973929 | 1977928 | 2066129 | 2070128 |
| 21 | 36206580 | 36206609 | 36260589 | 36260618 | 21 | 36206580 | 36210579 | 36260589 | 36264588 |
| 10 | 6520005 | 6520034 | 6577853 | 6577882 | 10 | 6516035 | 6520034 | 6577853 | 6581852 |
| 18 | 74756102 | 74756131 | 74845065 | 74845094 | 18 | 74756102 | 74760101 | 74845065 | 74849064 |
| 10 | 6454073 | 6454102 | 6577853 | 6577882 | 10 | 6450103 | 6454102 | 6577853 | 6581852 |
| 10 | 6448929 | 6448958 | 6577853 | 6577882 | 10 | 6448929 | 6452928 | 6577853 | 6581852 |
| 1 | 1977899 | 1977928 | 2125692 | 2125721 | 1 | 1973929 | 1977928 | 2125692 | 2129691 |
| 14 | 64356944 | 64856973 | 64805460 | 64805493 | 14 | 64852973 | 64856973 | 64805460 | 64331460 |
| 18 | 77135881 | 77135910 | 77156058 | 77156087 | 18 | 77131911 | 77135910 | 77152088 | 77156087 |
| 10 | 6391740 | 6391769 | 6577853 | 6577882 | 10 | 6391740 | 6395739 | 6577853 | 6581852 |
| 12 | 6473688 | 6473717 | 6494374 | 6494403 | 12 | 6469718 | 6473717 | 6490404 | 6494403 |
| 18 | 74845065 | 74845094 | 74864966 | 74864995 | 18 | 74845065 | 74849064 | 74860996 | 74864995 |
| 10 | 6515356 | 6515385 | 6577853 | 6577882 | 10 | 6515356 | 6519355 | 6577853 | 6581852 |
| 1 | 2035712 | 2035741 | 2125692 | 2125121 | 1 | 2035712 | 2039711 | 2125692 | 2129691 |
| 2 | 95655674 | 95655703 | 95691307 | 95691336 | 2 | 95651704 | 95655703 | 95691307 | 95695306 |
| 10 | 6427823 | 6427852 | 6577853 | 6577882 | 10 | 6427823 | 6431822 | 6577853 | 6581852 |
| 1 | 2483531 | 2483560 | 2539015 | 2539044 | 1 | 2479561 | 2483560 | 2539015 | 2543014 |
| 21 | 34696685 | 34596714 | 34746263 | 34745292 | 21 | 34596685 | 34700684 | 34746263 | 34750262 |
| 16 | 27367634 | 27367663 | 27460580 | 27460609 | 16 | 27367634 | 27371633 | 27460580 | 27464579 |
| 19 | 10326359 | 10326388 | 10368390 | 10368419 | 19 | 10326359 | 10330358 | 10368390 | 10372389 |
| 19 | 55449063 | 55449092 | 55486679 | 55486708 | 19 | 55449063 | 55453062 | 55482709 | 55486708 |
| 4 | 38794092 | 38794121 | 38904213 | 38904242 | 4 | 38790122 | 38794121 | 38904213 | 38908212 |
| 7 | 128578517 | 128578546 | 128592079 | 128592108 | 7 | 128574547 | 128578546 | 128588109 | 128592108 |
| 2 | 65604070 | 65604099 | 65634253 | 65634282 | 2 | 65604070 | 65608069 | 65630283 | 65634282 |
| 8 | 42092338 | 42092367 | 42202562 | 42202591 | 8 | 42088368 | 42092367 | 42202562 | 42206561 |
| 4 | 38788263 | 38788292 | 38859677 | 38859706 | 4 | 38784293 | 38788292 | 38855707 | 38859706 |
| 2 | 204566973 | 204567002 | 204624489 | 204624518 | 2 | 204566973 | 204570972 | 204624489 | 204628488 |
| 12 | 10289679 | 10289708 | 10351648 | 10351677 | 12 | 10289679 | 10293678 | 10347678 | 10351677 |
| 2 | 204566973 | 204567002 | 204645538 | 204545567 | 2 | 204566973 | 204570972 | 204645538 | 204649537 |
| 4 | 74601393 | 74601422 | 74662726 | 74662755 | 4 | 74601393 | 74605392 | 74658756 | 74662755 |
| 1 | 67639374 | 67639403 | 67673763 | 67573792 | 1 | 67639374 | 67643373 | 67669793 | 67673792 |
| 4 | 26109788 | 26109317 | 26147759 | 26147788 | 4 | 26105318 | 26109317 | 26143789 | 26147788 |
| 10 | 101933094 | 101933123 | 101989686 | 10198971S | 10 | 101933094 | 101937093 | 101985716 | 101989715 |

Example 1 - Table 6E. Stratifying between RA-MTX responders and non-responders

| Probe Location | | | | | 4 kb Sequence Location | | | |
|---|---|---|---|---|---|---|---|---|
| Chr | Start1 | End1 | Start2 | End2 | Chr | Start1 | End1 | Start2 | End2 |
| 12 | 111834072 | 111834101 | 111901271 | 111901300 | 12 | 111830102 | 111834101 | 111897301 | 111901300 |
| 12 | 66544383 | 66544412 | 66696510 | 66596539 | 12 | 56540413 | 66544412 | 65696510 | 66700509 |
| 2 | 204577870 | 204577899 | 204607547 | 204507576 | 2 | 204677870 | 204576869 | 204603577 | 204607576 |
| 2 | 204541606 | 204541635 | 204582161 | 204582190 | 2 | 204537636 | 204541635 | 204582161 | 204586160 |
| 19 | 39425901 | 39425930 | 39449597 | 39449626 | 19 | 39421931 | 39425930 | 39445627 | 39449626 |
| 2 | 113627760 | 113627789 | 113530289 | 113530318 | 2 | 113623789 | 113627789 | 113530289 | 113526289 |
| 12 | 66544383 | 66544412 | 66583104 | 66583133 | 12 | 66540413 | 66544412 | 66579134 | 66583133 |
| 5 | 102618306 | 102618335 | 102629447 | 102529476 | 5 | 102614336 | 102618335 | 102629447 | 102633446 |
| 4 | 78431568 | 78431597 | 78523781 | 78523810 | 4 | 78431568 | 78435567 | 78523/81 | 78527780 |
| 14 | 55507410 | 55507439 | 55586310 | 55586339 | 14 | 55507410 | 55511409 | 55582340 | 55586339 |
| 14 | 91451476 | 91451505 | 91527033 | 91527062 | 14 | 91447506 | 91451505 | 91523063 | 91527062 |
| 12 | 56741028 | 56741057 | 56754855 | 56754884 | 12 | 56737058 | 56741057 | 56754855 | 56758854 |
| 6 | 52026497 | 52026526 | 52049432 | 52049461 | 6 | 52026497 | 52030496 | 52049432 | 52053431 |

Example 2: A Method of Determining the Chromosome Interactions Relevant to a Companion Diagnostic as Pharmacodynamic Biomarker During the Inhibition of LSD1 in the Treatment of AML (Acute Myeloid Leukemia)

Source: Institute of Cancer Research UK.
Pharmacodynamic Biomarkers

Pharmacodynamic (PD) biomarkers are molecular indicators of drug effect on the target in an organism. A PD biomarker can be used to examine the link between drug regimen, target effect, and biological tumour response. Coupling new drug development with focused PD biomarker measurements provides critical data to make informed, early go/no-go decisions, to select rational combinations of targeted agents, and to optimise schedules of combination drug regimens. Use of PD endpoints also enhances the rationality and hypothesis-testing power throughout drug development, from selection of lead compounds in preclinical models to first-in-human trials (National Cancer Institute).

The inventors have discovered that chromosome signatures could be used as pharmacodynamic biomarkers to monitor response to a number of drugs at time points consistent with phenotypic changes observed.

EpiSwitch™ Markers—Ideal Pharmacodynamic Biomarkers

Work on BET (bromodomain and extra-terminal) inhibitors on MV4-11 cell lines has shown that BET inhibition causes the transcriptional repression of key oncogenes BCL2, CDK6, and C-MYC BET inhibitors like LSD1 inhibitors are epigenetic therapies, targeting the acetylated and methylation states of histones. As topological changes at loci precede any regulatory changes, the findings at the MYC locus with EpiSwitch™ show evidence of regulatory change with LSD1 inhibition. MV4-11 cell line harbours translocations that express MLL-AF4 and FLT3-ITD whereas THP-1 only expresses MLL-AF9.

EpiSwitch™ LSD1 Inhibition Biomarker Study for AML (Acute Myeloid Leukemia)

Epigenetic biomarkers identified by EpiSwitch™ platform are well suited for delineating epigenetic mechanisms of LSD1 demethylase and for stratification of different specificities of LSD1 inhibitors within and between cell lines. This work demonstrates that chromosome conformation signatures could be used as mechanism-linked predictive biomarkers in LSD1 inhibition. A standard LSD1 inhibitor is investigated in this study, tranylcypromine (TCP).

EpiSwitch™ LSD1 Pharmacodynamic Biomarker Discovery

The cells were treated with 1 uM of tranylcypromine (TCP). Two AML (acute myeloid leukemia) cell lines THP-1 and MV4-11 were tested with the above compound. Chromosome signatures identified in the vicinity of MYD88 gene in THP-1 cells are shown in Table 7. Chromosome signatures identified in the vicinity of MYD88 gene in MV4-11 cells are shown in Table 8. Each number combination, points to individual chromosome interaction. The positions across the gene have been created and selected based on restriction sites and other features of detection and primer efficiency and were then analysed for interactions. The result in tables 7 and 8 represent no signature detection. A signature detection is represented with the number 1. Below are the PCR EpiSwitch™ marker results for the MyD88 locus for cell lines THP-1 and MV4-11. FACS analysis was used to sort for the expression of CD11b±cells, as an indicator of differentiation. MyD88 and MYC loci were selected on the basis of previously published studies, as key genetic drivers of treatment changes at 72 hrs.

LSD1 Inhibitor (TCP) Experiments—Discovery Findings

The conformations that change at the later time point (72 hrs) relative to the untreated cells show the most consistency between the 2 cell types. These are the markers above the bold double line shown in the THP-1 data, and highlighted by the shaded cells in the MV4-11 data.

LSD1 inhibition removes a long range interaction with 5' upstream to the ORF of MYD88, changing the regulatory landscape for the locus.

LSD1 Inhibition Analysis Versus Gene Expression Data—Temporal and Structural Correlation of MYC Locus Conformations with Gene Expression (GEX)

MYC is the target gene that drives the AML (acute myeloid leukemia) pathology, but at 72 hrs treatment, the fold change is too small to be significant for a marker. The changes seen in Table 9 at the MYC locus at 72 hrs for GEX data correlates to the conformation changes identified at 72 hrs. The negative GEX change at MYC relative to the untreated cells is in keeping with the requirement to perturb MYC proliferation effect. The change is small also in keeping with the tight control elicited on this locus by numerous signal cascades.

Unlike GEX data above, the EpiSwitch™ biomarkers clearly detect changes in chromosome conformation signatures at 72 hr treatments correspondent with cells differentiation and their death by apoptosis (phenotypic change).

LSD1 Inhibition Analysis Versus Gene Expression Data—Temporal and Structural Correlation of MyD88 Locus Conformations with Gene Expression (GEX)

The changes seen at MyD88 at 72 hrs for the GEX data correlate to the conformation changes identified at 72 hrs. The GEX change is positive relative to untreated cells, which is in keeping with the differential seen in these AML (acute myeloid leukemia) cells after treatment with the LSD1 inhibitor.

Only 1.5 fold change observed at 72 hr treatment with TCP at MYD88 locus identified both by GEX and EpiSwitch™. This level of change is too affected by noise in microarray gene expression analysis. However, epigenetic changes observed for chromosome signatures are clean to follow a binary format of 0 or 1. The data shows distinct pattern of changes. Both MYC and MYD88 are epigenetic drivers that, as shown in the GEX data, may not present with the strong response in gene expression, but can be identified as key epigenetic changes are visible through chromosome signatures. These two genetic drivers define phenotypic changes required for successful therapy treatment. At 72 hrs cells differentiate and undergo apoptosis.

TABLE 7

THP cells - LSD1 Inhibitor (TCP) treated and untreated at 48 hrs and 72 hrs

| THP-1 | Untreated | TCP treatment 48 hr | TCP Treatment 72 hr |
|---|---|---|---|
| MYD88 1/29 | 1 | 1 | 0 |
| MYD88 7/27 | 1 | 1 | 0 |
| MYD88 9/17 | 1 | 1 | 0 |
| MYD88 3/27 | 1 | 1 | 0 |
| MYD88 1/13 | 1 | 1 | 0 |
| MYD88 17/29 | 1 | 1 | 0 |
| MYD88 3/19 | 1 | 1 | 0 |
| MYD88 5/21 | 1 | 1 | 0 |
| MYD88 5/29 | 1 | 1 | 0 |
| MYD88 3/31 | 1 | 1 | 0 |
| MYD88 7/23 | 1 | 1 | 1 |
| MYD88 3/7 | 1 | 1 | 1 |
| MYD88 1/25 | 0 | 0 | 1 |
| MYD88 3/25 | 0 | 1 | 1 |
| MYD88 1/27 | 0 | 1 | 1 |
| MYD88 3/11 | 0 | 1 | 1 |
| MYD88 11/27 | 0 | 1 | 1 |
| MYD88 9/25 | 0 | 1 | 0 |
| MYD88 13/25 | 0 | 1 | 1 |
| MYD88 3/15 | 0 | 1 | 0 |
| MYD88 13/29 | 0 | 1 | 0 |
| MYD88 7/11 | 0 | 1 | 0 |
| MYD88 7/31 | 0 | 1 | 0 |

TABLE 8

MV4-11 cells - LSD1 Inhibitor (TCP) treated and untreated at 48 hrs and 72 hrs

| MV4-11 | Untreated | TCP treatment 48hr | TCP Treatment 72 hr |
|---|---|---|---|
| MYD88 3/27 | 0 | 0 | 0 |
| MYD88 7/11 | 0 | 0 | 0 |
| MYD88 7/27 | 0 | 1 | 0 |
| MYD88 7/31 | 0 | 0 | 0 |
| MYD88 1/13 | 1 | 1 | 0 |
| MYD88 11/27 | 1 | 1 | 0 |
| MYD88 1/25 | 1 | 1 | 0 |
| MYD88 13/29 | 1 | 1 | 0 |
| MYD88 1/17 | 1 | 1 | 1 |
| MYD88 13/25 | 1 | 1 | 0 |
| MYD88 1/29 | 1 | 1 | 0 |

TABLE 8-continued

MV4-11 cells - LSD1 Inhibitor (TCP) treated and untreated at 48 hrs and 72 hrs

| MV4-11 | Untreated | TCP treatment 48hr | TCP Treatment 72 hr |
|---|---|---|---|
| MYD88 17/29 | 1 | 1 | 0 |
| MYD88 5/21 | 1 | 1 | 1 |
| MYD88 3/11 | 1 | 1 | 1 |
| MYD88 3/15 | 1 | 1 | 0 |
| MYD88 3/19 | 1 | 1 | 0 |
| MYD88 3/31 | 1 | 1 | 1 |
| MYD88 3/7 | 1 | 1 | 0 |
| MYD88 5/25 | 1 | 1 | 1 |
| MYD88 5/29 | 1 | 1 | 0 |
| MYD88 7/23 | 1 | 1 | 0 |
| MYD88 9/17 | 1 | 1 | 0 |
| MYD88 9/25 | 1 | 1 | 0 |

TABLE 9

Illumina Human HT-12 V4.0 expression beadchip GEX Data for MYC

| HUGO_SYN | TCP/un 3 h | TCP/un 12 h | TCP/un 72 h |
|---|---|---|---|
| MYC | 0.99 | 0.81 | −1.27 |

TABLE 10

Treatment with TCP

| MYC MV4-11 | Untreated | TCP treatment 48 hr | TCP Treatment 72 hr |
|---|---|---|---|
| MYCUS 1/MYCUS 23 | 1 | 1 | 0 |
| MYCUS 3/MYCUS 13 | 1 | 1 | 0 |
| MYCUS 5/MYCUS 21 | 1 | 1 | 0 |
| MYCUS 9/MYC 5 | 1 | 1 | 0 |

TABLE 11

Illumina Human HT-12 V4.0 expression beadchip GEX Data for MYD/38

| HUGO_SYN | TCP/un 3 h | 1TCP/un 12 h | ITCP/un 72 h |
|---|---|---|---|
| MyD88 | 1.07 | 11.13 | 11.53 |

TABLE 12

Treatment with TCP

| MyD88 MV4-11 | Untreated | TCP treatment 48 hr | TCP Treatment 72 hr |
|---|---|---|---|
| 1/13 | 1 | 1 | 0 |
| 11/27 | 1 | 1 | 0 |
| 1/25 | 1 | 1 | 0 |
| 13/29 | 1 | 1 | 0 |
| 5/29 | 1 | 1 | 0 |
| 7/23 | 1 | 1 | 0 |
| 9/17 | 1 | 1 | 0 |
| 9/25 | 1 | 1 | 0 |

Example 3: A Method of Determining the Chromosome Interactions which are Relevant to a Companion Diagnostic for Prognosis of Melanoma Relapse in Treated Patients (PCR Data)

Source: Mayo Clinic metastatic melanoma cohort, USA

A prognostic biomarker predicts the course or outcome (e.g. end, stabilisation or progression) of disease. This study discovers and validates chromosome signatures that could act as prognostic biomarkers for relapse to identify clear epigenetic chromosome conformation differences in monitored melanoma patients, who undergone surgery treatment, for signs of relapse or recovery, and to validate such biomarkers for potential to be prognostic biomarkers for monitoring relapse of melanoma. Here we want to present our example of validated prognostic use of chromosome conformation signatures in application to confirmed melanoma patients who have undergone treatment by the resection of the original growth in order to identify the candidates who are likely to relapse within 2 years of treatment.

224 melanoma patients were treated with surgery to remove their cancer. They were then observed for a period of two years with blood being drawn for analysis at >100 days after the surgery.

EpiSwitch™ Prognostic Biomarker Discovery

Chromosome signatures of 44 genes associated with melanoma and the rest of the genome for any disease-specific long range interaction by Next Generation Sequencing NGS were tested. Non-biased assessment of chromosome signatures associated with melanoma through deep sequencing provided initial pool of 2500 candidate markers. Further analysis by EpiSwitch™ platform on expanding sets of blood samples from melanoma patients and patients with non-melanoma skin cancers (NMSQ) as control, reduced the initial pool of candidate markers to 150. With further expansion on sample numbers it has been reduced to 32, as shown in Table 13.

TABLE 13

Number of EpiSwitch™ Markers screened and patients used.

| EpiSwitch™ Markers Screened | Melanoma Patients Used | NMSC Patients Used |
|---|---|---|
| 150 | 4 | 4 |
| 94 | 14 | 14 |
| 55 | 21 | 20 |
| 32 | 74 | 33 |

Prognosis of Relapse

Top 15 markers previously identified for stratification of melanoma from non-melanoma skin cancers comprise TBx2 7/15, TYR 1/9, TYR 13/17, TYR 3/11, TYR 3/23, P1611/19, P16 7/23, P16 9/29, MITF 35/51, MITF 43/61, MITF 49/55, BRAF 5/11, BRAF 27/31, BRAF 21/31, BRAF 13/21, which were taken from a total of 8 genes: TBx2; TYR; BRAF; MiTF; p 16; BRN2; p 21; TBx3

3C analysis of melanoma patients' epigenetic profiles revealed 150 chromosome signatures with a potential to be prognostic biomarkers, reduced to three in expanding sets of testing sample cohorts. The three chromosome signatures which show the switches in chromosome conformational signature highly consistent with treatment and 2 year outcome for relapse, and this are the best potential prognostic melanoma markers are: BRAF 5/11, p 16-11/19 and TYR 13/17. Finally, three chromosome signatures were carried out to the validation stage as prognostic biomarkers.

TABLE 14

EpiSwitch™ Prognostic signature for patients who relapsed 2 years after treatment (0 = No chromosome conformation detected, 1 = chromosome conformation detected) - Group A

| Sample ID | BRAF 5/11 | P16 11/19 | TYR 13/17 | Mel_gone |
|---|---|---|---|---|
| AZ250439M-2 | 1 | 1 | 1 | No |
| AZ250439M-1 | 1 | 1 | 1 | No |
| JB220262F-2 | 1 | 1 | 1 | No |
| JS150868F | 1 | 1 | 1 | No |
| KB200873F-2 | 1 | 1 | 1 | No |
| SW14101951F-1 | 1 | 1 | 1 | No |
| VW250929M-1 | 1 | 1 | 1 | No |
| AC130954F-1 | 1 | 1 | 1 | No |
| AC130954F-2 | 1 | 1 | 1 | No |
| GM271147M-2 | 1 | 1 | 1 | No |
| LW191048F-2 | 1 | 1 | 1 | No |
| LG040535M-2 | 1 | 0 | 1 | No |
| JB220262F-1 | 1 | 0 | 1 | No |
| RH070234F-2 | 1 | 0 | 1 | No |
| RH070234F-4 | 1 | 0 | 1 | No |
| GM271147M4 | 1 | 0 | 1 | No |
| LW191048F-1 | 1 | 0 | 1 | No |
| BB08111957F-2 | 1 | 1 | 0 | No |
| RH070234F-1 | 1 | 1 | 0 | No |
| RH070234F-1 | 1 | 1 | 0 | No |
| RD200666M-2 | 1 | 1 | 0 | No |
| RD200666M-1 | 1 | 1 | 0 | No |
| KB200873F-1 | 1 | 1 | 0 | No |
| VW250928M-2 | 1 | 1 | 0 | No |

Table 14 shows that relapse has been observed within two years after the treatment among the above patients. Through completely non-biased analysis of chromosome signatures these disease-specific three markers remained present and unchanged after treatment in majority of patients who relapsed after treatment.

Table 15 provides evidence that chromosome signatures change as a result of treatment to reflect more healthy profile. Through completely non-biased analysis of chromosome signatures the same disease-specific three markers have changed and were absent in majority of patients after treatment, with no signs of relapse for 2 years.

Table 16 shows that the same three prognostic biomarkers show a strong tendency to be absent in healthy population. From all melanoma specific biomarkers identified in initial discovery stage, only these three markers carried prognostic value due to their change after treatment, in that they were different from diagnostic markers.

These results confirm that the three identified chromosome signatures exemplify the evidence for chromosome signatures acting as valid and robust prognostic biomarkers.

TABLE 15

EpiSwitch™ Prognostic Signature for Successful Treatment in Melanoma Patients who did not relapse after 2 years (0 = No chromosome conformation detected, 1 = chromosome conformation detected) - Group B

| Sample ID | BRAF 5/11 | P16 11/19 | TYR 13/17 | Mel gone |
|---|---|---|---|---|
| DG04081968M-2 | 0 | 0 | 0 | Yes |
| DG04081968M-1 | 0 | 0 | 0 | Yes |
| JR08061937F-2 | 0 | 0 | 0 | Yes |
| EM110366F-4 | 0 | 0 | 0 | Yes |
| FS17051942M-2 | 0 | 0 | 0 | Yes |
| GS18081951M-1 | 0 | 0 | 0 | Yes |
| DB24021936M-1 | 0 | 0 | 0 | Yes |
| DB24021936M-2 | 0 | 0 | 0 | Yes |
| ML23131937M-2 | 0 | 0 | 0 | Yes |
| ML23131937M-1 | 0 | 0 | 0 | Yes |
| DM210555M-2 | 0 | 0 | 0 | Yes |

TABLE 15-continued

EpiSwitch ™ Prognostic Signature for Successful Treatment
in Melanoma Patients who did not relapse after
2 years (0 = No chromosome conformation detected,
1 = chromosome conformation detected) - Group B

| Sample ID | BRAF 5/11 | P16 11/19 | TYR 13/17 | Mel gone |
|---|---|---|---|---|
| DM210555M-1 | 0 | 0 | 0 | Yes |
| JS121060F-2 | 0 | 0 | 0 | Yes |
| JH280944M-2 | 0 | 0 | 0 | Yes |
| JH280944M-1 | 0 | 0 | 0 | Yes |
| RF15091934M-2 | 0 | 0 | 0 | Yes |
| GC23051957M-2 | 0 | 0 | 0 | Yes |
| PA24011941M-2 | 0 | 0 | 0 | Yes |
| PA24011941M-1 | 0 | 0 | 0 | Yes |
| MH12031946M-2 | 0 | 0 | 0 | Yes |
| MH12031946M-1 | 0 | 0 | 0 | Yes |
| AC17071938M-2 | 0 | 0 | 0 | Yes |
| AC17071938M-1 | 0 | 0 | 0 | Yes |
| TR080147M-2 | 0 | 0 | 0 | Yes |

TABLE 16

EpiSwitch ™ Reference Epigenetic Profile in Healthy Controls
(HC = Healthy Controls, 0 = No chromosome conformation
detected, 1 = chromosome conformation detected) - Group C

| Sample ID | BRAF 5/11 | P16 11/19 | TYR 13/17 | Condition |
|---|---|---|---|---|
| JP74(5)-1 | 0 | 0 | 0 | HC |
| JG80 (6)-1 | 0 | 0 | 0 | HC |
| JG80 (6)-2 | 0 | 0 | 0 | HC |
| MS80 (7)-1 | 0 | 0 | 0 | HC |
| MS80 (7)-2 | 0 | 0 | 0 | HC |
| RS86 (8)-1 | 0 | 0 | 0 | HC |
| ES86 (9)-1 | 0 | 0 | 0 | HC |
| DL (10)-1 | 0 | 0 | 0 | HC |
| RM81 (11)-1 | 0 | 0 | 0 | HC |
| CS (12)-1 | 0 | 0 | 0 | HC |
| CL84 (13)-1 | 0 | 0 | 0 | HC |
| ER83 (14)-1 | 0 | 0 | 0 | HC |
| AP57 (15)-1 | 0 | 0 | 0 | HC |
| AP57 (15)-2 | 0 | 0 | 0 | HC |
| SR86 (17)-1 | 0 | 0 | 0 | HC |
| YD80 (18)-1 | 0 | 0 | 0 | HC |
| KK69 (19)-1 | 0 | 0 | 0 | HC |
| KK69 (19)-2 | 0 | 0 | 0 | HC |
| RS84 (20)-1 | 0 | 0 | 0 | HC |
| AA85 (21)-1 | 0 | 0 | 0 | HC |
| AA85 (21)-2 | 0 | 0 | 0 | HC |
| AD75 (22)-1 | 0 | 0 | 0 | HC |
| JJ84 (23)-1 | 0 | 0 | 0 | HC |
| SP71 (24)-1 | 0 | 0 | 0 | HC |

Prognosis for Relapse (Residual Disease Monitoring in Treated Melanoma Patients)

Cross-validation for the 224 melanoma patients, observed for 2 years after the treatment for a relapse, on the basis of stratification with the three prognostic chromosome signatures from post-operational blood test. Table 17 shows the relevant confusion table.

TABLE 16b

| Classification | Result | 95% Confidence Interval (CI) |
|---|---|---|
| Sensitivity | 82.1% | 70.1%-89.4% |
| Specificity | 87.8% | 81.9%-92.1% |
| PPV | 71.0% | 59.4%-80.4% |
| NPV | 92.9% | 87.7%-96.1% |

TABLE 17

| | Confusion table | | |
|---|---|---|---|
| Group | A | B | Classified as |
| A | 49 | 11 | Still has melanoma |
| B | 20 | 144 | Re-categorised |

Predictive/Pharmacodynamic Biomarkers for Drug Response: Anti-PD-1 in Metastatic Melanoma Patients (Array Data)

Melanoma

Malignant melanoma is the least common, but most aggressive form of skin cancer. It occurs in melanocytes, cells responsible for synthesis of the dark pigment melanin. The majority of malignant melanomas are caused by heavy UV exposure from the sun. Most of the new melanoma cases are believed to be linked to behavioural changes towards UV exposure from sunlight and sunbeds. Globally, in 2012, melanoma occurred in 232,000 people and resulted in 55,000 deaths. Incidence rates are highest in Australia and New Zealand. The worldwide incidence has been increasing more rapidly amongst men than any other cancer type and has the second fastest incidence increase amongst women over the last decade. The survival rates are very good for individuals with stage 1 and 2 melanomas. However, only 7-19% of melanoma patients whose cancer has spread to distant lymph nodes or other parts of the body will live for more than 5 years. Currently, the only way to accurately diagnose melanoma is to perform an excision biopsy on the suspicious mole. The treatment includes surgical removal of the tumour. There is no melanoma screening programme in the UK, but educational programmes have been created to raise awareness of risks and symptoms of melanoma. There is a high demand for screening programmes in countries where melanoma incidence is very high e.g. in Australia. This work concerns biomarkers for diagnosis, prognosis, residual disease monitoring and companion diagnostics for melanoma immunotherapies.

Study Background

The major issue with all immunomodulators currently tested in the treatment of cancers is their low response rates. In the case of late melanoma, for anti-PD-1 or anti-PD-L1 monoclonal antibodies, the objective response rate is only 30-40%. Such therapy is in strong need of biomarkers predicting responders vs. non-responders. The PD-1 locus is regulated by cytokines epigenetically through resetting of long range chromosome conformation signatures.

OBD Technology

EpiSwitch™ platform technology is ideally suited for stratification of PD-1 epigenetic states prior to and in response to immunotherapy. An EpiSwitch™ array has been designed for analysis of >332 loci implicated in controls and modulation of response to anti-PD-1 treatment in melanoma patients.

Methods

Biomarker identification using EpiSwitch™ array analysis:
1. Chromosome conformations for 332 gene locations determined by EpiSwitch™ pattern recognition.
2. 14,000 EpiSwitch™ markers on PD1 screening array.

Samples

All patients have been previously treated with chemotherapy and anti-CTLA-4 therapy. Two time points considered pre-treatment (baseline samples) and post-treatment (12 week samples)

Discovery Cohort
  4 responders vs. 4 non-responders at baseline
  4 responders vs. 4 responders at 12 weeks (Matched)
Hypergeometric Analysis As the last step of the array data analysis, the hypergeometric analysis was carried out in order to identify regulatory hubs i.e. most densely regulated genes as being potential causative targets and preferred loci for stratification. The data is ranked by the Epigenetic Ratio for R vs R 12W (12W_FC_1), 1 in BL Binary indicates the loop is present in Responders vs Non-Responders, but when Responders baseline are compared to Responders at 12 weeks. The epigenetic ratio indicates that the presence of the loop is more abundant in the 12 week Responder patient samples. This indicates that there has been an expansion of this signature.

Summary

This epigenetic screen of anti-PD1 therapy for potential predictive and pharmacodynamic biomarkers provides a wealth of new regulatory knowledge, consistent with prior biological evidence. The work provides a rich pool of predictive and pharmacodynamic/response EpiSwitch™ markers to use in validation analysis. The results show presence of a defined epigenetic profile permissive for anti-PD-1 therapy. The epigenetic profile permissive for anti-PD1 therapy is present in naïve patients at baseline and is strengthened with treatment over 12 weeks period.

Further Information

This work concerns EpiSwitch™ as the basis for a diagnostic test to address the issue of poor melanoma diagnosis by general practitioners. 15 lead EpiSwitch™ biomarkers were screened and identified from an initial set of 86 patient samples representing true clinical setting. The biomarkers were then trained and validated in 2 independent patient cohorts: one from Australia (395 patients) and one from the Mayo Clinic (119 patients):
  119 independently and retrospectively annotated blood samples
  59 Melanoma Samples
  60 Controls (20 NMSC, 20 Benign Conditions, 20 Healthy Patients))
  2 Clinic collection in the USA
    95% Confidence Interval (CI)
    Sensitivity 90.0% 79.9%-95.3%
    Specificity 78.3% 66.4%-86.9%
    PPV 88.7% 77.4%-94.7%
    NPV 80.6% 69.65-88.3%
  68 EpiSwitch™ Markers identified by statistical processing as predictive biomarkers at baseline for anti-PD-1 therapy. (PD1-R vs NR BL). R is Responder, and NR Is Non-Responder. 63 EpiSwitch™ Markers identified by statistical processing as response biomarkers for anti-PD-1 therapy. (PD1 R-BL v R-12W). 10 Markers are both good candidates for predictive and response markers.

Fisher-Exact test results: top 8 predictive EpiSwitch™ Array Markers validated with the EpiSwitch™ PCR platform on the independent patient cohort (see Table 37). See Table 38 for the discerning markers from the Fisher-Exact analysis for PCR analysis between Responders at Baseline and Responders at 12 weeks. 1 is Conformation Present. 0 is Conformation Absent/Array: R12_W indicates that the conformation was present in the Responders at 12 weeks. The STAT5B_17_40403935_40406459_40464294_40468456_FR probe was measured in Responder v Non-Responder at Baseline and the conformation is present in the Responder. In this comparison the marker is in Responders at 12 weeks, this is the case as the concentrating of DNA used to detect the conformation in Responder vs Non Responder is greater than in Responder baseline v Responder at 12 weeks, indicating the Epigenetic Load has increased in the anti-PD-1 responding patients. Markers STAT5B and IL15 are of particular interest and are involved in key personalised medical and regulatory events responsible for the efficacies response to anti-PD1 therapies (see tables 39 to 40, 43 to 47).

The following Tables 36a to 36f, 37a, 37b, 38a, and 38b also pertain to Example 3 and are as follows:
  Table 36a. Top Probes—Anti PD1 (Melanoma)—responders
  Table 36b. Top Probes—Anti PD1 (Melanoma)—responders—probe sequences
  Table 36c. Top Probes—Anti PD1 (Melanoma)—Responders—Loci
  Table 36d. Top Probes—Anti PD1 (Melanoma) Non-responders
  Table 36e. Top Probes—Anti PD1 (Melanoma) Non-responders
  Table 36f. Top Probes—Anti PD1 (Melanoma) Non-responders—probes sequences and loci
  Table 37a. Anti-PD1: pharmacodynamic response markers
  Table 37b. Anti-PD1: pharmacodynamic response markers
  Table 38a. Anti-PD1: pharmacodynamic response markers—No difference in baseline Responders and baseline Non-Responders but show a significant change in 12 week Responder
  Table 38b. Probe location—Anti-PD1: pharmacodynamic response markers—No difference in baseline Responders and baseline Non-Responders but shows a significant change in 12 week Responders Indication Examples Example 4—Amyotrophic Lateral Sclerosis (ALS)

The motor neurone disease Amyotrophic lateral sclerosis (ALS or Lou Gehrig's disease) is a fatal neurodegenerative disease characterised by progressive death of the primary motor neurones in the central nervous system. Symptoms include muscle weakness and muscle wasting, difficulty in swallowing and undertaking everyday tasks. As the disease progresses, the muscles responsible for breathing gradually fail, causing difficulty in breathing, and finally death. ALS has an average prevalence of 2 per 100,000, but is higher in the UK and USA with up to 5 per 100,000. There are estimated to be over 50,000 patients in the USA and 5,000 patients in the UK with the condition. The mortality rate for ALS sufferers is high: the median survival from diagnosis with ALS (i.e. the time when 50% of patients have died) varies in different studies, but in the most reliable (unbiased) population studies it is about 22 months with a range of 18-30 months. With no known cure, treatment of ALS focuses on supportive care. There is only one drug currently approved for treatment, riluzole which provides a modest increase in lifespan for ALS patients but minimal improvement in symptoms. Despite intensive research into the biological basis of ALS, diagnosis and methods of treatment, as well as monitoring of disease progression remains a challenge. Such prognostic tests would greatly benefit ALS sufferers by allowing sub-stratification of patients according to the biological mediators of clinical heterogeneity, potentially allowing a more precise prognosis and care planning by identifying fast and slow progressors. OBD has been discovering EpiSwitch™ markers to stratify ALS vs. healthy controls, and fast progressing ALS vs. slow progressing ALS, to develop and validate diagnostic, prognostic and predictive EpiSwitch™ biomarkers for ALS.

Source: Northeast Amyotrophic Lateral Sclerosis Consortium (NEALS)—USA.

See Tables 1, 2, 18, and 42 and hereinafter for ALS Probes—EpiSwitch™ markers to stratify ALS vs. healthy controls. Table 27 shows the gene data for this indication.

Further work was performed to validate the top ALS array markers and identify primers that could study the interactions. Statistical analysis of the array markers informed shortlist selection for PCR based assay development. From the list of the best stratifying ALS array probes, 99 markers were taken to the PCR stage.

Primers were designed using Integrated DNA Technologies (IDT) software (and Primer3web version 4.0.0 software if required) from markers identified from the microarray. Primer testing was carried out on each primer set; each set was tested on a pooled subset of samples to ensure that appropriate primers could study the potential interactions. Presence of an amplified product from PCR was taken to indicate the presence of a ligated product, indicating that a particular chromosome interaction was taking place. If the primer testing was successful then the primer sets were taken through to screening.

The signature set was isolated using a combination of univariate (LIMMA package, R language) and multivariate (GLMNET package, R language) statistics and validated using logistic modelling within WEKA (Machine learning algorithms package). The best 10 stratifying PCR markers were selected for validation on 58 individuals (29×ALS; 29× Healthy controls—HC) using data from the Northeast Amyotrophic Lateral Sclerosis Consortium (NEALS). These were selected based on their Exact Fisher's P-value. A consistently good marker from all 3 tests was the EpiSwitch marker in CD36. The first 9 PCR markers shown in Table 41 stratified between ALS and HC with 90% rank discrimination index.

The ALS marker set was analysed against a small independent cohort of samples provided by Oxford University. Even in a small subset of samples stratification of the samples was shown based on the biomarkers. Four markers stratify the subset of 32 (16 ALS, 16 Healthy Control) samples with p-value<0.3. These core markers are ALS.21.23_2, DNM3.5.7_8, ALS.61.63_4 and NEALS.101.103_32, in genes EGFR, DNM3, CD36 and GLYCAM1 respectively. The Fisher-Exact test, GLMNET and Bayesian Logistic modelling marked CLIC4 as a valuable addition to the four core markers.

The sequences of the primers for the PCR markers given in Table 41 are provided in Table 42.

Example 5—Diabetes Mellitus (DM) Type II (T2DM)

Type 2 diabetes (also known as T2DM) is the most common form of diabetes. Diabetes may occur through either, the pancreas not producing enough hormone insulin which regulates blood sugar levels, or the body not being able to effectively use the hormone it produces due to reduced insulin sensitivity. Until recently, T2DM has only been diagnosed in adults, but it is now occurring in children and young adults. According to World Health Organisation (WHO), diabetes reached pandemic levels with 346 million sufferers worldwide and its incidence is predicted to double by 2030. In 2004 alone, approximately 3.4 million people died as a consequence of diabetes and its complications with the majority of deaths occurring in low- and middle-income countries. The incidence of T2DM is increasing due to an ageing population, changes in lifestyle such as lack of exercise and smoking, as well as diet and obesity. T2DM is not insulin dependent and can be controlled by changes in lifestyle such as diet, exercise and further aided with medication. Individuals treated with insulin are at a higher risk of developing severe hypoglycaemia (low blood glucose levels) and thus their medication and blood glucose levels require routine monitoring. Generally, older individuals with established T2DM are at a higher risk of cardiovascular disease (CVD) and other complications and thus usually require more treatment than younger adults with a recently-recognised disease. It has been estimated that seven million people in the UK are affected by pre-diabetic conditions, which increase the risk of progressing to T2DM. Such individuals are characterised by raised blood glucose levels, but are usually asymptomatic and thus may be overlooked for many years having a gradual impact on their health. Inventors develop prognostic stratifications for pre-diabetic state and T2DM. Presented herein are EpiSwitch™ markers to stratify pre-diabetic state (Pre-T2DM) vs. healthy controls, as well as the discovery of EpiSwitch™ markers to stratify T2DM vs. healthy control, and prognostic markers to stratify aggressive T2DM vs. slow T2DM.

Source: Norfolk and Norwich University Hospitals (NNUH), NHS Foundation Trust—Norwich UK See Tables 19a, 19b, 19c and 19d hereinafter for Pre-type 2 diabetes mellitus probes—EpiSwitch™ markers to stratify pre-type 2 diabetes vs. healthy controls. Table 28 shows the gene data.

See also Tables 20a, 20b, 20c, 20d hereinafter for Type 2 diabetes mellitus probes—EpiSwitch™ markers to stratify type 2 diabetes mellitus vs. healthy controls. Table 29 shows the gene data.

Example 6—Diabetes Mellitus Type I (T1DM)

Diabetes mellitus (DM) type 1 (also known as T1DM; formerly insulin-dependent diabetes or juvenile diabetes) is a form of diabetes that results from the autoimmune destruction of the insulin-producing beta cells in the pancreas. The classical symptoms are polyuria (frequent urination), polydipsia (increased thirst), polyphagia (increased hunger) and weight loss. Although, T1DM accounts for 5% of all diabetes cases, it is one of the most common endocrine and metabolic conditions among children. Its cause is unknown, but it is believed that both genetic factors and environmental triggers are involved. Globally, the number of people with T1DM is unknown, although it is estimated that about 80,000 children develop the disease each year. The development of new cases varies by country and region. The United States and northern Europe fall between 8-17 new cases per 100,000 per year. Treatment of diabetes involves lowering blood glucose and the levels of other known risk factors that damage blood vessels. Administration of insulin is essential for survival. Insulin therapy must be continued indefinitely and does not usually impair normal daily activities. Untreated, diabetes can cause many serious long-term complications such as heart disease, stroke, kidney failure, foot ulcers and damage to the eyes. Acute complications include diabetic ketoacidosis and coma. OBD's diabetes programme is focused on a development of EpiSwitch™ biomarkers for diagnostic and prognostic stratifications of T1DM.

Presented herein are EpiSwitch™ markers to stratify T1DM versus healthy controls.

Source: Caucasian samples collected by Procurement Company Tissue Solutions based in Glasgow (Samples collected in Russia); NEALS consortium controls (USA).

See Tables 21a, 21b, 21c and 21d hereinafter for Type 1 diabetes mellitus (T1DM) probes—EpiSwitch™ markers to stratify T1DM vs. healthy controls. Table 30 shows the gene data.

Example 7—Ulcerative Colitis (UC)

Ulcerative colitis (UC), a chronic inflammatory disease of the gastrointestinal tract, is the most common type of inflammatory disease of the bowel, with an incidence of 10 per 100,000 people annually, and a prevalence of 243 per 100,000. Although, UC can occur in people of any age, it is more likely to develop in people between the ages of 15 and 30 and older than 60. The exact cause of ulcerative colitis is unknown. However, it is believed that an overactive intestinal immune system, family history and environmental factors (e.g. emotional stress) may play a role in causing UC.

It is more prevalent in people of Caucasian and Ashkenazi Jewish origin than in other racial and ethnic subgroups. The most common signs and symptoms of this condition are diarrhoea with blood or pus and abdominal discomfort. It can also cause inflammation in joints, spine, skin, eyes, and the liver and its bile ducts. UC diagnosis is carried out through taking family history, physical exam, lab tests and endoscopy of large intestine. This lifelong disease is associated with a significant morbidity, and the potential for social and psychological sequelae particularly if poorly controlled. An estimated 30-60% of people with ulcerative colitis will have at least one relapse per year. About 80% of these are mild to moderate and about 20% are severe. Approximately 25% of people with UC will have one or more episodes of acute severe colitis in their lifetime. Of these, 20% will need a surgical removal of all or part of the colon (colectomy) on their first admission and 40% on their next admission. Although mortality rates have improved steadily over the past 30 years, acute severe colitis still has a mortality rate of up to 2%. Mortality is directly influenced by the timing of interventions, including medical therapy and colectomy.

Ulcerative colitis has a well-documented association with the development of colorectal cancer, with greatest risk in longstanding and extensive disease. Treatment of relapse may depend on the clinical severity, extent of disease and patient's preference and may include the use of aminosalicylates, corticosteroids or immunomodulators. The resulting wide choice of agents and dosing regimens has produced widespread heterogeneity in management across the UK, and emphasises the importance of comprehensive guidelines to help healthcare professionals provide consistent high quality care.

Presented herein are EpiSwitch™ markers to stratify UC versus healthy controls for a development of disease-specific signatures for UC.

Source: Caucasian samples collected by Procurement Company Tissue Solutions based in Glasgow (Samples collected in Russia); NEALS consortium controls (USA).

See Tables 22a, 22b, 22c and 22d hereinafter for Ulcerative colitis (UC) probes—EpiSwitch™ markers to stratify UC vs. healthy controls. Table 31 shows the gene data.

Example 8—Systemic Lupus Erythematosus (SLE)

Systemic lupus erythematosus (SLE), also known as discoid lupus or disseminated lupus erythematosus, is an autoimmune disease which affects the skin, joints, kidneys, brain, and other organs. Although "lupus" includes a number of different diseases, SLE is the most common type of lupus. SLE is a disease with a wide array of clinical manifestations including rash, photosensitivity, oral ulcers, arthritis, inflammation of the lining surrounding the lungs and heart, kidney problems, seizures and psychosis, and blood cell abnormalities. Symptoms can vary and can change over time and are not disease specific which makes diagnosis difficult. It occurs from infancy to old age, with peak occurrence between ages 15 and 40. The reported prevalence of SLE in the population is 20 to 150 cases per 100,000. In women, prevalence rates vary from 164 (white) to 406 (African American) per 100,000. Due to improved detection of mild disease, the incidence nearly tripled in the last 40 years of the 20th century. Estimated incidence rates are 1 to 25 per 100,000 in North America, South America, Europe and Asia. The exact cause of SLE is not known, but several factors have been associated with the disease. People with lupus often have family members with other autoimmune conditions. There may be environmental triggers like ultraviolet rays, certain medications, a virus, physical or emotional stress, and trauma. There is no cure for SLE and the treatment is to ease the symptoms. These will vary depending on expressed symptoms and may include anti-inflammatory medications, steroids, corticosteroids and anti-malarial drugs. Survival has been improving, suggesting that more or milder cases are being recognised. OBD has been developing prognostic signatures for SLE.

See Tables 23a, 23b, 23c and 23d for SLE probes— EpiSwitch™ markers to stratify SLE vs. healthy controls. Table 32 shows the gene data.

Source: Caucasian samples collected by Procurement Company Tissue Solutions based in Glasgow (Samples collected in US); NEALS consortium controls.

Example 9—Multiple Sclerosis (MS)

Multiple sclerosis (MS) is an acquired chronic immune-mediated inflammatory condition of the central nervous system (CNS), affecting both the brain and spinal cord. The cause of MS is unknown. It is believed that an abnormal immune response to environmental triggers in people who are genetically predisposed results in immune-mediated acute, and then chronic, inflammation. The initial phase of inflammation is followed by a phase of progressive degeneration of the affected cells in the nervous system. MS is more common among people in Europe, the United States, Canada, New Zealand, and sections of Australia and less common in Asia and the tropics. It affects approximately 100,000 people in the UK. In the US, the number of people with MS is estimated to be about 400,000, with approximately 10,000 new cases diagnosed every year. People with MS typically develop symptoms between the ages 20 and 40, experiencing visual and sensory disturbances, limb weakness, gait problems, and bladder and bowel symptoms. They may initially have partial recovery, but over time develop progressive disability. Although, there is no cure, there are many options for treating and managing MS. They include drug treatments, exercise and physiotherapy, diet and alternative therapies. MS is a potentially highly disabling disorder with considerable personal, social and economic consequences. People with MS live for many years after diagnosis with significant impact on their ability to work, as well as an adverse and often highly debilitating effect on their quality of life and that of their families.

OBD's MS programme involves looking at prognostic stratifications between primary progressive and relapsing-remitting MS.

The most common (approx. 90%) pattern of disease is relapsing-remitting MS (MSRR). Most people with this type of MS first experience symptoms in their early 20s. After that, there are periodic attacks (relapses), followed by partial or complete recovery (remissions). The pattern of nerves affected, severity of attacks, degree of recovery, and time between relapses all vary widely from person to person. Eventually, around two-thirds of people with relapsing-remitting MS enter a secondary progressive phase of MS. This occurs when there is a gradual accumulation of disability unrelated to relapses, which become less frequent or stop completely.

Presented herein are EpiSwitch™ monitoring markers to stratify MS patients who are responders to IFN-B treatment versus non-responders; EpiSwitch™ markers to stratify MSRR versus healthy controls and EpiSwitch™ markers to stratify MSRR (relapsing remitting type of MS) versus MSPP (primary progressive type of MS).

Source: Caucasian samples collected by procurement company Tissue Solutions, based in Glasgow (Samples collected in MS-RR: Russia: MS IFN-B R vs NR: USA); NEALS consortium controls (USA See Tables 24a, b, c and d hereinafter for Relapsing-Remitting Multiple Sclerosis (MSRR) probes—EpiSwitch™ markers to stratify MSRR vs. healthy controls. Table 33 shows the gene data.

See also Tables 25a, 25b, 25c and 25d hereinafter for Multiple Sclerosis (MS) probes—EpiSwitch™ monitoring markers to stratify MS patients who are (B) responders to IFN-B (IFN-beta) treatment vs. (A) non-responders. Table 34 shows the gene data.

Example 10—Neurofibromatosis (NF)

In patients with NF1 mutation transformation into malignant state is difficult to predict, as it is governed by epigenetic context of the patient. In NF2 mutants, prognosis of the disease is very reliable and strongly defined by the genetics itself. Presented herein are EpiSwitch™ markers to stratify Malignant Peripheral Nerve Sheath Tumours (MPNSTs) vs. Benign plexiform showing 329 top probes in enriched data.

Source: Belgium—University of Leuven

See Tables 26a and 26b hereinafter for Neurofibromatosis (NF) probes—EpiSwitch™ markers to stratify Benign plexiform vs. Malignant Peripheral Nerve Sheath Tumours (MPNSTs). Table 35 shows the gene data.

Example 11—Chromosome Interactions Relevant to Anti-PD1 Responsiveness in Different Cancers Table 47 shows the pattern of chromosome interactions present in responders to anti-PD1 (unless otherwise stated with NR (non-responder)) in individuals with particular cancers. The terminology used in the table is explained below.

DLBCL_ABC: Diffuse large B-cell lymphoma subtype activated B-cells

DLBCL_GBC: Diffuse large B-cell lymphoma subtype germinal centre B-cells

HCC: hepatocellular carcinoma

HCC_HEPB: hepatocellular carcinoma with hepatitis B virus

HCC_HEPC: hepatocellular carcinoma with hepatitis C virus

HEPB+R: Hepatitis B in remission

Pca_Class3: Prostate cancer stage 3

Pca_Class2: Prostate cancer stage 2

Pca_Class1: Prostate cancer stage 1

BrCa_Stg4: Breast cancer stage 4

BrCa_Stg3B: Breast cancer stage 3B

BrCa_Stg2A: Breast cancer stage 2A

BrCa_Stg2B: Breast cancer stage 2B

BrCa_Stg1A: Breast cancer stage 1A

BrCa_Stg1: Breast cancer stage 1

PD_1_R_Melanoma: Melanoma responder

PD_1_NR_Melanoma: Melanoma non responder

TABLE 18a

ALS Probes - EpiSwitch ™ markers to stratify ALS vs healthy controls

| Probe | GeneName | Probe_Count_Total | Probe_Count_Sig | HyperG_Stats | FDR_HyperG | Percent_Sig | logFC |
|---|---|---|---|---|---|---|---|
| 11_923549_925733_976127_979142_FR | AP2A2 | 19 | 8 | 0.006668 | 0.24512 | 42.11 | −0.74197 |
| 11_36524913_36530925_36605543_36609927_FR | RAG1 | 46 | 16 | 0.001656 | 0.127493 | 34.78 | −0.69372 |
| 1_161590754_161594100_161627152_161631654_RR | FCGR2B; FCGR3A | 106 | 33 | 9.75E−05 | 0.015455 | 31.13 | −0.68658 |
| 11_36531355_36534043_36605543_36609927_RR | RAG1 | 46 | 16 | 0.001656 | 0.127493 | 34.78 | −0.68331 |
| 11_36531355_36534043_36605543_36609927_FR | RAG1 | 46 | 16 | 0.001656 | 0.127493 | 34.78 | −0.66709 |
| 11_36588999_36590845_36605543_36609927_FR | RAG2; RAG1 | 10 | 4 | 0.064184 | 0.80436 | 40 | −0.66598 |
| 11_36583119_36588432_36605543_36609927_RR | RAG2; RAG1 | 10 | 4 | 0.064184 | 0.80436 | 40 | −0.66346 |
| 1_172061602_172067357_172083100_172087823_RF | DNM3 | 1004 | 200 | 0.000673 | 0.069123 | 19.92 | −0.64487 |
| 1_171936106_171939290_172083100_172087823_RF | DNM3 | 1004 | 200 | 0.000673 | 0.069123 | 19.92 | −0.63828 |
| 1_171811918_171813464_172083100_172087823_RF | DNM3 | 1004 | 200 | 0.000673 | 0.069123 | 19.92 | −0.6224 |
| 1_172083100_172087823_172151185_172154127_FF | DNM3 | 1004 | 200 | 0.000673 | 0.069123 | 19.92 | −0.62018 |
| 1_171887726_171889817_172083100_172087823_RF | DNM3 | 1004 | 200 | 0.000673 | 0.069123 | 19.92 | −0.6103 |
| 13_111748012_111752622_111942125_111944243_RR | ARHGEF7 | 71 | 20 | 0.007714 | 0.24512 | 28.17 | −0.59912 |
| 1_172083100_172087823_172212232_172223166_FF | DNM3 | 1004 | 200 | 0.000673 | 0.069123 | 19.92 | −0.58901 |
| 11_36489037_36490716_36605543_36609927_FR | RAG1 | 46 | 16 | 0.001656 | 0.127493 | 34.78 | −0.56054 |
| 16_31228760_31230406_31342509_31344379_FR | ITGAM | 42 | 12 | 0.031165 | 0.564628 | 28.57 | −0.5409 |
| X_153269405_153271257_153287046_153289165_RR | IRAKI | 3 | 2 | 0.070512 | 0.80436 | 66.67 | −0.51331 |
| 13_111748012_111752622_111822569_111834523_RR | ARHGET7 | 71 | 20 | 0.007714 | 0.24512 | 28.17 | −0.50678 |
| 1_172053648_172060321_172083100_172087823_RR | DNM3 | 1004 | 200 | 0.000673 | 0.069123 | 19.92 | −0.49381 |
| 6_112058283_112061400_112189648_112191961_RR | FYN | 286 | 61 | 0.013161 | 0.344967 | 21.33 | −0.49133 |
| 11_923549_925733_976127_979142_RR | AP2A2 | 19 | 8 | 0.006668 | 0.24512 | 42.11 | −0.48405 |
| 6_111995015_111999450_112042041_112045568_FR | FYN | 286 | 61 | 0.013161 | 0.344967 | 21.33 | −0.48326 |

TABLE 18a-continued

ALS Probes - EpiSwitch™ markers to stratify ALS vs healthy controls

| Probe | GeneName | Probe_Count_Total | Probe_Count_Sig | HyperG_Stats | FDR_HyperG | Percent_Sig | logFC |
|---|---|---|---|---|---|---|---|
| 1_198560813_198564901_198619228_198622003_FF | PTPRC | 140 | 33 | 0.015074 | 0.344967 | 23.57 | −0.46857 |
| 1198564901_19856746_198666515_198673906_FF | PTPRC | 140 | 33 | 0.015074 | 0.344967 | 23.57 | −0.46848 |
| 19_55146487_55148774_55168120_55169250_RR | LILRB4 | 9 | 4 | 0.044033 | 0.749763 | 44.44 | −0.45415 |
| 1_161590754_161594100_161613514_161615341_RR | FCGR2B; FCGR3A | 106 | 33 | 9.75E−05 | 0.015455 | 31.13 | −0.45064 |
| 10_6639985_6645189_6663527_6669234_RR | PRKCQ | 135 | 28 | 0.097688 | 0.81988 | 20.74 | −0.44815 |
| 1_161495318_161496726_161576950_161581654_RF | FCGR3A | 41 | 11 | 0.057992 | 0.80436 | 26.83 | −0.44617 |
| 6_111995015_111999450_112042041_112045568_RR | FYN | 286 | 61 | 0.013161 | 0.344967 | 21.33 | −0.44013 |
| 16_31342509_31344379_31355595_31363682_RF | ITGAM | 42 | 12 | 0.031165 | 0.564628 | 28.57 | −0.43779 |
| 6_111968389_111970413_111988059_111992304_RF | FYN | 286 | 61 | 0.013161 | 0.344967 | 21.33 | −0.43175 |
| 6_112042041_112045568_112210969_112216626_RF | FYN | 286 | 61 | 0.013161 | 0.344967 | 21.33 | −0.43125 |
| 6_111988059_111992304_112042041_112045568_RF | FYN | 286 | 61 | 0.013161 | 0.344967 | 21.33 | −0.4278 |
| 6_112008166_112013438_112042041_112045568_RR | FYN | 286 | 61 | 0.013161 | 0.344967 | 21.33 | −0.42596 |
| 6_112042041_112045568_112061400_112062959_RF | FYN | 286 | 61 | 0.013161 | 0.344967 | 21.33 | −0.42515 |
| 6_112042041_112045568_112058283_112061400_RF | FYN | 286 | 61 | 0.013161 | 0.344967 | 21.33 | −0.42322 |
| 6_112042041_112045568_112189648_112191961_RF | FYN | 286 | 61 | 0.013161 | 0.344967 | 21.33 | −0.4227 |
| 11_923549_925733_976127_979142_RF | AP2A2 | 19 | 8 | 0.006668 | 0.24512 | 42.11 | −0.41839 |
| 1_161496726_161500050_161560557_161562782_FF | FCGR3A | 41 | 11 | 0.057992 | 0.80436 | 26.83 | −0.41237 |
| 10_6474855_6481197_6530169_6531558_FR | PRKCQ | 135 | 28 | 0.097688 | 0.81988 | 20.74 | −0.41233 |
| 11_1010876_1013083_964245_969445_FF | AP2A2 | 19 | 8 | 0.006668 | 0.24512 | 42.11 | −0.41196 |
| 8_42121759_42128721_42138740_42142593_FR | IKBKB | 13 | 5 | 0.046252 | 0.749763 | 38.46 | −0.40929 |
| 6_112042041_112045568_112109707_112111662_RF | FYN | 286 | 61 | 0.013161 | 0.344967 | 21.33 | −0.40843 |
| 1_172053648_172060321_172094882_172096647_RR | DNM3 | 1004 | 200 | 0.000673 | 0.069123 | 19.92 | −0.40354 |
| 6_111982743_111987540_112042041_112045568_RR | FYN | 286 | 61 | 0.013161 | 0.344967 | 21.33 | −0.39579 |
| 6_112042041_112045568_112071383_112076102_RF | FYN | 286 | 61 | 0.013161 | 0.344967 | 21.33 | −0.39434 |
| 11_36507808_36510397_36605543_36609927_RR | RAG1 | 46 | 16 | 0.001656 | 0.127493 | 34.78 | −0.38968 |
| 1_198564901_198567426_198619228_198622.003_FF | PTPRC | 140 | 33 | 0.015074 | 0.344967 | 23.57 | −0.38595 |
| 12_54983093_54985391_55002281_55007763_RR | GLYCAM1 | 6 | 3 | 0.058173 | 0.80436 | 50 | −0.38567 |
| 1_172053648_172060321_172111598_172120521_RR | DNM3 | 1004 | 200 | 0.000673 | 0.069123 | 19.92 | −0.37565 |
| 1_161590754JL61594100_161627152_161631654_RR | FCGR2B; FCGR3A | 106 | 33 | 0.000098 | 0.015454931 | 31.13 | −0.68658 |
| 10_6474855_6481197_6530169_6531558_FR | PRKCQ | 135 | 28 | 0.097688 | 0.819879953 | 20.74 | −0.41233 |
| 7_55089963_55093430_55294211_55302386_RF | EGFR | 199 | 39 | 0.116519 | 0.819879953 | 19.6 | −0.450938 |

TABLE 18b

ALS Probes - EpiSwitch™ markers to stratify ALS is. healthy controls

| Probe | AveExpr | t | P. Value | adj. P. Val | B |
|---|---|---|---|---|---|
| 11_923549_925733_976127_979142_FR | −0.74197 | −6.35597 | 0.000138 | 0.044071 | 1.465965 |
| 11_36524913_36530925_36605543_36609927_FR | −0.69372 | −4.70509 | 0.001143 | 0.045761 | −0.49343 |
| 1_161590754_161594100_161627152_161631654_RR | −0.68658 | −5.74114 | 0.00029 | 0.044071 | 0.788561 |
| 11_36531355_36534043_36605543_36609927_RR | −0.68331 | −5.81653 | 0.000264 | 0.044071 | 0.874877 |
| 11_36531355_36534043_36605543_36609927_FR | −0.66709 | −4.3522 | 0.001888 | 0.049346 | −0.9712 |
| 11_36588999_36590845_36605543_36609927_FR | −0.66598 | −4.62622 | 0.001276 | 0.046471 | −0.59845 |
| 11_36583119_36588432_36605543_36609927_RR | −0.66346 | −4.90718 | 0.000864 | 0.045761 | −0.22922 |
| 1_172061602_172067357_172083100_172087823_RF | −0.64487 | −5.96817 | 0.000219 | 0.044071 | 1.045707 |
| 1_171936106_171939290_172083100_172087823_RF | −0.63828 | −5.97658 | 0.000217 | 0.044071 | 1.05507 |
| 1_171811918_171813464_172083100_172087823_RF | −0.6224 | −5.88362 | 0.000243 | 0.044071 | 0.950922 |
| 1_172083100_172087823_172151185_172154127_FF | −0.62018 | −5.9045 | 0.000237 | 0.044071 | 0.974434 |
| 1_171887726_171889817_172083100_172087823_RF | −0.6103 | −5.86877 | 0.000248 | 0.044071 | 0.934149 |
| 13_111748012_111752622_111942125_111944243_RR | −0.59912 | −5.06808 | 0.000695 | 0.045348 | −0.02376 |
| 1_172083100_172087823_172212232_172223166_FF | −0.58901 | −6.00417 | 0.00021 | 0.044071 | 1.085715 |
| 11_36489037_36490716_36605543_36609927_FR | −0.56054 | −4.51138 | 0.001502 | 0.046471 | −0.75317 |
| 16_31228760_31230406_31342509_31344379_ | −0.5409 | −6.15285 | 0.000175 | 0.044071 | 1.248786 |
| X_153269405_153271257_153287046_153289165_RR | 0.51331 | −4.49207 | 0.001544 | 0.046471 | −0.7794 |
| 13_111748012_111752622_111822569_111834523_RR | −0.50678 | −5.88851 | 0.000242 | 0.044071 | 0.956426 |
| 1_172053648_172060321_172083100_172087823_RF | −0.49381 | −5.07129 | 0.000692 | 0.045348 | −0.01971 |
| 6_112058283_112061400_112189648_112191961_RR | −0.49133 | −5.76674 | 0.000781 | 0.044071 | 0.817402 |
| 11_923549_925733_976127_979142_RR | −0.48405 | −4.33332 | 0.001941 | 0.049346 | −0.99734 |
| 6_111995015_111999450_112042041_112045568_FR | −0.48326 | −5.12181 | 0.000646 | 0.045348 | 0.043877 |
| 1_198560813_198564901_198619228_198622003_FF | −0.46848 | −5.53965 | 0.000374 | 0.045348 | 0.553299 |
| 1_198564901_198567426_198666515_198673906_FF | −0 46848 | −4.59704 | 0.00133 | 0.046471 | −0.63757 |
| 19_55146487_55148774_55168120_55169250_RR | −0.45415 | −3.59971 | 0.005845 | 0.066691 | −2.05425 |
| 1_161590754_161594100_161613S14_161615341_RR | −0.45064 | −4.47431 | 0.001584 | 0.046791 | −0.80357 |
| 10_6639985_6645189_6663527_6669234_RR | −0.44815 | −5.15219 | 0.000617 | 0.045348 | 0.086906 |
| 1_161495318_161496726_161576950_161581654_RF | −0.44617 | −6.57127 | 0.000107 | 0.044071 | 1.689256 |
| 6_111995015_111999450_112042041_112045568_RR | −0.44013 | −4.82984 | 0.000961 | 0.045761 | −0.32954 |
| 16_31342509_31344379_31355595_31363682_RF | −0.43779 | −5.32335 | 0.000495 | 0.045348 | 0.293243 |
| 6_111968389_111970413_111988059_111992304_RF | −0.43175 | −6.06363 | 0.000195 | 0.044071 | 1.151353 |
| 6_112042041_112045568_112210969_112216626_RF | −0.43125 | −4.84006 | 0.000947 | 0.045761 | −0.31623 |

TABLE 18b-continued

ALS Probes - EpiSwitch™ markers to stratify ALS is. healthy controls

| | | | | | |
|---|---|---|---|---|---|
| 6_111983059_111992304_112042041_112045568_FR | −0.4278 | −4.61927 | 0.001289 | 0.046471 | −0.60776 |
| 6_112008166_112013438_112042041_112045568_RR | −0.42596 | −4.40407 | 0.001752 | 0.048299 | −0.8997 |
| 6_112042041_112045568_112061400_112062959_RF | −0.42515 | −4.68527 | 0.001175 | 0.045761 | −0.51975 |
| 6_112042041_112045568_112058283_112061400_RF | −0.42322 | −4.26948 | 0.00213 | 0.050442 | −1.08611 |
| 6_112042041_112045568_112189648_112191961_RF | −0.4227 | −4.40459 | 0.001751 | 0.048299 | −0.89898 |
| 11_923549_975733_476177_979147_RF | −0.41839 | −5.24568 | 0.000548 | 0.045348 | 0.197959 |
| 1_161496726_161500050_161560557_161562782_FF | −0.41237 | −5.11609 | 0.000651 | 0.045348 | 0.036697 |
| 10_6474855_6481197_6530169_6531558_TR | −0.41233 | −6.13891 | 0.000178 | 0.044071 | 1.233651 |
| 11_1010876_1013083_964245_969445_FF | −0.41196 | −5.1686 | 0.000607 | 0.045348 | 0.102386 |
| 8_42121759_42128721_42138740_42142593_FR | −0.40929 | −5.61946 | 0.000338 | 0.045348 | 0.647288 |
| 6_112047041_117045568_112109707_112111662_RF | −0 40843 | −4.55006 | 0.001422 | 0.046471 | −0.70081 |
| 1_172053648_172060321_172094882_172096647_RR | −0.40354 | −3.84586 | 0.004005 | 0.059124 | −1.6911 |
| 6_111982743_111987540_112042041_112045568_RR | −0.39579 | −4.65594 | 0.001224 | 0.045896 | −0.55877 |
| 6_112042041_112045568_112071383_112076102_RF | −0.39434 | −4.24316 | 0.002213 | 0.05138 | −1.12291 |
| 11_36507808_36510397_36605543_36609927_RR | −0.38968 | −3.63982 | 0.005493 | 0.064718 | −1.99464 |
| 1_198564901_198567426_198619228_198677003_FF | −0.38595 | −4.19734 | 0.002367 | 0.05251 | −1.18721 |
| 12_54983093_54985391_55002281_55007763_RR | −0.38567 | −5.1471 | 0.000625 | 0.045348 | 0.075549 |
| 1_172053648_172060321_172111598_172120521_RR | −0.37565 | −3.78978 | 0.004362 | 0.060452 | −1.77314 |
| 1_161590754_161594100_161627152_161631654_KH | −0.68658 | −5.74114 | 0.000290 | 0.044071 | 0.788560 |
| 10_6474855_6431197_6530169_6531558_FR | −0.41233 | −6.13891 | 0.000178 | 0.044071 | 1.233651 |
| 7_55089963_55093430_55794711_55307386_RF | −0.45094 | −5.99775 | 7.84E−05 | 0.004052 | 1.891281 |

| Probe | FC | FC_1 | LS | Loop Detected |
|---|---|---|---|---|
| 11_923549_925733_976127_979142_FR | 0.597922 | −1.67246 | −1 | ALS |
| 11_36524913_36530925_36605543_36609927_FR | 0.618257 | −1.61745 | −1 | ALS |
| 1_161590754_161594100_161627152_161631654_RR | 0.621327 | −1.60946 | −1 | ALS |
| 11_36531355_36534043_36605543_36609927_RR | 0.622736 | −1.60582 | −1 | ALS |
| 11_36531355_36534043_36605543_36609927_FR | 0.629774 | −1.58787 | −1 | AI.S |
| 11_36588999_36590845_36605543_36609927_FR | 0.630261 | −1.58664 | −1 | ALS |
| 11_36583119_36588432_36605543_36609927_RR | 0.631364 | −1.58387 | −1 | ALS |
| 1_172061602_172067357_172083100_172087823_RF | 0.639548 | −1.5636 | −1 | ALS |
| 1_171936106_171939290_172083100_172087823_RF | 0.642477 | −1.55648 | −1 | ALS |
| 1_171811918_171813464_172083100_172087823_RF | 0.649591 | −1.53943 | −1 | ALS |
| 1_172083100_172087823_172151185_172154127_FF | 0.650591 | −1.53706 | −1 | ALS |
| 1_171887726_171889817_172083100_172087823_RF | 0.655059 | −1.52658 | −1 | ALS |
| 13_111748012_111752622_111942125_111944243_RR | 0.660154 | −1.5148 | −1 | ALS |
| 1_172083100_172087823_172212232_172223166_FF | 0.6648 | −1.50421 | −1 | ALS |
| 11_36489037_36490716_36605543_36609927_FR | 0.678046 | −1.47483 | −1 | ALS |
| 16_31228760_31230406_31342509_31344379_ FR | 0.687343 | −1.45488 | −1 | ALS |
| X_153269405_153271257_153287046_153289165_RR | 0.700615 | −1.42732 | −1 | ALS |
| 13_111748012_111752622_111822569_111834523_RR | 0.703792 | −1.42087 | −1 | ALS |
| 1_172053648_172060321_172083100_172087823_RR | 0.710146 | −1.40816 | −1 | ALS |
| 6_112058283_112061400 112189648_112191961_RR | 0.71137 | −1.40574 | −1 | ALS |
| 11_923549_925733_976127_979142_RR | 0.714966 | −1.39867 | −1 | ALS |
| 6_111995015_111999450_112042041_112045568_FR | 0.715362 | −1.39789 | −1 | ALS |
| 1_198560813_198619228_198619228_198622003_FF | 0.722683 | −1.38373 | −1 | ALS |
| 1_198564901_198567426_198666515_198673906_FF | 0.722726 | −1.38365 | −1 | ALS |
| 19_55146487_55148774_55168120_55169250_RR | 0.729942 | −1.36997 | −1 | ALS |
| 1_161590754_161594100_161613S14_161615341_RR | 0.73172 | −1.36664 | −1 | ALS |
| 10_6639985_6645189_6663527_6669234_RR | 0.732982 | −1.36429 | −1 | ALS |
| 1_161495318_161496726_161576950_161581654_RF | 0.733991 | −1.36241 | −1 | ALS |
| 6_111995015_111999450_112042041_112045568_RR | 0.737066 | −1.35673 | −1 | ALS |
| 16_31342509_31344379_31355595_31363682_RF | 0.738265 | −1.35453 | −1 | ALS |
| 6_111968389_111970413_111988059_111992304_RF | 0.741361 | −1.34887 | −1 | ALS |
| 6_112042041_112045568_112210969_112216626_RF | 0.741621 | −1.3484 | −1 | ALS |
| 6_111983059_111992304_112042041_112045568_FR | 0.743394 | −1.34518 | −1 | ALS |
| 6_112008166_112013438_112042041_112045568_RR | 0.744345 | 1.34346 | −1 | ALS |
| 6_112042041_112045568_112061400_112062959_RF | 0.744764 | −1.34271 | −1 | ALS |
| 6_112042041_112045568_112058283_112061400_RF | 0.745758 | −1.34092 | −1 | ALS |
| 6_112042041_112045568_112189648_112191961_RF | 0.746026 | −1.34044 | −1 | ALS |
| 11_923549_975733_476177_979147_RF | 0.748257 | −1.33644 | −1 | ALS |
| 1_161496726_161500050_161560557_161562782_FF | 0.751389 | −1.33087 | −1 | ALS |
| 10_6474855_6481197_6530169_6531558_TR | 0.751408 | −1.33084 | −1 | ALS |
| 11_1010876_1013083_964245_969445_FF | 0.751603 | −1.33049 | −1 | ALS |
| 8_42121759_42128721_42138740_42142593_FR | 0.752995 | 1.32803 | −1 | ALS |
| 6_112047041_117045568_112109707_112111662_RF | 0.753443 | −1.32724 | −1 | ALS |
| 1_172053648_172060321_172094882_172096647_RR | 0.756 | −1.32275 | −1 | ALS |
| 6_111982743_111987540_112042041_112045568_RR | 0.760075 | −1.31566 | −1 | ALS |
| 6_112042041_112045568_112071383_112076102_RF | 0.760836 | −1.31434 | −1 | ALS |
| 11_36507808_36510397_36605543_36609927_RR | 0.763301 | −1.3101 | −1 | ALS |
| 1_198564901_198567426_198619228_198677003_FF | 0.765274 | −1.30672 | −1 | ALS |
| 12_54983093_54985391_55002281_55007763_RR | 0.765425 | −1.30646 | −1 | ALS |
| 1_172053648_172060321_172111598_172120521_RR | 0.77076 | −1.29742 | −1 | ALS |

TABLE 18b-continued

ALS Probes - EpiSwitch™ markers to stratify ALS is. healthy controls

| | | | | |
|---|---|---|---|---|
| 1_161590754_161594100_161627152_161631654_KH | 0.621327 | −1.60946 | −1 | ALS |
| 10_6474855_6431197_6530169_6531558_FR | 0.751408 | −1.33084 | −1 | ALS |
| 7_55089963_55093430_55794711_55307386_RF | 0.731567 | −1.36693 | −1 | ALS |

TABLE 18c

ALS Probes - EpiSwitch™ markers to stratify ALS vs. healthy controls

| Probe | Probe sequence 60 mer |
|---|---|
| 11_923549_925733_976127_979142_FR | GCCTGCAGGGGGCGCCCCCGCGCCTGCCTCGACCACACATCCACATGGACGCATGGCAGG (SEQ ID NO: 104) |
| 11_36524913_36530925_36605543_36609927_FR | TTATCAACCCGGCGTCTGGAACAATCGCTCGATCCACACCACACCAGCAGTGGGGCACAA (SEQ ID NO: 105) |
| 1_161590754_161594100_161627152_161631654_RR | AGGACAGAGACCCCTAATTCCACCACCATCGACCCTTCTGCTTTCTCTCCAGGGGATGGC (SEQ ID NO: 106) |
| 11_36531355_36534043_36605543_36609927_RR | CCGCCCCTGTCCTCTCGCTTCCCGCTGGTCGATCCACACCACACCAGCAGTGGGGCACAA (SEQ ID NO: 107) |
| 11_36531355_36534043_36605543_36609927_FR | AGTTCTTTCTTGAATTCTTTCCTGATACTCGATCCACACCACACCAGCAGTGGGGCACAA (SEQ ID NO: 108) |
| 11_36588999_36590845_36605543_36609927_FR | CCTGTAGCTCTGATGTCAGATGGCAATGTCGATCCACACCACACCAGCAGTGGGGCACAA (SEQ ID NO: 109) |
| 11_36583119_36588432_36605543_36609927_RR | CCACCTCATAGGGGAGGGCTTTACTCAGTCGATCCACACCACACCAGCAGTGGGGCACAA (SEQ ID NO: 110) |
| 1_172061602_172067357_172083100_172087823_RF | TCACCTCTGTCACCCACCCGTTCCACTCTCGATAAAGCACTTAGAACATGGCATATACTC (SEQ ID NO: 111) |
| 1_171936106_171939290_172083100_172087823_RF | TCACCTCTGTCACCCACCCGTTCCACTCTCGAATAGCTCCTATTGTTATGGAGTGTAGCA (SEQ ID NO: 112) |
| 1_171811918_171813464_172083100_172087823_RF | TCACCTCTGTCACCCACCCGTTCCACTCTCGAATTAGGAATCAGCATTTCTTCCACTGAG (SEQ ID NO: 113) |
| 1_172083100_172087823_172151185_172154127_FF | TCACCTCTGTCACCCACCCGTTCCACTCTCGATGCTCTCTTAGTGTTCCAATTCTCAGCT (SEQ ID NO: 114) |
| 1_171887726_171889817_172083100_172087823_RF | TCACCTCTGTCACCCACCCGTTCCACTCTCGAAATAGTAAAATTTGATTATCAAAATTTT (SEQ ID NO: 115) |
| 13_111748012_111752622_111942125_111944243_RR | TCCGTGACCCCCACAGCCGGTCGCCACATCGATTATCCAGAAGCTTCTTTTTTTTTAACC (SEQ ID NO: 116) |
| 1_172083100_172087823_172212232_172223166_FF | TCACCTCTGTCACCCACCCGTTCCACTCTCGAGGCTGCAGTGAATCATAATCATAGCACT (SEQ ID NO: 117) |
| 11_36489037_36490716_36605543_36609927_FR | AGTGTTGGTGAGATATTGTCTCTCAGTTTCGATCCACACCACACCAGCAGTGGGGCACAA (SEQ ID NO: 118) |
| 16_31228760_31230406_31342509_31344379_FR | GGTGGCATCCCCATCACTTCTCCATGCCTCGAGGTCCCCAACCCCCTGCCGCTCATCGTG (SEQ ID NO: 119) |
| X_153269405_153271257_153287046_153289165_RR | TCCTGCCCACAGCCCCCGCTTTAGCCTCTCGAGAATGCTAACAGCACAGGATACAGTACT (SEQ ID NO: 120) |
| 13_111748012_111752622_111822569_111834523_RR | TCCGTGACCCCCACAGCCGGTCGCCACATCGAGTAGCTGAGATTACAGGCATGTACCACC (SEQ ID NO: 121) |
| 1_172053648_172060321_172083100_172087823_RR | CTCCACGTCACCCCATGTCAATTCCAAGTCGATGCCAGACACTCTTCTGGGGGTGGGGTG (SEQ ID NO: 122) |
| 6_112058283_112061400_112189648_112191961_RR | CCTCTGTCCACACCATTATTTTAAAGAGTCGACATGCCTTGCTTTACCATTGTTTAATTT (SEQ ID NO: 123) |
| 11_923549_925733_976127_979142_RR | AGTGGTACAATCATGAATCACTACAGCCTCGACCACACATCCACATGGACGCATGGCAGG (SEQ ID NO: 124) |
| 6_111995015_111999450_112042041_112045568_FR | CTCCCAAGGTAAACTCATTGCCGAAACCTCGAGTTGTTGCCACCCCACCCTCCTCAAACC (SEQ ID NO: 125) |

TABLE 18c-continued

ALS Probes - EpiSwitch ™ markers to stratify ALS vs. healthy controls

| Probe | Probe sequence 60 mer |
|---|---|
| 1_198560813_198564901_198619228_198622003_FF | TGTTTTTTATTGTTTGATGTCCAATGTATCGAGCCGCCCTTGACATAACACCATCTTTTA (SEQ ID NO: 126) |
| 1_198564901_198567426_198666515_198673906_FF | TTGAACCCAAGAGGTCACACCACTGCACTCGACGCCCAGCAAGTAGGCACAGTTCCAAT (SEQ ID NO: 127) |
| 19_55146487_55148774_55168120_55169250_RR | TTGGAGCCCCCTGCCCTGCACACACAGCTCGAGATTTGTCTTTCTGTTCCTGGCTTATTT (SEQ ID NO: 128) |
| 1_161590754_161594100_161613514_161615341_RR | AGGACAGAGACCCCTAATTCCACCACCATCGAACAACTGCAAACTCCACTCAACATCTTT (SEQ ID NO: 129) |
| 10_6639985_6645189_6663527_6669234_RR | AACCACACAACTGCTACTCACAATTCTTTCGAAACCAGAAGACCCAATATAATATCTAGT (SEQ ID NO: 130) |
| 1_161495318_161496726_161576950_161581654_RF | ACCCAGGATAAAACGCAGTGTTGACCGATCGAGGGCGTGGACTTCTACACGTCCATCACT (SEQ ID NO: 131) |
| 6_111995015_111999450_112042041_112045568_RR | GGCTTATCCATGCTTAAATTGATTAACGTCGAGTTGTTGCCACCCCACCCTCCTCAAACC (SEQ ID NO: 132) |
| 16_31342509_31344379_31355595_31363682_RF | AGTGGTCTCACCATGGCTTTCTTCCAATTCGAGGTCCCCAACCCCCTGCCGCTCATCGTG (SEQ ID NO: 133) |
| 6_111968389_111970413_111988059_111992304_RF | GGAACTGCATCCATACTTGTTACACATCTCGAACCGGAGTGGACGTGTGTCCACATGTAA (SEQ ID NO: 134) |
| 6_112042041_112045568_112210969_112216626_RF | ATCTAAACACAGTCCATGCTAAAAAGCTTCGAGTTGTTGCCACCCCACCCTCCTCAAACC (SEQ ID NO: 135) |
| 6_111988059_111992304_112042041_112045568_FR | GGAACTGCATCCATACTTGTTACACATCTCGAGTTGTTGCCACCCCACCCTCCTCAAACC (SEQ ID NO: 136) |
| 6_112008166_112013438_112042041_112045568_RR | CTCAGGAAGAAGTGGATCCCTGTTTCTTTCGAGTTGTTGCCACCCCACCCTCCTCAAACC (SEQ ID NO: 137) |
| 6_112042041_112045568_112061400_112062959_RF | AGTGTATTTTTCACTACACTAGTGGTTTTCGAGTTGTTGCCACCCCACCCTCCTCAAACC (SEQ ID NO: 138) |
| 6_112042041_112045568_112058283_112061400_RF | TAAATACAGATGAAACCAACTAATAGACTCGAGTTGTTGCCACCCCACCCTCCTCAAACC (SEQ ID NO: 139) |
| 6_112042041_112045568_112189648_112191961_RF | AGCTGGGCCCCAAAGGTTAAAAAGGACTTCGAGTTGTTGCCACCCCACCCTCCTCAAACC (SEQ ID NO: 140) |
| 11_923549_925733_976127_979142_RF | CCACGTGTCGCGGGCCTGAGTGTGCCCCTCGAGGCTGTAGTGATTCATGATTGTACCACT (SEQ ID NO: 141) |
| 1_161496726_161500050_161560557_161562782_FF | ACCTAGGATAAAAGGCAGTGTTGACCGATCGACACCCATATGAGCCCCACCCGGCTTCAA (SEQ ID NO: 142) |
| 10_6474855_6481197_6530169_6531558_FR | TTCCACCTGTAATACTGTGCCTGTATTCTCGAGCAGGCGCTCAACAAATACAACTTCCTT (SEQ ID NO: 143) |
| 11_1010876_1013083_964245_969445_FF | GTGCCCTCCTCGCCCCTGATGGGTCTGGTCGAGACCAGCCTCAACATGGAGAAACACCAT (SEQ ID NO: 144) |
| 8_42121759_42128721_42138740_42142593_FR | CCACCCCCGCCCCGGGGGAGTCGCCCGGTCGAGGGCCTGGCAAGAAGACAGAAGCCGACT (SEQ ID NO: 145) |
| 6_112042041_112045568_112109707_112111662_RF | AAGTCCTAAGAACACTGAAAATCTCAGATCGAGTTGTTGCCACCCCACCCTCCTCAAACC (SEQ ID NO: 146) |
| 1_172053648_172060321_172094882_172096647_RR | CTCCACGTCACCCCATGTCAATTCCAAGTCGAATACTCAAAACAGAATTTGATATTCAAA (SEQ ID NO: 147) |
| 6_111982743_111987540_112042041_112045568_RR | CCAAATCCGAACCTCCTCTGTGAAGCATTCGAGTTGTTGCCACCCCACCCTCCTCAAACC (SEQ ID NO: 148) |
| 6_112042041_112045568_112071383_112076102_RF | GTTAACAGTAATACGATGTTAAAAGGACTCGAGTTGTTGCCACCCCACCCTCCTCAAACC (SEQ ID NO: 149) |
| 11_36507808_36510397_36605543_36609927_RR | GGCTGGCGGATTACTTGAAGCCAGGAGTTCGATCCACACCACACCAGCAGTGGGGCACAA (SEQ ID NO: 150) |

TABLE 18c-continued

ALS Probes - EpiSwitch ™ markers to stratify ALS vs. healthy controls

| Probe | Probe sequence 60 mer |
|---|---|
| 1_198564901_198567426_198619228_198622003_FF | TTGAACCCAAGAGGTCACACCACTGCACTCGAGCCGCCCTTGACATAACACCATCTTT TA (SEQ ID NO: 151) |
| 12_54983093_54985391_55002281_55007763_RR | CCCCTAATTTAGCAAGCAGAAAGAGAACTCGATGCTTCATTTGACTCACACTCACATT TA (SEQ ID NO: 152) |
| 1_172053648_172060321_172111598_172120521_RR | CTCCACGTCACCCCATGTCAATTCCAAGTCGAAAATAAGTCGCTAGAGCCACATCAAG CA (SEQ ID NO: 153) |
| 1_161590754_161594100_161627152_161631654_RR | AGGACAGAGACCCCTAATTCCACCACCATCGACCCTTCTGCTTTCTCTCCAGGGGATG GC (SEQ ID NO: 154) |
| 10_6474855_6481197_6530169_6531558_FR | TTCCACCTGTAATACTGTGCCTGTATTCTCGAGCAGGCGCTCAACAAATACAACTTCC TT (SEQ ID NO: 155) |
| 7_55089963_55093430_55294211_55302386_RF | ACCAAACCCAAGGTCCGCTGCTCGCTGCTCGAATTCCCAACTGAGGGAGCTTTGTGGA AA (SEQ ID NO: 156) |

TABLE 18D

ALS Probes - EpiSwitch™ markers to stratify ALS v. healthy controls

| Probe | Chr | Start1 | End1 | Start2 | End2 |
|---|---|---|---|---|---|
| 11_923549_925733__976127_979142_FR | 11 | 925704 | 925733 | 976128 | 976157 |
| 11_36524913_36530925_36605543_36609927_FR | 11 | 36530896 | 36530925 | 36605544 | 36605573 |
| 1_161590754_161594100_161627152_161631_654_RR | 1 | 161590755 | 161590784 | 161627153 | 161627182 |
| 11_36531355_36534043_36605543_36609927_RR | 11 | 36531356 | 36531385 | 36605544 | 36605573 |
| 11_36531355_36534043_36605543_36609927_FR | 11 | 36534014 | 36534043 | 36605544 | 36605573 |
| 11_36588999_36590845_36605543_36609927_RR | 11 | 36590816 | 36590845 | 36605544 | 36605573 |
| 11_36583119_36588432_36605543_36609927_RR | 11 | 36583120 | 36583149 | 36605544 | 36605573 |
| 1_172061602_172067357_172083100_172087823_RF | 1 | 172061603 | 172061632 | 172087794 | 172087823 |
| 1_171936106_171939290_172083100_172087823_RF | 1 | 171936107 | 171936136 | 172087794 | 172087823 |
| 1_171811918_171813464_172083100_172087823_RF | 1 | 171811919 | 171811948 | 172087794 | 172087823 |
| 1_172083100_172087823_172151185_172154127_FF | 1 | 172087794 | 172087823 | 172154098 | 172154127 |
| 1_171887726_171889817_172083100_172087823_RF | 1 | 171887727 | 171887756 | 172087794 | 172087823 |
| 13_111748012_111752622_111942125_111944243_RR | 13 | 111748013 | 111748042 | 111942126 | 111942155 |
| 1_172083100_172087823_172212232_172223_156_FF | 1 | 172087794 | 172087823 | 172223137 | 172223166 |
| 11_36489037_3649071_36605543_36609927 | 11 | 36490687 | 36490716 | 36605544 | 36605573 |
| 16_31228760_31230406_31342509_31344379_FR | 16 | 31230377 | 31230406 | 31342510 | 31342539 |
| X_153269405_153271257_153287046_153289155_RR | X | 153269406 | 153269435 | 153287047 | 153287076 |
| 13_111748012_111752622_111822569_111834523_RR | 13 | 111748013 | 111748042 | 111822570 | 111822599 |
| 1_172053648_172060321_172083100_172087823_RR | 1 | 172053649 | 172053678 | 172083101 | 172083130 |
| 6_112058283_112061400_112189648_112191961_RR | 6 | 112058284 | 112058313 | 112189649 | 112189678 |
| 11_923549_925733_976127_979142_RR | 11 | 923550 | 923579 | 976128 | 976157 |
| 6_111995015_111999450_112042041_112045568_FR | 6 | 111999421 | 111999450 | 112042042 | 112042071 |
| 1_198560813_198564901_198619228_198622003_FF | 1 | 198564872 | 198564901 | 198621974 | 198622003 |
| 1_198564901_198567426_198666515_198673906_FF | | 198567397 | 198567426 | 198673877 | 198673906 |
| 19_55146487_55148774_55168120_55169250_RR | 19 | 55146488 | 55146517 | 55168121 | 55168150 |
| 1_161590754_161594100_161613514_161615341_RR | 1 | 161590755 | 161590784 | 161613515 | 161613544 |
| 10_6639985_6645189_6663527_6669234_RR | 10 | 6639986 | 6640015 | 6663528 | 6663557 |
| 1_161495318_161496726_161576950_161581654_RF | 1 | 161495319 | 161495348 | 161581625 | 161581654 |
| 6_111995015_111999450_112042041_112045568_RR | 6 | 111995016 | 111995045 | 112042042 | 112042071 |
| 16_31342509_31344379_31355595_31363682_RF | 16 | 31342510 | 31342539 | 31363653 | 31363682 |
| 6_111968389_111970413_111988059_111992304_RF | 6 | 111968390 | 111968419 | 111992275 | 111992304 |
| 6_112042041_112045568_112210969_112216626_RF | 6 | 112042042 | 112042071 | 112216597 | 112216626 |
| 6_111988059_111992304_112042041_112045568_FR | 6 | 111992275 | 111992304 | 112042042 | 112042071 |
| 6_112008166_112013438_112042041_112045568_RR | 6 | 112008196 | 112008196 | 112042042 | 112042071 |
| 6_112042041_11204556B_112061400_112062959_RF | 6 | 112042042 | 112042071 | 112062930 | 112062959 |
| 6_112042041_112045568_112058283_112061400_RF | 6 | 112042042 | 112042071 | 112061371 | 112061400 |
| 6_112042041_112045568_112189648_112191951_RF | 6 | 112042042 | 112042071 | 112191932 | 112191961 |
| 11_923549_925733_976127_979142_RF | 11 | 923550 | 923579 | 979113 | 979142 |
| 1_161496726_161500050_161560557_161562782_FF | 1 | 161500021 | 161500050 | 161562753 | 161562782 |
| 10_6474855_6481197_6530169_6531558_FR | 10 | 6481168 | 6481197 | 6530170 | 6530199 |
| 11_1010876_1013083_964245_969445_FF | 11 | 1013054 | 1013083 | 969416 | 969445 |
| 8_42121759_42128721_42138740_42142593_FR | 8 | 42128692 | 42128721 | 42138741 | 42138770 |
| 6_112042041_112045568_112109707_112111662_RF | 6 | 112042042 | 112042071 | 112111633 | 112111662 |
| 1_172053648_172060321_172094882_172096647_RR | 1 | 172053649 | 172053678 | 172094883 | 172094912 |
| 6_111982743_111987540_112042041_112045558_RR | 6 | 111982744 | 111982773 | 112042042 | 112042071 |
| 6_112042041_112045568_112071383_112076102_RF | 6 | 112042042 | 112042071 | 112076073 | 112076102 |
| 11_36507808_36510397_36605543_36609927_RR | 11 | 36507809 | 36507838 | 36605544 | 36605573 |

TABLE 18D-continued

ALS Probes - EpiSwitch™ markers to stratify ALS v. healthy controls

| | | | | | |
|---|---|---|---|---|---|
| 1_198564901_198567426_198619228_198622003_FF | 1 | 198567397 | 198567426 | 198621974 | 198622003 |
| 12_54983093_54985391_55002281_55007763_RR | 12 | 54983094 | 54983123 | 55002282 | 55002311 |
| 1_172053648_172060321_172111598_172120521_RR | 1 | 172053649 | 172053678 | 172111599 | 172111628 |
| 1_161590754_161594100_161627152_161631654_RR | 1 | 161590754 | 161590783 | 161627152 | 161627182 |
| 10_6474855_6481197_6530169_6531558_FR | 10 | 6481168 | 6481197 | 6530169 | 6530198 |
| 7_55089963_55093430_55294211_55302386_RF | 7 | 55089963 | 55089992 | 55302357 | 55302386 |

| | | 4 kb Sequence Location | | | |
|---|---|---|---|---|---|
| Probe | Chr | Start1 | End1 | Start2 | End2 |
| 11_923549_925733__976127_979142_FR | 11 | 921734 | 925733 | 976128 | 980127 |
| 11_36524913_36530925_36605543_36609927_FR | 11 | 36526926 | 36530925 | 36605544 | 36609543 |
| 1_161590754_161594100_161627152_161631_654_RR | 1 | 161590755 | 161594754 | 161627153 | 161631152 |
| 11_36531355_36534043_36605543_36609927_RR | 11 | 36531356 | 36535355 | 36605544 | 36609543 |
| 11_36531355_36534043_36605543_36609927_RR | 11 | 36530044 | 36534043 | 36605544 | 36609543 |
| 11_36588999_36590845_36605543_36609927_FR | 11 | 36586846 | 36590845 | 36605544 | 36609543 |
| 11_36583119_36588432_36605543_36609927_RR | 11 | 36583120 | 36587119 | 36605544 | 36609543 |
| 1_172061602_172067357_172083100_172087823_RF | 1 | 172061603 | 172065602 | 172083824 | 172087823 |
| 1_171936106_171939290_172083100_172087823_RF | 1 | 171936107 | 171940106 | 172083824 | 172087823 |
| 1_171811918_171813464_172083100_172087823_RF | 1 | 171811919 | 171815918 | 172083824 | 172087823 |
| 1_172083100_172087823_172151185_172154127_FF | 1 | 172083824 | 172087823 | 172150128 | 172154127 |
| 1_171887726_171889817_172083100_172087823_RF | 1 | 171887727 | 171891726 | 172083824 | 172087823 |
| 13_111748012_111752622_111942125_111944243_RR | 13 | 111748013 | 111752012 | 111942126 | 111946125 |
| 1_172083100_172087823_172212232_172223_156_FF | 1 | 172083824 | 172087823 | 172219167 | 172223166 |
| 11_36489037_3649071_36605543_36609927 | 11 | 36486717 | 36490716 | 36605544 | 36609543 |
| 16_31228760_31230406_31342509_31344379_FR | 16 | 31228407 | 31230406 | 31342510 | 31346509 |
| X_153269405_153271257_153287046_153289155_RR | X | 153269406 | 153273405 | 153287047 | 153291046 |
| 13_111748012_111752622_111822569_111834523_RR | 13 | 111748013 | 111752012 | 111822570 | 111826569 |
| 1_172053648_172060321_172083100_172087823_RR | 1 | 172053649 | 172057648 | 172083101 | 172087100 |
| 6_112058283_112061400_112189648_112191961_RR | 6 | 112058284 | 112061400 | 112189649 | 112193648 |
| 11_923549_925733_976127_979142_RR | 11 | 923550 | 927549 | 976128 | 980127 |
| 6_111995015_111999450_112042041_112045568_FR | 6 | 111995451 | 111999450 | 112042042 | 112046041 |
| 1_198560813_198564901_198619228_198622003_FF | 1 | 198560902 | 198564901 | 198618004 | 198622003 |
| 1_198564901_198567426_198666515_198673906_FF | 1 | 198563427 | 198567426 | 198669907 | 198673906 |
| 19_55146487_55148774_55168120_55169250_RR | 19 | 55146488 | 55150487 | 55168121 | 55172120 |
| 1_161590754_161594100_161613514_161615341_RR | 1 | 161590755 | 161594754 | 161613515 | 161617514 |
| 10_6639985_6645189_6663527_6669234_RR | 10 | 6639986 | 6643985 | 6663528 | 6667527 |
| 1_161495318_161496726_161576950_161581654_RF | 1 | 161495319 | 161499318 | 161577655 | 161581654 |
| 6_111995015_111999450_112042041_112045568_RR | 6 | 111995016 | 111999450 | 112042042 | 112046041 |
| 16_31342509_31344379_31355595_31363682_RF | 16 | 31342510 | 31346509 | 31359683 | 31363682 |
| 6_111968389_111970413_111988059_111992304_RF | 6 | 111968390 | 111972389 | 111988305 | 111992304 |
| 6_112042041_112045568_112210969_112216626_RF | 6 | 112042042 | 112046041 | 112212627 | 112216626 |
| 6_111988305_111992304_112042041_112045568_FR | 6 | 111988305 | 111992304 | 112042042 | 112046041 |
| 6_112008166_112013438_112042041_112045568_RR | 6 | 1120008167 | 112012166 | 112042042 | 112046041 |
| 6_112042041_11204556B_112061400_112062959_RF | 6 | 112042042 | 112046041 | 112058960 | 112062959 |
| 6_112042041_112045568_112058283_112061400_RF | 6 | 112042042 | 112046041 | 112057401 | 112061400 |
| 6_112042041_112045568_112189648_112191951_RF | 6 | 112042042 | 112046041 | 112187962 | 112191961 |
| 11_923549_925733_976127_979142_RF | 11 | 923550 | 927549 | 975143 | 979142 |
| 1_161496726_161500050_161560557_161562782_FF | 1 | 161496051 | 161500050 | 161558783 | 161562782 |
| 10_6474855_6481197_6530169_6531558_FR | 10 | 6477198 | 6481197 | 6530170 | 6534169 |
| 11_1010876_1013093_964245_969445_FF | 11 | 1009084 | 1013083 | 965446 | 969445 |
| 8_42121759_42128721_42138740_42142593_FR | 8 | 42124722 | 42128721 | 42138741 | 42142740 |
| 6_112042041_112045568_112109707_112111662_RF | 6 | 112042042 | 112046041 | 112107663 | 112111662 |
| 1_172053648_172060321_172094882_172096647_RR | 1 | 172053649 | 172057648 | 172094883 | 172098882 |
| 6_111982743_111987540_112042041_112045558_RR | 6 | 111982744 | 111986743 | 112042042 | 112046041 |
| 6_112042041_112045568_112071383_112076102_RF | 6 | 112042042 | 112046041 | 112072103 | 112076102 |
| 11_36507808_36510397_36605543_36609927_RR | 11 | 36507809 | 36511808 | 36605544 | 36609543 |
| 1_198564901_198567426_198619228_198622003_FF | 1 | 198563427 | 198567426 | 198618004 | 198622003 |
| 12_54983093_54985391_55002281_55007763_RR | 12 | 54983094 | 54987093 | 55002282 | 55006281 |
| 1_172053648_172060321_172111598_172120521_RR | 1 | 172053649 | 172057648 | 172111599 | 172115598 |
| 1_161590754_161594100_161627152_161631654_RR | 1 | 161590754 | 161594753 | 161627152 | 161631151 |
| 10_6474855_6481197_6530169_6531558_FR | 10 | 6477198 | 6481197 | 6530169 | 6534168 |
| 7_55089963_55093430_55294211_55302386_RF | 7 | 55089963 | 55093962 | 55298387 | 55302386 |

TABLE 19A

Pre-type 2 diabetes mellitus probes - EpiSwitch™ markers to stratify pre-type 2 diabetes vs. healthy controls

| Probe | GeneLocus | Probe_Count_Total | Probe_Count_Sig | HyperG_Stats | FDR_Hyper G | Percent_Sig | logFC |
|---|---|---|---|---|---|---|---|
| IGF2_11_2162616_2164979_2210793_2214417_RF | IGF2 | 20 | 6 | 0.013782 | 0.264753 | 30 | 0.477536 |
| ADCY5_3_123037100_123044621_123133741_123143812_RF | ADCY5 | 90 | 21 | 0.000309 | 0.032153 | 23.33 | 0.391689 |

TABLE 19A-continued

Pre-type 2 diabetes mellitus probes - EpiSwitch™ markers to stratify pre-type 2 diabetes vs. healthy controls

| Probe | GeneLocus | Probe_Count_Total | Probe_Count_Sig | HyperG_Stats | FDR_Hyper G | Percent_Sig | logFC |
|---|---|---|---|---|---|---|---|
| TASP1_20_13265932_13269301_13507251_13521471_RR | TASP1 | 172 | 30 | 0.003377 | 0.154079 | 17.44 | 0.356789 |
| TNFRSF1B_1_12241967_12245164_12269283_12270518_RR | TNFRSF1B | 12 | 5 | 0.005227 | 0.162271 | 41.67 | 0.345092 |
| SREBF1_17_17743896_17753157_17777190_17783023_RF | SREBF1 | 19 | 8 | 0.000366 | 0.032153 | 42.11 | 0.340726 |
| TSPAN8_1271690883_71707188_71850942_71857145_RF | TSPAN8 | 200 | 31 | 0.016203 | 0.295714 | 15.5 | 0.339978 |
| CYB5R4_6841553857_84562119_84611173_84616879_FF | CYB5R4 | 39 | 11 | 0.001648 | 0.085942 | 28.21 | 0.336289 |
| KCNJ11_11_17401446_17405499_1744519_17452295_RF | KCNJ11 | 22 | 9 | 0.000203 | 0.032153 | 40.91 | 0.325425 |
| PTPRD_9_9058670_9068143_9186543_9197535_FF | PTPRD | 171 | 28 | 0.010775 | 0.218484 | 16.37 | 0.325058 |
| ICAM1_19_10368390_10370561_10406169_10407761_RF | ICAM1 | 9 | 4 | 0.009728 | 0.218484 | 44.44 | 0.323175 |
| ABCC8_11_17401446_17405499_17445199_17452295_RF | ABCC8 | 22 | 7 | 0.005571 | 0.162271 | 31.82 | 0.322412 |
| CYP2C9_10_96661464_96668745_96741594_96747469_FR | CYP2C9 | 8 | 6 | 3.00E-05 | 0.010944 | 75 | 0.315667 |
| KCNJ11_11_17401446_17405499_17419957_17422762_RF | KCNJ11 | 22 | 9 | 0.000203 | 0.032153 | 40.91 | 0.313372 |
| LEP_7_127838673_127843908_127864269_127868140_RF | LEP | 19 | 6 | 0.010562 | 0.218484 | 31.58 | 0.308548 |
| CDKN2A_9_21967880_21969373_22029988_22034038_RR | CDKN2A | 13 | 6 | 0.001156 | 0.070344 | 46.15 | 0.306887 |
| CACNA1C_12_2099248_2111840_2394923_2398377_FR | CACNA1C | 197 | 33 | 0.004207 | 0.162271 | 16.75 | 0.306732 |
| PIK3R3_1_46633134_46639474_46678880_46685388_RF | PIK3R3 | 17 | 6 | 0.00578 | 0.162271 | 35.29 | 0.305924 |
| ABCC8_11_17445199_17452295_17545007_17546815_RF | ABCC8 | 22 | 7 | 0.005571 | 0.162271 | 31.82 | 0.30417 |
| CDKN2A_9_21967880_21969373_22029988_22034038_RF | CDKN2A | 13 | 6 | 0.001156 | 0.070344 | 46.15 | 0.30104 |
| KCNJ11_11_17419957_17422762_17445199_17452295_RR | KCNJ11 | 22 | 9 | 0.000203 | 0.032153 | 40.91 | 0.299727 |
| ICAM1_19_10341612_10343024_10406169_10407761_RF | ICAM1 | 9 | 4 | 0.009728 | 0.218484 | 44.44 | 0.298038 |
| SREBF1_17_17722022_17726360_17743896_17753157_RR | SREBF1 | 19 | 8 | 0.000366 | 0.032153 | 42.11 | 0.296794 |
| IGF2_11_2162616_2164979_2191728_2194389_FF | IGF2 | 20 | 6 | 0.013782 | 0.264753 | 30 | 0.293116 |
| ABCC8_11_17419957_17422762_17445199_17452295_RR | ABCC8 | 22 | 7 | 0.005571 | 0.162271 | 31.82 | 0.290947 |
| CACNA1C_12_2099248_2111840_2221145_2224077_FR | CACNA1C | 197 | 33 | 0.004207 | 0.162271 | 16.75 | 0.280753 |
| INS_11_2191728_2194389_2210793_2214417_RF | INS | 17 | 6 | 0.00578 | 0.162271 | 35.29 | 0.275842 |
| MAPK10_4_87459424_87462716_87493751_87502639_FF | MAPK10 | 171 | 28 | 0.010775 | 0.218484 | 16.37 | 0.274476 |
| PTPRD_9_8886566_8895563_9186543_9197535_FF | PTPRD | 171 | 28 | 0.010775 | 0.218484 | 16.37 | 0.273693 |
| CDKN2A_9_22005914_22007156_22029988_22034038_RF | CDKN2A | 13 | 6 | 0.001156 | 0.070344 | 46.15 | 0.273046 |
| LEP_7_127838673_127843908_127903727_127906543_RF | LEP | 19 | 6 | 0.010562 | 0.218484 | 31.58 | 0.272802 |
| TSPAN8_12_71559221_71564078_71667712_71675824_RR | TSPAN8 | 200 | 31 | 0.016203 | 0.295714 | 15.5 | 0.27188 |
| CYB5R4_6_84533887_84541872_84600402_84604101_RF | CYB5R4 | 39 | 11 | 0.001648 | 0.085942 | 28.21 | 0.271658 |
| CYP2C9_10_96661464_96668745_96755577_96760846_FF | CYP2C9 | 8 | 6 | 3.00E-05 | 0.010944 | 75 | 0.270453 |
| TSPAN8_12_71559221_71564078_71675824_71684278_RF | TSPAN8 | 200 | 31 | 0.016203 | 0.295714 | 15.5 | 0.266085 |
| CYB5R4_6_841533887_84541872_84611173_84616879_FF | CYB5R4 | 39 | 11 | 0.001648 | 0.085942 | 28.21 | 0.265364 |
| TASP1_20_13441063_13442565_13507251_13521471_FR | TASP1 | 172 | 30 | 0.003377 | 0.154079 | 17.44 | 0.255345 |
| KCNJ11_11_17430922_17433660_17445199_17452295_RR | KCNJ11 | 22 | 9 | 0.000203 | 0.032153 | 40.91 | 0.25388 |
| INS_11_2162616_2164979_2191728_2194389_RR | INS | 17 | 5 | 0.00578 | 0.162271 | 35.29 | 0.253761 |
| PTPRD_9_9551379_9564487_9852099_9857206_RR | PTPRD | 171 | 28 | 0.010775 | 0.218484 | 16.37 | 0.253043 |
| IGF2_11_2162616_2164979_2191728_2194389_RR | IGF2 | 20 | 6 | 0.013782 | 0.264753 | 30 | 0.251753 |
| TNFRSF1B_1_12241967_12245164_12274102_12277104_RF | TNFRSF1B | 12 | 5 | 0.005227 | 0.162271 | 41.67 | 0.251298 |
| TSPAN8_12_71667712_71675824_71850942_71857145_RF | TSPAN8 | 200 | 31 | 0.016203 | 0.295714 | 15.5 | 0.248869 |
| CACNA1C_12_2099248_2111840_2200229_2202042_RF | CACNA1C | 197 | 33 | 0.004207 | 0.162271 | 16.75 | 0.24864 |
| CYP2C9_10_96690028_96694118_96748928_96755577_FR | CYP2C9 | 8 | 6 | 3.00E-05 | 0.010944 | 75 | 0.247789 |
| TSPAN8_12_71559221_71564078_7169088_71707188_RR | TSPAN8 | 200 | 31 | 0.016203 | 0.295714 | 15.5 | 0.24768 |
| ABCC8_11_17445199_17452295_17514252_17516772_RF | ABCC8 | 22 | 7 | 0.005571 | 0.162271 | 31.82 | 0.247675 |
| ADCY5_3_123098260_123106114_123133741_123143812_RF | ADCY5 | 90 | 21 | 0.000309 | 0.032153 | 23.33 | 0.245589 |
| IGF2_11_2191728_2194389_2210793_2214417_RF | IGF2 | 20 | 6 | 0.013782 | 0.264753 | 30 | 0.244894 |
| SREBF1_17_17722022_17726360_17743896_17753157_FR | SREBF1 | 19 | 8 | 0.000366 | 0.032153 | 42.11 | 0.243916 |
| ABCC8_11_17445199_17452295_1753899_17541116_RF | ABCC8 | 22 | 7 | 0.005571 | 0.162271 | 31.82 | 0.243453 |

TABLE 19B

Pre-type 2 diabetes mellitus probes - Epi Switch™ markers to stratify pre-type 2 diabetes vs. healthy controls

| Probe | AveExpr | t | P.Value | adj.P.Val | B |
|---|---|---|---|---|---|
| IGF2_11_2162616_2164979_2210793_2214417_RF | 0.477536 | 3.535151 | 0.006208 | 0.083614 | -2.156406 |
| ADCY5_3_123037100_123044621_123133741_123143812_RF | 0.391689 | 3.616002 | 0.005464 | 0.080553 | -2.032765 |
| TASP1_20_13265932_13269301_13507251_13521471_RR | 0.356789 | 6.963954 | 6.09E-05 | 0.036169 | 2.219697 |
| TNFRSF1B_1_12241967_12245164_12269283_12270518_RR | 0.345092 | 5.317703 | 0.000458 | 0.047353 | 0.352959 |
| SREBF1_17_17743896_17753157_17777190_17783023_RF | 0.340726 | 5.383925 | 0.000419 | 0.046852 | 0.436391 |
| TSPAN8_12_71690883_7185094_71857145_RF | 0.339978 | 6.894591 | 6.59E-05 | 0.036169 | 2.149351 |
| CYB5R4_6_84553857_84562119_84611173_84616879_FF | 0.336456 | 4.684603 | 0.001097 | 0.053336 | -0.481351 |
| KCNJ11_11_17401446_17405499_17445199_17452295_RF | 0.325425 | 5.839875 | 0.000232 | 0.042245 | 0.991283 |
| PTPRD_9_9058670_9068143_9186543_9197535_FF | 0.325058 | 6.01299 | 0.000187 | 0.04041 | 1.193155 |
| ICAM1_19_10368390_10370561_10406169_10407761_RF | 0.323175 | 4.217282 | 0.002171 | 0.060012 | -1.139093 |
| ABCC8_11_17401446_17405499_17445199_17452295_RF | 0.322412 | 6.516205 | 0.000102 | 0.037879 | 1.753307 |
| CYP2C9_10_96661464_96668745_96741594_96747469_FR | 0.315667 | 5.688997 | 0.000282 | 0.042245 | 0.811417 |
| KCNJ11_11_17401446_17405499_17419957_17422762_RF | 0.313372 | 6.220593 | 0.000145 | 0.039036 | 1.428992 |
| LEP_7_127838673_127843908_127864269_127868140_RF | 0.308548 | 6.038536 | 0.000181 | 0.04041 | 1.22254 |
| CDKN2_9_21967880_21969373_22029988_22034038_RR | 0.306887 | 4.203439 | 0.002217 | 0.060605 | -1.159095 |
| CACNA1C_12_2099248_2111840_2394923_2398377_FR | 0.306732 | 6.600332 | 9.23E-05 | 0.037879 | 1.843184 |

TABLE 19B-continued

Pre-type 2 diabetes mellitus probes - Epi Switch™ markers to stratify pre-type 2 diabetes vs. healthy controls

| | | | | | |
|---|---|---|---|---|---|
| PIK3R3_1_46633134_46639474_46678880_46685388_RF | 0.305924 | 5.715643 | 0.000272 | 0.042245 | 0.843449 |
| ABCC8_11_17445199_17452295_17545007_17546815_RF | 0.30417 | 6.346622 | 0.000125 | 0.037879 | 1.568892 |
| CDKN2A_9_21967880_21969373_22029988_22034038_RF | 0.30104 | 3.555782 | 0.006008 | 0.083182 | -2.124789 |
| KCNJ11_11_17419957_17422762_17445199_17452295_RR | 0.299727 | 6.400185 | 0.000117 | 0.037879 | 1.627611 |
| ICAM1_19_10341612_10343024_10406169_10407761_RF | 0.298038 | 3.7795 | 0.004231 | 0.076034 | 1.785033 |
| SREBF1_17_17722022_17726360_17743896_17753157_RR | 0.296794 | 5.555377 | 0.000335 | 0.04429 | 0.649035 |
| IGF2_11_2162616_2164979_2191728_2194389_FF | 0.293116 | 4.660277 | 0.001136 | 0.053336 | -0.514728 |
| ABCC8_11_17419957_17422762_17445199_17452295_RR | 0.290947 | 5.099022 | 0.000615 | 0.049081 | 0.072288 |
| CACNA1C_12_2099248_2111840_2221145_2224007_FR | 0.280735 | 5.809957 | 0.000241 | 0.042245 | 0.955909 |
| INS_11_2191728_2194389_2210793_2214417_RF | 0.275842 | 4.673253 | 0.001115 | 0.053336 | -0.496912 |
| MAPK10_4_87459424_87462716_87493751_87502639_FF | 0.274476 | 4.833587 | 0.000889 | 0.053336 | -0.279053 |
| PTPRD_9_8886566_8895563_9185543_9197535_FF | 0.273693 | 4.733721 | 0.001023 | 0.053336 | -0.414255 |
| CDKN2A_9_22005914_22007156_22029988_22034038_RF | 0.273046 | 6.139505 | 0.00016 | 0.039221 | 1.337681 |
| LEP_7_127838673_127843908_127903727_127906543_RF | 0.272802 | 6.193991 | 0.00015 | 0.039186 | 1.399149 |
| TSPAN8_12_71559221_71564078_71667712_71675824_RR | 0.27188 | 4.533782 | 0.001363 | 0.055293 | -0.689833 |
| CVB5R4_6_84533887_84541872_84600402_84604101_RF | 0.271658 | 4.921912 | 0.000785 | 0.053336 | 0.160847 |
| CYP2C9_10_96661464_96668745_96755577_96760846_FF | 0.270453 | 4.918804 | 0.000789 | 0.053336 | -0.164985 |
| T5PAN8_12_71559221_71564078_71675824_71684278_RF | 0.266085 | 4.741123 | 0.001013 | 0.053336 | -0.404177 |
| CYB5R4_6_84533887_84541872_84611173_84616879_FF | 0.265364 | 3.734665 | 0.004537 | 0.076978 | -1.852645 |
| TASP1_20_13441063_13442565_13507251_13521471_FR | 0.255345 | 4.438612 | 0.001565 | 0.055431 | -0.823269 |
| KCNJ11_11_17430922_17433660_17445199_1745229_RR | 0.25388 | 5.45502 | 0.000382 | 0.046163 | 0.525154 |
| INS_11_2162616_2164979_2191728_2194389_FF | 0.253761 | 4.302499 | 0.001913 | 0.058469 | -1.016596 |
| PTPRD_9_9551379_9564487_9852099_9857206_RR | 0.253043 | 5.604223 | 0.000314 | 0.044166 | 0.708733 |
| IGF2_11_2162616_2164979_2191728_2194389_RR | 0.251753 | 4.52036 | 0.00139 | 0.055424 | -0.708564 |
| TNIFRSF1B_1_12241967_12245164_12274102_12277104_RF | 0.251298 | 5.26762 | 0.00049 | 0.048568 | 0.28938 |
| TSPAN8_12_71667712_71675824_71850942_71857145_RF | 0.248869 | 5.506825 | 0.000357 | 0.045219 | 0.589309 |
| CACNA1C_12_2099248_2111840_2200229_2202042_RF | 0.24864 | 4.853482 | 0.000864 | 0.053336 | -0.252315 |
| CYP2C9_10_96690028_96694118_96748928_96755577_FR | 0.247789 | 4.674106 | 0.001114 | 0.053336 | -0.495742 |
| TSPAN8_12_71559221_71564078_71690883_71707188_RR | 0.24768 | 4.287891 | 0.001955 | 0.058885 | -1.037516 |
| ABCC8_11_17445199_17452295_17514252_17516772_RF | 0.247675 | 5.217723 | 0.000524 | 0.048568 | 0.225622 |
| ADCY5_3_123098260_123106114_123133741_123143812_RF | 0.245589 | 4.056041 | 0.002768 | 0.065995 | -1.37385 |
| IGF2_11_2191728_2194389_2210793_2214417_RF | 0.244894 | 3.926099 | 0.003374 | 0.070388 | -1.565763 |
| SREBF1_17_17722022_17726360_17743896_17753157_FR | 0.243916 | 3.351811 | 0.008314 | 0.09188 | -2.439215 |
| ABCC8_11_17445199_17.452.295_17538995_17541116_RF | 0.243453 | 4.73022 | 0.001028 | 0.053336 | 0.419024 |

| Probe | FC | FC_1 | LS | Loop detected |
|---|---|---|---|---|
| IGF2_11_2162616_2164979_2210793_2214417_RF | 1.392363 | 1.392363 | 1 | pre-T2DM |
| ADCY5_3_123037100_123044621_123133741_123143812_RF | 1.311928 | 1.311928 | 1 | pre-T2DM |
| TASP1_20_13265932_13269301_13507251_13521471_RR | 1.280572 | 1.280572 | 1 | pre-T2DM |
| TNFRSF1B_1_12241967_12245164_12269283_12270518_RR | 1.270232 | 1.270232 | 1 | pre-T2DM |
| SREBF1_17_17743896_17753157_17777190_17783023_RF | 1.266394 | 1.266394 | 1 | pre-T2DM |
| TSPAN8_12_71690883_7185094_71857145_RF | 1.265738 | 1.265738 | 1 | pre-T2DM |
| CYB5R4_6_84553857_84562119_84611173_84616879_FF | 1.262505 | 1.262505 | 1 | pre-T2DM |
| KCNJ11_11_17401446_17405499_17445199_17452295_RF | 1.253034 | 1.253034 | 1 | pre-T2DM |
| PTPRD_9_9058670_9068143_9186543_9197535_FF | 1.252715 | 1.252715 | 1 | pre-T2DM |
| ICAM1_19_10368390_10370561_10406169_10407761_RF | 1.251081 | 1.251081 | 1 | pre-T2DM |
| ABCC8_11_17401446_17405499_17445199_17452295_RF | 1.250419 | 1.250419 | 1 | pre-T2DM |
| CYP2C9_10_96661464_96668745_96741594_96747469_FR | 1.244587 | 1.244587 | 1 | pre-T2DM |
| KCNJ11_11_17401446_17405499_17419957_17422762_RF | 1.242609 | 1.242609 | 1 | pre-T2DM |
| LEP_7_127838673_127843908_127864269_127868140_RF | 1.23846 | 1.23846 | 1 | pre-T2DM |
| CDKN2_9_21967880_21969373_22029988_22034038_RR | 1.237036 | 1.237036 | 1 | pre-T2DM |
| CACNA1C_12_2099248_2111840_2394923_2398377_FR | 1.236903 | 1.236903 | 1 | pre-T2DM |
| PIK3R3_1_46633134_46639474_46678880_46685388_RF | 1.23621 | 1.23621 | 1 | pre-T2DM |
| ABCC8_11_17445199_17452295_17545007_17546815_RF | 1.234708 | 1.234708 | 1 | pre-T2DM |
| CDKN2A_9_21967880_21969373_22029988_22034038_RF | 1.232032 | 1.232032 | 1 | pre-T2DM |
| KCNJ11_11_17419957_17422762_17445199_17452295_RR | 1.230911 | 1.230911 | 1 | pre-T2DM |
| ICAM1_19_10341612_10343024_10406169_10407761_RF | 1.229471 | 1.229471 | 1 | pre-T2DM |
| SREBF1_17_17722022_17726360_17743896_17753157_RR | 1.228411 | 1.228411 | 1 | pre-T2DM |
| IGF2_11_2162616_2164979_2191728_2194389_FF | 1.225284 | 1.225284 | 1 | pre-T2DM |
| ABCC8_11_17419957_17422762_17445199_17452295_RR | 1.223443 | 1.223443 | 1 | pre-T2DM |
| CACNA1C_12_2099248_2111840_2221145_2224007_FR | 1.214814 | 1.214814 | 1 | pre-T2DM |
| INS_11_2191728_2194389_2210793_2214417_RF | 1.210701 | 1.210701 | 1 | pre-T2DM |
| MAPK10_4_87459424_87462716_87493751_87502639_FF | 1.209554 | 1.209554 | 1 | pre-T2DM |
| PTPRD_9_8886566_8895563_9185543_9197535_FF | 1.208898 | 1.208898 | 1 | pre-T2DM |
| CDKN2A_9_22005914_22007156_22029988_22034038_RF | 1.208357 | 1.208357 | 1 | pre-T2DM |
| LEP_7_127838673_127843908_127903727_127906543_RF | 1.208152 | 1.208152 | 1 | pre-T2DM |
| TSPAN8_12_71559221_71564078_71667712_71675824_RR | 1.207381 | 1.207381 | 1 | pre-T2DM |
| CVB5R4_6_84533887_84541872_84600402_84604101_RF | 1.207194 | 1.207194 | 1 | pre-T2DM |
| CYP2C9_10_96661464_96668745_96755577_96760846_FF | 1.206187 | 1.206187 | 1 | pre-T2DM |
| T5PAN8_12_71559221_71564078_71675824_71684278_RF | 1.20254 | 1.20254 | 1 | pre-T2DM |
| CYB5R4_6_84533887_84541872_84611173_84616879_FF | 1.20194 | 1.20194 | 1 | pre-T2DM |
| TASP1_20_13441063_13442565_13507251_13521471_FR | 1.193621 | 1.193621 | 1 | pre-T2DM |
| KCNJ11_11_17430922_17433660_17445199_1745229_RR | 1.192409 | 1.192409 | 1 | pre-T2DM |
| INS_11_2162616_2164979_2191728_2194389_FF | 1.192311 | 1.192311 | 1 | pre-T2DM |
| PTPRD_9_9551379_9564487_9852099_9857206_RR | 1.191718 | 1.191718 | 1 | pre-T2DM |
| IGF2_11_2162616_2164979_2191728_2194389_RR | 1.190653 | 1.190653 | 1 | pre-T2DM |
| TNIFRSF1B_1_12241967_12245164_12274102_12277104_RF | 1.190277 | 1.190277 | 1 | pre-T2DM |

TABLE 19B-continued

Pre-type 2 diabetes mellitus probes - Epi Switch™ markers to stratify pre-type 2 diabetes vs. healthy controls

| | | | | |
|---|---|---|---|---|
| TSPAN8_12_71667712_71675824_71850942_71857145_RF | 1.188275 | 1.188275 | 1 | pre-T2DM |
| CACNA1C_12_2099248_2111840_2200229_2202042_RF | 1.88087 | 1.188087 | 1 | pre-T2DM |
| CYP2C9_10_96690028_96694118_96748928_96755577_FR | 1.187386 | 1.187386 | 1 | pre-T2DM |
| TSPAN8_12_71559221_71564078_71690883_71707188_RR | 1.187296 | 1.187296 | 1 | pre-T2DM |
| ABCC8_11_17445199_17452295_17514252_17516772_RF | 1.187292 | 1.187292 | 1 | pre-T2DM |
| ADCY5_3_123098260_123106114_123133741_123143812_RF | 1.185577 | 1.185577 | 1 | pre-T2DM |
| IGF2_11_2191728_2194389_2210793_2214417_RF | 1.185005 | 1.185005 | 1 | pre-T2DM |
| SREBF1_17_17722022_17726360_17743896_17753157_FR | 1.184203 | 1.184203 | 1 | pre-T2DM |
| ABCC8_11_17445199_17452.295_17538995_17541116_RF | 1.183822 | 1.183822 | 1 | pre-T2DM |

TABLE 19c

Pre-type 2 DM Probes - EpiSwitch ™ markers to stratify Pre-type 2 DM vs. healthy controls

| Probe | Probe sequence 60 mer |
|---|---|
| IGF2_11_2162616_2164979_2210793_2214417_RF | CTCCTCAAAAAAAAGAGGAGGCCCAGGCTCGAGACTCCAGAAAAATAGATTACAGGTTTG (SEQ ID NO: 157) |
| ADCY5_3_123037100_123044621_123133741_123143812_RF | TTTAGCCAAAAAGAAAAAAAGGTTCATTTCGAGAACCAGAGTCAAACTTAGACCCCAGGA (SEQ ID NO: 158) |
| TASP1_20_13265932_13269301_13507251_13521471_RR | TCCTTTCTTTTTTATTTTTTAAGCTGTTTCGATTCAACATTAATTCATTTTAGACTTCTC (SEQ ID NO: 159) |
| TNFRSF1B_1_12241967_12245164_12269283_12270518_RR | ACCAGCCCTGGGTTCTTAAGGATGGGTGTCGACCCCTGGCTCTGCCTGGGGTCTGGGCTT (SEQ ID NO: 160) |
| SREBF1_17_17743896_17753157_17777190_17783023_RF | ACATCTCAGACATGACTTTTGTGTTTCCTCGAGCCTTTTCGGGCAGGCGTCCAGCACGGG (SEQ ID NO: 161) |
| TSPAN8_12_71690883_71707188_71850942_71857145_RF | CTCAGACTGTATATTCTCTTAGCTTCAGTCGAGCTGTTTCTTTATATGGTCTCTGCTATC (SEQ ID NO: 162) |
| CYB5R4_6_84553857_84562119_84611173_84616879_FF | ATTATAACATTTATATATCATCTTTTCCTCGAGGTTGCAGTAAGCTGATCATGCCACTAC (SEQ ID NO: 163) |
| KCNJ11_11_17401446_17405499_17445199_17452295_RF | GACCAAACAGCTGTGGTTTGGCCATCACTCGAGAGAGAGCCTGTGTGAGGAGTGCAGTCA (SEQ ID NO: 164) |
| PTPRD_9_9058670_9068143_9186543_9197535_FF | CTTTTAGCTTTTACTTAGCATAATTTTCTCGAGAGGGTGGGGCAGGAGAATCTCTTGAAC (SEQ ID NO: 165) |
| ICAM1_19_10368390_10370561_10406169_10407761_RF | GGAAGGCCGAGGCGGCCAGATCACGAGGTCGAACCTCCTGATAACTTCAGCATTAACAGC (SEQ ID NO: 166) |
| ABCC8_11_17401446_17405499_17445199_17452295_RF | GACCAAACAGCTGTGGTTTGGCCATCACTCGAGAGAGAGCCTGTGTGAGGAGTGCAGTCA (SEQ ID NO: 167) |
| CYP2C9_10_96661464_96668745_96741594_96747469_FR | GAGTAGGTAAACAAAGCAGTCAGGAAGCTCGAGTCTTTGGTTTTCCCTAGATAATTAATA (SEQ ID NO: 168) |
| KCNJ11_11_17401446_17405499_17419957_17422762_RF | CTTAGAGCAAAGGCTAGGCTCAGTAATGTCGAGAGAGAGCCTGTGTGAGGAGTGCAGTCA (SEQ ID NO: 169) |
| LEP_7_127838673_127843908_127864269_127868140_RF | AGATCAAATCCAGTTTAAGGCTACTCCTTCGATTCATACACCATTCAGGGTATACAATAG (SEQ ID NO: 170) |
| CDKN2A_9_21967880_21969373_22029988_22034038_RR | TTGCGAGCCTCGCAGCCTCCGGAAGCTGTCGATTTTAAGTCTATTTTGTTAGATCTAAAG (SEQ ID NO: 171) |
| CACNA1C_12_2099248_2111840_2394923_2398377_FR | ACTGACAGTTTCTTGGGATTCTCCAGACTCGAGAGAGGCTGGTGCGCACCTACCCAGCGG (SEQ ID NO: 172) |
| PIK3R3_1_46633134_46639474_46678880_46685388_RF | CCACTCCCCCAGGCTTACCTGCGAGCCATCGAGGTGGGCCTGGGTTCTCGTGGAGGGAGA (SEQ ID NO: 173) |
| ABCC8_11_17445199_17452295_17545007_17546815_RF | CCATCCTGGACGCAGAATGTAGTCCCGTTCGAACAGAGCTGGGAGCTGGGCCTAGGCTA (SEQ ID NO: 174) |
| CDKN2A_9_21967880_21969373_22029988_22034038_RF | TGCTTTTTAAAAAATCAAAGGTGTAACTTCGACAGCTTCCGGAGGCTGCGAGGCTCGCAA (SEQ ID NO: 175) |
| KCNJ11_11_17419957_17422762_17445199_17452295_RR | TATGAGGCCCGGTTCCAGCAGAAGCTTCTCGAACAGAGCTGGGAGCTGGGGCCTAGGCTA (SEQ ID NO: 176) |

TABLE 19c-continued

Pre-type 2 DM Probes - EpiSwitch ™ markers to stratify Pre-type 2 DM vs. healthy controls

| Probe | Probe sequence 60 mer |
|---|---|
| ICAM1_19_10341612_10343024_10406169_10407761_RF | GGAAGGCCGAGGCGGCCAGATCACGAGGTCGAAAGCGCTCGGATTCAGCCTTC TCCCCGG (SEQ ID NO: 177) |
| SREBF1_17_17722022_17726360_17743896_17753157_RR | ATGGACAGTAGGCAGGATGAATAAGTGCTCGAGCCTTTTCGGGCAGGCGTCCA GCACGGG (SEQ ID NO: 178) |
| IGF2_11_2162616_2164979_2191728_2194389_FF | TAACGTCCAAGAAAATTATTGTGACCCGTCGAGAAGTCAGGGAGCGTCTAGGG CTTCTGG (SEQ ID NO: 179) |
| ABCC8_11_17419957_17422762_17445199_17452295_RR | TATGAGGCCCGGTTCCAGCAGAAGCTTCTCGAACAGAGCTGGGAGCTGGGGCC TAGGCTA (SEQ ID NO: 180) |
| CACNA1C_12_2099248_2111840_2221145_2224007_FR | ACTGACAGTTTCTTGGGATTCTCCAGACTCGAGGCCTGGAGAAGCCCAGGAGG AGGCGTG (SEQ ID NO: 181) |
| INS_11_2191728_2194389_2210793_2214417_RF | CTCCTCAAAAAAAGAGGAGGCCCAGGCTCGATCCCAGAGCCGTCCCAGGCCT GGACAGA (SEQ ID NO: 182) |
| MAPK10_4_87459424_87462716_87493751_87502639_FF | AGGCTGAACTTCAAATGTGATAATAACCTCGACTTAATTTTATTACAGCACTA ATATAAT (SEQ ID NO: 183) |
| PTPRD_9_8886566_8895563_9186543_9197535_FF | GACTTCAACTCACTATGAATAAATAAAATCGAGAGGGTGGGGCAGGAGAATCT CTTGAAC (SEQ ID NO: 184) |
| CDKN2A_9_22005914_22007156_22029988_22034038_RF | TGCTTTTTAAAAAATCAAAGGTGTAACTTCGAATTAGGTGGGTGGGGGTGGGA AATTGGG (SEQ ID NO: 185) |
| LEP_7_127838673_127843908_127903727_127906543_RF | ATAAGAAACTGAATTTAAATGCTCTCTTTCGATTCATACACCATTCAGGGTAT ACAATAG (SEQ ID NO: 186) |
| TSPAN8_12_71559221_71564078_71667712_71675824_RR | AAGGTCTTCAGCTTCACTCCTGAAGCCATCGAGTTCTGTACTTAAGCAAACAT TATCCTT (SEQ ID NO: 187) |
| CYB5R4_6_84533887_84541872_84600402_84604101_RF | CCATGTTGTAATATTGGATTTTATCATTCGATATAGTGGTTTCTAGGTATCA TGGTAAA (SEQ ID NO: 188) |
| CYP2C9_10_96661464_96668745_96755577_96760846_FF | GAGTAGGTAAACAAAGCAGTCAGGAAGCTCGATCCAGTGTGCTTTTCACTTCA GACCTTG (SEQ ID NO: 189) |
| TSPAN8_12_71559221_71564078_71675824_71684278_RF | AATATCTTTTCATTTTTGGTGAAGTCTTCGATGGCTTCAGGAGTGAAGCTGA AGACCTT (SEQ ID NO: 190) |
| CYB5R4_6_84533887_84541872_84611173_84616879_FF | TGTTCAATCAAAGGAAGGGATAACACTATCGAGGTTGCAGTAAGCTGATCATG CCACTAC (SEQ ID NO: 191) |
| TASP1_20_13441063_13442565_13507251_13521471_FR | GATGTTTATACAAGATTCATTCTTTCCATCGATTCAACATTAATTCATTTTAG ACTTCTC (SEQ ID NO: 192) |
| KCNJ11_11_17430922_17433660_17445199_17452295_RR | TTCCTTGAGGAATCAGTGATCAGGACTCTCGAACAGAGCTGGGAGCTGGGGCC TAGGCTA (SEQ ID NO: 193) |
| INS_11_2162616_2164979_2191728_2194389_FF | TAACGTCCAAGAAAATTATTGTGACCCGTCGAGAAGTCAGGGAGCGTCTAGGG CTTCTGG (SEQ ID NO: 194) |
| PTPRD_9_9551379_9564487_9852099_9857206_RR | TAGTACTACCACTGGAAAGCTAGAATATTCGATGCATTAAAATGTTCTCGGAA AGAGATA (SEQ ID NO: 195) |
| IGF2_11_2162616_2164979_2191728_2194389_RR | CAAACCTGTAATCTATTTTTCTGGAGTCTCGATCCCAGAGCCGTCCCAGGCCT GGACAGA (SEQ ID NO: 196) |
| TNFRSF1b_1_12241967_12245164_12274102_12277104_RF | GTTGAGGCTGCAATAAACCGTGATCAAGTCGACACCCATCCTTAAGAACCCAG GGCTGGT (SEQ ID NO: 197) |
| TSPAN8_12_71667712_71675824_71850942_71857145_RF | CTCAGACTGTATATTCTCTTAGCTTCAGTCGAGTTCTGTACTTAAGCAAACAT TATCCTT (SEQ ID NO: 198) |
| CACNA1C_12_2099248_2111840_2200229_2202042_RF | GGAAATGAGTCTCATGTCTAATTAAATGTCGAAGTTAAGGTTTCTTGGTTCAA GTGGTGT (SEQ ID NO: 199) |
| CYP2C9_10_96690028_96694118_96748928_96755577_FR | TGAGGTAGGCAGATCACAGGTCAGGAGATCGACCTCCATTACGGAGAGTTTCC TATGTTT (SEQ ID NO: 200) |
| TSPAN8_12_71559221_71564078_71690883_71707188_RR | AAGGTCTTCAGCTTCACTCCTGAAGCCATCGAGCTGTTTCTTTATATGGTCTC TGCTATC (SEQ ID NO: 201) |

TABLE 19c-continued

Pre-type 2 DM Probes - EpiSwitch ™ markers to stratify Pre-type 2 DM vs. healthy controls

| Probe | Probe sequence 60 mer |
|---|---|
| ABCC8_11_17445199_17452295_17514252_17516772_RF | TGGGCTCCTTCAGCCCCACATGCCTGGTTCGAACAGAGCTGGGAGCTGGGGCC TAGGCTA (SEQ ID NO: 202) |
| ADCY5_3_123098260_123106114_123133741_123143812_RF | TTTAGCCAAAAAGAAAAAAAGGTTCATTTCGAGGAATGTTTCCAAGCAATTCT CTCTGCT (SEQ ID NO: 203) |
| IGF2_11_2191728_2194389_2210793_2214417_RF | CTCCTCAAAAAAAGAGGAGGCCCAGGCTCGATCCCAGAGCCGTCCCAGGCCT GGACAGA (SEQ ID NO: 204) |
| SREBF1_17_17722022_17726360_17743896_17753157_FR | CCCTTTACCCCAGTCCGTGTGAGCCTCTTCGAGCCTTTTCGGGCAGGCGTCCA GCACGGG (SEQ ID NO: 205) |
| ABCC8_11_17445199_17452295_17538995_17541116_RF | GGATTACTTCCATGAGAAGCAATTAAAATCGAACAGAGCTGGGAGCTGGGGCC TAGGCTA (SEQ ID NO: 206) |

TABLE 19D

Pre-type 2 diabetes mellitus probes - EpiSwitch™ markers to stratify pre-type 2 diabetes vs. healthy controls

| Probe | Chr | Start1 | End1 | Start2 | End2 |
|---|---|---|---|---|---|
| IGF2_11_2162616_2164979_2210793_2214417_RF | 11 | 2162617 | 2162646 | 2214388 | 2214417 |
| ADCY5_3_123037101_123044621_123133741_123143812_RF | 3 | 123037101 | 123037130 | 123143783 | 123143812 |
| TASP1_20_13265932_13269301_13507251_13521471_RR | 20 | 13265933 | 13265962 | 13507252 | 13507281 |
| TNIFRSFB_1_12241967_12245164_12269283_12270518_RR | 1 | 12241968 | 12241997 | 12269284 | 12269313 |
| SREBF1_17_17743896_17753157_17777190_17783023_RF | 17 | 17743897 | 17743926 | 17782994 | 17783023 |
| TSPAN8_12_71690884_71707188_71850942_71857145_RF | 12 | 71690884 | 71690913 | 71857116 | 71857145 |
| CYB5R4_6_84553857_84562119_8461173_84616879_FF | 6 | 84562090 | 84562119 | 84616850 | 84616879 |
| KCNJ11_11_17401446_17405499_17445199_17452295_RF | 11 | 17401447 | 17401476 | 17452266 | 17452295 |
| PTPRD_9_9058670_9068143_9186543_9197535_FF | 9 | 9068114 | 9068143 | 9197506 | 9197535 |
| ICAM1_19_10368391_10370561_10406169_10407761_RF | 19 | 10368391 | 10368420 | 10407732 | 10407761 |
| ABCC8_11_17401446_17405499_17445199_17452295_RF | 11 | 17401447 | 17401476 | 17452266 | 17452295 |
| CYP2C9_10_96661464_96668745_96741594_96747469_FR | 10 | 96668716 | 96668745 | 96741595 | 96741624 |
| KCNJ11_11_17401446_17405499_17419957_17422762_RF | 11 | 17401447 | 17401476 | 17422733 | 17422762 |
| LEP_7_127838673_127843908_127864269_127868140_FF | 7 | 127838674 | 127838703 | 127868111 | 127868140 |
| CDKN2A_9_21967880_21969373_22029988_22034038_RR | 9 | 21967881 | 21967910 | 22029989 | 22030018 |
| CACNA1C_12_2099248_2111840_2394923_2398377_FR | 12 | 2111811 | 2111840 | 2394924 | 2394953 |
| PIK3R3_1_46633134_46639474_46678880_46688388_RF | 1 | 46633135 | 46633164 | 46685359 | 46685388 |
| ABCC8_11_17445199_17452295_17545007_17546815_RF | 11 | 17445200 | 17445229 | 17546786 | 17546815 |
| CDKN2A_9_21967880_21969373_22029988_22034038_RF | 9 | 21967881 | 21967910 | 22034009 | 22034038 |
| KCNJ11_11_17419957_17422762_17445199_17452295_RR | 11 | 17419958 | 17419987 | 17445200 | 17445229 |
| ICAM1_19_10341612_10343024_10406169_10407761_RF | 19 | 10341613 | 10341642 | 10407732 | 10407761 |
| SRFBF1_17_17722022_17726360_17743896_17753157_RR | 17 | 17722023 | 17722052 | 17743897 | 17743926 |
| IGF2_11_2162616_2164979_2191728_2194389_FF | 11 | 2164950 | 2164979 | 2194360 | 2194389 |
| ABCC8_11_17419957_17422762_17445199_17452295_RR | 11 | 17419958 | 17419987 | 17445200 | 17445229 |
| CACNA1C_12_2099248_2111840_2221145_2224007_FR | 12 | 2111811 | 2111840 | 2221146 | 2221175 |
| INS_11_2191728_2194389_2210793_2214417_RF | 11 | 2191729 | 2191758 | 2214388 | 2214417 |
| MAPK10_4_87459424_87462716_87493751_87502639_FF | 4 | 87462687 | 87462716 | 87502610 | 87502639 |
| PTPRD_9_8886566_8895563_9186543_9197535_FF | 9 | 8895534 | 8895563 | 9197506 | 9197535 |
| CDKN2A_9_22005914_22007156_22029988_22034038_RF | 9 | 22005915 | 22005944 | 22034009 | 22034038 |
| LEP_7_127838673_127843908_127903727_127906543_RF | 7 | 127838674 | 127838703 | 127906514 | 127906543 |
| TSPAN8_12_71559221_71564078_71667712_71675824_RF | 12 | 71559222 | 71559251 | 71667713 | 71667742 |
| CYB5R4_6_84533887_84541872_84600402_84604101_RF | 6 | 84533888 | 84533917 | 84604072 | 84604101 |
| CYP2C9_10_96661464_96668745_96755577_96760846_FF | 10 | 96668716 | 96668745 | 96760817 | 96760846 |
| TSPAN8_12_71559221_71564078_71675824_71634278_RF | 12 | 71559222 | 71559251 | 71684249 | 71684278 |
| CYB5R4_6_84541843_84541872_84611173_84615879_FF | 6 | 84541843 | 84541872 | 84616850 | 84616879 |
| TASP8_20_13441063_13442565_13507251_13521471_FR | 20 | 13442536 | 13442565 | 13507252 | 13507281 |
| KCNJ11_11_17430922_17433660_17445199_17452295_RR | 11 | 17430923 | 17430952 | 17445200 | 17445229 |
| INS_11_2162616_2164979_2191728_2194389_FF | 11 | 2164950 | 2164979 | 2194360 | 2194389 |
| PTPRD_9_9551379_9S64487_9852099_9857206_RR | 9 | 9551380 | 9551409 | 9852120 | 9852149 |
| IGF2_11_2162616_2164979_2191728_2194389_RR | 11 | 2162617 | 2162646 | 2191729 | 2191758 |
| TNFRSF1B_1_12241967_12245164_12274102_12277104_RF | 1 | 12241968 | 12241997 | 12277075 | 12277104 |
| TSPAN8_12_71667712_71675824_71850942_71857145_RF | 12 | 71667713 | 71667742 | 71857116 | 71857145 |
| CACNA1C_12_2099248_2111840_2200229_2202042_RF | 12 | 2099249 | 2099278 | 2202013 | 2202042 |
| CYP2C9_10_96690028_96694118_96748928_96755577_FR | 10 | 96694089 | 96694118 | 96748929 | 96748958 |
| TSPAN8_12_71559221_71564078_71690883_71707188_RR | 12 | 71559222 | 71559251 | 71690884 | 71690913 |
| ABCC8_11_1744519917452295_17514252_1751577_RF | 11 | 17445200 | 17445229 | 17516743 | 17516772 |
| ADCY5_3_123098260_123106114_123133741_123143812_RF | 3 | 123098261 | 123098290 | 123143783 | 123143812 |
| IGF2_11_2191728_2194389_2210793_2214417_RF | 11 | 2191729 | 2191758 | 2214388 | 2214417 |

TABLE 19D-continued

Pre-type 2 diabetes mellitus probes - EpiSwitch™ markers to stratify pre-type 2 diabetes vs. healthy controls

| Probe | | | | |
|---|---|---|---|---|
| SREBF1_17_17722022_17726360_l774389b_l7753157_FR | 17 | 17726331 17726360 | 17743897 | 17743926 |
| ABCC8_11_177445199_17452295_17538995_17541116_RF | 11 | 17445200 17445229 | 17541087 | 17541116 |

| | | 4 kb Sequence Location | | | |
|---|---|---|---|---|---|
| Probe | Chr | Start1 | End1 | Start2 | End2 |
| IGF2_11_2162616_2164979_2210793_2214417_RF | 11 | 2162617 | 2166616 | 2210418 | 2214417 |
| ADCY5_3_123037100_123044621_123133741_123143812_RF | 3 | 123037101 | 123041100 | 123139813 | 123143812 |
| TASP1_20_13265932_13269301_13507251_13521471_RR | 20 | 13265933 | 13269932 | 13507252 | 13511251 |
| TNIFRSFB_1_12241967_12245164_12269283_12270518_RR | 1 | 12241968 | 12245967 | 12269284 | 12273283 |
| SREBF1_17_17743896_17753157_17777190_17783023_RF | 17 | 17743897 | 17747896 | 17779024 | 17783023 |
| TSPAN8_12_71690883_71707188_71850942_71857145_RF | 12 | 71690884 | 71694883 | 71853146 | 71857145 |
| CYB5R4_6_84553857_84562119_8461173_84616879_FF | 6 | 84558120 | 84562119 | 84612880 | 84616879 |
| KCNJ11_11_17401446_17405499__17445199_17452295_RF | 11 | 17401447 | 17405446 | 17448296 | 17452295 |
| PTPRD_9_9058670_9068143_9186543_9197535_FF | 9 | 9064144 | 9068143 | 9193536 | 9197535 |
| ICAM1__19_10368390_10370561_10406169_10407761_RF | 19 | 10368391 | 10372390 | 10403762 | 10407761 |
| ABCC8_11_17401446_17405499_17445199_17452295_RF | 11 | 17401447 | 17405446 | 17448296 | 17452295 |
| CYP2C9_10_96664746_96668745_96741594_96747469_FR | 10 | 96664746 | 96668745 | 96741595 | 96745594 |
| KCNJ11_11_17401446_17405499_17419957_17422762_RF | 11 | 17401447 | 17405446 | 17418763 | 17422762 |
| LEP_7_127838673_127843908_127864269_127868140_RF | 7 | 127838674 | 127842673 | 127864141 | 127868140 |
| CDKN2A_9_21967880_21969373_22029988_22034038_RR | 9 | 21967881 | 21971880 | 22029989 | 22033988 |
| CACNA1C_12_2099248_2111840_2394923_2398377_FR | 12 | 2107841 | 2111840 | 2394924 | 2398923 |
| PIK3R3_1_46633134_46639474_46678880_46688388_RF | 1 | 46633135 | 46637134 | 46681389 | 46685388 |
| ABCC8_11_17445199_17452295_17545007_17546815_RF | 11 | 17445200 | 17449199 | 17542816 | 17546815 |
| CDKN2A_9_21967880_21969373_22029988_22034038_RF | 9 | 21967881 | 21971880 | 22030039 | 22034038 |
| KCNJ11_11_17419958_17422762_17445199_17452295_RF | 11 | 17419958 | 17422957 | 17445200 | 17449199 |
| ICAM1_19_10341612_10343024_10406169_10407761_RF | 19 | 10341613 | 10345612 | 10403762 | 10407761 |
| SRFBF1_17_17722022_17726360_17743896_17753157_RR | 17 | 17722023 | 17726022 | 17743897 | 17747896 |
| IGF2_11_2162616_2164979_2191728_2194389_FF | 11 | 2160980 | 2164979 | 2190390 | 2194389 |
| ABCC8_11_17419957_17422762_17445199_17452295_RR | 11 | 17419958 | 17422957 | 17445200 | 17449199 |
| CACNA1C_12_2099248_2111840_2221145_2224007_FR | 12 | 2107841 | 2111840 | 2221146 | 2225145 |
| INS_11_2191728_2194389_2210793_2214417_RF | 11 | 2191729 | 2195728 | 2210418 | 2214417 |
| MAPK10_4_87459424_87462716_87493751_87502639_FF | 4 | 87458717 | 87462716 | 87498640 | 87502639 |
| PTPRD_9_8886566_8895563_9186543_9197535_FF | 9 | 8891564 | 8895563 | 9193536 | 9197535 |
| CDKN2A_9_22005914_22007156_22029988_22034038_RF | 9 | 22005915 | 22009914 | 22030039 | 22034038 |
| LEP_7_127838673_127843908_127903727_127906543_RF | 7 | 127838674 | 127842673 | 127902544 | 127906543 |
| TSPAN8_12_71559221_71564078_71667712_71675824_RR | 12 | 71559222 | 71563221 | 71667713 | 71671712 |
| CYB5R4_6_84533887_84541872_84600402_84604101_RF | 6 | 84533888 | 84537887 | 84600102 | 84604101 |
| CYP2C9_10_96664746_96668745_96755577_96760846_FR | 10 | 96664746 | 96668745 | 96756847 | 96760846 |
| TSPAN8_12_71559221_71564078_71675824_71634278_RF | 12 | 71559222 | 71563221 | 71680279 | 71684278 |
| CYB5R4_6_84533887_84541872_84611173_84615879_FF | 6 | 84537873 | 84541872 | 84612880 | 84616879 |
| TASP8_20_13441063_13442565_13507251_13521471_FR | 20 | 13438566 | 13442565 | 13507252 | 13511251 |
| KCNJ11_11_17430923_17433660_17445199_17452295_RR | 11 | 17430923 | 17434922 | 17445200 | 17449199 |
| INS_11_2162616_2164979_2191728_2194389_FF | 11 | 2160980 | 2164979 | 2190390 | 2194389 |
| PTPRD_9_9551379_9S64487_9852099_9857206_RR | 9 | 9551380 | 9555379 | 9852100 | 9856099 |
| IGF2_11_2162616_2164979_2191728_2194389_RR | 11 | 2162617 | 2166616 | 2191729 | 2195728 |
| TNFRSF1B_1_12241967_12245164_12274102_12277104_RF | 1 | 12241968 | 12245967 | 12273105 | 12277104 |
| TSPAN8_12_71667713_71675824_71850942_71857145_RF | 12 | 71667713 | 71671712 | 71853146 | 73857145 |
| CACNA1C_12_2099248_2111840_2200229_2202042_RF | 12 | 2099249 | 2103248 | 2198043 | 2202042 |
| CYP2C9_10_96690028_96694118_96748928_96755577_FR | 10 | 96690119 | 96694118 | 96748929 | 96752928 |
| TSPAN8_12_71559221_71564078_71690883_71707188_RR | 12 | 71559222 | 71563221 | 71690884 | 71694883 |
| ABCC8_11_1744519917452295_17514252_1751577_RF | 11 | 17445200 | 17449199 | 17512773 | 17516772 |
| ADCY5_3_123098260_123106114_123133741_123143812_RF | 3 | 123098260 | 123102260 | 123139813 | 123143812 |
| IGF2_11_2191728_2194389_2210793_2214417_RF | 11 | 2191729 | 2195728 | 2210418 | 2214417 |
| SREBF1_17_17722022_17726360_l774389b_l7753157_FR | 17 | 17722361 | 17726360 | 17743897 | 17747896 |
| ABCC8_11_177445199_17452295_17538995_17541116_RF | 11 | 17445200 | 17449199 | 17537117 | 17541116 |

TABLE 20A

Type 2 diabetes mellitus probes - EpiSwitch™ markers to stratify type 2 diabetes mellitus vs. healthy controls

| Probe | GeneLocus | Probe_Count_Total | Probe_Count_Sig | HyperG_Stats | FDR_HyperG | Percent_Sig | logFC |
|---|---|---|---|---|---|---|---|
| ICAM1_19_10368390_10370561_10406169_10407761_RF | ICAMI | 9 | 5 | 0.001732 | 0.070257 | 55.56 | 0.454102 |
| SREBF1_17_17743896_17753157_17777190_17783023_RF | SREBF1 | 19 | 9 | 0.000113 | 0.013705 | 47.37 | 0.405312 |
| CAMK1D_10_12558950_12568337_12770482_12771684_FR | CAMK1D | 115 | 24 | 0.002791 | 0.092599 | 20.87 | 0.389359 |
| SLC2A2_3_170700264_170710807_170738889_170750047_RF | SLC2A2 | 5 | 4 | 0.000809 | 0.038824 | 80 | 0.37933 |
| ICAM1_19_10341612_10343024_10406169_10407761_RF | ICAMI | 9 | 5 | 0.001732 | 0.070257 | 55.56 | 0.374366 |
| SREBF1_17_17722022_17726360_17743896_17753157_RR | SREBF1 | 19 | 9 | 0.000113 | 0.013705 | 47.37 | 0.370578 |
| IDE_10_94207972_94216393_94322805_94330672_RR | IDE | 7 | 6 | 1.49E−05 | 0.004309 | 85.71 | 0.335806 |
| CACNA1C_12_2099248_2111840_2394923_2398377_FR | CACNA1C | 197 | 35 | 0.006212 | 0.174409 | 17.77 | 0.335327 |
| KCNJ11_11_17401446_17405499_17419957_17422762_RF | KCNJ11 | 22 | 8 | 0.002252 | 0.082207 | 36.36 | 0.334267 |

TABLE 20A-continued

Type 2 diabetes mellitus probes - EpiSwitch™ markers to stratify type 2 diabetes mellitus vs. healthy controls

| Probe | GeneLocus | Probe_Count_Total | Probe_Count_Sig | HyperG_Stats | FDR_HyperG | Percent_Sig | logFC |
|---|---|---|---|---|---|---|---|
| SREBF1_17_17754197_17760488_17777190_17783023_RF | SREBF1 | 19 | 9 | 0.000113 | 0.013705 | 47.37 | 0.305866 |
| CACNA1C_12_2099243_2111840_2221145_2224007_FR | CACNA1C | 197 | 35 | 0.006212 | 0.174409 | 17.77 | 0.304928 |
| CYB5R4_6_84553857_84562119_84611173_84616879_FF | CYB5R4 | 39 | 10 | 0.011329 | 0.217632 | 25.64 | 0.304406 |
| SLC2A2_3_170700264_170710807_170767515_170774153_RF | SLC2A2 | 5 | 4 | 0.000809 | 0.038824 | 80 | 0.304351 |
| KCNJ11_11_17419957_17422762_17452295_17453614_FR | KCNJ11 | 22 | 8 | 0.002252 | 0.082207 | 36.36 | 0.30432 |
| CAMK1D_10_12425560_12430245_12558950_12568337_RF | CAMK1D | 115 | 24 | 0.002791 | 0.092599 | 20.87 | 0.29721 |
| KCNJ11_11_17401446_17405499_17445199_17452295_FR | KCNJ11 | 22 | 8 | 0.002252 | 0.082207 | 36.36 | 0.294294 |
| CAMK1D_10_12558950_12568337_12609856_12611356_FR | CAMK1D | 115 | 24 | 0.002791 | 0.092599 | 20.87 | 0.293636 |
| CAMK1D_10_12509013_12511923_12558950_12568337_FR | CAMK1D | 115 | 24 | 0.002791 | 0.092599 | 20.87 | 0.288358 |
| VEGFA_6_43701600_43705478_43718880_43723783_RF | VEGFA | 16 | 6 | 0.006786 | 0.176922 | 37.5 | 0.285845 |
| ADCY5_3_123037100_123044621_123133741_123143812_RF | ADCY5 | 90 | 18 | 0.013754 | 0.230556 | 20 | 0.283847 |
| CAMK1D_10_12558950_12568337_12770482_12771684_RR | CAMK1D | 115 | 24 | 0.002791 | 0.092599 | 20.87 | 0.282717 |
| LTA_6_31498892_31502771_31552034_31554202_FF | LTA | 17 | 6 | 0.009477 | 0.192177 | 35.29 | 0.782028 |
| CYP2C9_10_96661464_96668745_96741594_96747469_FR | CYP2C9 | 8 | 5 | 0.000851 | 0.038824 | 62.5 | 0.281118 |
| CACNA1C_12_2099248_2111840_238331_2391100_RR | CACNA1C | 197 | 35 | 0.006212 | 0.174409 | 17.77 | 0.280559 |
| SREBF1_17_17722022_17726360_17743896_17753157_FR | SREBF1 | 19 | 9 | 0.000113 | 0.013705 | 47.37 | 0.279061 |
| CACNA1C_12_2099248_2111840_2255353_2257963_FF | CACNA1C | 197 | 35 | 0.006212 | 0.174409 | 17.77 | 0.276063 |
| CYB5A_18_71929777_71931243_71965803_71970158_FF | CYB5A | 19 | 6 | 0.016982 | 0.247935 | 31.58 | 0.275053 |
| IDE_10_94207972_94216393_94232614_94236267_RF | IDE | 7 | 6 | 1.49E-05 | 0.004309 | 85.71 | 0.270976 |
| TASP1_20_13265932_13269301_13507251_13521471_RR | TASP1 | 172 | 30 | 0.013787 | 0.230556 | 17.44 | 0.26783 |
| SDHB_1_17371319_17376758_17396655_17400949_FR | SDHB | 13 | 8 | 2.36E-05 | 0.004309 | 61.54 | 0.267658 |
| CYB5R4_6_84541872_84548862_84611173_84616879_FF | CYB5R4 | 39 | 10 | 0.011329 | 0.217632 | 25.64 | 0.265948 |
| CAMK1D_10_12584612_12587236_12806730_12814968_FF | CAMK1D | 115 | 24 | 0.002791 | 0.092599 | 20.87 | 0.262783 |
| CYB5R4_6_84533887_84541872_84611173_84616879_FF | CYB5R4 | 39 | 10 | 0.011329 | 0.217632 | 25.64 | 0.262369 |
| SREBF1_17_17722022_17726360_17754197_17760488_RR | SREBF1 | 19 | 9 | 0.000113 | 0.013705 | 47.37 | 0.258464 |
| SREBF1_17_17743896_17753157_17764809_17767745_FR | SREBF1 | 19 | 9 | 0.000113 | 0.013705 | 47.37 | 0.258278 |
| SDHB_1_17371319_17376758_17395655_17400949_RR | SDHB | 13 | 8 | 2.36E-05 | 0.004309 | 61.54 | 0.256686 |
| ADCY5_3_123098260_123106114_123133741_123143812_RF | ADCY5 | 90 | 18 | 0.013754 | 0.230556 | 20 | 0.256602 |
| CACNA1C_12_2099248_2111840_2371355_2375397_FF | CACNA1C | 197 | 35 | 0.006212 | 0.174409 | 17.77 | 0.251757 |
| CACNA1C_12_2099243_2111840_2249555_2251873_RF | CACNA1C | 197 | 35 | 0.006212 | 0.174409 | 17.77 | 0.250871 |
| CYP2C9_10_96690028_96694118_96755577_96760846_FF | CYP2C9 | 8 | 5 | 0.000851 | 0.038824 | 62.5 | 0.248438 |
| TASP1_20_13507251_13521471_13641645_1364731_FR | TASP1 | 172 | 30 | 0.013787 | 0.230556 | 17.44 | 0.246916 |
| CAMK1D_10_12392639_12394405_12558950_12568337_FR | CAMK1D | 115 | 24 | 0.002791 | 0.092599 | 20.87 | 0.246871 |
| AVP_20_3082527_3084991_3109305_3112452_RR | AVP | 8 | 4 | 0.00849 | 0.182297 | 50 | 0.245622 |
| CYP2C9_10_96661464_96668745_96755577_96760846_FF | CYP2C9 | 8 | 5 | 0.000851 | 0.038824 | 62.5 | 0.245603 |
| ICAM1_19_10341612_10343024_10368390_10370561_RR | ICAM1 | 9 | 5 | 0.001732 | 0.070257 | 55.56 | 0.245234 |
| LTA_6_31498892_31502771_31523234_31525915_RF | LTA | 17 | 6 | 0.009477 | 0.192177 | 35.29 | 0.242562 |
| VEGFA_6_43711156_43718584_43743156_43756590_RR | VEGFA | 16 | 6 | 0.006786 | 0.176922 | 37.5 | 0.241134 |
| CAMK1D_10_12558950_12568337_12770482_12771684_FF | CAMK1D | 115 | 24 | 0.002791 | 0.092599 | 20.87 | 0.240511 |
| TASP1_20_13279725_13285391_13489615_13507251_RF | TASP1 | 172 | 30 | 0.013787 | 0.230556 | 17.44 | 0.239337 |
| SDHB_1_17348194_17353079_17405102_17406505_FF | SDHB | 13 | 8 | 2.36E-05 | 0.004309 | 61.54 | 0.238395 |

TABLE 20B

Type 2 diabetes mellitus probes - EpiSwitch™ markers to stratify type 2 diabetes mellitus vs. healthy controls

| Probe | AveExpr | t | P.Value | adj.P.Val | B |
|---|---|---|---|---|---|
| ICAM1_19_10368390__10370561_10406169_10407761_RF | 0.434102 | 6.42338 | 0.000148 | 0.085141 | 1.368276 |
| SREBF1_17_17743896_17753157_17777190_17783023_RF | 0.405312 | 4.847753 | 0.001034 | 0.085141 | -0.376824 |
| CAMK1D_10_12558950_12568337_12770482_12771684_FR | 0.389359 | 7.082112 | 7.22E-05 | 0.085141 | 1.981818 |
| SLC2A2_3_170700264_170710807_170738889_170750047_RF | 0.37933 | 4.109419 | 0.0029 | 0.086908 | -1.33958 |
| ICAM1_19_10341612_10343024_10406169_10407761_RF | 0.374366 | 4.192347 | 0.002573 | 0.086505 | -1.226909 |
| SREBF1_17_17722022_17726360_17743896_17753157_FR | 0.370578 | 6.47337 | 0.00014 | 0.085141 | 1.417082 |
| IDE_10_94207972_94216393_94322805_94330672_RR | 0.335806 | 4.411221 | 0.001884 | 0.085141 | -0.934957 |
| CACNA1C_12_2099248_2111840_2394923_2398377_FR | 0.335327 | 6.941313 | 8.38E-05 | 0.085141 | 1.85594 |
| KCNJ11_11_17O1446_17405499JL7419957_17422762_RF | 0.334267 | 7.216543 | 6.27E-05 | 0.085141 | 2.099438 |
| SREBF1_17_177541S7_17760488_17777190_17783023_RF | 0.305866 | 4.192252 | 0.002573 | 0.086505 | -1.227037 |
| CACNA1C_12_2099248_2111840_2221145_2224007_FR | 0.304928 | 4.334594 | 0.0021 | 0.085141 | -1.036262 |
| CYB5R4_6_84553857_84562119_84611173_84616879_FF | 0.304406 | 3.987268 | 0.003466 | 0.086908 | -1.507539 |
| SLC2A2_3_170700264_170710807_170767515_170774153_RF | 0.304351 | 3.648477 | 0.005743 | 0.091143 | -1.985152 |
| KCNJ11_11_17419957_17422762_17452295_17453614_FR | 0.30432 | 5.539967 | 0.000423 | 0.085141 | 0.440492 |
| CAMK1D_10_12425560_12430245_12558950_12568337_RF | 0.29721 | 5.92423 | 0.000265 | 0.085141 | 0.859646 |
| KCNJ11_11_17401446_17405499_17445199_17452295_RF | 0.294294 | 6.734493 | 0.000105 | 0.085141 | 1.665928 |
| CAMK1D_10_12558950_12568337_1260S856_12611356_FR | 0.293636 | 6.449811 | 0.000144 | 0.085141 | 1.394129 |
| CAMK1D_10_12509013_12S11923_12558950_12568337_FR | 0.288358 | 3.608044 | 0.006106 | 0.091143 | -2.043232 |
| VEGFA_6_43701600_43705478_43718880_43723783_RF | 0.285845 | 3.220423 | 0.011102 | 0.098567 | -2.609928 |
| ADCY5_3_123037100_123044621_123133741_123143812_RF | 0.283847 | 5.443563 | 0.000477 | 0.085141 | 0.331754 |
| CAMK1D_10_12558950_12568337_12770482_12771684_RR | 0.282717 | 5.210694 | 0.000641 | 0.085141 | 0.062038 |
| LTA_6_31498892_31502771_31552034_31554202_FF | 0.782028 | 3.530375 | 0.006873 | 0.091324 | -2.155392 |
| CYP2C9_10_96661464_96668745_96741594_96747469_FR | 0.281118 | 3.845873 | 0.004271 | 0.086908 | -1.704835 |

TABLE 20B-continued

Type 2 diabetes mellitus probes - EpiSwitch™ markers to stratify type 2 diabetes mellitus vs. healthy controls

| | | | | | |
|---|---|---|---|---|---|
| CACNA1C_12_2099248_2111840_2383231_2391100_RR | 0.280559 | 4.641664 | 0.001368 | 0.085141 | −0.636294 |
| SREBF1_17_17722022_17726360_17743896_17753157_FR | 0.279061 | 3.327419 | 0.009397 | 0.093872 | −2.451875 |
| CACNA1C_12_2099248_2111840_2255353_2257963_FF | 0.276063 | 3.581668 | 0.006356 | 0.091143 | −2.081234 |
| CYB5A_18_71929777_71931243_71965803_71970158_FF | 0.275053 | 5.581719 | 0.000401 | 0.085141 | 0.487422 |
| IDE_10_94207972_94216393_94232614_94236267_RF | 0.270976 | 3.808438 | 0.004516 | 0.088035 | −1.757569 |
| TASP1_20_13265932_13269301_13507251_13521471_RR | 0.26783 | 4.183714 | 0.002605 | 0.086505 | −1.238586 |
| SDHB_1_17371319_17376758_17395655_17400949_FR | 0.267658 | 3.734784 | 0.005042 | 0.089145 | −1.861916 |
| CYB5R4_6_84541872_84548862_84611173_84616879_FF | 0.265948 | 3.914546 | 0.003857 | 0.086908 | −1.608634 |
| CAMK1D_10_12584612_12587236_12806730_12814088_FF | 0.262783 | 3.829993 | 0.004373 | 0.086908 | −1.72718 |
| CYB5R4_6_84533887_84541872_84611173_84616879_FF | 0.262369 | 3.516339 | 0.007022 | 0.091755 | −2.175742 |
| SREBF1_17_17722022_17726360_17754197_17760488_RR | 0.258464 | 4.593833 | 0.001461 | 0.085141 | −0.697539 |
| SREBF1_17_17743896_17753157_17764809_17767745_FR | 0.258278 | 4.299433 | 0.002207 | 0.085141 | −1.083076 |
| SDHB_1_17371319_17376758_17395655_17400949_RR | 0.256686 | 3.882266 | 0.004046 | 0.086908 | −1.653765 |
| ADCY5_3_123098260_123106114_123133741_123143812_RF | 0.256602 | 3.953353 | 0.003643 | 0.086908 | −1.554585 |
| CACNA1C_12_2099248_2111840_2371355_2375397_FF | 0.251757 | 5.392827 | 0.000508 | 0.085141 | 0.273777 |
| CACNA1C_12_2099248_2111840_2249555_2251873_RF | 0.250871 | 3.572509 | 0.006445 | 0.091143 | −2.094452 |
| CYP2C9_10_96690028_96694118_96755577_96760846_FF | 0.248438 | 5.685135 | 0.000353 | 0.085141 | 0.601853 |
| TASP1_20_13507251_13521471_13641645_13647312_FR | 0.246916 | 3.67084 | 0.005552 | 0.091143 | −1.953122 |
| CAMK1D_10_12392639_12394405_12558950_12568337_FR | 0.246871 | 4.321578 | 0.002139 | 0.085141 | −1.053568 |
| AVP_20_3082527_3084991_3109305_3112452_RR | 0.245622 | 3.833295 | 0.004351 | 0.086908 | −1.72253 |
| CYP2C9_10_96661464_96668745_96755577_96760846_FF | 0.245603 | 3.254351 | 0.010529 | 0.097267 | −2.559693 |
| ICAM1_19_10341612__10343024_10368390_10370561_RR | 0.245234 | 3.621185 | 0.005985 | 0.091143 | −2.024332 |
| LTA_6_31498892_31502771_31523234_31525915_RF | 0.242562 | 4.646403 | 0.001359 | 0.085141 | −0.630248 |
| VEGFA_6_43711156_43718584_43754116_43756590_RR | 0.241134 | 4.631302 | 0.001388 | 0.085141 | −0.649529 |
| CAMK1D_10_12558950_12568337_12770482_12771684_FF | 0.240511 | 5.225549 | 0.000629 | 0.085141 | 0.07952 |
| TASP1_20_13279725_13285391_13489615_13507251_RF | 0.239337 | 3.408863 | 0.008284 | 0.092903 | −2.332342 |
| SDHB_1_17348194_17353079_17405102_17406505_FF | 0.238395 | 4.19351 | 0.002568 | 0.086505 | −1.225337 |

| Probe | FC | FC_1 | LS | Loop detected |
|---|---|---|---|---|
| ICAM1_19_10368390__10370561_10406169_10407761_RF | 1.36993 | 1.36993 | 1 | T2DM |
| SREBF1_17_17743896_17753157_17777190_17783023_RF | 1.324375 | 1.324375 | 1 | T2DM |
| CAMK1D_10_12558950_12568337_12770482_12771684_FR | 1.309812 | 1.309812 | 1 | T2DM |
| SLC2A2_3_170700264_170710807_170738889_170750047_RF | 1.300738 | 1.300738 | 1 | T2DM |
| ICAM1_19_10341612_10343024_10406169_10407761_RF | 1.29627 | 1.29627 | 1 | T2DM |
| SREBF1_17_17722022_17726360_17743896_17753157_RR | 1.292871 | 1.292871 | 1 | T2DM |
| IDE_10_94207972_94216393_94322805_94330672_RR | 1.262082 | 1.262082 | 1 | T2DM |
| CACNA1C_12_2099248_2111840_2394923_2398377_FR | 1.261663 | 1.261663 | 1 | T2DM |
| KCNJ11_11_174O1446_17405499JL7419957_17422762_RF | 1.260737 | 1.260737 | 1 | T2DM |
| SREBF1_17_177541S7_17760488_17777190_17783023_RF | 1.23616 | 1.23616 | 1 | T2DM |
| CACNA1C_12_2099248_2111840_2221145_2224007_FR | 1.235357 | 1.235357 | 1 | T2DM |
| CYB5R4_6_84553857_84562119_84611173_84616879_FF | 1.23491 | 1.23491 | 1 | T2DM |
| SLC2A2_3_170700264_170710807_170767515_170774153_RF | 1.234863 | 1.234863 | 1 | T2DM |
| KCNJ11_11_17419957_17422762_17452295_17453614_FR | 1.234837 | 1.234837 | 1 | T2DM |
| CAMK1D_10_12425560_12430245_12558950_12568337_RF | 1.228766 | 1.228766 | 1 | T2DM |
| KCNJ11_11_17401446_17405499_17445199_17452295_RF | 1.226285 | 1.226285 | 1 | T2DM |
| CAMK1D_10_12558950_12568337_1260S856_12611356_FR | 1.225726 | 1.225726 | 1 | T2DM |
| CAMK1D_10_12209013_12S11923_12558950_12568337_FR | 1.221249 | 1.221249 | 1 | T2DM |
| VEGFA_6_43701600_43705478_43718880_43723783_RF | 1.219124 | 1.219124 | 1 | T2DM |
| ADCY5_3_123037100_123044621_123133741_123143812_RF | 1.217437 | 1.217437 | 1 | T2DM |
| CAMK1D_10_12558950_12568337_12770482_12771684_RR | 1.216484 | 1.216484 | 1 | T2DM |
| LTA_6_31498892_31502771_31552034_31554202_FF | 1.215903 | 1.215903 | 1 | T2DM |
| CYP2C9_10_96661464_96668745_96741594_96747469_FR | 1.215136 | 1.215136 | 1 | T2DM |
| CACNA1C_12_2099248_2111840_2383231_2391100_RR | 1.214666 | 1.214666 | 1 | T2DM |
| SREBF1_17_17722022_17726360_17743896_17753157_FR | 1.213405 | 1.213405 | 1 | T2DM |
| CACNA1C_12_2099248_2111840_2255353_2257963_FF | 1.210886 | 1.210886 | 1 | T2DM |
| CYB5A_18_71929777_71931243_71965803_71970158_FF | 1.210038 | 1.210038 | 1 | T2DM |
| IDE_10_94207972_94216393_94232614_94236267_RF | 1.206624 | 1.206624 | 1 | T2DM |
| TASP1_20_13265932_13269301_13507251_13521471_RR | 1.203995 | 1.203995 | 1 | T2DM |
| SDHB_1_17371319_17376758_17395655_17400949_FR | 1.203852 | 1.203852 | 1 | T2DM |
| CYB5R4_6_84541872_84548862_84611173_84616879_FF | 1.202426 | 1.202426 | 1 | T2DM |
| CAMK1D_10_12584612_12587236_12806730_12814088_FF | 1.199791 | 1.199791 | 1 | T2DM |
| CYB5R4_6_84533887_84541872_84611173_84616879_FF | 1.199447 | 1.199447 | 1 | T2DM |
| SREBF1_17_17722022_17726360_17754197_17760488_RR | 1.196205 | 1.196205 | 1 | T2DM |
| SREBF1_17_17743896_17753157_17764809_17767745_FR | 1.19605 | 1.19605 | 1 | T2DM |
| SDHB_1_17371319_17376758_17395655_17400949_RR | 1.194731 | 1.194731 | 1 | T2DM |
| ADCY5_3_123098260_123106114_123133741_123143812_RF | 1.194662 | 1.194662 | 1 | T2DM |
| CACNA1C_12_2099248_2111840_2371355_2375397_FF | 1.190656 | 1.190656 | 1 | T2DM |
| CACNA1C_12_2099248_2111840_2249555_2251873_RF | 1.189926 | 1.189926 | 1 | T2DM |
| CYP2C9_10_96690028_96694118_96755577_96760846_FF | 1.187921 | 1.187921 | 1 | T2DM |
| TASP1_20_13507251_13521471_13641645_13647312_FR | 1.186668 | 1.186668 | 1 | T2DM |
| CAMK1D_10_12392639_12394405_12558950_12568337_FR | 1.186631 | 1.186631 | 1 | T2DM |
| AVP_20_3082527_3084991_3109305_3112452_RR | 1.185604 | 1.185604 | 1 | T2DM |
| CYP2C9_10_96661464_96668745_96755577_96760846_FF | 1.185588 | 1.185588 | 1 | T2DM |
| ICAM1_19_10341612__10343024_10368390_10370561_RR | 1.185285 | 1.185285 | 1 | T2DM |
| LTA_6_31498892_31502771_31523234_31525915_RF | 1.183092 | 1.183092 | 1 | T2DM |
| VEGFA_6_43711156_43718584_43754116_43756590_RR | 1.181921 | 1.181921 | 1 | T2DM |
| CAMK1D_10_12558950_12568337_12770482_12771684_FF | 1.181411 | 1.181411 | 1 | T2DM |

TABLE 20B-continued

Type 2 diabetes mellitus probes - EpiSwitch™ markers to stratify type 2 diabetes mellitus vs. healthy controls

| | | | | |
|---|---|---|---|---|
| TASP1_20_13279725_13285391_13489615_13507251_RF | 1.18045 | 1.18045 | 1 | T2DM |
| SDHB_1_17348194_17353079_17405102_17406505_FF | 1.179679 | 1.179679 | 1 | T2DM |

TABLE 20c

Type 2 DM Probes - EpiSwitch ™ markers to stratify Type 2 DM vs. healthy controls

| Probe | Probe sequence 60 mer |
|---|---|
| ICAM1_19_10368390_10370561_10406169_10407761_RF | GGAAGGCCGAGGCGGCCAGATCACGAGGTCGAACCTCCTGATAACTTCAGCAT TAACAGC (SEQ ID NO: 207) |
| SREBF1_17_17743896_17753157_17777190_17783023_RF | ACATCTCAGACATGACTTTTGTGTTTCCTCGAGCCTTTTCGGGCAGGCGTCCA GCACGGG (SEQ ID NO: 208) |
| CAMK1D_10_12558950_12568337_12770482_12771684_FR | CGTGGTTCTTCAAGTTGTAGTTTAATTCTCGAGAGCAGTGTTTTAAGTGGTCT GACGGGA (SEQ ID NO: 209) |
| SLC2A2_3_170700264_170710807_170738889_170750047_RF | TTGGCTGTTTTCACTCAGTGAAATTCCTTCGAGCCCAGGAGGCAAAGGTTGCA GTGAGCT (SEQ ID NO: 210) |
| ICAM1_19_10341612_10343024_10406169_10407761_RF | GGAAGGCCGAGGCGGCCAGATCACGAGGTCGAAAGCGCTCGGATTCAGCCTTC TCCCCGG (SEQ ID NO: 211) |
| SREBF1_17_17722022_17726360_17743896_17753157_RR | ATGGACAGTAGGCAGGATGAATAAGTGCTCGAGCCTTTTCGGGCAGGCGTCCA GCACGGG (SEQ ID NO: 212) |
| IDE_10_94207972_94216393_94322805_94330672_RR | GGGTTTCACCATGTTGGCCTGGCTGGGCTCGAGACCAGCCTGGCCAACATGGT GAAACCA (SEQ ID NO: 213) |
| CACNA1C_12_2099248_2111840_2394923_2398377_FR | ACTGACAGTTTCTTGGGATTCTCCAGACTCGAGAGAGGCTGGTGCGCACCTAC CCAGCGG (SEQ ID NO: 214) |
| KCNJ11_11_17401446_17405499_17419957_17422762_RF | CTTAGAGCAAAGGCTAGGCTCAGTAATGTCGAGAGAGAGCCTGTGTGAGGAGT GCAGTCA (SEQ ID NO: 215) |
| SREBF1_17_17754197_17760488_17777190_17783023_RF | ACATCTCAGACATGACTTTTGTGTTTCCTCGAGTCTCACCAGGTCGGTCCTGA GCCACAC (SEQ ID NO: 216) |
| CACNA1C_12_2099248_2111840_2221145_2224007_FR | ACTGACAGTTTCTTGGGATTCTCCAGACTCGAGGCCTGGAGAAGCCCAGGAGG AGGCGTG (SEQ ID NO: 217) |
| CYB5R4_6_84553857_84562119_84611173_84616879_FF | ATTATAACATTTATATATCATCTTTTCCTCGAGGTTGCAGTAAGCTGATCATG CCACTAC (SEQ ID NO: 218) |
| SLC2A2_3_170700264_170710807_170767515_170774153_RF | GGAAAACAGGATTAAAAAAGAAATGGATTCGAGCCCAGGAGGCAAAGGTTGCA GTGAGCT (SEQ ID NO: 219) |
| KCNJ11_11_17419957_17422762_17452295_17453614_FR | CTTAGAGCAAAGGCTAGGCTCAGTAATGTCGAGCAAGCCTTGAGGCTGACACA GGACCTG (SEQ ID NO: 220) |
| CAMK1D_10_12425560_12430245_12558950_12568337_RF | CGTGGTTCTTCAAGTTGTAGTTTAATTCTCGAGCTTGTTATTTTCTCTTTCTT ACCTAGT (SEQ ID NO: 221) |
| KCNJ11_11_17401446_17405499_17445199_17452295_RF | GACCAAACAGCTGTGGTTTGGCCATCACTCGAGAGAGAGCCTGTGTGAGGAGT GCAGTCA (SEQ ID NO: 222) |
| CAMK1D_10_12558950_12568337_12609856_12611356_FR | CGTGGTTCTTCAAGTTGTAGTTTAATTCTCGAGCTTGAATCAGAATGGTCAAG ATACCTG (SEQ ID NO: 223) |
| CAMK1D_10_12509013_12511923_12558950_12568337_FR | TGTGTTAGGGTACCATTCTTCTTAAGTATCGAATCTGTACATCAACTTTGGAA AAACTAA (SEQ ID NO: 224) |
| VEGFA_6_43701600_43705478_43718880_43723783_RF | TCCTACAGAAGTTAAAATAGAGCTAGGGTCGAATTGGCCCGGGTCCCTGCTGG GCTGGAG (SEQ ID NO: 225) |
| ADCY5_3_123037100_123044621_123133741_123143812_RF | TTTAGCCAAAAGAAAAAAGGTTCATTTCGAGAACCAGAGTCAAACTTAGAC CCCAGGA (SEQ ID NO: 226) |
| CAMK1D_10_12558950_12568337_12770482_12771684_RR | TTAGTTTTTCCAAAGTTGATGTACAGATTCGAGAGCAGTGTTTTAAGTGGTCT GACGGGA (SEQ ID NO: 227) |
| LTA_6_31498892_31502771_31552034_31554202_FF | TGGTGAGCAGAAGGCTCCAGCTGTACGCTCGACGGCCCAGGGAAACTCAACC CATACTC (SEQ ID NO: 228) |

TABLE 20c-continued

Type 2 DM Probes - EpiSwitch ™ markers to stratify Type 2 DM vs. healthy controls

| Probe | Probe sequence 60 mer |
|---|---|
| CYP2C9_10_96661464_96668745_96741594_96747469_FR | GAGTAGGTAAACAAAGCAGTCAGGAAGCTCGAGTCTTTGGTTTTCCCTAGATAATTAATA (SEQ ID NO: 229) |
| CACNA1C_12_2099248_2111840_2383231_2391100_RR | ACACCACTTGAACCAAGAAACCTTAACTTCGAAGGAGTGGCATAAGGTCCCACTTGGGTG (SEQ ID NO: 230) |
| SREBF1_17_17722022_17726360_17743896_17753157_FR | CCCTTTACCCCAGTCCGTGTGAGCCTCTTCGAGCCTTTTCGGGCAGGCGTCCAGCACGGG (SEQ ID NO: 231) |
| CACNA1C_12_2099248_2111840_2255353_2257963_FF | ACTGACAGTTTCTTGGGATTCTCCAGACTCGAGGCAGGAGGACAGCTTGAGCCCGGGAGT (SEQ ID NO: 232) |
| CYB5A_18_71929777_71931243_71965803_71970158_FF | CCTAGGCAGATCACTTGAGTTCAGGAGTTCGAAACACTTGATCAAAACAGAATAACAGGT (SEQ ID NO: 233) |
| IDE_10_94207972_94216393_94232614_94236267_RF | ATCTTTTTTAAAAAATATATTTATTTATTCGAGCCCAGCCAGGCCAACATGGTGAAACCC (SEQ ID NO: 234) |
| TASP1_20_13265932_13269301_13507251_13521471_RR | TCCTTTCTTTTTTATTTTTTAAGCTGTTTCGATTCAACATTAATTCATTTTAGACTTCTC (SEQ ID NO: 235) |
| SDHB_1_17371319_17376758_17395655_17400949_FR | CCAGGATGTACTACACTGAATATCTAAGTCGAGGCCCAGGGGCTCCAGGAGGCACGCAC (SEQ ID NO: 236) |
| CYB5R4_6_84541872_84548862_84611173_84616879_FF | TCCCGATCACAGCTGAAGATTGGAAAGGTCGAGGTTGCAGTAAGCTGATCATGCCACTAC (SEQ ID NO: 237) |
| CAMK1D_10_12584612_12587236_12806730_12814088_FF | AGAAGCAATTGAGAAAAACCTCAGGTGTTCGACTACTATGTTGTTGATTTCTATCAAAGC (SEQ ID NO: 238) |
| CYB5R4_6_84533887_84541872_84611173_84616879_FF | TGTTCAATCAAAGGAAGGGATAACACTATCGAGGTTGCAGTAAGCTGATCATGCCACTAC (SEQ ID NO: 239) |
| SREBF1_17_17722022_17726360_17754197_17760488_RR | ATGGACAGTAGGCAGGATGAATAAGTGCTCGAGTCTCACCAGGTCGGTCCTGAGCCACAC (SEQ ID NO: 240) |
| SREBF1_17_17743896_17753157_17764809_17767745_FR | TTGCTTCTGTGAGAGAAGCAATTTCTTTTCGATTGTCTAGTGCAGAAGCAAGTCCTCCGA (SEQ ID NO: 241) |
| SDHB_1_17371319_17376758_17395655_17400949_RR | CTCCCCGTATCAAGAAATTTGCCATCTATCGAGGCCCAGGGGCTCCAGGAGGCACGCAC (SEQ ID NO: 242) |
| ADCY5_3_123098260_123106114_123133741_123143812_RF | TTTAGCCAAAAAGAAAAAAAGGTTCATTTCGAGGAATGTTTCCAAGCAATTCTCTCTGCT (SEQ ID NO: 243) |
| CACNA1C_12_2099248_2111840_2371355_2375397_FF | ACTGACAGTTTCTTGGGATTCTCCAGACTCGAAGGCATTGTTCTGGAGGTGGAGGAAGGG (SEQ ID NO: 244) |
| CACNA1C_12_2099248_2111840_2249555_2251873_RF | TCCTGACCAAGGATCCTGATCCTTGATATCGAAGTTAAGGTTTCTTGGTTCAAGTGGTGT (SEQ ID NO: 245) |
| CYP2C9_10_96690028_96694118_96755577_96760846_FF | TGAGGTAGGCAGATCACAGGTCAGGAGATCGATCCAGTGTGCTTTTCACTTCAGACCTTG (SEQ ID NO: 246) |
| TASP1_20_13507251_13521471_13641645_13647312_FR | CATGGTTATATACACATGTTAAAATTCATCGATTGAACCCTGGAGGAGGAGGTTGCAGTG (SEQ ID NO: 247) |
| CAMK1D_10_12392639_12394405_12558950_12568337_FR | AGGCGAGCTGATCACTTAAGTCAGGAGTTCGAATCTGTACATCAACTTTGGAAAAACTAA (SEQ ID NO: 248) |
| AVP_20_3082527_3084991_3109305_3112452_RR | CCCTTGTTTTCTGGAGATTCACTCTTCATCGAGATCAGCCCGGGCAACACAGCAAGACCC (SEQ ID NO: 249) |
| CYP2C9_10_96661464_96668745_96755577_96760846_FF | GAGTAGGTAAACAAAGCAGTCAGGAAGCTCGATCCAGTGTGCTTTTCACTTCAGACCTTG (SEQ ID NO: 250) |
| ICAM1_19_10341612_10343024_10368390_10370561_RR | CCGGGGAGAAGGCTGAATCCGAGCGCTTTCGAACCTCCTGATAACTTCAGCATTAACAGC (SEQ ID NO: 251) |
| LTA_6_31498892_31502771_31523234_31525915_RF | AGCAGCAGCGAGAAGCAGAGGGATCCCGTCGATGTCCATGCCTCGGCCAAATAGGTTGGT (SEQ ID NO: 252) |
| VEGFA_6_43711156_43718584_43754116_43756590_RR | AGCAGGATCGTTTCACAACCATGTGTGCTCGAGATATTCCGTAGTACATATTTATTTTTA (SEQ ID NO: 253) |

TABLE 20c-continued

Type 2 DM Probes - EpiSwitch ™ markers to stratify Type 2 DM vs. healthy controls

| Probe | Probe sequence 60 mer |
|---|---|
| CAMK1D_10_12558950_12568337_12770482_12771684_FF | CGTGGTTCTTCAAGTTGTAGTTTAATTCTCGAATATTTAATCTCTCTACACCA CTTAATC (SEQ ID NO: 254) |
| TASP1_20_13279725_13285391_13489615_13507251_RF | ATTTTTTGACAATTATAGTAGTATGGATTCGACCGCATCAAGCGCAAGGACTT CCGCTGG (SEQ ID NO: 255) |
| SDHB_1_17348194_17353079_17405102_17406505_FF | GGGTTTTATCACGTTGGCCAGGCTGGTCTCGAGACCAGCCTGGGCAACCCAGT GAAACCC (SEQ ID NO: 256) |

TABLE 20D

Type 2 diabetes mellitus probes - Epi Switch™ markers to stratify type 2 diabetes vs. healthy controls

| Probe | Chr | Start1 | End1 | Start2 | End2 |
|---|---|---|---|---|---|
| ICAM1_19_10368390_10370561_10406169_10407761_RF | 19 | 10368391 | 10368420 | 10407732 | 10407761 |
| SREBF1_17_17743896_17753157_17777190_17783023_RF | 17 | 17743897 | 17743926 | 17782994 | 17783023 |
| CAMK1D_10_12558950_12568337_12770482_12771684_FR | 10 | 12568308 | 12568337 | 12770483 | 12770512 |
| SLC2A2_3_170700264_170710807_170738889_170750047_RF | 3 | 170700265 | 170700294 | 170750018 | 170750047 |
| ICAM1_19_10341612_10343024_10406169_10407761_RF | 19 | 10341613 | 10341642 | 10407732 | 10407761 |
| SREBF1_17_17722022_17726360_17743896_17753157_RR | 17 | 17722023 | 17722052 | 17743897 | 17743926 |
| IDE_10_94207972_94216393_94322805_94330672_RR | 10 | 94207973 | 94208002 | 94322806 | 94322835 |
| CACNA1C_12_2099248_2111840_2394923_2398377_FR | 12 | 2111811 | 2111840 | 2394924 | 2394953 |
| KCNJ11_11_17401446_17405499_17419957_17422762_RF | 11 | 17401447 | 17401476 | 17422733 | 17422762 |
| SREBF1_17_17754197_17760488_17777190_17783023_RF | 17 | 17754198 | 17754227 | 17782994 | 17783023 |
| CACNA1C_12_2099248_2111840_2221145_2224007_FR | 12 | 2111811 | 2111840 | 2221146 | 2221175 |
| CYB5R4_6_84553857_84562119_84611173_84615879_FF | 6 | 84562090 | 84562119 | 84616850 | 84616879 |
| SLC2A2_3_170700264_170710807_170767515_170774153_RF | 3 | 170700265 | 170700294 | 170774124 | 170774153 |
| KCNJ11_11_17419957_17422762_17452295_17453614_FR | 11 | 17422733 | 17422762 | 17452296 | 17452325 |
| CAMK1D_10_12425560_12430245_12558950_12568337_RF | 10 | 12425561 | 12425590 | 12568308 | 12568337 |
| KCNJ11_11_17401446_17405499_17445199_17452295_RF | 11 | 17401447 | 17401476 | 17452266 | 17452295 |
| CAMK1D_10_12558950_12568337_12609856_12611356_FR | 10 | 12568308 | 12568337 | 12609857 | 12609886 |
| CAMK1D_10_12509013_12511923_12558950_12568337_FR | 10 | 12511894 | 12511923 | 12558951 | 12558980 |
| VEGFA_6_43701600_43705478_43718880_43723783_RF | 6 | 43701601 | 43701630 | 43723754 | 43723783 |
| ADCY5_3_123037100_123044621_123133741_123143812_RF | 3 | 123037101 | 123037130 | 123143783 | 123143812 |
| CAMK1D_10_12558950_12568337_12770482_12771684_RR | 10 | 12558951 | 12558980 | 12770483 | 12770512 |
| LTA_6_31498892_31502771_31552034_31554202_FF | 6 | 31502742 | 31502771 | 31554173 | 31554202 |
| CYP2C9_10_96661464_96668745_96741594_96747469_FR | 10 | 96668716 | 96668745 | 96741595 | 96741624 |
| CACNA1C_12_2099248_2111840_2383231_2391100_RR | 12 | 2099249 | 2099278 | 2383232 | 2383261 |
| SREBF1_17_17722022_17726360J17743896_17753157_FR | 17 | 17726331 | 17726360 | 17743897 | 17743926 |
| CACNA1C_12_2099248_2111840_2255353_2257953_FR | 12 | 2111811 | 2111840 | 2257934 | 2257963 |
| CYB5A_18_71929777_71931243_71965803_71970158_FF | 18 | 71931214 | 71931243 | 71970129 | 71970158 |
| IDE_10_94207972_94216393_94232614_94236267_RF | 10 | 94207973 | 94208002 | 94236238 | 94236267 |
| TASP1_20_13265932_13269301_13507251_13521471_RR | 20 | 13265933 | 13265962 | 13507252 | 13507281 |
| SDHB_1_17371319_17376758_17395655_17400949_FR | 1 | 17376729 | 17376758 | 17395656 | 17395685 |
| CYB5R4_6_84541872_84548862_84611173_84615879_FF | 6 | 84548833 | 84548862 | 84616850 | 84616879 |
| CAMK1D_10_12584612_12587236_12806730_12814088_FF | 10 | 12587207 | 12587236 | 12814059 | 12814088 |
| CYB5R4_6_84533887_84541872_84611173_84615879_FF | 6 | 84541843 | 84541872 | 84616850 | 84616879 |
| SREBF1_17_17722022_17726360_17754197_17760488_RR | 17 | 17722023 | 17722052 | 17754198 | 17754227 |
| SREBF1_17_17743896_17753157_17764809_17767745_FR | 17 | 17753128 | 17753157 | 17764810 | 17764839 |
| SDHB_1_17371319_17376758_17395655_17400949_RR | 1 | 17371320 | 17371349 | 17395656 | 17395685 |
| ADCY5_3_123098260_123106114_123133741_123143812_RF | 3 | 123098261 | 123098290 | 123143783 | 123143812 |
| CACNA1C_12_2099248_2111840_2371355_2375397_FF | 12 | 2111811 | 2111840 | 2375374 | 2375397 |
| CACNA1C_12_2099248_2111840_2249555_2251873_RF | 12 | 2099249 | 2099278 | 2251844 | 2251873 |
| CYP2C9_10_96690028_96694118_96755577_96760846_FF | 10 | 96694089 | 96694118 | 96760817 | 96760846 |
| TASP1_20_13507251_13521471_13641645_13647312_FR | 20 | 13521442 | 13521471 | 13641646 | 13641675 |
| CAMK1D_10_12392639_12394405_12558950_12568337_FR | 10 | 12392639 | 12394405 | 12558951 | 12558980 |
| AVP_20_3082527_3084991_3109305_3112452_RR | 20 | 3082528 | 3082557 | 3109306 | 3109335 |
| CYP2C9_10_96661464_96668745_96755577_96760846_FF | 10 | 96668716 | 96668745 | 96760817 | 96760846 |
| ICAM1_19_10341612_10343024_10368390_10370561_RR | 19 | 10341613 | 10341642 | 10368391 | 10368420 |
| LTA_6_31498892_31502771_31523234_31525915_RF | 6 | 31498892 | 31498922 | 31525886 | 31525915 |
| VEGFA_6_43711156_43718584_43754116_43756390_RR | 6 | 43711157 | 43711186 | 43754117 | 43754146 |
| CAMK1D_10_12558950_12568337_12770482_12771684_FF | 10 | 12568308 | 12568337 | 12771655 | 12771684 |
| TASP1_20_13279725_13285391_13489615_13507251_RF | 20 | 13279726 | 13279755 | 13507222 | 13507251 |
| SDHB_1_17348194_17353079_17405102_17406505_FF | 1 | 17353050 | 17353079 | 17406476 | 17406505 |

TABLE 20D-continued

Type 2 diabetes mellitus probes - Epi Switch™ markers to stratify type 2 diabetes vs. healthy controls

| Probe | Chr | Start1 | End1 | Start2 | End2 |
|---|---|---|---|---|---|
| ICAM1_19_10368390_10370561_10406169_10407761_RF | 19 | 10368391 | 10372390 | 10403762 | 10407761 |
| SREBF1_17_17743896_17753157_17777190_17783023_RF | 17 | 17743896 | 17747896 | 17779024 | 17783023 |
| CAMK1D_10_12558950_12568337_12770482_12771684_FR | 10 | 12564338 | 12568337 | 12770483 | 12774482 |
| SLC2A2_3_170700264_170710807_170738889_170750047_RF | 3 | 170700265 | 170704264 | 170746048 | 170750047 |
| ICAM1_19_10341612_10343024_10406169_10407761_RF | 19 | 10341613 | 10345612 | 10403762 | 10407761 |
| SREBF1_17_17722022_17726360_17743896_17753157_RR | 17 | 17722023 | 17726022 | 17743897 | 17747896 |
| IDE_10_94207972_94216393_94322805_94330672_RR | 10 | 94207973 | 94211972 | 94322806 | 94326805 |
| CACNA1C_12_2099248_2111840_2394923_2398377_FR | 12 | 2107841 | 2111840 | 2394924 | 2398923 |
| KCNJ11_11_17401446_17405499_17419957_17422762_RF | 11 | 17401447 | 17405446 | 17418763 | 17422762 |
| SREBF1_17_17754197_17760488_17777190_17783023_RF | 17 | 17754198 | 17758197 | 17779024 | 17783023 |
| CACNA1C_12_2099248_2111840_2221145_2224007_FR | 12 | 2107841 | 2111840 | 2221146 | 2225145 |
| CYB5R4_6_84553857_84562119_84611173_84615879_FF | 6 | 84558120 | 84562119 | 84612880 | 84616879 |
| SLC2A2_3_170700264_170710807_170767515_170774153_RF | 3 | 170700265 | 170704264 | 170770154 | 170774153 |
| KCNJ11_11_17419957_17422762_17452295_17453614_FR | 11 | 17418763 | 17422762 | 17452296 | 17456295 |
| CAMK1D_10_12425560_12430245_12558950_12568337_RF | 10 | 12425560 | 12430245 | 12564338 | 12568337 |
| KCNJ11_11_17401446_17405499_17445199_17452295_RF | 11 | 17401447 | 17405446 | 17448296 | 17452295 |
| CAMK1D_10_12558950_12568337_12609856_12611356_FR | 10 | 12564338 | 12568337 | 12609857 | 12613856 |
| CAMK1D_10_12509013_12511923_12558950_12568337_FR | 10 | 12507924 | 12511923 | 12558951 | 12562950 |
| VEGFA_6_43701600_43705478_43718880_43723783_RF | 6 | 43701601 | 43705600 | 43719784 | 43723783 |
| ADCY5_3_123037100_123044621_123133741_123143812_RF | 3 | 123037101 | 123041100 | 123139813 | 123143812 |
| CAMK1D_10_12558950_12568337_12770482_12771684_RR | 10 | 12558951 | 12562950 | 12770483 | 12774482 |
| LTA_6_31498892_31502771_31552034_31554202_FF | 6 | 31498772 | 31502771 | 31550203 | 31554202 |
| CYP2C9_10_96661464_96668745_96741594_96747469_FR | 10 | 96664746 | 96668745 | 96741595 | 96745594 |
| CACNA1C_12_2099248_2111840_2383231_2391100_RR | 12 | 2099249 | 2103248 | 2383232 | 2387231 |
| SREBF1_17_17722022_17726360J17743896_17753157_FR | 17 | 17722361 | 17726360 | 17743897 | 17747896 |
| CACNA1C_12_2099248_2111840_2255353_2257953_FF | 12 | 2107841 | 2111840 | 2253964 | 2257963 |
| CYB5A_18_71929277_71931243_71965803_71970158_FF | 18 | 71927244 | 71931243 | 71966159 | 71970158 |
| IDE_10_94207972_94216393_94232614_94236267_RF | 10 | 94207973 | 94211972 | 94232268 | 94236267 |
| TASP1_20_13265932_13269301_13507251_13521471_RR | 20 | 13265933 | 13269932 | 13507252 | 13511251 |
| SDHB_1_17371319_17376758_17395655_17400949_FR | 1 | 17372759 | 17376758 | 17395656 | 17399655 |
| CYB5R4_6_84541872_84548862_84611173_84615879_FF | 6 | 84544863 | 84548862 | 84612880 | 84616879 |
| CAMK1D_10_12584612_12587236_12806730_12814088_FF | 10 | 12583237 | 12587236 | 12810089 | 12814088 |
| CYB5R4_6_84533887_84541872_84611173_84615879_FF | 6 | 84537873 | 84541872 | 84612880 | 84616879 |
| SREBF1_17_17722022_17726360_17754197_17760488_RR | 17 | 17722023 | 17726022 | 17754198 | 17758197 |
| SREBF1_17_17743896_17753157_17764809_17767745_FR | 17 | 17749158 | 17753157 | 17764810 | 17768809 |
| SDHB_1_17371319_17376758_17395655_17400949_RR | 1 | 17371320 | 17375319 | 17395656 | 17399655 |
| ADCY5_3_123098260_123106114_123133741_123143812_RF | 3 | 123098261 | 123102260 | 123139813 | 123143812 |
| CACNA1C_12_2099248_2111840_2371355_2375397_FF | 12 | 2107841 | 2111840 | 2371398 | 2375397 |
| CACNA1C_12_2099248_2111840_2249555_2251873_RF | 12 | 2099249 | 2103248 | 2247874 | 2251873 |
| CYP2C9_10_96690028_96694118_96755577_96760846_FF | 10 | 96690119 | 96694118 | 96756847 | 96760846 |
| TASP1_20_13507251_13521471_13641645_13647312_FR | 20 | 13517472 | 13521471 | 13641646 | 13645645 |
| CAMK1D_10_12392639_12394405_12558950_12568337_FR | 10 | 12390406 | 12394405 | 12558951 | 12562950 |
| AVP_20_3082527_3084991_3109305_3112452_RR | 20 | 3082528 | 3086527 | 3109306 | 3113305 |
| CYP2C9_10_96661464_96668745__96755577_96760846_FF | 10 | 96664746 | 96668745 | 96756847 | 96760846 |
| ICAM1_19_10341612_10343024_10368390_10370561_RR | 19 | 10341613 | 10345612 | 10368391 | 10372300 |
| LTA_6_31498892_31502771_31523234_31525915_RF | 6 | 31498893 | 31502892 | 31521916 | 31525915 |
| VEGFA_6_43711156_43718584_43754116_43756390_RR | 6 | 43711157 | 43715156 | 43754117 | 43758116 |
| CAMK1D_10_12558950_12568337_12770482_12771684_FF | 10 | 12564338 | 12568337 | 12767685 | 12771684 |
| TASP1_20_13279725_13285391_13489615_13507251_RF | 20 | 13279726 | 13283725 | 13503252 | 13507251 |
| SDHB_1_17348194_17353079_17405102_17406505_FF | 1 | 17349080 | 17353079 | 17402506 | 17406505 |

TABLE 21A

Type 1 diabetes meilitus (T1DM) probes - EpiSwitch™ markers to stratify T1DM vs. healthy controls

| Probe | GeneLocus | Probe_Count_Total | Probe_Count_Sig | HyperG_Stats |
|---|---|---|---|---|
| 11_923549_925733_976127_979142_FR | AP2A2 | 16 | 5 | 0.059154368 |
| 3_3117964_3119702_3187910_3199411_RF | IL5RA | 7 | 3 | 0.060129293 |
| 16_4065887_4067896_4109379_4115518_FR | ADCY9 | 66 | 17 | 0.007121374 |
| 1_172083100_172087823_172151185_172154127_FF | DNM3 | 902 | 153 | 0.002933237 |
| 16_31228760_31230406_31342509_31344379_FR | ITGAM | 28 | 11 | 0.000764097 |
| 1_171936106_171939290_172083100_172087823_RF | DNM3 | 902 | 153 | 0.002933237 |
| 1_172061602_172067357_172083100_172087823_RF | DNM3 | 902 | 153 | 0.002933237 |
| 1_171811918_171813464_172083100_172087823_RF | DNM3 | 902 | 153 | 0.002933237 |
| 11_36531355_36534043_36605543_36609927_RR | RAG1 | 44 | 14 | 0.001755155 |
| 1_171887726_171889817_172083100_172087823_RF | DNM3 | 902 | 153 | 0.002933237 |
| 11_1010876_1013083_964245_969445_FF | AP2A2 | 16 | 5 | 0.059154368 |
| 1_172083100_172087823_172212232_172223166_FF | DNM3 | 902 | 153 | 0.002933237 |
| 6_32135728_32138270_32149729_32154447_FF | AGER | 3 | 3 | 0.002646464 |
| 16_4065887_4067896_4204978_4209511_FF | ADCY9 | 66 | 17 | 0.007121374 |

TABLE 21A-continued

Type 1 diabetes mellitus (T1DM) probes - EpiSwitch™ markers to stratify T1DM vs. healthy controls

| Probe | Gene | | | |
|---|---|---|---|---|
| 16_31342509_31344379_31355595_31363682_RF | ITGAM | 28 | 11 | 0.000764097 |
| 1_161590754_161594100_161627152_161631654_RR | FCGR2B; FCGR3A | 96 | 20 | 0.037659864 |
| 16_4004273_4006715_4065887_4067896_RF | ADCY9 | 66 | 17 | 0.007121374 |
| 16_4065887_4067896_4209511_4211354_FF | ADCY9 | 66 | 17 | 0.007121374 |
| 13_111748012_111752622_111942125_111944243_RR | ARHGEF7 | 61 | 17 | 0.002977018 |
| 19_10341612_10343024_10406169_10407761_FF | ICAM1 | 6 | 4 | 0.004341765 |
| 16_4044767_4047085_4065887_4067896_RF | ADCY9 | 66 | 17 | 0.007121374 |
| 16_4065887_4067896_4145870_4149370_FF | ADCY9 | 66 | 17 | 0.007121374 |
| 16_4065887_4067896_4169801_4171577_FF | ADCY9 | 66 | 17 | 0.007121374 |
| 16_4065887_4067896_4209511_4211354_FR | ADCY9 | 66 | 17 | 0.007121374 |
| 11_36524913_36530925_36605543_36609927_FR | RAG1 | 44 | 14 | 0.001755155 |
| 1_172053648_172060321_172083100_172087823_RR | DNM3 | 902 | 153 | 0.002933237 |
| 22_23509706_23512087_23566317_23569153_RR | BCR | 51 | 11 | 0.086137864 |
| 6_6621204_6623713_6637118_6642924_RR | LY86 | 53 | 14 | 0.01108912 |
| 1_198564901_198567426_198666515_198673906_FF | PTPRC | 138 | 28 | 0.022371015 |
| 11_36531355_36534043_36605543_36609927_FR | RAG1 | 44 | 14 | 0.001755155 |
| 8_131812677_131818201_131980638_131987302_FF | ADCY8 | 83 | 18 | 0.032875301 |
| 8_131812677_131818201_131974285_131980638_FR | ADCY8 | 83 | 18 | 0.032875301 |
| 8_131796786_131800910_131812677_131818201_RF | ADCY8 | 83 | 18 | 0.032875301 |
| X_19555372_19559004_19587789_19592813_FR | SH3KBP1 | 168 | 36 | 0.00435443 |
| 8_131812677_131818201_131926196_131933918_FR | ADCY8 | 83 | 18 | 0.032875301 |
| 8_131812677_131818201_132011208_132012836_FR | ADCY8 | 83 | 18 | 0.032875301 |
| 1_171805518_171810940_171986876_171988822_FF | DNM3 | 902 | 153 | 0.002933237 |
| 1_161576950_161581654_161627152_161631654_FR | FCGR2B; FCGR3A | 96 | 20 | 0.037659864 |
| X_19644496_19650796_19796774_19799668_RR | SH3KBP1 | 168 | 36 | 0.00435443 |
| 8_42099384_42103137_42121759_42128721_FF | IKBKB | 11 | 5 | 0.011285817 |
| 5_42419594_42423647_42597654_42505427_FR | GHR | 84 | 18 | 0.03663135 |
| 6_6569800_6579319_6621204_6623713_RR | LY86 | 53 | 14 | 0.01108912 |
| 8_131812677_131818201_132023344_132028736_FR | ADCY8 | 83 | 18 | 0.032875301 |
| 5_42419594_42423647_42515628_42519035_FF | GHR | 84 | 18 | 0.03663135 |
| 5_67483678_67490216_67602566_67610345_RF | PIK3R1 | 14 | 7 | 0.001348057 |
| 5_42419594_42423647_42519035_42531458_FR | GHR | 84 | 18 | 0.03663135 |
| 8_131812677_131818201_132011208_132012836_FF | ADCY8 | 83 | 18 | 0.032875301 |
| 5_42419594_42423647_42546292_42555639_FR | GHR | 84 | 18 | 0.03663135 |
| 16_4071891_4073711_4204978_4209511_RF | ADCY9 | 66 | 17 | 0.007121374 |
| 22_23509706_23512087_23570512_23575772_RR | BCR | 51 | 11 | 0.086137864 |

| Probe | FDR_HyperG | Percent_Sig | reps. | Avg_CV | logFC |
|---|---|---|---|---|---|
| 11_923549_925733_976127_979142_FR | 0.647796332 | 31.25 | 4 | 3.706 | −0.529758172 |
| 3_3117964_3119702_3187910_3199411_RF | 0.647796332 | 42.86 | 4 | 3.403 | −0.472211842 |
| 16_4065887_4067896_4109379_4115518_FR | 0.182781932 | 25.76 | 4 | 4.12 | −0.443525263 |
| 1_172083100_172087823_172151185_172154127_FF | 0.114615211 | 16.96 | 4 | 2.695 | −0.436858249 |
| 16_31228760_31230406_31342509_31344379_FR | 0.108117529 | 39.29 | 4 | 3.617 | −0.43527354 |
| 1_171936106_171939290_172083100_172087823_RF | 0.114615211 | 16.96 | 4 | 4.24 | −0.423950437 |
| 1_172061602_172067357_172083100_172087823_RF | 0.114615211 | 16.96 | 4 | 4.369 | −0.422397473 |
| 1_171811918_171813464_172083100_172087823_RF | 0.114615211 | 16.96 | 4 | 3.75 | −0.412452012 |
| 11_36531355_36534043_36605543_36609927_RR | 0.108117529 | 31.82 | 4 | 3.185 | −0.409161997 |
| 1_171887726_171889817_172083100_172087823_RF | 0.114615211 | 16.96 | 4 | 2.093 | −0.4080218 |
| 11_1010876_1013083_964245_969445_FF | 0.647796332 | 31.25 | 4 | 4.114 | −0.403895599 |
| 1_172083100_172087823_172212232_172223166_FF | 0.114615211 | 16.96 | 4 | 3.339 | −0.394277802 |
| 6_32135728_32138270_32149729_32154447_FF | 0.114615211 | 100 | 4 | 4.106 | −0.386842707 |
| 16_4065887_4067896_4204978_4209511_FF | 0.182781932 | 25.76 | 4 | 3.536 | −0.385489846 |
| 16_31342509_31344379_31355595_31363682_RF | 0.108117529 | 39.29 | 4 | 3.29 | −0.381926095 |
| 1_161590754_161594100_161627152_161631654_RR | 0.56343312 | 20.83 | 4 | 3.793 | −0.380537697 |
| 16_4004273_4006715_4065887_4067896_RF | 0.182781932 | 25.76 | 4 | 3.34 | −0.37973185 |
| 16_4065887_4067896_4209511_4211354_FF | 0.182781932 | 25.76 | 4 | 3.447 | −0.377158647 |
| 13_111748012_111752622_111942125_111944243_RR | 0.114615211 | 27.87 | 4 | 3.57 | −0.373760579 |
| 19_10341612_10343024_10406169_10407761_FF | 0.134116446 | 66.67 | 4 | 4.066 | −0.365760195 |
| 16_4044767_4047085_4065887_4067896_RF | 0.182781932 | 25.76 | 4 | 4.183 | −0.362629207 |
| 16_4065887_4067896_4145870_4149370_FF | 0.182781932 | 25.76 | 4 | 3.24 | −0.358825866 |
| 16_4065887_4067896_4169801_4171577_FF | 0.182781932 | 25.76 | 4 | 3.257 | −0.356727176 |
| 16_4065887_4067896_4209511_4211354_FR | 0.182781932 | 25.76 | 4 | 2.966 | −0.355168037 |
| 11_36524913_36530925_36605543_36609927_FR | 0.108117529 | 31.82 | 4 | 4.444 | −0.350562005 |
| 1_172053648_172060321_172083100_172087823_RR | 0.114615211 | 16.96 | 4 | 4.067 | −0.346486038 |
| 22_23509706_23512087_23566317_23569153_RR | 0.787292123 | 21.57 | 4 | 3.926 | −0.333558559 |
| 6_6621204_6623713_6637118_6642924_RR | 0.231735442 | 26.42 | 4 | 4.149 | −0.333492256 |
| 1_198564901_198567426_198666515_198673906_FF | 0.430642048 | 20.29 | 4 | 3.936 | −0.324552901 |
| 11_36531355_36534043_36605543_36609927_FR | 0.108117529 | 31.82 | 4 | 4.776 | −0.314053685 |
| 8_131812677_131818201_131980638_131987302_FF | 0.56343312 | 21.69 | 4 | 3.965 | −0.307426412 |
| 8_131812677_131818201_131974285_131980638_FR | 0.56343312 | 21.69 | 4 | 3.754 | −0.306962662 |
| 8_131796786_131800910_131812677_131818201_RF | 0.56343312 | 21.69 | 4 | 5.046 | −0.305084735 |
| X_19555372_19559004_19587789_19592813_FR | 0.134116446 | 21.43 | 4 | 8.54 | −0.303254166 |
| 8_131812677_131818201_131926196_131933918_FR | 0.56343312 | 21.69 | 4 | 2.272 | −0.300945102 |
| 8_131812677_131818201_132011208_132012836_FR | 0.56343312 | 21.69 | 4 | 3.877 | −0.299926052 |
| 1_171805518_171810940_171986876_171988822_FF | 0.114615211 | 16.96 | 4 | 5.663 | −0.297441732 |
| 1_161576950_161581654_161627152_161631654_FR | 0.56343312 | 20.83 | 4 | 5.054 | −0.293499837 |
| X_19644496_19650796_19796774_19799668_RR | 0.134116446 | 21.43 | 4 | 3.798 | −0.29153113 |

TABLE 21A-continued

Type 1 diabetes mellitus (T1DM) probes - EpiSwitch™ markers to stratify T1DM vs. healthy controls

| | | | | |
|---|---|---|---|---|
| 8_42099384_42103137_42121759_42128721_FF | 0.231735442 | 45.45 | 4 | 5.228 | −0.291180044 |
| 5_42419594_42423647_42597654_42605427_FR | 0.56343312 | 21.43 | 4 | 4.497 | −0.290654281 |
| 6_6569800_6579319_6621204_6623713_RR | 0.231735442 | 26.42 | 4 | 4.024 | −0.287951764 |
| 8_131812677_131818201_132023344_132028736_FR | 0.56343312 | 21.69 | 4 | 3.631 | −0.285057864 |
| 5_42419594_42423647_42515628_42519035_FF | 0.56343312 | 21.43 | 4 | 4.019 | −0.283604972 |
| 5_67483678_67490216_67602566_67610345_RF | 0.108117529 | 50 | 4 | 3.969 | −0.282353934 |
| 5_42419594_42423647_42519035_42531458_FR | 0.56343312 | 21.43 | 4 | 3.372 | −0.282109082 |
| 8_131812677_131818201_132011208_132012836_FF | 0.56343312 | 21.69 | 4 | 3.625 | −0.281315812 |
| 5_42419594_42423647_42546292_42555639_FR | 0.56343312 | 21.43 | 4 | 3.675 | −0.280553106 |
| 16_4071891_4073711_4204978_4209511_RF | 0.182781932 | 25.76 | 4 | 2.982 | −0.279952461 |
| 22_23509706_23512087_23570512_23575772_RR | 0.787292123 | 21.57 | 4 | 3.893 | −0.278366248 |

TABLE 21b

Type 1 diabetes mellitus (T1DM) probes - EpiSwitch ™ markers to stratify T1DM vs. healthy controls

| Probe | AveExpr | t | P.Value | adj.P.Val | B |
|---|---|---|---|---|---|
| 11_923549_925733_976127_979142_FR | −0.529758172 | −8.092940735 | 2.70E−06 | 0.002478464 | 5.056585897 |
| 3_3117964_3119702_3187910_3199411_RF | −0.472211842 | −7.326745164 | 7.60E−06 | 0.002478464 | 4.088814905 |
| 16_4065887_4067896_4109379_4115518_FR | −0.443525263 | −4.897708137 | 0.000334556 | 0.018676874 | 0.441359698 |
| 1_172083100_172087823_172151185_172154127_FF | −0.436858249 | −8.008643893 | 3.02E−06 | 0.002478464 | 4.954100461 |
| 16_31228760_31230406_31342509_31344379_FR | −0.43527354 | −7.895023881 | 3.51E−06 | 0.002478464 | 4.814434563 |
| 1_171936106_171939290_172083100_172087823_RF | −0.423950437 | −7.864029648 | 3.66E−06 | 0.002478464 | 4.776027833 |
| 1_172061602_172067357_172083100_172087823_RF | −0.422397473 | −7.776469372 | 4.11E−06 | 0.002478464 | 4.666809028 |
| 1_171811918_171813464_172083100_172087823_RF | −0.412452012 | −7.671544816 | 4.73E−06 | 0.002478464 | 4.534523533 |
| 11_36531355_36534043_36605543_36609927_RR | −0.409161997 | −6.819776394 | 1.57E−05 | 0.003231046 | 3.401963442 |
| 1_171887726_171889817_172083100_172087823_RF | −0.4080218 | −7.529429148 | 5.74E−06 | 0.002478464 | 4.352875105 |
| 11_1010876_1013083_964245_969445_FF | −0.403895599 | −6.684109098 | 1.91E−05 | 0.003629502 | 3.211628494 |
| 1_172083100_172087823_172212232_172223166_FF | −0.394277802 | −7.26361383 | 8.31E−06 | 0.002478464 | 4.005351851 |
| 6_32135728_32138270_32149729_32154447_FF | −0.386842707 | −5.731657165 | 8.33E−05 | 0.009736268 | 1.795575772 |
| 16_4065887_4067896_4204978_4209511_FF | −0.385489846 | −4.888681066 | 0.000339809 | 0.018728454 | 0.426143725 |
| 16_31342509_31344379_31355595_31363682_RF | −0.381926509 | −6.703010937 | 1.86E−05 | 0.003629502 | 3.238314557 |
| 1_161590754_161594100_161627152_161631654_RR | −0.380537697 | −6.631403849 | 2.07E−05 | 0.003810738 | 3.136930233 |
| 16_4004273_4006715_4065887_4067896_RF | −0.37973185 | −4.884889904 | 0.000342041 | 0.018732137 | 0.419749987 |
| 16_4065887_4067896_4209511_4211354_FF | −0.377158647 | −5.013405675 | 0.00027427 | 0.017323041 | 0.635364748 |
| 13_111748012_111752622_111942125_111944243_RR | −0.37376004 | −6.566614764 | 2.28E−05 | 0.003979612 | 3.044523931 |
| 19_10341612_10343024_10406169_10407761_FF | −0.365760195 | −6.847126759 | 1.51E−05 | 0.003231046 | 3.439997052 |
| 16_4044767_4047085_4065887_4067896_RF | −0.362629207 | −4.41276426 | 0.000784271 | 0.025038962 | −0.391357411 |
| 16_4065887_4067896_4145870_4149370_FF | −0.358825866 | −4.464550904 | 0.000715054 | 0.024359678 | −0.301020595 |
| 16_4065887_4067896_4168491_4171577_FF | −0.356727176 | −4.448531881 | 0.00073576 | 0.024772487 | −0.32893059 |
| 16_4065887_4067896_4209511_4211354_FR | −0.355168037 | −4.543545518 | 0.000621447 | 0.0233799 | −0.163840278 |
| 11_36524913_36530925_36605543_36609927_FR | −0.350562005 | −5.497779151 | 0.000121787 | 0.012585299 | 1.426356702 |
| 1_172053648_172060321_172083100_172087823_RR | −0.346486038 | −6.509010811 | 2.49E−05 | 0.004135312 | 2.961825036 |
| 22_23550876_23512087_23566317_23569153_RR | −0.333558579 | −6.257680647 | 3.64E−05 | 0.005431251 | 2.59501906 |
| 6_6621204_6623713_6637118_6642924_RR | −0.333492256 | −5.635209705 | 9.73E−05 | 0.010795146 | 1.644336465 |
| 1_198564901_198567426_198666515_198673906_FF | −0.324552901 | −5.625071996 | 9.89E−05 | 0.010835398 | 1.628356124 |
| 11_36531355_36534043_36605543_36609927_FR | −0.314053685 | −5.234700644 | 0.000188513 | 0.015535298 | 1.001070959 |
| 8_131812677_131818201_131980638_131987302_FF | −0.307426412 | −3.665767474 | 0.003071423 | 0.045822458 | −1.723581252 |
| 8_131812677_131818201_131974285_131980638_FR | −0.306962662 | −3.331746233 | 0.005739788 | 0.063202307 | −2.329928992 |
| 8_131796786_131800910_131812677_131818201_RF | −0.305084735 | −3.709790489 | 0.00282993 | 0.04428099 | −1.643918716 |
| X_19555372_19559004_19587789_19592813_FR | −0.303254166 | −4.451820709 | 0.000731458 | 0.024723863 | −0.323197898 |
| 8_131812677_131818201_131926196_131933918_FR | −0.300945102 | −3.610939996 | 0.003401862 | 0.048335494 | −1.822913931 |
| 8_131812677_131818201_132011208_132012836_FR | −0.299926052 | −3.822687959 | 0.002295478 | 0.039410264 | −1.440092801 |
| 1_171805618_171810940_171986876_171988822_FF | −0.297441732 | −4.378415333 | 0.000833987 | 0.025559591 | −0.45144788 |
| 1_161576950_161581654_161627152_161631654_FR | −0.293499837 | −4.993456509 | 0.000283792 | 0.017602604 | 0.602048693 |
| X_19644496_19650796_19796774_19799668_RR | −0.29153113 | −5.444999193 | 0.000132841 | 0.013212313 | 1.341873638 |
| 8_42099384_42103137_42121759_42128721_FF | −0.291180044 | −4.84874089 | 0.000364105 | 0.019220333 | 0.358685225 |
| 5_42419594_42423647_42597654_42605427_FR | −0.290654281 | −5.236418944 | 0.00018797 | 0.015535298 | 1.003882431 |
| 6_6569800_6579319_6621204_6623713_RR | −0.287951764 | −4.560501785 | 0.00060307 | 0.023192749 | −0.134494067 |
| 8_131812677_131818201_132023344_132028736_FR | −0.285057864 | −3.395159822 | 0.00509506 | 0.059532252 | −2.214691188 |
| 5_42419594_42423647_42515628_42519035_FF | −0.283604972 | −5.163591759 | 0.000212494 | 0.016129041 | 0.884839625 |
| 5_67483678_67490216_67602566_67610345_RF | −0.282353934 | −4.358632105 | 0.000864094 | 0.025847275 | −0.486117992 |
| 5_42419594_42423647_42519035_42531458_FR | −0.282109082 | −5.019367142 | 0.00027149 | 0.017273522 | 0.645309644 |
| 8_131812677_131818201_132011208_132012836_FF | −0.281315812 | −3.314316703 | 0.005931032 | 0.064089653 | −2.361599138 |
| 5_42419594_42423647_42546292_42555639_FR | −0.280553106 | −4.951991516 | 0.000304709 | 0.018144005 | 0.53261908 |
| 16_4071891_4073711_4204978_4209511_RF | −0.279952461 | −4.81303872 | 0.000387359 | 0.019869659 | 0.298198819 |
| 22_23509706_23512087_23570512_23575772_RR | −0.278366248 | −5.235317419 | 0.000188318 | 0.015535298 | 1.002080172 |

| Probe | FC | FC_1 | LS | Loop detected |
|---|---|---|---|---|
| 11_923549_925733_976127_979142_FR | 0.692670831 | −1.443687181 | −1 | T1DM |
| 3_3117964_3119702_3187910_3199411_RF | 0.720858579 | −1.387234652 | −1 | T1DM |
| 16_4065887_4067896_4109379_4115518_FR | 0.7353356 | −1.359923279 | −1 | T1DM |
| 1_172083100_172087823_172151185_172154127_FF | 0.738741613 | −1.35365327 | −1 | T1DM |

TABLE 21b-continued

Type 1 diabetes mellitus (T1DM) probes - EpiSwitch ™ markers to stratify T1DM vs. healthy controls

| | | | | |
|---|---|---|---|---|
| 16_31228760_31230406_31342509_31344379_FR | 0.739553519 | −1.352167184 | −1 | T1DM |
| 1_171936106_171939290_172083100_172087823_RF | 0.7453808 | −1.341596135 | −1 | T1DM |
| 1_172061602_172067357_172083100_172087823_RF | 0.746183584 | −1.340152774 | −1 | T1DM |
| 1_171811918_171813464_172083100_172087823_RF | 0.751345297 | −1.330945976 | −1 | T1DM |
| 11_36531355_36534043_36605543_36609927_RR | 0.753060669 | −1.327914258 | −1 | T1DM |
| 1_171887726_171889817_172083100_172087823_RF | 0.753656067 | −1.32686519 | −1 | T1DM |
| 11_1010876_1013083_964245_969445_FF | 0.755814657 | −1.323075692 | −1 | T1DM |
| 1_172083100_172087823_172212232_172223166_FF | 0.760870165 | −1.314284678 | −1 | T1DM |
| 6_32135728_32138270_32149729_32154447_FF | 0.764801518 | −1.307528785 | −1 | T1DM |
| 16_4065887_4067896_4204978_4209511_FF | 0.765519033 | −1.306303248 | −1 | T1DM |
| 16_31342509_31344379_31355595_31363682_RF | 0.767412359 | −1.303080395 | −1 | T1DM |
| 1_161590754_161594100_161627152_161631654_RR | 0.768151245 | −1.30182696 | −1 | T1DM |
| 16_4004273_4006715_4065887_4067896_RF | 0.768580431 | −1.301100001 | −1 | T1DM |
| 16_4065887_4067896_4209511_4211354_FF | 0.769952501 | −1.298781416 | −1 | T1DM |
| 13_111748012_111752622_111942125_111944243_RR | 0.771768155 | −1.295725917 | −1 | T1DM |
| 19_10341612_10343024_10406169_10407761_FF | 0.77605984 | −1.288560428 | −1 | T1DM |
| 16_4044767_4047085_4065887_4067896_RF | 0.777745902 | −1.28576698 | −1 | T1DM |
| 16_4065887_4067896_4145870_4149370_FF | 0.779798959 | −1.282381809 | −1 | T1DM |
| 16_4065887_4067896_4169801_4171577_FF | 0.780934159 | −1.280517683 | −1 | T1DM |
| 16_4065887_4067896_4209511_4211354_FR | 0.781778581 | −1.279134559 | −1 | T1DM |
| 11_36524913_36530925_36605543_36609927_FR | 0.784278521 | −1.275057232 | −1 | T1DM |
| 1_172053648_172060321_172083100_172087823_RR | 0.786497433 | −1.271459967 | −1 | T1DM |
| 22_23509706_23512087_23566317_23569153_RR | 0.793576627 | −1.260117757 | −1 | T1DM |
| 6_6621204_6623713_6637118_6642924_RR | 0.793613099 | −1.260059846 | −1 | T1DM |
| 1_198564901_198567426_198666515_198673906_FF | 0.798545821 | −1.252276292 | −1 | T1DM |
| 11_36531355_36534043_36605543_36609927_FR | 0.804378438 | −1.243195929 | −1 | T1DM |
| 8_131812677_131818201_131980638_131987302_FF | 0.808081992 | −1.237498187 | −1 | T1DM |
| 8_131812677_131818201_131974285_131980638_FR | 0.808341789 | −1.237100461 | −1 | T1DM |
| 8_131796786_131800910_131812677_131818201_RF | 0.809394676 | −1.2354912 | −1 | T1DM |
| X_19555372_19559004_19587789_19592813_FR | 0.810422331 | −1.233924537 | −1 | T1DM |
| 8_131812677_131818201_131926196_131933918_FR | 0.811720468 | −1.231951194 | −1 | T1DM |
| 8_131812677_131818201_132011208_132012836_FR | 0.812294031 | −1.231081311 | −1 | T1DM |
| 1_171805618_171810940_171986876_171988822_FF | 0.813694006 | −1.228963213 | −1 | T1DM |
| 1_161576950_161581654_161627152_161631654_FR | 0.815920313 | −1.225609884 | −1 | T1DM |
| X_19644496_19650796_19796774_19799668_RR | 0.817034481 | −1.223938553 | −1 | T1DM |
| 8_42099384_42103137_42121759_42128721_FF | 0.817233334 | −1.223640738 | −1 | T1DM |
| 5_42419594_42423647_42597654_42605427_FR | 0.817531214 | −1.223194886 | −1 | T1DM |
| 6_6569800_6579319_6621204_6623713_RR | 0.819064083 | −1.220905691 | −1 | T1DM |
| 8_131812677_131818201_132023344_132028736_FR | 0.820708691 | −1.218459133 | −1 | T1DM |
| 5_42419594_42423647_42515628_42519035_FF | 0.821535617 | −1.217232679 | −1 | T1DM |
| 5_67483678_67490216_67602566_67610345_RF | 0.822248323 | −1.216177609 | −1 | T1DM |
| 5_42419594_42423647_42519035_42531458_FR | 0.822387886 | −1.215971219 | −1 | T1DM |
| 8_131812677_131818201_132011208_132012836_FF | 0.822840202 | −1.215302798 | −1 | T1DM |
| 5_42419594_42423647_42546292_42555639_FR | 0.823275326 | −1.214660477 | −1 | T1DM |
| 16_4071891_4073711_4204978_4209511_RF | 0.823618157 | −1.214154875 | −1 | T1DM |
| 22_23509706_23512087_23570512_23575772_RR | 0.824524205 | −1.212820671 | −1 | T1DM |

TABLE 21c

Type 1 diabetes mellitus (T1DM) probes - EpiSwitch ™ markers to stratify T1DM vs. healthy controls

| Probe | Probes sequence 60 mer |
|---|---|
| 11_923549_925733_976127_979142_FR | GCCTGCAGGGGCGCCCCCGCGCCTGCCTCGACCACACATCCACATGGACGCATGGCAGG (SEQ ID NO: 257) |
| 3_3117964_3119702_3187910_3199411_RF | TGTACAATGTGCTACACCACTCACACCCTCGACAACTTCAGGTAGGAGTGAGTGATAGCT (SEQ ID NO: 258) |
| 16_4065887_4067896_4109379_4115518_FR | CGCCGGGCCGACACCCAGATTGTCTTCTTCGAAAAAAAAAAAAAAGAAAAAAAAAGAAA (SEQ ID NO: 259) |
| 1_172083100_172087823_172151185_172154127_FF | TCACCTCTGTCACCCACCCGTTCCACTCTCGATGCTCTCTTAGTGTTCCAATTCTCAGCT (SEQ ID NO: 260) |
| 16_31228760_31230406_31342509_31344379_FR | GGTGGCATCCCCATCACTTCTCCATGCCTCGAGGTCCCCAACCCCCTGCCGCTCATCGTG (SEQ ID NO: 261) |
| 1_171936106_171939290_172083100_172087823_RF | TCACCTCTGTCACCCACCCGTTCCACTCTCGAATAGCTCCTATTGTTATGGAGTGTAGCA (SEQ ID NO: 262) |
| 1_172061602_172067357_172083100_172087823_RF | TCACCTCTGTCACCCACCCGTTCCACTCTCGATAAAGCACTTAGAACATGGCATATACTC (SEQ ID NO: 263) |

TABLE 21c-continued

Type 1 diabetes mellitus (T1DM) probes - EpiSwitch ™ markers to stratify T1DM vs. healthy controls

| Probe | Probes sequence 60 mer |
|---|---|
| 1_171811918_171813464_172083100_172087823_RF | TCACCTCTGTCACCCACCCGTTCCACTCTCGAATTAGGAATCAGCATTTCTTCCACTGAG (SEQ ID NO: 264) |
| 11_36531355_36534043_36605543_36609927_RR | CCGCCCCTGTCCTCTCGCTTCCCGCTGGTCGATCCACACCACACCAGCAGTGGGGCACAA (SEQ ID NO: 265) |
| 1_171887726_171889817_172083100_172087823_RF | TCACCTCTGTCACCCACCCGTTCCACTCTCGAAATAGTAAAATTTGATTATCAAAATTTT (SEQ ID NO: 266) |
| 11_1010876_1013083_964245_969445_FF | GTGCCCTCCTCGCCCCTGATGGGTCTGGTCGAGACCAGCCTCAACATGGAGAAACACCAT (SEQ ID NO: 267) |
| 1_172083100_172087823_172212232_172223166_FF | TCACCTCTGTCACCCACCCGTTCCACTCTCGAGGCTGCAGTGAATCATAATCATAGCACT (SEQ ID NO: 268) |
| 6_32135728_32138270_32149729_32154447_FF | ACTGATGGCATCCCCGTGCGCTTCCGGTCGATGGGGCCAGGGGGCTATGGGGATAACCT (SEQ ID NO: 269) |
| 16_4065887_4067896_4204978_4209511_FF | CGCCGGGCCGACACCCACATTGTCTTCTTCGATCCCTGGGCTACAAGGTGGGCGATTCTG (SEQ ID NO: 270) |
| 16_31342509_31344379_31355595_31363682_RF | AGTGGTCTCACCATGGCTTTCTTCCAATTCGAGGTCCCCAACCCCCTGCCGCTCATCGTG (SEQ ID NO: 271) |
| 1_161590754_161594100_161627152_161631654_RR | AGGACAGAGACCCCTAATTCCACCACCATCGACCCTTCTGCTTTCTCTCCAGGGGATGGC (SEQ ID NO: 272) |
| 16_4004273_4006715_4065887_4067896_RF | CGCCGGGCCGACACCCACATTGTCTTCTTCGACATCCACTCTTCTGGGCATTCCCAGCCT (SEQ ID NO: 273) |
| 16_4065887_4067896_4209511_4211354_FF | CGCCGGGCCGACACCCACATTGTCTTCTTCGATTTGCATTTCCCTAATGATCGGTGATGT (SEQ ID NO: 274) |
| 13_111748012_111752622_111942125_111944243_RR | TCCGTGACCCCCACAGCCGGTCGCCACATCGATTATCCAGAAGCTTCTTTTTTTTTAACC (SEQ ID NO: 275) |
| 19_10341612_10343024_10406169_10407761_FF | TGCGGAAATGATGGACACTACACCTTCATCGACCTCGTGATCTGGCCGCCTCGGCCTTCC (SEQ ID NO: 276) |
| 16_4044767_4047085_4065887_4067896_RF | CGCCGGGCCGACACCCACATTGTCTTCTTCGATTTTATAGTATGTGAATTATATCTCAAC (SEQ ID NO: 277) |
| 16_4065887_4067896_4145870_4149370_FF | CGCCGGGCCGACACCCACATTGTCTTCTTCGAGTTCCTTGGAAGCTTTAATTTGCATTCC (SEQ ID NO: 278) |
| 16_4065887_4067896_4169801_4171577_FF | CGCCGGGCCGACACCCACATTGTCTTCTTCGAATCTCCCATCTGCTCTTTCAACCAAGCT (SEQ ID NO: 279) |
| 16_4065887_4067896_4209511_4211354_FR | CGCCGGGCCGACACCCACATTGTCTTCTTCGAACCCCTTTAAACCACTGACCTTGTCCCT (SEQ ID NO: 280) |
| 11_36524913_36530925_36605543_36609927_FR | TTATCAACCCGGCGTCTGGAACAATCGCTCGATCCACACCACACCAGCAGTGGGGCACAA (SEQ ID NO: 281) |
| 1_172053648_172060321_172083100_172087823_RR | CTCCACGTCACCCCATGTCAATTCCAAGTCGATGCCAGACACTCTTCTGGGGGTGGGGTG (SEQ ID NO: 282) |
| 22_23509706_23512087_23566317_23569153_RR | CATCCCATCCCCCAGGCTGAAATGTGAGTCGACTGTGGCCGCCACACAGTGGTCACTGCT (SEQ ID NO: 283) |
| 6_6621204_6623713_6637118_6642924_RR | CTCCCCTCTCCCCGGGCATGTGGGCCCTCGAACTGCAAAAAAAAAAAAAACAGAACTAA (SEQ ID NO: 284) |
| 1_198564901_198567426_198666515_198673906_FF | TTGAACCCAAGAGGTCACACCACTGCACTCGACGCCCAGCAAGTAGGCACAGTTCCCAAT (SEQ ID NO: 285) |
| 11_36531355_36534043_36605543_36609927_FR | AGTTCTTTCTTGAATTCTTTCCTGATACTCGATCCACACCACACCAGCAGTGGGGCACAA (SEQ ID NO: 286) |
| 8_131812677_131818201_131980638_131987302_FF | TCTTTAGCACCCGGGCCCCACAATTGTCTCGAAGCTTCTCTTCTGAACCTGGTGAAGCAG (SEQ ID NO: 287) |
| 8_131812677_131818201_131974285_131980638_FR | TCTTTAGCACCCGGGCCCCACAATTGTCTCGATGCTTTCATGGGACACTTTGAAAATAAA (SEQ ID NO: 288) |

TABLE 21c-continued

Type 1 diabetes mellitus (T1DM) probes - EpiSwitch ™ markers to stratify T1DM vs. healthy controls

| Probe | Probes sequence 60 mer |
|---|---|
| 8_131796786_131800910_131812677_131818201_RF | TCTTTAGCACCCGGGCCCCACAATTGTCTCGACCATATGGTCTTTGTTGTGACACTCAAC (SEQ ID NO: 289) |
| X_19555372_19559004_19587789_19592813_FR | AGAAACAGCTAACTGATCCCTAAACTCCTCGAGTTGAGATCTGGCGGCCTGAATGCTGGT (SEQ ID NO: 290) |
| 8_131812677_131818201_131926196_131933918_FR | TCTTTAGCACCCGGGCCCCACAATTGTCTCGATAAAATGTTAATAACGTTGTCAAGATTA (SEQ ID NO: 291) |
| 8_131812677_131818201_132011208_132012836_FR | TCTTTAGCACCCGGGCCCCACAATTGTCTCGATCTGCTGCGGTGGGTCCATAGACTGGCA (SEQ ID NO: 292) |
| 1_171805618_171810940_171986876_171988822_FF | GGCCAGAGCGCCGGCAAGAGCTCGGTGCTCGAAAAGAAAAAAAAAATACTAGGGGTAGG (SEQ ID NO: 293) |
| 1_161576950_161581654_161627152_161631654_FR | ACCCAGGATAAAACGCAGTGTTGACCGATCGACCCTTCTGCTTTCTCTCCAGGGGATGGC (SEQ ID NO: 294) |
| X_19644496_19650796_19796774_19799668_RR | TTCATTCATTCATTCATTCATTCATACATCGAAAGGCCAGTAGGTGTGATCTGAGGAAGG (SEQ ID NO: 295) |
| 8_42099384_42103137_42121759_42128721_FF | CAAGATAAAGGAAGAGTGAAATCCTGTCTCGACCGGGCGACTCCCCCGGGGCGGGGTGG (SEQ ID NO: 296) |
| 5_42419594_42423647_42597654_42605427_FR | GCGGCACTCGGCCTCTCCGCAGCAGTTCTCGAGGAAAGACTTACTAGGTCCTGCAGTATT (SEQ ID NO: 297) |
| 6_6569800_6579319_6621204_6623713_RR | TCCCCAGCCTGCTCTCTGGTAGACCTCTTCGAGGGCCCACATGCCCGGGGAGAGGGGAG (SEQ ID NO: 298) |
| 8_131812677_131818201_132023344_132028736_FR | TCTTTAGCACCCGGGCCCCACAATTGTCTCGAATCTAGGATAGACGCATGCAGCCCCTGG (SEQ ID NO: 299) |
| 5_42419594_42423647_42515628_42519035_FF | GCGGCACTCGGCCTCTCCGCAGCAGTTCTCGAATACCAAGAAAAAGTCACATGACTAACA (SEQ ID NO: 300) |
| 5_67483678_67490216_67602566_67610345_RF | CACTGCACCACCCTGTACATAAGTCCCCTCGACTTCAGCTCCAGTGAAGAAGACACTACT (SEQ ID NO: 301) |
| 5_42419594_42423647_42519035_42531458_FR | GCGGCACTCGGCCTCTCCGCAGCAGTTCTCGAGAGCCAGGAGGCTCTTGTGGTCTAATCT (SEQ ID NO: 302) |
| 8_131812677_131818201_132011208_132012836_FF | TCTTTAGCACCCGGGCCCCACAATTGTCTCGAGCTTCAGTTCCGGCATCTACAGAATGCT (SEQ ID NO: 303) |
| 5_42419594_42423647_42546292_42555639_FR | GCGGCACTCGGCCTCTCCGCAGCAGTTCTCGATTGAGCCTGAAAAATGAGGTGAAAAAAT (SEQ ID NO: 304) |
| 16_4071891_4073711_4204978_4209511_RF | CAGAATCGCCCACCTTGTAGCCCAGGGATCGACGGCAAGCCACTCACCCTCAGCCCTATC (SEQ ID NO: 305) |
| 22_23509706_23512087_23570512_23575772_RR | CATCCCATCCCCCAGGCTGAAATGTGAGTCGAGACTTCCTTTTTCATCTGTGGATCATTT (SEQ ID NO: 306) |

TABLE 21d

Type 1 diabetes mellitus (T1DM) probes - EpiSwitch ™ markers to stratify T1DM vs. healthy controls

| Probe | Chr | Probe Location | | | |
| | | Start1 | End1 | Start2 | End2 |
|---|---|---|---|---|---|
| 11_923549_925733_976127_979142_FR | 11 | 925704 | 925733 | 976128 | 976157 |
| 3_3117964_3119702_3187910_3199411_RF | 3 | 3117965 | 3117994 | 3199382 | 3199411 |
| 16_4065887_4067896_4109379_4115518_FR | 16 | 4067867 | 4067896 | 4109380 | 4109409 |
| 1_172083100_172087823_172151185_172154127_FF | 1 | 172087794 | 172087823 | 172154098 | 172154127 |
| 16_31228760_31230406_31342509_31344379_FR | 16 | 31230377 | 31230406 | 31342510 | 31342539 |
| 1_171936106_171939290_172083100_172087823_RF | 1 | 171936107 | 171936136 | 172087794 | 172087823 |
| 1_172061602_172067357_172083100_172087823_RF | 1 | 172061603 | 172061632 | 172087794 | 172087823 |
| 1_171811918_171813464_172083100_172087823_RF | 1 | 171811919 | 171811948 | 172087794 | 172087823 |
| 11_36531355_36534043_36605543_36609927_RR | 11 | 36531356 | 36531385 | 36605544 | 36605573 |
| 1_171887726_171889817_172083100_172087823_RF | 1 | 171887727 | 171887756 | 172087794 | 172087823 |
| 11_1010876_1013083_964245_969445_FF | 11 | 1013054 | 1013083 | 969416 | 969445 |

TABLE 21d-continued

Type 1 diabetes mellitus (T1DM) probes - EpiSwitch ™ markers to stratify T1DM vs. healthy controls

| Probe | Chr | | | | |
|---|---|---|---|---|---|
| 1_172083100_172087823_172212232_172223166 _FF | 1 | 172087794 | 172087823 | 172223137 | 172223166 |
| 6_32135728_32138270_32149729_32154447_FF | 6 | 32138241 | 32138270 | 32154418 | 32154447 |
| 16_4065887_4067896_4204978_4209511_FF | 16 | 4067867 | 4067896 | 4209482 | 4209511 |
| 16_31342509_31344379_31355595_31363682_RF | 16 | 31342510 | 31342539 | 31363653 | 31363682 |
| 1_161590754_161594100_161627152_161631654_RR | 1 | 161590755 | 161590784 | 161627153 | 161627382 |
| 16_4004273_4006715_4065887_4067896_RF | 16 | 4004274 | 4004303 | 4067867 | 4067896 |
| 16_4065887_4067896_4209511_4211354_FF | 16 | 4067867 | 4067896 | 4211325 | 4211354 |
| 13_111748012_111752622_111942125_111944243_RR | 13 | 111748013 | 111748042 | 111942126 | 111942155 |
| 19_10341612_10343024_10406169_10407761_FF | 19 | 10342995 | 10343024 | 10407732 | 10407761 |
| 16_4044767_4047085_4065887_4067896_RF | 16 | 4044768 | 4044797 | 4067867 | 4067896 |
| 16_4065887_4067896_4145870_4149370_FF | 16 | 4067867 | 4067896 | 4149341 | 4149370 |
| 16_4065887_4067896_4169801_4171577_FF | 16 | 4067867 | 4067896 | 4171548 | 4171577 |
| 16_4065887_4067896_4209511_4211354_FR | 16 | 4067867 | 4067896 | 4209512 | 4209541 |
| 11_36524913_36530925_36605543_36609927_FR | 11 | 36530896 | 36530925 | 36605544 | 36605573 |
| 1_172053648_172060321_172083100_172087823_RR | 1 | 172053649 | 172053678 | 172083101 | 172083130 |
| 22_23509706_23512087_23566317_23569153_RR | 22 | 23509707 | 23509736 | 23566318 | 23566347 |
| 6_6621204_6623713_6637118_6642924_RR | 6 | 6621205 | 6621234 | 6637119 | 6637148 |
| 1_198564901_198567426_198666515_198673906_FF | 1 | 198567397 | 198567426 | 198673877 | 198673906 |
| 11_36531355_36534043_36605543_36609927 FR | 11 | 36534014 | 36534043 | 36605544 | 36605573 |
| 8_131812677_131818201_131980638_131987302 FF | 8 | 131818172 | 131818201 | 131987273 | 131987302 |
| 8_131812677_131818201_131974285_131980638_FR | 8 | 131818172 | 131818201 | 131974286 | 131974315 |
| 8_131796786_131800910_131812677_131818201_RF | 8 | 131796787 | 131796816 | 131818172 | 131818201 |
| X_19555372_19559004_19587789_19592813_FR | X | 19558975 | 19559004 | 19587790 | 19587819 |
| 8_131812677_131818201_131926196_131933918_FR | 8 | 131818172 | 131818201 | 131926197 | 131926226 |
| 8_131812677_131818201_132011208_132012836_FR | 8 | 131818172 | 131818201 | 132011209 | 132011238 |
| 1_171805618_171810940_171986876_171988822_FF | 1 | 171810911 | 171810940 | 171988793 | 171988822 |
| 1_161576950_161581654_161627152_161631654_FR | 1 | 161581625 | 161581654 | 161627153 | 161627182 |
| X_19644496_19650796_19796774_19799668_RR | X | 19644497 | 19644526 | 19796775 | 19796804 |
| 8_42099384_42103137_42121759_42128721_FF | 8 | 42103108 | 42103137 | 42128692 | 42128721 |
| 5_42419594_42423647_42597654_42605427_FR | 5 | 42423618 | 42423647 | 42597655 | 42597684 |
| 6_6569800_6579319_6621204_6623713_RR | 6 | 6569801 | 6569830 | 6621205 | 6621234 |
| 8_131812677_131818201_132023344_132028736_FR | 8 | 131818172 | 131818201 | 132023345 | 132023374 |
| 5_42419594_42423647_42515628_42519035_FF | 5 | 42423618 | 42423647 | 42519006 | 42519035 |
| 5_67483678_67490216_67602566_67610345_RF | 5 | 67483679 | 67483708 | 67610316 | 67610345 |
| 5_42419594_42423647_42519035_42531458_FR | 5 | 42423618 | 42423647 | 42519036 | 42519065 |
| 8_131812677_131818201_132011208_132012836 _FF | 8 | 131818172 | 131818201 | 132012807 | 132012836 |
| 5_42419594_42423647_42546292_42555639_FR | 5 | 42423618 | 42423647 | 42546293 | 42546322 |
| 16_407y1891_4073711_204978_4209511_RF | 16 | 4071892 | 4071921 | 4209482 | 4209511 |
| 22_23509706_23512087_23570512_23575772_RR | 22 | 23509707 | 23509736 | 23570513 | 23570542 |

| | | 4 kb Sequence Location | | | |
|---|---|---|---|---|---|
| Probe | Chr | Start1 | End1 | Start2 | End2 |
| 11_923549_925733_976127_979142_FR | 11 | 921734 | 925733 | 976128 | 980127 |
| 3_3117964_3119702_3187910_3199411_RF | 3 | 3117965 | 3121964 | 3195412 | 3199411 |
| 16_4065887_4067896_4109379_4115518_FR | 16 | 4063897 | 4067896 | 4109380 | 4113379 |
| 1_172083100_172087823_172151185_172154127_FF | 1 | 172083824 | 172087823 | 172150128 | 172154127 |
| 16_31228760_31230406_31342509_31344379_FR | 16 | 31226407 | 31230406 | 31342510 | 31346509 |
| 1_171936106_171939290_172083100_172087823_RF | 1 | 171936107 | 171940106 | 172083824 | 172087823 |
| 1_172061602_172067357_172083100_172087823_RF | 1 | 172061603 | 172065602 | 172083824 | 172087823 |
| 1_171811918_171813464_172083100_172087823_RF | 1 | 171811919 | 171815918 | 172083824 | 172087823 |
| 11_36531355_36534043_36605543_36609927_RR | 11 | 36531356 | 36535355 | 36605544 | 36609543 |
| 1_171887726_171889817_172083100_172087823_RF | 1 | 171887727 | 171891726 | 172083824 | 172087823 |
| 11_1010876_1013083_964245_969445_FF | 11 | 1009084 | 1013083 | 965446 | 969445 |
| 1_172083100_172087823_172212232_172223166 _FF | 1 | 172083824 | 172087823 | 172219167 | 172223166 |
| 6_32135728_32138270_32149729_32154447_FF | 6 | 32134271 | 32138270 | 32150448 | 32154447 |
| 16_4065887_4067896_4204978_4209511_FF | 16 | 4063897 | 4067896 | 4205512 | 4209511 |
| 16_31342509_31344379_31355595_31363682_RF | 16 | 31342510 | 31346509 | 31359683 | 31363682 |
| 1_161590754_161594100_161627152_161631654_RR | 1 | 161590755 | 161594754 | 161627153 | 161631152 |
| 16_4004273_4006715_4065887_4067896_RF | 16 | 4004274 | 4008273 | 4063897 | 4067896 |
| 16_4065887_4067896_4209511_4211354_FF | 16 | 4063897 | 4067896 | 4207355 | 4211354 |
| 13_111748012_111752622_111942125_111944243_RR | 13 | 111748013 | 111752012 | 111942126 | 111946125 |
| 19_10341612_10343024_10406169_10407761_FF | 19 | 10339025 | 10343024 | 10403762 | 10407761 |
| 16_4044767_4047085_4065887_4067896_RF | 16 | 4044768 | 4048768 | 4063897 | 4067896 |
| 16_4065887_4067896_4145870_4149370_FF | 16 | 4063897 | 4067896 | 4145371 | 4149370 |
| 16_4065887_4067896_4169801_4171577_FF | 16 | 4063897 | 4067896 | 4167578 | 4171577 |
| 16_4065887_4067896_4209511_4211354_FR | 16 | 4063897 | 4067896 | 4209512 | 4213511 |
| 11_36524913_36530925_36605543_36609927_FR | 11 | 36526926 | 36530925 | 36605544 | 36609543 |
| 1_172053648_172060321_172083100_172087823_RR | 1 | 172053649 | 172057648 | 172083101 | 172087100 |
| 22_23509706_23512087_23566317_23569153_RR | 22 | 23509707 | 23513706 | 23566318 | 23570317 |
| 6_6621204_6623713_6637118_6642924_RR | 6 | 6621205 | 6625204 | 6637119 | 6641118 |
| 1_198564901_198567426_198666515_198673906_FF | 1 | 198563427 | 198567426 | 198669907 | 198673906 |
| 11_36531355_36534043_36605543 36609927 FR | 11 | 36530044 | 36534043 | 36605544 | 36609543 |
| 8_131812677_131818201_131980638_131987302 FF | 8 | 131814202 | 131818201 | 131983303 | 131987302 |
| 8_131812677_131818201_131974285_131980638_FR | 8 | 131814202 | 131818201 | 131974286 | 131978285 |
| 8_131796786_131800910_131812677_131818201_RF | 8 | 131796787 | 131800786 | 131814202 | 131818201 |
| X_19555372_19559004_19587789_19592813_FR | X | 19555005 | 19559004 | 19587790 | 19591789 |

TABLE 21d-continued

Type 1 diabetes mellitus (T1DM) probes - EpiSwitch ™ markers to stratify T1DM vs. healthy controls

| | | | | | |
|---|---|---|---|---|---|
| 8_131812677_131818201_131926196_131933918_FR | 8 | 131814202 | 131818201 | 131926197 | 131930196 |
| 8_131812677_131818201_132011208_132012836_FR | 8 | 131814202 | 131818201 | 132011209 | 132015208 |
| 1_171805618_171810940_171986876_171988822_FF | 1 | 171806941 | 171810940 | 171984823 | 171988822 |
| 1_161576950_161581654_161627152_161631654_FR | 1 | 161577655 | 161581654 | 161627153 | 161631152 |
| X_19644496_19650796_19796774_19799668_RR | X | 19644497 | 19648496 | 19796775 | 19800774 |
| 8_42099384_42103137_42121759_42128721_FF | 8 | 42099138 | 42103137 | 42124722 | 42128721 |
| 5_42419594_42423647_42597654_42605427_FR | 5 | 42419648 | 42423647 | 42597655 | 42601654 |
| 6_6569800_6579319_6621204_6623713_RR | 6 | 6569801 | 6573800 | 6621205 | 6625204 |
| 8_131812677_131818201_132023344_132028736_FR | 8 | 131814202 | 131818201 | 132023345 | 132027344 |
| 5_42419594_42423647_42515628_42519035_FF | 5 | 42419648 | 42423647 | 42515036 | 42519035 |
| 5_67483678_67490216_67602566_67610345_RF | 5 | 67483679 | 67487678 | 67606346 | 67610345 |
| 5_42419594_42423647_42519035_42531458_FR | 5 | 42419648 | 42423647 | 42519036 | 42523035 |
| 8_131812677_131818201_132011208_132012836_FF | 8 | 131814202 | 131818201 | 132008837 | 132012836 |
| 5_42419594_42423647_42546292_42555639_FR | 5 | 42419648 | 42423647 | 42546293 | 42550292 |
| 16_407y1891_4073711_204978_4209511_RF | 16 | 4071892 | 4075891 | 4205512 | 4209511 |
| 22_23509706_23512087_23570512_23575772_RR | 22 | 23509707 | 23513706 | 23570513 | 23574512 |

TABLE 22a

Ulcerative colitis (UC) probes - EpiSwitch ™ markers to stratify UC vs. healthy controls

| Probe | GeneLocus | Probe_Count_Total | Probe_Count_Sig | HyperG_Stats |
|---|---|---|---|---|
| 7_45584884_45588878_45736475_45743273_RF | ADCY1 | 30 | 12 | 0.004580887 |
| 1_161576950_161581654_161625371_161626958_FR | FCGR2B;FCGR3A | 96 | 33 | 0.000124986 |
| 7_55087969_55089963_55247129_55257611_RR | EGFR | 196 | 53 | 0.001552393 |
| 7_55087969_55089963_55276177_55281528_RF | EGFR | 196 | 53 | 0.001552393 |
| 7_55087969_55089963_55146890_55151406_RF | EGFR | 196 | 53 | 0.001552393 |
| 7_55087969_55089963_55113347_55115444_RR | EGFR | 196 | 53 | 0.001552393 |
| 1_161495318_161496726_161576950_161581654_RF | FCGR3A | 37 | 12 | 0.028212278 |
| 7_55087969_55089963_55159296_55163839_RF | EGFR | 196 | 53 | 0.001552393 |
| 19_6736190_6739207_6832841_6834447_FR | VAV1 | 16 | 7 | 0.016844872 |
| 22_22718523_22726462_22744564_22754970_FR | IGLV7-43 | 6 | 3 | 0.079534188 |
| 16_31228760_31230406_31342509_31344379 | ITGAM | 28 | 9 | 0.056781917 |
| 7_55087969_55089963_55294211_55302386_RR | EGFR | 196 | 53 | 0.001552393 |
| 19_10341612_10343024_10406169_10407761_FF | ICAM1 | 5 | 4 | 0.012352453 |
| 1_161543531_161545118_161576950_161581654_RF | FCGRB;FCGR3A | 96 | 33 | 0.000124986 |
| 1_161576950_161581654_161627152_161631654_FR | FCGR2B;FCGR3A | 96 | 33 | 0.000124986 |
| 7_55087969_55089963_55224588_55235839_RR | EGFR | 196 | 53 | 0.001552393 |
| 6_32135728_32138270_32149729_32154447_FF | AGER | 3 | 2 | 0.088576681 |
| 8_42121759_42128721_42138740_42142593_FR | IKBKB | 11 | 5 | 0.035894511 |
| 11_118135384_118142619_118155813_118161617_RR | CD3E | 9 | 4 | 0.065256334 |
| X_19555372_19559004_19587789_19592813_FR | SH3KBP1 | 168 | 49 | 0.000373076 |
| 1_161519223_161525894_161625371_161626958_RR | FCGR2B;FCGR3A | 96 | 33 | 0.000124986 |
| 7_55087969_55089963_55116799_55120169_RR | EGFR | 196 | 53 | 0.001552393 |
| 8_42099384_42103137_42121759_42128721_FF | IKBKB | 11 | 5 | 0.035894511 |
| 1_161576950_161581654_161625371_161626958_RR | FCGR2B;FCGR3A | 96 | 33 | 0.000124986 |
| 1_161519223_161525894_161543531_161545118_RR | FCGR2B;FCR3A | 96 | 33 | 0.000124986 |
| 10_98420739_98422156_98475835_98481698_FF | PIK3AP1 | 117 | 38 | 0.000157143 |
| 11_923549_925733_976127_979142_FR | AP2A2 | 16 | 6 | 0.056983687 |
| X_19747473_19749276_19778202_19779729_RF | SH3KBP1 | 168 | 49 | 0.000373076 |
| X_19555372_19559004_19801817_19808062_FF | SH3KBP1 | 168 | 49 | 0.000373076 |
| 7_55116799_55120169_55294211_55302386_RF | EGFR | 196 | 53 | 0.001552393 |
| 13_111740592_111744283_111955243_111957450_RR | ARHGEF7 | 61 | 18 | 0.022511064 |
| 13_111740592_111744283_111951910_111954429_RF | ARHGEF7 | 51 | 18 | 0.022511064 |
| 7_45584884_45588878_45641165_45652147_RR | ADCY1 | 30 | 12 | 0.004580887 |
| 7_55087969_55089963_55247129_55257611_RF | EGFR | 196 | 53 | 0.001552393 |
| 19_6698247_6701314_6736190_6739207_RF | C3 | 10 | 4 | 0.093434304 |
| 11_118135384_118142619_118155813_118161617_FR | CD3E | 9 | 4 | 0.065256334 |
| 11_65282265_65284907_65314616_65318092_RF | SCYL1 | 5 | 3 | 0.04594332 |
| 10_98397707_98399014_98464393_98468588_FF | PIK3AP1 | 117 | 38 | 0.000157143 |
| X_19555372_19559004_19778202_19779729_FF | SH3KBP1 | 168 | 49 | 0.000373076 |
| X_19747473_19749276_19801817_19808062_RR | SH3KBP1 | 168 | 49 | 0.000373076 |
| 7_55146890_55151406_55294211_55302386_RF | EGFR | 196 | 53 | 0.001552393 |
| 7_55146890_55151406_55276177_55281528_FF | EGFR | 196 | 53 | 0.001552393 |
| 7_55159296_55163839_55294211_55302386_FF | EGFR | 196 | 53 | 0.001552393 |
| 8_42121759_42128721_42152856_42153945_FF | IKBKB | 11 | 5 | 0.035894511 |
| 10_98426247_98429729_98475835_98481698_FF | PIK3AP1 | 117 | 38 | 0.000157143 |
| 7_55061795_55064635_55087969_55089953_FR | EGFR | 196 | 53 | 0.001552393 |
| 7_55061795_55064635_55159296_55163839_RF | EGFR | 196 | 53 | 0.001552393 |

TABLE 22a-continued

Ulcerative colitis (UC) probes - EpiSwitch ™ markers to stratify UC vs. healthy controls

| | | | | |
|---|---|---|---|---|
| 22_22707693_22711085_22732515_22734197_FF | IGLV7-43 | 6 | 3 | 0.079534188 |
| X_19652532_19655511_19778202_19779729_RF | SH3KBP1 | 168 | 49 | 0.000373076 |
| 13_111730571_111732652_111951910_111954429_FF | ARHGEF7 | 61 | 18 | 0.022511064 |

| Probe | FDR_HyperG | Percent_Sig | reps. | Avg_CV | logFC |
|---|---|---|---|---|---|
| 7_45584884_45588878_45736475_45743273_RF | 0.235152183 | 40 | 4 | 7.078 | −0.446398112 |
| 1_161576950_161581654_161625371_161626958_FR | 0.02420002 | 34.38 | 4 | 6.877 | −0.423285329 |
| 7_55087969_55089963_55247129_55257611_RR | 0.119534297 | 27.04 | 4 | 7.023 | −0.419269005 |
| 7_55087969_55089963_55276177_55281528_RF | 0.119534297 | 27.04 | 4 | 6.334 | −0.405109539 |
| 7_55087969_55089963_55146890_55151406_RF | 0.119534297 | 27.04 | 4 | 7.084 | −0.399784507 |
| 7_55087969_55089963_55113347_55115444_RR | 0.119534297 | 27.04 | 4 | 6.958 | −0.352217394 |
| 1_161495318_161496726_161576950_161581654_RF | 0.511140091 | 32.43 | 4 | 5.212 | −0.349947619 |
| 7_55087969_55089963_55159296_55163839_RF | 0.119534297 | 27.04 | 4 | 8.654 | −0.34865568 |
| 19_6736190_6739207_6832841_6834474_FR | 0.370587187 | 43.75 | 4 | 6.787 | −0.338622756 |
| 22_22718523_22726462_22744564_22754970_FR | 0.846404874 | 50 | 4 | 2.861 | −0.334996016 |
| 16_31228760_31230406_31342509_31344379 | 0.675037525 | 32.14 | 4 | 3.617 | −0.330551344 |
| 7_55087969_55089963_55294211_55302386_RR | 0.119534297 | 27.04 | 4 | 7.634 | −0.328896083 |
| 19_10341612_10343024_10406169_10407761 _FF | 0.300931881 | 66.67 | 4 | 4.066 | −0.325517106 |
| 1_161543531_161545118_161576950_161581654_RF | 0.02420002 | 34.38 | 4 | 6.008 | −0.320338689 |
| 1_161576950_161581654_161627152_161631654_FR | 0.02420002 | 34.38 | 4 | 5.054 | −0.318424708 |
| 7_55087969_55089963_55224588_55235839_RR | 0.119534297 | 27.04 | 4 | 5.298 | −0.314588705 |
| 6_32135728_32138270_32149729_32154447_FF | 0.846404874 | 66.67 | 4 | 4.106 | −0.313025185 |
| 8_42121759_42128721_42138740_42142593_FR | 0.552775462 | 45.45 | 4 | 4.556 | −0.308386023 |
| 11_118135384_118142619_118155813_118161617_RR | 0.744405584 | 44.44 | 3 | 2.805 | −0.298082914 |
| X_19555372_19559004_19587789_19592813_FR | 0.038302514 | 29.17 | 4 | 8.54 | −0.293447331 |
| 1_161519223_161525894_161576371_161626958_RR | 0.02420002 | 34.38 | 4 | 4.896 | −0.287540254 |
| 7_55087969_55089963_55116799_55120169_RR | 0.119534297 | 27.04 | 4 | 7.021 | −0.286823372 |
| 8_42099384_42103137_42121759_42128721_FF | 0.552775462 | 45.45 | 4 | 5.228 | −0.284393396 |
| 1_161576950_161581654_161625371_161526958_RR | 0.02420002 | 34.38 | 4 | 4.334 | −0.282643839 |
| 1_161519223_161525894_161543531_161545118_RR | 0.02420002 | 34.38 | 4 | 5.216 | −0.277758539 |
| 10_98420739_98422156_98475835_98481698_FF | 0.02420002 | 32.48 | 4 | 3.216 | −0.27713633 |
| 11_923549_925733_976127_979142_FR | 0.675037525 | 37.5 | 4 | 3.706 | −0.276532824 |
| X_19747473_19749276_19778202_19779729_RF | 0.038302514 | 29.17 | 4 | 15.829 | −0.272986417 |
| X_19555372_19559004_19801817_19808062_FF | 0.038302514 | 29.17 | 4 | 6.811 | −0.269931263 |
| 7_55116799_55120169_55294211_55302386_RF | 0.119534297 | 27.04 | 4 | 4.233 | −0.268950471 |
| 13_111740592_111744283_111955243_111957450_RR | 0.462227188 | 29.51 | 4 | 5.616 | −0.267816486 |
| 13_111740592_111744283_111951910_111954429_RF | 0.462227188 | 29.51 | 4 | 7.583 | −0.267054433 |
| 7_45584884_45588878_45641165_45652147_RR | 0.235152183 | 40 | 4 | 12.069 | −0.265005547 |
| 7_55087969_55089963_55247129_55257611_RF | 0.119534297 | 27.04 | 4 | 5.297 | −0.262657522 |
| 19_6698247_6701314_6736190_6739207_RF | 0.846404874 | 40 | 4 | 3.227 | −0.260946755 |
| 11_118135384_118142619_118155813_118161617_FR | 0.744405584 | 44.44 | 4 | 4.111 | −0.260502589 |
| 11_65282265_65284907_65314616_65318092 _RF | 0.59107768 | 60 | 4 | 5.079 | −0.260154428 |
| 10_98397707_98399014_98464393_98468588_FF | 0.02420002 | 32.48 | 4 | 6.946 | −0.259297107 |
| X_19555372_19559004_19778202_19779729_FF | 0.038302514 | 29.17 | 4 | 10.156 | −0.258850322 |
| X_19747473_19749276_19801817_19808062_RR | 0.038302514 | 29.17 | 4 | 19.347 | −0.258747317 |
| 7_55146890_55151406_55294211_55302386_RF | 0.119534297 | 27.04 | 4 | 4.893 | −0.258444556 |
| 7_55146890_55151406_55276177_55281528_FF | 0.119534297 | 27.04 | 4 | 18.078 | −0.257369248 |
| 7_55159296_55163839_55294211_55302386_FF | 0.119534297 | 27.04 | 4 | 7.722 | −0.2568125 |
| 8_42121759_42128721_42152856_42153945_FF | 0.552775462 | 45.45 | 3 | 5.25 | −0.255746698 |
| 10_98426247_98429729_98475835_98481698_FF | 0.02420002 | 32.48 | 4 | 4.164 | −0.255158509 |
| 7_55061795_55064635_55087969_55089953_FR | 0.119534297 | 27.04 | 4 | 4.1 | −0.254266064 |
| 7_55061795_55064635_55159296_55163839_RF | 0.119534297 | 27.04 | 4 | 3.739 | −0.254243219 |
| 22_22707693_22711085_22732515_22734197_FF | 0.846404874 | 50 | 4 | 11.929 | −0.2530292 |
| X_19652532_19655511_19778202_19779729_RF | 0.038302514 | 29.17 | 4 | 14.941 | −0.251445257 |
| 13_111730571_111732652_111951910_111954429_FF | 0.462227188 | 29.51 | 4 | 15.948 | −0.25127638 |

TABLE 22b

Ulcerative colitis {UC) probes –EpiSwitch ™ markers to stratify UC vs. healthy controls

| Probe | AveExpr | t | P.Value | adj.P.Val | B |
|---|---|---|---|---|---|
| 7_45584884_45588878_45736475_4574327 3_RF | −0.446398112 | −9.435638924 | 8.85E−06 | 0.004888244 | 4.153848344 |
| 1_161576950_161581654_161625371_1616 26958_FR | −0.423285329 | −9.204965599 | 1.07E−05 | 0.004888244 | 3.975717007 |
| 7_5 5087969_55089963_55247129_5525761 1 RR | −0.419269005 | −6.369833493 | 0.00016899 | 0.009683903 | 1.315750587 |
| 7_55087969_55089963_55276177_5528152 8 RF | −0.405109539 | −7.588326295 | 4.69E−05 | 0.006547249 | 2.575442784 |
| 7_55087969_55089963_55146890_5515140 6 RF | −0.399784507 | −5.530622454 | 0.000452878 | 0.012730546 | 0.327975654 |
| 7_55087969_55089963_55113347_5511544 4 RR | −0.352217394 | −5.963318431 | 0.000269342 | 0.011344149 | 0.850286475 |
| 1_161495318_161496726_161576950_1615 81654 RF | −0.349947619 | −8.588507383 | 1.83E−05 | 0.005775865 | 3.474436751 |
| 7_55087969_55089963_55159296_55163839_RF | −0.34865568 | −6.004819682 | 0.000256579 | 0.011156666 | 0.89890943 |
| 19_6736190_6739207_6832841_6834474_FR | −0.338622756 | −5.016498633 | 0.000868153 | 0.014251641 | −0.329969771 |
| 22_22718523_22726462_22744564_22754970_FR | −0.334996016 | −7.89866635 | 3.47E−05 | 0.006456046 | 2.866475514 |
| 16_31228760_31230406_31342509_31344379_FR | −0.330551344 | −8.609951248 | 1.80E−05 | 0.005775865 | 3.49251633 |
| 7_55087969_55089963_55294211_55302386_RR | −0.328896083 | −7.358953281 | 5.90E−05 | 0.007290908 | 2.352921549 |

TABLE 22b-continued

Ulcerative colitis {UC} probes –EpiSwitch ™ markers to stratify UC vs. healthy controls

| | | | | | |
|---|---|---|---|---|---|
| 19_10341612_10343024_10406169_10407761_FF | −0.325517106 | −8.528225011 | 1.94E−05 | 0.005775865 | 3.423355584 |
| 1_161543531_161545118_161576950_161581654_RF | −0.320338689 | −8.393511114 | 2.19E−05 | 0.0059132 | 3.307822028 |
| 1_161576950_161581654_161627152_161631654_FR | −0.318424708 | −8.126862.28 | 2.80E−05 | 0.006456046 | 3.073378688 |
| 7_55087969_55089963_55224588_55235839_RR | −0.314588705 | −5.391216831 | 0.000538302 | 0.012974733 | 0.153625606 |
| 6_32135728_32138270_32149729_32154447_FF | −0.313025185 | −5.602106309 | 0.000414904 | 0.012478833 | 0.41622014 |
| 8_42121759_42128721_42138740_42142593_FR | −0.308386023 | −7.622976448 | 4.53E−05 | 0.00653853 | 2.608502416 |
| 11_118135384_118142619_118155813_118161617_RR | −0.298082914 | −8.094870263 | 2.88E−05 | 0.006456046 | 3.044725378 |
| X_19555372_19559004_19587789_19592813_FR | −0.293447331 | −7.444102967 | 5.41E−05 | 0.006996488 | 2.436279661 |
| 1_161519223_161525894_161625371_161626968_RR | −0.287540254 | −7.03430515 | 8.23E−05 | 0.008172517 | 2.026741952 |
| 7_55087969_55089963_55116799_55120169_RR | −0.286823372 | −6.401828897 | 0.000163044 | 0.009583602 | 1.351378276 |
| 8_42099384_42103137_42121759_42128721_FF | −0.284393396 | −6.612254602 | 0.00012922 | 0.00920378 | 1.582121005 |
| 1_161576950_161581654_161625371_161626958_RR | −0.282643839 | −7.052682312 | 8.08E−05 | 0.008172517 | 2.045566049 |
| 1_161519223_161525894_161543531_161545118_RR | −0.277758539 | −7.444555354 | 5.41E−05 | 0.006996488 | 2.436720143 |
| 10_98420739_98422156_98475835_98481698_FF | −0.27713633 | −6.046853388 | 0.000244323 | 0.011126993 | 0.947897504 |
| 11_923549_925733_976127_979142_FR | −0.276532824 | −5.676486002 | 0.000379047 | 0.012018309 | 0.50721141 |
| X_19747473_19749276_19778202_19779729_RF | −0.272986417 | −5.696390475 | 0.000370035 | 0.012015418 | 0.531418605 |
| X_19555372_19559004_19801817_19808062_FF | −0.269931263 | −6.52881124 | 0.000141611 | 0.009455532 | 1.491358118 |
| 7_55116799_55120169_55294211_55302386_RF | −0.268950471 | −5.739838279 | 0.000351166 | 0.011815747 | 0.584050005 |
| 13_111740592_111744283_111955243_111957450_RR | −0.267816446 | −4.205996047 | 0.002616378 | 0.022984284 | −1.450517746 |
| 13_111740592_111744283_111951910_111954429_RF | −0.267054433 | −6.52226367 | 0.000142637 | 0.009455532 | 1.484195419 |
| 7_45584884_45588878_45641165_45652147_RR | −0.265005547 | −4.183322812 | 0.002702107 | 0.023242532 | −1.483290206 |
| 7_55087969_55089963_55247129_55257611_RF | −0.262657522 | −6.47694387 | 0.000149967 | 0.009455532 | 1.4344543 |
| 19_6698247_6701314_6736190_6739707_RF | −0.262048587 | −6.928808517 | 9.20E−05 | 0.008557251 | 1.91782663 |
| 11_118135384_118142619_118155813_118161617_FR | −0.260502589 | −6.591823929 | 0.00013214 | 0.00920378 | 1.559987043 |
| 11_65282265_65284907_65314616_65318092_RF | −0.260154428 | −6.459744124 | 0.000152857 | 0.009455532 | 1.415501514 |
| 10_98397707_98399014_98464393_98468588_FF | −0.259297107 | −6.141944944 | 0.000218896 | 0.010581613 | 1.057766824 |
| X_19555372_19559004_19778202_19779729_FF | −0.258850622 | −5.163588632 | 0.000717941 | 0.013426134 | −0.137531553 |
| X_19747473_19749276_19801817_19808062_RR | −0.258747317 | −5.628459403 | 0.000401793 | 0.012388987 | 0.448555164 |
| 7_55146890_55151406_55294211_55302386_RF | −0.258444556 | −5.48941519 | 0.000476478 | 0.012730546 | 0.27675066 |
| 7_55146890_55151406_55276177_55281528_FF | −0.257369248 | −6.856937539 | 9.93E−05 | 0.008748963 | 1.842787206 |
| 7_55159296_55163839_55294211_55302386_RF | −0.2568125 | −5.445425032 | 0.00050316 | 0.012730546 | 0.22177796 |
| 8_42121759_42128721_42152856_42153945_FF | −0.255746698 | −6.333295655 | 0.000176072 | 0.009766371 | 1.274887498 |
| 10_9842647_98429729_98475835_984816_98_FF | −0.255158509 | −5.308765695 | 0.000596982 | 0.01321755 | 0.049093344 |
| 7_55061795_55064635_55087969_55089963_FR | −0.254266064 | −6.603821021 | 0.000130416 | 0.00920378 | 1.572991286 |
| 7_55061795_55064635_55159296_55163839_FR | −0.254243219 | −5.394082975 | 0.000536379 | 0.012974733 | 0.157240388 |
| 22_22707693_22711065_22732515_22734197_FF | −0.2530292 | −4.020252229 | 0.003414746 | 0.026069411 | −1.721154237 |
| X_19652532_19655511_19778202_19779729_RF | −0.251445257 | −5.59071546 | 0.000420715 | 0.012478825 | 0.402210859 |
| 13_111730571_111732652_111951910_111954429_FF | −0.25127638 | −4.396690328 | 0.002000888 | 0.020387988 | −1.17786842 |

| Probe | FC | FC_1 | LS | Loop detected |
|---|---|---|---|---|
| 7_45584884_45588878_45736475_4574327 3_RF | 0.733872778 | −1.362634002 | −1 | UC |
| 1_161576950_161581654_161625371_1616 26958_FR | 0.745724513 | −1.340977777 | −1 | UC |
| 7_5 5087969_55089963_55247129_5525761 1_RR | 0.747803431 | −1.337249815 | −1 | UC |
| 7_55087969_55089963_55276177_5528152 8_RF | 0.755178953 | −1.324189448 | −1 | UC |
| 7_55087969_55089963_55146890_5515140 6_RF | 0.757971492 | −1.319310833 | −1 | UC |
| 7_55087969_55089963_55113347_5511544 4_RR | 0.783379134 | −1.276521108 | −1 | UC |
| 1_161495318_161496726_161576950_1615 81654_RF | 0.784612585 | −1.274514352 | −1 | UC |
| 7_55087969_55089963_55159296_55163839_RF | 0.785315523 | −1.27337353 | −1 | UC |
| 19_6736190_6739207_6832841_6834474_FR | 0.790795872 | −1.264548837 | −1 | UC |
| 22_22718523_22726462_22744564_22754970_FR | 0.792786326 | −1.261373926 | −1 | UC |
| 16_31228760_31230406_31342509_31344379_FR | 0.795232518 | −1.25749385 | −1 | UC |
| 7_55087969_55089963_55294211_55302386_RR | 0.796145443 | −1.256051904 | −1 | UC |
| 19_10341612_10343024_10406169_10407761_FF | 0.798012303 | −1.253113512 | −1 | UC |
| 1_161543531_161545118_161576950_161581654_RF | 0.800881839 | −1.248623643 | −1 | UC |
| 1_161576950_161581654_161627152_161631654_FR | 0.801945051 | −1.246968229 | −1 | UC |
| 7_55087969_55089963_55224588_55235839_RR | 0.804080192 | −1.243657051 | −1 | UC |
| 6_32135728_32138270_32149729_32154447_FF | 0.804952085 | −1.242309969 | −1 | UC |
| 8_42121759_42128721_42138740_42142593_FR | 0.807544673 | −1.238321585 | −1 | UC |
| 11_118135384_118142619_118155813_118161617_RR | 0.813332453 | −1.229509527 | −1 | UC |
| X_19555372_19559004_19587789_19592813_FR | 0.815950009 | −1.225565279 | −1 | UC |
| 1_161519223_161525894_161625371_161626968_RR | 0.819297743 | −1.220557493 | −1 | UC |
| 7_55087969_55089963_55116799_55120169_RR | 0.819704957 | −1.219951144 | −1 | UC |
| 8_42099384_42103137_42121759_42128721_FF | 0.821086775 | −1.217898071 | −1 | UC |
| 1_161576950_161581654_161625371_161626958_RR | 0.822083112 | −1.216422021 | −1 | UC |
| 1_161519223_161525894_161543531_161545118_RR | 0.824871594 | −1.2123099 | −1 | UC |
| 10_98420739_98422156_98475835_98481698_FF | 0.825227424 | −1.211787165 | −1 | UC |
| 11_923549_925733_976127_979142_FR | 0.825572704 | −1.211280358 | −1 | UC |
| X_19747473_19749276_19778202_19779729_RF | 0.827604608 | −1.208306467 | −1 | UC |
| X_19555372_19559004_19801817_19808062_FF | 0.829359059 | −1.205750379 | −1 | UC |
| 7_55116799_55120169_55294211_55302386_RF | 0.829923077 | −1.204930948 | −1 | UC |
| 13_111740592_111744283_111955243_111957450_RR | 0.830575668 | −1.203984222 | −1 | UC |
| 13_111740592_111744283_111951910_111954429_RF | 0.831014507 | −1.203348428 | −1 | UC |
| 7_45584884_45588878_45641165_45652147_RR | 0.832195535 | −1.20164067 | −1 | UC |
| 7_55087969_55089963_55247129_55257611_RF | 0.833551058 | −1.199686558 | −1 | UC |
| 19_6698247_6701314_6736190_6739707_RF | 0.83454008 | −1.198264797 | −1 | UC |
| 11_118135384_118142619_118155813_118161617_FR | 0.834797052 | −1.197895941 | −1 | UC |
| 11_65282265_65284907_65314616_65318092_RF | 0.834998535 | −1.197606891 | −1 | UC |

TABLE 22b-continued

Ulcerative colitis (UC) probes –EpiSwitch ™ markers to stratify UC vs. healthy controls

| | | | |
|---|---|---|---|
| 10_98397707_98399014_98464393_98468588_FF | 0.83549488 | −1.196895425 | −1 | UC |
| X_19555372_19559004_19778202_19779729_FF | 0.835753663 | −1.196524819 | −1 | UC |
| X_19747473_19749276_19801817_19808062_RR | 0.835813336 | −1.196439392 | −1 | UC |
| 7_55146890_55151406_55294211_55302386_RF | 0.835988756 | −1.196188337 | −1 | UC |
| 7_55146890_55151406_55276177_55281528_FF | 0.83661209 | −1.195297094 | −1 | UC |
| 7_55159296_55163839_55294211_55302386_FF | 0.836935008 | −1.194835908 | −1 | UC |
| 8_42121759_42128721_42152856_42153945_FF | 0.837553529 | −1.193953539 | −1 | UC |
| 10_9842647_98429729_98475835_984816_98 FF | 0.83789507 | −1.193466862 | −1 | UC |
| 7_55061795_55064635_55087969_55089963_FR | 0.838413548 | −1.192728817 | −1 | UC |
| 7_55061795_55064635_55159296_55163839_RF | 0.838426825 | −1.19270993 | −1 | UC |
| 22_22707693_22711085_22732515_22734197_FF | 0.839132653 | −1.191706694 | −1 | UC |
| X_19652532_19655511_19778202_19779729_RF | 0.840054447 | −1.190399031 | −1 | UC |
| 13_111730571_111732652_111951910_111954429_FF | 0.840152787 | −1.190259695 | −1 | UC |

TABLE 22c

Ulcerative colitis (UC) probes - EpiSwitch ™ markers to stratify UC vs. healthy controls

| Probe | Probe Sequence 60 mer |
|---|---|
| 7_45584884_45588878_45736475_45743273_RF | TCCATCCCCAACTTCAATGACTTCTACATCGACATAGTACTGAAAGTCTTTGCTAGAGTA (SEQ ID NO: 307) |
| 1_161576950_161581654_161625371_161626958_FR | ACCCAGGATAAAACGCAGTGTTGACCGATCGATTCTTGGGCCTTCCACCTTCACATTCTA (SEQ ID NO: 308) |
| 7_55087969_55089963_55247129_55257611_RR | AGACCCGGACGTCTCCGCGAGGCGGCCATCGAGGAAGGCTCCTCTGAGAAAGAGTCTGCT (SEQ ID NO: 309) |
| 7_55087969_55089963_55276177_55281528_RF | CTCCAGAAAGGACCTTTAAACACTCAGGTCGATGGCCGCCTCGCGGAGACGTCCGGGTCT (SEQ ID NO: 310) |
| 7_55087969_55089963_55146890_55151406_RF | TTCCTGAAAAAAATGGCTACTTATTAGTCGATGGCCGCCTCGCGGAGACGTCCGGGTCT (SEQ ID NO: 311) |
| 7_55087969_55089963_55113347_55115444_RR | AGACCCGGACGTCTCCGCGAGGCGGCCATCGAGTGTCAACATGATGGCACCTAAAGCTGT (SEQ ID NO: 312) |
| 1_161495318_161496726_161576950_161581654_RF | ACCCAGGATAAAACGCAGTGTTGACCGATCGAGGGCGTGGACTTCTACACGTCCATCACT (SEQ ID NO: 313) |
| 7_55087969_55089963_55159296_55163839_RF | CACTTTTTATAGAAGAGAAAGTGAAGATTCGATGGCCGCCTCGCGGAGACGTCCGGGTCT (SEQ ID NO: 314) |
| 19_6736190_6739207_6832841_6834474_FR | CCTTGGCGAAGGCGCGTCCTGGGTTGGATCGAAGTGTATGATCGCATGGCATTTTGTACA (SEQ ID NO: 315) |
| 22_22718523_22726462_22744564_22754970_FR | CCTTCCCTCGTATTCAGTGAGATTCATTTCGAACTCCTGACCTCAGGTGAGGTGATCCAC (SEQ ID NO: 316) |
| 16_31228760_31230406_31342509_31344379_FR | GGTGGCATCCCCATCACTTCTCCATGCCTCGAGGTCCCCAACCCCCTGCCGCTCATCGTG (SEQ ID NO: 317) |
| 7_55087969_55089963_55294211_55302386_RR | AGACCCGGACGTCTCCGCGAGGCGGCCATCGAATGATCAGTGATGTTGATTTTTTTTCT (SEQ ID NO: 318) |
| 19_10341612_10343024_10406169_10407761_FF | TGCGGAAATGATGGACACTACACCTTCATCGACCTCGTGATCTGGCCGCCTCGGCCTTCC (SEQ ID NO: 319) |
| 1_161543531_161545118_161576950_161581654_RF | ACCCAGGATAAAACGCAGTGTTGACCGATCGATTCTTGGGCCTTCCACCTTCACATTCTA (SEQ ID NO: 320) |
| 1_161576950_161581654_161627152_161631654_FR | ACCCAGGATAAAACGCAGTGTTGACCGATCGACCCTTCTGCTTTCTCTCCAGGGGATGGC (SEQ ID NO: 321) |
| 7_55087969_55089963_55224588_55235839_RR | AGACCCGGACGTCTCCGCGAGGCGGCCATCGACATATTTCCTGTTCCCTTGGAATAAAAA (SEQ ID NO: 322) |
| 6_32135728_32138270_32149729_32154447_FF | ACTGATGGCATCCCCCGTGCGCTTCCGGTCGATGGGGCCAGGGGGCTATGGGGATAACCT (SEQ ID NO: 323) |
| 8_42121759_42128721_42138740_42142593_FR | CCACCCCCGCCCCGGGGGAGTCGCCCGGTCGAGGGCCTGGCAAGAAGACAGAAGCCGACT (SEQ ID NO: 324) |

TABLE 22c-continued

Ulcerative colitis (UC) probes - EpiSwitch ™ markers to stratify UC vs. healthy controls

| Probe | Probe Sequence 60 mer |
|---|---|
| 11_118135384_118142619_118155813_118161617_RR | GAATTCCGACTCCCGTTTTGAAATTGTATCGAACTCCTGACCTCGGGTGACCCGTATGCC (SEQ ID NO: 325) |
| X_19555372_19559004_19587789_19592813_FR | AGAAACAGCTAACTGATCCCTAAACTCCTCGAGTTGAGATCTGGCGGCCTGAATGCTGGT (SEQ ID NO: 326) |
| 1_161519223_161525894_161625371_161626958_RR | CAGAATCACTCTGTGGAACCAAAGAGCTTCGATTCTTGGGCCTTCCACCTTCACATTCTA (SEQ ID NO: 327) |
| 7_55087969_55089963_55116799_55120169_RR | AGACCCGGACGTCTCCGCGAGGCGGCCATCGATTTTGCTGATGCAATACAGTTTTACAGG (SEQ ID NO: 328) |
| 8_42099384_42103137_42121759_42128721_FF | CAAGATAAAGGAAGAGTGAAATCCTGTCTCGACCGGGCGACTCCCCCGGGGCGGGGTGG (SEQ ID NO: 329) |
| 1_161576950_161581654_161625371_161626958_RR | AGTGATGGACTTGTAGAAGTCCACGCCCTCGATTCTTGGGCCTTCCACCTTCACATTCTA (SEQ ID NO: 330) |
| 1_161519223_161525894_161543531_161545118_RR | CAGAATCACTCTGTGGAACCAAAGAGCTTCGATTCTTGGGCCTTCCACCTTCACATTCTA (SEQ ID NO: 331) |
| 10_98420739_98422156_98475835_98481698_FF | GGCGGGTGGATCACCTGAGGTCAGGAGCTCGATCTCCTGACCTCGTGATCCGCCCGC)CTC (SEQ ID NO: 332 |
| 11_923549_925733_976127_979142_FR | GCCTGCAGGGGCGCCCCCGCGCCTGCCTCGACCACACATCCACATGGACGCATGGCAGG (SEQ ID NO: 333) |
| X_19747473_19749276_19778202_19779729_RF | CATGATAGTTAAGAGATCATATCTAGAATCGATACAGTTCATAATTTATGAACATGTGGA (SEQ ID NO: 334) |
| X_19555372_19559004_19801817_19808062_FF | AGAAACAGCTAACTGATCCCTAAACTCCTCGAGAGAGTCTTAAAAAGGGAACAAACCAAA (SEQ ID NO: 335) |
| 7_55116799_55120169_55294211_55302386_RF | ACCAAACCCAAGGTCCGCTGCTCGTGCTCGATTTTGCTGATGCAATACAGTTTTACAGG (SEQ ID NO: 336) |
| 13_111740592_111744283_111955243_111957450_RR | AGTGACCTAATCACAGCTCACCGGAGCCTCGAGGCCTTAGCTCCTCAAGGATACACATTT (SEQ ID NO: 337) |
| 13_111740592_111744283_111951910_111954429_RF | AATTCTGTTGGAAGAATAATTTAAAATATCGAGGCTCCGGTGAGCTGTGATTAGGTCACT (SEQ ID NO: 338) |
| 7_45584884_45588878_45641165_45652147_RR | TACTCTAGCAAAGACTTTCAGTACTATGTCGATGGTGATTTTACCTTGTGGAGCAATGGC (SEQ ID NO: 339) |
| 7_55087969_55089963_55247129_55257611_RF | AGCAAGAGGCTGAGCCTAACTCTCCCTTTCGATGGCCGCCTCGCGGAGACGTCCGGGTCT (SEQ ID NO: 340) |
| 19_6698247_6701314_6736190_6739207_RF | CCTTGGCGAAGGCGCGTCCTGGGTTGGATCGATCTCTTGACCTCACGATCCACCCGCCTC (SEQ ID NO: 341) |
| 11_118135384_118142619_118155813_118161617_FR | GCAGAGGGAATTGAGAGAAGTTAAGAGTTCGAACTCCTGACCTCGGGTGACCCGTATGCC (SEQ ID NO: 342) |
| 11_65282265_65284907_65314616_65318092_RF | GACACGGGCGCATCACGAGGTCAAGAGATCGATCTCTTGACCTGGTGATCTACCCGCCTC (SEQ ID NO: 343) |
| 10_98397707_98399014_98464393_98468588_FF | ATACTGACACACTATTCCACCCACAAAGTCGATAACATGTTTATAGAGAAATAGCCCTCT (SEQ ID NO: 344) |
| X_19555372_19559004_19778202_19779729_FF | AGAAACAGCTAACTGATCCCTAAACTCCTCGATTCTAGATATGATCTCTTAACTATCATG (SEQ ID NO: 345) |
| X_19747473_19749276_19801817_19808062_RR | TCCACATGTTCATAAATTATGAACTGTATCGAAATGTCTATTCATATTCATTAACTCAAG (SEQ ID NO: 346) |
| 7_55146890_55151406_55294211_55302386_RF | ACCAAACCCAAGGTCCGCTGCTCGTGCTCGAGATGGGGAAGGAAAGGTCAGAAGAGGAG (SEQ ID NO: 347) |
| 7_55146890_55151406_55276177_55281528_FF | TTCCTGAAAAAAATGGCTACTTATTAGTCGACCTGAGTGTTTAAAGGTCCTTTCTGGAG (SEQ ID NO: 348) |
| 7_55159296_55163839_55294211_55302386_FF | CACTTTTTATAGAAGAGAAAGTGAAGATTCGAGCAGCGAGCAGCGGACCTTGGGTTTGGT (SEQ ID NO: 349) |

TABLE 22c-continued

Ulcerative colitis (UC) probes - EpiSwitch ™ markers to stratify UC vs. healthy controls

| Probe | Probe Sequence 60 mer |
|---|---|
| 8_42121759_42128721_42152856_42153945_FF | CCACCCCGCCCCGGGGGAGTCGCCCGGTCGAACTCCGGACCTCGTGATCTGCCCAC CTC (SEQ ID NO: 350) |
| 10_98426247_98429729_98475835_98481698_FF | GAGGTGGGCGGATCCTAAGGTCAGGAGTTCGATCTCCTGACCTCGTGATCCGCCCGC CTC (SEQ ID NO: 351) |
| 7_55061795_55064635_55087969_55089963_FR | TTAACATGGTCTATGTGTCCCTGCATGATCGATGGCCGCCTCGCGGAGACGTCCGGG TCT (SEQ ID NO: 352) |
| 7_55061795_55064635_55159296_55163839_RF | CACTTTTTATAGAAGAGAAAGTGAAGATTCGACCTCCTGACCTCGGAACCACAATCA) CTC (SEQ ID NO: 353 |
| 22_22707693_22711085_22732515_22734197_FF | TTTTCCCTGGAAATCCTAGTTGGGGTGCTCGAGCCGCCAACGAGGATTTCTAGGAGA AGA (SEQ ID NO: 354) |
| X_19652532_19655511_19778202_19779729_RF | CATGATAGTTAAGAGATCATATCTAGAATCGACTGTGCAGCTATGCTGTTTTATGTG TAA (SEQ ID NO: 355) |
| 13_111730571_111732652_111951910_111954429_FF | TCTTTGTTACTGGAATATACGAATAAAATCGATATTTTAAATTATTCTTCCAACAGA ATT (SEQ ID NO: 356) |

TABLE 22d

Ulcerative colitis (UC) probes - EpiSwitch ™ markers to stratify UC vs. healthy controls

| Probe | Chr | Probe Location | | | |
|---|---|---|---|---|---|
| | | Start1 | End1 | Start2 | End2 |
| 7_45584884_45588878_45736475_45743273_RF | 7 | 45584885 | 45584914 | 45743244 | 45743273 |
| 1_161576950_161581654_161625371_161626958_FR | 1 | 161576950 | 161581654 | 161625372 | 161625401 |
| 7_55087969_55089963_55247129_55257611_RR | 7 | 55087970 | 55087999 | 55247130 | 55247159 |
| 7_55087969_55089963 55276177_55281528_RF | 7 | 55087970 | 55087999 | 55281499 | 55281528 |
| 7_55087969_55089963_55146890_55151406_RF | 7 | 55087970 | 55087999 | 55151377 | 55151406 |
| 7_55087969_55089963_55113347_55115444_RR | 7 | 55087970 | 55087999 | 55113348 | 55113377 |
| 1_161495318_161496726_161576950_161581654_RF | 1 | 161495319 | 161495348 | 161581625 | 161581654 |
| 7_55087969_55089963_55159296_55163839_RF | 7 | 55087970 | 55087999 | 55163810 | 55163839 |
| 19_6736190_6739207_6832841_6834474_FR | 19 | 6739178 | 6739207 | 6832842 | 6832871 |
| 22_22718523_22726462_22744564_22754970_FR | 22 | 22726433 | 22726462 | 22744565 | 22744594 |
| 16_31228760_31230406_31342509_31344379_FR | 16 | 31230377 | 31230406 | 31342510 | 31342539 |
| 7_55087969_55089963_55294211_55302386_RR | 7 | 55087970 | 55087999 | 55294212 | 55294241 |
| 19_10341612_10343024_10406169_10407761_FF | 19 | 10342995 | 10343024 | 10407732 | 10407761 |
| 1_161543531_161545118_161576950_161581654_RF | 1 | 161543532 | 161543561 | 161581625 | 161581654 |
| 1_161576950_161581654_161627152_161631654_FR | 1 | 161581625 | 161581654 | 161627153 | 161627182 |
| 7_55087969_55089963_55224588_55235839_RR | 7 | 55087970 | 55087999 | 55224589 | 55224618 |
| 6_32135728_32138270_32149729_32154447_FF | 6 | 32138241 | 32138270 | 32154418 | 32154447 |
| 8_42121759_42128721_42138740_42142593_FR | 8 | 42128692 | 42128721 | 42138741 | 42138770 |
| 11_118135384_118142619_118155813_1181616_17_RR | 11 | 118135385 | 118135414 | 118155814 | 118155843 |
| X_19555372_19559004_19587789_19592813_FR | X | 19558975 | 19559004 | 19587790 | 19587819 |
| 1_161519223_161525894_161625371_161626958_RR | 1 | 161519224 | 161519253 | 161625372 | 161625401 |
| 7_55087969_55089963_55116799_55120169_RR | 7 | 55087970 | 55087999 | 55116800 | 55116829 |
| 8_42099384_42103137_42121759_42128721_FF | 8 | 42103108 | 42103137 | 42128692 | 42128721 |
| 1_161576950_161581654_161625371_161626958_RR | 1 | 161576951 | 161576980 | 161625372 | 161625401 |
| 1_161519223_161525894_161543531_161545118_RR | 1 | 161519224 | 161519253 | 161543532 | 161543561 |
| 10_98420739_98422156_98475835_98481698_FF | 10 | 98422127 | 98422156 | 98481669 | 98481698 |
| 11_923549_925733_976127_979142_FR | 11 | 925704 | 925733 | 976128 | 976157 |
| X_19747473_19749276_19778202_19779729_RF | X | 19747474 | 19747503 | 19779700 | 19779729 |
| X_19555372_19559004_19801817_19808062_FF | X | 19558975 | 19559004 | 19808033 | 19808062 |
| 7_55116799_55120169_55294211_55302386_RF | 7 | 55116800 | 55116829 | 55302357 | 55302386 |
| 13_111740592_111744283_111955243_111957450_RR | 13 | 111740593 | 111740622 | 111955244 | 111955273 |
| 13_111740592_111744283_111951910_111954429_RF | 13 | 111740593 | 111740622 | 111954400 | 111954429 |
| 7_45584884_45588878_45641165_45652147_RR | 7 | 45584885 | 45584914 | 45641166 | 45641195 |
| 7_55087969_55089963_55247129_55257611_RF | 7 | 55087970 | 55087999 | 55257582 | 55257611 |
| 196698247_6701314_6736190_6739207_RF | 19 | 6698248 | 6698277 | 6739178 | 6739207 |
| 11_118135384_118142619_118155813_118161617_FR | 11 | 118142590 | 118142619 | 118155814 | 118155843 |
| 11_65282265_65284907_65314616_65318092_RF | 11 | 65282266 | 65282295 | 65318063 | 65318092 |
| 10_98397707_98399014_98464393_98468588_FF | 10 | 98398985 | 98399014 | 98468559 | 98468588 |
| X_19555372_19559004_19778202_19779729_FF | X | 19558975 | 19559004 | 19779700 | 19779729 |
| X_19747473_19749276_19801817_19808062_RR | X | 19747474 | 19747503 | 19801818 | 19801847 |
| 7_55146890_55151406_55294211_55302386_RF | 7 | 55146891 | 55146920 | 55302357 | 55302386 |
| 7_55146890_55151406_55276177_55281528_FF | 7 | 55151377 | 55151406 | 55281499 | 55281528 |
| 7_55159296_55163839_55294211_55302386_FF | 7 | 55163810 | 55163839 | 55302357 | 55302386 |
| 8_42121759_42128721_42152856_42153945_FF | 8 | 42128692 | 42128721 | 42153916 | 42153945 |

TABLE 22d-continued

Ulcerative colitis (UC) probes - EpiSwitch ™ markers to stratify UC vs. healthy controls

| | | | | | |
|---|---|---|---|---|---|
| 10_98426247_98429729_98475835_98481698_FF | 10 | 98429700 | 98429729 | 98481669 | 98481698 |
| 7_55061795_55064635_55087969_55089963_FR | 7 | 55064606 | 55064635 | 55087970 | 55087999 |
| 7_55061795_55064635_55159296_55163839_RF | 7 | 55061796 | 55061825 | 55163810 | 55163839 |
| 22_22707693_22711085_22732515_22734197_FF | 22 | 22711056 | 22711085 | 22734168 | 22734197 |
| X_19652532_19655511_19778202_19779729_RF | X | 19652533 | 19652562 | 19779700 | 19779729 |
| 13_111730571_111732652_111951910_111954429_FF | 13 | 111732623 | 111732652 | 111954400 | 111954429 |

| Probe | \multicolumn{5}{c}{4 kb Sequence Location} |

| Probe | Chr | Start1 | End1 | Start2 | End2 |
|---|---|---|---|---|---|
| 7_45584884_45588878_45736475_45743273_RF | 7 | 45584885 | 45588884 | 45739274 | 45743273 |
| 1_161576950_161581654_161625371_161626958_FR | 1 | 161577655 | 161581654 | 161625372 | 161629371 |
| 7_55087969_55089963_55247129_55257611_RR | 7 | 55087970 | 55091969 | 55247130 | 55251129 |
| 7_55087969_55089963_55276177_55281528_RF | 7 | 55087970 | 55091969 | 55277529 | 55281528 |
| 7_55087969_55089963_55146890_55151406_RF | 7 | 55087970 | 55091969 | 55147407 | 55151406 |
| 7_55087969_55089963_55113347_55115444_RR | 7 | 55087970 | 55091969 | 55113348 | 55117347 |
| 1_161495318_161496726_161576950_161581654_RF | 1 | 161495319 | 161499318 | 161577655 | 161581654 |
| 7_55087969_55089963_55159296_55163839_RF | 7 | 55087970 | 55091969 | 55159840 | 55163839 |
| 19_6736190_6739207_6832841_6834474_FR | 19 | 6735208 | 6739207 | 6832842 | 6836841 |
| 22_22718523_22726462_22744564_22754970_FR | 22 | 22722463 | 22726462 | 22744565 | 22748564 |
| 16_31228760_31230406_31342509_31344379_FR | 16 | 31226407 | 31230406 | 31342510 | 31346509 |
| 7_55087969_55089963_55294211_55302386_RR | 7 | 55087970 | 55091969 | 55294212 | 55298211 |
| 19_10341612_10343024_10406169_10407761_FF | 19 | 10339025 | 10343024 | 10403762 | 10407761 |
| 1_161543531_161545118_161576950_161581654_RF | 1 | 161543532 | 161547531 | 161577655 | 161581654 |
| 1_161576950_161581654_161627152_161631654_FR | 1 | 161577655 | 161581654 | 161627153 | 161631152 |
| 7_55087969_55089963_55224588_55235839_RR | 7 | 55087970 | 55091969 | 55224589 | 55228588 |
| 6_32135728_32138270_32149729_32154447_FF | 6 | 32134271 | 32138270 | 32150448 | 32154447 |
| 8_42121759_42128721_42138740_42142593_FR | 8 | 42124722 | 42128721 | 42138741 | 42142740 |
| 11_118135384_118142619_118155813_1181616_17_RR | 11 | 118135385 | 118139384 | 118155814 | 118159813 |
| X_19555372_19559004_19587789_19592813_FR | X | 19555005 | 19559004 | 19587790 | 19591789 |
| 1_161519223_161525894_161625371_161626958_RR | 1 | 161519224 | 161523223 | 161625372 | 161629371 |
| 7_55087969_55089963_55116799_55120169_RR | 7 | 55087970 | 55091969 | 55116800 | 55120799 |
| 8_42099384_42103137_42121759_42128721_FF | 8 | 42099138 | 42103137 | 42124722 | 42128721 |
| 1_161576950_161581654_161625371_161626958_RR | 1 | 161576951 | 161580950 | 161625372 | 161629371 |
| 1_161519223_161525894_161543531_161545118_RR | 1 | 161519224 | 161523223 | 161543532 | 161547531 |
| 10_98420739_98422156_98475835_98481698_FF | 10 | 98418157 | 98422156 | 98477699 | 98481698 |
| 11_923549_925733_976127_979142_FR | 11 | 921734 | 925733 | 976128 | 980127 |
| X_19747473_19749276_19778202_19779729_RF | X | 19747474 | 19751473 | 19775730 | 19779729 |
| X_19555372_19559004_19801817_19808062_FF | X | 19555005 | 19559004 | 19804063 | 19808062 |
| 7_55116799_55120169_55294211_55302386_RF | 7 | 55116800 | 55120799 | 55298387 | 55302386 |
| 13_111740592_111744283_111955243_111957450_RR | 13 | 111740593 | 111744592 | 111955244 | 111959243 |
| 13_111740592_111744283_111951910_111954429_RF | 13 | 111740593 | 111744592 | 111950430 | 111954429 |
| 7_45584884_45588878_45641165_45652147_RR | 7 | 45584885 | 45588884 | 45641166 | 45645165 |
| 7_55087969_55089963_55247129_55257611_RF | 7 | 55087970 | 55091969 | 55253612 | 55257611 |
| 196698247_6701314_6736190_6739207_RF | 19 | 6698248 | 6702247 | 6735208 | 6739207 |
| 11_118135384_118142619_118155813_118161617_FR | 11 | 118138620 | 118142619 | 118155814 | 118159813 |
| 11_65282265_65284907_65314616_65318092_RF | 11 | 65282266 | 65286265 | 65314093 | 65318092 |
| 10_98397707_98399014_98464393_98468588_FF | 10 | 98395015 | 98399014 | 98464589 | 98468588 |
| X_19555372_19559004_19778202_19779729_FF | X | 19555005 | 19559004 | 19775730 | 19779729 |
| X_19747473_19749276_19801817_19808062_RR | X | 19747474 | 19751473 | 19801818 | 19805817 |
| 7_55146890_55151406_55294211_55302386_RF | 7 | 55146891 | 55150890 | 55298387 | 55302386 |
| 7_55146890_55151406_55276177_55281528_FF | 7 | 55147407 | 55151406 | 55277529 | 55281528 |
| 7_55159296_55163839_55294211_55302386_FF | 7 | 55159840 | 55163839 | 55298387 | 55302386 |
| 8_42121759_42128721_42152856_42153945_FF | 8 | 42124722 | 42128721 | 42149946 | 42153945 |
| 10_98426247_98429729_98475835_98481698_FF | 10 | 98425730 | 98429729 | 98477699 | 98481698 |
| 7_55061795_55064635_55087969_55089963_FR | 7 | 55060636 | 55064635 | 55087970 | 55091969 |
| 7_55061795_55064635_55159296_55163839_RF | 7 | 55061796 | 55065795 | 55159840 | 55163839 |
| 22_22707693_22711085_22732515_22734197_FF | 22 | 22707086 | 22711085 | 22730198 | 22734197 |
| X_19652532_19655511_19778202_19779729_RF | X | 19652533 | 19656532 | 19775730 | 19779729 |
| 13_111730571_111732652_111951910_111954429_FF | 13 | 111728653 | 111732652 | 111950430 | 111954429 |

TABLE 23a

SLE probes - EpiSwitch ™ markers to stratify SLE vs. healthy controls

| Probe | GeneLocus | Probe_Count_Total | Probe_Count_Sig | HyperG_Stats |
|---|---|---|---|---|
| 1_243635945_243637780_243655019_243656128_RR | AKT3 | 329 | 64 | 0.046948 |
| 1_243655019_243656128_243727939_243733240_RF | AKT3 | 329 | 64 | 0.046948 |
| 1_243655019_243656128_243954381_243957141_RF | AKT3 | 329 | 64 | 0.046948 |
| 1_243655019_243656128_243680126_243690814_RF | AKT3 | 329 | 64 | 0.046948 |
| 1_243655019_243656128_243867949_243871515_RF | AKT3 | 329 | 64 | 0.046948 |
| 1_243655019_243656128_243860421_243862288_RF | AKT3 | 329 | 64 | 0.046948 |
| 14_24795078_24798615_24843066_24844509_RR | ADCY4 | 10 | 4 | 0.060426 |

TABLE 23a-continued

SLE probes - EpiSwitch ™ markers to stratify SLE vs. healthy controls

| Probe | Gene | | | |
|---|---|---|---|---|
| 1_243655019_243656128_243816190_243822519_RF | AKT3 | 329 | 64 | 0.046948 |
| 14_24795078_24798615_24825321_24828950_RR | ADCY4 | 10 | 4 | 0.060426 |
| 1_243655019_243656128_243938249_243942270_RF | AKT3 | 329 | 64 | 0.046948 |
| 11_923549_925733_976127_979142_FR | AP2A2 | 16 | 5 | 0.097194 |
| 1_243655019_243656128_243864025_243867879_RF | AKT3 | 329 | 64 | 0.046948 |
| 1_161590754_161594100_161627152_161631654_RR | FCGR2B;FCGR3A | 96 | 21 | 0.076199 |
| 1_243637780_243640834_243655019_243656128_RR | AKT3 | 329 | 64 | 0.046948 |
| 7_45584884_45588878_45736475_45743273_RF | ADCY1 | 30 | 11 | 0.004679 |
| 16_31228760_31230406_31342509_31344379_FR | ITGAM | 28 | 10 | 0.008518 |
| 5_7602410_7603529_7797003_7800572_FR | ADCY2 | 306 | 64 | 0.011305 |
| 1_243635945_243637780_243655019_243656128_FR | AKT3 | 329 | 64 | 0.046948 |
| 11_36583119_36588432_36605543_36609927_RR | RAG2;RAG1 | 10 | 5 | 0.012725 |
| 1_243655019_243656128_243784071_243785870_RF | AKT3 | 329 | 64 | 0.046948 |
| 1_243655019_243656128_243707136_243710471_RR | AKT3 | 329 | 64 | 0.046948 |
| 16_31342509_31344379_31355595_31363682_RF | ITGAM | 28 | 10 | 0.008518 |
| 13_111748012_111752622_111942125_111944243_RR | ARHGFF7 | 61 | 15 | 0.052278 |
| 11_36588999_36590845_36605543_36609927_FR | RAG2;RAG1 | 10 | 5 | 0.012725 |
| 1_243637780_243640834_243655019_243656128_FR | AKT3 | 329 | 64 | 0.046948 |
| 1_243655019_243656128_243784071_243785870_RR | AKT3 | 329 | 64 | 0.046948 |
| 1_243655019_243656128_243790811_243793831_RR | AKT3 | 329 | 64 | 0.046948 |
| 1_243655019_243656128_243669663_243671724_RF | AKT3 | 329 | 64 | 0.046948 |
| 1_243655019_243656128_243946602_243948601_RR | AKT3 | 329 | 64 | 0.046948 |
| 1_243655019_243656128_243674676_243579954_RR | AKT3 | 329 | 64 | 0.046948 |
| 5_140009798_140011363_140052701_140055063_FR | CD14 | 23 | 7 | 0.060939 |
| 1_243655019_243656128_243915703_243918596_RR | AKT3 | 329 | 64 | 0.046948 |
| 3_111125030_111133059_111238151_111244343_FF | CD96 | 121 | 31 | 0.003927 |
| 11_119059609_119061980_119165298_119170353_RF | CBL | 19 | 6 | 0.068591 |
| 1_243655019_243656128_243669663_243671724_RR | AKT3 | 329 | 64 | 0.046948 |
| 1_243655019_243656128_243816190_243822519_RR | AKT3 | 329 | 64 | 0.046948 |
| 1_243655019_243656128_243774056_243776138_RR | AKT3 | 329 | 64 | 0.046948 |
| 21_46345789_46346831_46359648_46362975_FF | ITGB2 | 7 | 3 | 0.085633 |
| 3_111080379_111085861_111238151_111244343_FF | CD96 | 121 | 31 | 0.003927 |
| 3_111054275_111073125_111238151_111244343_FF | CD96 | 121 | 31 | 0.003927 |
| 5_7602410_7603529_7787275_7792598_FF | ADCY2 | 306 | 64 | 0.011305 |
| 13_111748012_111752622_111822569_111834523_RR | ARHGFF7 | 61 | 15 | 0.052278 |
| 3_123010454_123013518_123033778_123037100_RF | ADCY5 | 123 | 29 | 0.016881 |
| 5_7520707_7525339_7602410_7603529_RF | ADCY2 | 306 | 64 | 0.011305 |
| 1_243655019_243656128_243954381_243957141_RR | AKT3 | 329 | 64 | 0.046948 |
| 21_46345789_46346831_46359648_46362975_FR | ITGB2 | 7 | 3 | 0.085633 |
| 6_111988059_111992304_112042041_112045568_FR | FYN | 278 | 67 | 0.000218 |
| 5_7425481_7432673_7602410_7603529_RF | ADCY2 | 306 | 64 | 0.011305 |
| 1_243655019_243656128_243760927_243763803_RF | AKT3 | 329 | 64 | 0.046948 |
| 11_923549_925733_976127_979142_RR | AP2A2 | 16 | 5 | 0.097194 |

| Probe | FDR_HyperG | Percent_Sig | reps. | Avg_CV | logFC |
|---|---|---|---|---|---|
| 1_243635945_243637780_243655019_243656128_RR | 0.964009 | 19.45 | 4 | 10.288 | −1.11091 |
| 1_243655019_243656128_243727939_243733240_RF | 0.964009 | 19.45 | 4 | 12.13 | −1.046316 |
| 1_243655019_243656128_243954381_243957141_RF | 0.964009 | 19.45 | 4 | 8.518 | −1.021078 |
| 1_243655019_243656128_243680126_243690814_RF | 0.964009 | 19.45 | 4 | 9.474 | −1.004448 |
| 1_243655019_243656128_243867949_243871515_RF | 0.964009 | 19.45 | 4 | 7.102 | −0.959208 |
| 1_243655019_243656128_243860421_243862288_RF | 0.964009 | 19.45 | 4 | 4.984 | −0.955948 |
| 14_24795078_24798615_24843066_24844509_RR | 0.976846 | 40 | 4 | 3.707 | −0.92139 |
| 1_243655019_243656128_243816190_243822519_RF | 0.964009 | 19.45 | 4 | 7.955 | −0.899817 |
| 14_24795078_24798615_24825321_24828950_RR | 0.976846 | 40 | 4 | 2.67 | −0.883452 |
| 1_243655019_243656128_243938249_243942270_RF | 0.964009 | 19.45 | 4 | 8.951 | −0.797775 |
| 11_923549_925733_976127_979142_FR | 1 | 31.25 | 4 | 3.706 | −0.750885 |
| 1_243655019_243656128_243864025_243867879_RF | 0.964009 | 19.45 | 4 | 7.444 | −0.7203 |
| 1_161590754_161594100_161627152_161631654_RR | 0.976846 | 21.88 | 4 | 3.793 | −0.718037 |
| 1_243637780_243640834_243655019_243656128_RR | 0.964009 | 19.45 | 4 | 3.009 | −0.708974 |
| 7_45584884_45588878_45736475_45743273_RF | 0.356305 | 36.67 | 4 | 7.078 | −0.694141 |
| 16_31228760_31230406_31342509_31344379_FR | 0.356305 | 35.71 | 4 | 3.617 | −0.685914 |
| 5_7602410_7603529_7797003_7800572_FR | 0.356305 | 20.92 | 4 | 3.224 | −0.683956 |
| 1_243635945_243637780_243655019_243656128_FR | 0.964009 | 19.45 | 4 | 6.732 | −0.673434 |
| 11_36583119_36588432_36605543_36609927_RR | 0.356305 | 50 | 4 | 3.345 | −0.662419 |
| 1_243655019_243656128_243784071_243785870_RF | 0.964009 | 19.45 | 4 | 4.885 | −0.655741 |
| 1_243655019_243656128_243707136_243710471_RR | 0.964009 | 19.45 | 4 | 4.221 | −0.634957 |
| 16_31342509_31344379_31355595 31363682_RF | 0.356305 | 35.71 | 4 | 3.29 | −0.634798 |
| 13_111748012_111752622_111942125_111944243_RR | 0.976846 | 24.59 | 4 | 3.57 | −0.629905 |
| 11_36588999_36590845_36605543_36609927_FR | 0.356305 | 50 | 4 | 3.56 | −0.616867 |
| 1_243637780_243640834_243655019_243656128_FR | 0.964009 | 19.45 | 4 | 5.632 | −0.609976 |
| 1_243655019_243656128_243784071_243785870_RR | 0.964009 | 19.45 | 4 | 3.8 | −0.605805 |
| 1_243655019_243656128_243790811_243793831_RR | 0.964009 | 19.45 | 4 | 4.891 | −0.603487 |
| 1_243655019_243656128_243669663_243671724_RF | 0.964009 | 19.45 | 4 | 5.918 | −0.603109 |
| 1_243655019_243656128_243946602_243948601_RR | 0.964009 | 19.45 | 4 | 4.691 | −0.598414 |
| 1_243655019_243656128_243674676_243579954_RR | 0.964009 | 19.45 | 4 | 4.312 | −0.594725 |
| 5_140009798_140011363_140052701_140055063_FR | 0.976846 | 30.43 | 4 | 3.095 | −0.56733 |
| 1_243655019_243656128_243915703_243918596_RR | 0.964009 | 19.45 | 4 | 4.647 | −0.565895 |

TABLE 23a-continued

SLE probes - EpiSwitch ™ markers to stratify SLE vs. healthy controls

| | | | | | |
|---|---|---|---|---|---|
| 3_111125030_111133059_111238151_111244343_FF | 0.356305 | 25.62 | 4 | 2.675 | −0.56071 |
| 11_119059609_119061980_119165298_119170353_RF | 0.976846 | 31.58 | 4 | 4.022 | −0.559209 |
| 1_243655019_243656128_243669663_243671724_RR | 0.964009 | 19.45 | 4 | 3.629 | −0.558549 |
| 1_243655019_243656128_243816190_243822519_RR | 0.964009 | 19.45 | 4 | 4.429 | −0.557515 |
| 1_243655019_243656128_243774056_243776138_RR | 0.964009 | 19.45 | 4 | 3.649 | −0.552494 |
| 21_46345789_46346831_46359648_46362975_FF | 0.976846 | 42.86 | 4 | 3.661 | −0.546289 |
| 3_111080379_111085861_111238151_111244343_FF | 0.356305 | 25.62 | 4 | 3.59 | −0.541985 |
| 3_111054275_111073125_111238151_111244343_FF | 0.356305 | 25.62 | 4 | 3.619 | −0.538482 |
| 5_7602410_7603529_7787275_7792598_FF | 0.356305 | 20.92 | 4 | 3.602 | −0.532192 |
| 13_111748012_111752622_111822569_111834523_RR | 0.976846 | 24.59 | 4 | 3.876 | −0.530585 |
| 3_123010454_123013518_123033778_123037100_RF | 0.43328 | 23.58 | 4 | 3.106 | −0.52203 |
| 5_7520707_7525339_7602410_7603529_RF | 0.356305 | 20.92 | 4 | 4.127 | −0.520443 |
| 1_243655019_243656128_243954381_243957141_RR | 0.964009 | 19.45 | 4 | 3.861 | −0.517294 |
| 21_46345789_46346831_46359648_46362975_FR | 0.976846 | 42.86 | 4 | 5.114 | −0.516056 |
| 6_111988059_111992304_112042041_112045568_FR | 0.067196 | 24.1 | 4 | 3.654 | −0.486999 |
| 5_7425481_7432673_7602410_7603529_RF | 0.356305 | 20.92 | 4 | 3.405 | −0.485758 |
| 1_243655019_243656128_243760927_243763803_RF | 0.964009 | 19.45 | 4 | 6.485 | −0.4791 |
| 11_923549_925733_976127_979142_RR | 1 | 31.25 | 4 | 3.228 | −0.477125 |

TABLE 23b

SLE probes - EpiSwitch ™ markers to stratify SLE vs. healthy controls

| Probe | AveExpr | t | P.Value | adj.P.Val | B |
|---|---|---|---|---|---|
| 1_243635945_743637780_243655019_743656128_RR | −1.11091 | −5.599889 | 0.001314 | 0.036644 | −0.448311 |
| 1_243655019_243656128_243727939_243733240_RF | −1.046316 | −6.292863 | 0.000708 | 0.036258 | 0.165125 |
| 1_243655019_243656128_243954381_243957141_RF | −1.021078 | −5.726179 | 0.001169 | 0.036644 | −0.331516 |
| 1_243655019_243656128_243680126_243690814_RF | −1.004448 | −5.274858 | 0.00179 | 0.036644 | −0.759704 |
| 1_243655019_243656128_243867949_243871515_RF | −0.959208 | −6.127974 | 0.000816 | 0.036258 | 0.025116 |
| 1_243655019_243656128_243860421_243862288_RF | −0.955948 | −5.470775 | 0.001483 | 0.036644 | −0.570123 |
| 14_24795078_24798615_24843066_24844509_RR | −0.92139 | −5.247772 | 0.001838 | 0.036644 | −0.786372 |
| 1_243655019_243656128_243816190_243822519_RF | −0.899817 | −5.808019 | 0.001085 | 0.03651 | −0.25705 |
| 14_24795078_24798615_24825321_24828950_RR | −0.883452 | −5.055018 | 0.002223 | 0.036852 | −0.979419 |
| 1_243655019_243656128_243938249_243942270_RF | −0.797775 | −5.316164 | 0.00172 | 0.036644 | −0.719252 |
| 11_923549_925733_976127_979142_FR | −0.750885 | −6.20439 | 0.000764 | 0.036258 | 0.090449 |
| 1_243655019_243656128_243864025_243867879_RF | −0.7203 | −5.090557 | 0.002146 | 0.036644 | −0.943392 |
| 1_161590754_161594100_161627152_161631654_RR | −0.718625 | −5.082248 | 0.002164 | 0.036652 | −0.951797 |
| 1_243637780_243640834_243655019_243656128_RR | −0.708974 | −5.13893 | 0.002045 | 0.036644 | −0.894671 |
| 7_45584884_45588878_45736475_45743273_RF | −0.694141 | −9.769901 | 6.04E−05 | 0.036258 | 2.430319 |
| 16_31228760_31230406_31342509_31344379_FR | −0.685914 | −5.332127 | 0.001693 | 0.036644 | −0.703688 |
| 5_7603956_7603529_7797003_7800572_FR | −0.683956 | −6.410403 | 0.000641 | 0.036258 | 0.26276 |
| 1_243635945_243637780_243655019_243656128_FR | −0.673434 | −4.942038 | 0.002491 | 0.036991 | −1.095274 |
| 11_36583119_36588432_36605543_36609927_RR | −0.662419 | −6.265955 | 0.000724 | 0.036258 | 0.142522 |
| 1_243655019_243656128_243784071_243785870_RF | −0.655741 | −4.92646 | 0.002531 | 0.037249 | −1.111407 |
| 1_243655019_243656128_243707136_243710471_RR | −0.634957 | −4.591917 | 0.003585 | 0.038783 | −1.467292 |
| 16_31342509_31344379_31355595_31363682_RF | −0.634798 | −4.822787 | 0.002815 | 0.037729 | −1.219761 |
| 13_111748012_111752622_111942125_111944243_RR | −0.629905 | −4.021529 | 0.006736 | 0.04662 | −2.11649 |
| 11_36588999_36590845_36605543_36609927_FR | −0.616867 | −6.119132 | 0.000823 | 0.036258 | 0.017506 |
| 1_243637780_243640834_243655019_243656128_FR | −0.609976 | −4.687394 | 0.003241 | 0.038485 | −1.363874 |
| 1_243655019_243656128_243784071_243785870_RR | −0.605805 | −4.459183 | 0.004134 | 0.039948 | −1.613554 |
| 1_243655019_243656128_243790811_243793831_RR | −0.603487 | −4.631626 | 0.003437 | 0.038567 | 1.424099 |
| 1_243655019_243656128_243669663_243671724_RF | −0.603109 | −5.448 | 0.001516 | 0.036644 | −0.591866 |
| 1_243655019_243656128_243946602_243948601_RR | −0.598414 | −4.44854 | 0.004182 | 0.04016 | −1.625407 |
| 1_243655019_243656128_243674676_243679954_RR | −0.594725 | −5.239517 | 0.001853 | 0.036644 | −0.794521 |
| 5_140009798_140011363_140052701_140055063_FR | −0.56733 | −4.725427 | 0.003114 | 0.038193 | −1.32309 |
| 1_243655019_243656128_243915703_243918596_RR | −0.565895 | −4.478155 | 0.00405 | 0.039553 | −1.59247 |
| 3_111125030_111133059_111238151_111244343_FF | −0.56071 | −5.792929 | 0.0011 | 0.036553 | −0.270709 |
| 11_119059609_119061980_119165298_119170353_RF | −0.559209 | −6.367158 | 0.000665 | 0.036258 | 0.227046 |
| 1_243655019_243656128_243669663_243671724_RR | −0.558549 | −4.215551 | 0.005406 | 0.043054 | −1.889601 |
| 1_243655019_243656128_243816190_243822519_RR | −0.557515 | −4.417923 | 0.004324 | 0.040194 | −1.659611 |
| 1_243655019_243656128_243774056_243776138_RR | −0.552494 | −4.570167 | 0.003669 | 0.038783 | −1.49106 |
| 21_46345789_46346831_46359648_46362975_FF | −0.546289 | −5.929646 | 0.000972 | 0.036258 | −0.148125 |
| 3_111080379_111085861_111238151_111244343_FF | −0.541985 | −5.838613 | 0.001055 | 0.036258 | −0.229456 |
| 3_111054275_111073125_111238151_111244343_FF | −0.538482 | −5.700713 | 0.001197 | 0.036644 | −0.354883 |
| 5_7602410_7603529_7787275_7792598_FF | −0.532192 | −9.313451 | 7.95E−05 | 0.036258 | 2.194884 |
| 13_111748012_111752622_111822569_111834523_RR | −0.530585 | −3.908474 | 0.007678 | 0.048749 | −2.251568 |
| 3_123010454_123013518_123033778_123037100_RF | −0.52203 | −7.099017 | 0.000367 | 0.036258 | 0.800425 |
| 5_7520707_7525339_7602410_7603529_RF | −0.520443 | −8.338933 | 0.000149 | 0.036258 | 1.637153 |
| 1_243655019_243656128_243954381_243957141_RR | −0.517294 | −4.34537 | 0.004681 | 0.041129 | −1.741283 |
| 21_46345789_46346831_46359648_46362975_FR | −0.516056 | −4.976539 | 0.002406 | 0.036852 | −1.059681 |
| 6_111988059_111992304_112042041_112045568_FR | −0.486999 | −7.427349 | 0.000286 | 0.036258 | 1.037454 |

TABLE 23b-continued

SLE probes - EpiSwitch ™ markers to stratify SLE vs. healthy controls

| | | | | | |
|---|---|---|---|---|---|
| 5_7425481_7432673_7602410_7603529_RF | −0.485758 | −9.720907 | 6.22E−05 | 0.036258 | 2.405775 |
| 1_243655019_243656128_243760927_243763803_RF | −0.4791 | −4.579671 | 0.003632 | 0.038783 | −1.480665 |
| 11_923549_925733_976127_979142_RR | −0.477125 | −3.945042 | 0.007358 | 0.048126 | 2.207646 |

| Probe | FC | FC_1 | LS | Loop detected |
|---|---|---|---|---|
| 1_243635945_743637780_243655019_743656128_RR | 0.463002 | −2.159818 | −1 | SLE |
| 1_243655019_243656128_243727939_243733240_RF | 0.484203 | −2.065249 | −1 | SLE |
| 1_243655019_243656128_243954381_243957141_RF | 0.492748 | −2.029435 | −1 | SLE |
| 1_243655019_243656128_243680126_243690814_RF | 0.498461 | −2.006175 | −1 | SLE |
| 1_243655019_243656128_243867949_243871515_RF | 0.514339 | −1.944242 | −1 | SLE |
| 1_243655019_243656128_243860421_243862288_RF | 0.515503 | −1.939854 | −1 | SLE |
| 14_24795078_24798615_24843066_24844509_RR | 0.528 | −1.893939 | −1 | SLE |
| 1_243655019_243656128_243816190_243822519_RF | 0.535955 | −1.86583 | −1 | SLE |
| 14_24795078_24798615_24825321_24828950_RR | 0.542069 | −1.844784 | −1 | SLE |
| 1_243655019_243656128_243938249_243942270_RF | 0.575236 | −1.738418 | −1 | SLE |
| 11_923549_925733_976127_979142_FR | 0.594239 | −1.682825 | −1 | SLE |
| 1_243655019_243656128_243864025_243867879_RF | 0.606971 | −1.647525 | −1 | SLE |
| 1_161590754_161594100_161627152_161631654_RR | 0.607924 | −1.644943 | −1 | SLE |
| 1_243637780_243640834_243655019_243656128_RR | 0.611755 | −1.634641 | −1 | SLE |
| 7_45584884_45588878_45736475_45743273_RF | 0.618077 | −1.617921 | −1 | SLE |
| 16_31228760_31230406_31342509_31344379_FR | 0.621612 | −1.608771 | −1 | SLE |
| 5_7602456_7603529_7797003_7800572_FR | 0.622456 | −1.606539 | −1 | SLE |
| 1_243635945_243637780_243655019_243656128_FR | 0.627012 | −1.594865 | −1 | SLE |
| 11_36583119_36588432_36605543_36609927_RR | 0.631818 | −1.582734 | −1 | SLE |
| 1_243655019_243656128_243784071_243785870_RF | 0.634749 | −1.575425 | −1 | SLE |
| 1_243655019_243656128_243707136_243710471_RR | 0.64396 | −1.552892 | −1 | SLE |
| 16_31342509_31344379_31355595_31363682_RF | 0.644031 | −1.552721 | −1 | SLE |
| 13_111748012_111752622_111942125_111944243_RR | 0.646219 | −1.547463 | −1 | SLE |
| 11_36588999_36590845_36605543_36609927_FR | 0.652085 | −1.533542 | −1 | SLE |
| 1_243637780_243640834_243655019_243656128_FR | 0.655207 | −1.526234 | −1 | SLE |
| 1_243655019_243656128_243784071_243785870_RR | 0.657105 | −1.521828 | −1 | SLE |
| 1_243655019_243656128_243790811_243793831_RF | 0.658161 | −1.519385 | −1 | SLE |
| 1_243655019_243656128_243669663_243671724_RF | 0.658334 | −1.518987 | −1 | SLE |
| 1_243655019_243656128_243946602_243948601_RR | 0.66048 | −1.514051 | −1 | SLE |
| 1_243655019_243656128_243674676_243679954_RR | 0.662171 | −1.510185 | −1 | SLE |
| 5_140009798_140011363_140052701_140055063_FR | 0.674865 | −1.481778 | −1 | SLE |
| 1_243655019_243656128_243915703_243918596_RR | 0.675536 | −1.480306 | −1 | SLE |
| 3_111125030_111133059_111238151_111244343_FF | 0.677968 | −1.474995 | −1 | SLE |
| 11_119059609_119061980_119165298_119170353_RF | 0.678674 | −1.473461 | −1 | SLE |
| 1_243655019_243656128_243669663_243671724_RR | 0.678985 | −1.472787 | −1 | SLE |
| 1_243655019_243656128_243816190_243822519_RR | 0.679472 | −1.471732 | −1 | SLt |
| 1_243655019_243656128_243774056_243776138_RR | 0.68184 | −1.466619 | −1 | SLE |
| 21_46345789_46346831_46359648_46362975_FF | 0.684779 | −1.460324 | −1 | SLE |
| 3_111080379_111085861_111238151_111244343_FF | 0.686825 | −1.455975 | −1 | SLE |
| 3_111054275_111073125_111238151_111244343_FF | 0.688495 | −1.452443 | −1 | SLE |
| 5_7602410_7603529_7787275_7792598_FF | 0.691503 | −1.446125 | −1 | SLE |
| 13_111748012_111752622_111822569_111834523_RR | 0.692274 | −1.444515 | −1 | SLE |
| 3_123010454_123013518_123033778_123037100_RF | 0.696391 | −1.435975 | −1 | SLE |
| 5_7520707_7525339_7602410_7603529_RF | 0.697158 | −1.434396 | −1 | SLE |
| 1_243655019_243656128_243954381_243957141_RR | 0.698681 | −1.431268 | −1 | SLE |
| 21_46345789_46346831_46359648_46362975_FR | 0.699281 | −1.430041 | −1 | SLE |
| 6 111988059_111992304_112042041_112045568_FR | 0.713508 | −1.401526 | −1 | SLE |
| 5_7425481_7432673_7602410_7603529_RF | 0.714122 | −1.400322 | −1 | SLE |
| 1_243655019_243656128_243760927_243763803_RF | 0.717425 | −1.393874 | −1 | SLE |
| 11_923549_925733_976127_979142_RR | 0.718408 | −1.391967 | −1 | SLE |

TABLE 23c

SLE probes - EpiSwitch ™ markers to stratify SLE vs. healthy controls

| Probe | Probe sequence 60 mer |
|---|---|
| 1_243635945_243637780_243655019_243656128_RR | CAAATAAATTAGAATGTATTTTCATTGCTCGAGCAGGTATTTTGGATGCGGTGCCG CCTG (SEQ ID NO: 357) |
| 1_243655019_243656128_243727939_243733240_RF | TACTGAAGAAGTCTTTGAAGAGATTTCTTCGAGCAGGTATTTTGGATGCGGTGCCG CCTG (SEQ ID NO: 358) |
| 1_243655019_243656128_243954381_243957141_RF | ATTTATTGACTCCCTAGGGTCTAGGAGCTCGAGCAGGTATTTTGGATGCGGTGCCG CCTG (SEQ ID NO: 359) |
| 1_243655019_243656128_243680126_243690814_RF | TGTTTTATAATCATTATAATTTTTTCTTTCGAGCAGGTATTTTGGATGCGGTGCCG CCTG (SEQ ID NO: 360) |

TABLE 23c-continued

SLE probes - EpiSwitch ™ markers to stratify SLE vs. healthy controls

| Probe | Probe sequence 60 mer |
|---|---|
| 1_243655019_243656128_243867949_243871515_RF | TAGAACTGAACATGTTTAAATGATATCGTCGAGCAGGTATTTTGGATGCGGTGCCG CCTG (SEQ ID NO: 361) |
| 1_243655019_243656128_243860421_243862288_RF | TTATACCAGATTTCAGGTGCCTAGCTGTTCGAGCAGGTATTTTGGATGCGGTGCCG CCTG (SEQ ID NO: 362) |
| 14_24795078_24798615_24843066_24844509_RR | CCCACCTCCCACCAGACAGTGGAAGCAGTCGAGTGCTGTGAGCAAAGAGGCCCTGG GCCA (SEQ ID NO: 363) |
| 1_243655019_243656128_243816190_243822519_RF | TTCCACTTATGTGATGTGTCTAAAGTAGTCGAGCAGGTATTTTGGATGCGGTGCCG CCTG (SEQ ID NO: 364) |
| 14_24795078_24798615_24825321_24828950_RR | CCCACCTCCCACCAGACAGTGGAAGCAGTCGAAGCAAAACTGTGGAGATTGGGTCG GTGA (SEQ ID NO: 365) |
| 1_243655019_243656128_243938249_243942270_RF | TGAATGGACCTCATCCTACCATTCTTTTTCGAGCAGGTATTTTGGATGCGGTGCCG CCTG (SEQ ID NO: 366) |
| 11_923549_925733_976127_979142_FR | GCCTGCAGGGGCGCCCCGCGCCTGCCTCGACCACACATCCACATGGACGCATGG CAGG (SEQ ID NO: 367) |
| 1_243655019_243656128_243864025_243867879_RF | CATCTCATGTGGATTCAGAAAAAGGTAGTCGAGCAGGTATTTTGGATGCGGTGCCG CCTG (SEQ ID NO: 368) |
| 1_161590754_161594100_161627152_161631654_RR | AGGACAGAGACCCCTAATTCCACCACCATCGACCCTTCTGCTTTCTCTCCAGGGGA TGGC (SEQ ID NO: 369) |
| 1_243637780_243640834_243655019_243656128_RR | TGCCCACCCAGACCTCCCGGCGGCTGCTTCGAGCAGGTATTTTGGATGCGGTGCCG CCTG (SEQ ID NO: 370) |
| 7_45584884_45588878_45736475_45743273_RF | TCCATCCCCAACTTCAATGACTTCTACATCGACATAGTACTGAAAGTCTTTGCTAG AGTA (SEQ ID NO: 371) |
| 16_31228760_31230406_31342509_31344379_FR | GGTGGCATCCCCATCACTTCTCCATGCCTCGAGGTCCCCAACCCCCTGCCGCTCAT CGTG (SEQ ID NO: 372) |
| 5_7602410_7603529_7797003_7800572_FR | CACTGCCCCACCTCTTACTGGCATCTCCTCGACCCCGTGCCAAGTCCCCGGGTGGT AGAG (SEQ ID NO: 373) |
| 1_243635945_243637780_243655019_243656128_FR | CGGCCGAGCCCGGGCCTAGTATCCAGAGTCGAGCAGGTATTTTGGATGCGGTGCCG CCTG (SEQ ID NO: 374) |
| 11_36583119_36588432_36605543_36609927_RR | CCACCTCATAGGGGAGGGCTTTACTCAGTCGATCCACACCACACCAGCAGTGGGGC ACAA (SEQ ID NO: 375) |
| 1_243655019_243656128_243784071_243785870_RF | GAGCAGTACCTAGCAAATAATTAGGTGTTCGAGCAGGTATTTTGGATGCGGTGCCG CCTG (SEQ ID NO: 376) |
| 1_243655019_243656128_243707136_243710471_RR | CAGGCGGCACCGCATCCAAAATACCTGCTCGAGTAGAGGTGTCTAATATGATGCAC CTAT (SEQ ID NO: 377) |
| 16_31342509_31344379_31355595_31363682_RF | AGTGGTCTCACCATGGCTTTCTTCCAATTCGAGGTCCCCAACCCCCTGCCGCTCAT CGTG (SEQ ID NO: 378) |
| 13_111748012_111752622_111942125_111944243_RR | TCCGTGACCCCCACAGCCGGTCGCCACATCGATTATCCAGAAGCTTCTTTTTTTTT AACC (SEQ ID NO: 379) |
| 11_36588999_36590845_36605543_36609927_FR | CCTGTAGCTCTGATGTCAGATGGCAATGTCGATCCACACCACACCAGCAGTGGGGC ACAA (SEQ ID NO: 380) |
| 1_243637780_243640834_243655019_243656128_FR | CCAAAGGTATTACAAACTCAGCCTTGGTTCGAGCAGGTATTTTGGATGCGGTGCCG CCTG (SEQ ID NO: 381) |
| 1_243655019_243656128_243784071_243785870_RR | CAGGCGGCACCGCATCCAAAATACCTGCTCGAGTATTGTGTTTGATACTTTGTTCT TGAT (SEQ ID NO: 382) |
| 1_243655019_243656128_243790811_243793831_RR | CAGGCGGCACCGCATCCAAAATACCTGCTCGAAGGGATTCTGACTTGATACAGGTC CAGA (SEQ ID NO: 383) |
| 1_243655019_243656128_243669663_243671724_RF | CTGCTGAACAGAGGTGCCTGCAGATGCGTCGAGCAGGTATTTTGGATGCGGTGCCG CCTG (SEQ ID NO: 384) |
| 1_243655019_243656128_243946602_243948601_RR | CAGGCGGCACCGCATCCAAAATACCTGCTCGATGGCCAATGATTTGATTAATTATG TCTA (SEQ ID NO: 385) |

TABLE 23c-continued

SLE probes - EpiSwitch ™ markers to stratify SLE vs. healthy controls

| Probe | Probe sequence 60 mer |
|---|---|
| 1_243655019_243656128_243674676_243679954_RR | CAGGCGGCACCGCATCCAAAATACCTGCTCGACAGTAGAATCTGCTGCCTGTGACC ATCT (SEQ ID NO: 386) |
| 5_140009798_140011363_140052701_140055063_FR | ATAAAGGTGGGGCAAAGGGTTGAATTGGTCGACGGGGCGGGTGGACGTGGAGCCAC AGTT (SEQ ID NO: 387) |
| 1_243655019_243656128_243915703_243918596_RR | CAGGCGGCACCGCATCCAAAATACCTGCTCGATGCTATAAATGTTACGGAAATTAT GTAC (SEQ ID NO: 388) |
| 3_111125030_111133059_111238151_111244343_FF | GGTCTCTGGTAATGGCCAAATAATCTAATCGACCGCCCTGCCCCCTACTGTGGAGT TCTA (SEQ ID NO: 389) |
| 11_119059609_119061980_119165298_119170353_RF | ACCGCCTCACCTCAGCTCTCCAGTGAGATCGATCCTTTGCTGCCTGATCGGTCTTC CTCT (SEQ ID NO: 390) |
| 1_243655019_243656128_243669663_243671724_RR | CAGGCGGCACCGCATCCAAAATACCTGCTCGATGTCCTCAAACCCATATAGGAAGT ACAT (SEQ ID NO: 391) |
| 1_243655019_243656128_243816190_243822519_RR | CAGGCGGCACCGCATCCAAAATACCTGCTCGATGCAACAAAAAGAGCTAACTATCC TAAA (SEQ ID NO: 392) |
| 1_243655019_243656128_243774056_243776138_RR | CAGGCGGCACCGCATCCAAAATACCTGCTCGATCAATAGACAAACATATATACACA TGTT (SEQ ID NO: 393) |
| 21_46345789_46346831_46359648_46362975_FF | GCCCGACCCTGAGCTCCAGAACAGACCATCGACCTCAACAGAGGTTTCTGAAGGGG GTCA (SEQ ID NO: 394) |
| 3_111080379_111085861_111238151_111244343_FF | ATACCAAGCCAGAGGTTTCTTGACTTAATCGACCGCCCTGCCCCCTACTGTGGAGT TCTA (SEQ ID NO: 395) |
| 3_111054275_111073125_111238151_111244343_FF | TACACAATGACTTCATTTTGTCCTCATATCGACCGCCCTGCCCCCTACTGTGGAGT TCTA (SEQ ID NO: 396) |
| 5_7602410_7603529_7787275_7792598_FF | CACTGCCCCACCTCTTACTGGCATCTCCTCGAGCTCCAGAGCTTTCCTCTGAGCCC ATGT (SEQ ID NO: 397) |
| 13_111748012_111752622_111822569_111834523_RR | TCCGTGACCCCCACAGCCGGTCGCCACATCGAGTAGCTGAGATTACAGGCATGTAC CACC (SEQ ID NO: 398) |
| 3_123010454_123013518_123033778_123037100_RF | TGCAGCCCACTCCCACAACAGGGAAGACTCGAACTCTCTCTGCCAGCCTCTCTGGG GGTG (SEQ ID NO: 399) |
| 5_7520707_7525339_7602410_7603529_RF | CACTGCCCCACCTCTTACTGGCATCTCCTCGACTGCCCTATTTTGTCTATAGATTA TTTC (SEQ ID NO: 400) |
| 1_243655019_243656128_243954381_243957141_RR | CAGGCGGCACCGCATCCAAAATACCTGCTCGACTCAAGGTTGCCACAAATCTTCAA TTTG (SEQ ID NO: 401) |
| 21_46345789_46346831_46359648_46362975_FR | GCCCGACCCTGAGCTCCAGAACAGACCATCGACTGCCGCGGGGTCGCGTCCTCTC CATC (SEQ ID NO: 402) |
| 6_111988059_111992304_112042041_112045568_FR | GGAACTGCATCCATACTTGTTACACATCTCGAGTTGTTGCCACCCCACCCTCCTCA AACC (SEQ ID NO: 403) |
| 5_7425481_7432673_7602410_7603529_RF | CACTGCCCCACCTCTTACTGGCATCTCCTCGAGCATTAAGTCTTGGATGCTGTTGT TCTA (SEQ ID NO: 404) |
| 1_243655019_243656128_243760927_243763803_RF | CAATACAACAGAATGCAGAGTCCAGAAATCGAGCAGGTATTTTGGATGCGGTGCCG CCTG (SEQ ID NO: 405) |
| 11_923549_925733_976127_979142_RR | AGTGGTACAATCATGAATCACTACAGCCTCGACCACACATCCACATGGACGCATGG CAGG (SEQ ID NO: 406) |

TABLE 23d

SLE probes - EpiSwitch ™ markers to stratify SLE vs. healthy controls

| | Probe location | | | | |
|---|---|---|---|---|---|
| Probe | Chr | Start1 | End1 | Start2 | End2 |
| 1_243635945_243637780_243655019_243656128_RR | 1 | 243635946 | 243635975 | 243655020 | 243655049 |
| 1_243655019_243656128_243727939_243733240_RF | 1 | 243655020 | 243655049 | 243733211 | 243733240 |
| 1_243655019_243656128_243954381_243957141_RF | 1 | 243655020 | 243655049 | 243957112 | 243957141 |
| 1_243655019_243656128_243680126_243690814_RF | 1 | 243655020 | 243655049 | 243690785 | 243690814 |
| 1_243655019_243656128_243867949_243871515_RF | 1 | 243655020 | 243655049 | 243871486 | 243871515 |
| 1_243655019_243656128_243860421_243862288_RF | 1 | 243655020 | 243655049 | 243862259 | 243862288 |
| 14_24795078_24798615_24843066_24844509_RR | 14 | 24795079 | 24795108 | 24843067 | 24843096 |
| 1_243655019_243656128_243816190_243822519_RF | 1 | 243655020 | 243655049 | 243822490 | 243822519 |
| 14_24795078_24795615_24825321_24828950_RR | 14 | 24795079 | 24795108 | 24825322 | 24825351 |
| 1_243655019_243656128_243938249_243942270_RF | 1 | 243655020 | 243655049 | 243942241 | 243942270 |
| 11_923549_925733_976127_979142_FR | 11 | 925704 | 925733 | 976128 | 976157 |
| 1_243655019_243656128_243864025_243867879_RF | 1 | 243655020 | 243655049 | 243867850 | 243867879 |
| 1_161590754_161594100_161627152_161631654_RR | 1 | 161590755 | 161590784 | 161627153 | 161627182 |
| 1_243637780_243640834_243655019_243656128_RR | 1 | 243637781 | 243637810 | 243655020 | 243655049 |
| 7_45584884_45588878_45736475_45743273_RF | 7 | 45584885 | 45584914 | 45743244 | 45743273 |
| 16_31228760_31230406_31342509_31344379_FR | 16 | 31230377 | 31230406 | 31342510 | 31342539 |
| 5_7602410_7603529_7797003_7800572_FR | 5 | 7603500 | 7603529 | 7797004 | 7797033 |
| 1_243635945_243637780_243655019_243656128_FR | 1 | 243637751 | 243637780 | 243655020 | 243655049 |
| 11_36583119_36588432_36605543_36609927_RR | 11 | 36583120 | 36583149 | 36605544 | 36605573 |
| 1_243655019_243656128_243784071_243785870_RF | 1 | 243655020 | 243655049 | 243785841 | 243785870 |
| 1_243655019_243656128_243707136_243710471_RR | 1 | 243655020 | 243655049 | 243707137 | 243707166 |
| 16_31342509_31344379_31355595_31363682_RF | 16 | 31342510 | 31342539 | 31363653 | 31363682 |
| 13_111748013_111752622_111942125_111944243_RR | 13 | 111748013 | 111748042 | 111942126 | 111942155 |
| 11_36588999_36590845_36605543_36609927_FR | 11 | 36590816 | 36590845 | 36605544 | 36605573 |
| 1_243637780_243640834_243655019_243656128_FR | 1 | 243640805 | 243640834 | 243655020 | 243655049 |
| 1_243655019_243656128_243784071_243785870_RR | 1 | 243655020 | 243655049 | 243784072 | 243784101 |
| 1_243655019_243656128_243790811_243793831_RR | 1 | 243655020 | 243655049 | 243790812 | 243790841 |
| 1_243655019_243656128_243669663_243671724_RF | 1 | 243655020 | 243655049 | 243671695 | 243671724 |
| 1_243655019_243656128_243946602_243948601_RR | 1 | 243655020 | 243655049 | 243946603 | 243946632 |
| 1_243655019_243656128_243674676_243679954_RR | 1 | 243655020 | 243655049 | 243674677 | 243674706 |
| 5_140009798_140011363_140052701_140055063_FR | 5 | 140011334 | 140011363 | 140052702 | 140052731 |
| 1_243655019_243656128_243915703_243918596_RR | 1 | 243655020 | 243655049 | 243915704 | 243915733 |
| 3_111125030_111133059_111238151_111244343_FF | 3 | 111133030 | 111133059 | 111244314 | 111244343 |
| 11_119059609_119061980_119165298_119170353_RF | 11 | 119059610 | 119059639 | 119170324 | 119170353 |
| 1_243655019_243656128_243669663_243671724_RR | 1 | 243655020 | 243655049 | 243669664 | 243669693 |
| 1_243655019_243656128_243816190_243822519_RR | 1 | 243655020 | 243655049 | 243816191 | 243816220 |
| 1_243655019_243656128_243774056_243776138_RR | 1 | 243655020 | 243655049 | 243774057 | 243774086 |
| 21_46345789_46346831_46359648_46362975_FF | 21 | 46346802 | 46346831 | 46362946 | 46362975 |
| 3_111080379_111085861_111238151_111244343_FF | 3 | 111085832 | 111085861 | 111244314 | 111244343 |
| 3_111073125_111073151_111244343_FF | 3 | 111073096 | 111073125 | 111244314 | 111244343 |
| 5_7602410_7603529_7787275_7792598_FF | 5 | 7603500 | 7603529 | 7792569 | 7792598 |
| 13_11748012_111752622_111822569_111834523_RR | 13 | 111748013 | 111748042 | 111822570 | 111822599 |
| 3_123010454_123013518_123033778_123037100_RF | 3 | 123010455 | 123010484 | 123037071 | 123037100 |
| 5_7520707_7525339_7602410_7603529_RF | 5 | 7520708 | 7520737 | 7603500 | 7603529 |
| 1_243655019_243656128_243954381_243957141_RR | 1 | 243655020 | 243655049 | 243954382 | 243954411 |
| 21_46345789_46346831_46359648_46362975_FR | 21 | 46346802 | 46346831 | 46359649 | 46359678 |
| 6_111988059_111992304_112042041_112045568_FR | 6 | 111992275 | 111992304 | 112042042 | 112042071 |
| 5_7425481_7432673_7602410_7603529_RF | 5 | 7425482 | 7425511 | 7603500 | 7603529 |
| 1_243655019_243656128_243760927_243763803_RF | 1 | 243655020 | 243655049 | 243763774 | 243763803 |
| 11_923549_925733_976127_979142_RR | 11 | 923550 | 923579 | 976128 | 976157 |

| | 4 kb sequence location | | | | |
|---|---|---|---|---|---|
| | Chr | Start1 | End1 | Start2 | End2 |
| 1_243635945_243637780_243655019_243656128_RR | 1 | 243635946 | 243639945 | 243655020 | 243659019 |
| 1_243655019_243656128_243727939_243733240_RF | 1 | 243655020 | 243659019 | 243729241 | 243733240 |
| 1_243655019_243656128_243954381_243957141_RF | 1 | 243655020 | 243659019 | 243953142 | 243957141 |
| 1_243655019_243656128_243680126_243690814_RF | 1 | 243655020 | 243659019 | 243686815 | 243690814 |
| 1_243655019_243656128_243867949_243871515_RF | 1 | 243655020 | 243659019 | 243867516 | 243871515 |
| 1_243655019_243656128_243860421_243862288_RF | 1 | 243655020 | 243659019 | 243858289 | 243862288 |
| 14_24795078_24798615_24843066_24844509_RR | 14 | 24795079 | 24799078 | 24843067 | 24847066 |
| 1_243655019_243656128_243816190_243822519_RF | 1 | 243655020 | 243659019 | 243818520 | 243822519 |
| 14_24795078_24795615_24825321_24828950_RR | 14 | 24795079 | 24799078 | 24825322 | 24829321 |
| 1_243655019_243656128_243938249_243942270_RF | 1 | 243655020 | 243659019 | 243938271 | 243942270 |
| 11_923549_925733_976127_979142_FR | 11 | 921734 | 925733 | 976128 | 980127 |
| 1_243655019_243656128_243864025_243867879_RF | 1 | 243655020 | 243659019 | 243863880 | 243867879 |
| 1_161590754_161594100_161627152_161631654_RR | 1 | 161590755 | 161594754 | 161627153 | 161631152 |
| 1_243637780_243640834_243655019_243656128_RR | 1 | 243637781 | 243641780 | 243655020 | 243659019 |
| 7_45584884_45588878_45736475_45743273_RF | 7 | 45584885 | 45588884 | 45739274 | 45743273 |
| 16_31228760_31230406_31342509_31344379_FR | 16 | 31226407 | 31230406 | 31342510 | 31346509 |
| 5_7602410_7603529_7797003_7800572_FR | 5 | 7599530 | 7603529 | 7797004 | 7801003 |
| 1_243635945_243637780_243655019_243656128_FR | 1 | 243633781 | 243637780 | 243655020 | 243659019 |
| 11_36583119_36588432_36605543_36609927_RR | 11 | 36583120 | 36587119 | 36605544 | 36609543 |

TABLE 23d-continued

SLE probes - EpiSwitch ™ markers to stratify SLE vs. healthy controls

| | | | | | |
|---|---|---|---|---|---|
| 1_243655019_243656128_243784071_243785870_RF | 1 | 243655020 | 243659019 | 243781871 | 243785870 |
| 1_243655019_243656128_243707136_243710471_RR | 1 | 243655020 | 243659019 | 243707137 | 243711136 |
| 16_31342509_31344379_31355595_31363682_RF | 16 | 31342510 | 31346509 | 31359683 | 31363682 |
| 13_111748012_111752622_111942125_111944243_RR | 13 | 111748013 | 111752012 | 111942126 | 111946125 |
| 11_36588999_36590845_36605543_36609927_FR | 11 | 36586846 | 36590845 | 36605544 | 36609543 |
| 1_243637780_243640834_243655019_243656128_FR | 1 | 243636835 | 243640834 | 243655020 | 243659019 |
| 1_243655019_243656128_243784071_243785870_RR | 1 | 243655020 | 243659019 | 243784072 | 243788071 |
| 1_243655019_243656128_243790811_243793831_RR | 1 | 243655020 | 243659019 | 243790812 | 243794811 |
| 1_243655019_243656128_243669663_243671724_RF | 1 | 243655020 | 243659019 | 243667725 | 243671724 |
| 1_243655019_243656128_243946603_243948601_RR | 1 | 243655020 | 243659019 | 243946603 | 243950602 |
| 1_243655019_243656128_243674676_243679954_RR | 1 | 243655020 | 243659019 | 243674677 | 243678676 |
| 5_140009798_140011363_140052701_140055063_FR | 5 | 140007364 | 140011363 | 140052702 | 140056701 |
| 1_243655019_243656128_243915703_243918596_RR | 1 | 243655020 | 243659019 | 243915704 | 243919703 |
| 3_111125030_111133059_111238151_111244343_FF | 3 | 111129060 | 111133059 | 111240344 | 111244343 |
| 11_119059609_119061980_119165298_119170353_RF | 11 | 119059610 | 119063609 | 119166354 | 119170353 |
| 1_243655019_243656128_243669663_243671724_RR | 1 | 243655020 | 243659019 | 243669664 | 243673663 |
| 1_243655019_243656128_243816190_243822519_RR | 1 | 243655020 | 243659019 | 243816191 | 243820190 |
| 1_243655019_243656128_243774056_243776138_RR | 1 | 243655020 | 243659019 | 243774057 | 243778056 |
| 21_46342789_46346831_46359648_46362975_FF | 21 | 46342832 | 46346831 | 46358976 | 46362975 |
| 3_111080379_111085861_111238151_111244343_FF | 3 | 111081862 | 111085861 | 111240344 | 111244343 |
| 3_111054275_111073125_111238151_111244343_FF | 3 | 111069126 | 111073125 | 111240344 | 111244343 |
| 5_7602410_7603529_7787275_7792598_FF | 5 | 7599530 | 7603529 | 7788599 | 7792598 |
| 13_11748012_111752622_111822569_111834523_RR | 13 | 111748013 | 111752012 | 111822570 | 111826569 |
| 3_123010454_123013518_123033778_123037100_RF | 3 | 123010455 | 123014454 | 123033101 | 123037100 |
| 5_7520707_7525339_7602410_7603529_RF | 5 | 7520708 | 7524707 | 7599530 | 7603529 |
| 1_243655019_243656128_243954381_243957141_RR | 1 | 243655020 | 243659019 | 243954382 | 243958381 |
| 21_46345789_46346831_46359648_46362975_FR | 21 | 46342832 | 46346831 | 46359649 | 46363648 |
| 6_111988059_111992304_112042041_112045568_FR | 6 | 111988305 | 111992304 | 112042042 | 112046041 |
| 5_7425481_7432673_7602410_7603529_RF | 5 | 7425482 | 7429481 | 7599530 | 7603529 |
| 1_243655019_243656128_243760927_243763803_RF | 1 | 243655020 | 243659019 | 243759804 | 243763803 |
| 11_923549_925733_976127_979142_RR | 11 | 923550 | 927549 | 976128 | 980127 |

TABLE 24a

Relapsing-Remitting Multiple Sclerosis (MSRR) probes - EpiSwitch ™ markers to stratify MSRR vs. healthy controls

| Probe | GeneLocus | Probe_Count_Total | Probe_Count_Sig | HyperG_Stats | FDR_HyperG | Percent_Sig | reps. | Avg_CV | logFC |
|---|---|---|---|---|---|---|---|---|---|
| 1_171811918_171813464_172083100_172087823_RF | DNM3 | 902 | 68 | 0.08859 | 1 | 7.54 | 4 | 3.75 | −0.549300177 |
| 1_171887726_171889817_172083100_172087823_RF | DNM3 | 902 | 68 | 0.08859 | 1 | 7.54 | 4 | 2.093 | −0.537146861 |
| 11_36588999_36590845_36605543_36609927_FR | RAG2; RAG1 | 10 | 3 | 0.022581 | 0.695488 | 30 | 4 | 3.56 | −0.537123703 |
| 11_36583119_36588432_36605543_36609927_RR | RAG2; RAG1 | 10 | 3 | 0.022581 | 0.695488 | 30 | 4 | 3.345 | −0.536970673 |
| 1_172083100_172087823_172151185_172154127_FF | DNM3 | 902 | 68 | 0.08859 | 1 | 7.54 | 4 | 2.695 | −0.52875345 |
| 1_172061602_172067357_172083100_172087823_RF | DNM3 | 902 | 68 | 0.08859 | 1 | 7.54 | 4 | 4.369 | −0.516042591 |
| 11_36531355_36534043_36605543_36609927_FR | RAG1 | 44 | 6 | 0.060775 | 1 | 13.64 | 4 | 4.776 | −0.514259356 |
| 11_36524913_36530925_36605543_36609927_FR | RAG1 | 44 | 6 | 0.060775 | 1 | 13.64 | 4 | 4.444 | −0.512456898 |
| X_19644496_19650796_19753406_19760963_RR | SH3KBP1 | 168 | 22 | 0.001083 | 0.136367 | 13.1 | 4 | 4.453 | −0.497267732 |
| X_19644496_19650796_19801817_19808062_RR | SH3KBP1 | 168 | 22 | 0.001083 | 0.136367 | 13.1 | 4 | 3.856 | −0.490178577 |
| 1_171936106_171939290_172083100_172087823_RF | DNM3 | 902 | 68 | 0.08859 | 1 | 7.54 | 4 | 4.24 | −0.489770025 |
| 1_172083100_172087823_172212232_172223166_FF | DNM3 | 902 | 68 | 0.08859 | 1 | 7.54 | 4 | 3.339 | −0.479550197 |
| 11_923549_925733_976127_979142_FR | AP2A2 | 16 | 3 | 0.079231 | 1 | 18.75 | 4 | 3.706 | −0.466762178 |
| 6_150252084_150255951_150278503_150282998_FF | ULBP1 | 13 | 4 | 0.007581 | 0.295659 | 30.77 | 4 | 3.854 | −0.465746785 |
| X_19644496_19650796_19796774_19799668_RR | SH3KBP1 | 168 | 22 | 0.001083 | 0.136367 | 13.1 | 4 | 3.798 | −0.457016079 |
| 11_36489037_36490716_36605543_36609927_FR | RAG1 | 44 | 6 | 0.060775 | 1 | 13.64 | 4 | 4.796 | −0.440356879 |
| 12_53578817_53581303_53603928_53605952_RF | ITGB7 | 1 | 1 | 0.064304 | 1 | 100 | 4 | 3.431 | −0.435531598 |
| 11_36531355_36534043_36605543_36609927_RR | RAG1 | 44 | 6 | 0.060775 | 1 | 13.64 | 4 | 3.185 | −0.42982656 |

TABLE 24a-continued

Relapsing-Remitting Multiple Sclerosis (MSRR) probes - EpiSwitch ™ markers to stratify MSRR vs. healthy controls

| Probe | GeneLocus | Probe_Count_Total | Probe_Count_Sig | HyperG_Stats | FDR_HyperG | Percent_Sig | reps. | Avg_CV | logFC |
|---|---|---|---|---|---|---|---|---|---|
| 10_6530169_6531558_6639985_6645189_FR | PRKCQ | 125 | 22 | 1.30E-05 | 0.003989 | 17.6 | 4 | 3.137 | -0.426811638 |
| 10_6530169_6531558_6632086_6637212_FR | PRKCQ | 125 | 22 | 1.30E-05 | 0.003989 | 17.6 | 4 | 2.911 | -0.424093073 |
| 11_923549_925733_976127_979142_RR | AP2A2 | 16 | 3 | 0.079231 | 1 | 18.75 | 4 | 3.228 | -0.41421442 |
| 20_43244575_43248985_43318009_43319077_FR | ADA | 7 | 2 | 0.069859 | 1 | 28.57 | 3 | 3.441 | -0.413256671 |
| 10_6510600_6515355_6530169_6531558_RF | PRKCQ | 125 | 22 | 1.30E-05 | 0.003989 | 17.6 | 4 | 4.194 | -0.400405262 |
| 6_112042041_112045568_112135380_112149905_RF | FYN | 278 | 29 | 0.006553 | 0.295659 | 10.43 | 4 | 3.36 | -0.399738531 |
| 6_112042041_112045568_112071383_112076102_RF | FYN | 278 | 29 | 0.006553 | 0.295659 | 10.43 | 4 | 2.355 | -0.394579607 |
| 19_40813634_40815315_40897327_40898354_RF | PLD3 | 5 | 2 | 0.036239 | 0.93013 | 40 | 4 | 6.096 | -0.389654595 |
| 6_111988059_111992304_112042041_112045568_FR | FYN | 278 | 29 | 0.006553 | 0.295659 | 10.43 | 4 | 3.654 | -0.389003289 |
| 11_36583119_36588432_36600417_36605543_RR | RAG2; RAG1 | 10 | 3 | 0.022581 | 0.695488 | 30 | 4 | 3.602 | -0.385757062 |
| 10_6474855_6481197_6632086_6637212_RR | PRKCQ | 125 | 22 | 1.30E-05 | 0.003989 | 17.6 | 4 | 3.662 | -0.385687884 |
| 1_171773003_171774629_171883013_171884075_FF | DNM3 | 902 | 68 | 0.08859 | 1 | 7.54 | 4 | 3.231 | -0.378954576 |
| 6_150252084_150255951_150307780_150309507_FF | ULBP1 | 13 | 4 | 0.007581 | 0.295659 | 30.77 | 4 | 4.266 | -0.376981869 |
| 10_6530169_6531558_6601540_6605133_FF | PRKCQ | 125 | 22 | 1.30E-05 | 0.003989 | 17.6 | 4 | 4.493 | -0.37476066 |
| 5_67483678_67490216_67602566_67610345_RF | PIK3R1 | 14 | 5 | 0.001328 | 0.136367 | 35.71 | 4 | 3.969 | -0.374337026 |
| 1_171813464_171818896_171883013_171884075_FF | DNM3 | 902 | 68 | 0.08859 | 1 | 7.54 | 4 | 3.041 | -0.373722216 |
| 1_172053648_172060321_172083100_172087823_RR | DNM3 | 902 | 68 | 0.08859 | 1 | 7.54 | 4 | 4.067 | -0.372802641 |
| 11_36507808_36510397_36605543_36609927_RR | RAG1 | 44 | 6 | 0.060775 | 1 | 13.64 | 4 | 4.148 | -0.370291136 |
| 6_112042041_112045568_112058283_112061400_RF | FYN | 278 | 29 | 0.006553 | 0.295659 | 10.43 | 4 | 3.078 | -0.368727065 |
| 6_112042041_112045568_112109707_112111662_RF | FYN | 278 | 29 | 0.006553 | 0.295659 | 10.43 | 4 | 4.037 | -0.367010214 |
| 19_10341612_10343024_10406169_10407761_FF | ICAM1 | 6 | 2 | 0.052074 | 1 | 33.33 | 4 | 4.066 | -0.364917001 |
| 6_112008166_112013438_112042041_112045568_RR | FYN | 278 | 29 | 0.006553 | 0.295659 | 10.43 | 4 | 4.186 | -0.361100403 |
| 10_6530159_6531558_6567582_6570484_FR | PRKCQ | 125 | 22 | 1.30E-05 | 0.003989 | 17.6 | 4 | 3.089 | -0.360875261 |
| X_19737340_19741050_19801817_19808062_RF | SH3KBP1 | 168 | 22 | 0.001083 | 0.136367 | 13.1 | 4 | 4.018 | -0.35429493 |
| 10_6474855_6481197_6663527_6669234_RR | PRKCQ | 125 | 22 | 1.30E-05 | 0.003989 | 17.6 | 4 | 3.669 | -0.346972125 |
| 10_6474855_6481197_6639985_6645189_RR | PRKCQ | 125 | 22 | 1.30E-05 | 0.003989 | 17.6 | 4 | 3.325 | -0.346904516 |
| 6_112042041_112045568_112210969_112216626_RF | FYN | 278 | 29 | 0.006553 | 0.295659 | 10.43 | 4 | 4.094 | -0.346182416 |
| X_19737340_19741050_19778202_19779729_RF | SH3KBP1 | 168 | 22 | 0.001083 | 0.136367 | 13.1 | 4 | 4.731 | -0.346178617 |
| 1_171770367_171771990_171883013_171884075_FF | DNM3 | 902 | 68 | 0.08859 | 1 | 7.54 | 4 | 3.37 | -0.345712766 |
| 5_7402050_7407728_7602410_7603529_RF | ADCY2 | 306 | 33 | 0.002281 | 0.175665 | 10.78 | 4 | 3.192 | -0.345212375 |
| 6_111982743_111987540_112042041_112045568_RR | FYN | 278 | 29 | 0.006553 | 0.295659 | 10.43 | 4 | 3.27 | -0.343509788 |
| 10_6530169_6531558_6639985_6645189_FF | PRKCQ | 125 | 22 | 1.30E-05 | 0.003989 | 17.6 | 4 | 4.012 | -0.341094327 |

TABLE 24b

Relapsing-Remitting Multiple Sclerosis (MSRR_probes - EpiSwitch ™ markers to stratify MSRR vs. healthy controls

| Probe | AveExpr | t | P.Value | adj.P.Val | B | FC | FC_1 | LS | Loop detected |
|---|---|---|---|---|---|---|---|---|---|
| 1_171811918_171813464_172083100_172087823_RF | -0.5493 | -4.878904 | 2.52E-05 | 0.016541 | 2.522812 | 0.683352 | -1.463376 | -1 | MSRR |
| 1_171887726_171889817_172083100_17208782.3_RF | -0.537147 | -4.776621 | 3.41E-05 | 0.016541 | 2.254684 | 0.689132 | -1.4511 | -1 | MSRR |
| 11_36588999_36590845_36605543_36609927_FR | -0.537124 | -4.759332 | 3.58E-05 | 0.016541 | 2.209419 | 0.689143 | -1.451077 | -1 | MSRR |
| 11_36583119_36588432_36605543_36609927_RR | -0.536971 | -4.754908 | 3.63E-05 | 0.016541 | 2.197839 | 0.689217 | -1.450923 | -1 | MSRR |
| 1_172083100_172087823_172151185_172154127_FF | -0.528753 | -4.671798 | 4.64E-05 | 0.020085 | 1.980532 | 0.693153 | -1.442682 | -1 | MSRR |

TABLE 24b-continued

Relapsing-Remitting Multiple Sclerosis (MSRR_probes - EpiSwitch ™ markers to stratify MSRR vs. healthy controls

| Probe | AveExpr | t | P.Value | adj.P.Val | B | FC | FC_1 | LS | Loop detected |
|---|---|---|---|---|---|---|---|---|---|
| 1_172061602_172067357_172083100_172087823_RF | −0.516043 | −4.577701 | 6.12E−05 | 0.023334 | 1.735112 | 0.699287 | −1.430027 | −1 | MSRR |
| 11_36531355_36534043_36605543_36609927_FR | −0.514259 | −4.546753 | 6.71E−05 | 0.023334 | 1.654558 | 0.700152 | −1.428261 | −1 | MSRR |
| 11_36524913_36530925_36605543_36609927_FR | −0.512457 | −4.551028 | 6.62E−05 | 0.023334 | 1.66568 | 0.701028 | −1.426477 | −1 | MSRR |
| X_19644496_19650796_19753406_19760963_RR | −0.497268 | −3.909962 | 0.000424 | 0.089384 | 0.02369 | 0.708447 | −1.411538 | −1 | MSRR |
| X_19644496_19650796_19801817_19808062_RR | −0.490179 | −3.837951 | 0.000519 | 0.098494 | −0.156436 | 0.711937 | −1.404619 | −1 | MSRR |
| 1_171936106_171939290_172083100_172087823_RF | −0.48977 | −4.328915 | 0.000127 | 0.040649 | 1.090307 | 0.712139 | −1.404221 | −1 | MSRR |
| 1_172083100_172087823_172212232_172223166_FF | −0.47955 | −4.25668 | 0.000156 | 0.048352 | 0.904453 | 0.717201 | −1.394309 | −1 | MSRR |
| 11_923549_925733_976127_979142_FR | −0.466762 | −4.078247 | 0.000262 | 0.068397 | 0.448614 | 0.723587 | −1.382004 | −1 | MSRR |
| 6_150252084_150255951_150278503_150282998_FF | −0.465747 | −4.05913 | 0.000277 | 0.068397 | 0.400082 | 0.724096 | −1.381032 | −1 | MSRR |
| X_19644496_19650796_19796774_19799668_RR | −0.457016 | −3.577031 | 0.001077 | 0.150238 | −0.799075 | 0.728491 | −1.3727 | −1 | MSRR |
| 11_36489037_36490716_36605543_36609927_FR | −0.440357 | −3.841588 | 0.000514 | 0.098494 | −0.147364 | 0.736952 | −1.35694 | −1 | MSRR |
| 12_53578817_53581303_53603928_53605952_RF | −0.435532 | −3.842051 | 0.000513 | 0.098494 | −0.146209 | 0.739421 | −1.352409 | −1 | MSRR |
| 11_36531355_36534043_36605543_36609927_RR | −0.429827 | −3.806914 | 0.000567 | 0.100546 | −0.233725 | 0.742351 | −1.347072 | −1 | MSRR |
| 10_6530169_6531558_6639985_6645189_FR | −0.426812 | −3.569871 | 0.001099 | 0.150238 | −0.816466 | 0.743904 | −1.344259 | −1 | MSRR |
| 10_6530169_6531558_6632086_6637212_FR | −0.424093 | −3.56223 | 0.001122 | 0.150238 | −0.83501 | 0.745307 | −1.341729 | −1 | MSRR |
| 11_923549_925733_976127_979142_RR | −0.414214 | −3.673148 | 0.000825 | 0.12543 | −0.564294 | 0.750428 | −1.332573 | −1 | MSRR |
| 20_43244575_43248985_43318009_43319077_FR | −0.413257 | −3.675048 | 0.00082 | 0.12543 | −0.559628 | 0.750926 | −1.331689 | −1 | MSRR |
| 10_6510600_6515355_6530169_6531558_RF | −0.400405 | −3.346683 | 0.002021 | 0.205187 | −1.351146 | 0.757645 | −1.319879 | −1 | MSRR |
| 6_112042041_112045568_112135380_112149905_RF | −0.399739 | −3.554581 | 0.001146 | 0.150238 | −0.853557 | 0.757996 | −1.319269 | −1 | MSRR |
| 6_112042041_112045568_112071383_112076102_RF | −0.39458 | −3.353416 | 0.001984 | 0.205187 | −1.33524 | 0.760711 | −1.31456 | −1 | MSRR |
| 19_40813634_40815315_40897327_40898354_RF | −0.389655 | −3.381122 | 0.001841 | 0.205187 | −1.269629 | 0.763312 | −1.31008 | −1 | MSRR |
| 6_111988059_111992304_112042041_11204556_FR | −0.389003 | −3.314793 | 0.002202 | 0.205187 | −1.42629 | 0.763657 | −1.309488 | −1 | MSRR |
| 11_36583119_36588432_36600417_36605543_RR | −0.385757 | −3.148846 | 0.003425 | 0.236519 | −1.81172 | 0.765377 | −1.306545 | −1 | MSRR |
| 10_6474855_6481197_6632086_6637212_RR | −0.385688 | −3.191411 | 0.003061 | 0.228339 | −1.713785 | 0.765414 | −1.306483 | −1 | MSRR |
| 1_171773003_171774629_171883013_171884075_FF | −0.378955 | −3.245663 | 0.00265 | 0.212785 | −1.588019 | 0.768995 | −1.300399 | −1 | MSRR |
| 6_150252084_150255951_150307780_150309507_FF | −0.376982 | −3.212931 | 0.002891 | 0.221395 | −1.66402 | 0.770047 | −1.298622 | −1 | MSRR |
| 10_6530169_6531558_6601540_6605133_FF | −0.374761 | −3.177187 | 0.003178 | 0.229196 | −1.746585 | 0.771233 | −1.296624 | −1 | MSRR |
| 5_67483678_67490216_67602566_67610345_RF | −0.374337 | −3.314195 | 0.002206 | 0.205187 | −1.427696 | 0.77146 | −1.296244 | −1 | MSRR |
| 1_171813464_171818896_171883013_171884075_FF | −0.373722 | −3.180371 | 0.003152 | 0.229184 | −1.739249 | 0.771789 | −1.295691 | −1 | MSRR |
| 1_172053648_172060321_172083100_172087823_RR | −0.372803 | −3.314532 | 0.002204 | 0.205187 | −1.426903 | 0.772281 | −1.294866 | −1 | MSRR |
| 11_36507808_36510397_36605543_36609927_RR | −0.370291 | −3.240667 | 0.002686 | 0.212785 | −1.599644 | 0.773626 | −1.292614 | −1 | MSRR |
| 6_112042041_112045568_112058283_112061400_RF | −0.368727 | −3.124672 | 0.00365 | 0.240436 | −1.867045 | 0.774466 | −1.291213 | −1 | MSRR |
| 6_112042041_112045568_112109707_112111662_RF | −0.36701 | −3.143782 | 0.003471 | 0.236519 | −1.823328 | 0.775388 | −1.289677 | −1 | MSRR |
| 19_10341612_10343024_10406169_10407761_FF | −0.364917 | −3.24435 | 0.002659 | 0.212785 | −1.591073 | 0.776514 | −1.287808 | −1 | MSRR |
| 6_112008166_112013438_11204041_112045568_RR | −0.3611 | −3.089639 | 0.004001 | 0.240436 | −1.946832 | 0.778571 | −1.284405 | −1 | MSRR |
| 10_6530169_6531558_6567582_6570484_FR | −0.360875 | −2.991279 | 0.005165 | 0.241157 | −2.168299 | 0.778692 | −1.284205 | −1 | MSRR |
| X_19737340_19741050_19801817_19808062_RF | −0.354295 | −3.129581 | 0.003604 | 0.240436 | −1.855828 | 0.782252 | −1.278361 | −1 | MSRR |
| 10_6474855_6481197_6663527_6669234_RR | −0.346972 | −2.851366 | 0.007382 | 0.259517 | −2.476483 | 0.786232 | −1.271888 | −1 | MSRR |
| 10_6474855_6481197_6639985_6645189_RR | −0.346905 | −2.865775 | 0.007118 | 0.258492 | −2.445132 | 0.786269 | −1.271829 | −1 | MSRR |
| 6_112042041_112045568_112210969_112716676_RF | −0.346182 | −2.979451 | 0.005325 | 0.241616 | −2.19467 | 0.786663 | −1.271192 | −1 | MSRR |
| X_19737340_19741050_19778202_19779729_RF | −0.346179 | −3.021513 | 0.004777 | 0.240831 | −2.100633 | 0.786665 | −1.271189 | −1 | MSRR |

TABLE 24b-continued

Relapsing-Remitting Multiple Sclerosis (MSRR_probes - EpiSwitch ™ markers to stratify MSRR vs. healthy controls

| Probe | AveExpr | t | P.Value | adj.P.Val | B | FC | FC_1 | LS | Loop detected |
|---|---|---|---|---|---|---|---|---|---|
| 1_171770367_171771990_171883013_171884075_FF | −0.345713 | −2.99466 | 0.005121 | 0.240831 | −2.160749 | 0.786919 | −1.270779 | −1 | MSRR |
| 5_7402050_7407728_7602410_7603529_RF | −0.345212 | −3.028269 | 0.004694 | 0.240831 | −2.085461 | 0.787192 | −1.270338 | −1 | MSRR |
| 6_111982743_111987540_112042041_112045568_RR | −0.34351 | −3.036106 | 0.0046 | 0.240831 | −2.06784 | 0.788122 | −1.26884 | −1 | MSRR |
| 10_6530169_6531558_6639985_6645189_FF | −0.341094 | −2.843592 | 0.007528 | 0.259517 | −2.49336 | 0.789442 | −1.265717 | −1 | MSRR |

TABLE 24c

Relapsing-Remitting Multiple Sclerosis (MSRR) probes - EpiSwitch ™ markers to stratify MSRR vs. healthy controls

| Probe | Probe sequence 60 mer |
|---|---|
| 1_171811918_171813464_172083100_172087823_RF | TCACCTCTGTCACCCACCCGTTCCACTCTCGAATTAGGAATCAGCATTTCTTCCACTGAG (SEQ ID NO: 407) |
| 1_171887726_171889817_172083100_172087823_RF | TCACCTCTGTCACCCACCCGTTCCACTCTCGAAATAGTAAAATTTGATTATCAAAATTTT (SEQ ID NO: 408) |
| 11_36588999_36590845_36605543_36609927_FR | CCTGTAGCTCTGATGTCAGATGGCAATGTCGATCCACACCACACCAGCAGTGGGGCACAA (SEQ ID NO: 409) |
| 11_36583119_36588432_36605543_36609927_RR | CCACCTCATAGGGGAGGGCTTTACTCAGTCGATCCACACCACACCAGCAGTGGGGCACAA (SEQ ID NO: 410) |
| 1_172083100_172087823_172151185_172154127_FF | TCACCTCTGTCACCCACCCGTTCCACTCTCGATGCTCTCTTAGTGTTCCAATTCTCAGCT (SEQ ID NO: 411) |
| 1_172061602_172067357_172083100_172087823_RF | TCACCTCTGTCACCCACCCGTTCCACTCTCGATAAAGCACTTAGAACATGGCATATACTC (SEQ ID NO: 412) |
| 11_36531355_36534043_36605543_36609927_FR | AGTTCTTTCTTGAATTCTTTCCTGATACTCGATCCACACCACACCAGCAGTGGGGCACAA (SEQ ID NO: 413) |
| 11_36524913_36530925_36605543_36609927_FR | TTATCAACCCGGCGTCTGGAACAATCGCTCGATCCACACCACACCAGCAGTGGGGCACAA (SEQ ID NO: 414) |
| X_19644496_19650796_19753406_19760963_RR | TTCATTCATTCATTCATTCATTCATACATCGATTCTCTATTTCATTTATTTCCACTGTAA (SEQ ID NO: 415) |
| X_19644496_19650796_19801817_19808062_RR | TTCATTCATTCATTCATTCATTCATACATCGAAATGTCTATTCATATTCATTAACTCAAG (SEQ ID NO: 416) |
| 1_171936106_171939290_172083100_172087823_RF | TCACCTCTGTCACCCACCCGTTCCACTCTCGAATAGCTCCTATTGTTATGGAGTGTAGCA (SEQ ID NO: 417) |
| 1_172083100_172087823_172212232_172223166_FF | TCACCTCTGTCACCCACCCGTTCCACTCTCGAGGCTGCAGTGAATCATAATCATAGCACT (SEQ ID NO: 418) |
| 11_923549_925733_976127_979142_FR | GCCTGCAGGGGCGCCCCGCGCCTGCCTCGACCACACATCCACATGGACGCATGGCAGG (SEQ ID NO: 419) |
| 6_150252084_150255951_150278503_150282998_FF | GGGTGGGATGGGACAGACACAAGAACTCTCGAGGTTGTAGACCTCATGGCTGGCACAAGT (SEQ ID NO: 420) |
| X_19644496_19650796_19796774_19799668_RR | TTCATTCATTCATTCATTCATTCATACATCGAAAGGCCAGTAGGTGTGATCTGAGGAAGG (SEQ ID NO: 421) |
| 11_36489037_36490716_36605543_36609927_FR | AGTGTTGGTGAGATATTGTCTCTCAGTTTCGATCCACACCACACCAGCAGTGGGGCACAA (SEQ ID NO: 422) |
| 12_53578817_53581303_53603928_53605952_RF | CCAACCCCACTCCCCAAGTACCCCACTCTCGAGTCAGGTACAGCGCTTGAGTCCATTGTG (SEQ ID NO: 423) |
| 11_36531355_36534043_36605543_36609927_RR | CCGCCCCTGTCCTCTCGCTTCCCGCTGGTCGATCCACACCACACCAGCAGTGGGGCACAA (SEQ ID NO: 424) |
| 10_6530169_6531558_6639985_6645189_FR | AGAGAGCTGGAGAAGAGGGCGAGAAGAGTCGAAAGAATTGTGAGTAGCAGTTGTGTGGTT (SEQ ID NO: 425) |

TABLE 24c-continued

Relapsing-Remitting Multiple Sclerosis (MSRR) probes - EpiSwitch ™ markers to stratify MSRR vs. healthy controls

| Probe | Probe sequence 60 mer |
|---|---|
| 10_6530169_6531558_6632086_6637212_FR | AGAGAGCTGGAGAAGAGGGCGAGAAGAGTCGATAAAGGAAAAAGTTCAGTAAAGTGTGAA (SEQ ID NO: 426) |
| 11_923549_925733_976127_979142_RR | AGTGGTACAATCATGAATCACTACAGCCTCGACCACACATCCACATGGACGCATGGCAGG (SEQ ID NO: 427) |
| 20_43244575_43248985_43318009_43319077_FR | TGGCATCCCATAGGCTTTATAGAGCAGGTCGACCTCCTGACCTCGTGATCCACCTGCCTC (SEQ ID NO: 428) |
| 10_6510600_6515355_6530169_6531558_RF | AGAGAGCTGGAGAAGAGGGCGAGAAGAGTCGAGGTATCTTTTTTCTCCGAAGGCTAGTAA (SEQ ID NO: 429) |
| 6_112042041_112045568_112135380_112149905_RF | ATCCACTTACATGAGGTACCTAGAGGAGTCGAGTTGTTGCCACCCCACCCTCCTCAAACC (SEQ ID NO: 430) |
| 6_112042041_112045568_112071383_112076102_RF | GTTAACAGTAATACGATGTTAAAAGGACTCGAGTTGTTGCCACCCCACCCTCCTCAAACC (SEQ ID NO: 431) |
| 19_40813634_40815315_40897327_40898354_RF | TGGGGAAGAGGAGCAAGTGTCAGGAAGATCGACTCATTTAATCCCCAAAACCATTCCATG (SEQ ID NO: 432) |
| 6_111988059_111992304_112042041_112045568_FR | GGAACTGCATCCATACTTGTTACACATCTCGAGTTGTTGCCACCCCACCCTCCTCAAACC (SEQ ID NO: 433) |
| 11_36583119_36588432_36600417_36605543_RR | CCACCTCATAGGGGAGGGCTTTACTCAGTCGAGCATTTGTGTGTGTATGTGTGAAGTATA (SEQ ID NO: 434) |
| 10_6474855_6481197_6632086_6637212_RR | TTTAAAGATGAGGGGAGGGAAGCAGGAGTCGATAAAGGAAAAAGTTCAGTAAAGTGTGAA (SEQ ID NO: 435) |
| 1_171773003_171774629_171883013_171884075_FF | TGTAATCTGTTTTGCTATCCAATCAAGATCGAGGTCCCCCCACCCCCACATGTCTCTACC (SEQ ID NO: 436) |
| 6_150252084_150255951_150307780_150309507_FF | GGGTGGGATGGGACAGACACAAGAACTCTCGAACACTCAGCTATCAGTTTTGTTGAGTTC (SEQ ID NO: 437) |
| 10_6530169_6531558_6601540_6605133_FF | AGAGAGCTGGAGAAGAGGGCGAGAAGAGTCGACTGAATATCTTCACTCTTGAGCCAAAGT (SEQ ID NO: 438) |
| 5_67483678_67490216_67602566_67610345_RF | CACTGCACCACCCTGTACATAAGTCCCCTCGACTTCAGCTCCAGTGAAGAAGACACTACT (SEQ ID NO: 439) |
| 1_171813464_171818896_171883013_171884075_FF | AAGCAGTTTTTATCATTTCATTAATCCTTCGAGGTCCCCCCACCCCCACATGTCTCTACC (SEQ ID NO: 440) |
| 1_172053648_172060321_172083100_172087823_RR | CTCCACGTCACCCCATGTCAATTCCAAGTCGATGCCAGACACTCTTCTGGGGGTGGGTG (SEQ ID NO: 441) |
| 11_36507808_36510397_36605543_36609927_RR | GGCTGGCGGATTACTTGAAGCCAGGAGTTCGATCCACACCACACCAGCAGTGGGGCACAA (SEQ ID NO: 442) |
| 6_112042041_112045568_112058283_112061400_RF | TAAATACAGATGAAACCAACTAATAGACTCGAGTTGTTGCCACCCCACCCTCCTCAAACC (SEQ ID NO: 443) |
| 6_112042041_112045568_112109707_112111662_RF | AAGTCCTAAGAACACTGAAAATCTCAGATCGAGTTGTTGCCACCCCACCCTCCTCAAACC (SEQ ID NO: 444) |
| 19_10341612_10343024_10406169_10407761_FF | TGCGGAAATGATGGACACTACACCTTCATCGACCTCGTGATCTGGCCGCCTCGGCCTTCC (SEQ ID NO: 445) |
| 6_112008166_112013438_112042041_112045568_RR | CTCAGGAAGAAGTGGATCCCTGTTTCTTTCGAGTTGTTGCCACCCCACCCTCCTCAAACC (SEQ ID NO: 446) |
| 10_6530169_6531558_6567582_6570484_FR | AGAGAGCTGGAGAAGAGGGCGAGAAGAGTCGAAGATGTCAAAAGGAAAAATGGAAATAGT (SEQ ID NO: 447) |
| X_19737340_19741050_19801817_19808062_RF | TTTGGTTTGTTCCCTTTTTAAGACTCTCTCGACTCACTCACATCTGCCTCATGATGGTTA (SEQ ID NO: 448) |
| 10_6474855_6481197_6663527_6669234_RR | TTTAAAGATGAGGGGAGGGAAGCAGGAGTCGAAACCAGAAGACCCAATATAATATCTAGT (SEQ ID NO: 449) |
| 10_6474855_6481197_6639985_6645189_RR | TTTAAAGATGAGGGGAGGGAAGCAGGAGTCGAAAGAATTGTGAGTAGCAGTTGTGTGGTT (SEQ ID NO: 450) |

TABLE 24c-continued

Relapsing-Remitting Multiple Sclerosis (MSRR) probes - EpiSwitch ™ markers to stratify MSRR vs. healthy controls

| Probe | Probe sequence 60 mer |
|---|---|
| 6_112042041_112045568_112210969_112216626_RF | ATCTAAACACAGTCCATGCTAAAAAGCTTCGAGTTGTTGCCACCCCACCCTCCTCAAA CC (SEQ ID NO: 451) |
| X_19737340_19741050_19778202_19779729_RF | CATGATAGTTAAGAGATCATATCTAGAATCGACTCACTCACATCTGCCTCATGATGGT TA (SEQ ID NO: 452) |
| 1_171770367_171771990_171883013_171884075_FF | CTTCACCAGACATTTTAAATAAAATCTATCGAGGTCCCCCCACCCCCACATGTCTCTA CC (SEQ ID NO: 453) |
| 5_7402050_7407728_7602410_7603529_RF | CACTGCCCCACCTCTTACTGGCATCTCCTCGAGACAATTCATTGAACCTGACTCATTT CT (SEQ ID NO: 454) |
| 6_111982743_111987540_112042041_112045568_RR | CCAAATCCGAACCTCCTCTGTGAAGCATTCGAGTTGTTGCCACCCCACCCTCCTCAAA CC (SEQ ID NO: 455) |
| 10_6530169_6531558_6639985_6645189_FF | AGAGAGCTGGAGAAGAGGGCGAGAAGAGTCGAATTGTGCTCCATTGTTACCTTTTTGT GT (SEQ ID NO: 456) |

TABLE 24d

Relapsing-Remitting Multiple Sclerosis (MSRR) probes - EpiSwitch ™ markers to stratify MSRR vs. healthy controls

| Probe | Probe Location | | | | |
|---|---|---|---|---|---|
| | Chr | Start1 | End1 | Start2 | End2 |
| 1_171811918_171813464_172083100_172087823_RF | 1 | 171811919 | 171811948 | 172087794 | 172087823 |
| 1_171887726_171889817_172083100_172087823_RF | 1 | 171887727 | 171887756 | 172087794 | 172087823 |
| 11_36588999_36590845_36605543_36609927_FR | 11 | 36588999 | 36590845 | 36605544 | 36605573 |
| 11_36583119_36588432_36605543_36609927_RR | 11 | 36583120 | 36583149 | 36605544 | 36605573 |
| 1_172083100_172087823_172151185_172154127_FF | 1 | 172087794 | 172087823 | 172154098 | 172154127 |
| 1_172061602_172067357_172083100_172087823_RF | 1 | 172061603 | 172061632 | 172087794 | 172087823 |
| 11_36531355_36534043_36605543_36609927_RR | 11 | 36534014 | 36534043 | 36605544 | 36605573 |
| 11_36524913_36530925_36605543_36609927_FR | 11 | 36530896 | 36530925 | 36605544 | 36605573 |
| X_19644496_19650796_19753406_19760963_RR | X | 19644497 | 19644526 | 19753407 | 19753436 |
| X_19644496_19650796_19801817_19808062_RR | X | 19644497 | 19644526 | 19801818 | 19801847 |
| 1_171936106_171939290_172083100_172087823_RF | 1 | 171936107 | 171936136 | 172087794 | 172087823 |
| 1_172083100_172087823_172212232_172223166_FF | 1 | 172087794 | 172087823 | 172223137 | 172223166 |
| 11_923549_925733_976127_979142_FR | 11 | 925704 | 925733 | 976128 | 976157 |
| 6_150252084_150255951_150278503_150282998_FF | 6 | 150255922 | 150255951 | 150282969 | 150282998 |
| X_19644496_19650796_19796774_39799668_RR | X | 19644497 | 19644526 | 19796775 | 19796804 |
| 11_36489037_36490716_36605543_36609927_FR | 11 | 36490687 | 36490716 | 36605544 | 36605573 |
| 12_53578817_53581303_53603928_53605952_RF | 12 | 53578818 | 53578847 | 53605923 | 53605952 |
| 11_36531355_36534043_36605543_36609927_RR | 11 | 36531356 | 36531385 | 36605544 | 36605573 |
| 10_6530169_6531558_6639985_6645189_FR | 10 | 6531529 | 6531558 | 6639986 | 6640015 |
| 10_6530169_6531558_6632086_6637212_FR | 10 | 6531529 | 6531558 | 6632087 | 6632116 |
| 11_923549_925733_976127_979142_RR | 11 | 923550 | 923579 | 976128 | 976157 |
| 20_43244575_43248985_43318009_4331907_FR | 20 | 43248956 | 43248985 | 43318010 | 43318039 |
| 10_6510600_6515355_6530169_6531558_RF | 10 | 6510601 | 6510630 | 6531529 | 6531558 |
| 6_112042041_112045568_112135380_112149905_RF | 6 | 112042042 | 112042071 | 112149876 | 112149905 |
| 6_112042041_112045568_112071383_112076102_RF | 6 | 112042042 | 112042071 | 112076073 | 112076102 |
| 19_40813634_40815315_40897327_40898354_RF | 19 | 40813635 | 40813664 | 40898325 | 40898354 |
| 6_111988059_111992304_112042041_112045568_FR | 6 | 111992275 | 111992304 | 112042042 | 112042071 |
| 11_36583119_36588432_36605543_36609927_RR | 11 | 36583120 | 36583149 | 36600418 | 36600447 |
| 10_6474855_6481197_6632086_6637212_RR | 10 | 6474856 | 6474885 | 6632087 | 6632116 |
| 1_171773003_171774629_171883013_171884075_FF | 1 | 171774600 | 171774629 | 171884046 | 171884075 |
| 6_150252084_150255951_150307780_150309507_FF | 6 | 150255922 | 150255951 | 150309478 | 150309507 |
| 10_6530169_6531558_6601540_6605133_FF | 10 | 6531529 | 6531558 | 6605104 | 6605133 |
| 5_67483678_67490216_67602566_67610345_RF | 5 | 67483679 | 67483708 | 67610316 | 67610345 |
| 1_171813464_171818896_171883013_171884075_FF | 1 | 171818867 | 171818896 | 171884046 | 171884075 |
| 1_172053648_172060321_172083100_172087823_RR | 1 | 172053649 | 172053678 | 172083101 | 172083130 |
| 11_36507808_36510397_36605543_36609927_FR | 11 | 36507809 | 36507838 | 36605544 | 36605573 |
| 6_112042041_112045568_112058283_112061400_RF | 6 | 112042042 | 112042071 | 112061371 | 112061400 |
| 6_112042041_112045568_112109707_112111662_RF | 6 | 112042042 | 112042071 | 112111633 | 112111662 |
| 19_10341612_10343024_10406169_10407761_FF | 19 | 10342995 | 10343024 | 10407732 | 10407761 |
| 6_112008166_112013438_112042041_112045568_RR | 6 | 112008167 | 112008196 | 112042042 | 112042071 |
| 10_6530169_6531558_6567582_6570484_FR | 10 | 6531529 | 6531558 | 6567583 | 6567612 |
| X_19737340_19741050_19801817_19808062_RF | X | 19737341 | 19737370 | 19808033 | 19808062 |
| 10_6474855_6481197_6663527_6669234_RR | 10 | 6474856 | 6474885 | 6663528 | 6663557 |
| 10_6474855_6481197_6639985_6645189_RR | 10 | 6474856 | 6474885 | 6639986 | 6640015 |
| 6_112042041_112045568_112210969_112216626_RF | 6 | 112042042 | 112042071 | 112216597 | 112216626 |

TABLE 24d-continued

Relapsing-Remitting Multiple Sclerosis (MSRR) probes - EpiSwitch ™ markers to stratify MSRR vs. healthy controls

| Probe | | | | | |
|---|---|---|---|---|---|
| X_19737340_19741050_19778202_19779729_RF | X | 19737341 | 19737370 | 19779700 | 19779729 |
| 1_171770367_171771990_171883013_171884075_FF | 1 | 171771961 | 171771990 | 171884046 | 171884075 |
| 5_7402050_7407728_7602410_7603529_RF | 5 | 7402051 | 7402080 | 7603500 | 7603529 |
| 6_111982743_111987540_112042041_112045568_RR | 6 | 111982744 | 111982773 | 112042042 | 112042071 |
| 10_6530169_6531558_6639985_6645189_FF | 10 | 6531529 | 6531558 | 6645160 | 6645189 |

| | | 4 kb Sequence Location | | | |
|---|---|---|---|---|---|
| Probe | Chr | Start1 | End1 | Start2 | End2 |
| 1_171811918_171813464_172083100_172087823_RF | 1 | 171811919 | 171815918 | 172083824 | 172087823 |
| 1_171887726_171889817_172083100_172087823_RF | 1 | 171887727 | 171891726 | 172083824 | 172087823 |
| 11_36588999_36590845_36605543_36609927_FR | 11 | 36586846 | 36590845 | 36605544 | 36609543 |
| 11_36583119_36588432_36605543_36609927_RR | 11 | 36583120 | 36587119 | 36605544 | 36609543 |
| 1_172083100_172087823_172151185_172154127_FF | 1 | 172083824 | 172087823 | 172150128 | 172154127 |
| 1_172061602_172067357_172083100_172087823_RF | 1 | 172061603 | 172065602 | 172083824 | 172087823 |
| 11_36531355_36534043_36605543_36609927_FR | 11 | 36530044 | 36534043 | 36605544 | 36609543 |
| 11_36524913_36530925_36605543_36609927_FR | 11 | 36526926 | 36530925 | 36605544 | 36609543 |
| X_19644496_19650796_19753406_19760963_RR | X | 19644497 | 19648496 | 19753407 | 19757406 |
| X_19644496_19650796_19801817_19808062_RR | X | 19644497 | 19648496 | 19801818 | 19805817 |
| 1_171936106_171939290_172083100_172087823_RF | 1 | 171936107 | 171940106 | 172083824 | 172087823 |
| 1_172083100_172087823_172212232_172223166_FF | 1 | 172083824 | 172087823 | 172219167 | 172223166 |
| 11_923549_925733_976127_979142_FR | 11 | 921734 | 925733 | 976128 | 980127 |
| 6_150252084_150255951_150278503_150282998_FF | 6 | 150251952 | 150255951 | 150278999 | 150282998 |
| X_19644496_19650796_19796774_39799668_RR | X | 19644497 | 19648496 | 19796775 | 19800774 |
| 11_36489037_36490716_36605543_36609927_FR | 11 | 36486717 | 36490716 | 36605544 | 36609543 |
| 12_53578817_53581303_53603928_53605952_RF | 12 | 53578818 | 53582817 | 53601953 | 53605952 |
| 11_36531355_36534043_36605543_36609927_RR | 11 | 36531356 | 36535355 | 36605544 | 36609543 |
| 10_6530169_6531558_6639985_6645189_FR | 10 | 6527559 | 6531558 | 6639986 | 6643985 |
| 10_6530169_6531558_6632086_6637212_FR | 10 | 6527559 | 6531558 | 6632087 | 6636086 |
| 11_923549_925733_976127_979142_RR | 11 | 923550 | 927549 | 976128 | 980127 |
| 20_43244575_43248985_43318009_4331907_FR | 20 | 43244986 | 43248985 | 43318010 | 43322009 |
| 10_6510600_6515355_6530169_6531558_RF | 10 | 6510601 | 6514600 | 6527559 | 6531558 |
| 6_112042041_112045568_112135380_112149905_RF | 6 | 112042042 | 112046041 | 112145906 | 112149905 |
| 6_112042041_112045568_112071383_112076102_RF | 6 | 112042042 | 112046041 | 112072103 | 112076102 |
| 19_40813634_40815315_40897327_40898354_RF | 19 | 40813635 | 40817634 | 40894355 | 40898354 |
| 6_111988059_111992304_112042041_112045568_FR | 6 | 111988305 | 111992304 | 112042042 | 112046041 |
| 11_36583119_36588432_36600417_36605543_RR | 11 | 36583120 | 36587119 | 36600418 | 36604417 |
| 10_6474855_6481197_6632086_6637212_RR | 10 | 6474856 | 6478855 | 6632087 | 6636086 |
| 1_171773003_171774629_171883013_171884075_FF | 1 | 171770630 | 171774629 | 171880076 | 171884075 |
| 6_150252084_150255951_150307780_150309507_FF | 6 | 150251952 | 150255951 | 150305508 | 150309507 |
| 10_6530169_6531558_6601540_6605133_FF | 10 | 6527559 | 6531558 | 6601134 | 6605133 |
| 5_67483678_67490216_67602566_67610345_RF | 5 | 67483679 | 67487678 | 67606346 | 67610345 |
| 1_171813464_171818896_171883013_171884075_FF | 1 | 171811918 | 171818896 | 171880076 | 171884075 |
| 1_172053648_172060321_172083100_172087823_RR | 1 | 172053649 | 172057648 | 172083101 | 172087100 |
| 11_36507808_36510397_36605543_36609927_RR | 11 | 36507809 | 36511808 | 36605544 | 36609543 |
| 6_112042041_112045568_112058283_112061400_RF | 6 | 112042042 | 112046041 | 112057401 | 112061400 |
| 6_112042041_112045568_112109707_112111662_RF | 6 | 112042042 | 112046041 | 112107663 | 112111662 |
| 19_10341612_10343024_10406169_10407761_FF | 19 | 10339025 | 10343024 | 10403762 | 10407761 |
| 6_112008166_112013438_112042041_112045568_RR | 6 | 112008167 | 112012166 | 112042042 | 112046041 |
| 10_6530169_6531558_6567582_6570484_FR | 10 | 6527559 | 6531558 | 6567583 | 6571582 |
| X_19737340_19741050_19801817_19808062_RF | X | 19737341 | 19741340 | 19804063 | 19808062 |
| 10_6474855_6481197_6663527_6669234_RR | 10 | 6474856 | 6478855 | 6663528 | 6667527 |
| 10_6474855_6481197_6639985_6645189_RR | 10 | 6474856 | 6478855 | 6639986 | 6643985 |
| 6_112042041_112045568_112210969_112216626_RF | 6 | 112042042 | 112046041 | 112212627 | 112216626 |
| X_19737340_19741050_19778202_19779729_RF | X | 19737341 | 19741340 | 19775730 | 19779729 |
| 1_171770367_171771990_171883013_171884075_FF | 1 | 171767991 | 171771990 | 171880076 | 171884075 |
| 5_7402050_7407728_7602410_7603529_RF | 5 | 7402051 | 7406050 | 7599530 | 7603529 |
| 6_111982743_111987540_112042041_112045568_RR | 6 | 111982744 | 111986743 | 112042042 | 112046041 |
| 10_6530169_6531558_6639985_6645189_FF | 10 | 6527559 | 6531558 | 6641190 | 6645189 |

TABLE 25a

Multiple Sclerosis (MS) probes - EpiSwitch ™ monitoring markers to stratify MS patients who are responders (B) to IFN-B treatment vs. non-responders (A)

| Probes | GeneLocus | Probe_Count_Total | Prob_Count_Sig | HyperG_Stats | FD_HyperG | Percent_Sig | logFC |
|---|---|---|---|---|---|---|---|
| | | A | | | | | |
| 14_24795078_24798515_24843066_24844509_RR | ADCY4 | 8 | 5 | 0.039348 | 0.471151 | 62.5 | −1.02593 |
| 14_24795078_24798615_24825321_24828950_RR | ADCY4 | 8 | 5 | 0.039348 | 0.471151 | 62.5 | −0.999378 |
| 11_923549_925733_976127_979142_FR | AP2A2 | 10 | 6 | 0.030192 | 0.478435 | 60 | −0.813494 |

TABLE 25a-continued

Multiple Sclerosis (MS) probes - EpiSwitch™ monitoring markers to stratify MS patients who are responders (B) to IFN-B treatment vs. non-responders (A)

| Probes | GeneLocus | Probe_Count_Total | Prob_Count_Sig | HyperG_Stats | FD_HyperG | Percent_Sig | logFC |
|---|---|---|---|---|---|---|---|
| 16_4065887_4067896_4209511_4211354_FR | ADCY9 | 60 | 30 | 0.000146 | 0.011194 | 50 | −0.771915 |
| 16_4065887_4067896_4145870_4149370_FF | ADCY9 | 60 | 30 | 0.000146 | 0.011194 | 50 | −0.76637 |
| 7_55087969_55089963_55116799_55120159_RR | EGFR | 196 | 77 | 0.00015 | 0.011194 | 39.29 | −0.756155 |
| 16_4065887_4067896_4169801_4171577_FF | ADCY9 | 60 | 30 | 0.000146 | 0.011194 | 50 | −0.752947 |
| 16_4004273_4006715_4065887_4067896_RF | ADCY9 | 60 | 30 | 0.000146 | 0.011194 | 50 | −0.73992 |
| 6_32135728_32138270_32149729_32154447_FF | AGER | 2 | 2 | 0.07449 | 0.599944 | 100 | −0.729578 |
| 16_4044767_4047085_4065887_4067896_RF | ADCY9 | 60 | 30 | 0.000146 | 0.011194 | 50 | −0.715327 |
| 6_167527869_167530791_167549754_167555064_FR | CCR6 | 11 | 6 | 0.051332 | 0.52748 | 54.55 | −0.711289 |
| 16_4071891_4073711_4204978_4209511_RF | ADCY9 | 60 | 30 | 0.000146 | 0.011194 | 50 | −0.704294 |
| 16_31255309_31261374_31329916_31335980_RF | ITGAM | 24 | 11 | 0.039526 | 0.471151 | 45.83 | −0.703943 |
| 7_45584884_45588878_45736475_45743273_RF | ADCY1 | 30 | 16 | 0.002216 | 0.073388 | 53.33 | −0.698983 |
| 7_55087969_55089963_55224588_55235839_RR | EGFR | 196 | 77 | 0.00015 | 0.011194 | 39.29 | −0.697432 |
| 16_4065887_4067896_4209511_4211354_FF | ADCY9 | 60 | 30 | 0.000146 | 0.011194 | 50 | −0.692904 |
| 1_161590754_161594100_161627152_161631654_RR | FCGR2B; FCGR3A | 95 | 41 | 0.000591 | 0.029335 | 43.16 | −0.688738 |
| 16_4065887_4067896_4204978_4209511_FF | ADCY9 | 60 | 30 | 0.000146 | 0.011194 | 50 | −0.673206 |
| 7_55087969_55089963_55146890_55151406_RF | EGFR | 196 | 77 | 0.00015 | 0.011194 | 39.29 | −0.670616 |
| 19_50479474_50480574_50495462_50498507_FF | SIGLEC16 | 5 | 4 | 0.021663 | 0.358647 | 80 | −0.661358 |
| 7_55087969_55089963_55159296_55163839_RF | FGFR | 196 | 77 | 0.00015 | 0.011194 | 39.29 | −0.66015 |
| 11_923549_925733_976127_979142_RF | AP2A2 | 10 | 6 | 0.030192 | 0.428435 | 60 | −0.648337 |
| 16_4065887_4067896_4109379_4115518_FR | ADCY9 | 60 | 30 | 0.000146 | 0.011194 | 50 | −0.642688 |
| 1_25048331_25049906_25138048_25141786_RR | CLIC4 | 171 | 60 | 0.014508 | 0.33256 | 35.09 | −0.628657 |
| 11_1010876_1013083_964245_969445_FF | AP2A2 | 10 | 6 | 0.030192 | 0.428435 | 60 | −0.626498 |
| B | | | | | | | |
| 19_55265127_55271536_55301130_55304400_FR | KIR2DL1; KIR2DL4; KIR3DL1; KIR2DL3 | 5 | 4 | 0.021663 | 0.358647 | 80 | 0.882342 |
| 15_45005395_45007515_45023742_45026509_FR | B2M | 18 | 8 | 0.089181 | 0.680673 | 44.44 | 0.79992 |
| 19_55265127_55271536_55301130_55304400_FF | KIR2DL1; KIR2DL4; KIR3DL1; KIR2DL3 | 5 | 4 | 0.021663 | 0.358647 | 80 | 0.784363 |
| 15_44986846_44994405_45005395_45007515_RF | B2M | 18 | 8 | 0.089181 | 0.680673 | 44.44 | 0.724237 |
| 15_44962061_44965177_45005395_45007515_RF | B2M | 18 | 8 | 0.089181 | 0.680673 | 44.44 | 0.703463 |
| 17_4709602_4710899_4724773_4727780_RR | PLD2 | 5 | 4 | 0.021663 | 0.358647 | 80 | 0.583764 |
| 15_44994405_44997599_45023742_45026509_RR | B2M | 18 | 8 | 0.089181 | 0.680673 | 44.44 | 0.560989 |
| 19_55275870_55279952_55301130_55304400_FF | KIR2DL1; KIR2DL4; KIR3DL1; KIR2DL3 | 5 | 4 | 0.021663 | 0.358647 | 80 | 0.549219 |
| 15_44986846_44994405_45005395_45007515_FF | B2M | 18 | 8 | 0.089181 | 0.680673 | 44.44 | 0.521549 |
| 1_207739376_207741296_207803544_207805928_RF | CR1 | 108 | 37 | 0.065707 | 0.593356 | 34.26 | 0.51017 |
| 2_65447148_65449472_65486660_65489594_FF | ACTR2 | 24 | 10 | 0.091366 | 0.680673 | 41.67 | 0.501463 |
| 1_9722966_9724614_9740102_9742515_RR | PIK3CD | 71 | 32 | 0.000945 | 0.040077 | 45.07 | 0.499905 |
| 20_1570332_1585721_1606778_1615074_RR | SIRPB1 | 2 | 2 | 0.07449 | 0.599944 | 100 | 0.497866 |
| 2_65429854_65434619_65447148_65449472_FR | ACTR2 | 24 | 10 | 0.091366 | 0.680673 | 41.67 | 0.48838 |
| 1_161588628_161590754_161603284_161607252_RR | FCGR2B; FCGR3A | 95 | 41 | 0.000591 | 0.029335 | 43.16 | 0.473798 |
| 1_25039149_25042248_25060201_25061315_RR | CLIC4 | 171 | 60 | 0.014508 | 0.33256 | 35.09 | 0.469989 |
| 19_6765111_6771260_6808215_6810512_FF | VAV1 | 16 | 9 | 0.013621 | 0.33256 | 56.25 | 0.461142 |
| 15_44986846_44994405_45005395_45007515_FR | B2M | 18 | 8 | 0.089181 | 0.680673 | 44.44 | 0.460579 |
| 1_25106841_25109990_25121474_25132059_RR | CLIC4 | 171 | 60 | 0.014508 | 0.33256 | 35.09 | 0.456162 |
| 1_207803544_207805928_207823127_207825662_FR | CR1 | 108 | 37 | 0.065707 | 0.593356 | 34.26 | 0.452664 |
| 1_161532168_161534007_161588628_161590754_RR | FCGR2B; FCGR3A | 95 | 41 | 0.000591 | 0.029335 | 43.16 | 0.451751 |
| 1_207803544_207805928_207823127_207825662_FF | CR1 | 108 | 37 | 0.065707 | 0.593356 | 34.26 | 0.449375 |
| 21_34811256_34815025_34867137_34868523_RR | IFNGR2 | 28 | 18 | 4.59E−05 | 0.006832 | 64.29 | 0.446599 |
| 2_65407538_65411209)_65486660_65489594_FF | ACTR2 | 24 | 10 | 0.091366 | 0.680573 | 41.67 | 0.430665 |
| 2_65429854_65434619_65461265_65464595_FF | ACTR2 | 24 | 10 | 0.091366 | 0.680673 | 41.67 | 0.427971 |

TABLE 25b

Multiple Sclerosis (MS) probes - EpiSwitch ™ monitoring markers to stratify MS patients who are responders (B) to IFN-B treatment vs. non-responders (A)

| Probes | AveExpr | t | P.Value | adj.P.Val | B |
|---|---|---|---|---|---|
| A | | | | | |
| 14_24795078_24798615_24843066_24844509_RR | −1.02593 | −8.353134 | 1.94E−07 | 0.001326 | 7.269095 |
| 14_24795078_24798615_24825321_24828950_RR | −0.999378 | −8.011946 | 3.44E−07 | 0.001326 | 6.753681 |
| 11_923549_925733_976127_979142_FR | −0.813494 | −6.68296 | 3.74E−06 | 0.002986 | 4.573795 |
| 16_4065887_4067896_4209511_4211354_FR | −0.771915 | −5.520398 | 3.67E−05 | 0.005146 | 2.441367 |
| 16_4065887_4067896_4145870_4149370_FF | −0.76637 | −5.439371 | 4.33E−05 | 0.005435 | 2.285404 |
| 7_55087969_55089963_55116799_55120169_RR | −0.756155 | −4.377827 | 0.000405 | 0.016027 | 0.172054 |
| 16_4065887_4067896_4169801_4171577_FF | −0.752947 | −5.697975 | 2.56E−05 | 0.004189 | 2.780024 |
| 16_4004273_4006715_4065887_4067896_RF | −0.73992 | −5.840209 | 1.92E−05 | 0.004189 | 3.048058 |
| 6_32135728_32138270_32149729_32154447_FF | −0.729578 | −5.804952 | 2.07E−05 | 0.004189 | 2.98189 |
| 16_4044767_4047085_4065887_4067896_RF | −0.715327 | −5.175447 | 7.47E−05 | 0.007103 | 1.771458 |
| 6_167527869_167530791_167549754_167555064_FR | −0.711289 | −5.75873 | 2.27E−05 | 0.004189 | 2.894871 |
| 16_4071891_4073711_4204978_4209511_RF | −0.704294 | −6.032689 | 1.31E−05 | 0.004179 | 3.406069 |
| 16_31255309_31261374_31329916_31335980_RF | −0.703943 | −5.996948 | 1.41E−05 | 0.004179 | 3.340008 |
| 7_45584884_45588878_45736475_45743273_RF | −0.698983 | −5.89072 | 1.74E−05 | 0.004189 | 3.142539 |
| 7_55087969_55089963_55224588_55235839_RR | −0.697432 | −4.563863 | 0.000272 | 0.013616 | 0.550153 |
| 16_4065887_4067896_4209511_4211354_FF | −0.692904 | −5.338064 | 5.34E−05 | 0.00614 | 2.089177 |
| 1_161590754_161594100_161627152_161631654_RR | −0.688738 | −5.719547 | 2.45E−05 | 0.004189 | 2.820863 |
| 16_4065887_4067896_4204978_4209511_FF | −0.673206 | −5.142187 | 8.01E−05 | 0.007264 | 1.706076 |
| 7_55087969_55089963_55146890_55151406_RF | −0.670616 | −3.987991 | 0.000943 | 0.023813 | −0.626034 |
| 19_50479474_50480574_50495462_50498507_FF | −0.661358 | −5.741299 | 2.35E−05 | 0.004189 | 2.861975 |
| 7_55087969_55089963_55159296_55163839_RF | −0.66015 | −4.047471 | 0.000828 | 0.022441 | −0.503956 |
| 11_923549_925733_976127_979142_RF | −0.648337 | −4.908682 | 0.000131 | 0.00981 | 1.243458 |
| 16_4065887_4067896_4109379_4115518_FR | −0.642688 | −4.6626 | 0.00022 | 0.011998 | 0.749772 |
| 1_25048331_25049906_25138048_25141786_RR | −0.628657 | −5.393526 | 4.76E−05 | 0.005734 | 2.19677 |
| 11_1010876_1013083_964245_969445_FF | −0.626498 | −4.803983 | 0.000163 | 0.010835 | 1.034127 |
| B | | | | | |
| 19_55265127_55271536_55301130_55304400_FR | 0.882342 | 7.654384 | 6.39E−07 | 0.001642 | 6.194412 |
| 15_45005395_45007515_45023742_45026509_FR | 0.79992 | 6.845926 | 2.76E−06 | 0.002986 | 4.856081 |
| 19_55265127_55271536_55301130_55304400_FF | 0.784363 | 6.631301 | 4.13E−06 | 0.002986 | 4.483437 |
| 15_44986846_44994405_45005395_45007515_RF | 0.724237 | 6.236561 | 8.81E−06 | 0.003975 | 3.779199 |
| 15_44962061_44965177_45005395_45007515_RF | 0.703463 | 5.83783 | 1.93E−05 | 0.004189 | 3.0436 |
| 17_4709602_4710899_4724773_4727780_RR | 0.583764 | 4.979741 | 0.000113 | 0.009131 | 1.384883 |
| 15_44994405_44997599_45023742_45026509_RR | 0.560989 | 4.537838 | 0.000287 | 0.013851 | 0.497407 |
| 19_55275870_55279952_55301130_55304400_FF | 0.549219 | 4.770727 | 0.000175 | 0.011147 | 0.967408 |
| 15_44986846_44994405_45005395_45007515_FF | 0.521549 | 4.339727 | 0.00044 | 0.016549 | 0.094345 |
| 1_207739376_207741296_207803544_207805928_RF | 0.51017 | 3.705654 | 0.001742 | 0.033948 | −1.20555 |
| 2_65447148_65449472_65486660_65489594_FF | 0.501463 | 4.32279 | 0.000456 | 0.016999 | 0.059773 |
| 1_9722966_9724614_9740102_9742515_RR | 0.499905 | 3.916502 | 0.001101 | 0.025709 | −0.772813 |
| 20_1570332_1585721_1606778_1615074_RR | 0.497866 | 4.140936 | 0.000676 | 0.019902 | −0.312278 |
| 2_65429854_65434619_65447148_65449472_FR | 0.48838 | 4.240472 | 0.000545 | 0.018315 | −0.108462 |
| 1_161588628_161590754_161603284_161607252_RR | 0.473798 | 4.078336 | 0.000775 | 0.021483 | −0.440632 |
| 1_25039149_25042248_25060201_25061315_RR | 0.469989 | 3.946322 | 0.001032 | 0.024818 | −0.711583 |
| 19_6765111_6771260_6808215_6810512_FF | 0.461142 | 3.8272 | 0.001337 | 0.028716 | −0.95617 |
| 15_44986846_44994405_45005395_45007515_FR | 0.460579 | 3.904482 | 0.00113 | 0.026088 | −0.797495 |
| 1_25106841_25109990_25121474_25132059_RR | 0.456162 | 3.950375 | 0.001023 | 0.024818 | −0.703261 |
| 21_34811256_34815025_34867137_34868525_RR | 0.446599 | 3.662075 | 0.001915 | 0.03533 | −1.294865 |
| 2_65407538_65411209_65486660_65489594_FF | 0.430665 | 3.625717 | 0.002073 | 0.036207 | −1.369322 |
| 2_65429854_65434619_65461265_65464595_FF | 0.427971 | 3.645565 | 0.001985 | 0.036019 | −1.328682 |

| Probes | FC | FC_1 | LS | Loop detected |
|---|---|---|---|---|
| A | | | | |
| 14_24795078_24798615_24843066_24844509_RR | 0.491094 | −2.036271 | −1 | IFN-B NR |
| 14_24795078_24798615_24825321_24828950_RR | 0.500216 | −1.999138 | −1 | IFN-B NR |
| 11_923549_925733_976127_979142_FR | 0.569002 | −1.757463 | −1 | IFN-B NR |
| 16_4065887_4067896_4209511_4211354_FR | 0.585639 | −1.707535 | −1 | IFN-B NR |
| 16_4065887_4067896_4145870_4149370_FF | 0.587895 | −1.700985 | −1 | IFN-B NR |
| 7_55087969_55089963_55116799_55120169_RR | 0.592072 | −1.688983 | −1 | IFN-B NR |
| 16_4065887_4067896_4169801_4171577_FF | 0.59339 | −1.685232 | −1 | IFN-B NR |
| 16_4004273_4006715_4065887_4067896_RF | 0.598773 | −1.670083 | −1 | IFN-B NR |
| 6_32135728_32138270_32149729_32154447_FF | 0.60308 | −1.658154 | −1 | IFN-B NR |
| 16_4044767_4047085_4065887_4067896_RF | 0.609067 | −1.641855 | −1 | IFN-B NR |
| 6_167527869_167530791_167549754_167555064_FR | 0.610774 | −1.637267 | −1 | IFN-B NR |
| 16_4071891_4073711_4204978_4209511_RF | 0.613743 | −1.629347 | −1 | IFN-B NR |
| 16_31255309_31261374_31329916_31335980_RF | 0.613892 | −1.628951 | −1 | IFN-B NR |
| 7_45584884_45588878_45736475_45743273_RF | 0.616006 | −1.62336 | −1 | IFN-B NR |
| 7_55087969_55089963_55224588_55235839_RR | 0.616669 | −1.621616 | −1 | IFN-B NR |
| 16_4065887_4067896_4209511_4211354_FF | 0.618607 | −1.616534 | −1 | IFN-B NR |
| 1_161590754_161594100_161627152_161631654_RR | 0.620396 | −1.611872 | −1 | IFN-B NR |
| 16_4065887_4067896_4204978_4209511_FF | 0.627112 | −1.594612 | −1 | IFN-B NR |
| 7_55087969_55089963_55146890_55151406_RF | 0.628238 | −1.591753 | −1 | IFN-B NR |

TABLE 25b-continued

Multiple Sclerosis (MS) probes - EpiSwitch ™ monitoring markers to stratify MS patients who are responders (B) to IFN-B treatment vs. non-responders (A)

| | | | | |
|---|---|---|---|---|
| 19_50479474_50480574_50495462_50498507_FF | 0.632283 | −1.581571 | −1 | IFN-B NR |
| 7_55087969_55089963_55159296_55163839_RF | 0.632812 | −1.580247 | −1 | IFN-B NR |
| 11_923549_925733_976127_979142_RF | 0.638015 | −1.56736 | −1 | IFN-B NR |
| 16_4065887_4067896_4109379_4115518_FR | 0.640518 | −1.561236 | −1 | IFN-B NR |
| 1_25048331_25049906_25138048_25141786_RR | 0.646778 | −1.546126 | −1 | IFN-B NR |
| 11_1010876_1013083_964245_969445_FF | 0.647747 | −1.543813 | −1 | IFN-B NR |
| B | | | | |
| 19_55265127_55271536_55301130_55304400_FR | 1.843366 | 1.843366 | 1 | IFN-B R |
| 15_45005395_45007515_45023742_45026509_FR | 1.741005 | 1.741005 | 1 | IFN-B R |
| 19_55265127_55271536_55301130_55304400_FF | 1.722331 | 1.722331 | 1 | IFN-B R |
| 15_44986846_44994405_45005395_45007515_RF | 1.652026 | 1.652026 | 1 | IFN-B R |
| 15_44962061_44965177_45005395_45007515_RF | 1.628409 | 1.628409 | 1 | IFN-B R |
| 17_4709602_4710899_4724773_4727780_RR | 1.498755 | 1.498755 | 1 | IFN-B R |
| 15_44994405_44997599_45023742_45026509_RR | 1.47528 | 1.47528 | 1 | IFN-B R |
| 19_55275870_55279952_55301130_55304400_FF | 1.463293 | 1.463293 | 1 | IFN-B R |
| 15_44986846_44994405_45005395_45007515_FF | 1.435495 | 1.435495 | 1 | IFN B R |
| 1_207739376_207741296_207803544_207805928_RF | 1.424218 | 1.424218 | 1 | IFN-B R |
| 2_65447148_65449472_65486660_65489594_FF | 1.415648 | 1.415648 | 1 | IFN-B R |
| 1_9722966_9724614_9740102_9742515_RR | 1.41412 | 1.41412 | 1 | IFN-B R |
| 20_1570332_1585721_1606778_1615074_RR | 1.412123 | 1.412123 | 1 | IFN-B R |
| 2_65429854_65434619_65447148_65449472_FR | 1.402869 | 1.402869 | 1 | IFN B R |
| 1_161588628_161590754_161603284_161607252_RR | 1.38876 | 1.38876 | 1 | IFN-B R |
| 1_25039149_25042248_25060201_25061315_RR | 1.385099 | 1.385099 | 1 | IFN-B R |
| 19_6765111_6771260_6808215_6810512_FF | 1.376632 | 1.376632 | 1 | IFN-B R |
| 15_44986846_44994405_45005395_45007515_FR | 1.376094 | 1.376094 | 1 | IFN B R |
| 1_25106841_25109990_25121474_25132059_RR | 1.371888 | 1.371888 | 1 | IFN-B R |
| 21_34811256_34815025_34867137_34868523_RR | 1.362824 | 1.362824 | 1 | IFN-B R |
| 2_65407538_65411209_65486660_65489594_FF | 1.347855 | 1.347855 | 1 | IFN-B R |
| 2_65429854_65434619_65461265_65464595_FF | 1.34534 | 1.34534 | 1 | IFN-B R |

TABLE 25c

Multiple Sclerosis (MS) probes - EpiSwitch ™ monitoring markers to stratify MS patients who are responders to IFN-B treatment (B) vs. non-responders (A)

| Probes | 60 mer Probe sequence |
|---|---|
| A | |
| 14_24795078_24798615_24843066_24844509_RR | CCCACCTCCCACCAGACAGTGGAAGCAGTCGAGTGCTGTGAGCAAAGAGGCCCTGGGCCA (SEQ ID NO: 457) |
| 14_24795078_24798615_24825321_24828950_RR | CCCACCTCCCACCAGACAGTGGAAGCAGTCGAAGCAAAACTGTGGAGATTGGGTCGGTGA (SEQ ID NO: 458) |
| 11_923549_925733_976127_979142_FR | GCCTGCAGGGGGCGCCCCCGCGCCTGCCTCGACCACACATCCACATGGACGCATGGCAGG (SEQ ID NO: 459) |
| 16_4065887_4067896_4209511_4211354_FR | CGCCGGGCCGACACCCACATTGTCTTCTTCGAACCCCTTTAAACCACTGACCTTGTCCCT (SEQ ID NO: 460) |
| 16_4065887_4067896_4145870_4149370_FF | CGCCGGGCCGACACCCACATTGTCTTCTTCGAGTTCCTTGGAAGCTTTAATTTGCATTCC (SEQ ID NO: 461) |
| 7_55087969_55089963_55116799_55120169_RR | AGACCCGGACGTCTCCGCGAGGCGGCCATCGATTTTGCTGATGCAATACAGTTTTACAGG (SEQ ID NO: 462) |
| 16_4065887_4067896_4169801_4171577_FF | CGCCGGGCCGACACCCACATTGTCTTCTTCGAATCTCCCATCTGCTCTTTCAACCAAGCT (SEQ ID NO: 463) |
| 16_4004273_4006715_4065887_4067896_RF | CGCCGGGCCGACACCCACATTGTCTTCTTCGACATCCACTCTTCTGGGCATTCCCAGCCT (SEQ ID NO: 464) |
| 6_32135728_32138270_32149729_32154447_FF | ACTGATGGCATCCCCCGTGCGCTTCCGGTCGATGGGGCCAGGGGGCTATGGGGATAACCT (SEQ ID NO: 465) |
| 16_4044767_4047085_4065887_4067896_RF | CGCCGGGCCGACACCCACATTGTCTTCTTCGATTTTATAGTATGTGAATTATATCTCAAC (SEQ ID NO: 466) |
| 6_167527869_167530791_167549754_167555064_FR | ACAGCTGCATCTTATGTCAGAAGAGTGTTCGACTCCAGTGAAGATTATTTTGTGTCAGTC (SEQ ID NO: 467) |

TABLE 25c-continued

Multiple Sclerosis (MS) probes - EpiSwitch ™ monitoring markers to stratify MS patients who are responders to IFN-B treatment (B) vs. non-responders (A)

| Probes | 60 mer Probe sequence |
|---|---|
| 16_4071891_4073711_4204978_4209511_RF | CAGAATCGCCCACCTTGTAGCCCAGGGATCGACGGCAAGCCACTCACCCTCAGCCCTATC (SEQ ID NO: 468) |
| 16_31255309_31261374_31329916_31335980_RF | CAAATCCCGGCTATCTCTTAGAATTGCATCGAGTTTATCTTGAGTTTATATATTTTAATG (SEQ ID NO: 469) |
| 7_45584884_45588878_45736475_45743273_RF | TCCATCCCCAACTTCAATGACTTCTACATCGACATAGTACTGAAAGTCTTTGCTAGAGTA (SEQ ID NO: 470) |
| 7_55087969_55089963_55224588_55235839_RR | AGACCCGGACGTCTCCGCGAGGCGGCCATCGACATATTTCCTGTTCCCTTGGAATAAAAA (SEQ ID NO: 471) |
| 16_4065887_4067896_4209511_4211354_FF | CGCCGGGCCGACACCCACATTGTCTTCTTCGATTTGCATTTCCCTAATGATCGGTGATGT (SEQ ID NO: 472) |
| 1_161590754_161594100_161627152_161631654_RR | AGGACAGAGACCCCTAATTCCACCACCATCGACCCTTCTGCTTTCTCTCCAGGGGATGGC (SEQ ID NO: 473) |
| 16_4065887_4067896_4204978_4209511_FF | CGCCGGGCCGACACCCACATTGTCTTCTTCGATCCCTGGGCTACAAGGTGGGCGATTCTG (SEQ ID NO: 474) |
| 7_55087969_55089963_55146890_55151406_RF | TTCCTGAAAAAAAATGGCTACTTATTAGTCGATGGCCGCCTCGCGGAGACGTCCGGGTCT (SEQ ID NO: 475) |
| 19_50479474_50480574_50495462_50498507_FF | AGCACAGGCAAGATGACCTTCAAGGTGCTCGACCCCACTGCTGGCCATCCCTACCTGCAT (SEQ ID NO: 476) |
| 7_55087969_55089963_55159296_55163839_RF | CACTTTTTATAGAAGAGAAAGTGAAGATTCGATGGCCGCCTCGCGGAGACGTCCGGGTCT (SEQ ID NO: 477) |
| 11_923549_925733_976127_979142_RF | CCACGTGTCGCGGGCCTGAGTGTGCCCCTCGAGGCTGTAGTGATTCATGATTGTACCACT (SEQ ID NO: 478) |
| 16_4065887_4067896_4109379_4115518_FR | CGCCGGGCCGACACCCACATTGTCTTCTTCGAAAAAAAAAAAAAAAGAAAAAAAAAGAAA (SEQ ID NO: 479) |
| 1_25048331_25049906_25138048_25141786_RR | GTGCCCACACTCCTCAGCCCTCCGGTGGTCGACCGCCTGGGCTCAACCAATCCTCCCATC (SEQ ID NO: 480) |
| 11_1010876_1013083_964245_969445_FF | GTGCCCTCCTCGCCCCTGATGGGTCTGGTCGAGACCAGCCTCAACATGGAGAAACACCAT (SEQ ID NO: 481) |
| B | |
| 19_55265127_55271536_55301130_55304400_FR | ATAGGCACCGAATAGATAAATAGATAGATCGATAGATAATAGATAGAAATATGCAGAAAG (SEQ ID NO: 482) |
| 15_45005395_45007515_45023742_45026509_FR | GCCAGAGTGGAAATGGAATTGGGAGAAATCGAAGAGTTTTAATATCTGCTGTAAACCTTG (SEQ ID NO: 483) |
| 19_55265127_55271536_55301130_55304400_FF | ATAGGCACCGAATAGATAAATAGATAGATCGAAGATTCTGACAATAACTAAGAGCAGAGG (SEQ ID NO: 484) |
| 15_44986846_44994405_45005395_45007515_RF | GCCAGAGTGGAAATGGAATTGGGAGAAATCGAAATGAGTCAAGGAAACTTACAAGCTTTT (SEQ ID NO: 485) |
| 15_44962061_44965177_45005395_45007515_RF | GCCAGAGTGGAAATGGAATTGGGAGAAATCGATTCGGACCACTGCATGAGAAGAGAGGCA (SEQ ID NO: 486) |
| 17_4709602_4710899_4724773_4727780_RR | ATCTTGGGTAACTAGGGAGTGGAGTTGTTCGACTTCGCCAGCTGAAGTGATCCTCCCACT (SEQ ID NO: 487) |
| 15_44994405_44997599_45023742_45026509_RR | ATTCCTAGACACATACAACCTGCCAAGATCGAAGAGTTTTAATATCTGCTGTAAACCTTG (SEQ ID NO: 488) |
| 19_55275870_55279952_55301130_55304400_FF | TACAGATTTTGGTATCTGAGTGGAGATCTCGAAGATTCTGACAATAACTAAGAGCAGAGG (SEQ ID NO: 489) |
| 15_44986846_44994405_45005395_45007515_FF | CTGTTCTGGTTTTGGATTTCTTCAAGGTTCGATTTCTCCCAATTCCATTTCCACTCTGGC (SEQ ID NO: 490) |
| 1_207739376_207741296_207803544_207805928_RF | CGAGGCGAGTGGATCATGAGTCAGGAGATCGATTTAAAAATAGTTTATTTTAATAATGTT (SEQ ID NO: 491) |

TABLE 25c-continued

Multiple Sclerosis (MS) probes - EpiSwitch ™ monitoring markers to stratify MS patients who are responders to IFN-B treatment (B) vs. non-responders (A)

| Probes | 60 mer Probe sequence |
|---|---|
| 2_65447148_65449472_65486660_65489594_FF | ATAAAGAAAATGCAGTACACATACACAATCGAGACCAGCCTGGTCAATACGGCAAAACCC (SEQ ID NO: 492) |
| 1_9722966_9724614_9740102_9742515_RR | GGCAGGTGGATCACCTGAGGTCAGGAGTTCGAACTCTTAACCTCAGGTGATCCACCCGCA (SEQ ID NO: 493) |
| 20_1570332_1585721_1606778_1615074_RR | GTAGTAGGGATTCATTCAAAAGCACCACTCGAGGATTTACGATGCAGTGCGACAACCCTG (SEQ ID NO: 494) |
| 2_65429854_65434619_65447148_65449472_FR | TATATTTATATCCCAGATTCAATCATCATCGAGACCAGCCTAGCTAACATGGTGAAACCC (SEQ ID NO: 495) |
| 1_161588628_161590754_161603284_161607252_RR | TGATAAACATCTTAACAGGAAACAGGGTTCGATTGTCATCCTCTAGGACTTACAGTTTCT (SEQ ID NO: 496) |
| 1_25039149_25042248_25060201_25061315_RR | GGCAGGCAGATCACTTGAGGTCAGGAGTTCGAACACCTGACCTCAGGTGATCTGCCCACC (SEQ ID NO: 497) |
| 19_6765111_6771260_6808215_6810512_FF | GGCAGGTGGATCACCTGAGGTCAGGAGTTCGAACTCCTGACCTCAGGGGATCCACCCACC (SEQ ID NO: 498) |
| 15_44986846_44994405_45005395_45007515_FR | CTGTTCTGGTTTTGGATTTCTTCAAGGTTCGAAAGCAGAATGTTTTGATCATGAGAAAAT (SEQ ID NO: 499) |
| 1_25106841_25109990_25121474_25132059_RR | AACAAATGTTTACCAAGTACCTACTATGTCGAAAATCAGATGGTTATAGGTGTGTGGCCT (SEQ ID NO: 500) |
| 1_207803544_207805928_207823127_207825662_FR | CGAGGCGAGTGGATCATGAGTCAGGAGATCGAAAGGTATCTGTCTTGGAAAAACCTTGAT (SEQ ID NO: 501) |
| 1_161532168_161534007_161588628_161590754_RR | AAAGATGTTGAGTGGAGTTTGCAGTTGTTCGAACCCTGTTTCCTGTTAAGATGTTTATCA (SEQ ID NO: 502) |
| 1_207803544_207805928_207823127_207825662_FF | CGAGGCGAGTGGATCATGAGTCAGGAGATCGACAATAAACTGAAGAGACAGCATTAATGT (SEQ ID NO: 503) |
| 21_34811256_34815025_34867137_34868523_RR | AAGGTGGGTGGATCATGAGGTCAGGAGTTCGAACCCCTGACCTCAAATGATCCACCTAGG (SEQ ID NO: 504) |
| 2_65407538_65411209_65486660_65489594_FF | AAGGAAGGAATCAAACACTTCTGAAAAGTCGAGACCAGCCTGGTCAATACGGCAAAACCC (SEQ ID NO: 505) |
| 2_65429854_65434619_65461265_65464595_FF | TATATTTATATCCCAGATTCAATCATCATCGAGACCAGTATGGGCAACACGGCAAGATTC (SEQ ID NO: 506) |

TABLE 25d

| Probes | Chr | Probe Location | | | |
|---|---|---|---|---|---|
| | | Start1 | End1 | Start2 | End2 |
| 14_24795078_24798615_24843066_24844509_RR | 14 | 24795079 | 24795108 | 24843067 | 24843096 |
| 14_24795078_24798615_24825321_24828950_RR | 14 | 24795079 | 24795108 | 24825322 | 24825351 |
| 11_923549_925733_976127_979142_FR | 11 | 925704 | 925733 | 976128 | 976157 |
| 16_4065887_4067896_4209511_4211354_FR | 16 | 4067867 | 4067896 | 4209512 | 4209541 |
| 16_4065887_4067396_4145870_4149370_FF | 16 | 4067867 | 4067896 | 4149341 | 4149370 |
| 7_55087969_55089963_55116799_55120169_RR | 7 | 55087970 | 55087999 | 55116800 | 55116829 |
| 16_4065887_4067896_4169801_4171577_FF | 16 | 4067867 | 4067896 | 4171548 | 4171577 |
| 16_4004273_4006715_4065887_4067896_RR | 16 | 4004274 | 4004303 | 4067867 | 4067896 |
| 6_32135728_32138270_32149729_32154447_FF | 6 | 32138241 | 32138270 | 32154418 | 32154447 |
| 16_4044767_4047085_4065887_4067896_RF | 16 | 4044768 | 4044797 | 4067867 | 4067896 |
| 6_167527869_167530791_167549754_167555064_FR | 6 | 167530762 | 167530791 | 167549755 | 167549784 |
| 16_4071891_4073711_4204978_4209511_RF | 16 | 4071892 | 4071921 | 4209482 | 4209511 |
| 16_31255309_31261374_31329916_31335980_RF | 16 | 31255310 | 31255339 | 31335951 | 31335980 |
| 7_45584884_45588878_45736475_45743273_RF | 7 | 45584885 | 45584914 | 45743244 | 45743273 |
| 7_55087969_55089963_55224588_55235839_RR | 7 | 55087970 | 55087999 | 55224589 | 55224618 |
| 16_4065887_4067896_4209511_4211354_RR | 16 | 4067867 | 4067896 | 4211325 | 4211354 |
| 1_161590754_161594100_161627152_161631654_RR | 1 | 161590755 | 161590784 | 161627153 | 161627182 |
| 16_4065887_4067896_4204978_4209511_FF | 16 | 4067867 | 4067896 | 4209482 | 4209511 |
| 7_55087969_55089963_55146890_55151406_RF | 7 | 55087970 | 55087999 | 55151377 | 55151406 |

TABLE 25d-continued

| | | | | | |
|---|---|---|---|---|---|
| 19_50479474_50480574_50495462_50498507_FF | 19 | 50480545 | 50480574 | 50498478 | 50498507 |
| 7_55087969_55089963_55159296_55163839_RF | 7 | 55087970 | 55087999 | 55163810 | 55163839 |

| | | 4 kb Sequence Location | | | |
|---|---|---|---|---|---|
| Probes | Chr | Start1 | End1 | Start2 | End2 |
| 14_24795078_24798615_24843066_24844509_RR | 14 | 24795079 | 24799078 | 24843067 | 24847066 |
| 14_24795078_24798615_24825321_24828950_RR | 14 | 24795079 | 24799078 | 24825322 | 24829321 |
| 11_923549_925733_976127_979142_FR | 11 | 921734 | 925733 | 976128 | 980127 |
| 16_4065887_4067896_4209511_4211354_FR | 16 | 4063897 | 4067896 | 4209512 | 4213511 |
| 16_4065887_4067396_4145870_4149370_FF | 16 | 4063897 | 4067896 | 4145371 | 4149370 |
| 7_55087969_55089963_55116799_55120169_RR | 7 | 55087970 | 55091969 | 55116800 | 55120799 |
| 16_4065887_4067896_4169801_4171577_FF | 16 | 4063897 | 4067896 | 4167578 | 4171577 |
| 16_4004273_4006715_4065887_4067896_RR | 16 | 4004274 | 4008273 | 4063897 | 4067896 |
| 6_32135728_32138270_32149729_32154447_FF | 6 | 32134271 | 32138270 | 32150448 | 32154447 |
| 16_4044767_4047085_4065887_4067896_RF | 16 | 4044768 | 4048767 | 4063897 | 4067896 |
| 6_167527869_167530791_167549754_167555064_FR | 6 | 167526792 | 167530791 | 167549755 | 167553754 |
| 16_4071891_4073711_4204978_4209511_RF | 16 | 4071892 | 4075891 | 4205512 | 4209511 |
| 16_31255309_31261374_31329916_31335980_RF | 16 | 31255310 | 31259309 | 31331981 | 31335980 |
| 7_45584884_45588878_45736475_45743273_RF | 7 | 45584885 | 45588884 | 45739274 | 45743273 |
| 7_55087969_55089963_55224588_55235839_RR | 7 | 55087970 | 55091969 | 55224589 | 55228588 |
| 16_4065887_4067896_4209511_4211354_RR | 16 | 4063897 | 4067896 | 4207355 | 4211354 |
| 1_161590754_161594100_161627152_161631654_RR | 1 | 161590755 | 161594754 | 161627153 | 161631152 |
| 16_4065887_4067896_4204978_4209511_FF | 16 | 4063897 | 4067896 | 4205512 | 4209511 |
| 7_55087969_55089963_55146890_55151406_RF | 7 | 55087970 | 55091969 | 55147407 | 55151406 |
| 19_50479474_50480574_50495462_50498507_FF | 19 | 50476575 | 50480574 | 50494508 | 50498507 |
| 7_55087969_55089963_55159296_55163839_RF | 7 | 55087970 | 55091969 | 55159840 | 55163839 |

TABLE 26a

Neurofibromatosis (NF) probes - EpiSwitch™ markers to stratify (A) Benign plexiform vs.
(B) Malignant Peripheral Nerve Sheath Tumours (MPNSTs)

| Probe | Loop LS detected | 60 mer Probe sequence |
|---|---|---|
| A | | |
| 10_114686118_114690592_114727613_114729725_FF | 1 Benign plexiform | AAGTCAATAAATCCCAAGCACACAACACTCGACCTTCATCACACAACAGTGCTCATAGGTTT (SEQ ID NO: 507) |
| 10_114686118_114690592_114743749_114745454_FF | 1 Benign plexiform | AAGTCAATAAATCCCAAGCACACAACACTCGAGGACCCTTCCACCCAAAAAAAGCAAGG (SEQ ID NO: 508) |
| 10_114686118_114690592_114773872_114776404_FF | 1 Benign plexiform | AAGTCAATAAATCCCAAGCACACAACACTCGAAGTCAGCTGGGATGAAGGAAGGAAAGA (SEQ ID NO: 509) |
| 10_114686118_114690592_114794603_114795614_FF | 1 Benign plexiform | AAGTCAATAAATCCCAAGCACACAACACTCGAAAGCAGCCACAGCAGTCAGTATATGTC (SEQ ID NO: 510) |
| 10_114686118_114690592_114804200_114807457_FF | 1 Benign plexiform | AAGTCAATAAATCCCAAGCACACAACACTCGAATAAATAGTATCTTTGCCCAATAATATG (SEQ ID NO: 511) |
| 10_114686118_114690592_114821603_114822761_FF | 1 Benign plexiform | AAGTCAATAAATCCCAAGCACACAACACTCGAATGTAAAATGAGACCTGATGCACAGT (SEQ ID NO: 512) |
| 10_114686118_114690592_114845287_114849773_FF | 1 Benign plexiform | AAGTCAATAAATCCCAAGCACACAACACTCGAGGCAAAGTGGGCATTTTCCAGCACCCTG (SEQ ID NO: 513) |
| 10_114686118_114690592_114885061_114889442_FF | 1 Benign plexiform | AAGTCAATAAATCCCAAGCACACAACACTCGAAATGGCTCCAGATTCCTGGCCGAGTAGG (SEQ ID NO: 514) |
| 11_128342943_128345136_128481262_128489818_FF | 1 Benign plexiform | ACCTGAATACATTGAGATTATTTTGCAATCGAGATCTGAGTGTGAGGGTGGGGGCTGAG (SEQ ID NO: 515) |
| 11_128410884_128413638_128489818_128498866_FF | 1 Benign plexiform | AAGTTGTGAAAATTTTATCTTACGTGATCGATGACACAAAGTGTGTTTAAATACAGGGT (SEQ ID NO: 516) |
| 5_131857043_131861763_131874140_131875551_RF | 1 Benign plexiform | GTATGTCAGGGTCAGAGGGGCAGAGGGGTCGAGAGGTCGAGGAGACTACTTAGGAATAATACAACAAA (SEQ ID NO: 517) |
| 5_131874140_131875551_131894531_131901964_FF | 1 Benign plexiform | GTATGTCAGGGTCAGAGGGGCAGAGGGGTCGAGAGTTCGAGAGGTCTAGCTACCCGGCAAACATCAAAT (SEQ ID NO: 518) |
| 5_131874140_131875551_131920774_131922322_FF | 1 Benign plexiform | GTATGTCAGGGTCAGAGGGGCAGAGGGGTCGAGAGGTCGACTTTAACATAATTAATTAAAATTATACT (SEQ ID NO: 519) |
| 5_131874140_131875551_131942647_131945574_FF | 1 Benign plexiform | GTATGTCAGGGTCAGAGGGGCAGAGGGGTCGAACTTTTTACCATGAGTCTTTTACTGAAAA (SEQ ID NO: 520) |

TABLE 26a-continued

Neurofibromatosis (NF) probes - EpiSwitch™ markers to stratify (A) Benign plexiform vs.
(B) Malignant Peripheral Nerve Sheath Tumours (MPNSTs)

| Probe | Loop LS detected | 60 mer Probe sequence |
|---|---|---|
| 5_131874140_131875551_131985852_131989475_FF | 1 Benign plexiform | GTATGTCAGGGTCAGAGGGGCAGAGTCGACTTTGATGAACAAAATGGATATCTAAC (SEQ ID NO: 521) |
| 5_131882513_131883559_131942647_131945574_FF | 1 Benign plexiform | GGTGGGTGGATTGGTTGAAGTCAGCAGTTCGAACTTTTACCATGACTTTTACTGAAAA (SEQ ID NO: 522) |
| 5_131882513_131883559_131966700_131972322_FF | 1 Benign plexiform | GGTGGGTGGATTGGTTGAAGTCAGCAGTTCGAACTGCCACCTTGTCCCTCTTCTATCACT (SEQ ID NO: 523) |
| 6_41890642_41893643_42057606_42059682_RR | 1 Benign plexiform | AGGGAGAGAGAGGAGTCTAAAGTTTATCTCGAGGGGTGGGAGGCATGTCTATTTGCTC (SEQ ID NO: 524) |
| 7_137557828_137562242_137656982_137661712_FF | 1 Benign plexiform | TTTACAATATCCCTTTTTAAGTGCAAAGTCGATGTTGATGTTGTGTGGGTGTGTACG (SEQ ID NO: 525) |
| 7_50818806_50825328_50840056_50842638_RR | 1 Benign plexiform | TGGTGAGGAGGGCAGTGTCCAAGGCAAGTCGATGCAAGAGTCCAGGACAGTCAAAGAAT (SEQ ID NO: 526) |
| 7_519231_522690_557100_558462_FF | 1 Benign plexiform | ATGGGTAAGTGATGAATGGGTGGATAGTTCGATGTTTAGATTTTCCCAACTGGGTTCTAT (SEQ ID NO: 527) |
| 7_519231_522690_594007_596370_FF | 1 Benign plexiform | ATGGGTAAGTGATGAATGGGTGGATAGTTCGACGTGCCCGAGGTCGTGGGGAACTGTTC (SEQ ID NO: 528) |
| 9_36907980_36909849_36932342_36938946_FF | 1 Benign plexiform | TTTTTTTTTTTTTAGATATAGGGTTTCGAGGTCGTAATCTGGCTGAGAGAGAGGGGTCT (SEQ ID NO: 529) |
| 9_36951690_36954534_36987524_36991745_RF | 1 Benign plexiform | CCCTGGACAGCAACTAAGCTGTCCTGGGTCGAGACTACTCAAATATTTTTATTTATTCT (SEQ ID NO: 530) |
| 9_36961116_36962831_37038244_37041179_FF | 1 Benign plexiform | AGACACACACTGAGACAGCTCAATCTGCTCGAGGATCAAAGGATGTTGTGTGAGGCTTGC (SEQ ID NO: 531) |
| B | | |
| 1_26993831_26995281_270500122_270527226_FF | -1 MPNSTs | GACCAGGCTGGAGTGCAGTGGCACAATCTCGAGCCACTGCACTCCATCCTGGGCAGCAGA (SEQ ID NO: 532) |
| 17_67495529_67497867_67514127_67521454_RF | -1 MPNSTs | GATTCCTTATAGTTTAAAATTAAATTATTCGAGTCTCTTAATGACCTGCGGAGATTGTAC (SEQ ID NO: 533) |
| 19_11040234_11041901_11194011_11195243_FF | -1 MPNSTs | CAGTCAGTTGGATCACCGAGGTTCAGGAGATCGATCTCCTGACCTCGTGATCCGCCCGCCTC (SEQ ID NO: 534) |
| 19_11062377_11065717_11194011_11195243_RF | -1 MPNSTs | GAGGCGGGCGGATCACGAGGTCAGGAGATCGATCTCCTGACCTCGTGATCCGCCCGCCTC (SEQ ID NO: 535) |

TABLE 26a-continued

Neurofibromatosis (NF) probes - EpiSwitch™ markers to stratify (A) Benign plexiform vs. (B) Malignant Peripheral Nerve Sheath Tumours (MPNSTs)

| Probe | Loop LS detected | 60 mer Probe sequence |
|---|---|---|
| 19_52666823_52670053_52700693_52702643_FF | -1 MPNSTs | GGGTTTCACCTTGTTAGCCAGGATGGTCTCGAGACCATCCTGGCTAACACGGTGAAACCC (SEQ ID NO: 536) |
| 21_39757299_39761915_39949058_39951313_FF | -1 MPNSTs | ACACTGATTAAATCTTAATTATTCCATTTCGATCCCTCAAGGATCAGGACTGTGTTGCAT (SEQ ID NO: 537) |
| 21_39757299_39761915_40055526_40064997_FF | -1 MPNSTs | ACACTGATTAAATCTTAATTATTCCATTTCGAGGGAATAATCTCCTAAACATTTCTGGTG (SEQ ID NO: 538) |
| 21_39762207_39763468_40021022_40024449_FF | -1 MPNSTs | CTTGGGCCCTATCTTATGTATGGAGCTGTCGAGTTTATGTTCTTACCCTGTTTCTCTTT (SEQ ID NO: 539) |
| 5_42377143_42386021_42652698_42659568_FF | -1 MPNSTs | ATGCTAAATTATGTAAAATGAATATGTTCGAGTTCATAGATACTCAAGGGCCCCTCAGT (SEQ ID NO: 540) |
| 5_42543850_42546292_42676184_42678827_RF | -1 MPNSTs | CAACAATTTTATTAATTTTCAACTTTCATCGATTTTATAAAATTATCAGTAATAACCTTT (SEQ ID NO: 541) |
| 6_41953588_41955459_42036433_42038022_RF | -1 MPNSTs | GAGGTGGGCAGATCACGAGGTCAGGAGATCGATCTCCTGACCTCGTGATCCGCCCGCCTC (SEQ ID NO: 542) |
| 6_41953588_41955459_42040682_42041908_RR | -1 MPNSTs | GAGGCGGGCCGATCACGAGGTCAGGAGATCGATCTCCCGACCTCGTGATCCGCCCGCCTC (SEQ ID NO: 543) |
| 7_116279520_116285670_116319380_116323843_RF | -1 MPNSTs | TGACACCATACATTTTATTTCTCCCTTCGAGAGATTTGTTATTAAGCTTCCGTCTCGTT (SEQ ID NO: 544) |
| 7_116279520_116285670_116419719_116422284_RF | -1 MPNSTs | AGTCCTTTATTTCTGTTACAATCTTAAATCGAGATTTTGTTATTAAGCTTCCGTCTCGTT (SEQ ID NO: 545) |
| 7_116308668_116319380_116371770_116373950_RR | -1 MPNSTs | TACCTTTTTAGAGCTATGTCATGTATGTTCGAACAGAGTTTACCACAGCTTTGCAGCGCG (SEQ ID NO: 546) |
| 7_137545600_137549019_137668037_137669463_RR | -1 MPNSTs | TGTATTCTGTATCACTTAGACTCTTCTTTCGAAGAAGGAATCTTAAACAAGAGAAGCAAG (SEQ ID NO: 547) |
| 7_50657698_50658729_50784135_50786449_FF | -1 MPNSTs | AGTTGTTTTTCCTTGAAAAGGGTTTACCTCGACGGTTACACAATTTCAGTATGCACGGGACT (SEQ ID NO: 548) |
| 8_108267104_108269307_108407566_108418839_RR | -1 MPNSTs | TTAACCTAGCAGATCTGGTTCTTCTGGTTCGAGGTATTTATATCACCTTGAGTATTATTT (SEQ ID NO: 549) |
| 8_108277745_108282069_108528062_108532217_FF | -1 MPNSTs | CCTAATAAAGAAAAAAAAATGAGTCCCTTCGAAGCACAAAGTTACAGGACATGGCATCCA (SEQ ID NO: 550) |
| 8_108444846_108453607_108528062_108532217_FF | -1 MPNSTs | TCCTTGGCCTGGTAATCTTTTCAATATTCGAAGCACAAAGTTACAGGACATGGCATCCA (SEQ ID NO: 551) |

TABLE 26a-continued

Neurofibromatosis (NF) probes - EpiSwitch™ markers to stratify (A) Benign plexiform vs.
(B) Malignant Peripheral Nerve Sheath Tumours (MPNSTs)

| Probe | Loop LS detected | 60 mer Probe sequence |
|---|---|---|
| 8_99432076_99435027_99521801_99527715_RF | -1 MPNSTs | CTGCTCCATGTCTGTATTCCTACTTTATTCGAAAGCATCTTTGTGTCATTGTCCATGCTC (SEQ ID NO: 552) |
| 8_99486386_99490632_99554813_99560156_FF | -1 MPNSTs | CCTAAACTAAGCTTGGGCTTAAGATCCATCGAAAGGATACTTTTATAGGAACCAGGCTAG (SEQ ID NO: 553) |
| 8_99521801_99527715_99826498_99828247_RF | -1 MPNSTs | ATATATATATATCACAATGCCTAAGGGATCGAATAGCTTTTTAAGAACAGTGTATAAAT (SEQ ID NO: 554) |
| 8_99541449_99550447_99646209_99658080_RR | -1 MPNSTs | CTCTCTGATTTGCCACATAAAGTAGGCATCGATTCCAAATAAATTAGTTGGTGATGTGGA (SEQ ID NO: 555) |
| 8_99792735_99799194_99962638_99967147_RF | -1 MPNSTs | ACTTCATGCACAAGTTAGGTATTTACTCTCGAGATTATAAACATTTTCATTTGGATTTTG (SEQ ID NO: 556) |

TABLE 26b

Neurofibromatosis (NF) probes - EpiSwitch ™ markers to stratify (A) Benign plexiform vs.
(B) Malignant Peripheral Nerve Sheath Tumours (MPNSTs)

| Probe | | Probe Location | | | |
|---|---|---|---|---|---|
| | Chr | Start1 | End1 | Start2 | End2 |
| A | | | | | |
| 10_114686118_114690592_114727613_114729725_FF | 10 | 114690563 | 114690592 | 114729696 | 114729725 |
| 10_114686118_114690592_114743749_114745454_FF | 10 | 114690563 | 114690592 | 114745425 | 114745454 |
| 10_114686118_114690592_114773872_114776404_FF | 10 | 114690563 | 114690592 | 114776375 | 114776404 |
| 10_114686118_114690592_114794603_114795614_FF | 10 | 114690563 | 114690592 | 114795585 | 114795614 |
| 10_114686118_114690592_114804200_114807457_FF | 10 | 114690563 | 114690592 | 114807428 | 114807457 |
| 10_114686118_114690592_114821603_114822761_FF | 10 | 114690563 | 114690592 | 114822732 | 114822761 |
| 10_114686118_114690592_114845287_114849773_FF | 10 | 114690563 | 114690592 | 114849744 | 114849773 |
| 10_114686118_114690592_114885061_114889442_FF | 10 | 114690563 | 114690592 | 114889413 | 114889442 |
| 11_128342943_128345136_128481262_128489818_FF | 11 | 128345107 | 128345136 | 128489789 | 128489818 |
| 11_128410884_128413638_128489818_128498866_FF | 11 | 128413609 | 128413638 | 128498837 | 128498866 |
| 5_131857043_131861763_131874140_131875551_RF | 5 | 131857044 | 131857073 | 131875522 | 131875551 |
| 5_131874140_131875551_131894531_131901964_FF | 5 | 131875522 | 131875551 | 131901935 | 131901964 |
| 5_131874140_131875551_131920774_131922322_FF | 5 | 131875522 | 131875551 | 131922293 | 131922322 |
| 5_131874140_131875551_131942647_131945574_FF | 5 | 131875522 | 131875551 | 131945545 | 131945574 |
| 5_131874140_131875551_131985852_131989475_FF | 5 | 131875522 | 131875551 | 131989446 | 131989475 |
| 5_131882513_131883559_131942647_131945574_FF | 5 | 131883530 | 131883559 | 131945545 | 131945574 |
| 5_131882513_131883559_131966700_131972322_FF | 5 | 131883530 | 131883559 | 131972293 | 131972322 |
| 6_41890642_41893643_42057606_42059682_RR | 6 | 41890643 | 41890672 | 42057607 | 42057636 |
| 7_137557828_137562242_137656982_137661712_FF | 7 | 137562213 | 137562242 | 137661683 | 137661712 |
| 7_50818806_50825328_50840056_50842638_RR | 7 | 50818807 | 50818836 | 50840057 | 50840086 |
| 7_519231_522690_557100_558462_FF | 7 | 522661 | 522690 | 558433 | 558462 |
| 7_519231_522690_594007_596370_FF | 7 | 522661 | 522690 | 596341 | 596370 |
| 9_36907980_36909849_36932342_36938946_FF | 9 | 36909820 | 36909849 | 36938917 | 36938946 |
| 9_36951690_36954534_36987524_36991745_RF | 9 | 36951691 | 36951720 | 36991716 | 36991745 |
| 9_36961116_36962831_37038244_37041179_FF | 9 | 36962802 | 36962831 | 37041150 | 37041179 |

| Probe | | 4 kb Sequence Location | | | |
|---|---|---|---|---|---|
| | Chr | Start1 | End1 | Start2 | End2 |
| 10_114686118_114690592_114727613_114729725_FF | 10 | 114686593 | 114690592 | 114725726 | 114729725 |
| 10_114686118_114690592_114743749_114745454_FF | 10 | 114686593 | 114690592 | 114741455 | 114745454 |
| 10_114686118_114690592_114773872_114776404_FF | 10 | 114686593 | 114690592 | 114772405 | 114776404 |
| 10_114686118_114690592_114794603_114795614_FF | 10 | 114686593 | 114690592 | 114791615 | 114795614 |
| 10_114686118_114690592_114804200_114807457_FF | 10 | 114686593 | 114690592 | 114803458 | 114807457 |
| 10_114686118_114690592_114821603_114822761_FF | 10 | 114686593 | 114690592 | 114818762 | 114822761 |
| 10_114686118_114690592_114845287_114849773_FF | 10 | 114686593 | 114690592 | 114845774 | 114849773 |
| 10_114686118_114690592_114885061_114889442_FF | 10 | 114686593 | 114690592 | 114885443 | 114889442 |
| 11_128342943_128345136_128481262_128489818_FF | 11 | 128341137 | 128345136 | 128485819 | 128489818 |
| 11_128410884_128413638_128489818_128498866_FF | 11 | 128409639 | 128413638 | 128494867 | 128498866 |
| 5_131857043_131861763_131874140_131875551_RF | 5 | 131857044 | 131861043 | 131871552 | 131875551 |
| 5_131874140_131875551_131894531_131901964_FF | 5 | 131871552 | 131875551 | 131897965 | 131901964 |
| 5_131874140_131875551_131920774_131922322_FF | 5 | 131871552 | 131875551 | 131918323 | 131922322 |
| 5_131874140_131875551_131942647_131945574_FF | 5 | 131871552 | 131875551 | 131941575 | 131945574 |
| 5_131874140_131875551_131985852_131989475_FF | 5 | 131871552 | 131875551 | 131985476 | 131989475 |
| 5_131882513_131883559_131942647_131945574_FF | 5 | 131879560 | 131883559 | 131941575 | 131945574 |
| 5_131882513_131883559_131966700_131972322_FF | 5 | 131879560 | 131883559 | 131968323 | 131972322 |
| 6_41890642_41893643_42057606_42059682_RR | 6 | 41890643 | 41894642 | 42057607 | 42061606 |
| 7_137557828_137562242_137656982_137661712_FF | 7 | 137558243 | 137562242 | 137657713 | 137661712 |
| 7_50818806_50825328_50840056_50842638_RR | 7 | 50818807 | 50822806 | 50840057 | 50844056 |
| 7_519231_522690_557100_558462_FF | 7 | 518691 | 522690 | 554463 | 558462 |
| 7_519231_522690_594007_596370_FF | 7 | 518691 | 522690 | 592371 | 596370 |
| 9_36907980_36909849_36932342_36938946_FF | 9 | 36905850 | 36909849 | 36934947 | 36938946 |
| 9_36951690_36954534_36987524_36991745_RF | 9 | 36951691 | 36955690 | 36987746 | 36991745 |
| 9_36961116_36962831_37038244_37041179_FF | 9 | 36958832 | 36962831 | 37037180 | 37041179 |

| Probe | | Probe Location | | | |
|---|---|---|---|---|---|
| | Chr | Start1 | End1 | Start2 | End2 |
| B | | | | | |
| 1_26993831_26995281_27050122_27052726_FF | 1 | 26995252 | 26995281 | 27052697 | 27052726 |
| 17_67495529_67497867_67514127_67521454_RF | 17 | 67495530 | 67495559 | 67521425 | 67521454 |
| 19_11040234_11041901_11194011_11195243_FF | 19 | 11041872 | 11041901 | 11195214 | 11195243 |
| 19_11062377_11065717_11194011_11195243_RF | 19 | 11062378 | 11062407 | 11195214 | 11195243 |
| 19_52666823_52670053_52700693_52702643_FF | 19 | 52670024 | 52670053 | 52702614 | 52702643 |
| 21_39757299_39761915_39949058_39951313_FF | 21 | 39761886 | 39761915 | 39951284 | 39951313 |
| 21_39757299_39761915_40055526_40064997_FF | 21 | 39761886 | 39761915 | 40064968 | 40064997 |
| 21_39762207_39763468_40021022_40024449_FF | 21 | 39763439 | 39763468 | 40024420 | 40024449 |
| 5_42377143_42386021_42652698_42659568_FF | 5 | 42385992 | 42386021 | 42659539 | 42659568 |

TABLE 26b-continued

Neurofibromatosis (NF) probes - EpiSwitch ™ markers to stratify (A) Benign plexiform vs.
(B) Malignant Peripheral Nerve Sheath Tumours (MPNSTs)

| | | | | | |
|---|---|---|---|---|---|
| 5_42543850_42546292_42676184_42678827_RF | 5 | 42543851 | 42543880 | 42678798 | 42678827 |
| 6_41953588_41955459_42036433_42038022_RF | 6 | 41953589 | 41953618 | 42037993 | 42038022 |
| 6_41953588_41955459_42040682_42041908_RR | 6 | 41953589 | 41953618 | 42040683 | 42040712 |
| 7_116279520_116285670_116319380_116323843_RF | 7 | 116279521 | 116279550 | 116323814 | 116323843 |
| 7_116279520_116285670_116419719_116422284_RF | 7 | 116279521 | 116279550 | 116422255 | 116422284 |
| 7_116308668_116319380_116371770_116373950_RR | 7 | 116308669 | 116308698 | 116371771 | 116371800 |
| 7_137545600_137549019_137668037_137669463_RR | 7 | 137545601 | 137545630 | 137668038 | 137668067 |
| 7_50657698_50658729_50784135_50786449_FF | 7 | 50658700 | 50658729 | 50786420 | 50786449 |
| 8_108267104_108269307_108407566_108418839_RR | 8 | 108267105 | 108267134 | 108407567 | 108407596 |
| 8_108277745_108282069_108528062_108532217_FF | 8 | 108282040 | 108282069 | 108532188 | 108532217 |
| 8_108444846_108453607_108528062_108532217_FF | 8 | 108453578 | 108453607 | 108532188 | 108532217 |
| 8_99432076_99435027_99521801_99527715_RF | 8 | 99432077 | 99432106 | 99527686 | 99527715 |
| 8_99486386_99490632_99554813_99560156_FF | 8 | 99490603 | 99490632 | 99560127 | 99560156 |
| 8_99521801_99527715_99826498_99828247_RF | 8 | 99521802 | 99521831 | 99828218 | 99828247 |
| 8_99541449_99550447_99646209_99658080_RR | 8 | 99541450 | 99541479 | 99646210 | 99646239 |
| 8_99792735_99799194_99962638_99967147_RF | 8 | 99792736 | 99792765 | 99967118 | 99967147 |

| | 4 kb Sequence Location | | | | |
|---|---|---|---|---|---|
| | Chr | Start1 | End1 | Start2 | End2 |
| 1_26993831_26995281_27050122_27052726_FF | 1 | 26991282 | 26995281 | 27048727 | 27052726 |
| 17_67495529_67497867_67514127_67521454_RF | 17 | 67495530 | 67499529 | 67517455 | 67521454 |
| 19_11040234_11041901_11194011_11195243_FF | 19 | 11037902 | 11041901 | 11191244 | 11195243 |
| 19_11062377_11065717_11194011_11195243_RF | 19 | 11062378 | 11066377 | 11191244 | 11195243 |
| 19_52666823_52670053_52700693_52702643_FF | 19 | 52666054 | 52670053 | 52698644 | 52702643 |
| 21_39757299_39761915_39949058_39951313_FF | 21 | 39757916 | 39761915 | 39947314 | 39951313 |
| 21_39757299_39761915_40055526_40064997_FF | 21 | 39757916 | 39761915 | 40060998 | 40064997 |
| 21_39762207_39763468_40021022_40024449_FF | 21 | 39759469 | 39763468 | 40020450 | 40024449 |
| 5_42377143_42386021_42652698_42659568_FF | 5 | 42382022 | 42386021 | 42655569 | 42659568 |
| 5_42543850_42546292_42676184_42678827_RF | 5 | 42543851 | 42547850 | 42674828 | 42678827 |
| 6_41953588_41955459_42036433_42038022_RF | 6 | 41953589 | 41957588 | 42034023 | 42038022 |
| 6_41953588_41955459_42040682_42041908_RR | 6 | 41953589 | 41957588 | 42040683 | 42044682 |
| 7_116279520_116285670_116319380_116323843_RF | 7 | 116279521 | 116283520 | 116319844 | 116323843 |
| 7_116279520_116285670_116419719_116422284_RF | 7 | 116279521 | 116283520 | 116418285 | 116422284 |
| 7_116308668_116319380_116371770_116373950_RR | 7 | 116308669 | 116312668 | 116371771 | 116375770 |
| 7_137545600_137549019_137668037_137669463_RR | 7 | 137545601 | 137549600 | 137668038 | 137672037 |
| 7_50657698_50658729_50784135_50786449_FF | 7 | 50654730 | 50658729 | 50782450 | 50786449 |
| 8_108267104_108269307_108407566_108418839_RR | 8 | 108267105 | 108271104 | 108407567 | 108411566 |
| 8_108277745_108282069_108528062_108532217_FF | 8 | 108278070 | 108282069 | 108528218 | 108532217 |
| 8_108444846_108453607_108528062_108532217_FF | 8 | 108449608 | 108453607 | 108528218 | 108532217 |
| 8_99432076_99435027_99521801_99527715_RF | 8 | 99432077 | 99436076 | 99523716 | 99527715 |
| 8_99486386_99490632_99554813_99560156_FF | 8 | 99486633 | 99490632 | 99556157 | 99560156 |
| 8_99521801_99527715_99826498_99828247_RF | 8 | 99521802 | 99525801 | 99824248 | 99828247 |
| 8_99541449_99550447_99646209_99658080_RR | 8 | 99541450 | 99545449 | 99646210 | 99650209 |
| 8_99792735_99799194_99962638_99967147_RF | 8 | 99792736 | 99796735 | 99963148 | 99967147 |

TABLE 27

ALS Gene Data

| GENE | Description | Comments | p-value |
|---|---|---|---|
| FCGR2B; FCGR3A | Fc Fragment Of IgG, Low Affinity IIb and IIa, Receptor | IgG binding | 9.75E−05 |
| CR1 | Complement Component (3b/4b) Receptor 1 (Knops Blood Group) | complement component C3b binding and complement component C4b receptor activity | 0.00010036 |
| DNM3 | Dynamin 3 | GTP binding and GTPase activity | 0.00067328 |
| RAG1 | Recombination Activating Gene 1 | ubiquitin-protein ligase activity and protein homodimerization activity | 0.00165575 |
| PIK3R1 | Phosphoinositide-3-Kinase, Regulatory Subunit 1 (Alpha) | protein phosphatase binding and 1-phosphatidylinositol binding | 0.00350494 |
| TRAF6 | TNF Receptor-Associated Factor 6, E3 Ubiquitin Protein Ligase | protein kinase binding and signal transducer activity | 0.00408044 |
| AP2A2 | Adaptor-Related Protein Complex 2, Alpha 2 Subunit | protein transporter activity and lipid binding | 0.00666831 |
| ARHGEF7 | Rho Guanine Nucleotide Exchange Factor (GEF) 7 | phospholipid binding and guanyl-nucleotide exchange factor activity | 0.00771418 |
| CLEC5A | C-Type Lectin Domain Family 5, Member A | carbohydrate binding and virus receptor activity | 0.00788381 |
| TREM1 | Triggering Receptor Expressed On Myeloid Cells 1 | receptor activity | 0.00795844 |
| FYN | FYN Oncogene Related To SRC, FGR, YES | ion channel binding and identical protein binding | 0.01316089 |
| KIR2DL4; KIR3DL1; KIR2DL3 | Killer Cell Immunoglobulin-Like Receptor, Two Domains, Long Cytoplasmic Tail, 4/Killer Cell Immunoglobulin-Like Receptor, Three Domains, Long Cytoplasmic Tail, 1/Killer Cell Immunoglobulin-Like Receptor, Two Domains, Long Cytoplasmic Tail, 3 | transmembrane signaling receptor activity/HLA-B specific inhibitory MHC class I receptor activity/antigen binding and receptor activity | 0.01380768 |

TABLE 27-continued

ALS Gene Data

| GENE | Description | Comments | p-value |
|---|---|---|---|
| PTPRC | Protein Tyrosine Phosphatase, Receptor Type, C | protein kinase binding and transmembrane receptor protein tyrosine phosphatase activity | 0.01507433 |
| ICAM1 | Intercellular Adhesion Molecule 1 | integrin binding and receptor activity | 0.01604022 |
| ULBP1 | UL16 Binding Protein 1 | antigen binding and natural killer cell lectin-like receptor binding | 0.01680033 |
| MYD88 | Myeloid Differentiation Primary Response 88 | identical protein binding and TIR domain binding | 0.028 |
| ITGAM | Integrin, Alpha M (Complement Component 3 Receptor 3 Subunit) | heparin binding and heparan sulfate proteoglycan binding | 0.03116451 |
| LILRB4 | Leukocyte Immunoglobulin-Like Receptor, Subfamily B (With TM And ITIM Domains), Member 4 | antigen binding and receptor activity | 0.04403324 |
| IKBKB | Inhibitor Of Kappa Light Polypeptide Gene Enhancer In B-Cells, Kinase Beta | protein heterodimerization activity and protein homodimerization activity | 0.04625161 |
| FCGR3A | Fc Fragment Of IgG, Low Affinity IIIa, Receptor (CD16a) | IgG binding | 0.0579917 |
| GLYCAM1 | Glycosylation Dependent Cell Adhesion Molecule 1 (Pseudogene) | regulation of immune response | 0.05817306 |
| DDOST | Dolichyl-Diphosphooligosaccharide-Protein Glycosyltransferase Subunit (Non-Catalytic) | oligosaccharyl transferase activity and dolichyl-diphosphooligosaccharide-protein glycotransferase activity | 0.06418361 |
| RAG2; RAG1 | Recombination Activating Gene 2 and 1 | chromatin binding and methylated histone residue binding/ubiquitin-protein ligase activity and protein homodimerization activity | 0.06418361 |
| VCAM1 | Vascular Cell Adhesion Molecule 1 | integrin binding and primary amine oxidase activity | 0.06418361 |
| IGKV3-11 | Immunoglobulin Kappa Variable 3-11 | antigen/protein binding | 0.07051211 |
| IGKV3-20 | Immunoglobulin Kappa Vaiiable 3-20 | antigen binding | 0.07051211 |
| IRAK1 | lnterleukin-1 Receptor-Associated Kinase 1 | protein serine/threonine kinase activity and protein homodimerization activity | 0.07051211 |
| SYK | Spleen Tyrosine Kinase | protein tyrosine kinase activity and protein kinase binding | 0.0812399 |
| FGFR1 | Fibroblast Growth Factor Receptor 1 | heparin binding and protein homodimerization activity | 0.08977269 |
| IGKV3-7 | Immunoglobulin Kappa Variable 3-7 (Non-Functional) | protein binding | 0.08977269 |
| PRKCQ | Protein Kinase C, Theta | ubiquitin-protein ligase activity and identical protein binding | 0.0976878 |
| GHR | Growth Hormone Receptor | protein phosphatase binding and protein homodimerization activity | 0.10265608 |
| SH3KBP1 | SH3-Domain Kinase Binding Protein 1 | SH3 domain binding | 0.11086917 |
| MS4A2 | Membrane-Spanning 4-Domains, Subfamily A, Member 2 | SH2 domain binding and protein kinase binding | 0.11608661 |
| EGFR | Epidermal Growth Factor Receptor | chromatin binding anddentical protein binding | 0.11651883 |
| BLNK | B-Cell Linker | SH3/SH2 adaptor activity and transmembrane receptor protein tyrosine kinase adaptor activity | 0.1175276 |
| CD96 | CD96 Molecule | protein binding | 0.12443215 |
| DAPP1 | Dual Adaptor Of Phosphotyrosine And 3-Phosphoinositides | phospholipid binding and phosphatidylinositol-3,4,5-trisphosphate binding | 0.1574769 |
| ART1 | ADP-Ribosyltransferase 1 | NAD(P)-+protein-arginine ADP-ribosyltransferase activity and NAD+ ADP-ribosyltransferase activity | 0.16237882 |
| C4B | Complement Component 4B | endopeptidase inhibitor activity | 0.16237882 |
| CCR2 | Chemokine (C-C Motif) Receptor 2 | C-C chemokine receptor activity and protein homodimerization activity | 0.16237882 |
| CD180 | CD180 Molecule | protein binding | 0.16237882 |
| CD274 | CD274 Molecule | protein binding | 0.16237882 |
| CD28 | CD28 Molecule | SH3/SH2 adaptor activity anddentical protein binding | 0.16237882 |
| CD3D | CD3d Molecule, Delta (CD3-TCR Complex) | transmembrane signaling receptor activity and protein heterodimerization | 0.16237882 |
| CD3G; CD3D | CD3g Molecule, Gamma (CD3-TCR Complex)/CD3d Molecule, Delta (CD3- TCR Complex) | activity receptor signaling complex scaffold activity and protein heterodimerization activity/transmembrane signaling receptor activity and protein heterodimerization activity | 0.16237882 |
| CD40LG | CD40 Ligand | CD40 receptor binding and cytokine activity | 0.16237882 |
| ICAM1; ICAM4 | Intercellular Adhesion Molecule 1 and 4 | integrin binding and receptor activity | 0.16237882 |
| IFITM1; IFITM2 | Interferon Induced Transmembrane Protein 1 and 2 | receptor signaling protein activity | 0,16237882 |
| IFITM3 | Interferon Induced Transmembrane Protein 3 | receptor signaling and protein binding activity | 0.16237882 |
| IGLC3; IGLC7; IGLC2; IGLC1; IGLC6 | Immunoglobulin Lambda Constant 3/7/2/1/6 | antigen binding | 0.16237882 |
| IKBKG | Inhibitor Of Kappa Light Polypeptide Gene Enhancer In B-Cells, Kinase Gamma | protein homodimerization activity and signal transducer activity | 0.16237882 |
| IRS2 | Insulin Receptor Substrate 2 | phospholipid binding and signal transducer activity | 0.16237882 |
| ITGA4 | Integrin, Alpha 4 (Antigen CD49D, Alpha 4 Subunit Of VLA-4 Receptor) | fibronectin binding | 0.16237882 |
| ITGAV | Integrin, Alpha V | protein kinase C binding and virus receptor activity | 0.16237882 |
| KIR2DS4; KIR3DL1 | Killer Cell Immunoglobulin-Like Receptor, Two Domains, Short Cytoplasmic Tail, 4/Killer Cell Immunoglobulin-Like Receptor, Three Domains, Long Cytoplasmic Tail, 1 | receptor activity/HLA-B specificnhibitory MHC class I receptor activity | 0.16237882 |
| LILRB2 | Leukocyte Immunoglobulin-Like Receptor, Subfamily B (With TM And ITIM Domains), Member 2 | MHC class I protein binding and receptor activity | 0.16237882 |

TABLE 27-continued

ALS Gene Data

| GENE | Description | Comments | p-value |
|---|---|---|---|
| PDCD1LG2 | Programmed Cell Death 1 Ligand 2 | protein binding | 0.16237882 |
| SIGIRR | Single Immunoglobulin And Toll-Interleukin 1 Receptor (TIR) Domain | protein binding | 0.16237882 |
| TLR1; TLR6 | Toll-Like Receptor 1 and 6 | transmembrane signaling receptor activity and protein heterodimerization activity | 0.16237882 |
| VPREB1 | Pre-B Lymphocyte 1 | antigen binding | 0.16237882 |
| DNM2 | Dynamin 2 | protein kinase binding and GTP binding | 0.16968984 |
| AGER | Advanced Glycosylation End Product-Specific Receptor | S100 protein binding and receptor activity | 0.1879858 |
| CCNO | Cyclin O | protein kinase binding and uracil DNA N-glycosylase activity | 0.1879858 |
| KRAS | Kirsten Rat Sarcoma Viral Oncogene Homolog | GDP binding and GTP binding | 0.1879858 |
| LILRB1 | Leukocyte Immunoglobulin-Like Receptor, Subfamily B (With TM And ITIM Domains), Member 1 | MHC class I protein binding and protein homodimerization activity | 0.1879858 |
| TLR2 | Toll-Like Receptor 2 | transmembrane signaling receptor activity and protein heterodimerization activity | 0.1879858 |
| B2M | beta-2-microglobulin | identical protein binding | 0.20978301 |
| ADCY4 | Adenylate Cyclase 4 | adenylate cyclase activity | 0.21283252 |
| IL7R | Interleukin 7 Receptor | antigen binding andnterleukin-7 receptor activity | 0.21283252 |
| CR1; CR2 | Complement Component (3b/4b) Receptor 1/Complement component C3b binding and complement component C4b receptor activity | complement component C3b binding and complement component C4b receptor activity/protein homo-dimerization activity and complement receptor activity | 0.25289217 |
| FCGR1A | Fc Fragment Of IgG, High Affinity Ia, Receptor (CD64) | IgG binding and receptor signaling protein activity | 0.2547195 |
| CCR6 | Chemokine (C-C Motif) Receptor 6 | C-C chemokine receptor activity and receptor activity | 0.25953148 |
| ITGB2 | Integrin, Beta 2 (Complement Component 3 Receptor 3 And 4 Subunit) | protein kinase binding and glycoprotein binding | 0.25953148 |
| RFXAP | Regulatory Factor X-Associated Protein | transcription coactivator activity and sequence-specific DNA binding transcription factor activity | 0.25953148 |
| ITGB5 | Integrin, Beta 5 | integrin binding and receptor activity | 0.27876985 |
| ADCY8 | Adenylate Cyclase 8 (Brain) | calcium- and calmodulin-responsive adenylate cyclase activity and adenylate cyclase activity | 0.29005636 |
| AICDA | Activation-Induced Cytidine Deaminase | cytidine deaminase activity | 0.29840344 |
| ATPIF1; PTAFR | ATPase Inhibitory Factor 1/Platelet-Activating Factor Receptor | enzymenhibitor activity and protein homodimerization activity/G-protein coupled receptor activity and lipopolysaccharide binding | 0.29840344 |
| CD3G | CD3g Molecule, Gamma (CD3-TCR Complex) | receptor signaling complex scaffold activity and protein heterodimerization activity | 0.29840344 |
| CD81 | CD81 Molecule | MHC class II protein complex binding | 0.29840344 |
| CFB | Complement Factor B | complement binding and serine-type endopeptidase activity | 0.29840344 |
| CXADR | Coxsackie Virus And Adenovirus Receptor | PDZ domain binding and identical protein binding | 0.29840344 |
| ERBB2 | V-Erb-B2 Avian Erythroblastic Leukemia Viral Oncogene Homolog 2 | protein C-terminus binding and identical protein binding | 0.29840344 |
| ERBB3 | V-Erb-B2 Avian Erythroblastic Leukemia Viral Oncogene Homolog 3 | protein heterodimerization activity and protein homodimerization activity | 0.29840344 |
| FCER1A | Fc Fragment Of IgE, High Affinity I, Receptor For; Alpha Polypeptide | IgE receptor activity and IgE binding | 0.29840344 |
| HCST | Hematopoietic Cell Signal Transducer | phosphatidylinositol 3-kinase binding | 0.29840344 |
| IGHV1-46 | Immunoglobulin Heavy Variable 1-46 | protein binding | 0.29840344 |
| IL3RA; CSF2RA | Interleukin 3 Receptor, Alpha (Low Affinity)/Colony Stimulating Factor 2 Receptor, Alpha, Low-Affinity | interleukin-3 receptor activity/cytokine receptor activity and receptor activity | 0.29840344 |
| ITGB7 | Integrin, Beta 7 | virus receptor activity | 0.29840344 |
| KIR2DS4; KIR3DL1; KIR3DL2 | Killer Cell Immunoglobulin-Like Receptor, Two Domains, Short Cytoplasmic Tail, 4/Killer Cell Immunoglobulin-Like Receptor, Three Domains, Long Cytoplasmic Tail, 1/ Killer Cell Immunoglobulin-Like Receptor, Three Domains, Long Cytoplasmic Tail, 2 | signalling activity/HLA-B specific inhibitory MHC class I receptor activity/Receptor on natural killer (NK) cells for HLA-A alleles | 0.29840344 |
| KIR3DL1 | Killer Cell Immunoglobulin-Like Receptor, Three Domains, Long Cytoplasmic Tail, 1 | HLA-B specific inhibitory MHC class I receptor activity | 0.29840344 |
| MADCAM1 | Mucosal Vascular Addressin Cell Adhesion Molecule 1 | protrein binding | 0.29840344 |
| MAP3K7 | Mitogen-Activated Protein Kinase Kinase Kinase 7 | protein serine/threonine kinase activity and protein kinase activity | 0.29840344 |
| NFKB2 | Nuclear Factor Of Kappa Light Polypeptide Gene Enhancer In B-Cells 2 (P49/P100) | transcription coactivator activity and sequence-specific DNA binding transcription factor activity | 0.29840344 |
| PDCD1 | Programmed Cell Death 1 | signal transducer activity | 0.29840344 |
| SIGLEC14 | Sialic Acid Binding Ig-Like Lectin 14 | protein binding | 0.29840344 |
| SIGLEC15 | Sialic Acid Binding Ig-Like Lectin 15 | protein binding | 0.29840344 |
| SIRPB1 | Signal-Regulatory Protein Beta 1 | protein binding | 0.29840344 |
| TIRAP | Toll-Interleukin 1 Receptor (TIR) Domain Containing Adaptor Protein | protein binding, bridging and protein homodimerization activity | 0.29840344 |
| TLR10 | Toll-Like Receptor 10 | transmembrane signaling receptor activity | 0.29840344 |
| TYROBP; HCST | TYRO Protein Tyrosine Kinase Binding Protein/ Hematopoietic Cell Signal Transducer | receptor signaling protein activity and identical protein binding/Hematopoietic Cell Signal Transducer | 0.29840344 |

TABLE 27-continued

ALS Gene Data

| GENE | Description | Comments | p-value |
| --- | --- | --- | --- |
| VAV1; C3 | Vav 1 Guanine Nucleotide Exchange Factor/ Complement Component 3 | sequence-specific DNA binding transcription factor activity and guanyl-nucleotide exchange factor activity/C5L2 anaphylatoxin chemotactic receptor binding and receptor binding | 0.29840344 |

TABLE 28

Pre-Type 2 Diabetes Gene Data

| GENE | Description | Table 28 Comments | p-value |
| --- | --- | --- | --- |
| ABCC8 | ATP-Binding Cassette, Sub-Family C (CFTR/MRP), Member 8 | ion channel binding andpotassiumon transmembrane transporter activity | 0.005571163 |
| ADCY5 | Adenylate Cyclase 5 | adenylate cyclase binding and protein heterodimerization activity | 0.000309237 |
| CACNA1C | Calcium Channel, Voltage-Dependent, L Type, Alpha 1C Subunit | alpha-actinin binding and calmodulin binding | 0.004207097 |
| CDKN2A | Cyclin-Dependent Kinase Inhibitor 2A | protein kinase binding and p53 binding | 0.001156338 |
| CYB5R4 | Cytochrome B5 Reductase 4 | NAD(P)H oxidase activity and heme binding | 0.001648199 |
| CYP2C9 | Cytochrome P450, Family 2, Subfamily C, Polypeptide 9 | electron carrier activity and heme binding | 3.00E−05 |
| DGKB | Diacylglycerol Kinase, Beta 90kDa | diacylglycerol kinase activity andcalciumon binding | 0.000440459 |
| ICAM1 | Intercellular Adhesion Molecule 1 | integrin binding and receptor activity | 0.009727539 |
| IGF2 | Insulin-Like Growth Factor 2 (Somatomedin A) | growth factor activity andnsulin receptor binding | 0.013781657 |
| INS | Insulin | protease binding anddentical protein binding | 0.005779532 |
| KCNJ11 | Potassium Inwardly-Rectifying Channel, Subfamily J, Member 11 | protein C-terminus binding andvoltage-gated potassium channel activity | 0.000203298 |
| LEP | Leptin | growth factor activity and peptide hormone receptor binding | 0.010562363 |
| MAPK10 | Mitogen-Activated Protein Kinase 10 | JUN kinase activity and MAP kinase kinase activity | 0.010774536 |
| PAX4 | Paired Box 4 | double-stranded DNA binding and sequence-specific DNA binding transcription factor activity | 0.009727539 |
| PIK3R3 | Phospnoinositide-3-Kinase, Regulatory Subunit 3 (Gamma) | 1 -phosphatidylinositol-3-kinase activity and phosphatidylinositol 3-kinase regulator activity | 0.005779532 |
| PTPRD | Protein Tyrosine Phosphatase, Receptor Type, D | transmembrane receptor protein tyrosine phosphatase activity and receptor binding | 0.010774536 |
| SREBF1 | Sterol Regulatory Element Binding Transcription Factor 1 | chromatin binding and sequence-specific DNA binding transcription factor activity | 0.00036609 |
| TASP1 | Taspase, Threonine Aspartase, 1 | threonine-type endopeptidase activity | 0.003377072 |
| TNFRSF1B | Tumor Necrosis Factor Receptor Superfamily, Member 1B | tumor necrosis factor-activated receptor activity and ubiquitin protein ligase binding | 0.005226941 |
| TSPAN8 | Tetraspanin 8 | signal transducer activity | 0.016203495 |
| ASIP | Agouti Signaling Protein | type 4 melanocortin receptor binding and receptor binding | 0.021488806 |
| INSR | Insulin Receptor | SH2 domain binding and GTP binding | 0.021488806 |
| CAMK1D | Calcium/Calmodulin-Dependent Protein Kinase ID | calmodulin binding and calmodulin-dependent protein kinase activity | 0.029182439 |
| UBA52P6 | Ubiquitin A-52 Residue Ribosomal Protein Fusion Product 1 Pseudogene 6 | pseudogene | 0.030482606 |
| SLC30A8 | Solute Carrier Family 30 (Zinc Transporter), Member 8 | zincon transmembrane transporter activityand protein homodimerization activity | 0.033480808 |
| CYB5A | Cytochrome B5 Type A (Microsomal) | cytochrome-c oxidase activity and enzyme binding | 0.041435693 |
| CDKN2B | Cyclin-Dependent Kinase Inhibitor 2B (P15, Inhibits CDK4) | cyclin-dependent protein serine/threonine kinasenhibitor activity and protein kinase binding | 0.059165859 |
| ZFAND6 | Zinc Finger, AN 1-Type Domain 6 | polyubiquitin binding | 0.059165859 |
| NOTCH2 | Neurogenic Locus Notch Homolog Protein 2 | receptor activity and calciumon binding | 0.064334474 |
| TIMP1 | Tissue Inhibitor Of Metalloproteinases 1 | metalloendopeptidasenhibitor activity | 0.063526643 |
| AGT | Angiotensinogen (Serpin Peptidase Inhibitor, Clade A, Member 8) | growth factor activity and hormone activity | 0.072394301 |
| HSD17B3 | Hydroxysteroid (17-Beta) Dehydrogenase 3 | testosterone 17-beta-dehydrogenase (NADP+) activity | 0.072394301 |
| RBP4 | Retinol Binding Protein 4, Plasma | retinal binding and protein heterodimerization activity | 0.072394301 |
| ADIPOR1 | Adiponectin Receptor 1 | protein kinase binding anddentical protein binding | 0.077957576 |
| AKT1 | V-Akt Murine Thymoma Viral Oncogene Homolog 1 | enzyme binding anddentical protein binding | 0.077957576 |
| VEGFA | Vascular Endothelial Growth Factor A | protein heterodimerization activity and protein homodimerization activity | 0.077957576 |
| ARAP1 | ArfGAP With RhoGAP Domain, Ankyrin Repeat And PH Domain 1 | ARF GTPase activator activity and phosphatidylinositol-3,4,5-trisphosphate binding | 0.091540286 |
| SUCLG2 | Succinate-CoA Ligase, GDP-Forming, Beta Subunit | succinate-CoA ligase (GDP-forming) activity and GTP binding | 0.204362567 |

TABLE 29

Type 2 Diabetes Gene Data

| GENE | Description | Table 29 Comments | p-value |
| --- | --- | --- | --- |
| IDE | Insulin-Degrading Enzyme | ATPase activity and protein homodimerization activity | 1.49E−05 |
| SDHB | Succinate Dehydrogenase Complex, Subunit B, Iron Sulfur (Ip) | electron carrier activity and 2ron, 2 sulfur cluster binding | 2.36E−05 |
| SREBF1 | Sterol Regulatory Element Binding Transcription Factor 1 | chromatin binding and sequence-specific DNA binding transcription factor activity | 0.00011264 |
| AGT | Angiotensinogen (Serpin Peptidase Inhibitor, Clade A, Member 8) | growth factor activity and hormone activity | 0.00043908 |
| CDKN2B-AS1 | CDKN2B Antisense RNA 1 | interacts with both polycomb repressive complex-1 (PRC1) and -2 (PRC2), and may function as a regulator for epigenetic transcriptional repression | 0.00054565 |
| ANKRD55 | Ankyrin Repeat Domain 55 | protein binding | 0.00065244 |
| SLC2A2 | Solute Carrier Family 2 (Facilitated Glucose Transporter), Member 2 | hexose transmembrane transporter activity and dehydroascorbic acid transporter activity | 0.00080874 |
| CYP2C9 | Cytochrome P450, Family 2, Subfamily C, Polypeptide 9 | electron carrier activity and heme binding | 0.00085093 |
| ICAM1 | Intercellular Adhesion Molecule 1 | integrin binding and receptor activity | 0.00173236 |
| KCNJ11 | Potassium Inwardly-Rectifying Channel, Subfamily J, Member 11 | protein C-terminus binding andvoltage-cated potassium channel activity | 0.00225223 |
| CAMK1D | Calcium/Calmodulin-Dependent Protein Kinase ID | calmodulin binding and calmodulin-dependent protein kinase activity | 0.00279065 |
| GIPR | Gastric Inhibitory Polypeptide Receptor | transmembrane signaling receptor activity and gastric inhibitory peptide receptor activity | 0.003136 |
| CACNA1C | Calcium Channel, Voltage-Dependent, L Type, Alpha 1C Subunit | alpha-actinin binding and calmodulin binding | 0.00621182 |
| VEGFA | Vascular Endothelial Growth Factor A | protein heterodimerization activity and protein homodimerization activity | 0.00678606 |
| GHRL | Ghrelin/Obestatin Prepropeptide | growth hormone-releasing hormone activity and G-protein coupled receptor binding | 0.00808286 |
| TLE1 | Transducin-Like Enhancer Of Split 1 (E(Sp1) Homolog, Drosophila) | chromatin binding and RNA polymerase II transcription corepressor activity | 0.00808286 |
| AVP | Arginine Vasopressin | protein kinase activity and receptor binding | 0.00849023 |
| LTA | Lymphotoxin Alpha | tumor necrosis factor receptor binding and receptor binding | 0.00947722 |
| CYB5R4 | Cytochrome B5 Reductase 4 | NAD(P)H oxidase activity and heme binding | 0.01132881 |
| ADCY5 | Adenylate Cyclase 5 | adenylate cyclase binding and protein heterodimerization activity | 0.0137542 |
| TASP1 | Taspase, Threonine Aspartase, 1 | hreonine-type endopeptidase activity | 0.01378654 |
| PAX4 | Paired Box 4 | double-stranded DNA binding and sequence-specific DNA binding transcription factor activity | 0.01389652 |
| DGKB | Diacylglycerol Kinase, Beta 90kDa | diacylglycerol kinase activity andcaldumon binding | 0.01468697 |
| SOCS2 | Suppressor Of Cytokine Signaling 2 | SH3/SH2 adaptor activity and growth hormone receptor binding | 0.01677982 |
| CYB5A | Cytochrome B5 Type A (Microsomal) | cytochrome-c oxidase activity and enzyme binding | 0.01698184 |
| SOCS3 | Suppressor Of Cytokine Signaling 3 | protein kinasenhibitor activity | 0.02282234 |
| TNF | Tumor Necrosis Factor | cytokine activity anddentical protein binding | 0.02282234 |
| H19 | H19, Imprinted Maternally Expressed Transcript (Non-Protein Coding) | expresses a non-coding RNA, and functions as a tumor suppressor | 0.02357461 |
| EDN1 | Endothelin 1 | endothelin A receptor binding and cytokine activity | 0.02779399 |
| HSD3B2 | Hydroxy-Delta-5-Steroid Dehydrogenase, 3 Beta- And Steroid Delta-lsomerase 2 | 3-beta-hydroxy-delta5-steroid dehydrogenase activity and steroid delta-isomerase activity | 0.02779399 |
| SELE | Selectin E | transmembrane signaling receptor activity and sialic acid binding | 0.03638118 |
| ADIPOQ | Adiponectin, C1Q And Collagen Domain Containing | protein homodimerization activity and receptor binding | 0.03775263 |
| GIP | Gastric Inhibitory Polypeptide | hormone activity | 0.03775263 |
| TCF7L2 | Transcription Factor 7-Like 2 (T-Cell Specific, HMG-Box) | chromatin binding and sequence-specific DNA binding transcription factor activity | 0.04116208 |
| NFKB1 | Nuclear Factor Of Kappa Light Polypeptide Gene Enhancer In B-Cells 1 | transcription factor binding andsequence-specific DNA binding transcription factor activity | 0.04503238 |
| MTOR | Mechanistic Target Of Rapamycin (Serine/Threonine Kinase) | drug binding and protein serine/threonine kinase activity | 0.05115907 |
| TSPAN8 | Tetraspanin 8 | signal transducer activity | 0.05432511 |
| GSTT1 | Glutathione S-Transferase Theta 1 | glutathione transferase activity and glutathione peroxidase activity | 0.05531008 |
| PRC1 | Protein Regulator Of Cytokinesis 1 | microtubule binding anddentical protein binding | 0.05531008 |
| VPS26A | Vacuolar Protein Sorting 26 Homolog A (S. Pombe) | protein transporter activity | 0.05531008 |
| KCNQ1 | Potassium Voltage-Gated Channel, KQT-Like Subfamily, Member 1 | calmodulin binding and voltage-gated potassium channel activity | 0.05682953 |
| ATP5A1 | ATP Synthase, HMitochondrial F1 Complex, Alpha Subunit 1, Cardiac Muscle | ATPase activity and proton-transporting ATPase activity, rotational mechanism | 0.06838534 |
| WFS1 | Wolfram Syndrome 1 (Wolframin) | ATPase binding and transporter activity | 0.0718483 |
| CCL2 | Chemokine (C-C Motif) Ligand 2 | heparin binding and receptor binding | 0.0726416 |
| ELOVL6 | ELOVL Fatty Acid Elongase 6 | transferase activity, transferring acyl groups other than amino-acyl groups | 0.0726416 |
| IL6 | Interleukin 6 (Interferon, Beta 2) | interleukin-6 receptor binding and cytokine activity | 0.0726416 |
| UCP2 | Uncoupling Protein 2 (Mitochondrial, Proton Carrier) | mitochondrial transporter proteins | 0.0726416 |
| ESR1 | Estrogen Receptor 1 | chromatin binding and sequence-specific DNA binding transcription factor activity | 0.07850912 |

TABLE 29-continued

Type 2 Diabetes Gene Data

| GENE | Description | Table 29 Comments | p-value |
|---|---|---|---|
| NR3C1 | Nuclear Receptor Subfamily 3, Group C, Member 1 (Glucocorticoid Receptor | protein dimerization activity and sequence-specific DNA binding transcription factor activity | 0.08595811 |
| ACADM | Acyl-CoA Dehydrogenase, C-4 To C-12 Straight Chain | acyl-CoA dehydrogenase activity anddentical protein binding | 0.08665649 |
| PNISR | PNN-Interacting Serine/Arginine-Rich Protein | poly(A) RNA binding | 0.08665649 |
| PTPRD | Protein Tyrosine Phosphatase, Receptor Type, D | transmembrane receptor protein tyrosine phosphatase activity and receptor binding | 0.08744676 |
| PSMG1 | Proteasome (Prosome, Macropain) Assembly Chaperone 1 | protein binding | 0.09956542 |
| LDLR | Low Density Lipoprotein Receptor | low-density lipoprotein particle binding and calciumon binding | 0.10538293 |
| PDHB | Pyruvate Dehydrogenase (Lipoamide) Beta | pyruvate dehydrogenase activity andpyruvate dehydrogenase (acetyl-transferring) activity | 0.10538293 |
| CCKAR | Cholecystokinin A Receptor | cholecystokinin receptor activity | 0.12483961 |
| INS | insulin | protease binding anddentical protein binding | 0.12483961 |
| MT1X | Metallothionein 1X | metalon binding | 0.12483961 |
| PIK3R3 | Phosphoinositide-3-Kinase, Regulatory Subunit 3 (Gamma) | 1-phosphatidylinositol-3-kinase activity and phosphatidylinositol 3-kinase regulator activity | 0.12483961 |
| SHBG | Sex Hormone-Binding Globulin | androgen binding and protein homodimerization activity | 0.12483961 |
| ZBED3 | Zinc Finger, BED-Type Containing 3 | DNA/protein/metalon binding | 012483961 |
| MAPK8IP1 | Mitogen-Activated Protein Kinase 8 Interacting Protein 1 | protein kinase binding and kinesin binding | 0.12560157 |
| CRHR1 | Corticotropin Releasing Hormone Receptor 1 | corticotrophin-releasing factor receptor activity and protein complex binding | 0.14071272 |
| CDK10 | Cyclin-Dependent Kinase 10 | cyclin-dependent protein serine/threonine kinase activity | 0.1462871 |
| CYBA | Cytochrome B-245, Alpha Polypeptide | protein heterodimerization activity and heme binding | 0.1462871 |
| GCDH | Glutaryl-CoA Dehydrogenase | fatty-acyl-CoA binding and flavin adenine dinucleotide binding | 0.1462871 |
| GPX1 | Glutathione Peroxidase 1 | SH3 domain binding and glutathione peroxidase activity | 0.1462871 |
| SLC9A1 | Solute Carrier Family 9, Subfamily A (NHE1, Cation Proton Antiporter 1), Member 1 | sodium hydrogen antiporter activityand calmodulin binding | 0.1462871 |
| ATF3 | Activating Transcription Factor 3 | identical protein binding and sequence-specific DNA binding transcription factor activity | 0.14660664 |
| CCR5 | Chemokine (C-C Motif) Receptor 5 (Gene/Pseudogene) | actin binding and coreceptor activity | 0.14660664 |
| FADS1 | Fatty Acid Desaturase 1 | oxidoreductase activity andron binding | 0.14660664 |
| AP3S2 | Adaptor-Related Protein Complex 3, Sigma 2 Subunit | protein transporter activity | 0.15374807 |
| CTRB1 | Chymotrypsinogen B1 | serine-type endopeptidase activity | 0.15374807 |
| CDKN2A | Cyclin-Dependent Kinase Inhibitor 2A | protein kinase binding and p53 binding | 0.18362238 |
| HLA-DQA1 | Major Histocompatibility Complex, Class II, DQ Alpha 1 | MHC class II receptor activity | 0.18970088 |
| SOD1 | Superoxide Dismutase 1, Soluble | copperon binding and protein homodimerization activity | 0.18970088 |
| RND3 | Rho Family GTPase 3 | GTP binding and GTPase activity | 0.19352045 |
| MAPK9 | Mitogen-Activated Protein Kinase 9 | transcription factor binding and mitogen-activated protein kinase kinase kinase binding | 0.19397784 |
| SDHA | Succinate Dehydrogenase Complex, Subunit A, Flavoprotein (Fp) | succinate dehydrogenase (ubiquinone) activity and flavin adenine dinucleotide binding | 0.19397784 |
| SOD2 | Superoxide Dismutase 2, Mitochondrial | oxygen binding anddentical protein binding | 0.21484978 |
| CARTPT | Cocaine And Amphetamine Regulated Transcript | protein binding | 0.21922992 |
| CCL13 | Chemokine (C-C Motif) Ligand 13 | chemokine activity and receptor binding | 0.23449781 |
| HSD17B3 | Hydroxysteroid (17-Beta) Dehydrogenase 3 | testosterone 17-beta-dehydrogenase (NADP+) activity | 0.24528753 |
| PDX1 | Pancreatic And Duodenal Homeobox 1 | chromatin binding and sequence-specific DNA binding transcription factor activity | 0.24528753 |
| SRC | V-Src Avian Sarcoma (Schmidt-Ruppin A-2) Viral Oncogene Homolog | protein kinase activity anddentical protein binding | 0.2470727 |
| GLIS3 | GLIS Family Zinc Finger 3 | sequence-specific DNA binding transcription factor activity | 0.25858972 |
| CDKN2B | Cyclin-Dependent Kinase Inhibitor 2B (P15, Inhibits CDK4) | cyclin-dependent protein serine/threonine kinasenhibitor activity and protein kinase binding | 0.27977809 |
| PIK3R2 | Phosphoinositide-3-Kinase, Regulatory Subunit 2 (Beta) | receptor tyrosine kinase binding and phosphatidylinositol 3-kinase regulator activity | 0.27977809 |
| ZFAND6 | Zinc Finger, AN 1-Type Domain 6 | polyubiquitin binding | 0.27977809 |

TABLE 30

Type 1 Diabetes Gent Data

| GENE | Description | Table 30 Comments | p-value |
|---|---|---|---|
| ITGAM | Integrin, Alpha M (Complement Component 3 Receptor 3 Subunit) | heparin binding and heparan sulfate proteoglycan binding | 0.0007641 |
| ULBP1 | UL16 Binding Protein 1 | antigen binding and natural killer cell lectin-like receptor binding | 0.000765 |
| P1K3R1 | Phosphoinositide-3-Kinase, Regulatory Subunit 1 (Alpha) | protein phosphatase binding and 1-phosphatidyiinositol binding | 0.00134806 |
| CCNO | Cyclin O | protein kinase binding and uracil DNA N-glycosylase activity | 0.00162587 |
| RAG1 | Recombination Activating Gene 1 | ubiquitin-protein ligase activity and protein homodimerization activity | 0.00175515 |
| AGER | Advanced Glycosylation End Product-Specific Receptor | S100 protein binding and receptor activity | 0.00264646 |
| DNM3 | Dynamin 3 | GTP binding and GTPase activity | 0.00293324 |
| ARHGEF7 | Rho Guanine Nucleotide Exchange Factor (GEF) 7 | phospholipid binding and guanyl-nucleotide exchange factor activity | 0.00297702 |

TABLE 30-continued

Type 1 Diabetes Gent Data

| GENE | Description | Table 30 Comments | p-value |
|---|---|---|---|
| ICAM1 | intercellular Adhesion Molecule 1 | integrin binding and receptor activity | 0.00434176 |
| SH3KBP1 | SH3-Domain Kinase Binding Protein 1 | SH3 domain binding | 0.00435443 |
| DARR1 | Dual Adaptor Of Rhosphotyrosine And 3-Phosphoinositides | phospholipid binding and phosphatidylinositol-3,4,5-trisphosphate binding | 0.00523553 |
| AOCY9 | Adenylate Cyclase 9 | adenylate cyclase activity | 0.00712137 |
| PLD1 | Phospholipase D1, Phosphatidylcholine-Specific | NAPE-specific phospholipase D activity and phosphatidylinositol binding | 0.00999977 |
| LY86 | lymphocyte Antigen 86 | mediate innate immune response to bacterial lipopolysaccharide (LPS) and cytokine production | 0.01108912 |
| IKBK3 | Inhibitor Of Kappa Light Polypeptide Gene Enhancer In B-Cells, Kinase Beta | protein heterodimerization activity and protein homodimerization activity | 0.01128582 |
| PTPRC | Protein Tyrosine Phosphatase, Receptor Type, C | protein kinase binding and transmembrane receptor protein tyrosine phosphatase activity | 0.02237102 |
| ADCY8 | Adenylate Cyclase 8 (Brain) | calcium- and calmodulin-responsive adenylate cyclase activity and adenylate cyclase activity | 0.0328753 |
| PRKCQ | Protein Kinase C, Theta | ubiquitin-protein ligase activity and identical protein binding | 0.03480357 |
| GHR | Growth Hormone Receptor | protein phosphatase binding and protein homodimerization activity | 0.03663135 |
| FCGR2B; FCGR3A | Fc Fragment Of IgG, Low Affinity IIb and IIIa, Receptor | IgG binding | 0.03765986 |
| VCAM1 | Vascular Cell Adhesion Molecule X | integrin binding and primary amine oxidase activity | 0.03841589 |
| TAP2; TAP1 | Transporter 2, ATP-Binding Cassette, Sub-Family B/ Transporter 1, ATP-Binding Cassette, Sub-Family B | transporter activity and MHC class I protein binding/ADP binding and protein homodimerization activity | 0.05214662 |
| CCR6 | Chemokine (C-C Motif) Receptor 6 | C-C chemokine receptor activity and receptor activity | 0.0539188 |
| AP2A2 | Adaptor-Related Protein Complex 2, Alpha 2 Subunit | protein transporter activity and lipid binding | 0.05915437 |
| PRKCSH | Protein Kinase C Substrate 80K-H | protein kinase C binding and calcium ion binding | 0.05915437 |
| DNMX | Dynamin 1 | phospholipid binding and identical protein binding | 0.06012929 |
| IL5RA | Interleukin 5 Receptor, Alpha | interleukin-5 receptor activity | 0.06012929 |
| PLCG1 | Phospholipase C, Gamma 1 | receptor signaling protein activity and calciumon binding | 0.06012929 |
| FCGR3A | Fc Fragment Of IgG. Low Affinity IIIa, Receptor (CD16a) | IgG binding | 6.06099381 |
| FCGR1A | Fc Fragment Of IgG, High Affinity Ia, Receptor (CD64) | IgG binding and receptor signaling protein activity | 0.07229075 |
| BCR | Breakpoint Cluster Region | protein serine/threonine kinase activity and enzyme binding | 0.03613786 |
| RAG1; TRAF6 | Recombination Activating Gene 1/TNF Receptor-Associated Factor 6, E3 Ubiquitin Protein Ligase | ubsquitin-protein ligase activity and protein homodimerization activity/ protein kinase binding and signal transducer activity | 0.08655541 |
| B2M | beta-2-microglobulin | identical protein binding | 0.08762339 |
| AP2B1 | Adaptor-Related Protein Complex 2, Beta 1 Subunit | clathrin binding and protein complex binding | 6 08822935 |
| CD38 | CD38 Molecule | phosphorus-oxygen lyase activity and NAD+ nucleosidase activity | 0.09202116 |
| KIT | V-Kit Hardy-Zuckerman 4 Feline Sarcoma Viral Oncogene Homolog | protein homodimerization activity and protease binding | 0.09202116 |
| CBL | Cbl Proto-Oncogene, E3 Ubiquitin Protein Ligase | ubiquitin-protem ligase activity and sequence-specific DNA binding transcription factor activity | 0.11131925 |
| TREM1 | Triggering Receptor Expressed On Myeloid Cells 1 | receptor activity | 0.11692072 |
| CDH1 | Cadherin 1, Type 1, E-Cadherin (Epithelial) | beta-catenin binding and calcium ion binding | 0.1313431 |
| AICDA | Activation-induced Cytidine Deaminase | cytidine deaminase activity | 0.13842069 |
| CD180 | CD180 Molecule | protein binding | 0.13842069 |
| C0274 | CD274 Molecule | protein binding | 0.13842069 |
| CD3D | CD3d Molecule, Delta (CD3-TCR Complex) | transmembrane signaling receptor- activity and protein heterodimerization activity | 0.13842069 |
| CD81 | CD81 Molecule | MHC class II protein complex binding | 0.13842069 |
| HCST | Hematopoietic Cell Signal Transducer | phosphatidylinositol 3-kinase binding | 0.13842069 |
| ITGAV | Integrin, Alpha V | protein kinase C binding and virus receptor activity | 0.13842069 |
| ITGB7 | Integrin, Beta 7 | virus receptor activity | 0.13842069 |
| NFKB2 | Nuclear Factor Of Kappa Light Polypeptide Gene Enhancer in B-Cells 2 (P49/P1Q0) | include transcription coactivator activity and sequence-specific DNA binding transcription factor activity | 0.13842069 |
| IRS1 | Insulin Receptor Substrate 1 | protein kinase C binding and phospholipid binding | 0.14381711 |
| SCYL1 | SCY1-Like 1 (S. Cerevisiae) | protein tyrosine kinase activity | 0.14381711 |
| SYK | Spleen Tyrosine Kinase | protein tyrosine kinase activity and protein kinase binding | 0.1709489 |
| FYN | FYN Oncogene Related To SRC, FGR, YES | ion channel binding and identical protein binding | 0.18657498 |
| HRAS | Harvey Rat Sarcoma Viral Oncogene Homolog | protein C-terminus binding and GTP binding | 0.19661222 |
| PVR | Poliovirus Receptor | receptor activity and cell adhesion molecule binding | 0.19661222 |
| LCK | Lymphocyte-Specific Protein Tyrosine Kinase | protein C-terminus binding and identical protein binding | 0.20079822 |
| PANX1 | Pannexin 1 | actin filament binding and protein heterodimerization activity | 6 20454126 |
| PPAPDC1A | Phosphatidic Acid Phosphatase Type 2 Domain Containing 1A | phosphatidate phosphatase activity | 0.23161338 |
| CR1 | Complement Component (3b/4b) Receptor 1 (Knops Blood Group) | complement component C3b binding and complement component C4b receptor activity | 0.23203701 |
| ADA | Adenosine Deaminase | purine nucleoside binding and adenosine deaminase activity | 0 25120539 |
| CHUK | Conserved Helix-Loop-Helix Ubiquitous Kinase | protein heterodimerization activity and protein, homodimerization activity | 0.25120539 |
| FGFR1 | Fibroblast Growth Factor Receptor 1 | heparin binding .and protein homodimerization activity | 0.25120539 |
| ITGB2 | Integrin, Beta 2 (Complement Component 3 Receptor 3 And 4 Subunit) | protein kinase binding antigiycoprotein binding | 0.25120539 |
| RFXAP | Regulatory Factor X-Associated Protein | transcription coactivator activity andsequence-spedfk: DNA binding transcription factor activity | 0.25120539 |

TABLE 30-continued

Type 1 Diabetes Gent Data

| GENE | Description | Table 30 Comments | p-value |
|---|---|---|---|
| TNFRSF13B | Tumor Necrosis Factor Receptor Superfamily, Member 13B | receptor activity | 0.25120539 |
| CD19 | CD19 Molecule | receptor signaling protein activity | 0.25769486 |
| CD74 | CD74 Molecule, Major Histocompatibility Complex, Class II Invariant Chain | cytokine receptor activity anddentical protein binding | 0.25769486 |
| FCER1A | Fc Fragment Of IgE, High Affinity I, Receptor For; Alpha Polypeptide | ig£ receptor activity andgE binding | 0.25769486 |
| PDCD1 | Programmed Cell Death 1 | signal transducer activity | 0.25769486 |
| PIK3AP1 | Phosphoinositide-3-Kinase Adaptor Protein 1 | phosphatidyfinositoi 3-kinase regulatory subunit binding and identical protein binding | 0.2609107 |
| PDPK1 | 3-Phosphoinositide Dependent Protein Kinase 1 | protein serine/threonine kinase activity andnsulin receptor binding | 0.26369181 |

TABLE 31

Ulcerative Colitis Gene Data

| GENE | Description | Table 31 Comments | p-value |
|---|---|---|---|
| FCGR28; FCGR3A | Fc Fragment Of IgG, Low Affinity IIb and IIIa, Receptor | IgG binding | 0.00012499 |
| PIK3AP1 | Phosphoinositide-3-Kinase Adaptor Protein 1 | phosphatidylinositol 3-kinase regulatory subunit binding and identical protein binding | 0.00015714 |
| SH3KBP1 | SH3-Domain Kinase Binding Protein 1 | SH3 domain binding | 0.00037308 |
| EGER | Epidermal Growth Factor Receptor | chromatin binding and identical protein binding | 0.00155239 |
| DLEU2 | Deleted In Lymphocytic Leukemia 2 (Non-Protein Coding) | RNA gene affiliated with the lncRNA class | 0.00226369 |
| ADCY1 | Adenylate Cyclase 1 (Brain) | calcium- and calmodulin-responsive adenylate cyclase activity and calmodulin binding | 0.00458089 |
| ZAP70 | Zeta-Chain (TCR) Associated Protein Kinase 70 kDa | phosphotyrosine binding and protein tyrosine kinase activity | 0.00706531 |
| CBLB | Cbl Proto-Oncogene B, E3 Ubiquitin Protein Ligase | signal transducer activity and calcium ion binding | 0.00835978 |
| CD96 | CD96 Molecule | protein binding | 0.00964315 |
| GLYCAM1 | Glycosvlation Dependent Cell Adhesion Molecule 1 (Pseudogene) | pseudogene affiliated with the lncRNA class | 0.01235245 |
| ICAM1 | Intercellular Adhesion Molecule 1 | Inregrin binding and receptor activity | 0.01235245 |
| TRAC | T Cell Receptor Alpha Constant | peptide antigen binding and MHC protein binding | 0.01235245 |
| FCGR1A | Fc Fragment Of IgG, High Affinity Ia, Receptor (CD64) | IgG binding and receptor signaling protein activity | 0.01270167 |
| VAV1 | Vav 1 Guanine Nucleotide Exchange Factor | sequence-specific DNA binding transcription factor activity and guanyl-nucleotide exchange factor activity | 0.01684487 |
| ARHGEF7 | Rho Guanine Nucleotide Exchange Factor (GEF) 7 | phospholipid binding and guanyl-nudeotide exchange factor activity | 0.02251106 |
| C4BPB | Complement Component 4 Binding Protein, Beta | controls activation of the complement cascade through the classical pathway | 0.02466186 |
| FCGR3A | Fc Fragment Of IgG, Low Affinity IIIa, Receptor (CD16a) | IgG binding | 0.02821228 |
| PLD1 | Phospholipase D1, Phosphatidylcholine-Specific | NAPE-specific, phospholipase D activity and phosphatidylinositol binding | 0.03197958 |
| NFKB1 | Nuclear Factor Of Kappa Light Polypeptide Gene Enhancer in B-Cells 1 | transcription factor binding and sequence-specific DNA binding transcription factor activity | 0.03543356 |
| IKBKB | Inhibitor Of Kappa Light Polypeptide Gene Enhancer in B-Cells, Kinase Seta | protein heterodimerization activity and protein homodimerization activity | 0.03589451 |
| IRS1 | Insulin Receptor Substrate 1 | protein kinase C binding and phospholipid binding | 0.04594332 |
| SCYL1 | SCY1-Like 1 (S. Cerevisiae) | protein tyrosine kinase activity | 0.04594332 |
| CD36 | CD36 Molecule (Thrombospondin Receptor) | lipid binding and transforming growth factor beta binding | 0.046058 |
| ITGAM | Integrin, Alpha M (Complement Component 3 Receptor 3 Subunit) | heparin binding and heparan sulfate proteoglycan binding | 0.05678192 |
| AP2A2 | Adaptor Related Protein Complex 2, Alpha 2 Subunit | protein transporter activity and lipid binding | 0.05698369 |
| CD3E | CD3e Molecule, Epsilon (CD3-TCR Complex) | SH3 domain binding and protein heterodimerization activity | 0.06525633 |
| IGLV7-43 | Immunoglobulin Lambda Variable 7-43 | antigen binding | 0.07953419 |
| IFI6 | Interferon, Alpha-Inducible Protein 6 | protein binding | 0.08776649 |
| AGER | Advanced Glycosylation End Product-Specific Receptor | S100 protein binding and receptor activity | 0.08857668 |
| TLR1; TLR10 | Toll-Like Receptor 1 and 10 | transmembrane signaling receptor activity and protein heterodimerization activity/transmembrane signaling receptor activity | 0.08857668 |
| PTGIR | Prostaglandin I2 (Prostacyclin) Receptor (IP) | G-protein coupled receptor activity and guanyl-nucleotide exchange factor activity | 0.09239109 |
| C3 | Complement Component 3 | C5L2 anaphylatoxin chemotactic receptor binding and receptor binding | 0.0334343 |
| PVRL2 | Poliovirus Receptor-Related 2 (Herpesvirus Entry Mediator B) | virus receptor activity and protein homodimerization activity | 0.0934343 |

TABLE 31-continued

Ulcerative Colitis Gene Data

| GENE | Description | Table 31 Comments | p-value |
|---|---|---|---|
| B2M | beta-2-microglobulin | identical protein binding | 0.1127473 |
| PDPK1 | 3-Phosphoinositide Dependent Protein Kinase 1 | protein serine/threonine kinase activity and insulin receptor binding | 0.11897734 |
| ADA | Adenosine Deaminase | purine nucleoside binding and adenosine deaminase activity | 0.12068843 |
| IL5RA | Interleukin 5 Receptor, Alpha | Interleukin-5 receptor activity | 0.12068843 |
| ITGB2 | Integrin, Beta 2 (Complement Component 3 Receptor 3 And 4 Subunit) | protein kinase binding and glycoprotein binding | 0.12068843 |
| CCR6 | Chemokine (C-C Motif) Receptor 6 | C-C chemokine receptor activity and receptor activity | 0.12631419 |
| FAS | Fas Cell Surface Death Receptor | receptor activity and identical protein binding | 0.12631419 |
| PTPRC | Protein Tyrosine Phosphatase, Receptor Type, C | protein kinase binding and transmembrane receptor protein tyrosine phosphatase activity | 0.12636817 |
| PRKCQ | Protein Kinase C, Theta | ubiquitin-protein ligase activity and identical protein binding | 0.14418364 |
| RAP1B | RAP1B, Member Of RAS Oncogene Family | GDP binding and GTP binding | 0.14746966 |
| CXCR5 | Chemokine (C-X-C Motif) Receptor 5 | G-protein coupled receptor activity and C-X-C chemokine receptor activity | 0.15588515 |
| FCGR3A; FCGR2A | Fc Fragment Of IgG; Low Affinity IIIa and IIa, Receptor | IgG binding | 0.15588515 |
| TREM2 | Triggering Receptor Expressed On Myeloid Cells 2 | lipopolysaccharide binding and receptor activity | 0.15588515 |
| AP2B1 | Adaptor-Related Protein Complex 2, Beta 1 Subunit | clathrin binding and protein complex binding | 0.15685807 |
| ITGAL | Integrin, Alpha L (Antigen CD11A (P180), Lymphocyte Function-Associated Antigen 1; Alpha Polypeptide) | cell adhesion molecule binding | 0.16324087 |
| CSF2RA | Colony Stimulating Factor 2 Receptor, Alpha, Low-Affinity (Granulocyte-Macrophage) | cytokine receptor activity and receptor activity | 0.16774645 |
| KIR2DL4; KIR3DL1; KIR2DL3 | Killer Cell Immunoglobulin-Like Receptor, Two Domains Long Cytoplasmic Tail, 3 and 4/Killer Cell Immunoglobulin-Like Receptor, Three Domains, Long Cytoplasmic Tail, 1 | receptor activity/HLA-B specific inhibitory MHC class I receptor activity | 0.16774645 |
| RASGRP1 | RAS Guanyl Releasing Protein 1 (Calcium And DAG-Regulated) | guanyl-nucleotide exchange factor activity and calcium ion binding | 0.16774645 |
| RAG1 | Recombination Activating Gene 1 | ubiquitin-protein ligase activity and protein homodimerization activity | 0.16996471 |
| CD274 | CD274 Molecule | protein binding | 0.18344493 |
| CD28 | CD28 Molecule | SH3/SH2 adaptor activity and identical protein binding | 0.18344493 |
| CD3D | CD3d Molecule, Delta (CD3-TCR Complex) | transmembrane signaling receptor activity and protein heterodimerization 1 activity | 0.18344493 |
| ITGAV | Integrin, Alpha V | protein kinase C binding and virus receptor activity | 0.18344493 |
| TIRAP | Toll-interleukin 1 Receptor (TIR) Domain Containing Adaptor Protein | protein binding, bridging and protein homodimerization activity | 0.18344493 |
| TYROBP | TYRO Protein Tyrosine Kinase Binding Protein | receptor signaling protein activity and identical protein binding | 0.18344493 |
| PRKCB | Protein Kinase C, Seta | chromatin binding and histone binding | 0.18954531 |
| ULBP1 | UL16 Binding Protein 1 | antigen binding and natural killer cell lectin-like receptor binding | 0.20345466 |
| AMICA1 | Adhesion Molecule, Interacts With CXADR Antigen 1 | cell adhesion molecule binding | 0.2189915 |
| TREM1 | Triggering Receptor Expressed On Myeloid Cells 1 | receptor activity | 0.2189915 |
| TAB3 | TGF-Beta Activated Kinase 1/MAP3K7 Binding Protein 3 | protein binding/zinc ion binding | 0.22139123 |
| PPAPDC1A | Phosphatidic Acid Phosphatase Type 2 Domain Containing 1A | phosphatidate phosphatase activity | 0.22331897 |
| ACP5 | Acid Phosphatase 5, Tartrate Resistant | ferrous iron binding and acid phosphatase activity | 0.2291797 |
| LAT | Linker For Activation Of T Cells | SH3/SH2 adaptor activity and protein kinase binding | 0.2291797 |
| SIGLEC16 | Sialic Acid Binding Ig-Like Lectin 16 (Gene/Pseudogene) | pseudogene affiliated with the lncRNA class | 0.2291797 |
| GINS1 | GINS Complex Subunit 1 (Psf1 Homolog) | plays a role in the Initiation of DNA replication, and progression of DNA replication forks | 0.24615224 |
| CDH1 | Cadherin 1, Type 1, E-Cadherin (Epithelial) | beta-catenin binding and calcium ion binding | 0.25428788 |
| CBL | Cbl Proto-Oncogene, E3 Ubiquitin Protein Ligase | ubiquitin-protein ligase activity and sequence-specific DNA binding transcription factor activity | 0.26058383 |
| GHR | Growth Hormone Receptor | protein phosphatase binding and protein homodimerization activity | 0.27057824 |
| ATPIF1 | ATPase Inhibitory Factor 1 | enzyme inhibitor activity and protein homodimerization activity | 0.27280173 |
| CD8A; CD8B | CD8a and 8b Molecules | protein homodimerization activity and coreceptor activity/MHC class I protein binding and coreceptor activity | 0.27280173 |
| IGKV3-15 | Immunoglobulin Kappa Variable 3-15 | protein binding | 0.27230173 |

TABLE 32

SLE Gene Data

| GENE | Description | Table 32. Comments | p-value |
|---|---|---|---|
| FYN | FYN Oncogene Related To SRC, FGR, YES | ion channel binding and identical protein binding | 0.00021817 |
| MKL1 | Megakaryoblastic Leukemia (Translocation) 1 | transcription regulatory region sequence-specific DNA binding and sequence-specific DNA binding transcription factor | 0.00055943 |
| CD96 | CD96 Molecule | activity protein binding | 0.00392655 |
| ADCY1 | Adenylate Cyclase 1 (Brain) | calcium- and calmodulin-responsive adenylate cyclase activity and calmodulin binding | 0.00467913 |
| PRKCQ | Protein Kinase C, Theta | ubiquitin-protein ligase activity and identical protein binding | 0.00655819 |
| TREM1 | Triggering Receptor Expressed On Myeloid Cells 1 | receptor activity | 0.0073133 |
| ITGAM | Integrin, Alpha M (Complement Component 3 Receptor 3 Subunit) | heparin binding and heparan sulfate proteoglycan binding | 0.00851784 |
| ULBP1 | UL16 Binding Protein 1 | antigen binding and natural killer cell lectin-like receptor binding | 0.01009946 |
| ADCY2 | Adenylate Cyclase 2 (Brain) | adenylate cyclase activity and protein heterodimerization activity | 0.01130513 |
| PLD1 | Phospholipase D1, Phosphatidylcholine-Specific | NAPE-specific phospholipase D activity and phosphatidylinositol binding | 0.01230118 |
| RAG2; RAG1 | Recombination Activating Gene 2 and 1 | chromatin binding and methylated histone residue binding/ ubiquitin-protein ligase activity and protein homodimerization activity | 0.01272518 |
| ADCY5 | Adenylate Cyclase 5 | adenylate cyclase binding and protein heterodimerization activity | 0.01688104 |
| CCNO | Cyclin O | protein kinase binding and uracil DNA N-glycosylase activity | 0.03134733 |
| MALT1 | Mucosa Associated Lymphoid Tissue Lymphoma Translocation Gene 1 | ubiquitin-protein ligase activity and peptidase activity | 0.04135861 |
| AKT3 | V-Akt Murine Thymoma Viral Oncogene Homolog 3 | protein serine/threonine kinase activity and protein kinase activity | 0.04694848 |
| ARHGEF7 | Rho Guanine Nucleotide Exchange Factor (GEF) 7 | phospholipid binding and guanyl-nucleotide exchange factor activity | 0.0522776 |
| CR1;CR2 | Complement Component (3b/4b) Receptor 1/ Complement Component (3d/Epstein Barr Virus) Receptor 2 | complement component C3b binding and complement component C4b receptor activity/protein homodimerization activity and complement receptor activity | 0.05535272 |
| ADCY4 | Adenylate Cyclase 4 | adenylate cyclase activity | 0.06042648 |
| CD14 | CD14 Molecule | lipoteichoic acid binding and lipopolysaccharide binding | 0.06093891 |
| TNFRSF13C | Tumor Necrosis Factor Receptor Superfamily, Member 13C | enhances B-cell survival in vitro and is a regulator of the peripheral B-cell population | 0.06802621 |
| CBL | Cbl Proto-Oncogene, E3 Ubiquitin Protein Ligase | ubiquitin-protein ligase activity and sequence-specific DNA binding transcription factor activity | 0.0685906 |
| SELL | Selectin L | carbohydrate binding and protease binding | 0.07467257 |
| FCGR2B; FCGR3A | Fc Fragment Of IgG, low Affinity IIb and IIIa, Receptor | IgG binding | 0.07619895 |
| SH3KBP1 | SH3-Domain Kinase Binding Protein 1 | SH3 domain binding | 0.0788614 |
| IKBKB | Inhibitor Of Kappa Light Polypeptide Gene Enhancer in B-Cells, Kinase Beta | protein heterodimerization activity and protein homodimerization activity | 0.08334932 |
| ADA | Adenosine Deaminase | purine nucleoside binding and adenosine deaminase activity | 0.08563263 |
| ITGB2 | Integrin, Beta 2 (Complement Component 3 Receptor 3 And 4 Subunit) | protein kinase binding and glycoprotein binding | 0.08563263 |
| TLR5 | Toll-Like Receptors | interleukin-1 receptor binding | 0.09151248 |
| AP2A2 | Adaptor-Related Protein Complex 2, Alpha 2 Subunit | protein transporter activity and lipid binding | 0.09719424 |
| PTPRC | Protein Tyrosine Phosphatase, Receptor Type, C | protein kinase binding and transmembrane receptor protein tyrosine phosphatase activity | 0.10051777 |
| CD55 | CD55 Molecule, Decay Accelerating Factor For Complement | enzyme inhibitor activity and virus receptor activity | 0.10406481 |
| CR1 | Complement Component (3b/4b) Receptor 1 | complement component C3b binding and complement component C4b receptor activity | 0.10918275 |
| DAPP1 | Dual Adaptor Of Phosphotyrosine And 3-Phosphoinositides | phospholipid binding and phosphatidylinositol-3,4,5-trisphosphate binding | 0.12045909 |
| FGFR4 | Fibroblast Growth Factor Receptor 4 | fibroblast growth factor binding and heparin binding | 0.12128 |
| IGKV1D-16 | Immunoglobulin Kappa Variable 1D-16 | protein binding | 0.12128 |
| IL7R | Interleukin 7 Receptor | antigen binding and interleukin-7 receptor activity | 0.12128 |
| KIR2DL4; KIR3DL1 | Killer Cell Immunoglobulin-Like Receptor, Two Domains, Short Cytoplasmic Tail, 4/ Killer Cell Immunoglobulin-Like Receptor, Three Domains, Long Cytoplasmic Tail, 1 | receptor activity/HLA-B specific inhibitory MHC class I receptor activity | 0.12128 |
| NFKB1 | Nuclear Factor Of Kappa Light Polypeptide Gene Enhancer in B-Cells 1 | transcription factor binding and sequence-specific DNA binding transcription factor activity | 0.12476294 |
| CDH1 | Cadherin 1, Type 1, E-Cadherin (Epithelial) | beta-catenin binding and calcium ion binding | 0.13542507 |
| RAG1 | Recombination Activating Gene 1 | ubiquitin-protein ligase activity and protein homodimerization activity | 0.15168578 |
| AICDA | Activation-Induced Cytidine Deaminase | cytidine deaminase activity | 0.15931656 |
| CD274 | CD274 Molecule | protein binding | 0.15931656 |
| ERBB2 | V Erb-B2 Avian Erythroblastic Leukemia Viral Oncogene Homolog 2 | protein C-terminus binding and identical protein binding | 0.15931656 |

TABLE 32-continued

SLE Gene Data

| GENE | Description | Table 32. Comments | p-value |
|---|---|---|---|
| HCST | Hematopoietic Cell Signal Transducer | phosphatidylinositol 3-kinase binding | 0.15931656 |
| IGLC3; IGLC7; IGLC2; IGLC1; IGLC6 | Immunoglobulin Lambda Constant 3/7/2/1/6 | antigen binding | 0.15931656 |
| IRS2 | Insulin Receptor Substrate 2 | phospholipid binding and signal transducer activity | 0.15931656 |
| ITGB7 | Integrin, Beta 7 | virus receptor activity | 0.15931656 |
| NFKB2 | Nuclear Factor Of Kappa Light Polypeptide Gene Enhancer in B-Cells 2 | transcription coactivator activity and sequence-specific DNA binding transcription factor activity | 0.15931656 |
| TLR1; TLR6 | Toll-Like Receptor 1 and 6 | transmembrane signaling receptor activity and protein heterodimerization activity | 0.15931656 |
| AP2B1 | Adaptor-Related Protein Complex 2, Beta 1 Subunit | clathrin binding and protein complex binding | 0.16253886 |
| EPHB4 | EPH Receptor B4 | ephrin receptor activity and transmembrane receptor protein tyrosine kinase activity | 0.17370523 |
| CD200R1 | CD200 Receptor 1 | protein binding | 0.18215624 |
| GUCY2D | Guanylate Cyclase 2D, Membrane (Retina-Specific) | receptor activity and identical protein binding | 0.18215624 |
| IRS1 | Insulin Receptor Substrate 1 | protein kinase C binding and phospholipid binding | 0.18215624 |
| SCYL1 | SCY1-Like 1 (S. Cerevisiae) | protein tyrosine kinase activity | 0.18215624 |
| TLR2 | Toll-Like Receptor 2 | transmembrane signaling receptor activity and protein heterodimerization activity | 0.18215624 |
| CD8A; CD8B | CD8a and 8b Molecules | protein homodimerization activity and coreceptor activity/ MHC class I protein binding and coreceptor activity | 0.20445582 |
| ICOS | Inducible T-Cell Co-Stimulator | protein binding | 0.20445582 |
| KLB | Klotho Beta | fibroblast growth factor binding and hydrolase activity, hydrolyzing O-glycosyl compounds | 0.20445582 |
| LYRLA2 | Lysophospholipase II | hydrolase activity | 0.20445582 |
| PIK3CD | Phosphatidylinositol-4,5-Bisphosphate 3-Kinase, Catalytic Subunit Delta | phosphatidylinositol 3-kinase activity and 1-phosphaticiylinositol-3- kinase activity | 0.20457531 |
| LY86 | Lymphocyte Antigen 86 | mediate innate immune response to bacterial lipopolysaccharide (LPS) and cytokine production | 0.21428543 |
| LYN | V-Yes-1 Yamaguchi Sarcoma Viral Related Oncogene Homolog | SH3 domain binding and enzyme binding | 0.21831744 |
| ACTR2 | ARP2 Actin-Related Protein 2 Homolog (Yeast) | actin binding | 0.23943002 |
| GLYCAM1 | Glycosylation Dependent Cell Adhesion Molecule 1 (Pseudogene) | pseudogene affiliated with the lncRNA class | 0.245558 |
| ICAM1 | Intercellular Adhesion Molecule 1 | integrin binding and receptor activity | 0.245558 |
| UNG | Uracil-DNA Glycosylase | uracil DNA N-glycosylase activity | 0.245558 |
| CCR6 | Chemokine (C-C Motif) Receptor 6 | C-C chemokine receptor activity and receptor activity | 0.24987076 |
| CD8B | CD8b Molecule | MHC class I protein binding and coreceptor activity | 0.24987076 |
| AKT2; PLD3 | V-Akt Murine Thymoma Viral Oncogene Homolog 2/Phospholipase O Family, Member 3 | protein serine/threonine kinase activity and kinase activity/phospholipase D activity and NAPE-specific phospholipase D activity | 0.29326681 |
| CD74 | CD74 Molecule, Major Histocompatibility Complex, Class II Invariant Chain | cytokine receptor activity and identical protein binding | 0.29326681 |
| SIGLEC15 | Sialic Acid Binding Ig-Like Lectin 15 | protein binding | 0.29326681 |
| FCGR1A | Fc Fragment Of IgG, High Affinity Ia, Receptor (CD64) | IgG binding and receptor signaling protein activity | 0.29654271 |

TABLE 33

Multiple Sclerosis. Relapse Remitting Gene Data

| GENE | Description | Table 33. Comments | p-value |
|---|---|---|---|
| PRKCQ | Protein Kinase C, Theta | ubiquitin-protein ligase activity and identical protein binding | 1.30E−05 |
| SH3KBP1 | SH3-Domain Kinase Binding Protein 1 | SH3 domain binding | 0.00108322 |
| PIK3R1 | Phosphoinositide-3-Kinase, Regulatory Subunit 1 (Alpha) | protein phosphatase binding and 1-phosphatidylinositol binding | 0.00132825 |
| ADCY2 | Adenylate Cyclase 2 (Brain) | adenylate cyclase activity and protein heterodimerization activity | 0.00228137 |
| PPAPDC1A | Phosphatidic Acid Phosphatase Type 2 Domain Containing 1A | phosphatidate phosphatase activity | 0.00458647 |
| FYN | FYN Oncogene Related To SRC, FGR, YES | ion channel binding and identical protein binding | 0.0065531 |
| ULBP1 | UL16 Binding Protein 1 | antigen binding and natural killer cell lectin-like receptor binding | 0.00758094 |
| ITGAM | Integrin, Alpha M (Complement Component 3 Receptor 3 Subunit) | heparin binding and heparan sulfate proteoglycan binding | 0.00767946 |
| KRAS | Kirsten Rat Sarcoma Viral Oncogene Homolog | GDP binding and GTP binding | 0.011855 |

TABLE 33-continued

Multiple Sclerosis. Relapse Remitting Gene Data

| GENE | Description | Table 33. Comments | p-value |
| --- | --- | --- | --- |
| RAG2; RAG1 | Recombination Activating Gene 2 and 1 | chromatin binding and methylated histone residue binding/ubiquitin-protein ligase activity and protein homodimerization activity | 0.02258078 |
| IRS1 | Insulin Receptor Substrate 1 | protein kinase C binding and phospholipid binding | 0.03623882 |
| PLD3 | Phospholipase D Family, Member 3 | phospholipase D activity and NAPE-specific phospholipase D activity | 0.03623882 |
| ICAM1 | Intercellular Adhesion Molecule 1 | integrin binding and receptor activity | 0.05207439 |
| PVR | Poliovirus Receptor | receptor activity and cell adhesion molecule binding | 0.05207439 |
| RAG1 | Recombination Activating Gene 1 | ubiquitin-protein ligase activity and protein homodimerization activity | 0.06077487 |
| IFNAR1 | interferon (Alpha, Beta And Omega) Receptor 1 | type I interferon receptor activity | 0.06430386 |
| ITGB7 | Integrin, Beta 7 | virus receptor activity | 0.06430386 |
| NFKB2 | Nuclear Factor Of Kappa Light Polypeptide Gene Enhancer In B-Cells 2 (P49/P100) | transcription coactivator activity and sequence-specific DNA binding transcription factor activity | 0.06430386 |
| ADA | Adenosine Deaminase | purine nucleoside binding and adenosine deaminase activity | 0.06985867 |
| TNFRSF13B | Tumor Necrosis Factor Receptor Superfamily, Member 13B | receptor activity | 0.06985867 |
| AP2A2 | Adaptor-Related Protein Complex 2; Alpha 2 Subunit | protein transporter activity and lipid binding | 0.07923074 |
| SYK | Spleen Tyrosine Kinase | protein tyrosine kinase activity and protein kinase binding | 0.07923074 |
| DNM3 | Dynamin 3 | GTP binding and GTPase activity | 0.08859048 |
| ARHGEF7 | Rho Guanine Nucleotide Exchange Factor (GEF) 7 | phospholipid binding and guanyl-nucleotide exchange factor activity | 0.09504564 |
| PTPRC | Protein Tyrosine Phosphatase, Receptor Type, C | protein kinase binding and transmembrane receptor protein tyrosine phosphatase activity | 0.10621879 |
| BCR | Breakpoint Cluster Region | protein serine/threonine kinase activity and enzyme binding | 0.10715318 |
| TREM1 | Triggering Receptor Expressed On Myeloid Cells 1 | receptor activity | 0.11004513 |
| ADCY1 | Adenylate Cyclase 1 (Brain) | calcium- and calmodulin-responsive adenylate cyclase activity and calmodulin binding | 0.12363153 |
| CD74 | CD74 Molecule, Major Histocompatibility Complex, Class II Invariant Chain | cytokine receptor activity and identical protein binding | 0.12447967 |
| PDCD1 | Programmed Cell Death 1 | signal transducer activity | 0.12447967 |
| TLR10 | Toll-Like Receptor 10 | transmembrane signaling receptor activity | 0.12447967 |
| ADCY4 | Adenylate Cyclase 4 | adenylate cyclase activity | 0.13191122 |
| CD8A; CD88 | CD8a and 8b Molecules | protein homodimerization activity and coreceptor activity/MHC class I protein binding and coreceptor activity | 0.13191122 |
| GINS2 | GINS Complex Subunit 2 (Psf2 Homolog) | ole in the initiation of DNA replication, and progression of DNA replication forks | 0.13386225 |
| LYN | V-Yes-1 Yamaguchi Sarcoma Viral Related Oncogene Homolog | SH3 domain binding and enzyme binding. | 0.14259452 |
| CLTA | Clathrin, Light Chain A | peptide binding and structural molecule activity | 0.15014664 |
| CCR6 | Chemokine (C-C Motif) Receptor 6 | C-C chemokine receptor activity and receptor activity | 0.15464838 |
| IKBKB | Inhibitor Of Kappa Light Polypeptide Gene Enhancer In B-Cells, Kinase Beta | protein heterodimerizstion activity and protein homodimerization activity | 0.15464838 |
| NFKB1 | Nuclear factor Of Kappa Light Polypeptide Gene Enhancer In B-Cells 1 | transcription factor binding and sequence-specific DNA binding transcription factor activity | 0.16493065 |
| AGER | Advanced Glycosylation End Product-Specific Receptor | S100 protein binding and receptor activity | 0.18079201 |
| ICOSLG; AIRE | Inducible T-Cell Co-Stimulator Ligand/ Autoimmune Regulator | receptor binding/transcription regulatory region DNA binding and identical protein binding | 0.18079201 |
| TAP2; TAP1 | Transporter 2, ATP-Blndlng Cassette, Sub-Family B/Transporter 1, ATP-Binding Cassette, Sub-Family B | transporter activity and MHC class I protein binding/ADP binding and protein homodimerization activity | 0.18079201 |
| TLR1; TLR10 | Toll-Like Receptor 1 and 10 | transmembrane signaling receptor activity and protein heterodimerization activity/transmembrane signaling receptor activity | 0.18079201 |
| B2M | beta-2-microglobulin | identical protein binding | 0.18119302 |
| CD14 | CD14 Molecule | lipoteichoic acid binding and lipopolysaccharide binding | 0.18119302 |
| CD226 | CD226 Molecule | protein kinase binding and cell adhesion molecule binding | 0.20195054 |
| KLRG1 | Killer Cell Lectin-Like Receptor Subfamily G, Member 1 | carbohydrate binding and receptor activity | 0.22617654 |
| IL6R | Interleukin 6 Receptor | interleukin-6 receptor binding and protein homodimerization activity | 0.22772527 |
| IL1RAP | Interleukin 1 Receptor Accessory Protein | interleukin-1 receptor activity and signal transducer activity | 0.23219152 |
| AP2S1 | Adaptor-Related Protein Complex 2, Sigma 1 Subunit | protein transporter activity and transporter activity | 0.23348849 |
| CD40 | CD40 Molecule, TNF Receptor Superfamily Member 5 | receptor activity and signal transducer activity | 0.23348849 |
| PRKCSH | Protein Kinase C Substrate 80K-H | protein kinase C binding and calcium ion binding | 0.27507189 |
| EGFR | Epidermal Growth Factor Receptor | chromatin binding and identical protein binding | 0.27872539 |
| CD59 | CD59 Molecule, Complement Regulatory Protein | complement binding | 0.28280091 |
| IGKV2-30 | Immunoglobulin Kappa Variable 2-30 | protein binding | 0.28280091 |
| KIR2DL1; | Killer Cell Immunoglobulin-Like Receptor, | receptor activity/HLA-B specific Inhibitory MHC class 1 receptor | 0.28280091 |

TABLE 33-continued

Multiple Sclerosis. Relapse Remitting Gene Data

| GENE | Description | Table 33. Comments | p-value |
|---|---|---|---|
| KIR2DL4; KIR3DL1; KIR2DL3 | Two Domains, Long Cytoplasmic Tail, 1,3 and 4/Killer Cell Immunoglobulin-Like Receptor, Three Domains, Long Cytoplasmic Tail, 1 | activity | |
| SIGLEC16 | Sialic Acid Binding Ig-Like Lectin 16 (Gene/Pseudogene) | pseudogene affiliated with the lncRNA class | 0.28280091 |
| TLR2 | Toll-Like Receptor 2 | transmembrane signaling receptor activity and protein heterodimerization activity | 0.28280091 |

TABLE 34

Multiple Sclerosis IFN-β Responder Gene Data

| GENE | Description | Table 34. Comments | p-value |
|---|---|---|---|
| TLR5 | Toll-Like Receptor 5 | interleukln-1 receptor binding | 4.96E−06 |
| IFNGR2 | Interferon Gamma Receptor 2 (Interferon Gamma Transducer 1) | interferon-gamma receptor activity | 4.59E−05 |
| ADCY9 | Adenylate Cyclase 9 | adenylate cyclase activity | 0.00014626 |
| EGFR | Epidermal Growth Factor Receptor | chromatin binding and identical protein binding | 0.00015025 |
| FCGR3A | Fc Fragment Of IgG, Low Affinity IIIa, Receptor (CD16a) | IgG binding | 0.0004003 |
| FCGR2B; FCGR3A | Fc Fragment Of IgG, Low Affinity IIb and IIIa, Receptor | IgG binding | 0.00059065 |
| PIK3CD | Phosphatidylinositol-4,5-Bisphosphate 3-Kinase, Catalytic Subunit Delta | phosphatidylinositol 3-kinase activity and 1-phosphatidylinositol-3-kinase activity | 0.00094547 |
| PDGFRA | Platelet-Derived Growth Factor Receptor, Alpha Polypeptide | platelet-derived growth factor receptor bindin gand protein homodimerization activity | 0.0010759 |
| ADCY1 | Adenylate Cyclase 1 (Brain) | calcium- and calmodulin-responsive adenylate cyclase activity and calmodulin binding | 0.00221641 |
| PTGIR | Prostaglandin I2 (Prostacyclin) Receptor (IP) | G-protein coupled receptor activity and guanyl-nucleotide exchange factor activity | 0.01047073 |
| ADCY8 | Adenylate Cyclase 8 (Brain) | calcium- and calmodulin-responsive adenylate cyclase activity and adenylate cyclase activity | 0.01116758 |
| VAV1 | Vav 1 Guanine Nucleotide Exchange Factor | sequence-specific DNA binding transcription factor activity and guanyl- nucleotide exchange factor activity | 0.0136214 |
| CLIC4 | Chloride Intracellular Channel 4 | chloride channel activity and voltage-gated chloride channel activity | 0.01450765 |
| IGKV3-20 | Immunoglobulin Kappa Variable 3-20 | antigen binding | 0.02031975 |
| ADA | Adenosine Deaminase | purine nucleoside binding and adenosine deaminase activity | 0.02166327 |
| KIR2DL1; KIR2DL4; KIR3DL1; KIR2DL3 | Killer Cell Immunoglobulin-Like Receptor, Two Domains, Long Cytoplasmic Tail, 1, 3 and 4/Killer Cell Immunoglobulin-Like Receptor, Three Domains, Long Cytoplasmic Tail, 1 | receptor activity/HLA-B specific inhibitory MHC class I receptor activity | 0.02166327 |
| PLD2 | Phospholipase D2 | NAPE-specific phospholipase D activity and phosphatidylinositol binding | 0.02166327 |
| SIGLEC16 | Sialic Acid Binding Ig-Like Lectin 16 (Gene/Pseudogene) | signallibg activity | 0.02166327 |
| CD34 | CD34 Molecule | sulfate binding and transcription factor binding | 0.0264282 |
| AR2A2 | Adaptor-Related Protein Complex 2, Alpha 2 Subunit | protein transporter activity and lipid binding | 0.0301917 |
| GINS1 | GINS Complex Subunit 1 (Psf1 Homolog) | protein binding | 0.0301917 |
| ULBP1 | UL16 Binding Protein 1 | antigen binding and natural killer cell lectin-like receptor binding | 0.0385112 |
| ADCY4 | Adenylate Cyclase 4 | adenylate cyclase activity | 0.03934766 |
| TREM1 | Triggering Receptor Expressed On Myeloid Cells 1 | receptor activity | 0.03934766 |
| ITGAM | Integrin, Alpha M (Complement Component 3 Receptor 3 Subunit) | heparin binding and heparan sulfate proteoglycan binding | 0.03952611 |
| CD55 | CD55 Molecule, Decay Accelerating Factor For Complement (Cromer Blood Group) | enzyme inhibitor activity and virus receptor activity | 0.0487537 |
| CR1;CR2 | Complement Component (3b/4b) Receptor 1 (Knops Blood Group)/Complement Component (3d/Epstein Barr Virus) Receptor 2 | complement component C3b binding and complement component C4b receptor activity/protein homodimerization activity and complement receptor activity | 0.05098024 |
| CCR6 | Chemokine (C-C Motif) Receptor 6 | C-C chemokine receptor activity and receptor activity | 0.05133199 |
| IL6ST | Interleukin 6 Signal Transducer (Gp130, Oncostatin M Receptor) | interleukin-6 receptor binding and protein homodimerization activity | 0.05133199 |
| CDH1 | Cadherin 1, Type 1, E-Cadherin (Epithelial) | beta-catenin binding and calcium ion binding | 0.05524598 |
| FCER1G | Fc Fragment Of igE, High Affinity I, Receptor For; Gamma Polypeptide | IgG binding and IgE receptor activity | 0.06443065 |

TABLE 34-continued

Multiple Sclerosis IFN-β Responder Gene Data

| GENE | Description | Table 34. Comments | p-value |
| --- | --- | --- | --- |
| ANGPTL2 | Angiopoietin-Like 2 | receptor binding | 0.06465591 |
| CR1 | Complement Component (3b/4b) Receptor 1 (Knops Blood Group) | complement component C3b binding and complement component C4b receptor activity | 0.06570725 |
| IFI6 | Interleukin 6 Signal Transducer (Gp130, Oncostatin M Receptor) | interleukin-6 receptor binding and protein homodimerization activity | 0.06840941 |
| AGER | Advanced Glycosylation End Product-Specific Receptor | S100 protein binding and receptor activity | 0.07448963 |
| IL2RB | Interleukin 2 Receptor, Beta | interleukin-2 receptor activity and interleukin-2 binding | 0.07448963 |
| SIRPB1 | Signal-Regulatory Protein Beta 1 | signallibg activity | 0.07448963 |
| C3 | Complement Component 3 | C5L2 anaphylatoxin chemotactic receptor binding and receptor binding | 0.07952454 |
| B2M | beta-2-microglobulin | identical protein binding | 0.089181 |
| ACTR2 | ARP2 Actin-Related Protein 2 Homolog (Yeast) | actin binding | 0.09136556 |
| AKT2 | V-Akt Murine Thymoma Viral Oncogene Homolog 2 | protein serine/threonine kinase activity and kinase activity | 0.10771954 |
| PAG1 | Phosphoprotein Associated With Glycosphingolipid Microdomains 1 | SH3/SH2 adaptor activity and SH2 domain binding | 0.10796035 |
| DNM2 | Dynamin 2 | protein kinase binding and GTP binding | 0.11207314 |
| IRAK2 | Interleukin-1 Receptor-Associated Kinase 2 | protein kinase activity and protein homodimerization activity | 0.11467884 |
| DLEU2 | Deleted In Lymphocytic Leukemia 2 (Non-Protein Coding) | affiliated with the lncRNA class | 0.11776746 |
| IL6R | Interleukin 6 Receptor | interleukin-6 receptor binding and protein homodimerization activity | 0.12113785 |
| GHR | Growth Hormone Receptor | protein phosphatase binding and protein homodimerization activity | 0.1256734 |
| KIR2DL4; KIR3DL1; KIR2DL3 | Killer Cell Immunoglobulin-Like Receptor, Two Domains, Long Cytoplasmic Tail, 4 and 3/ Killer Cell Immuncgiobuiin-Like Receptor, Three Domains, Long Cytoplasmic Tail, 1 | receptor activlty/HLA-B specific inhibitory MHC class I receptor activity | 0.14790547 |
| MS4A2 | Membrane-Spanning 4-Domains, Subfamily A, Member 2 | SH2 domain binding and protein kinase binding | 0.14790547 |
| CD8B | CD8b Molecule | MHC class I protein binding and coreceptor activity | 0.15470913 |
| FCGR1A | Fc Fragment Of IgG, High Affinity Ia, Receptor (CD64) | IgG binding and receptor signaling protein activity | 0.15470915 |
| IKBKB | Inhibitor Of Kappa Light Polypeptide Gene Enhancer in B-Cells, Kinase Beta | protein heterodimerization activity and protein homodimerization activity | 0.15470915 |
| PRKCQ | Protein Kinase C, Theta | ubiquitin-protein ligase activity and identical protein binding | 0.16963402 |
| C4BPB; C4BPA | Complement Component 4 Binding Protein, Beta and Alpha | both control activation of the complement cascade through the classical pathway | 0.18282939 |
| GUCY2D | Guanylate Cyclase 2D, Membrane (Retina-Specific) | receptor activity and identical protein binding | 0.18282939 |
| IL3RA | Interleukin 3 Receptor, Alpha (Low Affinity) | interleukln-3 receptor activity | 0.18282939 |
| IRAK1 | interleukin-1 Receptor-Associated Kinase 1 | protein serine/threonine kinase activity and protein homodimerization activity | 0.18282939 |
| TNFRSF13C | Tumor Necrosis Factor Receptor Superfamily, Member 13C | signallibg activity | 0.18282939 |
| RAR1B | RAP1B, Member Of RAS Oncogene Family | GDP binding and GTP binding | 0.18357409 |
| CD36 | CD36 Molecule (Thrombospondin Receptor) | lipid binding and transforming growth factor beta binding | 0.18747042 |
| IL21R | Interleukin 21 Receptor | interleukln-21 receptor activity | 0.20323726 |
| AP2S1 | Adaptor-Related Protein Complex 2, Sigma 1 Subunit | protein transporter activity and transporter activity | 0.20730949 |
| CRTAM | Cytotoxic And Regulatory T Cell Molecule | receptor binding | 0.20730949 |
| FGFR1 | Fibroblast Growth Factor Receptor 1 | heparin binding and protein homodimerization activity | 0.20730949 |
| GLYCAM1 | Glycosylation Dependent Cell Adhesion Molecule 1 (Pseudogene) | pseudogene affiliated with the lncENA class | 0.20730949 |
| JAK3 | Janus Kinase 3 | non-membrane spanning protein tyrosine kinase activity and protein tyrosine kinase activity | 0.20730949 |
| TRAC | T Cell Receptor Alpha Constant | peptide antigen binding and MHC protein binding | 0.20730949 |
| MRC2 | Mannose Receptor, C Type 2 | carbohydrate binding | 0.21155921 |
| AP2B1 | Adaptor-Related Protein Complex 2, Beta 1 Subunit | clathrin binding and protein complex binding | 0.22129944 |
| CBLB | Cbl Proto-Oncogene 3, E3 Ubiquitin Protein Ligase | signal transducer activity and calcium ion binding | 0.24873708 |
| FYN | FYN Oncogene Related To SRC FGR, YES | ion channel binding and identical protein binding | 0.24940226 |
| PRKCB | Protein Kinase C, Beta | chromatin binding and histone binding | 0.25190937 |
| AICDA | Activation-induced Cytidine Deaminase | cytidine deaminase activity | 0.27297508 |

TABLE 34-continued

Multiple Sclerosis IFN-β Responder Gene Data

| GENE | Description | Table 34. Comments | p-value |
|---|---|---|---|
| CD81 | CD81 Molecule | MHC class II protein complex binding | 0.27297508 |
| CLEC5A | C-Type Lectin Domain Family 5, Member A | carbohydrate binding and virus receptor activity | 0.27297508 |
| CXCR5 | Chemokine (C-X-C Motif) Receptor 5 | G-protein coupled receptor activity and C-X-C chemokine receptor activity | 0.27297508 |
| DONSON | Downstream Neighbor Of SON | molecular function | 0.27297508 |
| ERBB2 | V-Erb-B2 Avian Erythroblastic Leukemia Viral Oncogene Homolog 2 | protein C-terminus binding and identical protein binding | 0.27297508 |
| IGLC3; IGLC7; IGLC2; IGLC1; IGLC6 | Immunoglobulin Lambda Constant 3/7/2/1/6 | antigen binding | 0.27297508 |
| K1R2DS4; KIR3DL1 | Killer Cell Immunoglobulin-Like Receptor, Two Domains, Short Cytoplasmic Tail, 4/Killer Cell Immunoglobulin-Like Receptor, Three Domains, Long Cytoplasmic Tail, 1 | receptor activity/HLA-B specific inhibitory MHC class I receptor activity | 0.27297508 |
| NFKB2 | Nuclear Factor Of Kappa Light Polypeptide Gene Enhancer In B-Cells 2 (P49/P100) | transcription coactivator activity and sequence-specific DNA binding transcription factor activity | 0.27297508 |
| TIRAP | Toll-interleukin 1 Receptor (TIR) Domain Containing Adaptor Protein | protein binding, bridging and protein homodimerization activity | 0.27297508 |
| TLR1; TLR6 | Toll-Like Receptor 1 and 6 | transmembrane signaling receptor activity and protein heterodimerization activity | 0.27297508 |
| FAS | Fas Cell Surface Death Receptor | receptor activity and identical protein binding | 0.27996257 |
| CD96 | CD96 Molecule | protein binding | 0.28265813 |
| ATPIF1 | ATPase Inhibitory Factor 1 | enzyme inhibitor activity and protein homodimerization activity | 0.29257168 |
| ITGAL | Integrin, Alpha L (Antigen CD11A (P180), Lymphocyte Function- Associated Antigen 1; Alpha Polypeptide) | cell adhesion molecule binding | 0.29257168 |
| LILRB4 | Leukocyte immunoglobulin-Like Receptor, Subfamily B (With TM And ITIM Domains), Member 4 | antigen binding and receptor activity | 0.29257168 |
| ATK | Megakaryocyte-Associated Tyrosine Kinase | non-membrane spanning protein tyrosine kinase activity and protein tyrosine kinase activity | 0.29257168 |

TABLE 35

Neurofibromatosis

| GENE | Description | Table 35. Comments | p-value |
|---|---|---|---|
| PAX5 | Paired Box 5 | sequence-specific DNA binding transcription factor activity | 7.34E−05 |
| MAPK1 | Mitogen-Activated Protein Kinase 1 | phosphatase binding and protein serine/threonine kinase activity | 0.000242763 |
| TCF7L2 | Transcription Factor 7-like 2 (T-Cell Specific, HMG-Box) | chromatin binding and sequence-specific DNA binding transcription factor activity | 0.001722166 |
| RAD50 | DNA Repair Protein RAD50 | 3'-5' exonuclease activity and protein binding, bridging | 0.00248408 S |
| MET | Met Proto-Oncogene | hepatocyte growth factor-activated receptor activity and protein tyrosine kinase activity | 0.003610583 |
| HSPA1A | Heat Shock 70 kDa Protein 1A | stabilizes existing proteins against aggregation and mediates the folding of newly translated proteins | 0.003808074 |
| ETS1 | V-Ets Avian Erythroblastosis Virus E26 Oncogene Homolog 1 | transcription factor binding and sequence-specific DNA binding transcription factor activity | 0.005352442 |
| CCND3 | Cyclin D3 | protein kinase binding and cyclin-dependent protein serine/threonine kinase activity | 0.009209625 |
| PDGFA | Platelet-Derived Growth Factor Alpha Polypeptide | growth factor activity and protein homodimerizatlon activity | 0.013450723 |
| ANGPT1 | Angiopoietin 1 | receptor tyrosine kinase binding | 0.018084653 |
| YWNAE | Tyrosine 3-Monooxygenase/ Tryptophan 5-Monooxygenase Activation Protein, Epsilon | protein heterodimerizatlon activity and protein domain specific binding | 0.0195928 |
| IGF2 | Insulin-Like Growth Factor 2 (Somatomedin A) | growth factor activity and insulin receptor binding | 0.024402387 |
| CRLF2 | Cytokine Receptor-Like Factor 2 | protein binding | 0.024528379 |
| GSK3B | Glycogen Synthase Kinase 3 Beta | protein kinase binding and Identical protein binding | 0.025095831 |
| SMARCA4 | SWI/SNF Related, Matrix Associated, Actin Dependent Regulator of Chromatin, Subfamily A, Member 4 | chromatin binding and transcription corepressor activity | 0.039826881 |

TABLE 35-continued

Neurofibromatosis

| GENE | Description | Table 35. Comments | p-value |
|---|---|---|---|
| ARID1A | AT Rich Interactive Domain 1A (SWI-Like) | transcription coactivator activity and ligand-dependent nuclear receptor binding | 0.039899362 |
| PHLPP1 | PH Domain And Leucine Rich Repeat Protein Phosphatase 1 | phospholipid binding and phosphoprotein phosphatase activity | 0.045755956 |
| MAP2K6 | Mitogen-Activated Protein Kinase Kinase 6 | protein serine/threonine kinase activity and protein tyrosine kinase activity | 0.049695395 |
| CDKN1A | Cyclin-Dependent Kinase Inhibitor 1A (P21, Cip1) | cyclin-dependent protein serine/threonine kinase inhibitor activity and protein complex binding | 0.056825878 |
| CREB3L2 | CAMP Responsive Element Binding Protein 3-Like 2 | transcription regulatory region DNA binding and sequence-specific DNA binding transcription factor activity | 0.061543489 |
| MED12 | Mediator Complex Subunit 12 | chromatin binding and receptor activity | 0.065591011 |
| RPS6 | Ribosomal Protein S6 | structural constituent of ribosome and protein kinase binding | 0.065591011 |
| ERG | V-Ets Avian Erythroblastosis Virus E26 Oncogene Homolog | sequence-specific DNA binding transcription factor activity and signal transducer activity | 0.066666216 |
| STK3 | Serine/Threonine Kinase 3 | protein serine/threonine kinase activity and protein kinase activity | 0.071007547 |
| PPP2R1A | Protein Phosphatase 2, Regulatory Subunit A, Alpha | protein serine/threonine phosphatase activity and protein heterodimerization activity | 0.071334665 |
| HSP90AA1 | Heat Shock Protein 90 kDa Alpha (Cytosolic), Class A Member 1 | GTP binding and protein homodimerization activity | 0.07858404 |
| CRKL | V-Crk Avian Sarcoma Virus CT10 Oncogene Homolog-Like | SH3/SH2 adaptor activity and signal transducer activity | 0.081613204 |
| MEN1 | Multiple Endocrine Neoplasia I | sequence-specific DNA binding and transcription regulatory region DNA binding | 0.081613204 |
| TCF3 | Transcription Factor 3 | sequence-specific DNA binding and sequence-specific DNA binding transcription factor activity | 0.081613204 |
| GHR | Growth Hormone Receptor | protein phosphatase binding and protein homodimerization activity | 0.081618354 |
| GRB10 | Growth Factor Receptor-Bound Protein 10 | phospholipid binding and insulin receptor binding | 0.092067488 |
| CBLB | Methylmalonic Aciduria (Cobalamin Deficiency) ClbB Type | cob(il)alamin reductase activity and cob(i)yrinic acid a,c-diamide adenosyitransferase activity | 0.096651683 |
| IDH1 | Isocitrate Dehydrogenase 1 (NADP+), Soluble | magnesium ion binding and protein homodimerization activity | 0.103835035 |
| KDR | Kinase Insert Domain Receptor (A Type III Receptor Tyrosine Kinase) | transmembrane receptor protein tyrosine kinase activity and protein tyrosine kinase activity | 0.1177313 |
| LEPR | Leptin Receptor | cytokine receptor activity and identical protein binding | 0.137331474 |
| PAK1 | P21 Protein (Cdc42/Rac)-Activated Kinase 1 | protein kinase binding and identical protein binding | 0.145173658 |
| BRCA2 | Breast Cancer 2, Early Onset | histone acetyltransferase activity and single-stranded DNA binding | 0.154405702 |
| STAT5B | Signal Transducer And Activator Of Transcription 5B | sequence-specific DNA binding transcription factor activity activityand signal transducer | 0.155660564 |
| BAD | BCL2-Associated Agonist Of Cell Death | protein kinase binding and protein heterodimerization activity | 0.156265727 |
| E2F1 | Transcription Factor 1 | transcription factor binding and sequence-specific DNA binding transcription factor activity | 0.156265727 |
| NGFR | Nerve Growth Factor Receptor | ubiquitin protein ligase binding and signal transducer activity | 0.156265727 |
| APC | Adenomatous Polyposis Coli | beta-catenin binding and protein kinase binding | 0.161824001 |
| SPRED3 | Sprouty-Related, EVH1 Domain Containing 3 | signalling activity | 0.163428114 |
| FGFR2 | Fibroblast Growth Factor Receptor 2 | heparin binding and protein homodimerization activity | 0.171306539 |
| BDNF | Brain-Derived Neurotrophic Factor | growth factor activity and neurotrophin TRKB receptor binding | 0.176400063 |
| CASP2 | Caspase 2, Apoptosis-Related Cysteine Peptidase | cysteine-type endopeptidase activity and enzyme binding | 0.176400063 |
| VEGFA | Vascular Endothelial Growth Factor A | protein heterodimerization activity and protein homodimerization activity | 0.176400063 |
| NF2 | Neurofibromin 2 | cytoskeletal protein binding | 0.19198831 |
| CREBBL1 | CAMP Responsive Element Binding Protein 3-Like 1 | sequence-specific DNA binding and RNA polymerase II core promoter proximal region sequence-specific DNA binding transcription factor activity involved in positive regulation of transcription | 0.196225627 |
| SUZ12 | SUZ12 Polycomb Repressive Complex 2 Subunit | sequence-specific DNA binding and methylated histone residue binding | 0.221781006 |
| PAK2 | P21 Protein (Cdc42/R3c)-Activated Kinase 2 | protein kinase binding and identical protein binding | 0.232346927 |
| NGF | Nerve Growth Factor (Beta Polypeptide) | nerve growth factor receptor binding and growth factor activity | 0.240341223 |
| PML | Promyelocytic Leukemia | transcription coactivator activity and protein homodimerization activity | 0.240341223 |
| RELA | V-Rel Avian Reticuloendotheliosis Viral Oncogene Homolog A | identical protein binding and sequence-specific DNA binding transcription factor activity | 0.240341223 |
| EIF4B | Eukaryotic Translation Initiation Factor 4B | RNA binding and translation initiation factor activity | 0.252840719 |

TABLE 35-continued

Neurofibromatosis

| GENE | Description | Table 35. Comments | p-value |
|---|---|---|---|
| CDK6 | Cyclin-Dependent Kinase 6 | cyclin binding and cyclin-dependent protein serine/threonine kinase activity | 0.280990258 |
| CHUK | Conserved Helix-Loop-Helix Ubiquitous Kinase | protein heterodimerization activity and protein homodimerization activity | 0.285843285 |
| CASP7 | Caspase 7, Apoptosis-Related Cysteine Peptidase | cysteine-type peptidase activity and aspartic-type endopepridase activity | 0.288129068 |
| CCNA2 | Cyclin A2 | protein kinase binding | 0.288129068 |
| CDKN1B | Cyclin-Dependent Kinase inhibitor 1B (P27, Klp1) | cydin-dependent protein serine/threonine kinase inhibitor activity and protein phosphatase binding | 0.288129068 |
| CDKN2C | Cyclin-Dependent Kinase inhibitor 2C (P18, Inhibits CDK4) | cyclin-dependent protein serine/threonine kinase inhibitor activity and protein kinase binding | 0.2.88129068 |
| HRAS | Harvey Rat Sarcoma Viral Oncogene Homolog | protein C-terminus binding and GTP binding | 0.288129068 |
| SPRED1 | Sprouty-Related, EVH1 Domain Containing 1 | protein kinase binding and stem cell factor receptor binding | 0.288129068 |

TABLE 36a

Top Probes - Anti PD1 (Melanoma) - responders

| Probes | Gene Locus | Probe Count_Total | Probe Count_Sig | HyperG_Stats |
|---|---|---|---|---|
| PVRL1_11_119575859_119577309_119599998_119609544_FR | PVRL1 | 95 | 44 | 3.65E−05 |
| HLA-DQB1_6_32607972_32614493_32669132_32671838_RR | HLA-DQB1 | 12 | 8 | 0.004571 |
| HLA-DQB1_6_32607972_32614493_32630138_32632737_RR | HLA-DQB1 | 12 | 8 | 0.004571 |
| BOK_2_242498607_242505838_242528424_242532109_RF | BOK | 9 | 6 | 0.014565 |
| CSK_15_75042637_75047345_75083504_75088622_FR | CSK | 11 | 8 | 0.001994 |
| CSK_15_75042637_75047345_75075209_75080043_FF | CSK | 11 | 8 | 0.001994 |
| CSK_15_75042637_75047345J75072257_75074709_FR | CSK | 11 | 8 | 0.001994 |
| HLA-DQB1_6_32630138_32632737_32669132_32671838_RR | HLA-DQB1 | 12 | 8 | 0.004571 |
| STAT5B_17_40403935_40406459_40464294_40468456_FR | STAT5B | 20 | 12 | 0.001867 |
| BOK_2_242498607_242505838_242517411_242520415_RR | BOK | 9 | 6 | 0.014565 |
| PTPRA_20_2853761_2858838_2943750_2948659_RF | PTPRA | 137 | 57 | 0.000127 |
| FCGR2B_1_161562782_161569954_161615627_161622991_FR | FCGR2B | 72 | 28 | 0.017535 |
| BOK_2_242474875_242482300_242498607_242505838_RR | BOK | 9 | 6 | 0.014565 |
| FCCR2B_1_161519223_161525894_161562782_161569954_RF | FCGR2B | 72 | 28 | 0.017535 |
| HLA-DQB1_6_32634654_32639610_32669132_32671838_RR | HLA-DQB1 | 12 | 8 | 0.004571 |
| PTPRA_20_2853761_2858838_3001591_3004582_RF | PTPRA | 137 | 57 | 0.000127 |
| AKT1_14_105266348_105267359_105305709_105309658_FF | AKT1 | 18 | 11 | 0.002366 |
| PTPRA_20_2797355_2801691_3001591_3004582_RF | PTPRA | 137 | 57 | 0.000127 |
| FCGR2B_1_161534237_161535923_161562782_161569954_RF | FCGR2B | 72 | 28 | 0.017535 |
| BOK2_242454060_242458194_242498607_242505838_RR | BOK | 9 | 6 | 0.014565 |
| CSK_15_75042637_75047345_75075209_75080043_FR | CSK | 11 | 8 | 0.001994 |
| TNFRSF25_1_6521664_6526267_6554648_6558108_FR | TNFRSF25 | 23 | 16 | 2.37E−05 |
| SHH_7_155593268_155595881_155627543_155630456_FF | SHH | 25 | 12 | 0.019288 |
| PTPRA_20_2797355_2801691_2943750_2948659_RF | PTPRA | 137 | 57 | 0.000127 |
| TNFRSF25_1_6521664_6526267_6554648_6558108_FF | TNFRSF25 | 23 | 16 | 2.37E−05 |

| Probes | FDR_HyperG | Percent_Sig | Avg_CV |
|---|---|---|---|
| PVRL1_11_119575859_119577309_119599998_119609544_FR | 0.003027108 | 46 | 7.635 |
| HLA-DQB1_6_32607972_32614493_32669132_32671838_RR | 0.126456634 | 67 | 22.3213 |
| HLA-DQB1_6_32607972_32614493_32630138_32632737_RR | 0.126456634 | 67 | 11.4997 |
| BOK_2_242498607_242505838_242528424_242532109_RF | 0.185978822 | 67 | 12.1167 |
| CSK_15_75042637_75047345_75083504_75088622_FR | 0.066190912 | 73 | 4.2993 |
| CSK_15_75042637_75047345_75075209_75080043_FF | 0.066190912 | 73 | 3.5337 |
| CSK_15_75042637_75047345J75072257_75074709_FR | 0.066190912 | 73 | 7.7027 |
| HLA_DQB1_6_32630138_32632737_32669132_32671838_RR | 0.126456634 | 67 | 6.4587 |
| STAT5B_17_40403935_40406459_40464294_40468456_FR | 0.066190912 | 60 | 3.7883 |
| BOK_2_242498607_242505838_242517411_242520415_RR | 0.185978822 | 67 | 5.5887 |
| PTPRA_20_2853761_2858838_2943750_2948659_RF | 0.00842741 | 42 | 6.3143 |
| FCGR2B_1_161562782_161569954_161615627_161622991_FR | 0.207920508 | 39 | 7.6063 |
| BOK_2_242474875_242482300_242498607_242505838_RR | 0.185978822 | 67 | 5.514 |
| FCCR2B_1_161519223_161525894_161562782_161569954_RF | 0.207920508 | 39 | 11.9687 |
| HLA-DQB1_6_32634654_32639610_32669132_32671838_RR | 0.126456634 | 67 | 18.3157 |
| PTPRA_20_2853761_2858838_3001591_3004582_RF | 0.00842741 | 42 | 7.6363 |
| AKT1_14_105266348_105267359_105305709_105309658_FF | 0.071417842 | 61 | 11.7737 |
| PTPRA_20_2797355_2801691_3001591_3004582_RF | 0.0084274.1 | 42 | 11.6457 |
| FCGR2B_1_161534237_161535923_161562782_161569954_RF | 0.207920508 | 39 | 9.799 |
| BOK2_242454060_242458194_242498607_242505838_RR | 0.185978822 | 67 | 7.4167 |
| CSK_15_75042637_75047345_75075209_75080043_FR | 0.066190912 | 73 | 3.5587 |
| TNFRSF25_1_6521664_6526267_6554648_6558108_FR | 0.002619074 | 70 | 5.036 |

TABLE 36a-continued

Top Probes - Anti PD1 (Melanoma) - responders

| | | | |
|---|---|---|---|
| SHH_7_155593268_155595881_155627543_155630456_FF | 0.22081874 | 48 | 2.0403 |
| PTPRA_20_2797355_2801691_2943750_2948659_RF | 0.00842741 | 42 | 3.26 |
| TNFRSF25_1_6521664_6526267_6554648_6558108_FF | 0.002619074 | 70 | 3.634 |

| Probes | logFC | Ave Expr | t | B |
|---|---|---|---|---|
| PVRL1_11_119575859_119577309_119599998_119609544_FR | 1.226061632 | 1.226061632 | 5.78144807 | 0.132665646 |
| HLA-DQB1_6_32607972_32614493_32669132_32671838_RR | 1.087554243 | 1.087554243 | 4.681620255 | -1.14002515 |
| HLA-DQB1_6_32607972_32614493_32630138_32632737_RR | 1.063195633 | 1.063195633 | 3.723996585 | -2.400733019 |
| BOK_2_242498607_242505838_242528424_242532109_RF | 1.052556037 | 1.052556037 | 5.736345926 | 0.084050827 |
| CSK_15_75042637_75047345_75083504_75088622_FR | 1.017645742 | 1.017645742 | 10.5480604 | 3.93908303 |
| CSK_15_75042637_75047345_75075209_75080043_FF | 0.976259273 | 0.976259273 | 10.17749745 | 3.718233225 |
| CSK_15_75042637_75047345J75072257_75074709_FR | 0.956377371 | 0.956377371 | 8.607527484 | 2.66302761 |
| HLA-DQB1_6_32630138_32632737_32669132_32671838_RR | 0.947727381 | 0.947727381 | 6.812472203 | 1.167235963 |
| STAT5B_17_40403935_40406459_40464294_40468456_FR | 0.870424687 | 0.870424687 | 6.817040924 | 1.17150928 |
| BOK_2_242498607_242505838_242517411_242520415_RR | 0.80624455 | 0.80624455 | 6.460070524 | 0.829620615 |
| PTPRA_20_2853761_2858838_2943750_2948659_RF | 0.771442283 | 0.771442283 | 9.132304403 | 3.038874107 |
| FCGR2B_1_161562782_161569954_161615627_161622991_FR | 0.764546463 | 0.764546463 | 12.05142341 | 4.74221712 |
| BOK_2_242474875_242482300_242498607_242505838_FR | 0.7579354 | 0.7579354 | 6.572418004 | 0.938990195 |
| FCCR2B_1_161519223_161525894_161562782_161569954_RF | 0.753793658 | 0.753793658 | 10.0691174 | 3.651754924 |
| HLA-DQB1_6_32634654_32639610_32669132_32671838_RR | 0.744863383 | 0.744863383 | 12.87752031 | 5.127893879 |
| PTPRA_20_2853761_2858838_3001591_3004582_RF | 0.730046719 | 0.730046719 | 7.043346164 | 1.379956688 |
| AKT1_14_105266648_105267359_105305709_105309658_FF | 0.722145646 | 0.722145646 | 7.844164755 | 2.069431262 |
| PTPRA_20_2797355_2801691_3001591_3004582_RF | 0.708900064 | 0.708900064 | 8.071412072 | 2.252281349 |
| FCGR2B_1_161534237_161535923_161562782_161569954_RF | 0.705863487 | 0.705863487 | 11.77453541 | 4.604637192 |
| BOK2_242454060_242458194_242498607_242505838_RR | 0.697538177 | 0.697538177 | 5.281758629 | -0.422695361 |
| CSK_15_75042637_75047345_75075209_75080043_FR | 0.685347379 | 0.685347379 | 9.554135055 | 3.323606724 |
| TNFRSF25_1_6521664_6526267_6554648_6558108_FR | 0.683997693 | 0.683997693 | 4.543960331 | -1.31251778 |
| SHH_7_155593268_155595881_155627543_155630456_FF | 0.681239755 | 0.681239755 | 10.97966954 | 4.184300851 |
| PTPRA_20_2797355_2801691_2943750_2948659_RF | 0.665384587 | 0.665384587 | 7.762694435 | 2.00255201 |
| TNFRSF25_1_6521664_6526267_6554648_6558108_FF | 0.664203164 | 0.664203164 | 4.841523516 | -0.943405234 |

TABLE 36b

Top Probes - Anti PD1 (Melanoma) - responders - probe sequences

| Probes | FC | FC_1 | Loop LS | present | 60 mer |
|---|---|---|---|---|---|
| PVRL1_11_119575859_1195773091_119599998_119609544_FR | 2.33927526 | 2.33927526 | 1 | BL R | AGAAAATATAGTATTGATTGCTTTC AAGTCGATGCGCGCCCGCCGGGGC CCGGTCGGAGC (SEQ ID NO: 557) |
| HLA-DQB1_6_32607972_32614493_32669132_32671838_RR | 2.125134633 | 2.125134633 | 1 | BL R | TACTGTAGTAAGTTCTCTGAGGAGGA TATCGATTTTTTATTGTATCCTATAT TTTTTCTA (SEQ ID NO: 558) |
| HLA-DQB1_6_32607972_32614493_32630138_32632737_RR | 2.089554856 | 2.089554856 | 1 | BL R | TACTGTAGTAAGTTCTCTGAGGAGGA TATCGAAGTCTTGGATTAAGGTTCAT TCAACAAA (SEQ ID NO: 559) |
| BOK_2_242498607_242505838_242528424_242532109_RF | 2.074201477 | 2.074201477 | 1 | BL R | CACTTCCCCAACATAAGCCTCGGTCT CTTCGAGGGCGGGCCCGGCGGCCCCG GAGCAAAC (SEQ ID NO: 560) |
| CSK_15_75042637_75047345_75083504_75088622_FR | 2.024612404 | 2.024612404 | 1 | BL R | GAGTTCAGCGTGCCGCCGGGCGTGAA AGTCGAGGCATATTTGAGTTTAGGG AGGTGTTGC (SEQ ID NO: 561) |
| CSK_15_75042637_75047345_75075209_75080043_FF | 1.967357679 | 1.967357679 | 1 | BL R | GAGTTCAGCGTGCCGCCGGGCGTGA AAGTCGACTCTGGGCCCAGACCACA GAAGGAGGGG (SEQ ID NO: 562) |
| CSK_15_75042637_75047345_75072257_75074709_FR | 1.94043132 | 1.94043132 | 1 | BL R | GAGTTCAGCGTGCCGCCGGGCGTGA AAGTCGATTTGTTTATGGTTTTATC CCCAGTGCCT (SEQ ID NO: 563) |
| HLA-DQB1_6_32630138_32632737_32669132_32671838_RR | 1.928831852 | 1.928831852 | 1 | BL R | TTTGTTGAATGAACCTTAATCCAAGA CTTCGATTTTTTATTGTATCCTATAT TTTTTCTA (SEQ ID NO: 564) |
| STAT5B_17_40403935_40406459_40464294_40468456_FR | 1.82820099 | 1.82820099 | 1 | BL R | TTCCATAGATTACTTTTCAAATCATC CTTCGAAGCTGGCGGCTGAGGGCCCG GCGCCAAG (SEQ ID NO: 565) |

TABLE 36b -continued

Top Probes - Anti PD1 (Melanoma) - responders - probe sequences

| Probes | FC | FC_1 | Loop LS | present | 60 mer |
|---|---|---|---|---|---|
| BOK_2_242498607_242505838_ 242517411_242520415_RR | 1.748653628 | 1.748653628 | 1 | BL R | GTTTGCTCCGGGGCCGCCGGGCCCGC CCTCGATTTTAACACCACCATGGTTT GAATGAAT (SEQ ID NO: 566) |
| PTPRA_20_2853761_2858838_ 2943750_2948659_RF | 1.706975419 | 1.706975419 | 1 | BL R | TCCATTGTCTTATTCCAGTCTAGGCT TGTCGAGTTGCAGGCCGCCCTGGTGG CTAGACAT (SEQ ID NO: 567) |
| FCGR2B_1_161562782_161569954_ 161615627_161622991_FR | 1.698835854 | 1.698835854 | 1 | BL R | AAAAAACAATTATGTAATTGAAAACC CATCGAGGGGCTTACTAATGCCTTTT AGCTCCCT (SEQ ID NO: 568) |
| BOK_2_242474875_242482300_ 242498607_242505838_RR | 1.691068852 | 1.691068852 | 1 | BL R | GACCCCGGGAATTGGCTCCAGCACA TCTCGAGGGCGGGCCCGGCGGCCCCG GAGCAAAC (SEQ ID NO: 569) |
| FCGR2B_1_161519223_161525894_ 161562782_161569954_RF | 1.686221031 | 1.686221031 | 1 | BL R | AAAAAACAATTATGTAATTGAAAACC CATCGAAGCTCTTTGGTTCCACAGAG TGATTCTG (SEQ ID NO: 570) |
| HLA-DQB1_6_32634654_ 32639610_32669132_ 32671838_RR | 1.67581557 | 1.67581557 | 1 | BL R | AGGCATTCGTTCTTCAGCTCTTCTAT AATCGATTTTTTATTGTATCCTATAT TTTTTCTA (SEQ ID NO: 571) |
| PTPRA_20_2853761_2858838_ 3001591_3004582_RF | 1.658692805 | 1.658692805 | 1 | BL R | GCTCTTATAAATTATGTATTCAAAGA AATCGAGTTGCAGGCCGCCCTGGTGG CTAGACAT (SEQ ID NO: 572) |
| AKT1_14_105266348_105267359_ 105305709_105309658_FF | 1.649633626 | 1.649633626 | 1 | BL R | CCCGCGGCGGAGCTGCTACTGTTTA CTTTCGAAGCTTCTTCCTTTCGGCC CCCAGGCCTA (SEQ ID NO: 573) |
| PTPRA_20_2797355_2801691_ 3001591_3004582_RF | 1.634557427 | 1.634557427 | 1 | BL R | GCTCTTATAAATTATGTATTCAAAGA AATCGAACTGGCGGCAACCGCTGCAG CGCCTGCT (SEQ ID NO: 574) |
| FCGR2B_1_161534237_161535923_ 161562782_161569954_RF | 1.631120636 | 1.631120636 | 1 | BL R | AAAAAACAATTATGTAATTGAAAAC CCATCGAGGGGCTTACTAATGCCTT TTAGCTCCCT (SEQ ID NO: 575) |
| BOK_2_242454060_242458194_ 242498607_242505838_RR | 1.621735092 | 1.621735092 | 1 | BL R | TCTCCTGCCTACCACACTGTGAGAA AGCTCGAGGGCGGGCCCGGCGGCCC CGGAGCAAAC (SEQ ID NO:576) |
| CSK_15_75042637_75047345_ 75075209_75080043_FR | 1.608089138 | 1.608089138 | 1 | BL R | GAGTTCAGCGTGCCGCCGGGCGTGA AAGTCGAATTCTCCCAGGAGCCACT GTCAGAACCC (SEQ ID NO: 577) |
| TNFRSF25_1_6521664_6526267_ 6554648_6558108_FR | 1.606585424 | 1.606585424 | 1 | BL R | CCGCGCCCGCAGGGCCCGCCCCGCG CCGTCGACAATGTTATTCTTTGTTT CTCTTACCAA (SEQ ID NO: 578) |
| SHH_7_155593268_155595881_ 155627543_155630456_FF | 1.603517118 | 1.603517118 | 1 | BL R | GAAGGCCCGGTGCGCCCAGCTGTGC TCCTCGAGAACAGCCAGGCTAACAC GGAGAAACCC (SEQ ID NO: 579) |
| PTPRA_20_2797355_2801691_ 2943750_2948659_RF | 1.585991003 | 1.585991003 | 1 | BL R | TCCATTGTCTTATTCCAGTCTAGGC TTGTCGAACTGGCGGCAACCGCTGC AGCGCCTGCT (SEQ ID NO: 580) |
| TNFRSF25_1_6521664_6526267_ 6554648_6558108_FF | 1.584692766 | 1.584692766 | 1 | BL R | CCGCGCCCGCAGGGCCCGCCCCGCG CCGTCGATGTGTTGGAAGTCAGGGC GGCGGTGCCC (SEQ ID NO: 581) |

TABLE 36C

Top Probes - Anti PD1 (Melanoma) - Responders - Loci

| Probes | Chr | Start1 | End1 | Start2 | End2 |
|---|---|---|---|---|---|
| PVRL1_11_119575859_119577309_119599998_119609544_FR | 11 | 119577280 | 119577309 | 119599999 | 119600028 |
| HLA-DQB1_6_32607972_32614493_32669132_32671838_RR | 6 | 32607973 | 32608002 | 32669133 | 32669162 |

TABLE 36C-continued

Top Probes - Anti PD1 (Melanoma) - Responders - Loci

| | | | | | |
|---|---|---|---|---|---|
| HLA-DQB1_6_32607972_32614493_32630138_32632737_RR | 6 | 32607973 | 32608002 | 32630139 | 32630168 |
| BOK_2_242498607_242505838_242528424_242532109_RF | 2 | 242498608 | 242498637 | 242532080 | 242532109 |
| CSK_15_75042637_75047345_75083504_75088622_FR | 15 | 75047316 | 75047345 | 75083505 | 75083534 |
| CSK_15_75042637_75047345_75075209_75080043_FF | 15 | 75047316 | 75047345 | 75080014 | 75080043 |
| CSK_15_75042637_75047345J75072257_75074709_FR | 15 | 75047316 | 75047345 | 75072258 | 75072287 |
| HLA-DQB1_6_32630138_32632737_32669132_32671838_RR | 6 | 32630139 | 32630168 | 32669133 | 32669162 |
| STAT5B_17_40403935_40406459_40464294_40468456_FR | 17 | 40406430 | 40406459 | 40464295 | 40464324 |
| BOK_2_242498607_242505838_242517411_242520415_RR | 2 | 242498608 | 242498637 | 242517412 | 242517441 |
| PTPRA_20_2853761_2858838_2943750_2948659_RF | 20 | 2853762 | 2853791 | 2948630 | 2948659 |
| FCGR2B_1_161562782_161569954_161615627_161622991_FR | 1 | 161569925 | 161569954 | 161615628 | 161615657 |
| BOK_2_242474875_242482300_242498607_242505838_RR | 2 | 242454061 | 242454090 | 242498608 | 242498637 |
| FCCR2B_1_161519223_161525894_161562782_161569954_RF | 15 | 75047316 | 75047345 | 75075210 | 75075239 |
| HLA-DQB1_6_32634654_32639610_32669132_32671838_RR | 1 | 6526238 | 6526267 | 6554649 | 6554678 |
| PTPRA_20_2853761_2858838_3001591_3004582_RF | 7 | 155595852 | 155595881 | 155630427 | 155630456 |
| AKT1_14_105266348_105267359_105305709_105309658_FF | 20 | 2797356 | 2797385 | 2948630 | 2948659 |
| PTPRA_20_2797355_2801691_3001591_3004582_RF | 1 | 6526238 | 6526267 | 6558079 | 6558108 |
| FCGR2B_1_161534237_161535923_161562782_161569954_RF | 2 | 242454061 | 242454090 | 242498608 | 242498637 |
| BOK2_242454060_242458194_242498607_242505838_RR | 15 | 75047316 | 75047345 | 75075210 | 75075239 |
| CSK_15_75042637_75047345_75075209_75080043_FR | 1 | 6526238 | 6526267 | 6554649 | 6554678 |
| TNFRSF25_1_6521664_6526267_6554648_6558108_FR | 7 | 155595852 | 155595881 | 155630427 | 155630456 |
| SHH_7_155593268_155595881_155627543_155630456_FF | 20 | 2797356 | 2797385 | 2948630 | 2948659 |
| PTPRA_20_2797355_2801691_2943750_2948659_RF | 1 | 6526238 | 6526267 | 6558079 | 6558108 |
| TNFRSF25_1_6521664_6526267_6554648_6558108_FF | 2 | 242454061 | 242454090 | 242498608 | 242498637 |

| Probes | Chr | Start1 | End1 | Start2 | End2 |
|---|---|---|---|---|---|
| PVRL1_11_119575859_119577309_119599998_119609544_FR | 11 | 119573310 | 119577309 | 119599999 | 119603998 |
| HLA-DQB1_6_32607972_32614493_32669132_32671838_RR | 6 | 32607973 | 32611972 | 32669133 | 32673132 |
| HLA-DQB1_6_32607972_32614493_32630138_32632737_RR | 6 | 32607973 | 32611972 | 32630139 | 32634138 |
| BOK_2_242498607_242505838_242528424_242532109_RF | 2 | 242498608 | 242502607 | 242528110 | 242532109 |
| CSK_15_75042637_75047345_75083504_75088622_FR | 15 | 75043346 | 75047345 | 75083505 | 75087504 |
| CSK_15_75042637_75047345_75075209_75080043_FF | 15 | 75043346 | 75047345 | 75076044 | 75080043 |
| CSK_15_75042637_75047345J75072257_75074709_FR | 15 | 75043346 | 75047345 | 75072258 | 75076257 |
| HLA-DQB1_6_32630138_32632737_32669132_32671838_RR | 6 | 32630139 | 32634138 | 32669133 | 32673132 |
| STAT5B_17_40403935_40406459_40464294_40468456_FR | 17 | 40402460 | 40406459 | 40464295 | 40468294 |
| BOK_2_242498607_242505838_242517411_242520415_RR | 2 | 242498608 | 242502607 | 242517412 | 242521411 |
| PTPRA_20_2853761_2858838_2943750_2948659_RF | 20 | 2853762 | 2857761 | 2944660 | 2948659 |
| FCGR2B_1_161562782_161569954_161615627_161622991_FR | 1 | 161565955 | 161569954 | 161615628 | 161619627 |
| BOK_2_242474875_242482300_242498607_242505838_RR | 2 | 242454061 | 242458060 | 242498608 | 242502607 |
| FCCR2B_1_161519223_161525894_161562782_161569954_RF | 15 | 75043346 | 75047345 | 75075210 | 75079209 |
| HLA-DQB1_6_32634654_32639610_32669132_32671838_RR | 1 | 6522268 | 6526267 | 6554649 | 6558648 |
| PTPRA_20_2853761_2858838_3001591_3004582_RF | 7 | 155591882 | 155595881 | 155626457 | 155630456 |
| AKT1_14_105266348_105267359_105305709_105309658_FF | 20 | 2797356 | 2801355 | 2944660 | 2948659 |
| PTPRA_20_2797355_2801691_3001591_3004582_RF | 1 | 6522268 | 6526267 | 6554109 | 6558108 |
| FCGR2B_1_161534237_161535923_161562782_161569954_RF | 2 | 242454061 | 242458060 | 242498608 | 242502607 |
| BOK2_242454060_242458194_242498607_242505838_RR | 15 | 75043346 | 75047345 | 75075210 | 75079209 |
| CSK_15_75042637_75047345_75075209_75080043_FR | 1 | 6522268 | 6526267 | 6554649 | 6558648 |
| TNFRSF25_1_6521664_6526267_6554648_6558108_FR | 7 | 155591882 | 155595881 | 155626457 | 155630456 |
| SHH_7_155593268_155595881_155627543_155630456_FF | 20 | 2797356 | 2801355 | 2944660 | 2948659 |
| PTPRA_20_2797355_2801691_2943750_2948659_RF | 1 | 6522268 | 6526767 | 6554109 | 6558108 |
| TNFRSF25_1_6521664_6526267_6554648_6558108_FF | 2 | 242454061 | 242458060 | 242498608 | 242502607 |

TABLE 36d

Top Probes-Anti PD1 (Melanoma) Non-responders

| Probes | Gene Locus | Probe_Count_Total | Probe_Count_Sig | HyperG_Stats |
|---|---|---|---|---|
| PVRL1_11_119523735_119528121_119599998_119609544_RF | PVRL1 | 95 | 44 | 3.65E−05 |
| IL12B_5_158737480_158738589_158805563_158807407_FF | IL12B | 11 | 7 | 0.011584 |
| MYD88_3_38139864_38141788_38192489_38194027_RR | MYD88 | 18 | 10 | 0.009424 |
| PVRL1_11_119599998_119609544_119620830_119624585_FR | PVRL1 | 95 | 44 | 3.65E−05 |
| PIK3R3_1_46633134_46639474_46678880_46685388_FR | PIK3R3 | 55 | 24 | 0.005396 |
| CD6_11_60744556_60751199_60768894_60771404_RR | CD6 | 62 | 33 | 9.60E−06 |
| TREM1_6_41229998_41238663_41295986_41297320_RR | TREM1 | 32 | 15 | 0.012077 |
| PVRL1_11_119508824_119511197_119599998_119609544_RF | PVRL1 | 95 | 44 | 3.65E−05 |
| IL12B_5_158737480_158738689_158781589_158783887_FF | IL12B | 11 | 7 | 0.011584 |
| IL12A_3_159657523_159676447_159701524_159705330_FR | IL12A | 19 | 10 | 0.015159 |
| PVRL1_11_119599998_119609544_119640015_119642535_FR | PVRL1 | 95 | 44 | 3.65E−05 |
| CD6_11_60768894_60771404_60785339_60793057_RF | CD6 | 62 | 33 | 9.60E−06 |
| ILI2B_5_158737480_158738689_158805563_158807407_FR | IL12B | 11 | 7 | 0.011584 |
| PVRL1_11_119539363_119541214_119599998_119609544_RF | PVRL1 | 95 | 44 | 3.65E−05 |
| IL12A_3_159657523_159676447_159701524_159705330_RR | IL12A | 19 | 10 | 0.015159 |
| PVRL1_11_119479071_119480091_119599998_119609544_RF | PVRL1 | 95 | 44 | 3.65E−05 |
| PIK3CA_3_178832360_178841413_178871576_178873671_FF | PIK3CA | 25 | 13 | 0.006619 |

TABLE 36d-continued

Top Probes-Anti PD1 (Melanoma) Non-responders

| | | | | |
|---|---|---|---|---|
| PIK3R3_1_46609200_46612260_46633134_46639474_RF | PIK3R3 | 55 | 24 | 0.005396 |
| MYD88_3_38164895_38166955_38192489_38194027_RR | MYD88 | 18 | 10 | 0.009424 |
| PVRL1_11_119570787_119575859_119599998_119609544_RF | PVRL1 | 95 | 44 | 3.65E−05 |
| CD6_11_60744556_60751199_60768894_60771404_FR | CD6 | 62 | 33 | 9.60E−06 |
| PIK3R3_1_46488955_46494355_46633134_46639474_RF | PIK3R3 | 55 | 24 | 0.005396 |
| PVRL1_11_119599998_119609544_119620830_119624585_FF | PVRL1 | 95 | 44 | 3.65E−05 |
| PIK3R3_1_46633134_46639474_46662272_46666981_FR | PIK3R3 | 55 | 24 | 0.005396 |
| PIK3R3_1_46605407_46608166_46633134_46639474_RF | PIK3R3 | 55 | 24 | 0.005396 |

| Probes | FDR_HyperG | Percent_Sig | Avg_CV | logFC |
|---|---|---|---|---|
| PVRL1_11_119523735_119528121_119599998_119609544_RF | 0.003027108 | 46 | 5.822 | 0.534218713 |
| IL12B_5_158737480_158738589_158805563_158807407_FF | 0.182699883 | 64 | 4.1377 | 0.531233304 |
| MYD88_3_38139864_38141788_38192489_38194027_RR | 0.173813506 | 56 | 11.04 | 0.520757975 |
| PVRL1_11_119599998_119609544_119620830_119624585_FR | 0.003027108 | 46 | 5.2193 | 0.516406696 |
| PIK3R3_1_46633134_46639474_46678880_46685388_FR | 0.137801433 | 44 | 4.378 | 0.488392104 |
| CD6_11_60744556_60751199_60768894_60771404_RR | 0.001593482 | 53 | 3.2567 | 0.488334118 |
| TREM1_6_41229998_41238663_41295986_41297320_RR | 0.182699883 | 47 | 5.1013 | 0.486331515 |
| PVRL1_11_119508824_119511197_119599998_119609544_RF | 0.003027108 | 46 | 5.0377 | 0.480648315 |
| IL12B_5_158737480_158738689_158781589_158783887_FF | 0.182699883 | 64 | 4.282 | 0.476087861 |
| IL12A_3_159657523_159676447_159701524_159705330_FR | 0.186399228 | 53 | 0.9037 | 0.473957047 |
| PVRL1_11_119599998_119609544_119640015_119642535_FR | 0.003027108 | 46 | 6.073 | 0.470148979 |
| CD6_11_60768894_60771404_60785339_60793057_RF | 0.001593482 | 53 | 3.216 | 0.468856196 |
| ILI2B_5_158737480_158738689_158805563_158807407_FR | 0.182699883 | 64 | 6.2313 | 0.464794636 |
| PVRL1_11_119539363_119541214_119599998_119609544_RF | 0.003027108 | 46 | 5.525 | 0.460783807 |
| IL12A_3_159657523_159676447_159701524_159705330_RR | 0.186399228 | 53 | 3.6993 | 0.457786304 |
| PVRL1_11_119479071_119480091_119599998_119609544_RF | 0.003027108 | 46 | 3.7273 | 0.455986104 |
| PIK3CA_3_178832360_178841413_178871576_178873671_FF | 0.146507027 | 52 | 2.733 | 0.445211521 |
| PIK3R3_1_46609200_46612260_46633134_46639474_RF | 0.137801433 | 44 | 10.7787 | 0.443513439 |
| MYD88_3_38164895_38166955_38192489_38194027_RR | 0.173813506 | 56 | 2.8267 | 0.439771491 |
| PVRL1_11_119570787_119575859_119599998_119609544_RF | 0.003027108 | 46 | 4.0827 | 0.431853241 |
| CD6_11_60744556_60751199_60768894_60771404_FR | 0.001593482 | 53 | 5.8293 | −0.42873082 |
| PIK3R3_1_46488955_46494355_46633134_46639474_RF | 0.137801433 | 44 | 2.7617 | 0.427126062 |
| PVRL1_11_119599998_119609544_119620830_119624585_FF | 0.003027108 | 46 | 8.9813 | 0.424995751 |
| PIK3R3_1_46633134_46639474_46662272_46666981_FR | 0.137801433 | 44 | 5.5577 | 0.418086122 |
| PIK3R3_1_46605407_46608166_46633134_46639474_RF | 0.137801433 | 44 | 5.008 | 0.411050272 |

TABLE 36e

Top Probes - Anti PD1 (Melanoma) Non-responders

| Probes | Ave Expr | T | P. Value | adj.P.Val | B |
|---|---|---|---|---|---|
| PVRL1_11_119539363_119541214_119599998_119609544_RF | −0.534218713 | −9.570025943 | 2.35E−05 | 0.008847609 | 3.334045114 |
| IL12A_3_159657523_159676447_159701524_159705330_RR | −0.531233304 | −7.016342932 | 0.000181305 | 0.009942962 | 1.35541306 |
| PVRL1_11_119479071_119480091_119599998_119609544_RF | −0.520757975 | −3.831304203 | 0.006089906 | 0.044194094 | −2.252601523 |
| PIK3CA_3_178832360_178841413_178871576_178873671_FF | −0.516406696 | −8.795272062 | 4.14E−05 | 0.008847609 | 2.800356612 |
| PIK3R3_1_46609200_46612260_46633134_46639474_RF | −0.488392104 | −5.61212648 | 0.000725486 | 0.015727218 | −0.051375364 |
| MYD88_3_38164895_38166955_38192489_38194027_RR | −0.488334118 | −8.04736G963 | 7.46E−05 | 0.009617494 | 2.23318282 |
| PVRL1_11_119570787_119575859_119599998_119609544_RF | −0.486331515 | −8.738479042 | 4.32E−05 | 0.008847609 | 2.759158258 |
| CD6_11_60744556_60751199_60768894_60771404_FR | −0.480648315 | −8.6418614 | 4.66E−05 | 0.008945528 | 2.688386536 |
| PIK3R3_1_46488955_46494355_46633134_46639474_RF | −0.476087861 | −6.114799585 | 0.000430223 | 0.012658979 | 0.482977345 |
| PVRL1_11_119599998_119609544_119620830_119624585_FF | −0.473957047 | −7.58766065 | 0.000109483 | 0.00978135 | 1.856437949 |
| PIK3R3_1_46633134_46639474_46662272_46666981_FR | −0.470148979 | −8.578336694 | 4.89E−05 | 0.008945528 | 2.641380204 |
| PIK3R3_1_46605407_46608166_46633134_46639474_RF | −0.46886196 | −8.542957327 | 5.03E−05 | 0.008945528 | 2.615035493 |
| | −0.464794636 | −7.023464829 | 0.000180133 | 0.009942962 | 1.361894813 |
| PVRL1_11_119539363_119541214_119599998_119609544_RF | −0.460783807 | −8.332777274 | 5.93E−05 | 0.009591857 | 2.456053048 |
| PVRL1_11_119479071_119480091_119599998_119609544_RF | −0.455986104 | −7.517911586 | 0.000116245 | 0.00978135 | 1.797273524 |
| PIK3CA_3_ 178832360_178841413_178871576_178873671_FF | −0.445211521 | −7.531076446 | 0.000114934 | 0.00978135 | 1.808482074 |
| PIK3R3_1_46609200_46612260_46633134_46639474_RF | −0.443513439 | −5.674070937 | 0.000679088 | 0.015238097 | 0.016439762 |
| MYD88_3_38164895_38166955_381924893819402_RR | −0.439771491 | −7.048947048 | 0.00017601 | 0.009942962 | 1.38503639 |
| PVRL1_11_119570787_119575859_119599998_119609544_RF | −0.431853241 | −7.498223987 | 0.000118238 | 0.00978135 | 1.780475318 |
| CD6_11_60744556_60751199_60768894_60771404_FR | −0.42873082 | −7.398571649 | 0.000128932 | 0.00978135 | 1.694777806 |
| PIK3R3_1_46488955_46494355_46633134_46639474_RF | −0.427126062 | −4.901162068 | 0.001606582 | 0.0221991 | −0.871100352 |
| PVRL1_11_119599998_119609544_119620830_119624585_FF | −0.424995751 | −7.614744268 | 0.000106977 | 0.00978135 | 1.879266088 |
| PIK3R3_1_46633134_46639474_46662272_46666981_FR | −0.418086122 | −4.651195344 | 0.002160496 | 0.025812366 | −1.177891691 |
| PIK3R3_1_46605407_46608166_46633134_46639474_RF | −0.411050272 | −4.731761481 | 0.001961829 | 0.024339948 | −1.077937879 |

| Probes | | FC | FC_1 | LS | Loop present |
|---|---|---|---|---|---|
| PVRL1_11_119539363_119541214_119599998_119609544_RF | | 0.690532531 | −1.448157697 | −1 | BL NR |
| IL12A_3_159657523_159676447_159701524_159705330_RR | | 0.691962949 | −1.445164083 | −1 | BL NR |
| PVRL1_11_119479071_119480091_119599998_119609544_RF | | 0.697005539 | −1.434708829 | −1 | BL NR |
| PIK3CA_3_178832360_178841413_178871576_178873671_FF | | 0.699110934 | −1.430388156 | −1 | BL NR |
| PIK3R3_1_46609200_46612260_46633134_46639474_RF | | 0.712819098 | −1.402880481 | −1 | BL NR |

TABLE 36e-continued

Top Probes - Anti PD1 (Melanoma) Non-responders

| | | | | |
|---|---|---|---|---|
| MYD88_3_38164895_38166955_38192489_38194027_RR | 0.712847749 | −1.402824097 | −1 | BL NR |
| PVRL1_11_119570787_119575859_119599998_119609544_RF | 0.713837939 | −1.40087819 | −1 | BL NR |
| CD6_11_60744556_60751199_60768894_60771404_FR | 0.716655502 | −1.395370374 | −1 | BL NR |
| PIK3R3_1_46488955_46494355_46633134_46639474_RF | 0.718924482 | −1.39096668 | −1 | BL NR |
| PVRL1_11_119599998_119609544_119620830_119624585_FF | 0.719987095 | −1.388913783 | −1 | BL NR |
| PIK3R3_1_46633134_46639474_46662272_46666981_FR | 0.721890048 | −1.385252508 | −1 | BL NR |
| PIK3R3_1_46605407_46608166_46633134_46639474_RF | 0.722537216 | −1.384011755 | −1 | BL NR |
| | 0.724574211 | −1.380120883 | −1 | BL NR |
| PVRL1_11_119539363_119541214_119599998_119609544_RF | 0.726591399 | −1.376289344 | −1 | BL NR |
| PVRL1_11_119479071_119480091_119599998_119609944_RF | 0.729011711 | −1.371720076 | −1 | BL NR |
| PIK3CA_3_178832360_178841413_178871576_178873671_FF | 0.734476623 | −1.36151372 | −1 | BL NR |
| PIK3R3_1_46609200_46612260_46633134_46639474_RF | 0.735341627 | −1.359912133 | −1 | BL NR |
| MYD88_3_38164895_38166955_381924893819402_RR | 0.737251373 | −1.356389472 | −1 | BL NR |
| PVRL1_11_119570787_119575859_119599998_119609544_RF | 0.741308911 | −1.348965303 | −1 | BL NR |
| CD6_11_60744556_60751199_60768894_60771404_FR | 0.742915061 | −1.346048899 | −1 | BL NR |
| PIK3R3_1_46488955_46494355_46633134_46639474_RF | 0.74374189 | −1.344552476 | −1 | BL NR |
| PVRL1_11_119599998_119609544_119620830_119624585_FF | 0.744840925 | −1.342568549 | −1 | BL NR |
| PIK3R3_1_46633134_46639474_46662272_46666981_FR | 0.748416815 | −1.336153838 | −1 | BL NR |
| PIK3R3_1_46605407_46608166_46633134_46639474_RF | 0.752075669 | −1.32965344 | −1 | BL NR |

TABLE 36f

Top Probes - Anti PDI (Melanoma) Non-responders - probe sequences

| Probes | 60 mer |
|---|---|
| TNFRSF25_1_6521664_6526267_6541388_6544308_FF | CCGCGCCCGCAGGGCCCGCCCCGCGCCGTCGA GGCTTTCAAGGGATCCAGGGTGGGGTGC (SEQ ID NO: 582) |
| TNFRSF25_1_6521664_6526267_6554648_6558108_FR | CCGCGCCCGCAGGGCCCGCCCCGCGCCGTCGA CAATGTTATTCTTTGTTTCTCTTACCAA (SEQ ID NO: 583) |
| TNFRSF25_1_6521664_6526267_6554648_6558108_FF | CCGCGCCCGCAGGGCCCGCCCCGCGCCGTCGA TGTGTTGGAAGTCAGGGCGGCGGTGCCC (SEQ ID NO: 584) |
| BOK_2_242498607_242505838_242528424_242532109_RF | CACTTCCCCAACATAAGCCTCGGTCTCTTCGA GGGCGGGCCCGGCGGCCCCGGAGCAAAC (SEQ ID NO: 585) |
| TNFRSF25_1_6521664_6526267_6574084_6575375_FR | CCGCGCCCGCAGGGCCCGCCCCGCGCCGTCGA GAAGCATAAAGCAGGGACAGGTATGGAG (SEQ ID NO: 586) |
| BOK_2_242474875_242482300_242498607_242505838_RR | GACCCCCGGGAATTGGCTCCAGCACATCTCGA GGGCGGGCCCGGCGGCCCCGGAGCAAAC (SEQ ID NO: 587) |
| BOK_2_242498607_242505838_242517411_242520415_RR | GTTTGCTCCGGGGCCGCCGGGCCCGCCCTCGA TTTTAACACCACCATGGTTTGAATGAAT (SEQ ID NO: 588) |
| IRF1_5_131808352_131813604_131831068_131832754_FF | GTGTCTCGGCCCCCTGGGGCCCCACCCTTCGA TTTCCCTGTTGCCGCCGCGTTTGCAAGA (SEQ ID NO: 589) |
| BOK_2_242454060_242458194_242498607_242505838_RR | TCTCCTGCCTACCACACTGTGAGAAAGCTCGA GGGCGGGCCCGGCGGCCCCGGAGCAAAC (SEQ ID NO: 590) |
| CSK_15_75042637_75047345_75083504_75088622_FR | GAGTTCAGCGTGCCGCCGGGCGTGAAAGTCGA GGCATATTTGAGTTTAGGGAGGTGTTGC (SEQ ID NO: 591) |
| TNFRSF25_1_6521664_6526267_6554648_6558108_RF | GGGCACCGCCGCCCTGACTTCCAACACATCGA TCTCTGCCTCGCGCAGCCCCAGCGTGCG (SEQ ID NO: 592) |
| IKBKB_8_42121759_42128721_42148497_42149642_FR | CCACCCCCGCCCGGGGAGTCGCCCGGTCGA TTTCCAAAAGCTCACACATGGGTGCACA (SEQ ID NO: 593) |
| TNFRSF25_1_6510663_6512333_6554648_6558108_RF | GGGCACCGCCGCCCTGACTTCCAACACATCGA AGAATGGGTGGGGCCTTGCACCTCATAC (SEQ ID NO: 594) |
| IKBKB_8_42121759_42128721_42188562_42190317_FR | CCACCCCCGCCCGGGGAGTCGCCCGGTCGA CCCCCTGACATGGGGCTGCCTGGAGCAG (SEQ ID NO: 595) |
| TNFRSF25_1_6554648_6558108_6574084_6575375_FR | GGGCACCGCCGCCCTGACTTCCAACACATCGAG AAGCATAAAGCAGGGACAGGTATGGAG (SEQ ID NO: 596) |
| CSK_15_75042637_75047345_75075209_75080043_FF | GAGTTCAGCGTGCCGCCGGGCGTGAAAGTCGA CTCTGGGCCCAGACCACAGAAGGAGGGG (SEQ ID NO: 597) |

TABLE 36f-continued

Top Probes - Anti PDI (Melanoma) Non-responders - probe sequences

| Probes | 60 mer |
|---|---|
| ARHGEF7_13_111748012_111752622_111951910_111954429_RF | AATTCTGTTGGAAGAATAATTTAAAATATCGATGTGGCGACCGGCTGTGGGGGTCACGGA (SEQ ID NO: 598) |
| STAT5B_17_40403935_40406459_40464294_40468456_FR | TTCCATAGATTACTTTTCAAATCATCCTTCGAAGCTGGCGGCTGAGGGCCCGGCGCCAAG (SEQ ID NO: 599) |
| CSK_15_75042637_75047345_75072257_75074709_FR | GAGTTCAGCGTGCCGCCGGGCGTGAAAGTCGATTTGTTTATGGTTTTATCCCCAGTGCCT (SEQ ID NO: 600) |
| IRF3_19_50158039_50163617_50184391_50185455_RF | CACCCTCCCTTCTTCCTGGGCCCTCAGATCGACCCCCCCCACCCCCACCGGGCTGGCTGC (SEQ ID NO: 601) |
| IKBKB_8_42121759_42128721_42138740_42142593_FR | CCACCCCCGCCCCGGGGAGTCGCCCGGTCGAGGGCCTGGCAAGAAGACAGAAGCCGACT (SEQ ID NO: 602) |
| TRAF1_9_123675824_123681988_123698802_123702746_RF | TATGAGTAATAATTACAATTTCCCCCTTTCGACCTCCAGGTCCCCGCCACTTCCACGGC (SEQ ID NO: 603) |
| BAD_11_64023977_64025423_64060063_64064396_RR | CAGAAACTGCTGGTTGGGCTCATACTTTTCGAGGGCCAGCTCCCCGCACCCCCACCAAGC (SEQ ID NO: 604) |
| ICOSLG_21_45663614_45665471_45687442_45689916_FR | TTCCCCTGTAAGATTCATTTCCTGTGATTCGAGTCACAGCTGTAGTGGGTGGGGGGTGA (SEQ ID NO: 605) |
| ARHGEF7_13_111730571_111732652_111748012_111752622_FR | TCTTTGTTACTGGAATATACGAATAAAATCGATGTGGCGACCGGCTGTGGGGGTCACGGA (SEQ ID NO: 606) |

TABLE 36g

Top Probes - Anti PD1 (Melanoma) Non-responders - probes sequences and loci

| 60 mer | Chr | Start1 | End1 | Start2 | End2 | Chr | Start1 | End1 | Start2 | End2 |
|---|---|---|---|---|---|---|---|---|---|---|
| CCGCGCCCGCAGGGCCCGCCCCGCGCCGTCGAGGCTTTCAAGGGATCCAGGGTGGGGTGC (SEQ ID NO: 607) | 1 | 6526238 | 6526267 | 6544279 | 6544308 | 1 | 6522268 | 6526267 | 6540309 | 6544308 |
| CCGCGCCCGCAGGGCCCGCCCCGCGCCGTCGACAATGTTATTCTTTGTTTCTCTTACCAA (SEQ ID NO: 608) | 1 | 6526238 | 6526267 | 6554649 | 6554678 | 1 | 6522268 | 6526267 | 6554649 | 6558648 |
| CCGCGCCCGCAGGGCCCGCCCCGCGCCGTCGATGTGTTGGAAGTCAGGGCGGCGGTGCCC (SEQ ID NO: 609) | 1 | 6526238 | 6526267 | 6558079 | 6558108 | 1 | 6522268 | 6526267 | 6554109 | 6558108 |
| CACTTCCCCAACATAAGCCTCGGTCTCTTCGAGGGCGGGCCCGGCGGCCCCGGAGCAAAC (SEQ ID NO: 610) | 2 | 242498608 | 242498637 | 242532080 | 242532109 | 2 | 242498608 | 242502607 | 242528110 | 242532109 |
| CCGCGCCCGCAGGGCCCGCCCCGCGCCGTCGAGAAGCATAAAGCAGGGACAGGTATGGAG (SEQ ID NO: 611) | 1 | 6526238 | 6526267 | 6574085 | 6574114 | 1 | 6522268 | 6526267 | 6574085 | 6578084 |
| GACCCCCGGGAATTGGCTCCAGCACATCTCGAGGGCGGGCCCGGCGGCCCCGGAGCAAAC (SEQ ID NO: 612) | 2 | 242474876 | 242474905 | 242498608 | 242498637 | 2 | 242474876 | 242478875 | 242498608 | 242502607 |

TABLE 36g -continued

Top Probes - Anti PD1 (Melanoma) Non-responders - probes sequences and loci

| 60 mer | Chr | Start1 | End1 | Start2 | End2 | Chr | Start1 | End1 | Start2 | End2 |
|---|---|---|---|---|---|---|---|---|---|---|
| GTTTGCTCCGGGGCCGC CGGGCCCGCCCTCGATT TTAACACCACCATGGTT TGAATGAAT (SEQ ID NO: 613) | 2 | 242498608 | 242498637 | 242517412 | 242517441 | 2 | 242498608 | 242502607 | 242517412 | 242521411 |
| GTGTCTCGGCCCCCTGG GGCCCCACCCTTCGATT TCCCTGTTGCCGCCGCG TTTGCAAGA (SEQ ID NO: 614) | 5 | 131813575 | 131813604 | 131832725 | 131832754 | 5 | 131809605 | 131813604 | 131828755 | 131832754 |
| TCTCCTGCCTACCACAC TGTGAGAAAGCTCGAGG GCGGGCCCGGCGGCCCC GGAGCAAAC (SEQ ID NO: 615) | 2 | 242454061 | 242454090 | 242498608 | 242498637 | 2 | 242454061 | 242458060 | 242498608 | 242502607 |
| GAGTTCAGCGTGCCGCC GGGCGTGAAAGTCGAGG CATATTTGAGTTTAGGG AGGTGTTGC (SEQ ID NO: 616) | 15 | 75047316 | 75047345 | 75083505 | 75083534 | 15 | 75043346 | 75047345 | 75083505 | 75087504 |
| GGGCACCGCCGCCCTGA CTTCCAACACATCGATC TCTGCCTCGCGCAGCCC CAGCGTGCG (SEQ ID NO: 617) | 1 | 6521665 | 6521694 | 6558079 | 6558108 | 1 | 6521665 | 6525664 | 6554109 | 6558108 |
| CCACCCCCGCCCCGGGG GAGTCGCCCGGTCGATT TCCAAAAGCTCACACAT GGGTGCACA (SEQ ID NO: 618) | 8 | 42128692 | 42128721 | 42148498 | 42148527 | 8 | 42124722 | 4218721 | 42148498 | 42152497 |
| GGGCACCGCCGCCCTGA CTTCCAACACATCGAAG AATGGGTGGGGCCTTGC ACCTCATAC (SEQ ID NO: 619) | 1 | 6510664 | 6510693 | 6558079 | 6558108 | 1 | 6510664 | 6514663 | 6554109 | 6558108 |
| CCACCCCCGCCCCGGGG GAGTCGCCCGGTCGACC CCCTGACATGGGGCTGC CTGGAGCAG (SEQ ID NO: 620) | 8 | 42128692 | 42128721 | 42188563 | 42188592 | 8 | 42124722 | 42128721 | 42188563 | 42192562 |
| GGGCACCGCCGCCCTGA CTTCCAACACATCGAGA AGCATAAAGCAGGGACA GGTATGGAG (SEQ ID NO: 621) | 1 | 6558079 | 6558108 | 6574085 | 6574114 | 1 | 6554109 | 6558108 | 6574085 | 6578084 |
| GAGTTCAGCGTGCCGCC GGGCGTGAAAGTCGACT CTGGGCCCAGACCACAG AAGGAGGGG (SEQ ID NO:622) | 15 | 75047316 | 75047345 | 75080014 | 75080043 | 15 | 75043346 | 75047345 | 75076044 | 75080043 |
| AATTCTGTTGGAAGAAT AATTTAAAATATCGATG TGGCGACCGGCTGTGGG GGTCACGGA (SEQ ID NO: 623) | 13 | 111748013 | 111748042 | 111954400 | 111954429 | 13 | 111748013 | 111752012 | 111950430 | 111954429 |
| TTCCATAGATTACTTTT CAAATCATCCTTCGAAG CTGGCGGCTGAGGGCCC GGCGCCAAG (SEQ ID NO: 624) | 17 | 40406430 | 40406459 | 40464295 | 40464324 | 17 | 40402460 | 40406459 | 40464295 | 40468294 |

TABLE 36g -continued

Top Probes - Anti PD1 (Melanoma) Non-responders - probes sequences and loci

| 60 mer | Chr | Start1 | End1 | Start2 | End2 | Chr | Start1 | End1 | Start2 | End2 |
|---|---|---|---|---|---|---|---|---|---|---|
| GAGTTCAGCGTGCCGCC GGGCGTGAAAGTCGATT TGTTTATGGTTTTATCC CCAGTGCCT (SEQ ID NO: 625) | 15 | 75047316 | 75047345 | 75072258 | 75072287 | 15 | 75043346 | 75047345 | 75072258 | 75076257 |
| CACCCTCCCTTCTTCCT GGGCCCTCAGATCGACC CCCCCACCCCACCGG GCTGGCTGC (SEQ ID NO: 626) | 19 | 501578040 | 50158069 | 50185426 | 50185455 | 19 | 50158040 | 50162039 | 50181456 | 50185455 |
| CCACCCCGCCCCGGGG GAGTCGCCCGGTCGAGG GCCTGGCAAGAAGACA GAAGCCGACT (SEQ ID NO: 627) | 8 | 42128692 | 42128721 | 42138741 | 42138770 | 8 | 42124722 | 42128721 | 42138741 | 42142740 |
| TATGAGTAATAATTACA ATTTCCCCCTTTCGACCC TCCAGGTCCCCCGCCAC TTCCACGGC (SEQ ID NO: 628) | 9 | 123675825 | 123675857 | 123702717 | 123702746 | 9 | 123675825 | 123679824 | 123698747 | 12370276 |
| CAGAAACTGCTGGTTGG GCTCATACTTTTCGAGG GCCAGCTCCCCGCACCC CCACCAAGC (SEQ ID NO: 629) | 11 | 64023978 | 64024007 | 64060064 | 64060093 | 11 | 64023978 | 64027977 | 64060064 | 64064063 |
| TTCCCCTGTAAGATTCA TTTCCTGTGATTCGAGT CACAGCTGTAGTGGGGT GGGGGGTGA (SEQ ID NO: 630) | 21 | 45665442 | 45665471 | 45687443 | 45687472 | 21 | 45661472 | 45665471 | 45687443 | 45691442 |
| TCTTTGTTACTGGAATA TACGAATAAAATCGATG TGGCGACCGGCTGTGGG GGTCACGGA (SEQ ID NO: 631) | 13 | 111732623 | 111732652 | 111748013 | 111748042 | 13 | 111728653 | 111732652 | 111748013 | 111752012 |

1  2  3

TABLE 37a

Anti-PD1: pharmacodynamic response markers

| Probes | Gene Locus | X12w_adj. P.Val | X12w_FC_1 | X12w_LS | Loop detected | 60 mer |
|---|---|---|---|---|---|---|
| BAX_19_49417533_49419970_ 49471563_49474829_FF | BAX | 0.014 | 1.2508 | 1 | BL R | AAGGCAGGCAGATCAGGAGCTCAAGAGATC GAAAGAAAAAAAAAAAAAGCATAAAAATCCA (SEQ ID NO: 632) |
| BAX_19_49417533_49419970_ 49435499_49438567_FF | BAX | 0.014 | 1.2346 | 1 | BL R | AAGGCAGGCAGATCAGGAGCTCAAGAGATC GAACGCTAAGTGTAGTTTAACACCTACTAG (SEQ ID NO: 633) |
| CASP1_11_104941451_ 104946789_104994205_ 105005564_RR | CASP1 | 0.015 | 1.2201 | 1 | BL R | ATAGTAAAATGTGAAAATGTTACAGTTATC GAAGTTCAGCGAGTATATTTTACTGATAC (SEQ ID NO: 634) |
| NCK2_2_106375590_106379449_ 106457772_106460967_RR | NCK2 | 0.014 | 1.2178 | 1 | BL R | AAGGCCCAAGAACCAGGAATCTAGGTATTC GAAAAGCCCTAAAGTTGGCTTAATAAACTT (SEQ ID NO: 635) |
| JAM2_21_26994168_26998383_ 27012522_27024636_FR | JAM2 | 0.014 | 1.2083 | 1 | BL R | GGTGGGCAGATCACTTAAGGCCAGGAATTC GAATGCAAAACTCACTACCCACTGGTAAGA (SEQ ID NO: 636) |

TABLE 37a -continued

Anti-PD1: pharmacodynamic response markers

| Probes | Gene Locus | X12w_adj. P.Val | X12w_FC_1 | X12w_LS | Loop detected | 60 mer |
|---|---|---|---|---|---|---|
| JAM2_21_26994168_26998383_ 27070793_27073958_FF | JAM2 | 0.014 | 1.2076 | 1 | BL R | GGTGGGCAGATCACTTAAGGCCAGGAATTC GATTCTATCAACTCTAGAATTTTTTTAAAT (SEQ ID NO: 637) |
| BAX_19_49417533_49419970_ 49471563_49474829_FR | BAX | 0.014 | 1.2071 | 1 | BL R | AAGGCAGGCAGATCAGGAGCTCAAGAGATC GAGGTAAATGTGGGGGTTCTAGAACCCAGT (SEQ ID NO: 638) |
| JAM2_21_26994168_26998383_ 27075383_27076758_FF | JAM2 | 0.014 | 1.205 | 1 | BL R | GGTGGGCAGATCACTTAAGGCCAGGAATTC GAAATTCTTTCCTAATGCCAAGTGTGTTAT (SEQ ID NO: 639) |
| CXCL2_4_74949499_74952659_ 74968426_74975311_RR | CXCL2 | 0.014 | 1.2039 | 1 | BL R | GGTCCCCTGATTTCCATCCTAGTGCTTCTC GAAACATGTGCTCTGGAGATAAAGCGCCAA (SEQ ID NO: 640) |
| JAM2_21_26994168_26998383_ 27056447_27060410_FR | JAM2 | 0.014 | 1.2038 | 1 | BL R | GGTGGGCAGATCACTTAAGGCCAGGAATTC GATATTCAATAAAAGACCGGATGTGCAAAG (SEQ ID NO: 641) |
| JAM2_21_26994168_26998383_ 27056447_27060410_FF | JAM2 | 0.014 | 1.2033 | 1 | BL R | GGTGGGCAGATCACTTAAGGCCAGGAATTC GAGAAATGGTTTATCCAATTCATCCAAAAT (SEQ ID NO: 642) |
| JAM2_21_26994168_26998383_ 27047035_27050041_FR | JAM2 | 0.014 | 1.1995 | 1 | BL R | GGTGGGCAGATCACTTAAGGCCAGGAATTC GAGAGACTGTAAAGACATGTGTCTGCCTCT (SEQ ID NO: 643) |
| JAM2_21_26994168_26998383_ 27028107_27035825_FF | JAM2 | 0.015 | 1.1972 | 1 | BL R | GGTGGGCAGATCACTTAAGGCCAGGAATTC GATCACTTCTTAAAGGCCCTACCTCTTAAT (SEQ ID NO: 644) |
| IL2_4_123399246_123404439_ 123417475_123422774_FF | IL2 | 0.014 | 1.1962 | 1 | BL R | GTTGGGTTGAAGATGAAATCATAGGAAGTC GAGCTGTAACCTCTGCTTGGTATTCTCCCT (SEQ ID NO: 645) |
| JAM2_21_26994168_26998383_ 27028107_27035825_FR | JAM2 | 0.014 | 1.1953 | 1 | BL R | GGTGGGCAGATCACTTAAGGCCAGGAATTC GAAACACCAGCTCTCTTAAATCCTGTGCCT (SEQ ID NO: 646) |
| JAM2_21_26994168_26998383_ 27047035_27050041_FF | JAM2 | 0.014 | 1.1924 | 1 | BL R | GGTGGGCAGATCACTTAAGGCCAGGAATTC GAGGAAACCTCGGGGCAAAATAGGGAAAG (SEQ ID NO: 647) |
| BAX_19_49421751_49425642_ 49475136_49476327_RR | BAX | 0.015 | 1.1898 | 1 | BL R | TGAGAATGGAATAGATCAAAGGGAGGGTTC GAGACAAGGTCTCACTTTATCACCCAACCT (SEQ ID NO: 648) |
| JAM2_21_26994168_26998383_ 27070793_27073958_FR | JAM2 | 0.014 | 1.1879 | 1 | BL R | GGTGGGCAGATCACTTAAGGCCAGGAATTC GACTGTGTGCCCATGAAGAAAGAAGATGGG (SEQ ID NO: 649) |
| IL4_5_131966700_131972322_ 131985852_131989475_FR | IL4 | 0.024 | 1.1852 | 1 | BL R | AGTGATAGAAGAGGGACAAGGTGGCAGTTC GATTTTAAAACACGCTCTTCAATAAAAAGA (SEQ ID NO: 650) |
| CBLB_3_105390159_105394525_ 105627700_105635575_FF | CBLB | 0.015 | 1.1828 | 1 | BL R | AGCAGGGGATCACATAAGGCCAGGAGTTC GATAAAATAAATTAGAGAAGATATAAATAA (SEQ ID NO: 651) |
| JAM2_21_26994168_26998383_ 27080812_27083366_FF | JAM2 | 0.016 | 1.1816 | 1 | BL R | GGTGGGCAGATCACTTAAGGCCAGGAATTC GATTTCTGCTTCTCTCACAGCCCACATC (SEQ ID NO: 652) |
| NCK2_2_106344684_106358282_ 106457772_106460967_FR | NCK2 | 0.018 | 1.1805 | 1 | BL R | TCTTTGCAGATGTGTAAGATAAGGATGTC GAAAAGCCCTAAAGTTGGCTTAATAAACTT (SEQ ID NO: 653) |
| CXCL2_4_74949499_74952659_ 74983628_74990858_RR | CXCL2 | 0.015 | 1.1794 | 1 | BL R | GGTCCCCTGATTTCCATCCTAGTGCTTCTC GATGATATAATACTCTGCTGACTACATTTT (SEQ ID NO: 654) |

TABLE 37a -continued

Anti-PD1: pharmacodynamic response markers

| Probes | Gene Locus | X12w_adj. P.Val | X12w_FC_1 | X12w_LS | Loop detected | 60 mer |
|---|---|---|---|---|---|---|
| NCK2_2_106375590_106379449_ 106435340_106439151_RR | NCK2 | 0.015 | 1.1767 | 1 | BL R | AAGGCCCAAGAACCAGGAATCTAGGTATTC GACCACCTTAAAAGAAAAATCTCTTGGAAC (SEQ ID NO: 655) |
| CBLB_3_105390159_105394525_ 105606664_105615153_FR | CBLB | 0.015 | 1.176 | 1 | BL R | AGCAGGGGGATCACATAAGGCCAGGAGTTC GATGAACGTTTACCCAATTATTTCTAAACA (SEQ ID NO: 656) |

TABLE 37b

Anti-PD1: pharmacodynamic response markers

| Probes | Chr | Start1 | End1 | Start2 | End2 |
|---|---|---|---|---|---|
| BAX_19_49417533_49419970_49471563_49474829_FF | 19 | 49419941 | 49419970 | 49474800 | 49474829 |
| BAX_19_49417533_49419970_49435499_49438567_FF | 19 | 49419941 | 49419970 | 49438538 | 49438567 |
| CASP1_11_104941451_104946789_104994205_105005564_RR | 11 | 104941452 | 104941481 | 104994206 | 104994235 |
| NCK2_2_106375590_106379449_106457772_106460967_RR | 2 | 106375591 | 106375620 | 106457773 | 106457802 |
| JAM2_21_26994168_26998383_27012522_27024636_FR | 21 | 26998354 | 26998383 | 27012523 | 27012552 |
| JAM2_21_26994168_26998383_27070793_27073958_FF | 21 | 26998354 | 26998383 | 27073929 | 27073958 |
| BAX_19_49417533_49419970_49471563_49474829_FR | 19 | 49419941 | 49419970 | 49471564 | 49471593 |
| JAM2_21_26994168_26998383_27075383_27076758_FF | 21 | 26998354 | 26998383 | 27076729 | 27076758 |
| CXCL2_4_74949499_74952659_74968426_74975311_RR | 4 | 74949500 | 74949529 | 74968427 | 74968456 |
| JAM2_21_26994168_26998383_27056447_27060410_FR | 21 | 26998354 | 26998383 | 27056448 | 27056477 |
| JAM2_21_26994168_26998383_27056447_27060410_FF | 21 | 26998354 | 26998383 | 27060381 | 27060410 |
| JAM2_21_26994168_26998383_27047035_27050041_FR | 21 | 26998354 | 26998383 | 27047036 | 27047065 |
| JAM2_21_26994168_26998383_27028107_27035825_FF | 21 | 26998354 | 26998383 | 27035796 | 27035825 |
| IL2_4_123399246_123404439_123417475_123422774_FF | 4 | 123404410 | 123404439 | 123422745 | 123422774 |
| JAM2_21_26994168_26998383_27028107_27035825_FR | 21 | 26998354 | 26998383 | 27028108 | 27028137 |
| JAM2_21_26994168_26998383_27047035_27050041_FF | 21 | 26998354 | 26998383 | 27050012 | 27050041 |
| BAX_19_49421751_49425642_49475136_49476327_RR | 19 | 49421752 | 49421781 | 49475137 | 49475166 |
| JAM2_21_26994168_26998383_27070793_27073958_FR | 21 | 26998354 | 26998383 | 27070794 | 27070823 |
| IL4_5_131966700_131972322_131985852_131989475_FR | 5 | 131972293 | 131972322 | 131985853 | 131985882 |
| CBLB_3_105390159_105394525_105627700_105635575_FF | 3 | 105394496 | 105394525 | 105635546 | 105635575 |
| JAM2_21_26994168_26998383_27080812_27083366_FF | 21 | 26998354 | 26998383 | 27083337 | 27083366 |
| NCK2_2_106344684_106358282_106457772_106460967_FR | 2 | 106358253 | 106358282 | 106457773 | 106457802 |
| CXCL2_4_74949499_74952659_74983628_74990858_RR | 4 | 74949500 | 74949529 | 74983629 | 74983658 |
| NCK2_2_106375590_106379449_106435340_106439151_RR | 2 | 106375591 | 106375620 | 106435341 | 106435370 |
| CBLB_3_105390159_105394525_105606664_105615153_FR | 3 | 105394496 | 105394525 | 105606665 | 105606694 |

| Probes | Chr | Start1 | End1 | Start2 | End2 |
|---|---|---|---|---|---|
| BAX_19_49417533_49419970_49471563_49474829_FF | 19 | 49415971 | 49419970 | 49470830 | 5E+07 |
| BAX_19_49417533_49419970_49435499_49438567_FF | 19 | 49415971 | 49419970 | 49434568 | 5E+07 |
| CASP1_11_104941451_104946789_104994205_105005564_RR | 11 | 104941452 | 104945451 | 104994206 | 1E+08 |
| NCK2_2_106375590_106379449_106457772_106460967_RR | 2 | 106375591 | 106379590 | 106457773 | 1E+08 |
| JAM2_21_26994168_26998383_27012522_27024636_FR | 21 | 26994384 | 26998383 | 27012523 | 3E+07 |
| JAM2_21_26994168_26998383_27070793_27073958_FF | 21 | 26994384 | 26998383 | 27069959 | 3E+07 |
| BAX_19_49417533_49419970_49471563_49474829_FR | 19 | 49415971 | 49419970 | 49471564 | 5E+07 |
| JAM2_21_26994168_26998383_27075383_27076758_FF | 21 | 26994384 | 26998383 | 27072759 | 3E+07 |
| CXCL2_4_74949499_74952659_74968426_74975311_RR | 4 | 74949500 | 74953499 | 74968427 | 7E+07 |
| JAM2_21_26994168_26998383_27056447_27060410_FR | 21 | 26994384 | 26998383 | 27056448 | 3E+07 |
| JAM2_21_26994168_26998383_27056447_27060410_FF | 21 | 26994384 | 26998383 | 27056411 | 3E+07 |
| JAM2_21_26994168_26998383_27047035_27050041_FR | 21 | 26994384 | 26998383 | 27047036 | 3E+07 |
| JAM2_21_26994168_26998383_27028107_27035825_FF | 21 | 26994384 | 26998383 | 27031826 | 3E+07 |
| IL2_4_123399246_123404439_123417475_123422774_FF | 4 | 123400440 | 123404439 | 123418775 | 1E+07 |
| JAM2_21_26994168_26998383_27028107_27035825_FR | 21 | 26994384 | 26998383 | 27028108 | 3E+07 |
| JAM2_21_26994168_26998383_27047035_27050041_FF | 21 | 26994384 | 26998383 | 27046042 | 3E+07 |
| BAX_19_49421751_49425642_49475136_49476327_RR | 19 | 49421752 | 49425751 | 49475137 | 5E+07 |
| JAM2_21_26994168_26998383_27070793_27073958_FR | 21 | 26994384 | 26998383 | 27070794 | 3E+07 |
| IL4_5_131966700_131972322_131985852_131989475_FR | 5 | 131968323 | 131972322 | 131985853 | 1E+07 |
| CBLB_3_105390159_105394525_105627700_105635575_FF | 3 | 105390526 | 105394525 | 105631576 | 1E+07 |
| JAM2_21_26994168_26998383_27080812_27083366_FF | 21 | 26994384 | 26998383 | 27079367 | 3E+07 |
| NCK2_2_106344684_106358282_106457772_106460967_FR | 2 | 106354283 | 106358282 | 106457773 | 1E+07 |
| CXCL2_4_74949499_74952659_74983628_74990858_RR | 4 | 74949500 | 74953499 | 74983629 | 7E+07 |
| NCK2_2_106375590_106379449_106435340_106439151_RR | 2 | 106375591 | 106379590 | 106435341 | 1E+07 |
| CBLB_3_105390159_105394525_105606664_105615153_FR | 3 | 105390526 | 105394525 | 105606665 | 1E+07 |

TABLE 38a

Anti-PD1: pharmacodynamic response markers
No difference in baseline Responders and baseline
Non-Responders but show a significant change in 12 week Responder

| Probes | Gene Locus | X12w_adj. P.Val | X12w_FC_1 | X12w_LS | Loop dected | 60 mer |
|---|---|---|---|---|---|---|
| MAP3K14_17_43375304_43380378_ 43409961_43415408_FF | MAP3K14 | 0.085 | -1.382 | -1 | 12 W | R GATGCGGACTGTTTCCTGCTTTGATTTATC GACTTCTTATTTCTATTTTGTGACTTAGGA (SEQ ID NO: 657) |
| MAP3K14_17_43360790_43364282_ 43375304_43380378_RF | MAP3K14 | 0.065 | -1.366 | -1 | 12 W | R GATGCGGACTGTTTCCTGCTTTGATTTATC GACACAGTGTGTCTGAAGTTTGGGGTGGTA (SEQ ID NO: 658) |
| MAP3K14_17_43375304_43380378_ 43399352_43402185_FR | MAP3K14 | 00062 | -1.365 | -1 | 12 W | R GATGCGGACTGTTTCCTGCTTTGATTTATC GATATCTCCCTCCTTTCGCTTCTTCCTTTC (SEQ ID NO: 659) |
| MAP3K14_17_43375304_43380378_ 43416164_43419166_FF | MAP3K14 | 0.077 | -1.348 | -1 | 12 W | R GATGCGGACTGTTTCCTGCTTTGATTTATC GAGTCATTAAGAGACTCTCCGCCTGGGTGG (SEQ ID NO: 660) |
| PRKCQ_10_6474855_6481197_ 6530169_6531558_FF | PRKCQ | 0.014 | -1.332 | -1 | 12 W | R TTCCACCTGTAATACTGTGCCTGTATTCTC GACTCTTCTCGCCCTCTTCTCCAGCTCTCT (SEQ ID NO: 661) |
| SIRPA_20_1838201_1841874_ 1872135_1877996_FF | SIRPA | 0.014 | -1.296 | -1 | 12 W | R TAAAGTACTGTGTCCCACATATAAGTACTC GACCAAGAAATTCATTCTTACCTCCTAAGA (SEQ ID NO: 662) |
| MAPK1_22_22175466_22178188_ 22210841_22217782_RR | MAPK1 | 0.019 | -1.232 | -1 | 12 W | R ACCCCACCAATCTATAATAAGATTGATTTC GACACAAGGGTTTGTAACAAAAAACAAAAA (SEQ ID NO: 663) |
| SIRPA_20_1857090_1859261_ 1905279_1911608_FF | SIRPA | 0.014 | -1.219 | -1 | 12 W | R AGCGCTTTATTTGTCAGGACGATAGACCTC GACAATGTCCTATTCTTCCAGAAACTCATT (SEQ ID NO: 664) |
| CBLB_3_105466912_105471108_ 105514190_105519713_FR | CBLC | 0.039 | -1.217 | -1 | 12 W | R TTATTACTTTATTCTGACTGAATATCATTC GAAAGAAACCAAAAACACAAGTATACATCA (SEQ ID NO: 665) |
| CBLB_3_105442255_105450516_ 105471108_105479961_RR | CBLB | 0.018 | -1.211 | -1 | 12 W | R TATCCTTTGGTTTAGAAGTATTTCTTATTC GACAAAATTTTAACATGTTATGCAGTTACA (SEQ ID NO: 666) |
| PRKCQ_10_6474855_6481197_ 6544129_6548414_RF | PRKCQ | 0.014 | -1.211 | -1 | 12 W | R TTCAGCTATTCACTGGTTTTTCTTCAGATC GACTCCTGCTTCCCTCCCCTCATCTTTAAA (SEQ ID NO: 667) |
| CBLB_3_105471108_105479961_ 105538128_105544723_RF | CBLB | 0.023 | -1.21 | -1 | 12 W | R TCCAGTACAATAAACAATGTACCAAAGATC GACAAAATTTTAACATGTTATGCAGTTACA (SEQ ID NO: 668) |
| IGKC_2_89162710_89164067_ 89175040_89179794_FF | IGKC | 0.019 | -1.204 | -1 | 12 W | R TAAACTCTGACATTGCCTATTAGCATTCTC GAATGCATGGCTCACTGTAACCTCCAACTC (SEQ ID NO: 669) |
| CBLB_3_105442255_105450516_ 105466912_105471108_RR | CBLB | 0.047 | -1.202 | -1 | 12 W | R TATCCTTTGGTTTAGAAGTATTTCTTATTC GACAACTACTGGCTTAAAAAGGCAAACA (SEQ ID NO: 670) |
| PRKCQ_10_6474855_6481197_ 6593817_6595662_RF | PRKCQ | 0.016 | -1.202 | -1 | 12 W | R TACCTCCTTGGGAACATATTTGAGAGTTTC GACTCCTGCTTCCCTCCCCTCATCTTTAAA (SEQ ID NO: 671) |
| SIRPA_20_1905279_1911608_ 1931241_1933334_RF | SIRPA | 0.014 | -1.201 | -1 | 12 W | R ACACTTGATTTTTGCTTTCCAAGCTGACTC GAGACATCTAAGAAGGTCCAGCCAGATGTT (SEQ ID NO: 672) |
| SIRPA_20_1872135_1877996_ 1900304_1902024_RR | SIRPA | 0.014 | -1.199 | -1 | 12 W | R GCGCCCTATTTCCACCTTGTGCCTTCTGTC GACACACCAAGATGTCACGGAGGAGTCTGT (SEQ ID NO: 673) |
| NCK2_2_106403393_106408079_ 106473847_106478190_RR | NCK2 | 0.016 | -1.193 | -1 | 12 W | R CCAGCTGAAGTTTCGCAGGTCCCCTGCTTC GAGTAGGCCAATCCCATTTTTGGCGAAAAC (SEQ ID NO: 674) |

TABLE 38a -continued

Anti-PD1: pharmacodynamic response markers
No difference in baseline Responders and baseline
Non-Responders but show a significant change in 12 week Responder

| Probes | Gene Locus | X12w_adj. P.Val | X12w_FC_1 | X12w_LS | Loop dected | 60 mer |
|---|---|---|---|---|---|---|
| PRKCQ_10_6474855_6481197_ 6593817_6595662_RF | PRKCQ | 0.016 | -1.202 | -1 | 12 W R | TACCTCCTTGGGAACATATTTGAGAGTTTC GACTCCTGCTTCCCTCCCCTCATCTTTAAA (SEQ ID NO: 675) |
| SIRPA_20_1905279_1911608_ 1931241_1933334_RF | SIRPA | 0.014 | -1.201 | -1 | 12 W R | ACACTTGATTTTTGCTTTCCAAGCTGACTC GAGACATCTAAGAAGGTCCAGCCAGATGTT (SEQ ID NO: 676) |
| SIRPA_20_1872135_1877996_ 1900304_1902024_RR | SIRPA | 0.014 | -1.199 | -1 | 12 W R | GCGCCCTATTTCCACCTTGTGCCTTCTGTC GACACACCAAGATGTCACGGAGGAGTCTGT (SEQ ID NO: 677) |
| NCK2_2_106403393_106408079_ 106473847_106478190_RR | NCK2 | 0.016 | -1.193 | -1 | 12 W R | CCAGCTGAAGTTTCGCAGGTCCCCTGCTTC GAGTAGGCCAATCCCATTTTTGGCGAAAAC (SEQ ID NO: 678) |
| PRKCQ_10_6474855_6481197_ 6601540_6605133_RF | PRKCQ | 0.018 | -1.191 | -1 | 12 W R | ACTTTGGCTCAAGAGTGAAGATATTCAGTC GACTCCTGCTTCCCTCCCCTCATCTTTAAA (SEQ ID NO: 679) |
| MAPK1_22_22122470_22123582_ 22210841_22217782_FR | MAPK1 | 0.041 | -1.19 | -1 | 12 W R | TTCCTTAGGCAAGTCATCCAATTCCATGTC GACACAAGGGTTTGTAACAAAAAACAAAAA (SEQ ID NO: 680) |
| SIRPA_20_1830612_1833775_ 1872135_1877996_RF | SIRPA | 0.05 | -1.189 | -1 | 12 W R | TCTTAGGAGGTAAGAATGAATTTCTTGGTC GAACTCCTGACCAGGAGGCTGGGAGGGGGT (SEQ ID NO: 681) |
| CASP7_10_115416083_115421410_ 115478671_115481421_FF | CASP7 | 0.021 | -1.188 | -1 | 12 W R | CATCATTTTAATAGGTGCAAGAGTTCCGTC GAACGCCCATACCTGTGGGAATCAAGCAAT (SEQ ID NO: 682) |
| NCK2_2_106383183_106387147_ 106435340_106439151_RF | NCK2 | 0.015 | -1.188 | -1 | 12 W R | AAAAACAAAAAAGCCAATTCTGTACCCCTC GAACCAGCCCTGGCTCTGTCCCCAGACCTT (SEQ ID NO: 683) |
| SIRPA_20_1872135_1877996_ 1905279_1911608_RR | SIRPA | 0.014 | -1.188 | -1 | 12 W R | GCGCCCTATTTCCACCTTGTGCCTTCTGTC GAGACATCTAAGAAGGTCCAGCCAGATGTT (SEQ ID NO: 684) |
| PQRKCQ_10_6474855_6481197_ 6510600_6515355_RF | PRKCQ | 0.016 | -1.185 | -1 | 12 W R | TTGATTATTTCAGGTTGACAGCTGTAAATC GACTCCTGCTTCCCTCCCCTCATCTTTAAA (SEQ ID NO: 685) |

TABLE 38b

Probe location - Anti-PD1: pharmacodynamic response markers -No difference in baseline
Responders and baseline Non-Responders but show a significant change in 12 week Responder

| Probes | Chr | Start1 | End1 | Start2 | End2 |
|---|---|---|---|---|---|
| PRKCQ_10_6474855_6481197_6544129_6548414_RF | 10 | 6474856 | 6474885 | 6548385 | 6548414 |
| CBLB_3_105471108_105479961_105538128_105544723_RF | 3 | 105471109 | 105471138 | 105544694 | 105544723 |
| IGKC_2_89162710_89164067_89175040_89179794_FF | 2 | 89164038 | 89164067 | 89179765 | 89179794 |
| CBLB_3_105442255_105450516_105466912_105471108_RR | 3 | 105442256 | 105442285 | 105466913 | 105466942 |
| PRKCQ_10_6474855_6481197_6593817_6595662_RF | 10 | 6474856 | 6474885 | 6595633 | 6595662 |
| SIRPA_20_1905279_1911608_1931241_1933334_RF | 20 | 1905280 | 1905309 | 1933305 | 1933334 |
| SIRPA_20_1872135_1877996_190030/1_1902024_RR | 20 | 1872136 | 1872165 | 1900304 | 1900334 |
| NCK2_2_106403393_106408079_106473847_106478190_RR | 2 | 106403394 | 106403423 | 106473848 | 106473877 |
| PRKCQ_10_6474855_6481197_6601540_6605133_RF | 10 | 6474856 | 6474885 | 6605104 | 6605133 |
| MAPK1_22_22122470_22123582_2221084122217782_FR | 22 | 22123553 | 22123582 | 22210842 | 22210871 |
| SIRPA_20_1830612_1833775_1872135_1877996_RF | 20 | 1830613 | 1830642 | 1877967 | 1877996 |
| CASP7_10_115416083_115421410_115478671_115481421_FF | 10 | 115421381 | 115421410 | 115481392 | 115481421 |
| NCK2_2_106383183_106387147_106435340_106439151_RF | 2 | 106383184 | 106383213 | 106439122 | 106439151 |
| SIRPA_20_1872135_1877996_1905279_1911608_RR | 20 | 1872136 | 1872165 | 1905280 | 1905309 |
| PRKCQ_10_6474855_6481197_6510600_6515355_RF | 10 | 6474856 | 6474885 | 6515326 | 6515355 |

TABLE 38b-continued

Probe location - Anti-PD1: pharmacodynamic response markers - No difference in baseline Responders and baseline Non-Responders but show a significant change in 12 week Responder

| Probes | Chr | Start1 | End1 | Start2 | End2 |
|---|---|---|---|---|---|
| PRKCQ_10_6474855_6481197_6544129_6548414_RF | 10 | 6474856 | 6478855 | 6544415 | 7E+06 |
| CBLB_3_105471108_105479961_105538128_105544723_RF | 3 | 105471109 | 105475108 | 105540724 | 1E+08 |
| IGKC_2_89162710_89164067_89175040_89179794_FF | 2 | 89160068 | 89164067 | 89175795 | 9E+07 |
| CBLB_3_105442255_105450516_105466912_105471108_RR | 3 | 105442256 | 105446255 | 105466913 | 1E+08 |
| PRKCQ_10_6474855_6481197_6593817_6595662_RF | 10 | 6474856 | 6478855 | 6591663 | 7E+06 |
| SIRPA_20_1905279_1911608_1931241_1933334_RF | 20 | 1905280 | 1909279 | 1929335 | 2E+06 |
| SIRPA_20_1872135_1877996_190030/1_1902024_RR | 20 | 1872136 | 1876135 | 1900305 | 2E+06 |
| NCK2_2_106403393_106408079_106473847_106478190_RR | 2 | 106403394 | 106407393 | 106473848 | 1E+08 |
| PRKCQ_10_6474855_6481197_6601540_6605133_RF | 10 | 6474856 | 6478855 | 6601134 | 7E+06 |
| MAPK1_22_22122470_22123582_2221084122217782_FR | 22 | 22119583 | 22123582 | 22210842 | 2E+07 |
| SIRPA_20_1830612_1833775_1872135_1877996_RF | 20 | 1830613 | 1834612 | 1873997 | 2E+06 |
| CASP7_10_115416083_115421410_115478671_115481421_FF | 10 | 115417411 | 115421410 | 115477422 | 1E+08 |
| NCK2_2_106383183_106387147_106435340_106439151_RF | 2 | 106383184 | 106387183 | 106435152 | 1E+08 |
| SIRPA_20_1872135_1877996_1905279_1911608_RR | 20 | 1872136 | 1876135 | 1905280 | 2E+06 |
| PRKCQ_10_6474855_6481197_6510600_6515355_RF | 10 | 6474856 | 6478855 | 6511356 | 7E+06 |

TABLE 39

| Array Interaction | Outer Primers | Inner Primers | Chi.Square | p.value |
|---|---|---|---|---|
| IL15_4_142530356_142539177_142656375_142659066_RF | IL15-70/72 | IL15-69/71 | 4.8 | 0.129 |
| MYD88_3_38139864_38141788_38192489_3819402.7_RR | MYD88-10/12 | MYD88-9/11 | 4.8 | 0.129 |
| HLA-DQB1_6_32607972_32614493_32630138_32632737_RR | H LA-DQB1-86/88 | HLA-DQB1-85/87 | 4.8 | 0.135 |
| STAT5B_17_40403935_40406459_40464294_404G8456_FR | STAT5B-74/76 | STAT5B-73/75 | 4.8 | 0.142 |
| IL12B_5_158737480_158738689_158781589_158783887_FF | IL12B -30/32 | IL12B-29/31 | 4.8 | 0.143 |
| PVRL1_11_119599998_119609544_119620830_119624585_FR | PVRL1-14/16 | PVRL1-13/15 | 4.8 | 0.147 |
| PIK3R3_1_46633134_46639474_46678880_46685388_FR | PIK3R3-18/20 | PIK3R3-17/19 | 2.667 | 0.426 |
| CD6_11_60744556_60751199_60768894_60771404_RR | CD6-22/24 | CD6-21/23 | 2.667 | 0.443 |

TABLE 40

| | | Responder | | | | Non-Responder | | | |
|---|---|---|---|---|---|---|---|---|---|
| PCR Probe | GeneLocus | 1370 (BL) | 1372 (BL) | 1393 (BL) | 1414 (BL) | 1482 (BL) | 1426 (BL) | 1458 (BL) | 1440 (BL) |
| IL15-69/71 | IL15 | 1 | 1 | 1 | 1 | 0 | 0 | 1 | 0 |
| STAT5B-73/75 | STAT5B | 1 | 1 | 1 | 1 | 0 | 0 | 0 | 1 |
| HLA-DQB1-85/87 | HLA-DQB1 | 1 | 1 | 0 | 1 | 0 | 0 | 0 | 0 |
| MYD88-9/11 | MYD88 | 1 | 1 | 1 | 1 | 1 | 0 | 0 | 0 |
| IL12B-29/31 | IL12B | 1 | 0 | 0 | 0 | 1 | 1 | 1 | 1 |
| PVRL1-13/15 | PVRL1 | 0 | 0 | 1 | 0 | 1 | 1 | 1 | 1 |

| PCR Probe | Array Probe | Array |
|---|---|---|
| IL15-69/71 | IL15_4_142530356_142539177_142656375_142659066_RF | R |
| STAT5B-73/75 | STAT5B_17_40403935_40406459_40464294_404G8456_FR | R |
| HLA-DQB1-85/87 | HLA-DQB1_6_32607972_32614493_32630138_32632737_RR | R |
| MYD88-9/11 | MYD88_3_38139864_38141788_38192489_38194027_RR | NR |
| IL12B-29/31 | IL12B_5_158737480_158738689_158781589_158783887_FF | NR |
| PVRL1-13/15 | PVRL1_11_119599998_119609544_119620830_119624585_FR | NR |

TABLE 41

Top ALS PCR Markers

| No | PCR Marker | Corresponding Array Probe | Gene | GLMNET | GLMNET_1 |
|---|---|---|---|---|---|
| 1 | ALS.61.63_8 | 7_80060926_80068170_80299255_80301429_RF | CD36 | 0.257668 | 0.272798 |
| 2 | NEALS.213.215_8 | 6_149533510_149536508_149623404_149626512_RF | TAB2 | 0.237181 | 0.271083 |
| 3 | NEALS.101.103_32 | 12_54983093_54985391__55002281_55007763_RR | GLYCAM1 | 0.237255 | 0.261601 |
| 4 | NEALS.249.251_4 | 17_73313347_73315473_73407153_73409693_FR | GRB2 | 0.162296 | 0.180288 |
| 5 | NEALS.45.47_8 | 6_112058283_112061400_112189648_112191961_RR | FYN | 0.148914 | 0.170383 |
| 6 | ALS.49.51_4 | 1_198660142_198665086_198737979_198744955_RR | PTPRC | 0.150202 | 0.16467 |
| 7 | NEALS.65.67_8 | 1_172053648_172060321_172083100_172087823_RR | DNM3 | 0.114247 | 0.131721 |
| 8 | NEALS.97.99_16 | 8_42121759_42128721_42138740_42142593_FR | IKBKB | 0.082939 | 0.099489 |
| 9 | DNM3.5.7_16 | 1_171936106_171939290_171988822_171992948_RF | DNM3 | 0.062.886 | 0.07767 |
| 10 | CLIC41.3_1 | 1_25106841_25109990_25142389_25144224_RF | CLIC4 | 0.272660 | 0.1432879 |

TABLE 41-continued

Top ALS PCR Markers

| | | | | | |
|---|---|---|---|---|---|
| 11 | NEALS.5.7_64 | 1_161590754_161594100_161627152_161631654_RR | FCGR2B; FCGR3A_1 | 0 | |
| 12 | NEALS.57.59_1 | 10_6474855_6481197_6530169_6531558_FR | PRKCQ_10 | 0.043413 | |
| 13 | ALS.21.23_32 | 7_55089963_55093430_55294211_55302386_RF | EGFR_7 | 0 | |

| No | FP | Coef | S.E. | Wald | Pr(>|Z|) |
|---|---|---|---|---|---|
| 1 | 0.003 | −1.779 | 0.803 | −2.2 | 0.027 |
| 2 | 0.098 | −0.857 | 0.935 | −0.9 | 0.36 |
| 3 | 0.213 | −0.958 | 0.943 | −1 | 0.31 |
| 4 | 0.055 | −0.811 | 0.912 | −0.9 | 0.374 |
| 5 | 0.276 | −2.087 | 0.931 | −2.2 | 0.025 |
| 6 | 0.027 | −1.706 | 1.423 | −1.2 | 0.231 |
| 7 | 0.142 | −2.023 | 0.915 | −2.2 | 0.027 |
| 8 | 0.117 | −1.395 | 1.32 | −1.1 | 0.291 |
| 9 | 0.185 | −0.609 | 1.09 | −0.6 | 0.576 |
| 10 | 1 | 0.7161 | 1.243 | 0.58 | 0.565 |
| 11 | | | | | |
| 12 | | | | | |
| 13 | | | | | |

TABLE 42a

Primer Sequences of top PCR markers

| No | PCR Marker | PCR Primer 1 Sequence | PCR Primer 2 Sequence |
|---|---|---|---|
| 1 | ALS.61.63_8 | GGAACCTCGCTGTCCATAAAC (SEQ ID NO: 686) | TCTGTATGCAAGTCCTGATGTTTC (SEQ ID NO: 687) |
| 2 | NEALS.213.215_8 | GGTAGGAGTGTGCCTTATTAAC (SEQ ID NO: 688) | GAGGCTGTTAGGCATTCTAAG (SEQ ID NO: 689) |
| 3 | NEALS.101.103_32 | GAAACCAACCCTATCTGTAAAC (SEQ ID NO: 690) | AAAGAAAGGAGGCTGTGG (SEQ ID NO: 691) |
| 4 | NEALS.249.251_4 | GCTCTGGACTGCCTTTAAC (SEQ ID NO: 692) | AAGTCAGACTCCTCTTCTCTAC (SEQ ID NO: 693) |
| 5 | NEALS.45.47_8 | GTGAAACTAAGCCCTCAACC (SEQ ID NO: 694) | TACCCTCCTTCCATTCAGAC (SEQ ID NO: 695) |
| 6 | ALS.49.51_4 | GCTACAGAGGTGAAGGAGATC (SEQ ID NO: 696) | AAGTCTGGAGCTGGGCAAAG (SEQ ID NO: 697) |
| 7 | NEALS.65.67_8 | GAAACAGCATTCTTGCCAAC (SEQ ID NO: 698) | GCTTCATGAGAGAGTGAGAAC (SEQ ID NO: 699) |
| 8 | NEALS.97.99_16 | AAAGAGAACAGGGTGTAACG (SEQ ID NO: 700) | GAGCCGGGAATAAACGAC (SEQ ID NO: 701) |
| 9 | DNM3.5.7_16 | AGGTCTAGGGTTCAGGGCTC (SEQ ID NO: 702) | GGGTTCATTTGACTGGACTGG (SEQ ID NO: 703) |
| 10 | CLIC4_1.3_1 | GCCAGTGTGACAAGATTGCC (SEQ ID NO: 704) | GACATCAGTGGAGGGAGGAAC (SEQ ID NO: 705) |
| 11 | NEALS.5.7_64 | ATGCCTGCAACTTAAGGAC (SEQ ID NO: 706) | GAGGACAAAGAGATAGCTTACTG (SEQ ID NO: 707) |
| 12 | NEALS.57.59_1 | CTGTCTAGAGTCCAGATCTTTC (SEQ ID NO: 708) | AAACTACAGGTGAGGGTTG (SEQ ID NO: 709) |
| 13 | ALS.21.23_32 | TGACTTGTCCACCTTCACCC (SEQ ID NO: 710) | TACGGCAGTGTGGGTCTAAC (SEQ ID NO: 711) |

TABLE 42b

ALS Probes - EpSwtch™ markers to stratify ALS vs. healthy controls

| Probe | Probe sequence 60 mer |
|---|---|
| 7_80060926_80068170_80299255_80301429_RF | AAATACAATTGAAATAAAAATAATCTTGTCGAAGCAAGGGCTTCCAGGTCATAGGTGGAT (SEQ ID NO: 712) |
| 6_149533510_149536508_149623404_149626512_RF | GTTACTGGGCTCACCACAAGCTTAAAATCGAACGCTGCCAGCATTAGAACCTATTTGTT (SEQ ID NO: 713) |
| 17_73313347_73315473_73407153_73409693_FR | AAAAAGGCACTATGAAAAAACAACATGCTCGAACTCCTGACCTCAGATGATCCACACACC (SEQ ID NO: 714) |

TABLE 42b -continued

ALS Probes - EpSwtch™ markers to stratify ALS vs. healthy controls

| Probe | Probe sequence 60 mer |
|---|---|
| 1_198660142_198665086_198737979_198744955_RR | CAAACAAGAATAAAGAGTAGAGGGTGTTTC GAGAATCTTCAACTTTTTGTATCTTCTATT (SEQ ID NO: 715) |
| 1_171936106_171939290_171988822_171992948_RF | CTCTTTGGAATGTCAGTTATTCAAATATC GAATAGCTCCTATTGTTATGGAGTGTAGCA (SEQ ID NO: 716) |
| 1_25106841_25109990_25142389_25144224_RF | TATCTCAGCTTTTGGCCTGTCTCAGCTTTC GACATAGTAGGTACTTGGTAAACATTTGTT (SEQ ID NO: 717) |

TABLE 42c

ALS Probes - EpiSwitch™ markers to stratify AL5 vs. healthy controls: Probes

| | Probe Location | | | | |
|---|---|---|---|---|---|
| Probe | Chr | Start1 | End1 | Start2 | End2 |
| 7_80060926_80068170_80299255_80301429_RF | 7 | 80060926 | 80060955 | 80301398 | 80301429 |
| 6_149533510_149536508_149623404_149626512_RF | 6 | 149533510 | 149533539 | 149626481 | 149626512 |
| 17_73313347_73315473_73407153_73409693_FR | 17 | 73315444 | 73315473 | 73407154 | 73407183 |
| 1__198660142._198G65086_198737979_198744955_RR | 1 | 198660143 | 198660172 | 198737980 | 198738009 |
| 1_171936106_171939290_171988822_171992948_RF | 1 | 171936106 | 171936135 | 171992917 | 171992948 |
| 1_2510684125109990_2514238925144224_RF | 1 | 25106841 | 25106870 | 25144195 | 25144224 |

| | 4 kb Sequence Location | | | | |
|---|---|---|---|---|---|
| Probe | Chr | Start1 | End1 | Start2 | End2 |
| 7_80060926_80068170_80299255_80301429_RF | 7 | 80060926 | 80064925 | 80297430 | 80301429 |
| 6_149533510_149536508_149623404_149626512_RF | 6 | 149533510 | 149537509 | 149622513 | 149626512 |
| 17_73313347_73315473_73407153_73409693_FR | 17 | 73311474 | 73315473 | 73407154 | 73411153 |
| 1__198660142._198G65086_198737979_198744955_RR | 1 | 198660143 | 198664142 | 198737980 | 198741979 |
| 1_171936106_171939290_171988822_171992948_RF | 1 | 171936106 | 171940105 | 171988949 | 171992948 |
| 1_2510684125109990_2514238925144224_RF | 1 | 25106841 | 25110840 | 25140225 | 25144224 |

TABLE 42d

| PCR Marker | Probe | GeneName | HyperG_Stats | P.Value | FC |
|---|---|---|---|---|---|
| ALS.61.63_8 | 7_80060926_80068170_80299255_80301429_RF | CD36 | 0.755369 | 0.00012 | 1.311151 |
| NEALS.213.215_8 | 6_149533510_149536508_149623404_149626512_RF | TAB2 | 0.955552 | 0.00568 | 0.915476 |
| NEALS.101.103_3 | 12_54983093_54985391_55002281_55007763_RR | GLYCAM1 | 0.058173 | 0.000625 | 0.765425 |
| NEALS.249.251_4 | 17_73313347_73315473_73407153_73409693_FR | GRB2 | 0.979786 | 0.071514 | 0946013 |
| NEALS.45.47_8 | 6_112058283_112061400_112189648_112191961_RR | FYN | 0.013161 | 0.000281 | 0.71137 |
| ALS.49.51_4 | 1_198660142_198665086_198737979_198744955_RR | PTPRC | 0.015074 | 0.000819 | 1.265845 |
| NEALS.65.67_8 | 1_172053648_172060321_172083100_172087823_RR | DNM3 | 0.000673 | 0.000692 | 0.710146 |
| NEALS.97.99_16 | 8_42121759_42128721_42138740_42142593_FR | IKBKB | 0.046252 | 0.000338 | 0.752995 |
| DNM3.5.7_16 | 1_171936106_171939290_171988822_171992948_RF | DNM3 | 0.000673 | 0.002108 | 1.354848 |
| CLIC4 1.3_1 | 1_25106841_25109990_25142389_25144224_RF | CLIC4 | 0.616734 | 0.012406 | 1.389081 |

TABLE 43

| Probe | GeneLocus | adj.P.Val | FC_1 | LS R/NR |
|---|---|---|---|---|
| IL15_4_142530356_142539177_142656375_142659066_RF | IL15 | 0.012659 | 1.789825 | 1 Responder |
| MYD88_3_38139864_38141788_38192489_38194027_RR | MYD88 | 0.044194 | -1.43471 | -1 BL NR |
| HLA-DQB1_6_32607972_32614493_32630138_32632737_RR | HLA-DQB1 | 0.047009 | 2.089555 | 1 BL R |
| IL12B_5_158737480_158738689_158781589_158783887_FF | IL12B | 0.012659 | -1.39097 | -1 BL NR |
| PVRL1_11_119599998_119609544_119620830_119624585_FR | PVRL1 | 0.008848 | -1.43039 | -1 BL NR |
| PIK3R3_1_46633134_46639474_46678880_46685388_RF | PIK3R3 | 0.043255 | 1.197964 | 1 BL R |
| CD6_11_60744556_60751199_60768894_60771404_RR | CD6 | 0.009617 | -1.40282 | -1 BL NR |
| STAT5B_17_40403935_40406459_40464294_40468456_FR | STAT5B | 0.031193 | -1.43489 | -1 12W R |

TABLE 44

| Array Interaction | PCR Primer 1 Sequence | PCR Primer 2 Sequence |
|---|---|---|
| Responder Versus Non Responder | | |
| >IL15_4_142530356_142539177_142656375_142659066_RF | TGAGTAACACAAAGCATCTG (SEQ ID NO: 718) | AGTGACTGGCTATGTTCC (SEQ ID NO: 719) |
| >MYD88_3_38139864_38141788_38192489_38194027_RR | CTGGTGAT-TTGTGTGACTTTG (SEQ ID NO: 720) | AGGGAAGATGTGGAGGAG (SEQ ID NO: 721) |
| >HLA-DQB1_6_32607972_32614493_32630138_32632737_RR | GTACGACTCCAGCCAAATG (SEQ ID NO: 722) | GCTGTCTGTTACTAGATTGCAC (SEQ ID NO: 723) |
| >IL12B_5_158737480_158738689_158781589_158783887_FF | ACCTTGCAAGAAGCACAG (SEQ ID NO: 724) | ATGATACTTCCCAACTGACAC (SEQ ID NO: 725) |
| >PVRL1_11_119599998_119609544_119620830_119624585_FR | AGGAGCATCCATATCAAGTG (SEQ ID NO: 726) | CTGCCATGTCTGACTATCC (SEQ ID NO: 727) |
| >PIK3R3_1_46633134_46639474_46678880_46685388_FR | CAGTGAAGAAGCCATCATCG (SEQ ID NO: 728) | GCTTAGAGAAATACACCAGCAG (SEQ ID NO: 729) |
| >CD6_11_60744556_60751199_60768894_60771404_RR | ATGGGCAGCATTTCTCAC (SEQ ID NO: 730) | AGGGACGATTTATATGACTTGC (SEQ ID NO: 731) |
| Responder Baseline Versus 12 WKS | | |
| >STAT5B_17_40403935_40406459_40464294_40468456_FR | GTGCTGGTATGTACCTGTAATC (SEQ ID NO: 732) | GAGGGTTGAGAAGCATCTTG (SEQ ID NO: 733) |

TABLE 45

| Probe | Gene Locus | adj.P.Val | FC_1 | LS | R/NR |
|---|---|---|---|---|---|
| IL15_4_142530356_142539177_142656375_142659066_RF | IL15 | 0.012658979 | 1.78982 | 1 | R |

| Probe sequence |
|---|
| 60 mer |

(SEQ ID NO: 734)
TGTAAACTGTAATATCAAAAATTCAAAATCGAAGAGTTGATTTACTTATTAACATTAGAA

| Chr | Start1 | End1 | Start2 | End2 | Chr | Start1 | End1 | Start2 | End2 |
|---|---|---|---|---|---|---|---|---|---|
| 4 | 142530357 | 142530386 | 142659035 | 142659066 | 4 | 142530357 | 142534356 | 142655067 | 142659066 |

TABLE 46a

| Probe | Gene Name | Probe_Count_Total | Probe_Count_Sig | HyperG_Stats |
|---|---|---|---|---|
| MYD88_3_38139864_38141788_38192489_38194027_RR | MYD88 | 18 | 10 | 0.009423624 |
| HLA-DQB1_6_32607972_32614493_32630138_32632737_RR | HLA-DQB1 | 12 | 8 | 0.004570722 |
| IL12B_5_158737480_158738689_158781589_158783887_FF | IL12B | 11 | 7 | 0.011584493 |
| PVRL1_11_119599998_119609544_119620830_119624585_FR | PVRL1 | 95 | 44 | 3.65E−05 |
| PIK3R3_1_46633134_46639474_46678880_46685388_RF | PIK3R3 | 55 | 24 | 0.005395839 |
| CD6_11_60744556_60751199_60768894_60771404_RR | CD6 | 62 | 33 | 9.60E−06 |
| STAT5B_17_40403935_40406459_40464294_40468456_FR | STAT5B | 20 | 9 | 0.025471082 |

| Probe | FDR_HyperG | Percent_Sig | logFC |
|---|---|---|---|
| MYD88_3_38139864_38141788_38192489_38194027_RR | 0.173813506 | 55.56 | −0.520757975 |
| HLA-DQB1_6_32607972_32614493_32630138_32632737_RR | 0.126456634 | 66.67 | 1.063195633 |
| IL12B_5_158737480_158738689_158781589_158783887_FF | 0.182699883 | 63.64 | −0.476087861 |
| PVRL1_11_119599998_119609544_119620830_119624585_FR | 0.003027108 | 46.32 | −0.516406696 |
| PIK3R3_1.46633134_46639474_46678880_46685388_RF | 0.137801433 | 43.64 | 0.260584827 |
| CD6_11_60744556_60751199_60768894_60771404_RR | 0.001593482 | 53.23 | −0.488334118 |
| STAT5B_17_40403935_40406459_40464294_40468456_FR | 0.255659576 | 45 | −0.5209394 |

TABLE 46b

| Probe | AveExpr | t | P.Value | adj.P. Val | B |
|---|---|---|---|---|---|
| MYD88_3_38139864_38141788_38192489_38194027_RR | −0.52076 | −3.83130 | 0.006090 | 0.04419 | −2.25260 |
| HLA-DQB1_6_32607972_32614493_32630138_32632737_RR | 1.063196 | 3.72400 | 0.007027 | 0.04701 | −2.40073 |
| IL12B_5_158737480_158738689_158781589_158783887_FF | −0.47609 | −6.11480 | 0.000430 | 0.01266 | 0.48298 |
| PVRL1_11_119599998_119609544_119620830_119624585_FR | −0.51647 | −8.79527 | 4.14E−05 | 0.00885 | 2.80036 |
| PIK3R3_1_46633134_46639474_46678880_46685388_RF | 0.26059 | 3.86924 | 0.005792 | 0.04325 | −2.20062 |
| CD6_11_60744556_60751199_60768894_60771404_RR | −0.48834 | −8.04736 | 7.46E−05 | 0.00962 | 2.2332 |
| STAT5B_17_40403935_40406459_40464294_40468456_FR | −0.52094 | −4.11268 | 0.004912 | 0.03119 | −1.91703 |

| Probe | FC | FC_1 | LS | Loop detected |
|---|---|---|---|---|
| MYD88_3_38139864_38141788_38192489_38194027_RR | 0.69701 | −1.43471 | −1 | BL NR |
| HLA-DQB1_6_32607972_32614493_32630138_32632737_RR | 2.08955 | 2.08955 | 1 | BL R |
| IL12B_5_158737480_158738689_158781589_158783887_FF | 0.71892 | −1.391- | −1 | BL NR |
| PVRL1_11_119599998_119609544_119620830_119624585_FR | 0.69911 | −1.43039 | −1 | BL NR |
| PIK3R3_1_46633134_46639474_46678880_46685388_RF | 1.19796 | 1.19796 | 1 | BL R |
| CD6_11_60744556_60751199_60768894_60771404_RR | 0.71285 | −1.40282 | −1 | BL NR |
| STAT5B_17_40403935_40406459_40464294_40468456_FR | 0.69692 | −1.43489 | −1 | 12W R |

TABLE 46c

| Probes | 60 mer |
|---|---|
| MYD88_3_38139864_38141788_38192489_38194027_RR | ACTTTTATAGTGAAAAGTGCCATTTGAGTC GACTGTGATTGAATGTAAAAGGTTTTAAAT (SEQ ID NO: 735) |
| HLA-DQB1_6_32607972_32614493_32630138_32632737_RR | TACTGTAGTAAGTTCTCTGAGGAGGATATC GAAGTCTTGGATTAAGGTTCATTCAACAAA (SEQ ID NO: 736) |
| IL1213_5_158737480_158738689_158781589_158783887_FF | TCCATTTGAAGGATGAGAAAACTGAGGCTC GAGGCTTAGAAAGTTTCATTTGGTTGCTCA (SEQ ID NO: 737) |
| PVRL1_11_119599998_119609544_119620830_119624585_FR | TTTTAAACCCAGGTGCACACACAAGAGCTC GAAGCAGGAATCCTGGTTCTGTTCCCAGGC (SEQ ID NO: 738) |
| PIK3R3_1_46633134_46639474_46678880_46685388_RF | CCACTCCCCCAGGCTTACCTGCGAGCCATC GAGGTGGGCCTGGGTTCTCGTGGAGGGAGA (SEQ ID NO: 739) |
| CD6_11_60744556_60751199_60768894_60771404_RR | TCACTCATTCTAGATCCCTCTGTAAAGTTC GAACTCTGGACCTTGTGATCCACCCACCTT (SEQ ID NO: 740) |
| STAT5B_17_40403935_40406459_40464294_40468456_FR | TTCCATAGATTACTTTTCAAATCATCCTTC GAAGCTGGCGGCTGAGGGCCCGGCGCCAAG (SEQ ID NO: 741) |

| Probes | Chr | Start1 | End1 | Start2 | End2 |
|---|---|---|---|---|---|
| MYD88_3_38139864_38141788_38192489_38194027_RR | 3 | 38139865 | 38139894 | 38192490 | 38192519 |
| HLA_DQB1_6_32607972_32614493_32630138_32632737_RR | 6 | 32607973 | 32608002 | 32630139 | 32630168 |
| IL12B_5_158737480_158738689_158781589_158783887_FF | 5 | 1.59E+08 | 1.59E+08 | 1.59E+08 | 1.59E+08 |
| PVRL1_11_119599998_119609544_119620830_119624585_FR | 11 | 1.2E+08 | 1.2E+08 | 1.2E+08 | 1.2E+08 |
| PIK3R3_1_46633134_46639474_46678880_46685388_RF | 1 | 46633135 | 46633164 | 46685359 | 46685388 |
| CD6_11_60744556_60751199_60768894_60771404_RR | 11 | 60744557 | 60744586 | 60768895 | 60768924 |
| STAT5B_17_40403935_40406459_40464294_40468456_FR | 17 | 40406430 | 40406459 | 40464295 | 40464324 |

| Probes | Chr | Start1 | End1 | Start2 | End2 |
|---|---|---|---|---|---|
| MYD88_3_38139864_38141788_38192489_38194027_RR | 3 | 38139865 | 38143864 | 38192490 | 38196489 |
| HLA-DQB1_6_32607972_32614493_32630138_32632737_RR | 6 | 32607973 | 32611972 | 32630139 | 32634138 |
| IL12B_5_158737480_158738689_158781589_158783887_FF | 5 | 1.59E+08 | 1.59E+08 | 1.59E+08 | 1.59E+08 |
| PVRL1_11_119599998_119609544_119620830_119624585_FR | 11 | 1.2E+08 | 1.2E+08 | 1.2E+08 | 1.2E+08 |
| PIK3R3_1_46633134_46639474_46678880_46685388_RF | 1 | 46633135 | 46637134 | 46681389 | 46685388 |
| CD6_11_60744556_60751199_60768894_60771404_RR | 11 | 60744557 | 60748556 | 60768895 | 60772894 |
| STAT5B_17_40403935_40406459_40464294_40468456_FR | 17 | 40402460 | 40406459 | 40464295 | 40468294 |

TABLE 47

| Table 47. Patients | IL15-69/ 71-1 | PVRL1-13/ 15_2 | IL12B-29/ 31_1 | STAT5B-317/ 75-2 | STAT5B-73/ 75_2 | HLA-DQB1-85/ 87_1 | MYD88-9/ 11_1 |
|---|---|---|---|---|---|---|---|
| Benign_Thryoid_1 | 0 | 1 | 1 | 0 | 0 | 0 | 0 |
| Benign Thryoid_2 | 0 | 1 | 0 | 1 | 1 | 0 | 1 |
| Benign_Thryoid_3 | 0 | 1 | 0 | 0 | 1 | 1 | 0 |
| Benign_Thryoid_4 | 0 | 1 | 0 | 0 | 0 | 0 | 0 |
| Benign_Thryoid_5 | 1 | 1 | 0 | 0 | 1 | 0 | 0 |
| Malignant_Thryoid_1 | 0 | 1 | 1 | 1 | 0 | 0 | 0 |
| Malignant_Thryoid_2 | 1 | 1 | 1 | 0 | 1 | 0 | 0 |
| Malignant_Thryoid_3 | 1 | 1 | 1 | 0 | 0 | 0 | 1 |
| Malignant_Thryoid_4 | 0 | 0 | 1 | 0 | 1 | 0 | 0 |
| Malignant_Thryoid_5 | 0 | 0 | 1 | 0 | 0 | 0 | 0 |
| DLBCL_ABC_1 | 0 | 1 | 1 | 0 | 1 | 0 | 0 |
| DLBCL_ABC_2 | 0 | 1 | 1 | 0 | 0 | 0 | 1 |
| DLBCL_ABC_3 | 1 | 1 | 1 | 0 | 1 | 0 | 0 |
| DLBCL_ABC_4 | 1 | 1 | 1 | 1 | 0 | 0 | 0 |
| DLBCL_ABC_5 | 1 | 1 | 1 | 0 | 0 | 0 | 0 |
| DLBCL_ABC_6 | 1 | 1 | 1 | 0 | 1 | 1 | 1 |
| DLBCL_ABC_7 | 0 | 1 | 1 | 0 | 0 | 0 | 1 |
| DLBCL_ABC_8 | 0 | 0 | 1 | 1 | 0 | 0 | 1 |
| DLBCL_ABC_9 | 1 | 1 | 1 | 0 | 1 | 0 | 1 |
| DLBCL_ABC_10 | 1 | 1 | 0 | 1 | 0 | 0 | 0 |
| DLBCL_GBC_1 | 1 | 1 | 1 | 0 | 1 | 0 | 1 |
| DLBCL_GBC_2 | 1 | 1 | 1 | 1 | 1 | 1 | 1 |
| DLBCL_GBC_3 | 1 | 1 | 1 | 0 | 1 | 0 | 0 |
| DLBCL_GBC_4 | 1 | 1 | 0 | 0 | 1 | 0 | 1 |
| DLBCL_GBC_5 | 0 | 1 | 0 | 0 | 0 | 0 | 0 |
| DLBCL_GBC_6 | 1 | 1 | 1 | 0 | 0 | 0 | 0 |
| DLBCL_GBC_7 | 1 | 1 | 1 | 0 | 0 | 1 | 0 |
| DLBCL_GBC_8 | 1 | 1 | 1 | 0 | 1 | 1 | 0 |
| DLBCL_GBC_9 | 0 | 1 | 1 | 0 | 0 | 0 | 0 |
| DLBCL_GBC_10 | 1 | 1 | 1 | 0 | 0 | 0 | 1 |
| HCC_HEPB_1 | 0 | 0 | 1 | 1 | 1 | 0 | 1 |
| HCC_HEPB_2 | 0 | 1 | 0 | 0 | 0 | 0 | 1 |
| HCC_HEPB_3 | 0 | 0 | 1 | 0 | 0 | 0 | 0 |
| HCC_HEPC_1 | 1 | 1 | 1 | 1 | 1 | 0 | 0 |
| HCC_HEPC_2 | 1 | 1 | 1 | 1 | 1 | 0 | 1 |
| HCC_HEPC_3 | 0 | 1 | 0 | 0 | 0 | 0 | 0 |
| HCC_1 | 0 | 0 | 0 | 1 | 0 | 0 | 0 |
| HCC_2 | 1 | 1 | 1 | 1 | 1 | 0 | 1 |
| HCC_3 | 0 | 1 | 1 | 1 | 0 | 0 | 0 |
| HEPB + R_1 | 0 | 1 | 1 | 1 | 0 | 0 | 1 |
| Pca_Class3_1 | 0 | 0 | 1 | 0 | 0 | 0 | 1 |
| Pca_Class3_2 | 0 | 1 | 1 | 0 | 1 | 0 | 1 |
| Pca_Class3_3 | 0 | 1 | 0 | 1 | 1 | 0 | 1 |
| Pca_Class3_4 | 1 | 1 | 1 | 0 | 0 | 1 | 1 |
| Pca_Class2_1 | 1 | 1 | 1 | 0 | 1 | 0 | 1 |
| Pca_Class2_2 | 0 | 1 | 0 | 0 | 0 | 0 | 1 |
| Pca__Class2_3 | 1 | 1 | 1 | 0 | 0 | 0 | 1 |
| Pca_Class1_1 | 0 | 1 | 1 | 0 | 1 | 1 | 0 |
| Pca_Class1_2 | 1 | 1 | 1 | 1 | 1 | 0 | 1 |
| Pca_Class1_3 | 1 | 1 | 1 | 0 | 1 | 1 | 1 |
| BrCa_Stg4_1 | 1 | 0 | 1 | 0 | 0 | 0 | 1 |
| BrCa_Stg4_2 | 1 | 1 | 1 | 1 | 0 | 0 | 0 |
| BrCa_Stg4_3 | 1 | 1 | 1 | 0 | 0 | 0 | 0 |
| BrCa_Stg3B_1 | 0 | 1 | 1 | 0 | 0 | 0 | 0 |
| BrCa_Stg3B_2 | 1 | 1 | 1 | 0 | 1 | 0 | 1 |
| BrCa_Stg2A_1 | 1 | 1 | 1 | 1 | 1 | 0 | 1 |
| BrCa_Stg2B_1 | 1 | 1 | 1 | 1 | 0 | 0 | 0 |
| BrCa_Stg1A_1 | 0 | 0 | 1 | 0 | 0 | 0 | 0 |
| BrCa_Stg1A_2 | 0 | 1 | 1 | 1 | 1 | 0 | 0 |
| BrCa_Stg1_1 | 0 | 1 | 1 | 0 | 0 | 0 | 0 |
| PD_1_R_Melanoma | 1 | 0 | 0 | 0 | 1 | 1 | 1 |
| PD_1_NR_Melanoma | 0 | 1 | 1 | 1 | 0 | 0 | 0 |

TABLE 48

P-values

| | Condition | No All/gp | P-value Top range | Mid range | Bottom |
|---|---|---|---|---|---|
| Table 18 | ALS | 61/20 | 0.0058-0.0013 | 0.0013-0.0004 | 0.0004-0.00011 |
| Table 19 | preT2 DM | 50/17 | 0.0083-0.0013 | 0.0013-0.0004 | 0.0004-0.00006 |
| Table 20 | T2DM | 50/17 | 0.011-0.0043 | 0.0043-0.001 | 0.001-0.00006 |
| Table 21 | T1DM | 50/17 | 0.0059-0.0006 | 0.00039-0.0001 | $0.0001-2.7 \times 10^{-6}$ |

TABLE 48-continued

| Table 22 | UC | 50/17 | 0.0034-0.00040 | 0.00038-0.0001 | $9.9 \times 10^{-5}$-$8 \times 10^{-6}$ |
| --- | --- | --- | --- | --- | --- |
| Table 23 | SLE | 50/17 | 0.0077-0.0031 | 0.0028-0.001 | $0.001$-$6 \times 10^{-5}$ |
| Table 24 | MSRR | 50/17 | 0.0075-0.00306 | 0.0029-0.00082 | $0.000567$-$2 \times 10^{-5}$ |
| Table 25 | IFN-B R | 50/17 | 0.0061-0.00068 | $0.0005$-$2.6 \times 10^{-5}$ | $1.9 \times 10^{-5}$-$2 \times 10^{-7}$ |
| Table 6 | RA-MTX | 50/17 | $0.021$-$0.0103_{(17)}$ | $0.0096$-$0.0024_{(35)}$ | 0.0018-0.00011 |
| Table 36e | antiPDINR | 25/8 | 0.0061-0.0004 | 0.00018-0.000107 | $7.46 \times 10^{-5}$-$2 \times 10^{-5}$ |
| Table 27 | ALS | 97/33 | 0.298-0.21 (28) | 0.19-0.102 (66) | $0.097$-$9.7 \times 10^{-5}$ |
| Table 28 | preT2 DM | 39/13 | 0.204-0.059(13) | 0.04-0.0097 (26) | $0.00578$-$3 \times 10^{-5}$ |
| Table 29 | T2 DM | 89/33 | 0.28-0.14 (27) | 0.126-0.017 (66) | $0.0147$-$1.5 \times 10^{-5}$ |
| Table 30 | T1 DM | 70/23 | 0.26-0.144 (22) | 0.138-0.052 (47) | 0.038-0.0007 |
| Table 31 | UC | 75/25 | 0.273-0.183(22) | 0.167-0.079 (48) | 0.065-0.0001 |
| Table 32 | SLE | 73/24 | 0.2965-0.17 (23) | 0.163-0.083 (49) | 0.079-0.0002 |
| Table 33 | MSRR | 58/19 | 0.28-0.1807(19) | 0.165-0.079 (38) | $0.0698$-$1.3 \times 10^{-5}$ |
| Table 34 | IFN-B R | 89/30 | 0.29-0.203(29) | 0.187-0.064 (59) | $0.055$-$5 \times 10^{-5}$ |
| Table 35 | NeurFib | 63/21 | 0.289-0.171 (20) | 0.163-0.065 (43) | $0.057$-$7 \times 10^{-5}$ |

| | P-values | | | |
| --- | --- | --- | --- | --- |
| | Adj-P Top range | Mid range | Bottom | Range boundaries |
| Table 18 | 0.067-0.046 | 0.046-0.045 | 0.045-0.044 | 0.0013; 0.0004 |
| Table 19 | 0.008 | 0.055-0.046 | 0.046-0.036 | 0.0013; 0.0004 |
| Table 20 | 0.0986-0.087 | 0.087-0.085141 | 0.085141 | 0.0043; 0.001 |
| Table 21 | 0.0641-0.0232 | 0.0199-0.01084 | 0.0097-0.0025 | 0.0005; 0.0001 |
| Table 22 | 0.026-0.012 | 0.0118-0.009 | 0.0087-0.0048 | 0.0004; 0.00001 |
| Table 23 | 0.049-0.038 | 0.0378-0.03651 | 0.036258 | 0.003; 0.001 |
| Table 24 | 0.26-0.228 | 0.213-0.100 | 0.985-0.0165 | 0.003; 0.0006 |
| Table 25 | 0.0598-0.0214 | 0.0119-0.0051 | 0.0042-0.0013 | 0.0005; 0.00002 |
| Table 6 | | | | 0.01; 0.002 |
| Table 36e | | | | 0.0002; 0.0001 up to 0.0004; 0.0001 |
| Table 27 | | | | 0.2; 0.1 |
| Table 28 | | | | 0.04; 0.006 |
| Table 29 | | | | 0.13; 0.015 |
| Table 30 | | | | 0.14; 0.04 |
| Table 31 | | | | 0.17; 0.07 |
| Table 32 | | | | 0.17; 0.08 |
| Table 33 | | | | 0.18; 0.07 |
| Table 34 | | | | 0.2; 0.06 |
| Table 35 | | | | 0.17; 0.06 |

TABLE 49

Data for additional anti-PD1 probe

| Probe | Sequence |
| --- | --- |
| STAT5B_17_40388884_40391941_40464294_40468456_RR | TACAGTCTTTGTAGATGCAGAGTAG CGTTCGAAGCTGGCGGCTGAGGGCC CGGCGCCAAG (SEQ ID NO:742) |

| logFC | AveExpr | t | P.Value | adj.P.Val | B | FC | FC_1 | LS | Chi_Square |
| --- | --- | --- | --- | --- | --- | --- | --- | --- | --- |
| 0.5443091 | 0.5443091 | 6.64801232 | 0.00025533 | 0.01131185 | 1.01165877 | 1.45832179 | 1.45832179 | 1 | 0.138 |

| PCR Probe | STAT5B-317/75-2 | Gene Locus | STAT5B |
| --- | --- | --- | --- |

| Primer | Primer Sequence |
| --- | --- |
| STAT5B-317 | CTGCCCGTAAATAAGCAGAAG (SEQ ID NO:743) |
| STAT5B-75 | GAGGGTTGAGAAGCATCTTG (SEQ ID NO:744) |

The invention claimed is:

1. A method of typing a human comprising detecting the presence or absence of the following 5 epigenetic chromosome interactions which relate to predisposition to amyotrophic lateral sclerosis (ALS) disease
   (i) the chromosome interaction formed by chromosome positions 171936106 to 171936135 coming together with chromosome positions 171992917 to 171992948 on chromosome 1;
   (ii) the chromosome interaction formed by chromosome positions 25106841 to 25106870 coming together with chromosome positions 25144195 to 25144224 on chromosome 1;
   (iii) the chromosome interaction formed by chromosome positions 80060926 to 80060955 coming together with chromosome positions 80301398 to 80301429 on chromosome 7;
   (iv) the chromosome interaction formed by chromosome positions 54983094 to 54983123 coming together with chromosome positions 55002282 to 55002311 on chromosome 12; and
   (v) the chromosome interaction formed by chromosome positions 198660143 to 198660172 coming together with chromosome positions 198737980 to 198738009 on chromosome 1.

2. A method of treatment and/or prophylaxis of a human comprising administering a therapeutic agent for ALS disease to the individual wherein said individual has been identified as being in need of said therapeutic agent by the method of claim 1.

3. The method according to claim 1, wherein detecting of the presence or absence of the chromosome interactions is by a method comprising the steps of:

(i) in vitro cross-linking of chromosome regions which have come together in a chromosome interaction;
   (ii) subjecting said cross-linked DNA to restriction digestion cleavage with an enzyme; and
   (iii) ligating said cross-linked cleaved DNA ends to form the ligated nucleic acids.

4. The method according to claim 3, wherein said ligated DNA is detected by PCR or by use of a probe.

5. The method according to claim 4, wherein said probe has at least 70% identity to any of the following probes

```
                                              (SEQ ID NO: 716)
TCTCTTTGGAATGTCAGTTATTCAAATATC
GAATAGCTCCTATTGTTATGGAGTGTAGCA;

(SEQ ID NO: 717)
TATCTCAGCTTTTGGCCTGTCTCAGCTTTC
GACATAGTAGGTACTTGGTAAACATTTGTT;

(SEQ ID NO: 712)
AAATACAATTGAAATAAAAATAATCTTGTC
GAAGCAAGGGCTTCCAGGTCATAGGTGGAT;

(SEQ ID NO: 152)
CCCCTAATTTAGCAAGCAGAAAGAGAACTC
GATGCTTCATTTGACTCACACTCACATTTA;
or (SEQ ID NO: 715)
CAAACAAGAATAAAGAGTAGAGGGTGTTTC
GAGAATCTTCAACTTTTTGTATCTTCTATT.
```

* * * * *

UNITED STATES PATENT AND TRADEMARK OFFICE
CERTIFICATE OF CORRECTION

| | |
|---|---|
| PATENT NO. | : 11,434,522 B1 |
| APPLICATION NO. | : 15/738476 |
| DATED | : September 6, 2022 |
| INVENTOR(S) | : Ewan Hunter, Aroul Ramadass and Alexandre Akoulitchev |

It is certified that error appears in the above-identified patent and that said Letters Patent is hereby corrected as shown below:

On the Title Page

Item (30) Foreign Application Priority Data, the second Application GB 1511080:
Please delete "Jun. 26, 2015" and replace with --Jun. 24, 2015--.

Signed and Sealed this
Twenty-second Day of November, 2022

Katherine Kelly Vidal
*Director of the United States Patent and Trademark Office*

SEQUENCE LISTING

<160> NUMBER OF SEQ ID NOS: 744

<210> SEQ ID NO 1
<211> LENGTH: 60
<212> TYPE: DNA
<213> ORGANISM: Homo sapiens

<400> SEQUENCE: 1

```
tgttttttgg ctgcataaat gtcttctttc gaaataatca tcaaaatatt tttcattgac    60
```

<210> SEQ ID NO 2
<211> LENGTH: 60
<212> TYPE: DNA
<213> ORGANISM: Homo sapiens

<400> SEQUENCE: 2

```
caccccatc tcctttgct gactctcttc gatgaatcca ttttttgga aatagatgat      60
```

<210> SEQ ID NO 3
<211> LENGTH: 60
<212> TYPE: DNA
<213> ORGANISM: Homo sapiens

<400> SEQUENCE: 3

```
caccccatc tcctttgct gactctcttc gaactgtggc aattttaact tttcaaattg     60
```

<210> SEQ ID NO 4
<211> LENGTH: 60
<212> TYPE: DNA
<213> ORGANISM: Homo sapiens

<400> SEQUENCE: 4

```
caccccatc tcctttgct gactctcttc gaggcatgat ttgagtcttg acagaagttc     60
```

<210> SEQ ID NO 5
<211> LENGTH: 60
<212> TYPE: DNA
<213> ORGANISM: Homo sapiens

<400> SEQUENCE: 5

```
tgccagtatt ttattgagga tttttgcatc gagattgggt tgcatcatgt tggccaggct   60
```

<210> SEQ ID NO 6
<211> LENGTH: 60
<212> TYPE: DNA
<213> ORGANISM: Homo sapiens

<400> SEQUENCE: 6

```
tgttttttgg ctgcataaat gtcttctttc gaactcatgg gcacaagcaa tcctcccacc   60
```

<210> SEQ ID NO 7
<211> LENGTH: 60
<212> TYPE: DNA
<213> ORGANISM: Homo sapiens

<400> SEQUENCE: 7

```
tgccagtatt ttattgagga tttttgcatc gaacagatgg agggaagagg ggatagctcc   60
```

<210> SEQ ID NO 8
<211> LENGTH: 60
<212> TYPE: DNA
<213> ORGANISM: Homo sapiens

<400> SEQUENCE: 8

```
tgccctagag atctgtggaa ctttgaactc gagtcaaaga gatatcaaga gcttctatca   60
```

<210> SEQ ID NO 9
<211> LENGTH: 60
<212> TYPE: DNA
<213> ORGANISM: Homo sapiens

-continued

<400> SEQUENCE: 9
cacccccatc tccctttgct gactctcttc gagggcagaa tgagcctcag acatctccag    60

<210> SEQ ID NO 10
<211> LENGTH: 60
<212> TYPE: DNA
<213> ORGANISM: Homo sapiens

<400> SEQUENCE: 10
tctcctgcct gattgccctg ccagaacttc gatttgggct atagtgttgt tccagtctaa    60

<210> SEQ ID NO 11
<211> LENGTH: 60
<212> TYPE: DNA
<213> ORGANISM: Homo sapiens

<400> SEQUENCE: 11
cacccccatc tccctttgct gactctcttc gatcttgaag agatctcttc ttagcaaagc    60

<210> SEQ ID NO 12
<211> LENGTH: 60
<212> TYPE: DNA
<213> ORGANISM: Homo sapiens

<400> SEQUENCE: 12
cacccccatc tccctttgct gactctcttc gaaatatttt tgcttgagct cctgtctcat    60

<210> SEQ ID NO 13
<211> LENGTH: 60
<212> TYPE: DNA
<213> ORGANISM: Homo sapiens

<400> SEQUENCE: 13
taggcgcaca tgcacacagc tcgcctcttc gacccaggaa gatccaaagg aggaactgag    60

<210> SEQ ID NO 14
<211> LENGTH: 60
<212> TYPE: DNA
<213> ORGANISM: Homo sapiens

<400> SEQUENCE: 14
cccccacccc catcccagga aattggtttc gatgagagaa ggcaagagaa catggggtct    60

<210> SEQ ID NO 15
<211> LENGTH: 60
<212> TYPE: DNA
<213> ORGANISM: Homo sapiens

<400> SEQUENCE: 15
tgccagtatt ttattgagga tttttgcatc gagttcaaag ttccacagat ctctagggca    60

<210> SEQ ID NO 16
<211> LENGTH: 60
<212> TYPE: DNA
<213> ORGANISM: Homo sapiens

<400> SEQUENCE: 16
ctaaaaatta catccaggaa atgagatatc gaaagaagac atttatgcag ccaaaaaaca    60

<210> SEQ ID NO 17
<211> LENGTH: 60
<212> TYPE: DNA
<213> ORGANISM: Homo sapiens

<400> SEQUENCE: 17
taggcgcaca tgcacacagc tcgcctcttc gatgtacaag ctgcctattg atagactttc    60

<210> SEQ ID NO 18
<211> LENGTH: 60
<212> TYPE: DNA
<213> ORGANISM: Homo sapiens

<400> SEQUENCE: 18
aaagttgtgc aatcaggcaa gtcaagattc gaaagaagac atttatgcag ccaaaaaaca    60

<210> SEQ ID NO 19
<211> LENGTH: 60
<212> TYPE: DNA
<213> ORGANISM: Homo sapiens

<400> SEQUENCE: 19 caccccatc tccctttgct gactctcttc gagtggtgag cagccaaacc agggttcact    60

<210> SEQ ID NO 20
<211> LENGTH: 60
<212> TYPE: DNA
<213> ORGANISM: Homo sapiens

<400> SEQUENCE: 20
gggtcttgct atgttgccca ggctggcctc gagatcagcc tgggcaacac ggtgaaaacc    60

<210> SEQ ID NO 21
<211> LENGTH: 60
<212> TYPE: DNA
<213> ORGANISM: Homo sapiens

<400> SEQUENCE: 21
ctggtttagt cttgggagag tgtatgtgtc gagttaagcc atctgcaaat agcaagagag    60

<210> SEQ ID NO 22
<211> LENGTH: 60
<212> TYPE: DNA
<213> ORGANISM: Homo sapiens

<400> SEQUENCE: 22
agccttgcat cccagggatg aagcccactc gagatataga ttgagcccca gttttggag    60

<210> SEQ ID NO 23
<211> LENGTH: 60
<212> TYPE: DNA
<213> ORGANISM: Homo sapiens

<400> SEQUENCE: 23
atcgtgtggg ctgtgtgtgg cagactgttc gaaatcggaa gcctctctga aggtccaagg    60

<210> SEQ ID NO 24
<211> LENGTH: 60
<212> TYPE: DNA
<213> ORGANISM: Homo sapiens

<400> SEQUENCE: 24
tgccagtatt ttattgagga tttttgcatc gaattcctgg gtttatatcc caatcattgt    60

<210> SEQ ID NO 25
<211> LENGTH: 60
<212> TYPE: DNA

<213> ORGANISM: Homo sapiens

<400> SEQUENCE: 25 caccccatc tccctttgct gactctcttc gatattggtg tatattcaaa gggtacttga    60

<210> SEQ ID NO 26
<211> LENGTH: 60
<212> TYPE: DNA
<213> ORGANISM: Homo sapiens

<400> SEQUENCE: 26
tgatcactgt ttcctatgag gatacagctc gaggggcagg gggcggtcct gggccaggcg    60

<210> SEQ ID NO 27
<211> LENGTH: 60
<212> TYPE: DNA
<213> ORGANISM: Homo sapiens

<400> SEQUENCE: 27
aacttatgat tctaatcttg aatgtctgtc gatctatgag gaaatgcccc cagcctccca    60

<210> SEQ ID NO 28
<211> LENGTH: 60
<212> TYPE: DNA
<213> ORGANISM: Homo sapiens

<400> SEQUENCE: 28
cataatgcat gtgcatgaaa actaatcttc gatctatgag gaaatgcccc cagcctccca    60

<210> SEQ ID NO 29
<211> LENGTH: 60
<212> TYPE: DNA
<213> ORGANISM: Homo sapiens

<400> SEQUENCE: 29
atcagtaagc tggtcagcta cccatgaatc gatctatgag gaaatgcccc cagcctccca    60

<210> SEQ ID NO 30
<211> LENGTH: 60
<212> TYPE: DNA
<213> ORGANISM: Homo sapiens

<400> SEQUENCE: 30
gtgtcccaat ttctagtgca ctgtgaactc gacctcgcgg gaggggtgcc aggccgcatc    60

<210> SEQ ID NO 31
<211> LENGTH: 60
<212> TYPE: DNA
<213> ORGANISM: Homo sapiens

<400> SEQUENCE: 31
ccggggcttc tcgtttaaga attctttgtc gatctatgag gaaatgcccc cagcctccca    60

<210> SEQ ID NO 32
<211> LENGTH: 60
<212> TYPE: DNA
<213> ORGANISM: Homo sapiens

<400> SEQUENCE: 32
gtctttgaag aaggactaat gcttagtatc gagtgcagcg ccggtgggcc agcactgctg    60

<210> SEQ ID NO 33
<211> LENGTH: 60

```
<212> TYPE: DNA
<213> ORGANISM: Homo sapiens

<400> SEQUENCE: 33
gttcatttaa acattttatt atgtatattc gaggggccag gcttttatac ccccatctga    60

<210> SEQ ID NO 34
<211> LENGTH: 60
<212> TYPE: DNA
<213> ORGANISM: Homo sapiens

<400> SEQUENCE: 34
ttctccacag ccggccggtc cttggcagtc gaggggcagg gggcggtcct gggccaggcg    60

<210> SEQ ID NO 35
<211> LENGTH: 60
<212> TYPE: DNA
<213> ORGANISM: Homo sapiens

<400> SEQUENCE: 35
gcaacacata caacgactaa tcttctttc gacgccgagg agctctgcag tgggggcgta    60

<210> SEQ ID NO 36
<211> LENGTH: 60
<212> TYPE: DNA
<213> ORGANISM: Homo sapiens

<400> SEQUENCE: 36
gtaggtgctg agtaagtgag cacttgcctc gaggggcagg gggcggtcct gggccaggcg    60

<210> SEQ ID NO 37
<211> LENGTH: 60
<212> TYPE: DNA
<213> ORGANISM: Homo sapiens

<400> SEQUENCE: 37
cagaaagacc ttgcaatcat acggtgcttc gacgccgagg agctctgcag tgggggcgta    60

<210> SEQ ID NO 38
<211> LENGTH: 60
<212> TYPE: DNA
<213> ORGANISM: Homo sapiens

<400> SEQUENCE: 38
tactgtgctg tgctcgtcaa agagtatgtc gatctatgag gaaatgcccc cagcctccca    60

<210> SEQ ID NO 39
<211> LENGTH: 60
<212> TYPE: DNA
<213> ORGANISM: Homo sapiens

<400> SEQUENCE: 39
cagaaattaa tcaaatgcaa gtgcaccctc gaccacccaa gggctgagga gtgcgggcac    60

<210> SEQ ID NO 40
<211> LENGTH: 60
<212> TYPE: DNA
<213> ORGANISM: Homo sapiens

<400> SEQUENCE: 40
aagggaccta gtcccctatt aagatttctc gaggggccag gcttttatac ccccatctga    60

<210> SEQ ID NO 41
```

```
<211> LENGTH: 60
<212> TYPE: DNA
<213> ORGANISM: Homo sapiens

<400> SEQUENCE: 41
cctgccgaga cacgggacgt gggattgctc gatctatgag gaaatgcccc cagcctccca    60

<210> SEQ ID NO 42
<211> LENGTH: 60
<212> TYPE: DNA
<213> ORGANISM: Homo sapiens

<400> SEQUENCE: 42
ccaaagctcg ctttcttaac cactatgctc gaggggccag gcttttatac ccccatctga    60

<210> SEQ ID NO 43
<211> LENGTH: 60
<212> TYPE: DNA
<213> ORGANISM: Homo sapiens

<400> SEQUENCE: 43
tgaattgtgt agcgtaagaa tttatatctc gaagtttgtg aactggcagg tggacgggga    60

<210> SEQ ID NO 44
<211> LENGTH: 60
<212> TYPE: DNA
<213> ORGANISM: Homo sapiens

<400> SEQUENCE: 44
acctgatctg gggaagatta ggaattgttc gaaaccaatt tcctgggatg ggggtggggg    60

<210> SEQ ID NO 45
<211> LENGTH: 60
<212> TYPE: DNA
<213> ORGANISM: Homo sapiens

<400> SEQUENCE: 45
gcaagaggat ctcttgaggc ccaggagttc gaggggccag gcttttatac ccccatctga    60

<210> SEQ ID NO 46
<211> LENGTH: 60
<212> TYPE: DNA
<213> ORGANISM: Homo sapiens

<400> SEQUENCE: 46
tatcaagtga tccaaaaggc tgccagtgtc gaggggcagg gggcggtcct gggccaggcg    60

<210> SEQ ID NO 47
<211> LENGTH: 60
<212> TYPE: DNA
<213> ORGANISM: Homo sapiens

<400> SEQUENCE: 47
aagggaccta gtcccctatt aagatttctc gaaaccaatt tcctgggatg ggggtggggg    60

<210> SEQ ID NO 48
<211> LENGTH: 60
<212> TYPE: DNA
<213> ORGANISM: Homo sapiens

<400> SEQUENCE: 48
tatggacttt gtagtctcat atcaaagctc gaaaccaatt tcctgggatg ggggtggggg    60
```

```
<210> SEQ ID NO 49
<211> LENGTH: 60
<212> TYPE: DNA
<213> ORGANISM: Homo sapiens

<400> SEQUENCE: 49
aaaaataatc tggctctaca cttaggattc gaaaccaatt tcctgggatg ggggtggggg    60

<210> SEQ ID NO 50
<211> LENGTH: 60
<212> TYPE: DNA
<213> ORGANISM: Homo sapiens

<400> SEQUENCE: 50
tgatcactgt ttcctatgag gatacagctc gaggggcagg gggcggtcct gggccaggcg    60

<210> SEQ ID NO 51
<211> LENGTH: 60
<212> TYPE: DNA
<213> ORGANISM: Homo sapiens

<400> SEQUENCE: 51
aacctggaga acgccaagcg cttcgccatc gaggggcagg gggcggtcct gggccaggcg    60

<210> SEQ ID NO 52
<211> LENGTH: 60
<212> TYPE: DNA
<213> ORGANISM: Homo sapiens

<400> SEQUENCE: 52
ctacctttgt ggcacttggt acagcaaatc gacgggcccc gtgaggcggg ggcgggaccc    60

<210> SEQ ID NO 53
<211> LENGTH: 60
<212> TYPE: DNA
<213> ORGANISM: Homo sapiens

<400> SEQUENCE: 53
catcaattat aactcacctt acagatcatc gacgggcccc gtgaggcggg ggcgggaccc    60

<210> SEQ ID NO 54
<211> LENGTH: 60
<212> TYPE: DNA
<213> ORGANISM: Homo sapiens

<400> SEQUENCE: 54
tgatcactgt ttcctatgag gatacagctc gaagattagg taaaggtggg gacgcggaga    60

<210> SEQ ID NO 55
<211> LENGTH: 60
<212> TYPE: DNA
<213> ORGANISM: Homo sapiens

<400> SEQUENCE: 55
gaaaggtaat tgcccccaat atttattttc gaaacagatc gggcggctcg ggttacacac    60

<210> SEQ ID NO 56
<211> LENGTH: 60
<212> TYPE: DNA
<213> ORGANISM: Homo sapiens

<400> SEQUENCE: 56
ttctccacag ccggccggtc cttggcagtc gaggggcagg gggcggtcct gggccaggcg    60
```

<210> SEQ ID NO 57
<211> LENGTH: 60
<212> TYPE: DNA
<213> ORGANISM: Homo sapiens

<400> SEQUENCE: 57
cgtgtcccaa tttctagtgc actgtgaact cgacctcgcg ggaggggtgc caggccgcat    60

<210> SEQ ID NO 58
<211> LENGTH: 60
<212> TYPE: DNA
<213> ORGANISM: Homo sapiens

<400> SEQUENCE: 58
cctctcttct aaaaggtctc aacatcactc gactggagag cccggggcct cgcgccgctt    60

<210> SEQ ID NO 59
<211> LENGTH: 60
<212> TYPE: DNA
<213> ORGANISM: Homo sapiens

<400> SEQUENCE: 59
gtttcccctt gatgctcaga gaaaggcctc gaaacagatc gggcggctcg ggttacacac    60

<210> SEQ ID NO 60
<211> LENGTH: 60
<212> TYPE: DNA
<213> ORGANISM: Homo sapiens

<400> SEQUENCE: 60
cataatgcat gtgcatgaaa actaatcttc gatctatgag gaaatgcccc cagcctccca    60

<210> SEQ ID NO 61
<211> LENGTH: 60
<212> TYPE: DNA
<213> ORGANISM: Homo sapiens

<400> SEQUENCE: 61
agatgtgtaa gtcaccaggg agtgcattcg cgacctcgcg ggaggggtgc caggccgcat    60

<210> SEQ ID NO 62
<211> LENGTH: 60
<212> TYPE: DNA
<213> ORGANISM: Homo sapiens

<400> SEQUENCE: 62
gtaatggtgc catcatagct caagctcctc gatctatgag gaaatgcccc cagcctccca    60

<210> SEQ ID NO 63
<211> LENGTH: 60
<212> TYPE: DNA
<213> ORGANISM: Homo sapiens

<400> SEQUENCE: 63
aatacaaagg atggtatatt ttgcatattc gatctatgag gaaatgcccc cagcctccca    60

<210> SEQ ID NO 64
<211> LENGTH: 60
<212> TYPE: DNA
<213> ORGANISM: Homo sapiens

<400> SEQUENCE: 64
cctctcttct aaaaggtctc aacatcactc gatggtgcgg gaggtggccg gcagggttgg    60

<210> SEQ ID NO 65
<211> LENGTH: 60
<212> TYPE: DNA
<213> ORGANISM: Homo sapiens

<400> SEQUENCE: 65
ataattcttc ctggcacata ataagtattc gaatcgggcg ggttccggcg tgggtttcag    60

<210> SEQ ID NO 66
<211> LENGTH: 60
<212> TYPE: DNA
<213> ORGANISM: Homo sapiens

<400> SEQUENCE: 66
tctaaaggga tttccactat atgtagattc gaggggcgtg tgcgcgcgtg gcggggcccg    60

<210> SEQ ID NO 67
<211> LENGTH: 60
<212> TYPE: DNA
<213> ORGANISM: Homo sapiens

<400> SEQUENCE: 67
aacttatgat tctaatcttg aatgtctgtc gatctatgag gaaatgcccc cagcctccca    60

<210> SEQ ID NO 68
<211> LENGTH: 60
<212> TYPE: DNA
<213> ORGANISM: Homo sapiens

<400> SEQUENCE: 68
gaggtgggca gatcacgggg tcagggtatc gaggcccatc actggcgggg agacgggagg    60

<210> SEQ ID NO 69
<211> LENGTH: 60
<212> TYPE: DNA
<213> ORGANISM: Homo sapiens

<400> SEQUENCE: 69
actgaatatg aaaaaaaatg taaaaattat cgacctcgcg ggaggggtgc caggccgcat    60

<210> SEQ ID NO 70
<211> LENGTH: 60
<212> TYPE: DNA
<213> ORGANISM: Homo sapiens

<400> SEQUENCE: 70
gattttatag caaatttaca aaaatgagtc gatctatgag gaaatgcccc cagcctccca    60

<210> SEQ ID NO 71
<211> LENGTH: 60
<212> TYPE: DNA
<213> ORGANISM: Homo sapiens

<400> SEQUENCE: 71
accaagagtt ggacccccctt tttgatgttc gatggtgcgg gaggtggccg gcagggttgg    60

<210> SEQ ID NO 72
<211> LENGTH: 60
<212> TYPE: DNA
<213> ORGANISM: Homo sapiens

<400> SEQUENCE: 72
tatattgcta tctactagca aaggataatc gaagaggttc agggcggtgc ccgcggcgct       60

<210> SEQ ID NO 73
<211> LENGTH: 60
<212> TYPE: DNA
<213> ORGANISM: Homo sapiens

<400> SEQUENCE: 73
atcagtaagc tggtcagcta cccatgaatc gatctatgag gaaatgcccc cagcctccca       60

<210> SEQ ID NO 74
<211> LENGTH: 60
<212> TYPE: DNA
<213> ORGANISM: Homo sapiens

<400> SEQUENCE: 74
tgaaaacagt tcatcctgag tttcagtctc gaagattagg taaaggtggg gacgcggaga       60

<210> SEQ ID NO 75
<211> LENGTH: 60
<212> TYPE: DNA
<213> ORGANISM: Homo sapiens

<400> SEQUENCE: 75
gtgcagagcg agagcggggc agaggcggtc gaaactggga gaattcatct gaaatgatta       60

<210> SEQ ID NO 76
<211> LENGTH: 60
<212> TYPE: DNA
<213> ORGANISM: Homo sapiens

<400> SEQUENCE: 76
gaggcaggca gatcatgagg tcaggagttc gagccctgga ccccaggcca gctaatgagg       60

<210> SEQ ID NO 77
<211> LENGTH: 60
<212> TYPE: DNA
<213> ORGANISM: Homo sapiens

<400> SEQUENCE: 77
gctcactgca acctccacct cccaggttcg cgaacctcct gataacttca gcattaacag       60

<210> SEQ ID NO 78
<211> LENGTH: 60
<212> TYPE: DNA
<213> ORGANISM: Homo sapiens

<400> SEQUENCE: 78
agggtcttgc tatgttgccc aggctggcct cgagatcagc ctgggcaaca cggtgaaaac       60

<210> SEQ ID NO 79
<211> LENGTH: 60
<212> TYPE: DNA
<213> ORGANISM: Homo sapiens

<400> SEQUENCE: 79
tgtaatataa gcatagctca ctgcagcctc gaagcatttg tacgacattc tcatcttctt       60

<210> SEQ ID NO 80
<211> LENGTH: 60
<212> TYPE: DNA
<213> ORGANISM: Homo sapiens

<400> SEQUENCE: 80
acagaggagc gaggcccgat ccttactttc gaactcctga cctcgtgatc tgcccacctc    60

<210> SEQ ID NO 81
<211> LENGTH: 60
<212> TYPE: DNA
<213> ORGANISM: Homo sapiens

<400> SEQUENCE: 81
gggtttcacc atgttagcca ggatggtctc gatctcctga cctcatgatc cgcctgcctc    60

<210> SEQ ID NO 82
<211> LENGTH: 60
<212> TYPE: DNA
<213> ORGANISM: Homo sapiens

<400> SEQUENCE: 82
gcatttcacc atgttggtga ggctggtctc gaagagttca cacgtgtcca aatttggtgg    60

<210> SEQ ID NO 83
<211> LENGTH: 60
<212> TYPE: DNA
<213> ORGANISM: Homo sapiens

<400> SEQUENCE: 83
ctgggatcac aggcatgtgc caccatgctc gacaagaata gtctccttgt ttctgaacat    60

<210> SEQ ID NO 84
<211> LENGTH: 60
<212> TYPE: DNA
<213> ORGANISM: Homo sapiens

<400> SEQUENCE: 84
gtatttctgg ttctagatcc ttgaggaatc gagcagaagg agtctctccc tgaggccacc    60

<210> SEQ ID NO 85
<211> LENGTH: 60
<212> TYPE: DNA
<213> ORGANISM: Homo sapiens

<400> SEQUENCE: 85
cgaggcgggc ggatcacgag gtcaggagat cgaccccac gttctcacca cctgtttctt    60

<210> SEQ ID NO 86
<211> LENGTH: 60
<212> TYPE: DNA
<213> ORGANISM: Homo sapiens

<400> SEQUENCE: 86
gtatttctgg ttctagatcc ttgaggaatc gacctcctgg gctcaaccta tcctcccacc    60

<210> SEQ ID NO 87
<211> LENGTH: 60
<212> TYPE: DNA
<213> ORGANISM: Homo sapiens

<400> SEQUENCE: 87
gggtttcact gtgttagcca ggatggtctc gacctccctg gctcaagtga tcttcccacc    60

<210> SEQ ID NO 88
<211> LENGTH: 60
<212> TYPE: DNA
<213> ORGANISM: Homo sapiens -continued

```
<400> SEQUENCE: 88
tgccctagag atctgtggaa ctttgaactc gatatatgaa aatagttttt taattataaa      60

<210> SEQ ID NO 89
<211> LENGTH: 60
<212> TYPE: DNA
<213> ORGANISM: Homo sapiens

<400> SEQUENCE: 89
ggtgggggaa tcacttgagg tcagaagttc gagaccatcc tgggcaacat ggtaaaaccc      60

<210> SEQ ID NO 90
<211> LENGTH: 60
<212> TYPE: DNA
<213> ORGANISM: Homo sapiens

<400> SEQUENCE: 90
aatggcacga tcacggctca ctgcagcctc gaatgttact gacagtggac acagtaagaa      60

<210> SEQ ID NO 91
<211> LENGTH: 60
<212> TYPE: DNA
<213> ORGANISM: Homo sapiens

<400> SEQUENCE: 91
gagttttgcc atgttgccca ggctggtctc gagaacagcc tggccaacat ggtgaaaccc      60

<210> SEQ ID NO 92
<211> LENGTH: 60
<212> TYPE: DNA
<213> ORGANISM: Homo sapiens

<400> SEQUENCE: 92
aggtctcact atgttgcccg ggctggtctc gacgccgagg agctctgcag tgggggcgta      60

<210> SEQ ID NO 93
<211> LENGTH: 60
<212> TYPE: DNA
<213> ORGANISM: Homo sapiens

<400> SEQUENCE: 93
gggtttcacc atgttggcga ggctggtctc gaactcctga cctcaggtga tccgcctgcc      60

<210> SEQ ID NO 94
<211> LENGTH: 60
<212> TYPE: DNA
<213> ORGANISM: Homo sapiens

<400> SEQUENCE: 94
ggtgggtgga tcacctgagg tcaggagttc gacctaaggg tggtcataat tctgctgctg      60

<210> SEQ ID NO 95
<211> LENGTH: 60
<212> TYPE: DNA
<213> ORGANISM: Homo sapiens

<400> SEQUENCE: 95
gggtctcaca gccttcagag ctgagagcct aggcttcagt gagccataat cacgccacta      60

<210> SEQ ID NO 96
<211> LENGTH: 60
<212> TYPE: DNA
<213> ORGANISM: Homo sapiens
```

<400> SEQUENCE: 96
ctttgggagg ccaaggtgag tggattgctc gacatctcat ttgataggat taagtcaacg    60

<210> SEQ ID NO 97
<211> LENGTH: 60
<212> TYPE: DNA
<213> ORGANISM: Homo sapiens

<400> SEQUENCE: 97
aggtctcact atgttgcccg ggctggtctc gaacagcagc gtgtgcgccg acagcgcgcc    60

<210> SEQ ID NO 98
<211> LENGTH: 60
<212> TYPE: DNA
<213> ORGANISM: Homo sapiens

<400> SEQUENCE: 98
tctgtcgccc aggttggagt acagtggctc gaggatgtcc tattttgcca ccttatctaa    60

<210> SEQ ID NO 99
<211> LENGTH: 60
<212> TYPE: DNA
<213> ORGANISM: Homo sapiens

<400> SEQUENCE: 99
ttatatctcc tacctccaag cctggcagtc gattccaaag tgaagcaaaa aaaaaacttc    60

<210> SEQ ID NO 100
<211> LENGTH: 60
<212> TYPE: DNA
<213> ORGANISM: Homo sapiens

<400> SEQUENCE: 100
aaagaccctg tctctaaata aatagaacat cgagatcatg ccactgcact ccagcctggg    60

<210> SEQ ID NO 101
<211> LENGTH: 60
<212> TYPE: DNA
<213> ORGANISM: Homo sapiens

<400> SEQUENCE: 101
ggggtttttc catgttagtc aggctggtct aatggctccc ttaccttgct ggctgtgggc    60

<210> SEQ ID NO 102
<211> LENGTH: 60
<212> TYPE: DNA
<213> ORGANISM: Homo sapiens

<400> SEQUENCE: 102
agtggcatga tcacagctca ctgccacctc gaaaccaaac cctgtgactt caacacccaa    60

<210> SEQ ID NO 103
<211> LENGTH: 60
<212> TYPE: DNA
<213> ORGANISM: Homo sapiens

<400> SEQUENCE: 103
ccctccctca acatgcaggg attacaattc gaagatggtc tgaaggaagc aattgggaaa    60

<210> SEQ ID NO 104
<211> LENGTH: 60
<212> TYPE: DNA

<213> ORGANISM: Homo sapiens

<400> SEQUENCE: 104
gcctgcaggg ggcgccccg cgcctgcctc gaccacacat ccacatggac gcatggcagg    60

<210> SEQ ID NO 105
<211> LENGTH: 60
<212> TYPE: DNA
<213> ORGANISM: Homo sapiens

<400> SEQUENCE: 105
ttatcaaccc ggcgtctgga acaatcgctc gatccacacc acaccagcag tggggcacaa    60

<210> SEQ ID NO 106
<211> LENGTH: 60
<212> TYPE: DNA
<213> ORGANISM: Homo sapiens

<400> SEQUENCE: 106
aggacagaga ccctaattc caccaccatc gaccttctg ctttctctcc aggggatggc    60

<210> SEQ ID NO 107
<211> LENGTH: 60
<212> TYPE: DNA
<213> ORGANISM: Homo sapiens

<400> SEQUENCE: 107
ccgcccctgt cctctcgctt cccgctggtc gatccacacc acaccagcag tggggcacaa    60

<210> SEQ ID NO 108
<211> LENGTH: 60
<212> TYPE: DNA
<213> ORGANISM: Homo sapiens

<400> SEQUENCE: 108 agttcttct tgaattcttt cctgatactc gatccacacc acaccagcag tggggcacaa    60

<210> SEQ ID NO 109
<211> LENGTH: 60
<212> TYPE: DNA
<213> ORGANISM: Homo sapiens

<400> SEQUENCE: 109
cctgtagctc tgatgtcaga tggcaatgtc gatccacacc acaccagcag tggggcacaa    60

<210> SEQ ID NO 110
<211> LENGTH: 60
<212> TYPE: DNA
<213> ORGANISM: Homo sapiens

<400> SEQUENCE: 110
ccacctcata ggggagggct ttactcagtc gatccacacc acaccagcag tggggcacaa    60

<210> SEQ ID NO 111
<211> LENGTH: 60
<212> TYPE: DNA
<213> ORGANISM: Homo sapiens

<400> SEQUENCE: 111
tcacctctgt cacccacccg ttccactctc gataaagcac ttagaacatg gcatatactc    60

<210> SEQ ID NO 112
<211> LENGTH: 60

```
<212> TYPE: DNA
<213> ORGANISM: Homo sapiens

<400> SEQUENCE: 112
tcacctctgt cacccacccg ttccactctc gaatagctcc tattgttatg gagtgtagca    60

<210> SEQ ID NO 113
<211> LENGTH: 60
<212> TYPE: DNA
<213> ORGANISM: Homo sapiens

<400> SEQUENCE: 113
tcacctctgt cacccacccg ttccactctc gaattaggaa tcagcatttc ttccactgag    60

<210> SEQ ID NO 114
<211> LENGTH: 60
<212> TYPE: DNA
<213> ORGANISM: Homo sapiens

<400> SEQUENCE: 114
tcacctctgt cacccacccg ttccactctc gatgctctct tagtgttcca attctcagct    60

<210> SEQ ID NO 115
<211> LENGTH: 60
<212> TYPE: DNA
<213> ORGANISM: Homo sapiens

<400> SEQUENCE: 115
tcacctctgt cacccacccg ttccactctc gaaatagtaa aatttgatta tcaaaatttt    60

<210> SEQ ID NO 116
<211> LENGTH: 60
<212> TYPE: DNA
<213> ORGANISM: Homo sapiens

<400> SEQUENCE: 116
tccgtgaccc ccacagccgg tcgccacatc gattatccag aagcttcttt ttttttaacc    60

<210> SEQ ID NO 117
<211> LENGTH: 60
<212> TYPE: DNA
<213> ORGANISM: Homo sapiens

<400> SEQUENCE: 117
tcacctctgt cacccacccg ttccactctc gaggctgcag tgaatcataa tcatagcact    60

<210> SEQ ID NO 118
<211> LENGTH: 60
<212> TYPE: DNA
<213> ORGANISM: Homo sapiens

<400> SEQUENCE: 118
agtgttggtg agatattgtc tctcagtttc gatccacacc acaccagcag tggggcacaa    60

<210> SEQ ID NO 119
<211> LENGTH: 60
<212> TYPE: DNA
<213> ORGANISM: Homo sapiens

<400> SEQUENCE: 119
ggtggcatcc ccatcacttc tccatgcctc gaggtcccca accccctgcc gctcatcgtg    60

<210> SEQ ID NO 120
```

```
<211> LENGTH: 60
<212> TYPE: DNA
<213> ORGANISM: Homo sapiens

<400> SEQUENCE: 120
tcctgcccac agccccgct ttagcctctc gagaatgcta acagcacagg atacagtact      60

<210> SEQ ID NO 121
<211> LENGTH: 60
<212> TYPE: DNA
<213> ORGANISM: Homo sapiens

<400> SEQUENCE: 121
tccgtgaccc ccacagccgg tcgccacatc gagtagctga gattacaggc atgtaccacc      60

<210> SEQ ID NO 122
<211> LENGTH: 60
<212> TYPE: DNA
<213> ORGANISM: Homo sapiens

<400> SEQUENCE: 122
ctccacgtca ccccatgtca attccaagtc gatgccagac actcttctgg gggtggggtg      60

<210> SEQ ID NO 123
<211> LENGTH: 60
<212> TYPE: DNA
<213> ORGANISM: Homo sapiens

<400> SEQUENCE: 123
cctctgtcca caccattatt ttaaagagtc gacatgcctt gctttaccat tgtttaattt      60

<210> SEQ ID NO 124
<211> LENGTH: 60
<212> TYPE: DNA
<213> ORGANISM: Homo sapiens

<400> SEQUENCE: 124
agtggtacaa tcatgaatca ctacagcctc gaccacacat ccacatggac gcatggcagg      60

<210> SEQ ID NO 125
<211> LENGTH: 60
<212> TYPE: DNA
<213> ORGANISM: Homo sapiens

<400> SEQUENCE: 125
ctcccaaggt aaactcattg ccgaaacctc gagttgttgc caccccaccc tcctcaaacc      60

<210> SEQ ID NO 126
<211> LENGTH: 60
<212> TYPE: DNA
<213> ORGANISM: Homo sapiens

<400> SEQUENCE: 126
tgttttttat tgtttgatgt ccaatgtatc gagccgccct tgacataaca ccatctttta      60

<210> SEQ ID NO 127
<211> LENGTH: 60
<212> TYPE: DNA
<213> ORGANISM: Homo sapiens

<400> SEQUENCE: 127
ttgaacccaa gaggtcacac cactgcactc gacgcccagc aagtaggcac agttcccaat      60
```

```
<210> SEQ ID NO 128
<211> LENGTH: 60
<212> TYPE: DNA
<213> ORGANISM: Homo sapiens

<400> SEQUENCE: 128
ttggagcccc ctgccctgca cacacagctc gagatttgtc tttctgttcc tggcttattt      60

<210> SEQ ID NO 129
<211> LENGTH: 60
<212> TYPE: DNA
<213> ORGANISM: Homo sapiens

<400> SEQUENCE: 129
aggacagaga ccctaattc caccaccatc gaacaactgc aaactccact caacatcttt       60

<210> SEQ ID NO 130
<211> LENGTH: 60
<212> TYPE: DNA
<213> ORGANISM: Homo sapiens

<400> SEQUENCE: 130
aaccacacaa ctgctactca caattctttc gaaaccagaa gacccaatat aatatctagt      60

<210> SEQ ID NO 131
<211> LENGTH: 60
<212> TYPE: DNA
<213> ORGANISM: Homo sapiens

<400> SEQUENCE: 131
acccaggata aaacgcagtg ttgaccgatc gagggcgtgg acttctacac gtccatcact      60

<210> SEQ ID NO 132
<211> LENGTH: 60
<212> TYPE: DNA
<213> ORGANISM: Homo sapiens

<400> SEQUENCE: 132
ggcttatcca tgcttaaatt gattaacgtc gagttgttgc caccccaccc tcctcaaacc      60

<210> SEQ ID NO 133
<211> LENGTH: 60
<212> TYPE: DNA
<213> ORGANISM: Homo sapiens

<400> SEQUENCE: 133
agtggtctca ccatggcttt cttccaattc gaggtcccca accccctgcc gctcatcgtg      60

<210> SEQ ID NO 134
<211> LENGTH: 60
<212> TYPE: DNA
<213> ORGANISM: Homo sapiens

<400> SEQUENCE: 134
ggaactgcat ccatacttgt tacacatctc gaaccggagt ggacgtgtgt ccacatgtaa      60

<210> SEQ ID NO 135
<211> LENGTH: 60
<212> TYPE: DNA
<213> ORGANISM: Homo sapiens

<400> SEQUENCE: 135
atctaaacac agtccatgct aaaaagcttc gagttgttgc caccccaccc tcctcaaacc      60
```

<210> SEQ ID NO 136
<211> LENGTH: 60
<212> TYPE: DNA
<213> ORGANISM: Homo sapiens

<400> SEQUENCE: 136
ggaactgcat ccatacttgt tacacatctc gagttgttgc caccccaccc tcctcaaacc    60

<210> SEQ ID NO 137
<211> LENGTH: 60
<212> TYPE: DNA
<213> ORGANISM: Homo sapiens

<400> SEQUENCE: 137
ctcaggaaga agtggatccc tgtttctttc gagttgttgc caccccaccc tcctcaaacc    60

<210> SEQ ID NO 138
<211> LENGTH: 60
<212> TYPE: DNA
<213> ORGANISM: Homo sapiens

<400> SEQUENCE: 138
agtgtatttt tcactacact agtggttttc gagttgttgc caccccaccc tcctcaaacc    60

<210> SEQ ID NO 139
<211> LENGTH: 60
<212> TYPE: DNA
<213> ORGANISM: Homo sapiens

<400> SEQUENCE: 139
taaatacaga tgaaaccaac taatagactc gagttgttgc caccccaccc tcctcaaacc    60

<210> SEQ ID NO 140
<211> LENGTH: 60
<212> TYPE: DNA
<213> ORGANISM: Homo sapiens

<400> SEQUENCE: 140
agctgggccc caaaggttaa aaaggacttc gagttgttgc caccccaccc tcctcaaacc    60

<210> SEQ ID NO 141
<211> LENGTH: 60
<212> TYPE: DNA
<213> ORGANISM: Homo sapiens

<400> SEQUENCE: 141
ccacgtgtcg cgggcctgag tgtgcccctc gaggctgtag tgattcatga ttgtaccact    60

<210> SEQ ID NO 142
<211> LENGTH: 60
<212> TYPE: DNA
<213> ORGANISM: Homo sapiens

<400> SEQUENCE: 142
acctaggata aaaggcagtg ttgaccgatc gacacccata tgagcccac ccggcttcaa     60

<210> SEQ ID NO 143
<211> LENGTH: 60
<212> TYPE: DNA
<213> ORGANISM: Homo sapiens

<400> SEQUENCE: 143
ttccacctgt aatactgtgc ctgtattctc gagcaggcgc tcaacaaata caacttcctt    60

<210> SEQ ID NO 144
<211> LENGTH: 60
<212> TYPE: DNA
<213> ORGANISM: Homo sapiens

<400> SEQUENCE: 144
gtgccctcct cgcccctgat gggtctggtc gagaccagcc tcaacatgga gaaacaccat    60

<210> SEQ ID NO 145
<211> LENGTH: 60
<212> TYPE: DNA
<213> ORGANISM: Homo sapiens

<400> SEQUENCE: 145 ccaccccgc cccgggggag tcgcccggtc gagggcctgg caagaagaca gaagccgact    60

<210> SEQ ID NO 146
<211> LENGTH: 60
<212> TYPE: DNA
<213> ORGANISM: Homo sapiens

<400> SEQUENCE: 146
aagtcctaag aacactgaaa atctcagatc gagttgttgc caccccaccc tcctcaaacc    60

<210> SEQ ID NO 147
<211> LENGTH: 60
<212> TYPE: DNA
<213> ORGANISM: Homo sapiens

<400> SEQUENCE: 147
ctccacgtca cccatgtca attccaagtc gaatactcaa aacagaattt gatattcaaa     60

<210> SEQ ID NO 148
<211> LENGTH: 60
<212> TYPE: DNA
<213> ORGANISM: Homo sapiens

<400> SEQUENCE: 148
ccaaatccga acctcctctg tgaagcattc gagttgttgc caccccaccc tcctcaaacc    60

<210> SEQ ID NO 149
<211> LENGTH: 60
<212> TYPE: DNA
<213> ORGANISM: Homo sapiens

<400> SEQUENCE: 149
gttaacagta atacgatgtt aaaaggactc gagttgttgc caccccaccc tcctcaaacc    60

<210> SEQ ID NO 150
<211> LENGTH: 60
<212> TYPE: DNA
<213> ORGANISM: Homo sapiens

<400> SEQUENCE: 150
ggctggcgga ttacttgaag ccaggagttc gatccacacc acaccagcag tggggcacaa    60

<210> SEQ ID NO 151
<211> LENGTH: 60
<212> TYPE: DNA
<213> ORGANISM: Homo sapiens

<400> SEQUENCE: 151

```
ttgaacccaa gaggtcacac cactgcactc gagccgccct tgacataaca ccatctttta    60

<210> SEQ ID NO 152
<211> LENGTH: 60
<212> TYPE: DNA
<213> ORGANISM: Homo sapiens

<400> SEQUENCE: 152
cccctaattt agcaagcaga aagagaactc gatgcttcat ttgactcaca ctcacattta    60

<210> SEQ ID NO 153
<211> LENGTH: 60
<212> TYPE: DNA
<213> ORGANISM: Homo sapiens

<400> SEQUENCE: 153
ctccacgtca ccccatgtca attccaagtc gaaaataagt cgctagagcc acatcaagca    60

<210> SEQ ID NO 154
<211> LENGTH: 60
<212> TYPE: DNA
<213> ORGANISM: Homo sapiens

<400> SEQUENCE: 154
aggacagaga cccctaattc caccaccatc gacccttctg ctttctctcc aggggatggc    60

<210> SEQ ID NO 155
<211> LENGTH: 60
<212> TYPE: DNA
<213> ORGANISM: Homo sapiens

<400> SEQUENCE: 155
ttccacctgt aatactgtgc ctgtattctc gagcaggcgc tcaacaaata caacttcctt    60

<210> SEQ ID NO 156
<211> LENGTH: 60
<212> TYPE: DNA
<213> ORGANISM: Homo sapiens

<400> SEQUENCE: 156
accaaaccca aggtccgctg ctcgctgctc gaattcccaa ctgagggagc tttgtggaaa    60

<210> SEQ ID NO 157
<211> LENGTH: 60
<212> TYPE: DNA
<213> ORGANISM: Homo sapiens

<400> SEQUENCE: 157
ctcctcaaaa aaaagaggag gcccaggctc gagactccag aaaaatagat tacaggtttg    60

<210> SEQ ID NO 158
<211> LENGTH: 60
<212> TYPE: DNA
<213> ORGANISM: Homo sapiens

<400> SEQUENCE: 158
tttagccaaa aagaaaaaaa ggttcatttc gagaaccaga gtcaaactta gaccccagga    60

<210> SEQ ID NO 159
<211> LENGTH: 60
<212> TYPE: DNA
<213> ORGANISM: Homo sapiens

<400> SEQUENCE: 159
```

```
tcctttctttt tttatttttt aagctgtttc gattcaacat taattcattt tagacttctc    60
```

<210> SEQ ID NO 160
<211> LENGTH: 60
<212> TYPE: DNA
<213> ORGANISM: Homo sapiens

<400> SEQUENCE: 160

```
accagccctg ggttcttaag gatgggtgtc gaccctggc tctgcctggg gtctgggctt    60
```

<210> SEQ ID NO 161
<211> LENGTH: 60
<212> TYPE: DNA
<213> ORGANISM: Homo sapiens

<400> SEQUENCE: 161

```
acatctcaga catgactttt gtgtttcctc gagcctttc gggcaggcgt ccagcacggg    60
```

<210> SEQ ID NO 162
<211> LENGTH: 60
<212> TYPE: DNA
<213> ORGANISM: Homo sapiens

<400> SEQUENCE: 162

```
ctcagactgt atattctctt agcttcagtc gagctgtttc tttatatggt ctctgctatc    60
```

<210> SEQ ID NO 163
<211> LENGTH: 60
<212> TYPE: DNA
<213> ORGANISM: Homo sapiens

<400> SEQUENCE: 163

```
attataacat ttatatatca tcttttcctc gaggttgcag taagctgatc atgccactac    60
```

<210> SEQ ID NO 164
<211> LENGTH: 60
<212> TYPE: DNA
<213> ORGANISM: Homo sapiens

<400> SEQUENCE: 164

```
gaccaaacag ctgtggtttg gccatcactc gagagagagc ctgtgtgagg agtgcagtca    60
```

<210> SEQ ID NO 165
<211> LENGTH: 60
<212> TYPE: DNA
<213> ORGANISM: Homo sapiens

<400> SEQUENCE: 165

```
cttttagctt ttacttagca taattttctc gagagggtgg ggcaggagaa tctcttgaac    60
```

<210> SEQ ID NO 166
<211> LENGTH: 60
<212> TYPE: DNA
<213> ORGANISM: Homo sapiens

<400> SEQUENCE: 166

```
ggaaggccga ggcggccaga tcacgaggtc gaacctcctg ataacttcag cattaacagc    60
```

<210> SEQ ID NO 167
<211> LENGTH: 60
<212> TYPE: DNA
<213> ORGANISM: Homo sapiens

```
<400> SEQUENCE: 167
gaccaaacag ctgtggtttg gccatcactc gagagagagc ctgtgtgagg agtgcagtca    60

<210> SEQ ID NO 168
<211> LENGTH: 60
<212> TYPE: DNA
<213> ORGANISM: Homo sapiens

<400> SEQUENCE: 168
gagtaggtaa acaaagcagt caggaagctc gagtctttgg ttttccctag ataattaata    60

<210> SEQ ID NO 169
<211> LENGTH: 60
<212> TYPE: DNA
<213> ORGANISM: Homo sapiens

<400> SEQUENCE: 169
cttagagcaa aggctaggct cagtaatgtc gagagagagc ctgtgtgagg agtgcagtca    60

<210> SEQ ID NO 170
<211> LENGTH: 60
<212> TYPE: DNA
<213> ORGANISM: Homo sapiens

<400> SEQUENCE: 170
agatcaaatc cagtttaagg ctactccttc gattcataca ccattcaggg tatacaatag    60

<210> SEQ ID NO 171
<211> LENGTH: 60
<212> TYPE: DNA
<213> ORGANISM: Homo sapiens

<400> SEQUENCE: 171
ttgcgagcct cgcagcctcc ggaagctgtc gattttaagt ctattttgtt agatctaaag    60

<210> SEQ ID NO 172
<211> LENGTH: 60
<212> TYPE: DNA
<213> ORGANISM: Homo sapiens

<400> SEQUENCE: 172
actgacagtt tcttgggatt ctccagactc gagagaggct ggtgcgcacc tacccagcgg    60

<210> SEQ ID NO 173
<211> LENGTH: 60
<212> TYPE: DNA
<213> ORGANISM: Homo sapiens

<400> SEQUENCE: 173
ccactccccc aggcttacct gcgagccatc gaggtgggcc tgggttctcg tggagggaga    60

<210> SEQ ID NO 174
<211> LENGTH: 60
<212> TYPE: DNA
<213> ORGANISM: Homo sapiens

<400> SEQUENCE: 174
ccatcctgga cgcagaatgt agtcccgttc gaacagagct gggagctggg gcctaggcta    60

<210> SEQ ID NO 175
<211> LENGTH: 60
<212> TYPE: DNA
<213> ORGANISM: Homo sapiens
```

-continued

<400> SEQUENCE: 175 tgcttttaa aaaatcaaag gtgtaacttc gacagcttcc ggaggctgcg aggctcgcaa     60

<210> SEQ ID NO 176
<211> LENGTH: 60
<212> TYPE: DNA
<213> ORGANISM: Homo sapiens

<400> SEQUENCE: 176
tatgaggccc ggttccagca gaagcttctc gaacagagct gggagctggg gcctaggcta     60

<210> SEQ ID NO 177
<211> LENGTH: 60
<212> TYPE: DNA
<213> ORGANISM: Homo sapiens

<400> SEQUENCE: 177
ggaaggccga ggcggccaga tcacgaggtc gaaagcgctc ggattcagcc ttctccccgg     60

<210> SEQ ID NO 178
<211> LENGTH: 60
<212> TYPE: DNA
<213> ORGANISM: Homo sapiens

<400> SEQUENCE: 178
atggacagta ggcaggatga ataagtgctc gagcctttc gggcaggcgt ccagcacggg     60

<210> SEQ ID NO 179
<211> LENGTH: 60
<212> TYPE: DNA
<213> ORGANISM: Homo sapiens

<400> SEQUENCE: 179
taacgtccaa gaaaattatt gtgacccgtc gagaagtcag ggagcgtcta gggcttctgg     60

<210> SEQ ID NO 180
<211> LENGTH: 60
<212> TYPE: DNA
<213> ORGANISM: Homo sapiens

<400> SEQUENCE: 180
tatgaggccc ggttccagca gaagcttctc gaacagagct gggagctggg gcctaggcta     60

<210> SEQ ID NO 181
<211> LENGTH: 60
<212> TYPE: DNA
<213> ORGANISM: Homo sapiens

<400> SEQUENCE: 181
actgacagtt tcttgggatt ctccagactc gaggcctgga gaagcccagg aggaggcgtg     60

<210> SEQ ID NO 182
<211> LENGTH: 60
<212> TYPE: DNA
<213> ORGANISM: Homo sapiens

<400> SEQUENCE: 182
ctcctcaaaa aaagaggag gcccaggctc gatcccagag ccgtcccagg cctggacaga     60

<210> SEQ ID NO 183
<211> LENGTH: 60
<212> TYPE: DNA

<213> ORGANISM: Homo sapiens

<400> SEQUENCE: 183
aggctgaact tcaaatgtga taataacctc gacttaattt tattacagca ctaatataat    60

<210> SEQ ID NO 184
<211> LENGTH: 60
<212> TYPE: DNA
<213> ORGANISM: Homo sapiens

<400> SEQUENCE: 184
gacttcaact cactatgaat aaataaaatc gagagggtgg ggcaggagaa tctcttgaac    60

<210> SEQ ID NO 185
<211> LENGTH: 60
<212> TYPE: DNA
<213> ORGANISM: Homo sapiens

<400> SEQUENCE: 185 tgcttttaa aaaatcaaag gtgtaacttc gaattaggtg ggtgggggtg ggaaattggg    60

<210> SEQ ID NO 186
<211> LENGTH: 60
<212> TYPE: DNA
<213> ORGANISM: Homo sapiens

<400> SEQUENCE: 186
ataagaaact gaatttaaat gctctctttc gattcataca ccattcaggg tatacaatag    60

<210> SEQ ID NO 187
<211> LENGTH: 60
<212> TYPE: DNA
<213> ORGANISM: Homo sapiens

<400> SEQUENCE: 187
aaggtcttca gcttcactcc tgaagccatc gagttctgta cttaagcaaa cattatcctt    60

<210> SEQ ID NO 188
<211> LENGTH: 60
<212> TYPE: DNA
<213> ORGANISM: Homo sapiens

<400> SEQUENCE: 188
ccatgttgta atattggatt tttatcattc gatatagtgg tttctaggta tcatggtaaa    60

<210> SEQ ID NO 189
<211> LENGTH: 60
<212> TYPE: DNA
<213> ORGANISM: Homo sapiens

<400> SEQUENCE: 189
gagtaggtaa acaaagcagt caggaagctc gatccagtgt gcttttcact tcagaccttg    60

<210> SEQ ID NO 190
<211> LENGTH: 60
<212> TYPE: DNA
<213> ORGANISM: Homo sapiens

<400> SEQUENCE: 190
aatatctttt cattttttgg tgaagtcttc gatggcttca ggagtgaagc tgaagacctt    60

<210> SEQ ID NO 191
<211> LENGTH: 60

```
<212> TYPE: DNA
<213> ORGANISM: Homo sapiens

<400> SEQUENCE: 191
tgttcaatca aaggaaggga taacactatc gaggttgcag taagctgatc atgccactac      60

<210> SEQ ID NO 192
<211> LENGTH: 60
<212> TYPE: DNA
<213> ORGANISM: Homo sapiens

<400> SEQUENCE: 192
gatgtttata caagattcat tctttccatc gattcaacat taattcattt tagacttctc      60

<210> SEQ ID NO 193
<211> LENGTH: 60
<212> TYPE: DNA
<213> ORGANISM: Homo sapiens

<400> SEQUENCE: 193
ttccttgagg aatcagtgat caggactctc gaacagagct gggagctggg gcctaggcta      60

<210> SEQ ID NO 194
<211> LENGTH: 60
<212> TYPE: DNA
<213> ORGANISM: Homo sapiens

<400> SEQUENCE: 194
taacgtccaa gaaaattatt gtgacccgtc gagaagtcag ggagcgtcta gggcttctgg      60

<210> SEQ ID NO 195
<211> LENGTH: 60
<212> TYPE: DNA
<213> ORGANISM: Homo sapiens

<400> SEQUENCE: 195
tagtactacc actggaaagc tagaatattc gatgcattaa aatgttctcg gaaagagata      60

<210> SEQ ID NO 196
<211> LENGTH: 60
<212> TYPE: DNA
<213> ORGANISM: Homo sapiens

<400> SEQUENCE: 196
caaacctgta atctattttt ctggagtctc gatcccagag ccgtcccagg cctggacaga      60

<210> SEQ ID NO 197
<211> LENGTH: 60
<212> TYPE: DNA
<213> ORGANISM: Homo sapiens

<400> SEQUENCE: 197
gttgaggctg caataaaccg tgatcaagtc gacacccatc cttaagaacc cagggctggt      60

<210> SEQ ID NO 198
<211> LENGTH: 60
<212> TYPE: DNA
<213> ORGANISM: Homo sapiens

<400> SEQUENCE: 198
ctcagactgt atattctctt agcttcagtc gagttctgta cttaagcaaa cattatcctt      60

<210> SEQ ID NO 199
```

```
<211> LENGTH: 60
<212> TYPE: DNA
<213> ORGANISM: Homo sapiens

<400> SEQUENCE: 199
ggaaatgagt ctcatgtcta attaaatgtc gaagttaagg tttcttggtt caagtggtgt    60

<210> SEQ ID NO 200
<211> LENGTH: 60
<212> TYPE: DNA
<213> ORGANISM: Homo sapiens

<400> SEQUENCE: 200
tgaggtaggc agatcacagg tcaggagatc gacctccatt acggagagtt tcctatgttt    60

<210> SEQ ID NO 201
<211> LENGTH: 60
<212> TYPE: DNA
<213> ORGANISM: Homo sapiens

<400> SEQUENCE: 201
aaggtcttca gcttcactcc tgaagccatc gagctgtttc tttatatggt ctctgctatc    60

<210> SEQ ID NO 202
<211> LENGTH: 60
<212> TYPE: DNA
<213> ORGANISM: Homo sapiens

<400> SEQUENCE: 202
tgggctcctt cagccccaca tgcctggttc gaacagagct gggagctggg gcctaggcta    60

<210> SEQ ID NO 203
<211> LENGTH: 60
<212> TYPE: DNA
<213> ORGANISM: Homo sapiens

<400> SEQUENCE: 203
tttagccaaa aagaaaaaaa ggttcatttc gaggaatgtt tccaagcaat tctctctgct    60

<210> SEQ ID NO 204
<211> LENGTH: 60
<212> TYPE: DNA
<213> ORGANISM: Homo sapiens

<400> SEQUENCE: 204
ctcctcaaaa aaagaggag gcccaggctc gatcccagag ccgtcccagg cctggacaga    60

<210> SEQ ID NO 205
<211> LENGTH: 60
<212> TYPE: DNA
<213> ORGANISM: Homo sapiens

<400> SEQUENCE: 205 cccttttaccc cagtccgtgt gagcctcttc gagccttttc gggcaggcgt ccagcacggg    60

<210> SEQ ID NO 206
<211> LENGTH: 60
<212> TYPE: DNA
<213> ORGANISM: Homo sapiens

<400> SEQUENCE: 206
ggattacttc catgagaagc aattaaaatc gaacagagct gggagctggg gcctaggcta    60
```

```
<210> SEQ ID NO 207
<211> LENGTH: 60
<212> TYPE: DNA
<213> ORGANISM: Homo sapiens

<400> SEQUENCE: 207
ggaaggccga ggcggccaga tcacgaggtc gaacctcctg ataacttcag cattaacagc    60

<210> SEQ ID NO 208
<211> LENGTH: 60
<212> TYPE: DNA
<213> ORGANISM: Homo sapiens

<400> SEQUENCE: 208
acatctcaga catgactttt gtgtttcctc gagccttttc gggcaggcgt ccagcacggg    60

<210> SEQ ID NO 209
<211> LENGTH: 60
<212> TYPE: DNA
<213> ORGANISM: Homo sapiens

<400> SEQUENCE: 209
cgtggttctt caagttgtag tttaattctc gagagcagtg ttttaagtgg tctgacggga    60

<210> SEQ ID NO 210
<211> LENGTH: 60
<212> TYPE: DNA
<213> ORGANISM: Homo sapiens

<400> SEQUENCE: 210
ttggctgttt tcactcagtg aaattccttc gagcccagga ggcaaaggtt gcagtgagct    60

<210> SEQ ID NO 211
<211> LENGTH: 60
<212> TYPE: DNA
<213> ORGANISM: Homo sapiens

<400> SEQUENCE: 211
ggaaggccga ggcggccaga tcacgaggtc gaaagcgctc ggattcagcc ttctccccgg    60

<210> SEQ ID NO 212
<211> LENGTH: 60
<212> TYPE: DNA
<213> ORGANISM: Homo sapiens

<400> SEQUENCE: 212
atggacagta ggcaggatga ataagtgctc gagccttttc gggcaggcgt ccagcacggg    60

<210> SEQ ID NO 213
<211> LENGTH: 60
<212> TYPE: DNA
<213> ORGANISM: Homo sapiens

<400> SEQUENCE: 213
gggtttcacc atgttggcct ggctgggctc gagaccagcc tggccaacat ggtgaaacca    60

<210> SEQ ID NO 214
<211> LENGTH: 60
<212> TYPE: DNA
<213> ORGANISM: Homo sapiens

<400> SEQUENCE: 214
actgacagtt tcttgggatt ctccagactc gagagaggct ggtgcgcacc tacccagcgg    60
```

<210> SEQ ID NO 215
<211> LENGTH: 60
<212> TYPE: DNA
<213> ORGANISM: Homo sapiens

<400> SEQUENCE: 215
cttagagcaa aggctaggct cagtaatgtc gagagagagc ctgtgtgagg agtgcagtca    60

<210> SEQ ID NO 216
<211> LENGTH: 60
<212> TYPE: DNA
<213> ORGANISM: Homo sapiens

<400> SEQUENCE: 216
acatctcaga catgactttt gtgtttcctc gagtctcacc aggtcggtcc tgagccacac    60

<210> SEQ ID NO 217
<211> LENGTH: 60
<212> TYPE: DNA
<213> ORGANISM: Homo sapiens

<400> SEQUENCE: 217
actgacagtt tcttgggatt ctccagactc gaggcctgga aagcccagg aggaggcgtg    60

<210> SEQ ID NO 218
<211> LENGTH: 60
<212> TYPE: DNA
<213> ORGANISM: Homo sapiens

<400> SEQUENCE: 218
attataacat ttatatatca tcttttcctc gaggttgcag taagctgatc atgccactac    60

<210> SEQ ID NO 219
<211> LENGTH: 60
<212> TYPE: DNA
<213> ORGANISM: Homo sapiens

<400> SEQUENCE: 219
ggaaaacagg attaaaaaag aaatggattc gagcccagga ggcaaaggtt gcagtgagct    60

<210> SEQ ID NO 220
<211> LENGTH: 60
<212> TYPE: DNA
<213> ORGANISM: Homo sapiens

<400> SEQUENCE: 220
cttagagcaa aggctaggct cagtaatgtc gagcaagcct tgaggctgac acaggacctg    60

<210> SEQ ID NO 221
<211> LENGTH: 60
<212> TYPE: DNA
<213> ORGANISM: Homo sapiens

<400> SEQUENCE: 221
cgtggttctt caagttgtag tttaattctc gagcttgtta ttttctcttt cttacctagt    60

<210> SEQ ID NO 222
<211> LENGTH: 60
<212> TYPE: DNA
<213> ORGANISM: Homo sapiens

<400> SEQUENCE: 222
gaccaaacag ctgtggtttg ccatcactc gagagagagc ctgtgtgagg agtgcagtca    60

<210> SEQ ID NO 223
<211> LENGTH: 60
<212> TYPE: DNA
<213> ORGANISM: Homo sapiens

<400> SEQUENCE: 223
cgtggttctt caagttgtag tttaattctc gagcttgaat cagaatggtc aagatacctg    60

<210> SEQ ID NO 224
<211> LENGTH: 60
<212> TYPE: DNA
<213> ORGANISM: Homo sapiens

<400> SEQUENCE: 224
tgtgttaggg taccattctt cttaagtatc gaatctgtac atcaactttg gaaaaactaa    60

<210> SEQ ID NO 225
<211> LENGTH: 60
<212> TYPE: DNA
<213> ORGANISM: Homo sapiens

<400> SEQUENCE: 225
tcctacagaa gttaaaatag agctagggtc gaattggccc gggtccctgc tgggctggag    60

<210> SEQ ID NO 226
<211> LENGTH: 60
<212> TYPE: DNA
<213> ORGANISM: Homo sapiens

<400> SEQUENCE: 226
tttagccaaa aagaaaaaaa ggttcatttc gagaaccaga gtcaaactta daccccagga    60

<210> SEQ ID NO 227
<211> LENGTH: 60
<212> TYPE: DNA
<213> ORGANISM: Homo sapiens

<400> SEQUENCE: 227
ttagtttttc caaagttgat gtacagattc gagagcagtg ttttaagtgg tctgacggga    60

<210> SEQ ID NO 228
<211> LENGTH: 60
<212> TYPE: DNA
<213> ORGANISM: Homo sapiens

<400> SEQUENCE: 228
tggtgagcag aaggctccag ctgtacgctc gacggcccag ggaaactcaa acccatactc    60

<210> SEQ ID NO 229
<211> LENGTH: 60
<212> TYPE: DNA
<213> ORGANISM: Homo sapiens

<400> SEQUENCE: 229
gagtaggtaa acaaagcagt caggaagctc gagtctttgg ttttccctag ataattaata    60

<210> SEQ ID NO 230
<211> LENGTH: 60
<212> TYPE: DNA
<213> ORGANISM: Homo sapiens

<400> SEQUENCE: 230

```
acaccacttg aaccaagaaa ccttaacttc gaaggagtgg cataaggtcc cacttgggtg    60

<210> SEQ ID NO 231
<211> LENGTH: 60
<212> TYPE: DNA
<213> ORGANISM: Homo sapiens

<400> SEQUENCE: 231
ccctttaccc cagtccgtgt gagcctcttc gagccttttc gggcaggcgt ccagcacggg    60

<210> SEQ ID NO 232
<211> LENGTH: 60
<212> TYPE: DNA
<213> ORGANISM: Homo sapiens

<400> SEQUENCE: 232
actgacagtt tcttgggatt ctccagactc gaggcaggag gacagcttga gcccgggagt    60

<210> SEQ ID NO 233
<211> LENGTH: 60
<212> TYPE: DNA
<213> ORGANISM: Homo sapiens

<400> SEQUENCE: 233
cctaggcaga tcacttgagt tcaggagttc gaaacacttg atcaaaacag aataacaggt    60

<210> SEQ ID NO 234
<211> LENGTH: 60
<212> TYPE: DNA
<213> ORGANISM: Homo sapiens

<400> SEQUENCE: 234 atcttttta aaaatatat ttatttattc gagcccagcc aggccaacat ggtgaaaccc    60

<210> SEQ ID NO 235
<211> LENGTH: 60
<212> TYPE: DNA
<213> ORGANISM: Homo sapiens

<400> SEQUENCE: 235
tcctttcttt tttattttttt aagctgtttc gattcaacat taattcattt tagacttctc    60

<210> SEQ ID NO 236
<211> LENGTH: 60
<212> TYPE: DNA
<213> ORGANISM: Homo sapiens

<400> SEQUENCE: 236
ccaggatgta ctacactgaa tatctaagtc gaggcccagg ggctccagga ggccacgcac    60

<210> SEQ ID NO 237
<211> LENGTH: 60
<212> TYPE: DNA
<213> ORGANISM: Homo sapiens

<400> SEQUENCE: 237
tcccgatcac agctgaagat tggaaaggtc gaggttgcag taagctgatc atgccactac    60

<210> SEQ ID NO 238
<211> LENGTH: 60
<212> TYPE: DNA
<213> ORGANISM: Homo sapiens

<400> SEQUENCE: 238
```
agaagcaatt gagaaaaacc tcaggtgttc gactactatg ttgttgattt ctatcaaagc    60

<210> SEQ ID NO 239
<211> LENGTH: 60
<212> TYPE: DNA
<213> ORGANISM: Homo sapiens

<400> SEQUENCE: 239
tgttcaatca aaggaaggga taacactatc gaggttgcag taagctgatc atgccactac    60

<210> SEQ ID NO 240
<211> LENGTH: 60
<212> TYPE: DNA
<213> ORGANISM: Homo sapiens

<400> SEQUENCE: 240
atggacagta ggcaggatga ataagtgctc gagtctcacc aggtcggtcc tgagccacac    60

<210> SEQ ID NO 241
<211> LENGTH: 60
<212> TYPE: DNA
<213> ORGANISM: Homo sapiens

<400> SEQUENCE: 241
ttgcttctgt gagagaagca atttcttttc gattgtctag tgcagaagca agtcctccga    60

<210> SEQ ID NO 242
<211> LENGTH: 60
<212> TYPE: DNA
<213> ORGANISM: Homo sapiens

<400> SEQUENCE: 242
ctccccgtat caagaaattt gccatctatc gaggcccagg ggctccagga ggccacgcac    60

<210> SEQ ID NO 243
<211> LENGTH: 60
<212> TYPE: DNA
<213> ORGANISM: Homo sapiens

<400> SEQUENCE: 243
tttagccaaa aagaaaaaaa ggttcatttc gaggaatgtt tccaagcaat tctctctgct    60

<210> SEQ ID NO 244
<211> LENGTH: 60
<212> TYPE: DNA
<213> ORGANISM: Homo sapiens

<400> SEQUENCE: 244
actgacagtt tcttgggatt ctccagactc gaaggcattg ttctggaggt ggaggaaggg    60

<210> SEQ ID NO 245
<211> LENGTH: 60
<212> TYPE: DNA
<213> ORGANISM: Homo sapiens

<400> SEQUENCE: 245
tcctgaccaa ggatcctgat ccttgatatc gaagttaagg tttcttggtt caagtggtgt    60

<210> SEQ ID NO 246
<211> LENGTH: 60
<212> TYPE: DNA
<213> ORGANISM: Homo sapiens

```
<400> SEQUENCE: 246
tgaggtaggc agatcacagg tcaggagatc gatccagtgt gcttttcact tcagaccttg    60

<210> SEQ ID NO 247
<211> LENGTH: 60
<212> TYPE: DNA
<213> ORGANISM: Homo sapiens

<400> SEQUENCE: 247
catggttata tacacatgtt aaaattcatc gattgaaccc tggaggagga ggttgcagtg    60

<210> SEQ ID NO 248
<211> LENGTH: 60
<212> TYPE: DNA
<213> ORGANISM: Homo sapiens

<400> SEQUENCE: 248
aggcgagctg atcacttaag tcaggagttc gaatctgtac atcaactttg gaaaaactaa    60

<210> SEQ ID NO 249
<211> LENGTH: 60
<212> TYPE: DNA
<213> ORGANISM: Homo sapiens

<400> SEQUENCE: 249
cccttgtttt ctggagattc actcttcatc gagatcagcc cgggcaacac agcaagaccc    60

<210> SEQ ID NO 250
<211> LENGTH: 60
<212> TYPE: DNA
<213> ORGANISM: Homo sapiens

<400> SEQUENCE: 250
gagtaggtaa acaaagcagt caggaagctc gatccagtgt gcttttcact tcagaccttg    60

<210> SEQ ID NO 251
<211> LENGTH: 60
<212> TYPE: DNA
<213> ORGANISM: Homo sapiens

<400> SEQUENCE: 251
ccggggagaa ggctgaatcc gagcgctttc gaacctcctg ataacttcag cattaacagc    60

<210> SEQ ID NO 252
<211> LENGTH: 60
<212> TYPE: DNA
<213> ORGANISM: Homo sapiens

<400> SEQUENCE: 252
agcagcagcg agaagcagag ggatcccgtc gatgtccatg cctcggccaa ataggttggt    60

<210> SEQ ID NO 253
<211> LENGTH: 60
<212> TYPE: DNA
<213> ORGANISM: Homo sapiens

<400> SEQUENCE: 253
agcaggatcg tttcacaacc atgtgtgctc gagatattcc gtagtacata tttattttta    60

<210> SEQ ID NO 254
<211> LENGTH: 60
<212> TYPE: DNA
<213> ORGANISM: Homo sapiens
```

<400> SEQUENCE: 254
cgtggttctt caagttgtag tttaattctc gaatatttaa tctctctaca ccacttaatc            60

<210> SEQ ID NO 255
<211> LENGTH: 60
<212> TYPE: DNA
<213> ORGANISM: Homo sapiens

<400> SEQUENCE: 255 atttttttgac aattatagta gtatggattc gaccgcatca agcgcaagga cttccgctgg            60

<210> SEQ ID NO 256
<211> LENGTH: 60
<212> TYPE: DNA
<213> ORGANISM: Homo sapiens

<400> SEQUENCE: 256
gggttttatc acgttggcca ggctggtctc gagaccagcc tgggcaaccc agtgaaaccc            60

<210> SEQ ID NO 257
<211> LENGTH: 60
<212> TYPE: DNA
<213> ORGANISM: Homo sapiens

<400> SEQUENCE: 257
gcctgcaggg ggcgccccg cgcctgcctc gaccacacat ccacatggac gcatggcagg            60

<210> SEQ ID NO 258
<211> LENGTH: 60
<212> TYPE: DNA
<213> ORGANISM: Homo sapiens

<400> SEQUENCE: 258
tgtacaatgt gctacaccac tcacaccctc gacaacttca ggtaggagtg agtgatagct            60

<210> SEQ ID NO 259
<211> LENGTH: 60
<212> TYPE: DNA
<213> ORGANISM: Homo sapiens

<400> SEQUENCE: 259
cgccgggccg acacccacat tgtcttcttc gaaaaaaaaa aaaaagaaa aaaaagaaa            60

<210> SEQ ID NO 260
<211> LENGTH: 60
<212> TYPE: DNA
<213> ORGANISM: Homo sapiens

<400> SEQUENCE: 260
tcacctctgt cacccacccg ttccactctc gatgctctct tagtgttcca attctcagct            60

<210> SEQ ID NO 261
<211> LENGTH: 60
<212> TYPE: DNA
<213> ORGANISM: Homo sapiens

<400> SEQUENCE: 261
ggtggcatcc ccatcacttc tccatgcctc gaggtcccca accccctgcc gctcatcgtg            60

<210> SEQ ID NO 262
<211> LENGTH: 60
<212> TYPE: DNA

<213> ORGANISM: Homo sapiens

<400> SEQUENCE: 262
tcacctctgt cacccacccg ttccactctc gaatagctcc tattgttatg gagtgtagca    60

<210> SEQ ID NO 263
<211> LENGTH: 60
<212> TYPE: DNA
<213> ORGANISM: Homo sapiens

<400> SEQUENCE: 263
tcacctctgt cacccacccg ttccactctc gataaagcac ttagaacatg gcatatactc    60

<210> SEQ ID NO 264
<211> LENGTH: 60
<212> TYPE: DNA
<213> ORGANISM: Homo sapiens

<400> SEQUENCE: 264
tcacctctgt cacccacccg ttccactctc gaattaggaa tcagcatttc ttccactgag    60

<210> SEQ ID NO 265
<211> LENGTH: 60
<212> TYPE: DNA
<213> ORGANISM: Homo sapiens

<400> SEQUENCE: 265
ccgcccctgt cctctcgctt cccgctggtc gatccacacc acaccagcag tggggcacaa    60

<210> SEQ ID NO 266
<211> LENGTH: 60
<212> TYPE: DNA
<213> ORGANISM: Homo sapiens

<400> SEQUENCE: 266
tcacctctgt cacccacccg ttccactctc gaaatagtaa aatttgatta tcaaaatttt    60

<210> SEQ ID NO 267
<211> LENGTH: 60
<212> TYPE: DNA
<213> ORGANISM: Homo sapiens

<400> SEQUENCE: 267
gtgccctcct cgccctgat gggtctggtc gagaccagcc tcaacatgga gaaacaccat    60

<210> SEQ ID NO 268
<211> LENGTH: 60
<212> TYPE: DNA
<213> ORGANISM: Homo sapiens

<400> SEQUENCE: 268
tcacctctgt cacccacccg ttccactctc gaggctgcag tgaatcataa tcatagcact    60

<210> SEQ ID NO 269
<211> LENGTH: 60
<212> TYPE: DNA
<213> ORGANISM: Homo sapiens

<400> SEQUENCE: 269
actgatggca tccccgtgc gcttccggtc gatggggcca gggggctatg gggataacct    60

<210> SEQ ID NO 270
<211> LENGTH: 60

```
<212> TYPE: DNA
<213> ORGANISM: Homo sapiens

<400> SEQUENCE: 270
cgccgggccg acacccacat tgtcttcttc gatccctggg ctacaaggtg ggcgattctg    60

<210> SEQ ID NO 271
<211> LENGTH: 60
<212> TYPE: DNA
<213> ORGANISM: Homo sapiens

<400> SEQUENCE: 271
agtggtctca ccatggcttt cttccaattc gaggtcccca accccctgcc gctcatcgtg    60

<210> SEQ ID NO 272
<211> LENGTH: 60
<212> TYPE: DNA
<213> ORGANISM: Homo sapiens

<400> SEQUENCE: 272
aggacagaga ccctaattc caccaccatc gacccttctg ctttctctcc aggggatggc     60

<210> SEQ ID NO 273
<211> LENGTH: 60
<212> TYPE: DNA
<213> ORGANISM: Homo sapiens

<400> SEQUENCE: 273
cgccgggccg acacccacat tgtcttcttc gacatccact cttctgggca ttcccagcct    60

<210> SEQ ID NO 274
<211> LENGTH: 60
<212> TYPE: DNA
<213> ORGANISM: Homo sapiens

<400> SEQUENCE: 274
cgccgggccg acacccacat tgtcttcttc gatttgcatt ccctaatga tcggtgatgt     60

<210> SEQ ID NO 275
<211> LENGTH: 60
<212> TYPE: DNA
<213> ORGANISM: Homo sapiens

<400> SEQUENCE: 275
tccgtgaccc ccacagccgg tcgccacatc gattatccag aagcttcttt tttttttaacc   60

<210> SEQ ID NO 276
<211> LENGTH: 60
<212> TYPE: DNA
<213> ORGANISM: Homo sapiens

<400> SEQUENCE: 276
tgcggaaatg atggacacta caccttcatc gacctcgtga tctggccgcc tcggccttcc    60

<210> SEQ ID NO 277
<211> LENGTH: 60
<212> TYPE: DNA
<213> ORGANISM: Homo sapiens

<400> SEQUENCE: 277
cgccgggccg acacccacat tgtcttcttc gattttatag tatgtgaatt atatctcaac    60

<210> SEQ ID NO 278
```

```
<211> LENGTH: 60
<212> TYPE: DNA
<213> ORGANISM: Homo sapiens

<400> SEQUENCE: 278
cgccgggccg acacccacat tgtcttcttc gagttccttg aaagctttaa tttgcattcc    60

<210> SEQ ID NO 279
<211> LENGTH: 60
<212> TYPE: DNA
<213> ORGANISM: Homo sapiens

<400> SEQUENCE: 279
cgccgggccg acacccacat tgtcttcttc gaatctccca tctgctcttt caaccaagct    60

<210> SEQ ID NO 280
<211> LENGTH: 60
<212> TYPE: DNA
<213> ORGANISM: Homo sapiens

<400> SEQUENCE: 280
cgccgggccg acacccacat tgtcttcttc gaaccccttt aaaccactga ccttgtccct    60

<210> SEQ ID NO 281
<211> LENGTH: 60
<212> TYPE: DNA
<213> ORGANISM: Homo sapiens

<400> SEQUENCE: 281
ttatcaaccc ggcgtctgga acaatcgctc gatccacacc acaccagcag tggggcacaa    60

<210> SEQ ID NO 282
<211> LENGTH: 60
<212> TYPE: DNA
<213> ORGANISM: Homo sapiens

<400> SEQUENCE: 282
ctccacgtca ccccatgtca attccaagtc gatgccagac actcttctgg gggtggggtg    60

<210> SEQ ID NO 283
<211> LENGTH: 60
<212> TYPE: DNA
<213> ORGANISM: Homo sapiens

<400> SEQUENCE: 283
catcccatcc cccaggctga aatgtgagtc gactgtggcc gccacacagt ggtcactgct    60

<210> SEQ ID NO 284
<211> LENGTH: 60
<212> TYPE: DNA
<213> ORGANISM: Homo sapiens

<400> SEQUENCE: 284
ctcccctctc ccccgggcat gtgggccctc gaactgcaaa aaaaaaaaaa acagaactaa    60

<210> SEQ ID NO 285
<211> LENGTH: 60
<212> TYPE: DNA
<213> ORGANISM: Homo sapiens

<400> SEQUENCE: 285
ttgaacccaa gaggtcacac cactgcactc gacgcccagc aagtaggcac agttcccaat    60
```

```
<210> SEQ ID NO 286
<211> LENGTH: 60
<212> TYPE: DNA
<213> ORGANISM: Homo sapiens

<400> SEQUENCE: 286
agttctttct tgaattcttt cctgatactc gatccacacc acaccagcag tggggcacaa    60

<210> SEQ ID NO 287
<211> LENGTH: 60
<212> TYPE: DNA
<213> ORGANISM: Homo sapiens

<400> SEQUENCE: 287
tctttagcac ccgggcccca caattgtctc gaagcttctc ttctgaacct ggtgaagcag    60

<210> SEQ ID NO 288
<211> LENGTH: 60
<212> TYPE: DNA
<213> ORGANISM: Homo sapiens

<400> SEQUENCE: 288
tctttagcac ccgggcccca caattgtctc gatgctttca tgggacactt tgaaaataaa    60

<210> SEQ ID NO 289
<211> LENGTH: 60
<212> TYPE: DNA
<213> ORGANISM: Homo sapiens

<400> SEQUENCE: 289
tctttagcac ccgggcccca caattgtctc gaccatatgg tctttgttgt gacactcaac    60

<210> SEQ ID NO 290
<211> LENGTH: 60
<212> TYPE: DNA
<213> ORGANISM: Homo sapiens

<400> SEQUENCE: 290
agaaacagct aactgatccc taaactcctc gagttgagat ctggcggcct gaatgctggt    60

<210> SEQ ID NO 291
<211> LENGTH: 60
<212> TYPE: DNA
<213> ORGANISM: Homo sapiens

<400> SEQUENCE: 291
tctttagcac ccgggcccca caattgtctc gataaaatgt taataacgtt gtcaagatta    60

<210> SEQ ID NO 292
<211> LENGTH: 60
<212> TYPE: DNA
<213> ORGANISM: Homo sapiens

<400> SEQUENCE: 292
tctttagcac ccgggcccca caattgtctc gatctgctgc ggtgggtcca tagactggca    60

<210> SEQ ID NO 293
<211> LENGTH: 60
<212> TYPE: DNA
<213> ORGANISM: Homo sapiens

<400> SEQUENCE: 293
ggccagagcg ccggcaagag ctcggtgctc gaaaagaaaa aaaaaatact aggggggtagg    60
```

```
<210> SEQ ID NO 294
<211> LENGTH: 60
<212> TYPE: DNA
<213> ORGANISM: Homo sapiens

<400> SEQUENCE: 294
acccaggata aaacgcagtg ttgaccgatc gacccttctg ctttctctcc aggggatggc    60

<210> SEQ ID NO 295
<211> LENGTH: 60
<212> TYPE: DNA
<213> ORGANISM: Homo sapiens

<400> SEQUENCE: 295
ttcattcatt cattcattca ttcatacatc gaaaggccag taggtgtgat ctgaggaagg    60

<210> SEQ ID NO 296
<211> LENGTH: 60
<212> TYPE: DNA
<213> ORGANISM: Homo sapiens

<400> SEQUENCE: 296
caagataaag gaagagtgaa atcctgtctc gaccgggcga ctcccccggg gcggggtgg    60

<210> SEQ ID NO 297
<211> LENGTH: 60
<212> TYPE: DNA
<213> ORGANISM: Homo sapiens

<400> SEQUENCE: 297
gcggcactcg gcctctccgc agcagttctc gaggaaagac ttactaggtc ctgcagtatt    60

<210> SEQ ID NO 298
<211> LENGTH: 60
<212> TYPE: DNA
<213> ORGANISM: Homo sapiens

<400> SEQUENCE: 298
tccccagcct gctctctggt agacctcttc gagggcccac atgcccgggg gagaggggag    60

<210> SEQ ID NO 299
<211> LENGTH: 60
<212> TYPE: DNA
<213> ORGANISM: Homo sapiens

<400> SEQUENCE: 299
tctttagcac ccgggcccca caattgtctc gaatctagga tagacgcatg cagcccctgg    60

<210> SEQ ID NO 300
<211> LENGTH: 60
<212> TYPE: DNA
<213> ORGANISM: Homo sapiens

<400> SEQUENCE: 300
gcggcactcg gcctctccgc agcagttctc gaataccaag aaaaagtcac atgactaaca    60

<210> SEQ ID NO 301
<211> LENGTH: 60
<212> TYPE: DNA
<213> ORGANISM: Homo sapiens

<400> SEQUENCE: 301
cactgcacca ccctgtacat aagtcccctc gacttcagct ccagtgaaga agacactact    60
```

<210> SEQ ID NO 302
<211> LENGTH: 60
<212> TYPE: DNA
<213> ORGANISM: Homo sapiens

<400> SEQUENCE: 302
gcggcactcg gcctctccgc agcagttctc gagagccagg aggctcttgt ggtctaatct    60

<210> SEQ ID NO 303
<211> LENGTH: 60
<212> TYPE: DNA
<213> ORGANISM: Homo sapiens

<400> SEQUENCE: 303
tctttagcac ccgggcccca caattgtctc gagcttcagt tccggcatct acagaatgct    60

<210> SEQ ID NO 304
<211> LENGTH: 60
<212> TYPE: DNA
<213> ORGANISM: Homo sapiens

<400> SEQUENCE: 304
gcggcactcg gcctctccgc agcagttctc gattgagcct gaaaaatgag gtgaaaaat    60

<210> SEQ ID NO 305
<211> LENGTH: 60
<212> TYPE: DNA
<213> ORGANISM: Homo sapiens

<400> SEQUENCE: 305
cagaatcgcc caccttgtag cccagggatc gacggcaagc cactcaccct cagccctatc    60

<210> SEQ ID NO 306
<211> LENGTH: 60
<212> TYPE: DNA
<213> ORGANISM: Homo sapiens

<400> SEQUENCE: 306
catcccatcc cccaggctga aatgtgagtc gagacttcct ttttcatctg tggatcattt    60

<210> SEQ ID NO 307
<211> LENGTH: 60
<212> TYPE: DNA
<213> ORGANISM: Homo sapiens

<400> SEQUENCE: 307
tccatcccca acttcaatga cttctacatc gacatagtac tgaaagtctt tgctagagta    60

<210> SEQ ID NO 308
<211> LENGTH: 60
<212> TYPE: DNA
<213> ORGANISM: Homo sapiens

<400> SEQUENCE: 308
acccaggata aaacgcagtg ttgaccgatc gattcttggg ccttccacct tcacattcta    60

<210> SEQ ID NO 309
<211> LENGTH: 60
<212> TYPE: DNA
<213> ORGANISM: Homo sapiens

<400> SEQUENCE: 309
agacccggac gtctccgcga ggcggccatc gaggaaggct cctctgagaa agagtctgct    60

<210> SEQ ID NO 310
<211> LENGTH: 60
<212> TYPE: DNA
<213> ORGANISM: Homo sapiens

<400> SEQUENCE: 310
ctccagaaag gacctttaaa cactcaggtc gatggccgcc tcgcggagac gtccgggtct    60

<210> SEQ ID NO 311
<211> LENGTH: 60
<212> TYPE: DNA
<213> ORGANISM: Homo sapiens

<400> SEQUENCE: 311
ttcctgaaaa aaaatggcta cttattagtc gatggccgcc tcgcggagac gtccgggtct    60

<210> SEQ ID NO 312
<211> LENGTH: 60
<212> TYPE: DNA
<213> ORGANISM: Homo sapiens

<400> SEQUENCE: 312
agacccggac gtctccgcga ggcggccatc gagtgtcaac atgatggcac ctaaagctgt    60

<210> SEQ ID NO 313
<211> LENGTH: 60
<212> TYPE: DNA
<213> ORGANISM: Homo sapiens

<400> SEQUENCE: 313
acccaggata aaacgcagtg ttgaccgatc gagggcgtgg acttctacac gtccatcact    60

<210> SEQ ID NO 314
<211> LENGTH: 60
<212> TYPE: DNA
<213> ORGANISM: Homo sapiens

<400> SEQUENCE: 314
cactttttat agaagagaaa gtgaagattc gatggccgcc tcgcggagac gtccgggtct    60

<210> SEQ ID NO 315
<211> LENGTH: 60
<212> TYPE: DNA
<213> ORGANISM: Homo sapiens

<400> SEQUENCE: 315
ccttggcgaa ggcgcgtcct gggttggatc gaagtgtatg atcgcatggc attttgtaca    60

<210> SEQ ID NO 316
<211> LENGTH: 60
<212> TYPE: DNA
<213> ORGANISM: Homo sapiens

<400> SEQUENCE: 316
ccttccctcg tattcagtga gattcatttc gaactcctga cctcaggtga ggtgatccac    60

<210> SEQ ID NO 317
<211> LENGTH: 60
<212> TYPE: DNA
<213> ORGANISM: Homo sapiens

<400> SEQUENCE: 317

```
ggtggcatcc ccatcacttc tccatgcctc gaggtcccca accccctgcc gctcatcgtg    60

<210> SEQ ID NO 318
<211> LENGTH: 60
<212> TYPE: DNA
<213> ORGANISM: Homo sapiens

<400> SEQUENCE: 318
agacccggac gtctccgcga ggcggccatc gaatgatcag tgatgttgat ttttttttct    60

<210> SEQ ID NO 319
<211> LENGTH: 60
<212> TYPE: DNA
<213> ORGANISM: Homo sapiens

<400> SEQUENCE: 319
tgcggaaatg atggacacta caccttcatc gacctcgtga tctggccgcc tcggccttcc    60

<210> SEQ ID NO 320
<211> LENGTH: 60
<212> TYPE: DNA
<213> ORGANISM: Homo sapiens

<400> SEQUENCE: 320
acccaggata aaacgcagtg ttgaccgatc gattcttggg ccttccacct tcacattcta    60

<210> SEQ ID NO 321
<211> LENGTH: 60
<212> TYPE: DNA
<213> ORGANISM: Homo sapiens

<400> SEQUENCE: 321
acccaggata aaacgcagtg ttgaccgatc gacccttctg ctttctctcc aggggatggc    60

<210> SEQ ID NO 322
<211> LENGTH: 60
<212> TYPE: DNA
<213> ORGANISM: Homo sapiens

<400> SEQUENCE: 322
agacccggac gtctccgcga ggcggccatc gacatatttc ctgttccctt ggaataaaaa    60

<210> SEQ ID NO 323
<211> LENGTH: 60
<212> TYPE: DNA
<213> ORGANISM: Homo sapiens

<400> SEQUENCE: 323
actgatggca tccccgtgc gcttccggtc gatggggcca gggggctatg gggataacct    60

<210> SEQ ID NO 324
<211> LENGTH: 60
<212> TYPE: DNA
<213> ORGANISM: Homo sapiens

<400> SEQUENCE: 324 ccaccccgc cccgggggag tcgcccggtc gagggcctgg caagaagaca gaagccgact    60

<210> SEQ ID NO 325
<211> LENGTH: 60
<212> TYPE: DNA
<213> ORGANISM: Homo sapiens
```

<400> SEQUENCE: 325
gaattccgac tcccgttttg aaattgtatc gaactcctga cctcgggtga cccgtatgcc    60

<210> SEQ ID NO 326
<211> LENGTH: 60
<212> TYPE: DNA
<213> ORGANISM: Homo sapiens

<400> SEQUENCE: 326
agaaacagct aactgatccc taaactcctc gagttgagat ctggcggcct gaatgctggt    60

<210> SEQ ID NO 327
<211> LENGTH: 60
<212> TYPE: DNA
<213> ORGANISM: Homo sapiens

<400> SEQUENCE: 327
cagaatcact ctgtggaacc aaagagcttc gattcttggg ccttccacct tcacattcta    60

<210> SEQ ID NO 328
<211> LENGTH: 60
<212> TYPE: DNA
<213> ORGANISM: Homo sapiens

<400> SEQUENCE: 328
agacccggac gtctccgcga ggcggccatc gattttgctg atgcaataca gttttacagg    60

<210> SEQ ID NO 329
<211> LENGTH: 60
<212> TYPE: DNA
<213> ORGANISM: Homo sapiens

<400> SEQUENCE: 329
caagataaag gaagagtgaa atcctgtctc gaccgggcga ctcccccggg gcggggtgg     60

<210> SEQ ID NO 330
<211> LENGTH: 60
<212> TYPE: DNA
<213> ORGANISM: Homo sapiens

<400> SEQUENCE: 330
agtgatggac ttgtagaagt ccacgccctc gattcttggg ccttccacct tcacattcta    60

<210> SEQ ID NO 331
<211> LENGTH: 60
<212> TYPE: DNA
<213> ORGANISM: Homo sapiens

<400> SEQUENCE: 331
cagaatcact ctgtggaacc aaagagcttc gattcttggg ccttccacct tcacattcta    60

<210> SEQ ID NO 332
<211> LENGTH: 60
<212> TYPE: DNA
<213> ORGANISM: Homo sapiens

<400> SEQUENCE: 332
ggcgggtgga tcacctgagg tcaggagctc gatctcctga cctcgtgatc cgcccgcctc    60

<210> SEQ ID NO 333
<211> LENGTH: 60
<212> TYPE: DNA
<213> ORGANISM: Homo sapiens

```
<400> SEQUENCE: 333
gcctgcaggg ggcgccccg cgcctgcctc gaccacacat ccacatggac gcatggcagg    60

<210> SEQ ID NO 334
<211> LENGTH: 60
<212> TYPE: DNA
<213> ORGANISM: Homo sapiens

<400> SEQUENCE: 334
catgatagtt aagagatcat atctagaatc gatacagttc ataatttatg aacatgtgga    60

<210> SEQ ID NO 335
<211> LENGTH: 60
<212> TYPE: DNA
<213> ORGANISM: Homo sapiens

<400> SEQUENCE: 335
agaaacagct aactgatccc taaactcctc gagagagtct taaaaggga acaaaccaaa     60

<210> SEQ ID NO 336
<211> LENGTH: 60
<212> TYPE: DNA
<213> ORGANISM: Homo sapiens

<400> SEQUENCE: 336
accaaaccca aggtccgctg ctcgctgctc gattttgctg atgcaataca gttttacagg    60

<210> SEQ ID NO 337
<211> LENGTH: 60
<212> TYPE: DNA
<213> ORGANISM: Homo sapiens

<400> SEQUENCE: 337
agtgacctaa tcacagctca ccggagcctc gaggccttag ctcctcaagg atacacattt    60

<210> SEQ ID NO 338
<211> LENGTH: 60
<212> TYPE: DNA
<213> ORGANISM: Homo sapiens

<400> SEQUENCE: 338
aattctgttg gaagaataat ttaaaatatc gaggctccgg tgagctgtga ttaggtcact    60

<210> SEQ ID NO 339
<211> LENGTH: 60
<212> TYPE: DNA
<213> ORGANISM: Homo sapiens

<400> SEQUENCE: 339
tactctagca aagactttca gtactatgtc gatggtgatt ttaccttgtg gagcaatggc    60

<210> SEQ ID NO 340
<211> LENGTH: 60
<212> TYPE: DNA
<213> ORGANISM: Homo sapiens

<400> SEQUENCE: 340
agcaagaggc tgagcctaac tctcccttc gatggccgcc tcgcggagac gtccgggtct     60

<210> SEQ ID NO 341
<211> LENGTH: 60
<212> TYPE: DNA
```

<213> ORGANISM: Homo sapiens

<400> SEQUENCE: 341
ccttggcgaa ggcgcgtcct gggttggatc gatctcttga cctcacgatc cacccgcctc    60

<210> SEQ ID NO 342
<211> LENGTH: 60
<212> TYPE: DNA
<213> ORGANISM: Homo sapiens

<400> SEQUENCE: 342
gcagagggaa ttgagagaag ttaagagttc gaactcctga cctcgggtga cccgtatgcc    60

<210> SEQ ID NO 343
<211> LENGTH: 60
<212> TYPE: DNA
<213> ORGANISM: Homo sapiens

<400> SEQUENCE: 343
gacacgggcg catcacgagg tcaagagatc gatctcttga cctggtgatc tacccgcctc    60

<210> SEQ ID NO 344
<211> LENGTH: 60
<212> TYPE: DNA
<213> ORGANISM: Homo sapiens

<400> SEQUENCE: 344
atactgacac actattccac ccacaaagtc gataacatgt ttatagagaa atagccctct    60

<210> SEQ ID NO 345
<211> LENGTH: 60
<212> TYPE: DNA
<213> ORGANISM: Homo sapiens

<400> SEQUENCE: 345
agaaacagct aactgatccc taaactcctc gattctagat atgatctctt aactatcatg    60

<210> SEQ ID NO 346
<211> LENGTH: 60
<212> TYPE: DNA
<213> ORGANISM: Homo sapiens

<400> SEQUENCE: 346
tccacatgtt cataaattat gaactgtatc gaaatgtcta ttcatattca ttaactcaag    60

<210> SEQ ID NO 347
<211> LENGTH: 60
<212> TYPE: DNA
<213> ORGANISM: Homo sapiens

<400> SEQUENCE: 347
accaaaccca aggtccgctg ctcgctgctc gagatgggga aggaaaggtc agaagaggag    60

<210> SEQ ID NO 348
<211> LENGTH: 60
<212> TYPE: DNA
<213> ORGANISM: Homo sapiens

<400> SEQUENCE: 348
ttcctgaaaa aaaatggcta cttattagtc gacctgagtg tttaaaggtc ctttctggag    60

<210> SEQ ID NO 349
<211> LENGTH: 60

```
<212> TYPE: DNA
<213> ORGANISM: Homo sapiens

<400> SEQUENCE: 349 cacttttat agaagagaaa gtgaagattc gagcagcgag cagcggacct tgggtttggt      60

<210> SEQ ID NO 350
<211> LENGTH: 60
<212> TYPE: DNA
<213> ORGANISM: Homo sapiens

<400> SEQUENCE: 350 ccaccccgc cccggggag tcgcccggtc gaactccgga cctcgtgatc tgcccacctc       60

<210> SEQ ID NO 351
<211> LENGTH: 60
<212> TYPE: DNA
<213> ORGANISM: Homo sapiens

<400> SEQUENCE: 351
gaggtgggcg atcctaagg tcaggagttc gatctcctga cctcgtgatc cgcccgcctc     60

<210> SEQ ID NO 352
<211> LENGTH: 60
<212> TYPE: DNA
<213> ORGANISM: Homo sapiens

<400> SEQUENCE: 352
ttaacatggt ctatgtgtcc ctgcatgatc gatggccgcc tcgcggagac gtccgggtct    60

<210> SEQ ID NO 353
<211> LENGTH: 60
<212> TYPE: DNA
<213> ORGANISM: Homo sapiens

<400> SEQUENCE: 353
cactttttat agaagagaaa gtgaagattc gacctcctga cctcggaacc acaatcactc    60

<210> SEQ ID NO 354
<211> LENGTH: 60
<212> TYPE: DNA
<213> ORGANISM: Homo sapiens

<400> SEQUENCE: 354
ttttccctgg aaatcctagt tggggtgctc gagccgccaa cgaggatttc taggagaaga    60

<210> SEQ ID NO 355
<211> LENGTH: 60
<212> TYPE: DNA
<213> ORGANISM: Homo sapiens

<400> SEQUENCE: 355
catgatagtt aagagatcat atctagaatc gactgtgcag ctatgctgtt ttatgtgtaa    60

<210> SEQ ID NO 356
<211> LENGTH: 60
<212> TYPE: DNA
<213> ORGANISM: Homo sapiens

<400> SEQUENCE: 356
tctttgttac tggaatatac gaataaaatc gatattttaa attattcttc caacagaatt    60

<210> SEQ ID NO 357
```

```
<211> LENGTH: 60
<212> TYPE: DNA
<213> ORGANISM: Homo sapiens

<400> SEQUENCE: 357
caaataaatt agaatgtatt ttcattgctc gagcaggtat tttggatgcg gtgccgcctg      60

<210> SEQ ID NO 358
<211> LENGTH: 60
<212> TYPE: DNA
<213> ORGANISM: Homo sapiens

<400> SEQUENCE: 358
tactgaagaa gtctttgaag agatttcttc gagcaggtat tttggatgcg gtgccgcctg      60

<210> SEQ ID NO 359
<211> LENGTH: 60
<212> TYPE: DNA
<213> ORGANISM: Homo sapiens

<400> SEQUENCE: 359
atttattgac tccctagggt ctaggagctc gagcaggtat tttggatgcg gtgccgcctg      60

<210> SEQ ID NO 360
<211> LENGTH: 60
<212> TYPE: DNA
<213> ORGANISM: Homo sapiens

<400> SEQUENCE: 360
tgttttataa tcattataat tttttctttc gagcaggtat tttggatgcg gtgccgcctg      60

<210> SEQ ID NO 361
<211> LENGTH: 60
<212> TYPE: DNA
<213> ORGANISM: Homo sapiens

<400> SEQUENCE: 361
tagaactgaa catgttaaa tgatatcgtc gagcaggtat tttggatgcg gtgccgcctg      60

<210> SEQ ID NO 362
<211> LENGTH: 60
<212> TYPE: DNA
<213> ORGANISM: Homo sapiens

<400> SEQUENCE: 362
ttataccaga tttcaggtgc ctagctgttc gagcaggtat tttggatgcg gtgccgcctg      60

<210> SEQ ID NO 363
<211> LENGTH: 60
<212> TYPE: DNA
<213> ORGANISM: Homo sapiens

<400> SEQUENCE: 363
cccacctccc accagacagt ggaagcagtc gagtgctgtg agcaaagagg ccctgggcca      60

<210> SEQ ID NO 364
<211> LENGTH: 60
<212> TYPE: DNA
<213> ORGANISM: Homo sapiens

<400> SEQUENCE: 364
ttccacttat gtgatgtgtc taaagtagtc gagcaggtat tttggatgcg gtgccgcctg      60
```

```
<210> SEQ ID NO 365
<211> LENGTH: 60
<212> TYPE: DNA
<213> ORGANISM: Homo sapiens

<400> SEQUENCE: 365
cccacctccc accagacagt ggaagcagtc gaagcaaaac tgtggagatt gggtcggtga    60

<210> SEQ ID NO 366
<211> LENGTH: 60
<212> TYPE: DNA
<213> ORGANISM: Homo sapiens

<400> SEQUENCE: 366
tgaatggacc tcatcctacc attcttttc gagcaggtat tttggatgcg gtgccgcctg    60

<210> SEQ ID NO 367
<211> LENGTH: 60
<212> TYPE: DNA
<213> ORGANISM: Homo sapiens

<400> SEQUENCE: 367
gcctgcaggg ggcgccccg cgcctgcctc gaccacacat ccacatggac gcatggcagg    60

<210> SEQ ID NO 368
<211> LENGTH: 60
<212> TYPE: DNA
<213> ORGANISM: Homo sapiens

<400> SEQUENCE: 368
catctcatgt ggattcagaa aaggtagtc gagcaggtat tttggatgcg gtgccgcctg    60

<210> SEQ ID NO 369
<211> LENGTH: 60
<212> TYPE: DNA
<213> ORGANISM: Homo sapiens

<400> SEQUENCE: 369
aggacagaga ccctaattc caccaccatc gacccttctg ctttctctcc agggatggc     60

<210> SEQ ID NO 370
<211> LENGTH: 60
<212> TYPE: DNA
<213> ORGANISM: Homo sapiens

<400> SEQUENCE: 370
tgcccaccca gacctcccgg cggctgcttc gagcaggtat tttggatgcg gtgccgcctg    60

<210> SEQ ID NO 371
<211> LENGTH: 60
<212> TYPE: DNA
<213> ORGANISM: Homo sapiens

<400> SEQUENCE: 371
tccatcccca acttcaatga cttctacatc gacatagtac tgaaagtctt tgctagagta    60

<210> SEQ ID NO 372
<211> LENGTH: 60
<212> TYPE: DNA
<213> ORGANISM: Homo sapiens

<400> SEQUENCE: 372
ggtggcatcc ccatcacttc tccatgcctc gaggtcccca accccctgcc gctcatcgtg    60
```

<210> SEQ ID NO 373
<211> LENGTH: 60
<212> TYPE: DNA
<213> ORGANISM: Homo sapiens

<400> SEQUENCE: 373
cactgcccca cctcttactg gcatctcctc gaccccgtgc caagtccccg ggtggtagag    60

<210> SEQ ID NO 374
<211> LENGTH: 60
<212> TYPE: DNA
<213> ORGANISM: Homo sapiens

<400> SEQUENCE: 374
cggccgagcc cgggcctagt atccagagtc gagcaggtat tttggatgcg gtgccgcctg    60

<210> SEQ ID NO 375
<211> LENGTH: 60
<212> TYPE: DNA
<213> ORGANISM: Homo sapiens

<400> SEQUENCE: 375
ccacctcata ggggagggct ttactcagtc gatccacacc acaccagcag tggggcacaa    60

<210> SEQ ID NO 376
<211> LENGTH: 60
<212> TYPE: DNA
<213> ORGANISM: Homo sapiens

<400> SEQUENCE: 376
gagcagtacc tagcaaataa ttaggtgttc gagcaggtat tttggatgcg gtgccgcctg    60

<210> SEQ ID NO 377
<211> LENGTH: 60
<212> TYPE: DNA
<213> ORGANISM: Homo sapiens

<400> SEQUENCE: 377
caggcggcac cgcatccaaa atacctgctc gagtagaggt gtctaatatg atgcacctat    60

<210> SEQ ID NO 378
<211> LENGTH: 60
<212> TYPE: DNA
<213> ORGANISM: Homo sapiens

<400> SEQUENCE: 378
agtggtctca ccatggcttt cttccaattc gaggtcccca accccctgcc gctcatcgtg    60

<210> SEQ ID NO 379
<211> LENGTH: 60
<212> TYPE: DNA
<213> ORGANISM: Homo sapiens

<400> SEQUENCE: 379
tccgtgaccc ccacagccgg tcgccacatc gattatccag aagcttcttt ttttttaacc    60

<210> SEQ ID NO 380
<211> LENGTH: 60
<212> TYPE: DNA
<213> ORGANISM: Homo sapiens

<400> SEQUENCE: 380
cctgtagctc tgatgtcaga tggcaatgtc gatccacacc acaccagcag tggggcacaa    60

```
<210> SEQ ID NO 381
<211> LENGTH: 60
<212> TYPE: DNA
<213> ORGANISM: Homo sapiens

<400> SEQUENCE: 381
ccaaaggtat tacaaactca gccttggttc gagcaggtat tttggatgcg gtgccgcctg    60

<210> SEQ ID NO 382
<211> LENGTH: 60
<212> TYPE: DNA
<213> ORGANISM: Homo sapiens

<400> SEQUENCE: 382
caggcggcac cgcatccaaa atacctgctc gagtattgtg tttgatactt tgttcttgat    60

<210> SEQ ID NO 383
<211> LENGTH: 60
<212> TYPE: DNA
<213> ORGANISM: Homo sapiens

<400> SEQUENCE: 383
caggcggcac cgcatccaaa atacctgctc gaagggattc tgacttgata caggtccaga    60

<210> SEQ ID NO 384
<211> LENGTH: 60
<212> TYPE: DNA
<213> ORGANISM: Homo sapiens

<400> SEQUENCE: 384
ctgctgaaca gaggtgcctg cagatgcgtc gagcaggtat tttggatgcg gtgccgcctg    60

<210> SEQ ID NO 385
<211> LENGTH: 60
<212> TYPE: DNA
<213> ORGANISM: Homo sapiens

<400> SEQUENCE: 385
caggcggcac cgcatccaaa atacctgctc gatggccaat gatttgatta attatgtcta    60

<210> SEQ ID NO 386
<211> LENGTH: 60
<212> TYPE: DNA
<213> ORGANISM: Homo sapiens

<400> SEQUENCE: 386
caggcggcac cgcatccaaa atacctgctc gacagtagaa tctgctgcct gtgaccatct    60

<210> SEQ ID NO 387
<211> LENGTH: 60
<212> TYPE: DNA
<213> ORGANISM: Homo sapiens

<400> SEQUENCE: 387
ataaaggtgg ggcaaagggt tgaattggtc gacggggcgg gtggacgtgg agccacagtt    60

<210> SEQ ID NO 388
<211> LENGTH: 60
<212> TYPE: DNA
<213> ORGANISM: Homo sapiens

<400> SEQUENCE: 388
```

```
caggcggcac cgcatccaaa atacctgctc gatgctataa atgttacgga aattatgtac        60
```

<210> SEQ ID NO 389
<211> LENGTH: 60
<212> TYPE: DNA
<213> ORGANISM: Homo sapiens

<400> SEQUENCE: 389

```
ggtctctggt aatggccaaa taatctaatc gaccgccctg cccctactg tggagttcta         60
```

<210> SEQ ID NO 390
<211> LENGTH: 60
<212> TYPE: DNA
<213> ORGANISM: Homo sapiens

<400> SEQUENCE: 390

```
accgcctcac ctcagctctc cagtgagatc gatcctttgc tgcctgatcg gtcttcctct        60
```

<210> SEQ ID NO 391
<211> LENGTH: 60
<212> TYPE: DNA
<213> ORGANISM: Homo sapiens

<400> SEQUENCE: 391

```
caggcggcac cgcatccaaa atacctgctc gatgtcctca aacccatata ggaagtacat       60
```

<210> SEQ ID NO 392
<211> LENGTH: 60
<212> TYPE: DNA
<213> ORGANISM: Homo sapiens

<400> SEQUENCE: 392

```
caggcggcac cgcatccaaa atacctgctc gatgcaacaa aaagagctaa ctatcctaaa       60
```

<210> SEQ ID NO 393
<211> LENGTH: 60
<212> TYPE: DNA
<213> ORGANISM: Homo sapiens

<400> SEQUENCE: 393

```
caggcggcac cgcatccaaa atacctgctc gatcaataga caaacatata tacacatgtt       60
```

<210> SEQ ID NO 394
<211> LENGTH: 60
<212> TYPE: DNA
<213> ORGANISM: Homo sapiens

<400> SEQUENCE: 394

```
gcccgaccct gagctccaga acagaccatc gacctcaaca gaggtttctg aaggggtca       60
```

<210> SEQ ID NO 395
<211> LENGTH: 60
<212> TYPE: DNA
<213> ORGANISM: Homo sapiens

<400> SEQUENCE: 395

```
ataccaagcc agaggtttct tgacttaatc gaccgccctg cccctactg tggagttcta       60
```

<210> SEQ ID NO 396
<211> LENGTH: 60
<212> TYPE: DNA
<213> ORGANISM: Homo sapiens

<400> SEQUENCE: 396

```
tacacaatga cttcattttg tcctcatatc gaccgccctg cccctactg tggagttcta    60
```

<210> SEQ ID NO 397
<211> LENGTH: 60
<212> TYPE: DNA
<213> ORGANISM: Homo sapiens

<400> SEQUENCE: 397

```
cactgcccca cctcttactg gcatctcctc gagctccaga gctttcctct gagcccatgt    60
```

<210> SEQ ID NO 398
<211> LENGTH: 60
<212> TYPE: DNA
<213> ORGANISM: Homo sapiens

<400> SEQUENCE: 398

```
tccgtgaccc ccacagccgg tcgccacatc gagtagctga gattacaggc atgtaccacc    60
```

<210> SEQ ID NO 399
<211> LENGTH: 60
<212> TYPE: DNA
<213> ORGANISM: Homo sapiens

<400> SEQUENCE: 399

```
tgcagcccac tcccacaaca gggaagactc gaactctctc tgccagcctc tctgggggtg    60
```

<210> SEQ ID NO 400
<211> LENGTH: 60
<212> TYPE: DNA
<213> ORGANISM: Homo sapiens

<400> SEQUENCE: 400

```
cactgcccca cctcttactg gcatctcctc gactgcccta ttttgtctat agattatttc    60
```

<210> SEQ ID NO 401
<211> LENGTH: 60
<212> TYPE: DNA
<213> ORGANISM: Homo sapiens

<400> SEQUENCE: 401

```
caggcggcac cgcatccaaa atacctgctc gactcaaggt tgccacaaat cttcaatttg    60
```

<210> SEQ ID NO 402
<211> LENGTH: 60
<212> TYPE: DNA
<213> ORGANISM: Homo sapiens

<400> SEQUENCE: 402

```
gcccgaccct gagctccaga acagaccatc gactgccgcg ggggtcgcgt cctctccatc    60
```

<210> SEQ ID NO 403
<211> LENGTH: 60
<212> TYPE: DNA
<213> ORGANISM: Homo sapiens

<400> SEQUENCE: 403

```
ggaactgcat ccatacttgt tacacatctc gagttgttgc caccccaccc tcctcaaacc    60
```

<210> SEQ ID NO 404
<211> LENGTH: 60
<212> TYPE: DNA
<213> ORGANISM: Homo sapiens -continued

```
<400> SEQUENCE: 404
cactgcccca cctcttactg gcatctcctc gagcattaag tcttggatgc tgttgttcta    60

<210> SEQ ID NO 405
<211> LENGTH: 60
<212> TYPE: DNA
<213> ORGANISM: Homo sapiens

<400> SEQUENCE: 405
caatacaaca gaatgcagag tccagaaatc gagcaggtat tttggatgcg gtgccgcctg    60

<210> SEQ ID NO 406
<211> LENGTH: 60
<212> TYPE: DNA
<213> ORGANISM: Homo sapiens

<400> SEQUENCE: 406
agtggtacaa tcatgaatca ctacagcctc gaccacacat ccacatggac gcatggcagg    60

<210> SEQ ID NO 407
<211> LENGTH: 60
<212> TYPE: DNA
<213> ORGANISM: Homo sapiens

<400> SEQUENCE: 407
tcacctctgt cacccacccg ttccactctc gaattaggaa tcagcatttc ttccactgag    60

<210> SEQ ID NO 408
<211> LENGTH: 60
<212> TYPE: DNA
<213> ORGANISM: Homo sapiens

<400> SEQUENCE: 408
tcacctctgt cacccacccg ttccactctc gaaatagtaa aatttgatta tcaaaatttt    60

<210> SEQ ID NO 409
<211> LENGTH: 60
<212> TYPE: DNA
<213> ORGANISM: Homo sapiens

<400> SEQUENCE: 409
cctgtagctc tgatgtcaga tggcaatgtc gatccacacc acaccagcag tggggcacaa    60

<210> SEQ ID NO 410
<211> LENGTH: 60
<212> TYPE: DNA
<213> ORGANISM: Homo sapiens

<400> SEQUENCE: 410
ccacctcata ggggagggct ttactcagtc gatccacacc acaccagcag tggggcacaa    60

<210> SEQ ID NO 411
<211> LENGTH: 60
<212> TYPE: DNA
<213> ORGANISM: Homo sapiens

<400> SEQUENCE: 411
tcacctctgt cacccacccg ttccactctc gatgctctct tagtgttcca attctcagct    60

<210> SEQ ID NO 412
<211> LENGTH: 60
<212> TYPE: DNA
<213> ORGANISM: Homo sapiens
```

```
<400> SEQUENCE: 412
tcacctctgt cacccacccg ttccactctc gataaagcac ttagaacatg gcatatactc    60

<210> SEQ ID NO 413
<211> LENGTH: 60
<212> TYPE: DNA
<213> ORGANISM: Homo sapiens

<400> SEQUENCE: 413
agttctttct tgaattcttt cctgatactc gatccacacc acaccagcag tggggcacaa    60

<210> SEQ ID NO 414
<211> LENGTH: 60
<212> TYPE: DNA
<213> ORGANISM: Homo sapiens

<400> SEQUENCE: 414
ttatcaaccc ggcgtctgga acaatcgctc gatccacacc acaccagcag tggggcacaa    60

<210> SEQ ID NO 415
<211> LENGTH: 60
<212> TYPE: DNA
<213> ORGANISM: Homo sapiens

<400> SEQUENCE: 415
ttcattcatt cattcattca ttcatacatc gattctctat ttcatttatt tccactgtaa    60

<210> SEQ ID NO 416
<211> LENGTH: 60
<212> TYPE: DNA
<213> ORGANISM: Homo sapiens

<400> SEQUENCE: 416
ttcattcatt cattcattca ttcatacatc gaaatgtcta ttcatattca ttaactcaag    60

<210> SEQ ID NO 417
<211> LENGTH: 60
<212> TYPE: DNA
<213> ORGANISM: Homo sapiens

<400> SEQUENCE: 417
tcacctctgt cacccacccg ttccactctc gaatagctcc tattgttatg gagtgtagca    60

<210> SEQ ID NO 418
<211> LENGTH: 60
<212> TYPE: DNA
<213> ORGANISM: Homo sapiens

<400> SEQUENCE: 418
tcacctctgt cacccacccg ttccactctc gaggctgcag tgaatcataa tcatagcact    60

<210> SEQ ID NO 419
<211> LENGTH: 60
<212> TYPE: DNA
<213> ORGANISM: Homo sapiens

<400> SEQUENCE: 419
gcctgcaggg ggcgcccccg cgcctgcctc gaccacacat ccacatggac gcatggcagg    60

<210> SEQ ID NO 420
<211> LENGTH: 60
<212> TYPE: DNA
```

<213> ORGANISM: Homo sapiens

<400> SEQUENCE: 420
gggtgggatg ggacagacac aagaactctc gaggttgtag acctcatggc tggcacaagt    60

<210> SEQ ID NO 421
<211> LENGTH: 60
<212> TYPE: DNA
<213> ORGANISM: Homo sapiens

<400> SEQUENCE: 421
ttcattcatt cattcattca ttcatacatc gaaaggccag taggtgtgat ctgaggaagg    60

<210> SEQ ID NO 422
<211> LENGTH: 60
<212> TYPE: DNA
<213> ORGANISM: Homo sapiens

<400> SEQUENCE: 422
agtgttggtg agatattgtc tctcagtttc gatccacacc acaccagcag tggggcacaa    60

<210> SEQ ID NO 423
<211> LENGTH: 60
<212> TYPE: DNA
<213> ORGANISM: Homo sapiens

<400> SEQUENCE: 423
ccaaccccac tccccaagta ccccactctc gagtcaggta cagcgcttga gtccattgtg    60

<210> SEQ ID NO 424
<211> LENGTH: 60
<212> TYPE: DNA
<213> ORGANISM: Homo sapiens

<400> SEQUENCE: 424
ccgcccctgt cctctcgctt cccgctggtc gatccacacc acaccagcag tggggcacaa    60

<210> SEQ ID NO 425
<211> LENGTH: 60
<212> TYPE: DNA
<213> ORGANISM: Homo sapiens

<400> SEQUENCE: 425
agagagctgg agaagagggc gagaagagtc gaaagaattg tgagtagcag ttgtgtggtt    60

<210> SEQ ID NO 426
<211> LENGTH: 60
<212> TYPE: DNA
<213> ORGANISM: Homo sapiens

<400> SEQUENCE: 426
agagagctgg agaagagggc gagaagagtc gataaaggaa aaagttcagt aaagtgtgaa    60

<210> SEQ ID NO 427
<211> LENGTH: 60
<212> TYPE: DNA
<213> ORGANISM: Homo sapiens

<400> SEQUENCE: 427
agtggtacaa tcatgaatca ctacagcctc gaccacacat ccacatggac gcatggcagg    60

<210> SEQ ID NO 428
<211> LENGTH: 60

```
<212> TYPE: DNA
<213> ORGANISM: Homo sapiens

<400> SEQUENCE: 428
tggcatccca taggctttat agagcaggtc gacctcctga cctcgtgatc cacctgcctc    60

<210> SEQ ID NO 429
<211> LENGTH: 60
<212> TYPE: DNA
<213> ORGANISM: Homo sapiens

<400> SEQUENCE: 429
agagagctgg agaagagggc gagaagagtc gaggtatctt ttttctccga aggctagtaa    60

<210> SEQ ID NO 430
<211> LENGTH: 60
<212> TYPE: DNA
<213> ORGANISM: Homo sapiens

<400> SEQUENCE: 430
atccacttac atgaggtacc tagaggagtc gagttgttgc caccccaccc tcctcaaacc    60

<210> SEQ ID NO 431
<211> LENGTH: 60
<212> TYPE: DNA
<213> ORGANISM: Homo sapiens

<400> SEQUENCE: 431
gttaacagta atacgatgtt aaaaggactc gagttgttgc caccccaccc tcctcaaacc    60

<210> SEQ ID NO 432
<211> LENGTH: 60
<212> TYPE: DNA
<213> ORGANISM: Homo sapiens

<400> SEQUENCE: 432
tggggaagag gagcaagtgt caggaagatc gactcattta atccccaaaa ccattccatg    60

<210> SEQ ID NO 433
<211> LENGTH: 60
<212> TYPE: DNA
<213> ORGANISM: Homo sapiens

<400> SEQUENCE: 433
ggaactgcat ccatacttgt tacacatctc gagttgttgc caccccaccc tcctcaaacc    60

<210> SEQ ID NO 434
<211> LENGTH: 60
<212> TYPE: DNA
<213> ORGANISM: Homo sapiens

<400> SEQUENCE: 434
ccacctcata ggggagggct ttactcagtc gagcatttgt gtgtgtatgt gtgaagtata    60

<210> SEQ ID NO 435
<211> LENGTH: 60
<212> TYPE: DNA
<213> ORGANISM: Homo sapiens

<400> SEQUENCE: 435
tttaaagatg aggggaggga agcaggagtc gataaaggaa aaagttcagt aaagtgtgaa    60

<210> SEQ ID NO 436
```

```
<211> LENGTH: 60
<212> TYPE: DNA
<213> ORGANISM: Homo sapiens

<400> SEQUENCE: 436
tgtaatctgt tttgctatcc aatcaagatc gaggtccccc cacccccaca tgtctctacc    60

<210> SEQ ID NO 437
<211> LENGTH: 60
<212> TYPE: DNA
<213> ORGANISM: Homo sapiens

<400> SEQUENCE: 437
gggtgggatg ggacagacac aagaactctc gaacactcag ctatcagttt tgttgagttc    60

<210> SEQ ID NO 438
<211> LENGTH: 60
<212> TYPE: DNA
<213> ORGANISM: Homo sapiens

<400> SEQUENCE: 438
agagagctgg agaagagggc gagaagagtc gactgaatat cttcactctt gagccaaagt    60

<210> SEQ ID NO 439
<211> LENGTH: 60
<212> TYPE: DNA
<213> ORGANISM: Homo sapiens

<400> SEQUENCE: 439
cactgcacca ccctgtacat aagtcccctc gacttcagct ccagtgaaga agacactact    60

<210> SEQ ID NO 440
<211> LENGTH: 60
<212> TYPE: DNA
<213> ORGANISM: Homo sapiens

<400> SEQUENCE: 440
aagcagtttt tatcatttca ttaatccttc gaggtccccc cacccccaca tgtctctacc    60

<210> SEQ ID NO 441
<211> LENGTH: 60
<212> TYPE: DNA
<213> ORGANISM: Homo sapiens

<400> SEQUENCE: 441
ctccacgtca ccccatgtca attccaagtc gatgccagac actcttctgg gggtggggtg    60

<210> SEQ ID NO 442
<211> LENGTH: 60
<212> TYPE: DNA
<213> ORGANISM: Homo sapiens

<400> SEQUENCE: 442
ggctggcgga ttacttgaag ccaggagttc gatccacacc acaccagcag tggggcacaa    60

<210> SEQ ID NO 443
<211> LENGTH: 60
<212> TYPE: DNA
<213> ORGANISM: Homo sapiens

<400> SEQUENCE: 443
taaatacaga tgaaaccaac taatagactc gagttgttgc caccccaccc tcctcaaacc    60
```

```
<210> SEQ ID NO 444
<211> LENGTH: 60
<212> TYPE: DNA
<213> ORGANISM: Homo sapiens

<400> SEQUENCE: 444
aagtcctaag aacactgaaa atctcagatc gagttgttgc caccccaccc tcctcaaacc    60

<210> SEQ ID NO 445
<211> LENGTH: 60
<212> TYPE: DNA
<213> ORGANISM: Homo sapiens

<400> SEQUENCE: 445
tgcggaaatg atggacacta caccttcatc gacctcgtga tctggccgcc tcggccttcc    60

<210> SEQ ID NO 446
<211> LENGTH: 60
<212> TYPE: DNA
<213> ORGANISM: Homo sapiens

<400> SEQUENCE: 446
ctcaggaaga agtggatccc tgtttctttc gagttgttgc caccccaccc tcctcaaacc    60

<210> SEQ ID NO 447
<211> LENGTH: 60
<212> TYPE: DNA
<213> ORGANISM: Homo sapiens

<400> SEQUENCE: 447
agagagctgg agaagagggc gagaagagtc gaagatgtca aaaggaaaaa tggaaatagt    60

<210> SEQ ID NO 448
<211> LENGTH: 60
<212> TYPE: DNA
<213> ORGANISM: Homo sapiens

<400> SEQUENCE: 448
tttggtttgt tccctttta agactctctc gactcactca catctgcctc atgatggtta    60

<210> SEQ ID NO 449
<211> LENGTH: 60
<212> TYPE: DNA
<213> ORGANISM: Homo sapiens

<400> SEQUENCE: 449
tttaaagatg agggagggga agcaggagtc gaaaccagaa gacccaatat aatatctagt    60

<210> SEQ ID NO 450
<211> LENGTH: 60
<212> TYPE: DNA
<213> ORGANISM: Homo sapiens

<400> SEQUENCE: 450
tttaaagatg agggagggga agcaggagtc gaaagaattg tgagtagcag ttgtgtggtt    60

<210> SEQ ID NO 451
<211> LENGTH: 60
<212> TYPE: DNA
<213> ORGANISM: Homo sapiens

<400> SEQUENCE: 451
atctaaacac agtccatgct aaaaagcttc gagttgttgc caccccaccc tcctcaaacc    60
```

<210> SEQ ID NO 452
<211> LENGTH: 60
<212> TYPE: DNA
<213> ORGANISM: Homo sapiens

<400> SEQUENCE: 452
catgatagtt aagagatcat atctagaatc gactcactca catctgcctc atgatggtta    60

<210> SEQ ID NO 453
<211> LENGTH: 60
<212> TYPE: DNA
<213> ORGANISM: Homo sapiens

<400> SEQUENCE: 453
cttcaccaga cattttaaat aaaatctatc gaggtccccc caccccaca tgtctctacc    60

<210> SEQ ID NO 454
<211> LENGTH: 60
<212> TYPE: DNA
<213> ORGANISM: Homo sapiens

<400> SEQUENCE: 454
cactgcccca cctcttactg gcatctcctc gagacaattc attgaacctg actcatttct    60

<210> SEQ ID NO 455
<211> LENGTH: 60
<212> TYPE: DNA
<213> ORGANISM: Homo sapiens

<400> SEQUENCE: 455
ccaaatccga acctcctctg tgaagcattc gagttgttgc caccccaccc tcctcaaacc    60

<210> SEQ ID NO 456
<211> LENGTH: 60
<212> TYPE: DNA
<213> ORGANISM: Homo sapiens

<400> SEQUENCE: 456
agagagctgg agaagagggc gagaagagtc gaattgtgct ccattgttac cttttttgtgt    60

<210> SEQ ID NO 457
<211> LENGTH: 60
<212> TYPE: DNA
<213> ORGANISM: Homo sapiens

<400> SEQUENCE: 457
cccacctccc accagacagt ggaagcagtc gagtgctgtg agcaaagagg ccctgggcca    60

<210> SEQ ID NO 458
<211> LENGTH: 60
<212> TYPE: DNA
<213> ORGANISM: Homo sapiens

<400> SEQUENCE: 458
cccacctccc accagacagt ggaagcagtc gaagcaaaac tgtggagatt gggtcggtga    60

<210> SEQ ID NO 459
<211> LENGTH: 60
<212> TYPE: DNA
<213> ORGANISM: Homo sapiens

<400> SEQUENCE: 459
gcctgcaggg ggcgccccg cgcctgcctc gaccacacat ccacatggac gcatggcagg    60

```
<210> SEQ ID NO 460
<211> LENGTH: 60
<212> TYPE: DNA
<213> ORGANISM: Homo sapiens

<400> SEQUENCE: 460
cgccgggccg acacccacat tgtcttcttc gaacccctt aaaccactga ccttgtccct    60

<210> SEQ ID NO 461
<211> LENGTH: 60
<212> TYPE: DNA
<213> ORGANISM: Homo sapiens

<400> SEQUENCE: 461
cgccgggccg acacccacat tgtcttcttc gagttccttg gaagctttaa tttgcattcc    60

<210> SEQ ID NO 462
<211> LENGTH: 60
<212> TYPE: DNA
<213> ORGANISM: Homo sapiens

<400> SEQUENCE: 462
agacccggac gtctccgcga ggcggccatc gattttgctg atgcaataca gttttacagg    60

<210> SEQ ID NO 463
<211> LENGTH: 60
<212> TYPE: DNA
<213> ORGANISM: Homo sapiens

<400> SEQUENCE: 463
cgccgggccg acacccacat tgtcttcttc gaatctccca tctgctcttt caaccaagct    60

<210> SEQ ID NO 464
<211> LENGTH: 60
<212> TYPE: DNA
<213> ORGANISM: Homo sapiens

<400> SEQUENCE: 464
cgccgggccg acacccacat tgtcttcttc gacatccact cttctgggca ttcccagcct    60

<210> SEQ ID NO 465
<211> LENGTH: 60
<212> TYPE: DNA
<213> ORGANISM: Homo sapiens

<400> SEQUENCE: 465
actgatggca tcccccgtgc gcttccggtc gatggggcca gggggctatg gggataacct    60

<210> SEQ ID NO 466
<211> LENGTH: 60
<212> TYPE: DNA
<213> ORGANISM: Homo sapiens

<400> SEQUENCE: 466
cgccgggccg acacccacat tgtcttcttc gattttatag tatgtgaatt atatctcaac    60

<210> SEQ ID NO 467
<211> LENGTH: 60
<212> TYPE: DNA
<213> ORGANISM: Homo sapiens

<400> SEQUENCE: 467
```

```
acagctgcat cttatgtcag aagagtgttc gactccagtg aagattattt tgtgtcagtc    60

<210> SEQ ID NO 468
<211> LENGTH: 60
<212> TYPE: DNA
<213> ORGANISM: Homo sapiens

<400> SEQUENCE: 468
cagaatcgcc caccttgtag cccagggatc gacggcaagc cactcaccct cagccctatc    60

<210> SEQ ID NO 469
<211> LENGTH: 60
<212> TYPE: DNA
<213> ORGANISM: Homo sapiens

<400> SEQUENCE: 469
caaatcccgg ctatctctta gaattgcatc gagtttatct tgagtttata tattttaatg    60

<210> SEQ ID NO 470
<211> LENGTH: 60
<212> TYPE: DNA
<213> ORGANISM: Homo sapiens

<400> SEQUENCE: 470
tccatcccca acttcaatga cttctacatc gacatagtac tgaaagtctt tgctagagta    60

<210> SEQ ID NO 471
<211> LENGTH: 60
<212> TYPE: DNA
<213> ORGANISM: Homo sapiens

<400> SEQUENCE: 471
agacccggac gtctccgcga ggcggccatc gacatatttc ctgttccctt ggaataaaaa    60

<210> SEQ ID NO 472
<211> LENGTH: 60
<212> TYPE: DNA
<213> ORGANISM: Homo sapiens

<400> SEQUENCE: 472
cgccgggccg acaccacat tgtcttcttc gatttgcatt tccctaatga tcggtgatgt    60

<210> SEQ ID NO 473
<211> LENGTH: 60
<212> TYPE: DNA
<213> ORGANISM: Homo sapiens

<400> SEQUENCE: 473
aggacagaga ccctaattc caccaccatc gacccttctg ctttctctcc aggggatggc    60

<210> SEQ ID NO 474
<211> LENGTH: 60
<212> TYPE: DNA
<213> ORGANISM: Homo sapiens

<400> SEQUENCE: 474
cgccgggccg acacccacat tgtcttcttc gatccctggg ctacaaggtg ggcgattctg    60

<210> SEQ ID NO 475
<211> LENGTH: 60
<212> TYPE: DNA
<213> ORGANISM: Homo sapiens

<400> SEQUENCE: 475
```

```
ttcctgaaaa aaaatggcta cttattagtc gatggccgcc tcgcggagac gtccgggtct    60
```

<210> SEQ ID NO 476
<211> LENGTH: 60
<212> TYPE: DNA
<213> ORGANISM: Homo sapiens

<400> SEQUENCE: 476

```
agcacaggca agatgacctt caaggtgctc gaccccactg ctggccatcc ctacctgcat    60
```

<210> SEQ ID NO 477
<211> LENGTH: 60
<212> TYPE: DNA
<213> ORGANISM: Homo sapiens

<400> SEQUENCE: 477

```
cacttttat agaagagaaa gtgaagattc gatggccgcc tcgcggagac gtccgggtct     60
```

<210> SEQ ID NO 478
<211> LENGTH: 60
<212> TYPE: DNA
<213> ORGANISM: Homo sapiens

<400> SEQUENCE: 478

```
ccacgtgtcg cgggcctgag tgtgcccctc gaggctgtag tgattcatga ttgtaccact    60
```

<210> SEQ ID NO 479
<211> LENGTH: 60
<212> TYPE: DNA
<213> ORGANISM: Homo sapiens

<400> SEQUENCE: 479

```
cgccgggccg acacccacat tgtcttcttc gaaaaaaaaa aaaaagaaa aaaaagaaa      60
```

<210> SEQ ID NO 480
<211> LENGTH: 60
<212> TYPE: DNA
<213> ORGANISM: Homo sapiens

<400> SEQUENCE: 480

```
gtgcccacac tcctcagccc tccggtggtc gaccgcctgg gctcaaccaa tcctcccatc    60
```

<210> SEQ ID NO 481
<211> LENGTH: 60
<212> TYPE: DNA
<213> ORGANISM: Homo sapiens

<400> SEQUENCE: 481

```
gtgccctcct cgcccctgat gggtctggtc gagaccagcc tcaacatgga gaaacaccat    60
```

<210> SEQ ID NO 482
<211> LENGTH: 60
<212> TYPE: DNA
<213> ORGANISM: Homo sapiens

<400> SEQUENCE: 482

```
ataggcaccg aatagataaa tagatagatc gatagataat agatagaaat atgcagaaag    60
```

<210> SEQ ID NO 483
<211> LENGTH: 60
<212> TYPE: DNA
<213> ORGANISM: Homo sapiens

```
<400> SEQUENCE: 483
gccagagtgg aaatggaatt gggagaaatc gaagagtttt aatatctgct gtaaaccttg    60

<210> SEQ ID NO 484
<211> LENGTH: 60
<212> TYPE: DNA
<213> ORGANISM: Homo sapiens

<400> SEQUENCE: 484
ataggcaccg aatagataaa tagatagatc gaagattctg acaataacta agagcagagg    60

<210> SEQ ID NO 485
<211> LENGTH: 60
<212> TYPE: DNA
<213> ORGANISM: Homo sapiens

<400> SEQUENCE: 485
gccagagtgg aaatggaatt gggagaaatc gaaatgagtc aaggaaactt acaagctttt    60

<210> SEQ ID NO 486
<211> LENGTH: 60
<212> TYPE: DNA
<213> ORGANISM: Homo sapiens

<400> SEQUENCE: 486
gccagagtgg aaatggaatt gggagaaatc gattcggacc actgcatgag aagagaggca    60

<210> SEQ ID NO 487
<211> LENGTH: 60
<212> TYPE: DNA
<213> ORGANISM: Homo sapiens

<400> SEQUENCE: 487
atcttgggta actagggagt ggagttgttc gacttcgcca gctgaagtga tcctcccact    60

<210> SEQ ID NO 488
<211> LENGTH: 60
<212> TYPE: DNA
<213> ORGANISM: Homo sapiens

<400> SEQUENCE: 488
attcctagac acatacaacc tgccaagatc gaagagtttt aatatctgct gtaaaccttg    60

<210> SEQ ID NO 489
<211> LENGTH: 60
<212> TYPE: DNA
<213> ORGANISM: Homo sapiens

<400> SEQUENCE: 489
tacagatttt ggtatctgag tggagatctc gaagattctg acaataacta agagcagagg    60

<210> SEQ ID NO 490
<211> LENGTH: 60
<212> TYPE: DNA
<213> ORGANISM: Homo sapiens

<400> SEQUENCE: 490
ctgttctggt tttggatttc ttcaaggttc gatttctccc aattccattt ccactctggc    60

<210> SEQ ID NO 491
<211> LENGTH: 60
<212> TYPE: DNA
<213> ORGANISM: Homo sapiens
```

<400> SEQUENCE: 491
cgaggcgagt ggatcatgag tcaggagatc gatttaaaaa tagtttattt taataatgtt    60

<210> SEQ ID NO 492
<211> LENGTH: 60
<212> TYPE: DNA
<213> ORGANISM: Homo sapiens

<400> SEQUENCE: 492
ataaagaaaa tgcagtacac atacacaatc gagaccagcc tggtcaatac ggcaaaaccc    60

<210> SEQ ID NO 493
<211> LENGTH: 60
<212> TYPE: DNA
<213> ORGANISM: Homo sapiens

<400> SEQUENCE: 493
ggcaggtgga tcacctgagg tcaggagttc gaactcttaa cctcaggtga tccacccgca    60

<210> SEQ ID NO 494
<211> LENGTH: 60
<212> TYPE: DNA
<213> ORGANISM: Homo sapiens

<400> SEQUENCE: 494
gtagtaggga ttcattcaaa agcaccactc gaggatttac gatgcagtgc gacaaccctg    60

<210> SEQ ID NO 495
<211> LENGTH: 60
<212> TYPE: DNA
<213> ORGANISM: Homo sapiens

<400> SEQUENCE: 495
tatatttata tcccagattc aatcatcatc gagaccagcc tagctaacat ggtgaaaccc    60

<210> SEQ ID NO 496
<211> LENGTH: 60
<212> TYPE: DNA
<213> ORGANISM: Homo sapiens

<400> SEQUENCE: 496
tgataaacat cttaacagga aacagggttc gattgtcatc ctctaggact tacagtttct    60

<210> SEQ ID NO 497
<211> LENGTH: 60
<212> TYPE: DNA
<213> ORGANISM: Homo sapiens

<400> SEQUENCE: 497
ggcaggcaga tcacttgagg tcaggagttc gaacacctga cctcaggtga tctgcccacc    60

<210> SEQ ID NO 498
<211> LENGTH: 60
<212> TYPE: DNA
<213> ORGANISM: Homo sapiens

<400> SEQUENCE: 498
ggcaggtgga tcacctgagg tcaggagttc gaactcctga cctcagggga tccacccacc    60

<210> SEQ ID NO 499
<211> LENGTH: 60
<212> TYPE: DNA

<213> ORGANISM: Homo sapiens

<400> SEQUENCE: 499
ctgttctggt tttggatttc ttcaaggttc gaaagcagaa tgttttgatc atgagaaaat    60

<210> SEQ ID NO 500
<211> LENGTH: 60
<212> TYPE: DNA
<213> ORGANISM: Homo sapiens

<400> SEQUENCE: 500
aacaaatgtt taccaagtac ctactatgtc gaaaatcaga tggttatagg tgtgtggcct    60

<210> SEQ ID NO 501
<211> LENGTH: 60
<212> TYPE: DNA
<213> ORGANISM: Homo sapiens

<400> SEQUENCE: 501
cgaggcgagt ggatcatgag tcaggagatc gaaaggtatc tgtcttggaa aaaccttgat    60

<210> SEQ ID NO 502
<211> LENGTH: 60
<212> TYPE: DNA
<213> ORGANISM: Homo sapiens

<400> SEQUENCE: 502
aaagatgttg agtggagttt gcagttgttc gaaccctgtt tcctgttaag atgtttatca    60

<210> SEQ ID NO 503
<211> LENGTH: 60
<212> TYPE: DNA
<213> ORGANISM: Homo sapiens

<400> SEQUENCE: 503
cgaggcgagt ggatcatgag tcaggagatc gacaataaac tgaagagaca gcattaatgt    60

<210> SEQ ID NO 504
<211> LENGTH: 60
<212> TYPE: DNA
<213> ORGANISM: Homo sapiens

<400> SEQUENCE: 504
aaggtgggtg gatcatgagg tcaggagttc gaacccctga cctcaaatga tccacctagg    60

<210> SEQ ID NO 505
<211> LENGTH: 60
<212> TYPE: DNA
<213> ORGANISM: Homo sapiens

<400> SEQUENCE: 505
aaggaaggaa tcaaacactt ctgaaaagtc gagaccagcc tggtcaatac ggcaaaaccc    60

<210> SEQ ID NO 506
<211> LENGTH: 60
<212> TYPE: DNA
<213> ORGANISM: Homo sapiens

<400> SEQUENCE: 506
tatatttata tcccagattc aatcatcatc gagaccagta tgggcaacac ggcaagattc    60

<210> SEQ ID NO 507
<211> LENGTH: 60

```
<212> TYPE: DNA
<213> ORGANISM: Homo sapiens

<400> SEQUENCE: 507
aagctcaata atcccaagc acacacactc gaccttcatc acaacagtgc tcataggttt    60

<210> SEQ ID NO 508
<211> LENGTH: 60
<212> TYPE: DNA
<213> ORGANISM: Homo sapiens

<400> SEQUENCE: 508
aagctcaata atcccaagc acacacactc gaggacccct ccacccaaaa aaaagcaagg    60

<210> SEQ ID NO 509
<211> LENGTH: 60
<212> TYPE: DNA
<213> ORGANISM: Homo sapiens

<400> SEQUENCE: 509
aagctcaata atcccaagc acacacactc gaagtcagct gggatgaagg aagggaaaga    60

<210> SEQ ID NO 510
<211> LENGTH: 60
<212> TYPE: DNA
<213> ORGANISM: Homo sapiens

<400> SEQUENCE: 510
aagctcaata atcccaagc acacacactc gaaagcagcc acaggcagtc agtatatgtc    60

<210> SEQ ID NO 511
<211> LENGTH: 60
<212> TYPE: DNA
<213> ORGANISM: Homo sapiens

<400> SEQUENCE: 511
aagctcaata atcccaagc acacacactc gaataaatag tatctttgcc caataatatg    60

<210> SEQ ID NO 512
<211> LENGTH: 60
<212> TYPE: DNA
<213> ORGANISM: Homo sapiens

<400> SEQUENCE: 512
aagctcaata atcccaagc acacacactc gaatgtaaaa tgagagacct gatgcacagt    60

<210> SEQ ID NO 513
<211> LENGTH: 60
<212> TYPE: DNA
<213> ORGANISM: Homo sapiens

<400> SEQUENCE: 513
aagctcaata atcccaagc acacacactc gaggcaaagt gggcattttc cagcaccctg    60

<210> SEQ ID NO 514
<211> LENGTH: 60
<212> TYPE: DNA
<213> ORGANISM: Homo sapiens

<400> SEQUENCE: 514
aagctcaata atcccaagc acacacactc gaaatggctc cagattcctg gccgagtagg    60

<210> SEQ ID NO 515
```

```
<211> LENGTH: 60
<212> TYPE: DNA
<213> ORGANISM: Homo sapiens

<400> SEQUENCE: 515
acctgaatac attgagatta ttttgcaatc gagatctgag tgtgagggtg gggggctgag    60

<210> SEQ ID NO 516
<211> LENGTH: 60
<212> TYPE: DNA
<213> ORGANISM: Homo sapiens

<400> SEQUENCE: 516
aaggttgtga aaattttatc ttacgtgatc gatgacacaa agtgtgttta aatacagggt    60

<210> SEQ ID NO 517
<211> LENGTH: 60
<212> TYPE: DNA
<213> ORGANISM: Homo sapiens

<400> SEQUENCE: 517
gtatgtcagg ggtcagaggg ggcagaggtc gaggagacta cttaggaata atacaacaaa    60

<210> SEQ ID NO 518
<211> LENGTH: 60
<212> TYPE: DNA
<213> ORGANISM: Homo sapiens

<400> SEQUENCE: 518
gtatgtcagg ggtcagaggg ggcagaggtc gaggacctag ctacccggca aacatcaaat    60

<210> SEQ ID NO 519
<211> LENGTH: 60
<212> TYPE: DNA
<213> ORGANISM: Homo sapiens

<400> SEQUENCE: 519
gtatgtcagg ggtcagaggg ggcagaggtc gactttaaca taatttatta aaattatact    60

<210> SEQ ID NO 520
<211> LENGTH: 60
<212> TYPE: DNA
<213> ORGANISM: Homo sapiens

<400> SEQUENCE: 520
gtatgtcagg ggtcagaggg ggcagaggtc gaacttttac catgagtctt ttactgaaaa    60

<210> SEQ ID NO 521
<211> LENGTH: 60
<212> TYPE: DNA
<213> ORGANISM: Homo sapiens

<400> SEQUENCE: 521
gtatgtcagg ggtcagaggg ggcagaggtc gactttgatg aacaaaaatg gatatctaac    60

<210> SEQ ID NO 522
<211> LENGTH: 60
<212> TYPE: DNA
<213> ORGANISM: Homo sapiens

<400> SEQUENCE: 522
ggtgggtgga ttggttgaag tcagcagttc gaacttttac catgagtctt ttactgaaaa    60
```

```
<210> SEQ ID NO 523
<211> LENGTH: 60
<212> TYPE: DNA
<213> ORGANISM: Homo sapiens

<400> SEQUENCE: 523
ggtgggtgga ttggttgaag tcagcagttc gaactgccac cttgtccctc ttctatcact    60

<210> SEQ ID NO 524
<211> LENGTH: 60
<212> TYPE: DNA
<213> ORGANISM: Homo sapiens

<400> SEQUENCE: 524
agggagagag aggagtctaa agtttatctc gaggggtgg gagggcatgt ctatttgctc    60

<210> SEQ ID NO 525
<211> LENGTH: 60
<212> TYPE: DNA
<213> ORGANISM: Homo sapiens

<400> SEQUENCE: 525
tttacaatat ccctttttaa gtgcaaagtc gatggttgat gttgtgtgtg ggtgtgtacg    60

<210> SEQ ID NO 526
<211> LENGTH: 60
<212> TYPE: DNA
<213> ORGANISM: Homo sapiens

<400> SEQUENCE: 526
tggtgaggag ggcagtgtcc aaggcaagtc gatgcaagag tcccaggaca gtcaaagaat    60

<210> SEQ ID NO 527
<211> LENGTH: 60
<212> TYPE: DNA
<213> ORGANISM: Homo sapiens

<400> SEQUENCE: 527
atgggtaagt gatgaatggg tggatagttc gatgtttaga ttttcccaac tgggttctat    60

<210> SEQ ID NO 528
<211> LENGTH: 60
<212> TYPE: DNA
<213> ORGANISM: Homo sapiens

<400> SEQUENCE: 528
atgggtaagt gatgaatggg tggatagttc gacgtgccgg aggtgcgtgg ggaactgttc    60

<210> SEQ ID NO 529
<211> LENGTH: 60
<212> TYPE: DNA
<213> ORGANISM: Homo sapiens

<400> SEQUENCE: 529
tttttttttt tttttagat atagggtttc gaggctaatc tggctgagag aggagggtct    60

<210> SEQ ID NO 530
<211> LENGTH: 60
<212> TYPE: DNA
<213> ORGANISM: Homo sapiens

<400> SEQUENCE: 530
ccctggacag caactaagct gtcctgggtc gagactactc aaatattttt atttatttct    60
```

<210> SEQ ID NO 531
<211> LENGTH: 60
<212> TYPE: DNA
<213> ORGANISM: Homo sapiens

<400> SEQUENCE: 531
agacacacac tgagacagct caatctgctc gaggatcaaa ggatgttgtg tgaggcttgc    60

<210> SEQ ID NO 532
<211> LENGTH: 60
<212> TYPE: DNA
<213> ORGANISM: Homo sapiens

<400> SEQUENCE: 532
gaccaggctg gagtgcagtg gcacaatctc gagccactgc actccatcct gggcagcaga    60

<210> SEQ ID NO 533
<211> LENGTH: 60
<212> TYPE: DNA
<213> ORGANISM: Homo sapiens

<400> SEQUENCE: 533
gattccttat agtttaaaat taaattattc gagtctctta atgacctgcg agattgtac    60

<210> SEQ ID NO 534
<211> LENGTH: 60
<212> TYPE: DNA
<213> ORGANISM: Homo sapiens

<400> SEQUENCE: 534
cagtcaggtg gatcacgagg tcaggagatc gatctcctga cctcgtgatc cgcccgcctc    60

<210> SEQ ID NO 535
<211> LENGTH: 60
<212> TYPE: DNA
<213> ORGANISM: Homo sapiens

<400> SEQUENCE: 535
gaggcgggcg gatcacgagg tcaggagatc gatctcctga cctcgtgatc cgcccgcctc    60

<210> SEQ ID NO 536
<211> LENGTH: 60
<212> TYPE: DNA
<213> ORGANISM: Homo sapiens

<400> SEQUENCE: 536
gggtttcacc ttgttagcca ggatggtctc gagaccatcc tggctaacac ggtgaaaccc    60

<210> SEQ ID NO 537
<211> LENGTH: 60
<212> TYPE: DNA
<213> ORGANISM: Homo sapiens

<400> SEQUENCE: 537
acactgatta aatcttaatt attccatttc gatccctcaa ggatcaggac tgtgttgcat    60

<210> SEQ ID NO 538
<211> LENGTH: 60
<212> TYPE: DNA
<213> ORGANISM: Homo sapiens

<400> SEQUENCE: 538
acactgatta aatcttaatt attccatttc gagggaataa tctcctaaac atttctggtg    60

<210> SEQ ID NO 539
<211> LENGTH: 60
<212> TYPE: DNA
<213> ORGANISM: Homo sapiens

<400> SEQUENCE: 539
cttgggccct atcttatgta tggagctgtc gagtttatgt tcttaccctt gtttctcttt    60

<210> SEQ ID NO 540
<211> LENGTH: 60
<212> TYPE: DNA
<213> ORGANISM: Homo sapiens

<400> SEQUENCE: 540
atgctaaatt atgtaaaatg aatatgttc gagttcatag atactcaagg gcccctcagt    60

<210> SEQ ID NO 541
<211> LENGTH: 60
<212> TYPE: DNA
<213> ORGANISM: Homo sapiens

<400> SEQUENCE: 541
caacaatttt attaattttc aactttcatc gattttataa aattatcagt aataaccttt    60

<210> SEQ ID NO 542
<211> LENGTH: 60
<212> TYPE: DNA
<213> ORGANISM: Homo sapiens

<400> SEQUENCE: 542
gaggtgggca gatcacgagg tcaggagatc gatctcctga cctcgtgatc cgcccgcctc    60

<210> SEQ ID NO 543
<211> LENGTH: 60
<212> TYPE: DNA
<213> ORGANISM: Homo sapiens

<400> SEQUENCE: 543
gaggcgggcg gatcacgagg tcaggagatc gatctcccga cctcgtgatc cgcccgcctc    60

<210> SEQ ID NO 544
<211> LENGTH: 60
<212> TYPE: DNA
<213> ORGANISM: Homo sapiens

<400> SEQUENCE: 544
tgacaccata cattttattt ctcccttctc gagattttgt tattaagctt ccgtctcgtt    60

<210> SEQ ID NO 545
<211> LENGTH: 60
<212> TYPE: DNA
<213> ORGANISM: Homo sapiens

<400> SEQUENCE: 545
agtcctttat ttctgttaca atcttaaatc gagattttgt tattaagctt ccgtctcgtt    60

<210> SEQ ID NO 546
<211> LENGTH: 60
<212> TYPE: DNA
<213> ORGANISM: Homo sapiens

<400> SEQUENCE: 546

```
tacctttta gagctatgtc atgtatgttc gaacagagtt taccacagct ttgcagcgcg       60
```

<210> SEQ ID NO 547
<211> LENGTH: 60
<212> TYPE: DNA
<213> ORGANISM: Homo sapiens

<400> SEQUENCE: 547

```
tgtattctgt atcacttaga ctcttctttc gaagaaggaa tcttaaacaa gagaagcaag       60
```

<210> SEQ ID NO 548
<211> LENGTH: 60
<212> TYPE: DNA
<213> ORGANISM: Homo sapiens

<400> SEQUENCE: 548

```
agttgttttt ccttgaaaag ggtttacctc gacggttaca atttcagtat gcacgggact       60
```

<210> SEQ ID NO 549
<211> LENGTH: 60
<212> TYPE: DNA
<213> ORGANISM: Homo sapiens

<400> SEQUENCE: 549

```
ttaacctagc agatctggtt cttctggttc gaggtattta tatcaccttg agtattattt       60
```

<210> SEQ ID NO 550
<211> LENGTH: 60
<212> TYPE: DNA
<213> ORGANISM: Homo sapiens

<400> SEQUENCE: 550

```
cctaataaag aaaaaaaaat gagtcccttc gaagcacaaa gttacaggac atggcatcca       60
```

<210> SEQ ID NO 551
<211> LENGTH: 60
<212> TYPE: DNA
<213> ORGANISM: Homo sapiens

<400> SEQUENCE: 551

```
tcctttggcc tggtaatctt ttcaatattc gaagcacaaa gttacaggac atggcatcca       60
```

<210> SEQ ID NO 552
<211> LENGTH: 60
<212> TYPE: DNA
<213> ORGANISM: Homo sapiens

<400> SEQUENCE: 552

```
ctgctccatg tctgtattcc tactttattc gaaagcatct tgtgtcatt gtccatgctc        60
```

<210> SEQ ID NO 553
<211> LENGTH: 60
<212> TYPE: DNA
<213> ORGANISM: Homo sapiens

<400> SEQUENCE: 553

```
cctaaactaa gcttgggctt aagatccatc gaaaggatac ttttatagga accaggctag       60
```

<210> SEQ ID NO 554
<211> LENGTH: 60
<212> TYPE: DNA
<213> ORGANISM: Homo sapiens

<400> SEQUENCE: 554

```
atatatatat atcacaatgc ctaagggatc gaatagcttt ttaagaacag tgtataaaat    60
```

<210> SEQ ID NO 555
<211> LENGTH: 60
<212> TYPE: DNA
<213> ORGANISM: Homo sapiens

<400> SEQUENCE: 555

```
ctctctgatt tgccacataa agtaggcatc gattccaaat aaattagttg gtgatgtgga    60
```

<210> SEQ ID NO 556
<211> LENGTH: 60
<212> TYPE: DNA
<213> ORGANISM: Homo sapiens

<400> SEQUENCE: 556

```
acttcatgca caagttaggt atttactctc gagattataa acattttcat ttggattttg    60
```

<210> SEQ ID NO 557
<211> LENGTH: 60
<212> TYPE: DNA
<213> ORGANISM: Homo sapiens

<400> SEQUENCE: 557

```
agaaaatata gtattgattg ctttcaagtc gatgcgcgcc cgccggggcc cggtcggagc    60
```

<210> SEQ ID NO 558
<211> LENGTH: 60
<212> TYPE: DNA
<213> ORGANISM: Homo sapiens

<400> SEQUENCE: 558

```
tactgtagta agttctctga ggaggatatc gattttttat tgtatcctat attttttcta    60
```

<210> SEQ ID NO 559
<211> LENGTH: 60
<212> TYPE: DNA
<213> ORGANISM: Homo sapiens

<400> SEQUENCE: 559

```
tactgtagta agttctctga ggaggatatc gaagtcttgg attaaggttc attcaacaaa    60
```

<210> SEQ ID NO 560
<211> LENGTH: 60
<212> TYPE: DNA
<213> ORGANISM: Homo sapiens

<400> SEQUENCE: 560

```
cacttcccca acataagcct cggtctcttc gagggcgggc ccggcggccc cggagcaaac    60
```

<210> SEQ ID NO 561
<211> LENGTH: 60
<212> TYPE: DNA
<213> ORGANISM: Homo sapiens

<400> SEQUENCE: 561

```
gagttcagcg tgccgccggg cgtgaaagtc gaggcatatt tgagtttagg gaggtgttgc    60
```

<210> SEQ ID NO 562
<211> LENGTH: 60
<212> TYPE: DNA
<213> ORGANISM: Homo sapiens

```
<400> SEQUENCE: 562
gagttcagcg tgccgccggg cgtgaaagtc gactctgggc ccagaccaca gaaggagggg      60

<210> SEQ ID NO 563
<211> LENGTH: 60
<212> TYPE: DNA
<213> ORGANISM: Homo sapiens

<400> SEQUENCE: 563
gagttcagcg tgccgccggg cgtgaaagtc gatttgttta tggttttatc cccagtgcct      60

<210> SEQ ID NO 564
<211> LENGTH: 60
<212> TYPE: DNA
<213> ORGANISM: Homo sapiens

<400> SEQUENCE: 564
tttgttgaat gaaccttaat ccaagacttc gattttttat tgtatcctat attttttcta      60

<210> SEQ ID NO 565
<211> LENGTH: 60
<212> TYPE: DNA
<213> ORGANISM: Homo sapiens

<400> SEQUENCE: 565
ttccatagat tacttttcaa atcatccttc gaagctggcg gctgagggcc cggcgccaag      60

<210> SEQ ID NO 566
<211> LENGTH: 60
<212> TYPE: DNA
<213> ORGANISM: Homo sapiens

<400> SEQUENCE: 566
gtttgctccg gggccgccgg gcccgccctc gattttaaca ccaccatggt ttgaatgaat      60

<210> SEQ ID NO 567
<211> LENGTH: 60
<212> TYPE: DNA
<213> ORGANISM: Homo sapiens

<400> SEQUENCE: 567
tccattgtct tattccagtc taggcttgtc gagttgcagg ccgccctggt ggctagacat      60

<210> SEQ ID NO 568
<211> LENGTH: 60
<212> TYPE: DNA
<213> ORGANISM: Homo sapiens

<400> SEQUENCE: 568
aaaaaacaat tatgtaattg aaaacccatc gaggggctta ctaatgcctt ttagctccct      60

<210> SEQ ID NO 569
<211> LENGTH: 60
<212> TYPE: DNA
<213> ORGANISM: Homo sapiens

<400> SEQUENCE: 569
gacccccggg aattggctcc agcacatctc gagggcgggc ccggcggccc cggagcaaac      60

<210> SEQ ID NO 570
<211> LENGTH: 60
<212> TYPE: DNA
<213> ORGANISM: Homo sapiens
```

<400> SEQUENCE: 570
aaaaaacaat tatgtaattg aaaacccatc gaagctcttt ggttccacag agtgattctg    60

<210> SEQ ID NO 571
<211> LENGTH: 60
<212> TYPE: DNA
<213> ORGANISM: Homo sapiens

<400> SEQUENCE: 571
aggcattcgt tcttcagctc ttctataatc gatttttat tgtatcctat attttttcta    60

<210> SEQ ID NO 572
<211> LENGTH: 60
<212> TYPE: DNA
<213> ORGANISM: Homo sapiens

<400> SEQUENCE: 572
gctcttataa attatgtatt caaagaaatc gagttgcagg ccgccctggt ggctagacat    60

<210> SEQ ID NO 573
<211> LENGTH: 60
<212> TYPE: DNA
<213> ORGANISM: Homo sapiens

<400> SEQUENCE: 573
cccgcggcgg agctgctact gtttactttc gaagcttctt cctttcggcc cccaggccta    60

<210> SEQ ID NO 574
<211> LENGTH: 60
<212> TYPE: DNA
<213> ORGANISM: Homo sapiens

<400> SEQUENCE: 574
gctcttataa attatgtatt caaagaaatc gaactggcgg caaccgctgc agcgcctgct    60

<210> SEQ ID NO 575
<211> LENGTH: 60
<212> TYPE: DNA
<213> ORGANISM: Homo sapiens

<400> SEQUENCE: 575
aaaaaacaat tatgtaattg aaaacccatc gagggctta ctaatgcctt ttagctccct    60

<210> SEQ ID NO 576
<211> LENGTH: 60
<212> TYPE: DNA
<213> ORGANISM: Homo sapiens

<400> SEQUENCE: 576
tctcctgcct accacactgt gagaaagctc gagggcgggc ccggcggccc cggagcaaac    60

<210> SEQ ID NO 577
<211> LENGTH: 60
<212> TYPE: DNA
<213> ORGANISM: Homo sapiens

<400> SEQUENCE: 577
gagttcagcg tgccgccggg cgtgaaagtc gaattctccc aggagccact gtcagaaccc    60

<210> SEQ ID NO 578
<211> LENGTH: 60
<212> TYPE: DNA

```
<213> ORGANISM: Homo sapiens

<400> SEQUENCE: 578
ccgcgcccgc agggcccgcc ccgcgccgtc gacaatgtta ttctttgttt ctcttaccaa    60

<210> SEQ ID NO 579
<211> LENGTH: 60
<212> TYPE: DNA
<213> ORGANISM: Homo sapiens

<400> SEQUENCE: 579
gaaggcccgg tgcgcccagc tgtgctcctc gagaacagcc aggctaacac ggagaaaccc    60

<210> SEQ ID NO 580
<211> LENGTH: 60
<212> TYPE: DNA
<213> ORGANISM: Homo sapiens

<400> SEQUENCE: 580
tccattgtct tattccagtc taggcttgtc gaactggcgg caaccgctgc agcgcctgct    60

<210> SEQ ID NO 581
<211> LENGTH: 60
<212> TYPE: DNA
<213> ORGANISM: Homo sapiens

<400> SEQUENCE: 581
ccgcgcccgc agggcccgcc ccgcgccgtc gatgtgttgg aagtcagggc ggcggtgccc    60

<210> SEQ ID NO 582
<211> LENGTH: 60
<212> TYPE: DNA
<213> ORGANISM: Homo sapiens

<400> SEQUENCE: 582
ccgcgcccgc agggcccgcc ccgcgccgtc gaggctttca agggatccag ggtggggtgc    60

<210> SEQ ID NO 583
<211> LENGTH: 60
<212> TYPE: DNA
<213> ORGANISM: Homo sapiens

<400> SEQUENCE: 583
ccgcgcccgc agggcccgcc ccgcgccgtc gacaatgtta ttctttgttt ctcttaccaa    60

<210> SEQ ID NO 584
<211> LENGTH: 60
<212> TYPE: DNA
<213> ORGANISM: Homo sapiens

<400> SEQUENCE: 584
ccgcgcccgc agggcccgcc ccgcgccgtc gatgtgttgg aagtcagggc ggcggtgccc    60

<210> SEQ ID NO 585
<211> LENGTH: 60
<212> TYPE: DNA
<213> ORGANISM: Homo sapiens

<400> SEQUENCE: 585
cacttcccca acataagcct cggtctcttc gagggcgggc ccggcggccc cggagcaaac    60

<210> SEQ ID NO 586
<211> LENGTH: 60
```

```
<212> TYPE: DNA
<213> ORGANISM: Homo sapiens

<400> SEQUENCE: 586
ccgcgcccgc agggcccgcc ccgcgccgtc gagaagcata aagcagggac aggtatggag       60

<210> SEQ ID NO 587
<211> LENGTH: 60
<212> TYPE: DNA
<213> ORGANISM: Homo sapiens

<400> SEQUENCE: 587
gaccccgggg aattggctcc agcacatctc gagggcgggc ccggcggccc cggagcaaac       60

<210> SEQ ID NO 588
<211> LENGTH: 60
<212> TYPE: DNA
<213> ORGANISM: Homo sapiens

<400> SEQUENCE: 588
gtttgctccg ggccgccgg gcccgccctc gattttaaca ccaccatggt ttgaatgaat        60

<210> SEQ ID NO 589
<211> LENGTH: 60
<212> TYPE: DNA
<213> ORGANISM: Homo sapiens

<400> SEQUENCE: 589
gtgtctcggc ccctggggc ccaccccttc gatttccctg ttgccgccgc gtttgcaaga       60

<210> SEQ ID NO 590
<211> LENGTH: 60
<212> TYPE: DNA
<213> ORGANISM: Homo sapiens

<400> SEQUENCE: 590
tctcctgcct accacactgt gagaaagctc gagggcgggc ccggcggccc cggagcaaac       60

<210> SEQ ID NO 591
<211> LENGTH: 60
<212> TYPE: DNA
<213> ORGANISM: Homo sapiens

<400> SEQUENCE: 591
gagttcagcg tgccgccggg cgtgaaagtc gaggcatatt tgagtttagg gaggtgttgc       60

<210> SEQ ID NO 592
<211> LENGTH: 60
<212> TYPE: DNA
<213> ORGANISM: Homo sapiens

<400> SEQUENCE: 592
gggcaccgcc gccctgactt ccaacacatc gatctctgcc tcgcgcagcc ccagcgtgcg       60

<210> SEQ ID NO 593
<211> LENGTH: 60
<212> TYPE: DNA
<213> ORGANISM: Homo sapiens

<400> SEQUENCE: 593 ccaccccgc ccgggggag tcgcccggtc gatttccaaa agctcacaca tgggtgcaca        60

<210> SEQ ID NO 594
```

```
<211> LENGTH: 60
<212> TYPE: DNA
<213> ORGANISM: Homo sapiens

<400> SEQUENCE: 594
gggcaccgcc gccctgactt ccaacacatc gaagaatggg tggggccttg cacctcatac      60

<210> SEQ ID NO 595
<211> LENGTH: 60
<212> TYPE: DNA
<213> ORGANISM: Homo sapiens

<400> SEQUENCE: 595 ccaccccgc cccgggggag tcgcccggtc gaccccctga catggggctg cctggagcag       60

<210> SEQ ID NO 596
<211> LENGTH: 60
<212> TYPE: DNA
<213> ORGANISM: Homo sapiens

<400> SEQUENCE: 596
gggcaccgcc gccctgactt ccaacacatc gagaagcata aagcagggac aggtatggag      60

<210> SEQ ID NO 597
<211> LENGTH: 60
<212> TYPE: DNA
<213> ORGANISM: Homo sapiens

<400> SEQUENCE: 597
gagttcagcg tgccgccggg cgtgaaagtc gactctgggc ccagaccaca gaaggagggg     60

<210> SEQ ID NO 598
<211> LENGTH: 60
<212> TYPE: DNA
<213> ORGANISM: Homo sapiens

<400> SEQUENCE: 598
aattctgttg gaagaataat ttaaaatatc gatgtggcga ccggctgtgg gggtcacgga     60

<210> SEQ ID NO 599
<211> LENGTH: 60
<212> TYPE: DNA
<213> ORGANISM: Homo sapiens

<400> SEQUENCE: 599
ttccatagat tacttttcaa atcatccttc gaagctggcg gctgagggcc cggcgccaag     60

<210> SEQ ID NO 600
<211> LENGTH: 60
<212> TYPE: DNA
<213> ORGANISM: Homo sapiens

<400> SEQUENCE: 600
gagttcagcg tgccgccggg cgtgaaagtc gatttgttta tggttttatc cccagtgcct    60

<210> SEQ ID NO 601
<211> LENGTH: 60
<212> TYPE: DNA
<213> ORGANISM: Homo sapiens

<400> SEQUENCE: 601
caccctccct tcttcctggg ccctcagatc gaccccccc accccaccg ggctggctgc       60
```

```
<210> SEQ ID NO 602
<211> LENGTH: 60
<212> TYPE: DNA
<213> ORGANISM: Homo sapiens

<400> SEQUENCE: 602 ccaccccgc cccgggggag tcgcccggtc gagggcctgg caagaagaca gaagccgact      60

<210> SEQ ID NO 603
<211> LENGTH: 60
<212> TYPE: DNA
<213> ORGANISM: Homo sapiens

<400> SEQUENCE: 603
tatgagtaat aattacaatt tccccctttc gacctccagg tccccgcca cttccacggc      60

<210> SEQ ID NO 604
<211> LENGTH: 60
<212> TYPE: DNA
<213> ORGANISM: Homo sapiens

<400> SEQUENCE: 604
cagaaactgc tggttgggct catactttc gagggccagc tccccgcacc cccaccaagc     60

<210> SEQ ID NO 605
<211> LENGTH: 60
<212> TYPE: DNA
<213> ORGANISM: Homo sapiens

<400> SEQUENCE: 605
ttcccctgta agattcattt cctgtgattc gagtcacagc tgtagtgggg tgggggtga     60

<210> SEQ ID NO 606
<211> LENGTH: 60
<212> TYPE: DNA
<213> ORGANISM: Homo sapiens

<400> SEQUENCE: 606
tctttgttac tggaatatac gaataaaatc gatgtggcga ccggctgtgg gggtcacgga     60

<210> SEQ ID NO 607
<211> LENGTH: 60
<212> TYPE: DNA
<213> ORGANISM: Homo sapiens

<400> SEQUENCE: 607
ccgcgcccgc agggcccgcc ccgcgccgtc gaggctttca agggatccag ggtggggtgc     60

<210> SEQ ID NO 608
<211> LENGTH: 60
<212> TYPE: DNA
<213> ORGANISM: Homo sapiens

<400> SEQUENCE: 608
ccgcgcccgc agggcccgcc ccgcgccgtc gacaatgtta ttctttgttt ctcttaccaa     60

<210> SEQ ID NO 609
<211> LENGTH: 60
<212> TYPE: DNA
<213> ORGANISM: Homo sapiens

<400> SEQUENCE: 609
ccgcgcccgc agggcccgcc ccgcgccgtc gatgtgttgg aagtcagggc ggcggtgccc     60
```

<210> SEQ ID NO 610
<211> LENGTH: 60
<212> TYPE: DNA
<213> ORGANISM: Homo sapiens

<400> SEQUENCE: 610
cacttcccca acataagcct cggtctcttc gagggcgggc ccggcggccc cggagcaaac    60

<210> SEQ ID NO 611
<211> LENGTH: 60
<212> TYPE: DNA
<213> ORGANISM: Homo sapiens

<400> SEQUENCE: 611
ccgcgcccgc agggcccgcc ccgcgccgtc gagaagcata aagcagggac aggtatggag    60

<210> SEQ ID NO 612
<211> LENGTH: 60
<212> TYPE: DNA
<213> ORGANISM: Homo sapiens

<400> SEQUENCE: 612
gacccccggg aattggctcc agcacatctc gagggcgggc ccggcggccc cggagcaaac    60

<210> SEQ ID NO 613
<211> LENGTH: 60
<212> TYPE: DNA
<213> ORGANISM: Homo sapiens

<400> SEQUENCE: 613
gtttgctccg gggccgccgg gcccgccctc gattttaaca ccaccatggt ttgaatgaat    60

<210> SEQ ID NO 614
<211> LENGTH: 60
<212> TYPE: DNA
<213> ORGANISM: Homo sapiens

<400> SEQUENCE: 614
gtgtctcggc ccctggggc cccacccttc gatttccctg ttgccgccgc gtttgcaaga    60

<210> SEQ ID NO 615
<211> LENGTH: 60
<212> TYPE: DNA
<213> ORGANISM: Homo sapiens

<400> SEQUENCE: 615
tctcctgcct accacactgt gagaaagctc gagggcgggc ccggcggccc cggagcaaac    60

<210> SEQ ID NO 616
<211> LENGTH: 60
<212> TYPE: DNA
<213> ORGANISM: Homo sapiens

<400> SEQUENCE: 616
gagttcagcg tgccgccggg cgtgaaagtc gaggcatatt tgagtttagg gaggtgttgc    60

<210> SEQ ID NO 617
<211> LENGTH: 60
<212> TYPE: DNA
<213> ORGANISM: Homo sapiens

<400> SEQUENCE: 617
gggcaccgcc gccctgactt ccaacacatc gatctctgcc tcgcgcagcc ccagcgtgcg    60

<210> SEQ ID NO 618
<211> LENGTH: 60
<212> TYPE: DNA
<213> ORGANISM: Homo sapiens

<400> SEQUENCE: 618 ccaccccgc cccgggggag tcgcccggtc gatttccaaa agctcacaca tgggtgcaca    60

<210> SEQ ID NO 619
<211> LENGTH: 60
<212> TYPE: DNA
<213> ORGANISM: Homo sapiens

<400> SEQUENCE: 619
gggcaccgcc gccctgactt ccaacacatc gaagaatggg tggggccttg cacctcatac    60

<210> SEQ ID NO 620
<211> LENGTH: 60
<212> TYPE: DNA
<213> ORGANISM: Homo sapiens

<400> SEQUENCE: 620 ccaccccgc cccgggggag tcgcccggtc gaccccctga catggggctg cctggagcag    60

<210> SEQ ID NO 621
<211> LENGTH: 60
<212> TYPE: DNA
<213> ORGANISM: Homo sapiens

<400> SEQUENCE: 621
gggcaccgcc gccctgactt ccaacacatc gagaagcata aagcagggac aggtatggag    60

<210> SEQ ID NO 622
<211> LENGTH: 60
<212> TYPE: DNA
<213> ORGANISM: Homo sapiens

<400> SEQUENCE: 622
gagttcagcg tgccgccggg cgtgaaagtc gactctgggc ccagaccaca gaaggagggg    60

<210> SEQ ID NO 623
<211> LENGTH: 60
<212> TYPE: DNA
<213> ORGANISM: Homo sapiens

<400> SEQUENCE: 623
aattctgttg gaagaataat ttaaaatatc gatgtggcga ccggctgtgg gggtcacgga    60

<210> SEQ ID NO 624
<211> LENGTH: 60
<212> TYPE: DNA
<213> ORGANISM: Homo sapiens

<400> SEQUENCE: 624
ttccatagat tacttttcaa atcatccttc gaagctggcg gctgagggcc cggcgccaag    60

<210> SEQ ID NO 625
<211> LENGTH: 60
<212> TYPE: DNA
<213> ORGANISM: Homo sapiens

<400> SEQUENCE: 625

```
gagttcagcg tgccgccggg cgtgaaagtc gatttgttta tggttttatc cccagtgcct      60
```

<210> SEQ ID NO 626
<211> LENGTH: 60
<212> TYPE: DNA
<213> ORGANISM: Homo sapiens

<400> SEQUENCE: 626

```
caccctccct tcttcctggg ccctcagatc gaccccccc accccaccg ggctggctgc      60
```

<210> SEQ ID NO 627
<211> LENGTH: 60
<212> TYPE: DNA
<213> ORGANISM: Homo sapiens

<400> SEQUENCE: 627

```
ccacccccgc cccgggggag tcgcccggtc gagggcctgg caagaagaca gaagccgact      60
```

<210> SEQ ID NO 628
<211> LENGTH: 60
<212> TYPE: DNA
<213> ORGANISM: Homo sapiens

<400> SEQUENCE: 628

```
tatgagtaat aattacaatt tccccctttc gacctccagg tcccccgcca cttccacggc      60
```

<210> SEQ ID NO 629
<211> LENGTH: 60
<212> TYPE: DNA
<213> ORGANISM: Homo sapiens

<400> SEQUENCE: 629

```
cagaaactgc tggttgggct catacttttc gagggccagc tccccgcacc cccaccaagc      60
```

<210> SEQ ID NO 630
<211> LENGTH: 60
<212> TYPE: DNA
<213> ORGANISM: Homo sapiens

<400> SEQUENCE: 630

```
ttcccctgta agattcattt cctgtgattc gagtcacagc tgtagtgggg tgggggtga      60
```

<210> SEQ ID NO 631
<211> LENGTH: 60
<212> TYPE: DNA
<213> ORGANISM: Homo sapiens

<400> SEQUENCE: 631

```
tctttgttac tggaatatac gaataaaatc gatgtggcga ccggctgtgg gggtcacgga      60
```

<210> SEQ ID NO 632
<211> LENGTH: 60
<212> TYPE: DNA
<213> ORGANISM: Homo sapiens

<400> SEQUENCE: 632

```
aaggcaggca gatcaggagc tcaagagatc gaaagaaaaa aaaaaaagca taaaaatcca      60
```

<210> SEQ ID NO 633
<211> LENGTH: 60
<212> TYPE: DNA
<213> ORGANISM: Homo sapiens

<400> SEQUENCE: 633

```
aaggcaggca gatcaggagc tcaagagatc gaacgctaag tgtagtttaa cacctactag    60
```

<210> SEQ ID NO 634
<211> LENGTH: 60
<212> TYPE: DNA
<213> ORGANISM: Homo sapiens

<400> SEQUENCE: 634

```
atagtaaaat gtgaaaatgt tacagttatc gaagttcagc gagtatattt ttactgatac    60
```

<210> SEQ ID NO 635
<211> LENGTH: 60
<212> TYPE: DNA
<213> ORGANISM: Homo sapiens

<400> SEQUENCE: 635

```
aaggcccaag aaccaggaat ctaggtattc gaaaagccct aaagttggct taataaactt    60
```

<210> SEQ ID NO 636
<211> LENGTH: 60
<212> TYPE: DNA
<213> ORGANISM: Homo sapiens

<400> SEQUENCE: 636

```
ggtgggcaga tcacttaagg ccaggaattc gaatgcaaaa ctcactaccc actggtaaga    60
```

<210> SEQ ID NO 637
<211> LENGTH: 60
<212> TYPE: DNA
<213> ORGANISM: Homo sapiens

<400> SEQUENCE: 637

```
ggtgggcaga tcacttaagg ccaggaattc gattctatca actctagaat tttttttaaat   60
```

<210> SEQ ID NO 638
<211> LENGTH: 60
<212> TYPE: DNA
<213> ORGANISM: Homo sapiens

<400> SEQUENCE: 638

```
aaggcaggca gatcaggagc tcaagagatc gaggtaaatg tgggggttct agaacccagt    60
```

<210> SEQ ID NO 639
<211> LENGTH: 60
<212> TYPE: DNA
<213> ORGANISM: Homo sapiens

<400> SEQUENCE: 639

```
ggtgggcaga tcacttaagg ccaggaattc gaaattcttt cctaatgcca agtgtgttat    60
```

<210> SEQ ID NO 640
<211> LENGTH: 60
<212> TYPE: DNA
<213> ORGANISM: Homo sapiens

<400> SEQUENCE: 640

```
ggtcccctga tttccatcct agtgcttctc gaaacatgtg ctctggagat aaagcgccaa    60
```

<210> SEQ ID NO 641
<211> LENGTH: 60
<212> TYPE: DNA
<213> ORGANISM: Homo sapiens

<400> SEQUENCE: 641
ggtgggcaga tcacttaagg ccaggaattc gatattcaat aaaagaccgg atgtgcaaag    60

<210> SEQ ID NO 642
<211> LENGTH: 60
<212> TYPE: DNA
<213> ORGANISM: Homo sapiens

<400> SEQUENCE: 642
ggtgggcaga tcacttaagg ccaggaattc gagaaatggt ttatccaatt catccaaaat    60

<210> SEQ ID NO 643
<211> LENGTH: 60
<212> TYPE: DNA
<213> ORGANISM: Homo sapiens

<400> SEQUENCE: 643
ggtgggcaga tcacttaagg ccaggaattc gagagactgt aaagacatgt gtctgcctct    60

<210> SEQ ID NO 644
<211> LENGTH: 60
<212> TYPE: DNA
<213> ORGANISM: Homo sapiens

<400> SEQUENCE: 644
ggtgggcaga tcacttaagg ccaggaattc gatcacttct taaaggccct acctcttaat    60

<210> SEQ ID NO 645
<211> LENGTH: 60
<212> TYPE: DNA
<213> ORGANISM: Homo sapiens

<400> SEQUENCE: 645
gttgggttga agatgaaatc ataggaagtc gagctgtaac ctctgcttgg tattctccct    60

<210> SEQ ID NO 646
<211> LENGTH: 60
<212> TYPE: DNA
<213> ORGANISM: Homo sapiens

<400> SEQUENCE: 646
ggtgggcaga tcacttaagg ccaggaattc gaaacaccag ctctcttaaa tcctgtgcct    60

<210> SEQ ID NO 647
<211> LENGTH: 60
<212> TYPE: DNA
<213> ORGANISM: Homo sapiens

<400> SEQUENCE: 647
ggtgggcaga tcacttaagg ccaggaattc gaggaaaacc tcggggcaaa atagggaaag    60

<210> SEQ ID NO 648
<211> LENGTH: 60
<212> TYPE: DNA
<213> ORGANISM: Homo sapiens

<400> SEQUENCE: 648
tgagaatgga atagatcaaa gggagggttc gagacaaggt ctcactttat cacccaacct    60

<210> SEQ ID NO 649
<211> LENGTH: 60
<212> TYPE: DNA
<213> ORGANISM: Homo sapiens

<400> SEQUENCE: 649
ggtgggcaga tcacttaagg ccaggaattc gactgtgtgc ccatgaagaa agaagatggg    60

<210> SEQ ID NO 650
<211> LENGTH: 60
<212> TYPE: DNA
<213> ORGANISM: Homo sapiens

<400> SEQUENCE: 650
agtgatagaa gagggacaag gtggcagttc gattttaaaa cacgctcttc aataaaaaga    60

<210> SEQ ID NO 651
<211> LENGTH: 60
<212> TYPE: DNA
<213> ORGANISM: Homo sapiens

<400> SEQUENCE: 651
agcaggggga tcacataagg ccaggagttc gataaaataa attagagaag atataaataa    60

<210> SEQ ID NO 652
<211> LENGTH: 60
<212> TYPE: DNA
<213> ORGANISM: Homo sapiens

<400> SEQUENCE: 652
ggtgggcaga tcacttaagg ccaggaattc gatttctctg cttctctcac agcccacatc    60

<210> SEQ ID NO 653
<211> LENGTH: 60
<212> TYPE: DNA
<213> ORGANISM: Homo sapiens

<400> SEQUENCE: 653
tctttgcaga tgttgtaaga taaggatgtc gaaaagccct aaagttggct taataaactt    60

<210> SEQ ID NO 654
<211> LENGTH: 60
<212> TYPE: DNA
<213> ORGANISM: Homo sapiens

<400> SEQUENCE: 654
ggtcccctga tttccatcct agtgcttctc gatgatataa tactctgctg actacatttt    60

<210> SEQ ID NO 655
<211> LENGTH: 60
<212> TYPE: DNA
<213> ORGANISM: Homo sapiens

<400> SEQUENCE: 655
aaggcccaag aaccaggaat ctaggtattc gaccacctta aaagaaaaat ctcttggaac    60

<210> SEQ ID NO 656
<211> LENGTH: 60
<212> TYPE: DNA
<213> ORGANISM: Homo sapiens

<400> SEQUENCE: 656
agcaggggga tcacataagg ccaggagttc gatgaacgtt tacccaatta tttctaaaca    60

<210> SEQ ID NO 657
<211> LENGTH: 60
<212> TYPE: DNA

```
<213> ORGANISM: Homo sapiens

<400> SEQUENCE: 657
gatgcggact gtttcctgct ttgatttatc gacttcttat ttctattttg tgacttagga    60

<210> SEQ ID NO 658
<211> LENGTH: 60
<212> TYPE: DNA
<213> ORGANISM: Homo sapiens

<400> SEQUENCE: 658
gatgcggact gtttcctgct ttgatttatc gacacagtgt gtctgaagtt tggggtggta    60

<210> SEQ ID NO 659
<211> LENGTH: 60
<212> TYPE: DNA
<213> ORGANISM: Homo sapiens

<400> SEQUENCE: 659
gatgcggact gtttcctgct ttgatttatc gatatctccc tcctttcgct tcttcctttc    60

<210> SEQ ID NO 660
<211> LENGTH: 60
<212> TYPE: DNA
<213> ORGANISM: Homo sapiens

<400> SEQUENCE: 660
gatgcggact gtttcctgct ttgatttatc gagtcattaa gagactctcc gcctgggtgg    60

<210> SEQ ID NO 661
<211> LENGTH: 60
<212> TYPE: DNA
<213> ORGANISM: Homo sapiens

<400> SEQUENCE: 661
ttccacctgt aatactgtgc ctgtattctc gactcttctc gccctcttct ccagctctct    60

<210> SEQ ID NO 662
<211> LENGTH: 60
<212> TYPE: DNA
<213> ORGANISM: Homo sapiens

<400> SEQUENCE: 662
taaagtactg tgtcccacat ataagtactc gaccaagaaa ttcattctta cctcctaaga    60

<210> SEQ ID NO 663
<211> LENGTH: 60
<212> TYPE: DNA
<213> ORGANISM: Homo sapiens

<400> SEQUENCE: 663
accccaccaa tctataataa gattgatttc gacacaaggg tttgtaacaa aaacaaaaa     60

<210> SEQ ID NO 664
<211> LENGTH: 60
<212> TYPE: DNA
<213> ORGANISM: Homo sapiens

<400> SEQUENCE: 664
agcgctttat ttgtcaggac gatagacctc gacaatgtcc tattcttcca gaaactcatt    60

<210> SEQ ID NO 665
<211> LENGTH: 60
```

```
<212> TYPE: DNA
<213> ORGANISM: Homo sapiens

<400> SEQUENCE: 665
ttattacttt attctgactg aatatcattc gaaagaaacc aaaaacacaa gtatacatca      60

<210> SEQ ID NO 666
<211> LENGTH: 60
<212> TYPE: DNA
<213> ORGANISM: Homo sapiens

<400> SEQUENCE: 666
tatcctttgg tttagaagta tttcttattc gacaaaattt taacatgtta tgcagttaca      60

<210> SEQ ID NO 667
<211> LENGTH: 60
<212> TYPE: DNA
<213> ORGANISM: Homo sapiens

<400> SEQUENCE: 667
ttcagctatt cactggtttt tcttcagatc gactcctgct tccctcccct catctttaaa      60

<210> SEQ ID NO 668
<211> LENGTH: 60
<212> TYPE: DNA
<213> ORGANISM: Homo sapiens

<400> SEQUENCE: 668
tccagtacaa taaacaatgt accaaagatc gacaaaattt taacatgtta tgcagttaca      60

<210> SEQ ID NO 669
<211> LENGTH: 60
<212> TYPE: DNA
<213> ORGANISM: Homo sapiens

<400> SEQUENCE: 669
taaactctga cattgcctat tagcattctc gaatgcatgg ctcactgtaa cctccaactc      60

<210> SEQ ID NO 670
<211> LENGTH: 60
<212> TYPE: DNA
<213> ORGANISM: Homo sapiens

<400> SEQUENCE: 670
tatcctttgg tttagaagta tttcttattc gacaactact ggcttaaaaa aggcaaaaca      60

<210> SEQ ID NO 671
<211> LENGTH: 60
<212> TYPE: DNA
<213> ORGANISM: Homo sapiens

<400> SEQUENCE: 671
tacctccttg ggaacatatt tgagagtttc gactcctgct tccctcccct catctttaaa      60

<210> SEQ ID NO 672
<211> LENGTH: 60
<212> TYPE: DNA
<213> ORGANISM: Homo sapiens

<400> SEQUENCE: 672
acacttgatt tttgctttcc aagctgactc gagacatcta agaaggtcca gccagatgtt      60

<210> SEQ ID NO 673
```

```
<211> LENGTH: 60
<212> TYPE: DNA
<213> ORGANISM: Homo sapiens

<400> SEQUENCE: 673
gcgccctatt tccaccttgt gccttctgtc gacacaccaa gatgtcacgg aggagtctgt    60

<210> SEQ ID NO 674
<211> LENGTH: 60
<212> TYPE: DNA
<213> ORGANISM: Homo sapiens

<400> SEQUENCE: 674
ccagctgaag tttcgcaggt ccctgcttc gagtaggcca atcccatttt tggcgaaaac    60

<210> SEQ ID NO 675
<211> LENGTH: 60
<212> TYPE: DNA
<213> ORGANISM: Homo sapiens

<400> SEQUENCE: 675
tacctccttg ggaacatatt tgagagtttc gactcctgct tccctcccct catctttaaa    60

<210> SEQ ID NO 676
<211> LENGTH: 60
<212> TYPE: DNA
<213> ORGANISM: Homo sapiens

<400> SEQUENCE: 676
acacttgatt tttgctttcc aagctgactc gagacatcta agaaggtcca gccagatgtt    60

<210> SEQ ID NO 677
<211> LENGTH: 60
<212> TYPE: DNA
<213> ORGANISM: Homo sapiens

<400> SEQUENCE: 677
gcgccctatt tccaccttgt gccttctgtc gacacaccaa gatgtcacgg aggagtctgt    60

<210> SEQ ID NO 678
<211> LENGTH: 60
<212> TYPE: DNA
<213> ORGANISM: Homo sapiens

<400> SEQUENCE: 678
ccagctgaag tttcgcaggt ccctgcttc gagtaggcca atcccatttt tggcgaaaac    60

<210> SEQ ID NO 679
<211> LENGTH: 60
<212> TYPE: DNA
<213> ORGANISM: Homo sapiens

<400> SEQUENCE: 679
actttggctc aagagtgaag atattcagtc gactcctgct tccctcccct catctttaaa    60

<210> SEQ ID NO 680
<211> LENGTH: 60
<212> TYPE: DNA
<213> ORGANISM: Homo sapiens

<400> SEQUENCE: 680
ttccttaggc aagtcatcca attccatgtc gacacaaggg tttgtaacaa aaaacaaaaa    60
```

```
<210> SEQ ID NO 681
<211> LENGTH: 60
<212> TYPE: DNA
<213> ORGANISM: Homo sapiens

<400> SEQUENCE: 681
tcttaggagg taagaatgaa tttcttggtc gaactcctga ccaggaggct gggaggggt      60

<210> SEQ ID NO 682
<211> LENGTH: 60
<212> TYPE: DNA
<213> ORGANISM: Homo sapiens

<400> SEQUENCE: 682
catcatttta ataggtgcaa gagttccgtc gaacgcccat acctgtggga atcaagcaat     60

<210> SEQ ID NO 683
<211> LENGTH: 60
<212> TYPE: DNA
<213> ORGANISM: Homo sapiens

<400> SEQUENCE: 683
aaaaacaaaa aagccaattc tgtacccctc gaaccagccc tggctctgtc cccagacctt    60

<210> SEQ ID NO 684
<211> LENGTH: 60
<212> TYPE: DNA
<213> ORGANISM: Homo sapiens

<400> SEQUENCE: 684
gcgccctatt tccaccttgt gccttctgtc gagacatcta agaaggtcca gccagatgtt    60

<210> SEQ ID NO 685
<211> LENGTH: 60
<212> TYPE: DNA
<213> ORGANISM: Homo sapiens

<400> SEQUENCE: 685
ttgattattt caggttgaca gctgtaaatc gactcctgct tccctcccct catctttaaa    60

<210> SEQ ID NO 686
<211> LENGTH: 21
<212> TYPE: DNA
<213> ORGANISM: Homo sapiens

<400> SEQUENCE: 686
ggaacctcgc tgtccataaa c                                              21

<210> SEQ ID NO 687
<211> LENGTH: 24
<212> TYPE: DNA
<213> ORGANISM: Homo sapiens

<400> SEQUENCE: 687
tctgtatgca agtcctgatg tttc                                           24

<210> SEQ ID NO 688
<211> LENGTH: 22
<212> TYPE: DNA
<213> ORGANISM: Homo sapiens

<400> SEQUENCE: 688
ggtaggagtg tgccttatta ac                                             22
```

```
<210> SEQ ID NO 689
<211> LENGTH: 21
<212> TYPE: DNA
<213> ORGANISM: Homo sapiens

<400> SEQUENCE: 689
gaggctgtta ggcattctaa g                                       21

<210> SEQ ID NO 690
<211> LENGTH: 22
<212> TYPE: DNA
<213> ORGANISM: Homo sapiens

<400> SEQUENCE: 690
gaaaccaacc ctatctgtaa ac                                      22

<210> SEQ ID NO 691
<211> LENGTH: 18
<212> TYPE: DNA
<213> ORGANISM: Homo sapiens

<400> SEQUENCE: 691
aaagaaagga ggctgtgg                                           18

<210> SEQ ID NO 692
<211> LENGTH: 19
<212> TYPE: DNA
<213> ORGANISM: Homo sapiens

<400> SEQUENCE: 692
gctctggact gcctttaac                                          19

<210> SEQ ID NO 693
<211> LENGTH: 22
<212> TYPE: DNA
<213> ORGANISM: Homo sapiens

<400> SEQUENCE: 693
aagtcagact cctcttctct ac                                      22

<210> SEQ ID NO 694
<211> LENGTH: 20
<212> TYPE: DNA
<213> ORGANISM: Homo sapiens

<400> SEQUENCE: 694
gtgaaactaa gccctcaacc                                         20

<210> SEQ ID NO 695
<211> LENGTH: 20
<212> TYPE: DNA
<213> ORGANISM: Homo sapiens

<400> SEQUENCE: 695
taccctcctt ccattcagac                                         20

<210> SEQ ID NO 696
<211> LENGTH: 21
<212> TYPE: DNA
<213> ORGANISM: Homo sapiens

<400> SEQUENCE: 696
gctacagagg tgaaggagat c                                       21
```

```
<210> SEQ ID NO 697
<211> LENGTH: 20
<212> TYPE: DNA
<213> ORGANISM: Homo sapiens

<400> SEQUENCE: 697
aagtctggag ctgggcaaag                                               20

<210> SEQ ID NO 698
<211> LENGTH: 20
<212> TYPE: DNA
<213> ORGANISM: Homo sapiens

<400> SEQUENCE: 698
gaaacagcat tcttgccaac                                               20

<210> SEQ ID NO 699
<211> LENGTH: 21
<212> TYPE: DNA
<213> ORGANISM: Homo sapiens

<400> SEQUENCE: 699
gcttcatgag agagtgagaa c                                             21

<210> SEQ ID NO 700
<211> LENGTH: 20
<212> TYPE: DNA
<213> ORGANISM: Homo sapiens

<400> SEQUENCE: 700
aaagagaaca gggtgtaacg                                               20

<210> SEQ ID NO 701
<211> LENGTH: 18
<212> TYPE: DNA
<213> ORGANISM: Homo sapiens

<400> SEQUENCE: 701
gagccgggaa taaacgac                                                 18

<210> SEQ ID NO 702
<211> LENGTH: 20
<212> TYPE: DNA
<213> ORGANISM: Homo sapiens

<400> SEQUENCE: 702
aggtctaggg ttcagggctc                                               20

<210> SEQ ID NO 703
<211> LENGTH: 21
<212> TYPE: DNA
<213> ORGANISM: Homo sapiens

<400> SEQUENCE: 703
gggttcattt gactggactg g                                             21

<210> SEQ ID NO 704
<211> LENGTH: 20
<212> TYPE: DNA
<213> ORGANISM: Homo sapiens

<400> SEQUENCE: 704
```

-continued gccagtgtga caagattgcc                                           20

<210> SEQ ID NO 705
<211> LENGTH: 21
<212> TYPE: DNA
<213> ORGANISM: Homo sapiens

<400> SEQUENCE: 705
gacatcagtg gagggaggaa c                                         21

<210> SEQ ID NO 706
<211> LENGTH: 19
<212> TYPE: DNA
<213> ORGANISM: Homo sapiens

<400> SEQUENCE: 706
atgcctgcaa cttaaggac                                            19

<210> SEQ ID NO 707
<211> LENGTH: 23
<212> TYPE: DNA
<213> ORGANISM: Homo sapiens

<400> SEQUENCE: 707
gaggacaaag agatagctta ctg                                       23

<210> SEQ ID NO 708
<211> LENGTH: 22
<212> TYPE: DNA
<213> ORGANISM: Homo sapiens

<400> SEQUENCE: 708
ctgtctagag tccagatctt tc                                        22

<210> SEQ ID NO 709
<211> LENGTH: 19
<212> TYPE: DNA
<213> ORGANISM: Homo sapiens

<400> SEQUENCE: 709
aaactacagg tgagggttg                                            19

<210> SEQ ID NO 710
<211> LENGTH: 20
<212> TYPE: DNA
<213> ORGANISM: Homo sapiens

<400> SEQUENCE: 710
tgacttgtcc accttcaccc                                           20

<210> SEQ ID NO 711
<211> LENGTH: 20
<212> TYPE: DNA
<213> ORGANISM: Homo sapiens

<400> SEQUENCE: 711
tacggcagtg tgggtctaac                                           20

<210> SEQ ID NO 712
<211> LENGTH: 60
<212> TYPE: DNA
<213> ORGANISM: Homo sapiens

<400> SEQUENCE: 712

```
aaatacaatt gaaataaaaa taatcttgtc gaagcaaggg cttccaggtc ataggtggat    60
```

<210> SEQ ID NO 713
<211> LENGTH: 60
<212> TYPE: DNA
<213> ORGANISM: Homo sapiens

<400> SEQUENCE: 713

```
tgttactggg ctcaccacaa gcttaaaatc gaacgctgcc agcattagaa cctatttgtt    60
```

<210> SEQ ID NO 714
<211> LENGTH: 60
<212> TYPE: DNA
<213> ORGANISM: Homo sapiens

<400> SEQUENCE: 714

```
aaaaaggcac tatgaaaaaa caacatgctc gaactcctga cctcagatga tccacacacc    60
```

<210> SEQ ID NO 715
<211> LENGTH: 60
<212> TYPE: DNA
<213> ORGANISM: Homo sapiens

<400> SEQUENCE: 715

```
caaacaagaa taaagagtag agggtgtttc gagaatcttc aactttttgt atcttctatt    60
```

<210> SEQ ID NO 716
<211> LENGTH: 60
<212> TYPE: DNA
<213> ORGANISM: Homo sapiens

<400> SEQUENCE: 716

```
tctctttgga atgtcagtta ttcaaatatc gaatagctcc tattgttatg gagtgtagca    60
```

<210> SEQ ID NO 717
<211> LENGTH: 60
<212> TYPE: DNA
<213> ORGANISM: Homo sapiens

<400> SEQUENCE: 717

```
tatctcagct tttggcctgt ctcagctttc gacatagtag gtacttggta aacatttgtt    60
```

<210> SEQ ID NO 718
<211> LENGTH: 20
<212> TYPE: DNA
<213> ORGANISM: Homo sapiens

<400> SEQUENCE: 718

```
tgagtaacac aaagcatctg                                                20
```

<210> SEQ ID NO 719
<211> LENGTH: 18
<212> TYPE: DNA
<213> ORGANISM: Homo sapiens

<400> SEQUENCE: 719

```
agtgactggc tatgttcc                                                  18
```

<210> SEQ ID NO 720
<211> LENGTH: 21
<212> TYPE: DNA
<213> ORGANISM: Homo sapiens

```
<400> SEQUENCE: 720
ctggtgattt gtgtgacttt g                                          21

<210> SEQ ID NO 721
<211> LENGTH: 18
<212> TYPE: DNA
<213> ORGANISM: Homo sapiens

<400> SEQUENCE: 721
agggaagatg tggaggag                                              18

<210> SEQ ID NO 722
<211> LENGTH: 19
<212> TYPE: DNA
<213> ORGANISM: Homo sapiens

<400> SEQUENCE: 722
gtacgactcc agccaaatg                                             19

<210> SEQ ID NO 723
<211> LENGTH: 22
<212> TYPE: DNA
<213> ORGANISM: Homo sapiens

<400> SEQUENCE: 723
gctgtctgtt actagattgc ac                                         22

<210> SEQ ID NO 724
<211> LENGTH: 18
<212> TYPE: DNA
<213> ORGANISM: Homo sapiens

<400> SEQUENCE: 724
accttgcaag aagcacag                                              18

<210> SEQ ID NO 725
<211> LENGTH: 21
<212> TYPE: DNA
<213> ORGANISM: Homo sapiens

<400> SEQUENCE: 725
atgatacttc ccaactgaca c                                          21

<210> SEQ ID NO 726
<211> LENGTH: 20
<212> TYPE: DNA
<213> ORGANISM: Homo sapiens

<400> SEQUENCE: 726
aggagcatcc atatcaagtg                                            20

<210> SEQ ID NO 727
<211> LENGTH: 19
<212> TYPE: DNA
<213> ORGANISM: Homo sapiens

<400> SEQUENCE: 727
ctgccatgtc tgactatcc                                             19

<210> SEQ ID NO 728
<211> LENGTH: 20
<212> TYPE: DNA
<213> ORGANISM: Homo sapiens
```

```
<400> SEQUENCE: 728
cagtgaagaa gccatcatcg                                            20

<210> SEQ ID NO 729
<211> LENGTH: 22
<212> TYPE: DNA
<213> ORGANISM: Homo sapiens

<400> SEQUENCE: 729
gcttagagaa ataccaccagc ag                                        22

<210> SEQ ID NO 730
<211> LENGTH: 18
<212> TYPE: DNA
<213> ORGANISM: Homo sapiens

<400> SEQUENCE: 730
atgggcagca tttctcac                                              18

<210> SEQ ID NO 731
<211> LENGTH: 22
<212> TYPE: DNA
<213> ORGANISM: Homo sapiens

<400> SEQUENCE: 731
agggacgatt tatatgactt gc                                         22

<210> SEQ ID NO 732
<211> LENGTH: 22
<212> TYPE: DNA
<213> ORGANISM: Homo sapiens

<400> SEQUENCE: 732
gtgctggtat gtacctgtaa tc                                         22

<210> SEQ ID NO 733
<211> LENGTH: 20
<212> TYPE: DNA
<213> ORGANISM: Homo sapiens

<400> SEQUENCE: 733
gagggttgag aagcatcttg                                            20

<210> SEQ ID NO 734
<211> LENGTH: 60
<212> TYPE: DNA
<213> ORGANISM: Homo sapiens

<400> SEQUENCE: 734
tgtaaactgt aatatcaaaa attcaaaatc gaagagttga tttacttatt aacattagaa    60

<210> SEQ ID NO 735
<211> LENGTH: 60
<212> TYPE: DNA
<213> ORGANISM: Homo sapiens

<400> SEQUENCE: 735 actttatag tgaaaagtgc catttgagtc gactgtgatt gaatgtaaaa ggttttaaat     60

<210> SEQ ID NO 736
<211> LENGTH: 60
<212> TYPE: DNA
```

```
<213> ORGANISM: Homo sapiens

<400> SEQUENCE: 736
tactgtagta agttctctga ggaggatatc gaagtcttgg attaaggttc attcaacaaa     60

<210> SEQ ID NO 737
<211> LENGTH: 60
<212> TYPE: DNA
<213> ORGANISM: Homo sapiens

<400> SEQUENCE: 737
tccatttgaa ggatgagaaa actgaggctc gaggcttaga aagtttcatt tggttgctca     60

<210> SEQ ID NO 738
<211> LENGTH: 60
<212> TYPE: DNA
<213> ORGANISM: Homo sapiens

<400> SEQUENCE: 738
ttttaaaccc aggtgcacac acaagagctc gaagcaggaa tcctggttct gttcccaggc     60

<210> SEQ ID NO 739
<211> LENGTH: 60
<212> TYPE: DNA
<213> ORGANISM: Homo sapiens

<400> SEQUENCE: 739
ccactccccc aggcttacct gcgagccatc gaggtgggcc tgggttctcg tggagggaga     60

<210> SEQ ID NO 740
<211> LENGTH: 60
<212> TYPE: DNA
<213> ORGANISM: Homo sapiens

<400> SEQUENCE: 740
tcactcattc tagatccctc tgtaaagttc gaactctgga ccttgtgatc cacccacctt     60

<210> SEQ ID NO 741
<211> LENGTH: 60
<212> TYPE: DNA
<213> ORGANISM: Homo sapiens

<400> SEQUENCE: 741
ttccatagat tactttcaa atcatccttc gaagctggcg gctgagggcc cggcgccaag      60

<210> SEQ ID NO 742
<211> LENGTH: 60
<212> TYPE: DNA
<213> ORGANISM: Homo sapiens

<400> SEQUENCE: 742
tacagtcttt gtagatgcag agtagcgttc gaagctggcg gctgagggcc cggcgccaag     60

<210> SEQ ID NO 743
<211> LENGTH: 21
<212> TYPE: DNA
<213> ORGANISM: Homo sapiens

<400> SEQUENCE: 743
ctgcccgtaa ataagcagaa g                                               21

<210> SEQ ID NO 744
<211> LENGTH: 20
```

```
<212> TYPE: DNA
<213> ORGANISM: Homo sapiens

<400> SEQUENCE: 744
gagggttgag aagcatcttg                                                    20
```